United States Patent
Blanchetot et al.

(10) Patent No.: US 11,117,959 B2
(45) Date of Patent: Sep. 14, 2021

(54) IL-6 BINDING MOLECULES

(71) Applicant: argenx BVBA, Zwijnaarde (BE)

(72) Inventors: Christophe Blanchetot, Destelbergen (BE); Johannes De Haard, Oudelande (NL); Torsten Dreier, Sint-Martens-Latem (BE); Natalie De Jonge, Aalst (BE); Sebastian Paul Van Der Woning, Bachte-Maria-Leerne (BE); Nicolas Ongenae, Gentbrugge (BE)

(73) Assignee: argenx BVBA

( * ) Notice: Subject to any disclaimer, the term of this patent is extended or adjusted under 35 U.S.C. 154(b) by 30 days.

(21) Appl. No.: 16/239,321

(22) Filed: Jan. 3, 2019

(65) Prior Publication Data

US 2019/0233509 A1    Aug. 1, 2019

Related U.S. Application Data

(62) Division of application No. 14/403,135, filed as application No. PCT/IB2013/054271 on May 23, 2013, now Pat. No. 10,183,995.

(60) Provisional application No. 61/720,102, filed on Oct. 30, 2012, provisional application No. 61/650,883, filed on May 23, 2012.

(30) Foreign Application Priority Data

Nov. 14, 2012   (WO) ................ PCT/IB2012/056424

(51) Int. Cl.
| | | |
|---|---|---|
| *C07K 16/24* | (2006.01) | |
| *A61K 39/395* | (2006.01) | |
| *A61K 39/00* | (2006.01) | |

(52) U.S. Cl.
CPC .......... *C07K 16/248* (2013.01); *A61K 39/395* (2013.01); *A61K 2039/505* (2013.01); *C07K 2317/21* (2013.01); *C07K 2317/22* (2013.01); *C07K 2317/24* (2013.01); *C07K 2317/34* (2013.01); *C07K 2317/55* (2013.01); *C07K 2317/565* (2013.01); *C07K 2317/73* (2013.01); *C07K 2317/76* (2013.01); *C07K 2317/92* (2013.01); *C07K 2317/94* (2013.01)

(58) Field of Classification Search
CPC ............ A61K 2039/505; A61K 39/395; A61K 39/3955; C07K 16/248; C07K 2317/22; C07K 2317/76; C07K 2317/70; C07K 2317/72
See application file for complete search history.

(56) References Cited

U.S. PATENT DOCUMENTS

| | | |
|---|---|---|
| 4,741,900 A | 5/1988 | Alvarez et al. |
| 4,816,397 A | 3/1989 | Boss et al. |
| 4,816,567 A | 3/1989 | Cabilly et al. |
| 5,225,539 A | 7/1993 | Winter |
| 5,314,995 A | 5/1994 | Fell et al. |
| 5,460,785 A | 10/1995 | Rhodes et al. |
| 5,530,101 A | 6/1996 | Queen et al. |
| 5,565,332 A | 10/1996 | Hoogenboom et al. |
| 5,585,089 A | 12/1996 | Queen et al. |
| 5,648,260 A | 7/1997 | Winter et al. |
| 5,739,277 A | 4/1998 | Presta et al. |
| 5,807,715 A | 9/1998 | Morrison et al. |
| 5,834,250 A | 11/1998 | Wells et al. |
| 5,869,046 A | 2/1999 | Presta et al. |
| 6,096,871 A | 8/2000 | Presta et al. |
| 6,121,022 A | 9/2000 | Presta et al. |
| 6,193,980 B1 | 2/2001 | Estahiou et al. |
| 6,194,551 B1 | 6/2001 | Idusogie et al. |
| 6,277,375 B1 | 8/2001 | Ward |
| 6,528,624 B1 | 3/2003 | Idusogie et al. |
| 6,538,124 B1 | 3/2003 | Idusogie et al. |
| 6,602,977 B1 | 8/2003 | Ljungqvist et al. |
| 6,673,901 B2 | 1/2004 | Koide |
| 6,703,199 B1 | 3/2004 | Koide |
| 6,737,056 B1 | 5/2004 | Presta |
| 6,740,734 B1 | 5/2004 | Nilsson et al. |
| 6,821,505 B2 | 11/2004 | Ward |
| 6,998,253 B1 | 2/2006 | Presta et al. |
| 7,078,490 B2 | 7/2006 | Koide |
| 7,083,784 B2 | 8/2006 | Dall'Acqua et al. |

(Continued)

FOREIGN PATENT DOCUMENTS

| | | |
|---|---|---|
| EP | 0239400 | 9/1987 |
| EP | 0396387 | 11/1990 |

(Continued)

OTHER PUBLICATIONS

Fischer et al. The Two Faces of IL-6 in the Tumor Microenvironment. Semin Immunol. Feb. 2014; 26(1): 38-47 (Year: 2014).*

(Continued)

*Primary Examiner* — Vanessa L. Ford
*Assistant Examiner* — Sandra E Dillahunt
(74) *Attorney, Agent, or Firm* — Lathrop GPM LLP; James H. Velema, Esq.

(57) ABSTRACT

The present invention provides binding molecules (e.g., antibodies or antigen binding fragments thereof) that specifically bind to and inhibit the biological activity of IL-6 (e.g., human, mouse and non-human primate IL-6). In a preferred embodiment, the antibodies or antigen binding fragments of the invention bind to IL-6 and inhibit its binding to an IL-6 receptor. Such antibodies or antigen binding fragments are particularly useful for treating IL-6-associated diseases or disorders (e.g., inflammatory disease and cancer).

15 Claims, 18 Drawing Sheets

Specification includes a Sequence Listing.

(56) References Cited

U.S. PATENT DOCUMENTS

| | | | |
|---|---|---|---|
| 7,119,171 | B2 | 10/2006 | Koide |
| 8,075,889 | B2 | 12/2011 | Gelinas et al. |
| 8,163,881 | B2 | 4/2012 | Ober |
| 8,198,414 | B2 | 6/2012 | Cruvvys et al. |
| 8,444,976 | B2 | 5/2013 | Dreier et al. |
| 2002/0102208 | A1 | 8/2002 | Chinn et al. |
| 2004/0132028 | A1 | 7/2004 | Stumpp et al. |
| 2011/0086770 | A1 | 4/2011 | Wild et al. |
| 2012/0034212 | A1 | 2/2012 | Bowen et al. |

FOREIGN PATENT DOCUMENTS

| | | | | |
|---|---|---|---|---|
| EP | | 0519596 | 12/1992 | |
| EP | | 0592106 | 4/1994 | |
| WO | WO 1988007089 | | 9/1988 | |
| WO | WO 1989012624 | | 12/1989 | |
| WO | WO 1991009967 | | 7/1991 | |
| WO | WO 1991014438 | | 10/1991 | |
| WO | WO 1992008495 | | 5/1992 | |
| WO | WO 1996014339 | | 5/1996 | |
| WO | WO 1998005787 | | 2/1998 | |
| WO | WO 1998023289 | | 6/1998 | |
| WO | WO 1998052976 | | 11/1998 | |
| WO | WO 1999016873 | | 4/1999 | |
| WO | WO 1999051642 | | 10/1999 | |
| WO | WO 1999058572 | | 11/1999 | |
| WO | WO 2000009560 | | 2/2000 | |
| WO | WO 2000032767 | | 6/2000 | |
| WO | WO 2000034317 | | 6/2000 | |
| WO | WO 2000042072 | | 7/2000 | |
| WO | WO 2000063243 | | 10/2000 | |
| WO | WO 2001064942 | | 9/2001 | |
| WO | WO 2002020565 | | 3/2002 | |
| WO | WO 2002044215 | | 6/2002 | |
| WO | WO 2002060919 | | 8/2002 | |
| WO | WO 2002088171 | | 11/2002 | |
| WO | WO 2003074569 | | 9/2003 | |
| WO | WO 2004016750 | | 2/2004 | |
| WO | WO 2004029207 | | 4/2004 | |
| WO | WO 2004035752 | | 4/2004 | |
| WO | WO 2004044011 | | 5/2004 | |
| WO | WO 2004063351 | | 7/2004 | |
| WO | WO 2004074455 | | 9/2004 | |
| WO | WO 2004099249 | | 11/2004 | |
| WO | WO 2005018572 | | 3/2005 | |
| WO | WO 2005019254 | | 3/2005 | |
| WO | WO 2005040217 | | 5/2005 | |
| WO | WO 2005047327 | | 5/2005 | |
| WO | WO 2005070963 | | 8/2005 | |
| WO | WO 2005077981 | | 8/2005 | |
| WO | WO 2005092925 | | 10/2005 | |
| WO | WO 2005123780 | | 12/2005 | |
| WO | WO 2006019447 | | 2/2006 | |
| WO | WO 2006047350 | | 5/2006 | |
| WO | WO 2006083275 | | 8/2006 | |
| WO | WO 2006085967 | | 8/2006 | |
| WO | WO 2006119115 | | 11/2006 | |
| WO | WO 2007066082 | | 6/2007 | |
| WO | WO 2007104529 | | 9/2007 | |
| WO | WO 2008019061 | A2 | 2/2008 | |
| WO | WO-2008019061 | A2 * | 2/2008 | ............... A61P 9/14 |
| WO | WO 2008065378 | | 6/2008 | |
| WO | WO 2008144763 | | 11/2008 | |
| WO | WO 2010056948 | | 5/2010 | |

OTHER PUBLICATIONS

Hume et al. A Protective Role for IL-6 in Staphylococcal Microbial Keratitis. Investigative Ophthalmology & Visual Science, Nov. 2006, vol. 47, No. 11 (Year: 2006).*

Song et al. Antitumor efficacy of the anti-interleukin-6 (IL-6) antibody siltuximab in mouse xenograft models of lung cancer. J Thorac Oncol. Jul. 2014 ; 9(7): 974-982 (Year: 2014).*

Dorff et al. Clinical and Correlative Results of SWOG S0354: A Phase II Trial of CNTO328 (Siltuximab), a Monoclonal Antibody against Interleukin-6, in Chemotherapy-Pretreated Patients with Castration-Resistant Prostate Cancer. Clin Cancer Res. 2010; 16(11); 3028-34 (Year: 2010).*

Sieperetal. Assessment of short-term symptomatic efficacy of tocilizumab in ankylosing spondylitis: results of randomised, placebo-controlled trials. Ann Rheum Dis 2014; 73:95-100 (Year: 2014).*

Rovin et al. A Multicenter, Randomized, Double-Blind, Placebo-Controlled Study to Evaluate the Efficacy and Safety of Treatment With Sirukumab (CNTO 136) in Patients With Active Lupus Nephritis. Arthritis Rheumatol. Sep. 2016; 68(9): 2174-2183 (Year: 2016 ).*

"Antibodies—Abysis—new database." www.bioinf.org.uk : Dr. Andrew C.R. Martin's Group, Nov. 16, 2015, pp. 1-8.

Baca et al., "Antibody Humanization Using Monovalent Phage Display," The Journal of Biological Chemistry, Apr. 18, 1997, pp. 10678-10684, vol. 272, No. 16.

Beste et al., "Small antibody-like proteins with prescribed ligand specificities derived from the lipocalin fold," Proc. Natl. Acad. Sci. USA, Mar. 1999, pp. 1898-1903, vol. 96.

Binz et al., "High-affinity binders selected from designed ankyrin repeat proteins libraries," Nat. Biotechnol., May 2004, pp. 575-582, vol. 22, No. 5.

Boulanger et al. Hexameric Structure and Assembly of the Interleukin-6/IL-6 a-Receptor/gp130 Complex. Science, 2003, pp. 2101-2104, vol. 300.

Bowie et al. Deciphering the Message in Protein Sequences: Tolerance to Amino Acid Substitutions. Science, 247:1306-1310, 1990.

Brown et al. Tolerance to single, but not multiple, amino acid replacements in antibody VH CDR2. Journal of Immunology, May 1996;156(9):3285-91.

Brummell et al., "Probing the Combining Site of an Anti-Carbohydrate Antibody by Saturation-Mutagenesis: Role of the Heavy-Chain CDR3 Residues," Biochem., 1993, pp. 1180-1187, vol. 32.

Burks et al., "In vitro scanning saturation mutagenesis of an antibody binding pocket," Proc. Natl. Acad. Sci., Jan. 1997, pp. 412-417, vol. 94.

"Canonicals—Chothia Canonical Assignment," www.bioinf.org. uk : Dr. Andrew C.R. Martin's Group, Nov. 16, 2015, pp. 1-2.

Casset et al. A peptide mimetic of an anti-CD4 monoclonal antibody by rational design. Biochemical and Biophysical Research Communications, 307:198-205, 2003.

Chapman, Andrew P., "PEGylated antibodies and antibody fragments for improved therapy: a review," Advanced Drug Delivery Reviews, 2002, pp. 531-545, vol. 54.

Chinn, Paul, U.S. Appl. No. 09/259,338, filed Mar. 1, 1999, 48 pages.

Chomczynski et al., "Single-Step Method of RNA Isolation by Acid Guanidinium Thiocyanate-Phenol-Chloroform Extraction," Anal. Biochem., 1987, pp. 156-159, vol. 162.

Chothia et al., "Canonical Structures for the Hypervariable Regions of Immunoglobulins," J. Biol., 1987, pp. 901-917, vol. 196.

Chothia et al., "Structural Repertoire of the Human VH Segments," J. Mol. Biol., 1992, pp. 799-817, vol. 227.

Colman. Effects of amino acid sequence changes on antibody-antigen interactions. Research in Immunology, 145:33-36, 1994.

Correia, "Stability of IgG isotypes in serum", mABS, vol. 2, Jan. 1, 2010, pp. 221-232.

De Haard et al., "A Large Non-immunized Human Fab Fragment Phage Library That Permits Rapid Isolation and Kinetic Analysis of High Affinity Antibodies," The Journal of Biological Chemistry, Jun. 25, 1999, pp. 18218-18230, vol. 274, No. 26.

Ehlers et al., "Identification of Single Amino Acid Residues of Human IL-6 Involved in Receptor Binding and Signal Intitiation", Journal of Interferon and Cytokine Research, 1996, pp. 569-576, vol. 16.

Fulciniti et al., "A High-Affinity Fully Human Anti-IL-6 mAb, 1339, for the Treatment of Multiple Myeloma", Clinical Cancer Research, 2009, pp. 7144-7151, vol. 15.

(56) References Cited

OTHER PUBLICATIONS

GenBank 10834984, "interleukin-6 precursor [*Homo sapiens*]," NCBI Reference Sequence: NP_000591.1, accessed on Nov. 16, 2015, 3 pages.

GenBank 13624311, "interleukin-6 isoform 1 precursor [*Mus musculus*]," NCBI Reference Sequence: NP_112445.1, accessed on Nov. 16, 2015, 3 pages.

Gentz et al., "Bioassay for trans-activation using purified human immunodeficiency virus tat-encoded protein: Tarns-activation requires mRNA synthesis," Proc. Natl. Acad. Sci. USA, Feb. 1989, pp. 821-824, vol. 86.

Gillies et al., "High-level expression of chimeric antibodies using adapted cDNA variable region cassettes," J. Immunol. Methods, 1989, pp. 191-202, vol. 125.

Grotzinger et al., "The family of the IL-6-Type Cytokines: Specificity and Promiscuity of the Receptor Complexes", Proteins: Structure, Function and Bioinformatics, 1997, pp. 96-109, vol. 27.

Hammacher et al. "Structure-function analysis of human IL-6: identification of two distinct regions that are important for receptor binding," Protein Science: a publication of the Protein Society, 1994, pp. 2280-2293, vol. 3, No. 12.

Helle et al., "Functional discrimination between interleukin 6 and interleukin 1," Eur. J. Immunol., 1988, pp. 1535-1540, vol. 18.

Human Vk Germline Sequences (Vbase), http://www.bioc.uzh.ch/antibody/Sequences/GermlinesNBase_hVK.html, 1 page.

Jones, Elizabeth W., "Bipartite Structure of the ade3 Locus of *Saccharomyces cerevisiae*," Genetics, Feb. 1977, pp. 209-223, vol. 85.

Jones, Elizabeth W., "Proteinase Mutants of *Saccharomyces cerevisiae*," Genetics, Jan. 1977, pp. 23-33, vol. 85.

Kabat et al., "Unusual Distributions of Amino Acids in Complementarity-determining (Hypervariable) Segments of Heavy and Light Chains of Immunoglobulins and Their Possible Roles in Specificity of Antibody-combining Sites," J. Biol. Chem., 1977, pp. 6609-6616, vol. 252, No. 19.

Kalai et al., "Analysis of the Human Interleukin-6/Human Interleukin-6 Receptor Binding Interface at the Amino Acid Level: Proposed Mechanism of Interaction", Blood, 1997, pp. 1319-1333, vol. 89.

Kingsman et al., Replication in *Saccharomyces cerevisiae* of Plasmid pBR313 Carrying DNA from the Yeast trp1 Region, Gene, 1979, pp. 141-152, vol. 7.

Klein, et al., "Somatic Mutations of the Immunoglobulin Framework Are Generally Required for Broad and Potent HIV-1 Neutralization", Cell, vol. 153(1), Mar. 1, 2013, pp. 126-138.

Kobayashi et al., "Tryptophan H33 plays an important role in pryimidine (6-4) pyrimidone photoproduct binding by a high-affinity antibody," Protein Eng., 1999, pp. 879-884, vol. 12, No. 10.

Koide et al., "The Fibronectin Type III Domain as a Scaffold for Novel Binding Proteins," J. Mol. Biol., 1998, pp. 1141-1151, vol. 284.

Lefranc et al., "IMGT, the international ImMunoGeneTics database," Nucleic Acids Research, 1999, pp. 209-212, vol. 27, No. 1.

Legendre et al., "TEM-1 β-lactamase as a scaffold for protein recognition and assay," Protein Science, 2002, pp. 1506-1518, vol. 11.

Leong et al., "Adapting Pharmacokinetic Properties of a Humanized Anti-Interleukin-8 Antibody for Therapeutic Applications using Site-Specific Pegylation," Cytokine, 2001, pp. 106-119, vol. 16, No. 3.

MacCallum et al. Antibody-antigen Interactions: Contact Analysis and Binding Site Topography. Journal of Molecular Biology, 1996, pp. 732-745, vol. 262.

Martin et al., "Structural Families in Loops of Homologous Proteins: Automatic Classification, Modelling and Application to Antibodies," J. Mol. Biol., 1996, pp. 800-815, vol. 263.

Mimura, et al., "The influence of glycosylation on the thermal stability and effector function expression of human IgG1-Fc: properties of a series of truncated glycoforms", Molecular Immunology, vol. 37(12-13), Sep. 1, 2000, pp. 697-706.

Morea et al., "Antibody Modeling: Implications for Engineering and Design," Methods, 2000, pp. 267-279, vol. 20.

Morrison et al., "Chimeric human antibody molecules: Mouse antigen-binding domains with human constant region domains," Proc. Natl. Acad. Sci., Nov. 1984, pp. 851-855, vol. 81.

Morrison, Sherie L., "Transfectomas Provide Novel Chimeric Antibodies," Science, 1985, pp. 1202-1207, vol. 229, No. 4719.

Neuberger et al., "Recombinant antibodies possessing novel effector functions," Nature, 1984, pp. 604-608, vol. 312.

Nord et al., "Binding proteins selected from combinatorial libraries of an a-Helical bacterial receptor domain," Nat. Biotechnol., 1997, pp. 772-777, vol. 15.

Oi et al., "Overview: Chimeric Antibodies," Biotechniques, 1986, pp. 214-221, vol. 4, No. 3.

Ono et al., "The humanized anti-HM1.24 antibody effectively kills multiple myeloma cells by human effector cell-mediated cytotoxicity," Mol. Immunol., 1999, pp. 387-395, vol. 36.

Padlan, Eduardo A., "A Possible Procedure for Reducing the Immunogenicity of Antibody Variable Domains while Preserving their Ligand-Binding Properties," Molecular Immunology, 1991, pp. 489-498, vol. 28, No. 4/5.

Pancer et al., "Somatic diversification of variable lymphocyte receptors in the agnathan sea lamprey," Nature, Jul. 8, 2004, pp. 174-180, vol. 430.

Panni et al., "In Vitro Evolution of Recognition Specificity Mediated by SH3 Domains Reveals Target Recognition Rules," J. Biol. Chem., Jun. 14, 2002, pp. 21666-21674, vol. 277 No. 24.

Paul. Fundamental Immunology, 3rd Edition, Raven Press, New York, Chapter 8, pp. 292-295, 1993 (Year: 1993).

Pietersz et al., "The use of monoclonal antibody conjugates for the diagnosis and treatment of cancer," Immunol. Cell Biol. 1987, pp. 111-125, vol. 65 (Pt. 2).

Presta. Molecular engineering and design of therapeutic antibodies. Current Opinion in Immunology. 20(4): 460-470. Aug. 2008.

Qu et al., "Humanization of Immu31, an α-Fetoprotein-specific Antibody," Clin. Cancer Res., Oct. 1999 (Suppl.), pp. 3095-3100, vol. 5.

Ridgeway, Anthony A.G., "Mammalian Expression Vectors", Biotechnology, Chapter 24, 1987, pp. 467-492, Reading, Mass.

Riechmann et al., "Reshaping human antibodies for therapy," Nature, 1988, pp. 323-327, vol. 332.

Roguska et al., "Humanization of murine monoclonal antibodies through variable domain resurfacing," Proc. Natl. Acad. Sci. USA, Feb. 1994, pp. 969-973, vol. 9.

Rudikoff et al. Single amino acid substitution altering antigen-binding specificity. PNAS USA, 79(6):1979-1983, Mar. 1982.

Schlehuber et al., "Keynote Review: Lipocalins in drug discovery: from natural ligand-binding proteins to 'anticalins'," Drug Discov. Today, Jan. 2005, pp. 23-33, vol. 10, No. 1.

Schneider et al., "Mutagenesis and selection of PDZ domains that bind new protein targets," Nat. Biotechnol, Feb. 1999, pp. 170-175, vol. 17.

Schwantner et al., "Direct Determination of the Interleukin-6 Binding Epitope of the Interleukin-6 Receptor by NMR Spectroscopy", Journal of Biological Chemistry, 2004, pp. 571-576, vol. 279.

Somers et al., "1.9 Å crystal structure of interleukin 6: implications for a novel mode of receptor dimerization and signaling," The EMBO Journal, 1997, pp. 989-997, vol. 16, No. 5.

Stinchcomb et al., "Isolation and characterisation of a yeast chromosomal replicator," Nature, 1979, pp. 39-43, vol. 282.

Stoop et al., "Engineering of a macromolecular scaffold to develop specific protease inhibitors," Nat. Biotechnol., Sep. 2003, pp. 1063-1068, vol. 21, No. 9.

Strohl. Optimization of Fe-mediated effector functions of monoclonal antibodies. Current Opinion in Biotechnology. 20:685-691, Nov. 2009.

Studnicka et al., "Human-engineered monoclonal antibodies retain full specific binding activity by preserving non-CDR complementarity-modulating residues," Protein Engineering, 1994, pp. 805-814, vol. 7, No. 6.

(56) References Cited

OTHER PUBLICATIONS

Takeda et al., "Construction of chimaeric processed immunoglobulin genes containing mouse variable and human constant region sequences," Nature, 1985, pp. 452-454, vol. 314.

Tomlinson et al., "The Structural repertoire of the human Vk domain," The EMBO Journal, 1995, pp. 4628-4638, vol. 14, No. 18.

Tramontano et al., "Framework Residue 71 is a Major Determinant of the Position and Conformation of the Second Hypervariable Region in the VH Domains of Immunoglobins," J. Mol. Biol, 1990, pp. 175-182, vol. 215.

Tramontano et al., "Structural Determinants of the Conformations of Medium-Sized Loops in Proteins," Proteins, 1989, pp. 382-394, vol. 6.

Tschemper et al., "Sequence of a yeast DNA fragment containing a chromosomal replicator and the TRP1 gene," Gene, 1980, pp. 157-166, vol. 10.

Tsurushita et al., "Humanization of a chicken! anti-IL-12 monoclonal antibody," Journal of Immunological Methods, 2004, pp. 9-19, vol. 295.

Vajdos et al. Comprehensive functional maps of the antigen-binding site of an anti-ErbB2 antibody obtained with shotgun scanning mutagenesis. Journal of Molecular Biology, Jul. 5, 2002;320(2):415-28.

Van Snick et al., "Purification and NH2-terminal amino acid sequence of a T-cell-derived lymphokine with growth factor activity for B-Cell hybridomas," Proc. Natl. Acad. Sci. USA, Dec. 1986, pp. 9679-9683, vol. 83.

Varghese et al, "Structure of the extracellular domains of the human interleukin-6 receptor a-chain", PNAS, 2002, pp. 15959-15964, vol. 99.

Vita et al., "Scorpian toxins as natural scaffolds for protein engineering," Proc. Natl. Acad. Sci. USA, Jul. 1995, pp. 6404-6408, vol. 92.

Weir et al., "Formatting antibody fragments to mediate specific therapeutic functions," Biochem. Soc. Transactions, 2002, pp. 512-516, vol. 30, Part 4.

Williams et al., "Sequence and Evolution of the Human Germline V Repertoire," J_ Mal. Biol., 1996, pp. 220-232, vol. 264.

Wilson et al., "The Structure of an Antigenic Determinant in a Protein," Cell, Jul. 1984, pp. 767-778, vol. 37.

Wu et al., "Humanization of a Murine Monoclonal Antibody by Simultaneous Optimization of Framework and CDR Residues", J. Mol. Biol., 1999, 294: 151-162.

U.S. Appl. No. 14/403,135, filed May 23, 2013 / 2015/0140011 / May 21, 2015 / U.S. Pat. No. 10,183,995, Jan. 22, 2019, Christophe Blanchetot.

\* cited by examiner

The VL (VL2) belongs to the human 6λ-1-5 canonical structure class

The VH (VH4) belongs to the human 3-1 canonical structure class

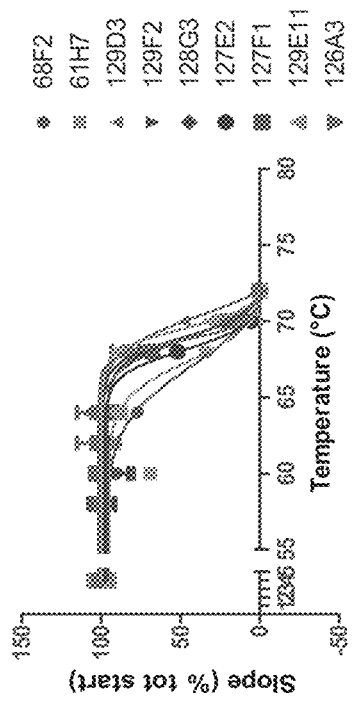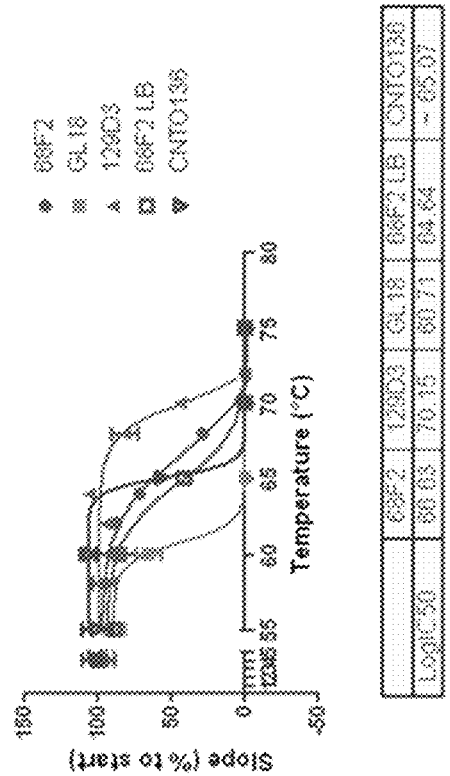
Fig. 7A
Fig. 7B

Figure 9

| | | VL | VH | TOTAL DRB1 SCORE |
|---|---|---|---|---|
| 1 | 111A7 | 2.77 | 2.35 | 5.12 |
| 2 | Humira | 2.47 | 5.04 | 7.51 |
| 3 | 104G5ML | 2.14 | 5.58 | 7.72 |
| 4 | 129E11 | 5.58 | 3.72 | 9.30 |
| 5 | CAT18 | 2.50 | 7.34 | 9.84 |
| 6 | ALDER | 6.08 | 4.25 | 10.33 |
| 7 | 127F1 | 6.08 | 4.25 | 10.34 |
| 8 | 104C1 | 2.73 | 7.98 | 10.71 |
| 9 | 104C1COMBA | 2.73 | 8.03 | 10.76 |
| 10 | 129D3 | 4.91 | 6.69 | 11.60 |
| 11 | 61H7 | 4.54 | 7.12 | 11.66 |
| 12 | 133E5 | 6.54 | 5.29 | 11.83 |
| 13 | Herceptin | 6.22 | 5.89 | 12.11 |
| 14 | CNTO136 | 5.70 | 6.56 | 12.26 |
| 15 | 68F2 | 6.54 | 5.85 | 12.39 |
| 16 | Synagis | 5.29 | 7.40 | 12.69 |
| 17 | 103A1ML | 4.54 | 8.22 | 12.76 |
| 18 | Campath | 4.84 | 9.42 | 14.26 |
| 19 | HuA33 | 6.41 | 9.07 | 15.48 |
| 20 | Remicade | 7.57 | 9.72 | 17.28 |
| 21 | CNTO328 | 9.71 | 10.69 | 20.40 |
| 22 | Rituxan | 8.71 | 11.71 | 20.42 |
| 23 | OKT3 | 14.17 | 34.39 | 48.56 |

Fig. 10A

```
                       CDR1                                                 CDR2                                                    CDR3
VH_68F2   1 EVQLQESGGGPGLVKPSQTLSLTCTVSGGSIT/TRYYAMS/WIRQPPGKGLEWMG/VIDYDGDTYYSPSLKS/RTSISWDTSKNQFSLQLSSVTPEDTAVYYCAR/DPDVTGPHYDY/WGQGTQVTVSS
VH_129D3  1 QVQLQESGGGPGLVKPSQTLSLTCTVSGGSIT/SRYYAMS/WIRQPPGKGLEWIG/VIDYDGDTYYSPSLKS/RVSISWDTSKNQFSLKLSSVTPADTAVYYCAR/DPDVTGPHYDY/WGQGTMVTVSS
                  1                 2                     3                                4                              5                         6

CDR1                                              CDR2                                            CDR3
VL_68F2   1 QSALTQPPLVSGTPGQTVTISC/AGANNDIGTYAYVS/WIQQLPGTAPKLLIY/KVTTRAS/GIPSRFSGSKSGNTASLTISGLQSEDEADYC/ASYRNFNRAV/FGRGTKLTVL
VL_129D3  1 QSALTQPPSVSGTPGQSVTISC/AGANNDIGTYAYVS/WIQQLPGTAPKLMIY/KVTTRAS/GIPDRFSGSKSGNTASLTISGLQAEDEADYC/ASYRNFNRAV/FGTGKLTVL
                   1              2                3              4                     5                         6    7
```

Fig. 10B

```
                       CDR1                                                    CDR2                                               CDR3
VH_111A7  1 EVQLLESGGGLVQPGGSLRLSCAASGFTFS/SYAMS/WVRQAPGKGPEWVS/RISAGGGSTYYGDSVKG/RFTISRDNSKNTLYLQMNSLRAEDTAVYYCAN/RAGWGMGDY/WGQGTLVTVSS
VH_61H7   1 EVQLVESGGGLVQPGGSLRLSCAASGFTFS/SYAMY/WVRQAPGKGLEWVS/AISAGGGSTYYGDSVKG/RFTISRDNAKNTVYLQMNSLKPEDTAVYYCAN/RAGWGMGDY/WGQGTQVTVSS
                  1                 2       3                    4                   5    67                           8

CDR1                                               CDR2                                            CDR3
VL_111A7  1 QTVVTQEPSFSVSPGGTVTLRC/GLSSGSVTASNYPG/WYQQTPGQAPRALIY/STMDRHS/GVPDRFSGSISGNKAALTITGAQAEDEADYC/ALDIGRITE/FGGGTQLTVL
VL_61H7   1 QTVVTQEPSLSVSPGGTVTLRC/GLSSGSVTASNYPG/WFQQRPGQAPRALIY/STMDRHS/GVPSRFSGSISGNKAALTITGAQPEDEADYC/ALDIGRITE/FGGGTRLTVL
                   1              2                 3              4                     5
```

Fig. 11A

```
                    CDR1                                          CDR2                                                 CDR3
VH_CNTO136 : EVQLVESGGGLVQPGGSLRLSCAASGFTFS/PFAMS/WVRQAPGKGLEWVA/KISPGGSWTYYSDTVYG/RFTISRDNAKNSLYLQMNSLRAEDTAVYYCAR/QLWGYYALDI/WGQGTLVTVSS
VH_CNTO328 : EVQLVESGGGKLLRPGGSLRLSCAASGFTFS/SFAMS/WFRQSPEKRLEWVA/EISSGGSYTYYPDTVTG/RFTISRDNAKNTLYLEMSSLRSEDTAMYYCAR/GLWGYYALDY/WGQGTSVTVTSS
             1 2 3                         4                    5 6 7 8                9 0 1 2 3                                        4
                                                                                       9 0 1 2 3
                          CDR1                                       CDR2                                         CDR3
VK_CNTO328 : QIVLIQSPAIMSASPGEKVTMTC/SASSSVSYMY/WYQQKPGSSPRKLLIY/DTSNLAS/GVPVRFSGSGSGTSYSLTISRMEAEDAATYYC/QQWSGYPYT/FGGGTKLEIK
VK_CNTO136 : EIVLTQSPATLSLSPGERATLSC/SASISVSYMY/WYQQKPGQAPRLLIY/DMSNLAS/GIPARFSGSGSGTDFTLTISSLEFEDFAVYYC/MQWSGYPYT/FGGGTKVEIK
             1 2   3 4 5            6 7 8 9              0 1              2 3             4 5 6    7 8 9 0 1                   2
```

Fig. 11B

```
                       CDR1                                         CDR2                                                CDR3
VH_rabbit : -QSLEESGGRLVTPGTPLTLTCTASGFSLS/RYTVT/WVRQAPGKGLEWIG/IIYGSDETAYAYAFWAIG/RFTISKTST--TVDLKMTSLTAADTATYFCAR/DFSSDWDAKFNL/WGQGTLVTVSS
VH_human  : EVQLVESGGGLVQPGGSLRLSCAASGFSLS/RYTVT/WVRQAPGKGLEWVG/IIYGSDETAYAYAFWAIG/RFTISRDNSKNTLYLQMNSLRAEDTAVYYCAR/DFSSDWDAKFNL/-------
             1 2 3 4   5 6 7 8 9 0 1                          2                  3 4 5 6 7 8 9 0 1 2 3 4              5 6
                       CDR1                                      CDR2                                      CDR3
VK_rabbit : AYDMTQTPASVSAAVGGTVTIKC/QASQSIRNELS/WYQQKPGQRPKLLIY/RASTLAS/GVSSRFKGSGSGTEFTLTISDLECADAATYYC/QQGYSLRNIDNAFGGGTEVVVK
VK_human  : -IQMTQSPSSLSASVGDRVTITC/QASQSIRNELS/WYQQKPGKAFPKLLIY/RASTLAS/GVPSRFSGSGSGTDFTLTISSLQPDFATYYC/QQGYSLRNIDNA--------
             1 2 3   4 5 6 7 8 9 0                    1 2           3 4 5         6 7 8 9 0
```

IL-6 BINDING MOLECULES

RELATED APPLICATIONS

This application is a divisional application of U.S. application Ser. No. 14/403,135, filed on Nov. 21, 2014, now U.S. Pat. No. 10,183,995, which is a national stage of International Patent Application No. PCT/IB2013/054271, filed on May 23, 2013, which claims priority to U.S. Provisional Application Ser. No. 61/650,883, filed May 23, 2012, U.S. Provisional Application Ser. No. 61/720,102, filed Oct. 30, 2012, and International Patent Application No. PCT/IB2012/056424, filed on Nov. 14, 2012, the entire contents of all of which are incorporated herein by reference.

BACKGROUND

Interleukin-6 (IL-6) is a major proinflammatory cytokine. It is responsible for the proliferation and differentiation of immunocompetent and hematopoietic cells. Human IL-6 is a single glycoprotein consisting of 212 amino acids with two N-linked glycosylation sites, and has a molecular weight of about 26 kDa. The structure of IL-6 comprises four α-helical domains with a motif of four cysteine residues which are necessary for its tertiary structure. IL-6 signalling is mediated by the binding of IL-6 to either soluble or surface bound IL-6 receptor alpha chain (IL-6Rα), enabling interaction of the complex with the cell surface transmembrane gp130 subunit that mediates intracellular signalling.

IL-6 is implicated in the pathogenesis of inflammatory diseases, including inflammatory autoimmune diseases such as rheumatoid arthritis (RA), spondylosing arthropathy, systemic lupus erythematosus (SLE), inflammatory bowel disease (IBD) and Castleman's disease. IL-6 is also implicated in the pathogenesis of cancers, including prostate cancer, diffuse large cell lymphoma, multiple myeloma, and renal cell cancer. A role for IL-6 in promoting cancer-related anorexia, oral mucositis and cachexia has also been reported.

Although IL-6 binding molecules derived from immunization of non-human animals are known in the art, these molecules have typically required extensive antibody engineering (e.g., CDR grafting and humanization) to reduce their immunogenicity. Moreover, the resulting humanized variants typically suffer from sub-optimal binding affinity to the IL-6 target and require extensive antibody engineering and affinity maturation in an attempt to restore IL-6 binding affinity. The end result is that most IL-6 antibodies exhibit sub-optimal binding affinity to the IL-6 target.

Therefore, given the importance of IL-6 in disease pathogenesis and the shortcomings of known IL-6 antibodies, there is clearly a need in the art for improved (e.g., minimally engineered) IL-6 agents that can inhibit the biological activity of IL-6, and hence treat diseases associated with IL-6 activity.

SUMMARY OF THE INVENTION

The present invention improves upon the state of the art by providing binding molecules (e.g., antibodies or antigen binding fragments thereof) with improved binding profiles that specifically bind to IL-6 (e.g., human and non-human primate IL-6) with high binding affinity (e.g., picomolar binding affinity) and potently inhibit its biological activity (e.g., binding to an IL-6 receptor). In certain exemplary embodiments, the IL-6 binding molecules of the invention are derived from the conventional antibody repertoire of a camelid species (e.g., llama) that has been subjected to active immunization with the IL-6 antigen. For example, the camelid-derived IL-6 binding molecules of the invention may comprise paired VH/VL domains or other alternative frameworks wherein one or more hypervariable loops (e.g., H1, H2, H3, L1, L2 and/or L3) of the VH or VL domains are derived from the camelid species. Moreover, in certain embodiments, at least one of the hypervariable loops adopt a canonical fold (or combination of canonical folds) that is identical or substantially identical to that of a human antibody. Such binding molecules exhibit high human homology (sequence and structure) and are therefore particularly useful for treating IL-6-associated diseases or disorders (e.g., inflammatory disease and cancer) due to their low immunogenicity. Surprisingly, the IL-6 antibodies of the invention exhibit high binding affinity, manufacturability and thermal stability without the need for extensive and time-consuming antibody engineering and affinity maturation that is typically required of known IL-6 antibodies.

Accordingly, in one aspect, the invention provides, a binding molecule that specifically binds to IL-6, the binding molecule comprising at least one antibody CDR, wherein the CDR comprises at least one amino acid residue that is buried in the F229 cavity or the F279 cavity on IL-6 when the binding molecule is bound to IL-6. In certain embodiments, the binding molecule comprises a VH domain, the VH domain having an amino acid at position 98, according to Kabat, that is buried in the F229 cavity on IL-6 when the antibody or fragment is bound to IL-6. In one particular embodiment, the amino acid at position 98 is a tryptophan. In certain embodiments, the binding molecule comprises a VL domain, the VL domain having an amino acid at position 30, according to Kabat, that is buried in the F229 cavity on IL-6 when the antibody or fragment is bound to IL-6. In one particular embodiment, the amino acid at position 30 is a tyrosine. In certain embodiments, the binding molecule comprises a VH domain, the VH domain having an amino acid at position 99, according to Kabat, that is buried in the F279 cavity on IL-6 when the antibody or fragment is bound to IL-6. In one particular embodiment, the amino acid at position 99 is a valine.

In certain embodiments, the binding molecule comprises a VH domain and a VL domain, said VH domain comprising hypervariable loops H1, H2 and H3, wherein said VH domain polypeptide is paired with a VL domain comprising hypervariable loops L1, L2 and L3 wherein at least one of hypervariable loops H1-H3 and L1-L3 are obtained from a conventional antibody of a *Lama* species by active immunization of the *Lama* species with the IL-6 antigen. In one particular embodiment, at least one of the hypervariable loops H1, H2, L1, L2 and L3 exhibits a predicted or actual canonical fold structure which is identical or substantially identical to a corresponding canonical fold structure of a H1, H2, L1, L2 or L3 hypervariable loop which occurs in a human antibody.

In one particular embodiment, at least one of the hypervariable loops H1 and H2 each exhibit a predicted or actual canonical fold structure which is identical or substantially identical to the corresponding human canonical fold structure. In one particular embodiment, at least one of the hypervariable loops L1, L2 and L3 each exhibit a predicted or actual canonical fold structure which is identical or substantially identical to the corresponding human canonical fold structure. In one particular embodiment, at least one of the hypervariable loops H1 and H2 form a combination of predicted or actual canonical fold structures which is identical or substantially identical to a corresponding combination of canonical fold structures known to occur in a human germline VH domain. In one particular embodiment, at least one of the hypervariable loops H1 and H2 form a combination of canonical fold structures corresponding to a combination of human canonical fold structures selected from the group consisting of 1-1, 1-2, 1-3, 1-4, 1-6, 2-1, 3-1 and 3-5.

In one particular embodiment, at least one of the hypervariable loops L1 and L2 form a combination of predicted or actual canonical fold structures which is identical or substantially identical to a corresponding combination of canonical fold structures known to occur in human germline VL domains. In one particular embodiment, at least one of the hypervariable loops L1 and L2 form a combination of canonical fold structures corresponding to a combination of human canonical fold structures selected from the group consisting of 11-7, 13-7(A,B,C), 14-7 (A,B), 12-11, 14-11, 12-12, 2-1, 3-1, 4-1 and 6-1.

In certain embodiments, the binding molecule comprises a VH domain and a VL domain, wherein the VH domain and/or VL domain of the binding molecule exhibits a sequence identity of 90% or greater, with one or more corresponding human VH or VL domains across framework regions FR1, FR2, FR3 and FR4. In certain embodiments, the binding molecule comprises a VH domain and a VL domain and is a germlined variant of a parental binding molecule, wherein one or both of the VH domain and VL domain of the binding molecule comprise a total of between 1 and 10 amino acid substitutions across the framework regions as compared to the corresponding VH domain and VL domain of the parental non-human antibody. In one particular embodiment the parental binding molecule is a conventional camelid antibody. In certain embodiments, the binding molecule is an antibody or antigen binding fragment thereof.

In certain embodiments, the binding molecule comprises a VH domain, the VH domain comprising the HCDR3 amino acid sequence set forth in SEQ ID NO: 500 [$X_1$PDVVTGFHYD$X_2$], or sequence variant thereof, wherein:
$X_1$ is any amino acid, preferably D or Y;
$X_2$ is any amino acid, preferably Y or N; and
wherein the sequence variant comprises one, two or three amino acid substitutions in the recited sequence. In one particular embodiment, the HCDR3 amino acid amino acid sequence is selected from the group consisting of SEQ ID NO: 497-499.

In certain embodiments, the VH domain further comprises the HCDR2 amino acid sequence set forth in SEQ ID NO: 507 [VI$X_1$Y$X_2X_3$DTYYSPSL$X_4$S], or sequence variant thereof, wherein:
X1 is any amino acid, preferably D, Y or N;
X2 is any amino acid, preferably D or E;
X3 is any amino acid, preferably A or G;
X4 is any amino acid, preferably E or K; and
wherein the sequence variant comprises one, two or three amino acid substitutions in the recited sequence. In one particular embodiment, the HCDR2 amino acid amino acid sequence is selected from the group consisting of SEQ ID NO: 501-506.

In certain embodiments, the VH domain further comprises the HCDR1 amino acid sequence set forth in SEQ ID NO: 512 [$X_1X_2$YY$X_3$W$X_4$], or sequence variant thereof, wherein:
X1 is any amino acid, preferably T, S or P;
X2 is any amino acid, preferably R or S;
X3 is any amino acid, preferably A or V;
X4 is any amino acid, preferably S or T; and
wherein the sequence variant comprises one, two or three amino acid substitutions in the recited sequence. In one particular embodiment, the HCDR1 amino acid sequence is selected from the group consisting of SEQ ID NO: 508-511.

In certain embodiments, the binding molecule comprises a VH domain comprising the HCDR3, HCDR2 and HCDR1 amino acid amino acid sequences set forth in SEQ ID NO: 497, 501 and 508, respectively.

In certain embodiments, the binding molecule further comprises a VL domain, wherein the VL domain comprises the LCDR3 amino acid sequence set forth in SEQ ID NO: 524 [ASY$X_1X_2X_3X_4X_5X_6X_7$], or sequence variant thereof, wherein:
X1 is any amino acid, preferably R or K;
X2 is any amino acid, preferably N, H, R, S, D, T or Y;
X3 is any amino acid, preferably F, Y, T, S or R;
X4 is any amino acid, preferably N or I;
X5 is any amino acid, preferably N or D;
X6 is any amino acid, preferably V, N, G or A;
X7 is any amino acid, preferably V or I; and
wherein the sequence variant comprises one, two or three amino acid substitutions in the recited sequence. In one particular embodiment, the LCDR3 amino acid amino acid sequence is selected from the group consisting of SEQ ID NO: 513-523.

In certain embodiments, the VL domain further comprises the LCDR2 amino acid sequence set forth in SEQ ID NO: 535 [$X_1$V$X_2X_3$R$X_4$S], or sequence variant thereof, wherein:
X1 is any amino acid, preferably R, K, D, A or E;
X2 is any amino acid, preferably S, N or T;
X3 is any amino acid, preferably T, K or Y;
X4 is any amino acid, preferably A, T or V; and
wherein the sequence variant comprises one, two or three amino acid substitutions in the recited sequence. In one particular embodiment, the LCDR2 amino acid amino acid sequence is selected from the group consisting of SEQ ID NO: 525-534.

In certain embodiments, the VL domain further comprises the LCDR1 amino acid sequence set forth in SEQ ID NO: 542 [AG$X_1X_2X_3$D$X_4$G$X_5X_6X_7$YVS], or sequence variant thereof, wherein
X1 is any amino acid, preferably A or T;
X2 is any amino acid, preferably S or N;
X3 is any amino acid, preferably S, E or N;
X4 is any amino acid, preferably V or I;
X5 is any amino acid, preferably G, Y, T or F;
X6 is any amino acid, preferably G or Y;
X7 is any amino acid, preferably N, D or A; and
wherein the sequence variant comprises one, two or three amino acid substitutions in the recited sequence.

In one particular embodiment, the LCDR1 amino acid amino acid sequence is selected from the group consisting of SEQ ID NO: 538-541. In certain embodiments, the binding molecule comprises a VL domain comprising the comprising the LCDR3, LCDR2 and LCDR1 amino acid amino acid sequences set forth in SEQ ID NO: 513, 525 and 536, respectively. In certain embodiments, the binding molecule comprises: a VH domain having the HCDR3, HCDR2 and HCDR1 amino acid amino acid sequences set forth in SEQ ID NO: 497, 501 and 508, respectively; and a VL domain having the LCDR3, LCDR2 and LCDR1 amino acid amino acid sequences set forth in SEQ ID NO: 513, 525 and 536, respectively.

In certain embodiments, the binding molecule comprises a VH domain with at least 85% sequence identity to the amino acid sequence set forth in SEQ ID NO: 152. In certain embodiments, the binding molecule comprises a VH domain amino acid sequence is selected from the group consisting of SEQ ID NO: 127-232 and 569-571. In certain embodiments, the binding molecule comprises a VH domain amino acid sequence is SEQ ID NO: 152. In certain embodiments, the binding molecule comprises a VL domain with at least 85% sequence identity to the amino acid sequence set forth in SEQ ID NO: 416. In certain embodiments, the binding molecule comprises a VL domain amino acid sequence is selected from the group consisting of SEQ ID NO: 391-496. In certain embodiments, the binding molecule comprises a VL domain amino acid sequence is SEQ ID NO: 416. In certain embodiments, the binding molecule comprises: a VH domain having the amino acid sequences set forth in SEQ ID NO: 152; and a VL domain having the amino acid sequence set forth in SEQ ID NO: 416.

In certain embodiments, the binding molecule comprises the H1 and H2 loops form a combination of canonical fold structures corresponding to the 3-1 combination of human canonical fold structures as found in a human 1ACY antibody structure.

In certain embodiments, the binding molecule comprises the L1 and L2 loops form a combination of canonical fold structures corresponding to the 6λ-1 combination of human canonical fold structures as found in a human 3MUG antibody structure. In certain embodiments, the binding molecule comprises the L1, L2 and L3 loops form a combination of canonical fold structures corresponding to the 6λ-1-5 combination of human canonical fold structures as found in the human 3MUG antibody structure.

In certain embodiments, the binding molecule comprises a VH domain, the VH domain comprising the HCDR3 amino acid sequence set forth in SEQ ID NO: 544 [RAGX$_1$GX$_2$G], or sequence variant thereof, wherein:

X$_1$ is any amino acid, preferably W;
X2 is any amino acid, preferably M, A, L, S or N; and
wherein the sequence variant comprises one, two or three amino acid substitutions in the recited sequence. In one particular embodiment, the HCDR3 amino acid amino acid sequence is selected from the group consisting of SEQ ID NO: 543, SEQ ID NO: 566, SEQ ID NO:567, and SEQ ID NO:568.

In certain embodiments, the VH domain further comprises the HCDR2 amino acid sequence set forth in SEQ ID NO: 554 [X$_1$ISX$_2$X$_3$GX$_4$SX$_5$X$_6$YX$_7$DSVKG], or sequence variant thereof, wherein:

X1 is any amino acid, preferably A, P or R;
X2 is any amino acid, preferably A or S;
X3 is any amino acid, preferably S or G;
X4 is any amino acid, preferably G or V;
X5 is any amino acid, preferably A or T;
X6 is any amino acid, preferably Y, N or S;
X7 is any amino acid, preferably G, A or T; and
wherein the sequence variant comprises one, two or three amino acid substitutions in the recited sequence. In one particular embodiment, the HCDR2 amino acid amino acid sequence is selected from the group consisting of SEQ ID NO: 545-553.

In certain embodiments, the VH domain further comprises the HCDR1 amino acid sequence set forth in SEQ ID NO: 562 [X$_1$X$_2$X$_3$X$_4$X$_5$], or sequence variant thereof, wherein:

X1 is any amino acid, preferably S or T;
X2 is any amino acid, preferably H or Y;
X3 is any amino acid, preferably A or R;
X4 is any amino acid, preferably M or L;
X5 is any amino acid, preferably S or Y; and
wherein the sequence variant comprises one, two or three amino acid substitutions in the recited sequence. In one particular embodiment, the HCDR1 amino acid amino acid sequence is selected from the group consisting of SEQ ID NO: 555-561.

In certain embodiments, the VH domain comprises a HCDR3 having an amino acid amino acid sequence selected from the group consisting of SEQ ID NO:543, 566, 567, and 568, and the HCDR2 and HCDR1 amino acid amino acid sequences set forth in SEQ ID NO: 545 and 555, respectively. In certain embodiments, the binding molecule further comprises a VL domain, wherein the VL domain comprises the LCDR3 amino acid sequence set forth in SEQ ID NO: 563, or sequence variant thereof, wherein the sequence variant comprises one, two or three amino acid substitutions in the recited sequence. In certain embodiments, the VL domain further comprises the LCDR2 amino acid sequence set forth in SEQ ID NO: 564, or sequence variant thereof, wherein the sequence variant comprises one, two or three amino acid substitutions in the recited sequence. In certain embodiments, the VL domain further comprises the LCDR1 amino acid sequence set forth in SEQ ID NO: 565, or sequence variant thereof, wherein the sequence variant comprises one, two or three amino acid substitutions in the recited sequence. In certain embodiments, the VL domain comprises the LCDR3, LCDR2 and LCDR1 amino acid amino acid sequences set forth in SEQ ID NO: 563, 564 and 565, respectively. In certain embodiments, the binding molecule comprises a VH domain having the HCDR3, HCDR2 and HCDR1 amino acid amino acid sequences set forth in SEQ ID NO: 544, 545 and 555, respectively; and a VL domain having the LCDR3, LCDR2 and LCDR1 amino acid amino acid sequences set forth in SEQ ID NO: 563, 564 and 565, respectively. In certain embodiments, the binding molecule comprises a VH domain with at least 85% sequence identity to the amino acid sequence set forth in SEQ ID NO: 86. In certain embodiments, the binding molecule comprises a VH domain having the amino acid sequence is selected from the group consisting of SEQ ID NO: 39-126 and 569-571. In certain embodiments, the binding molecule comprises a VH domain having the amino acid sequence is selected from SEQ ID NO: 86, SEQ ID NO:569, SEQ ID NO:570 and SEQ ID NO:571. In certain embodiments, the binding molecule comprises a VL domain with at least 85% sequence identity to the amino acid sequence set forth in SEQ ID NO: 350. In certain embodiments, the binding molecule comprises a VL domain having the amino acid sequence is selected from the group consisting of SEQ ID NO: 303-390. In certain embodiments, the binding molecule comprises a VL domain having the amino acid sequence is SEQ ID NO: 350. In certain embodiments, the binding molecule comprises: a VH domain having the amino acid sequences set forth in SEQ ID NO: 86, SEQ ID NO:569, SEQ ID NO:570 or SEQ ID NO:571; and a VL domain having the amino acid sequences set forth in SEQ ID NO: 350.

In certain embodiments, the binding molecule comprises the H1 and H2 loops form a combination of canonical fold structures corresponding to the 1-3 combination of human canonical fold structures as found in a human 1DFB antibody structure. In certain embodiments, the binding molecule comprises the L1 and L2 loops form a combination of canonical fold structures corresponding to the 7λ-1 combination of human canonical fold structures as found in a human 1MFA antibody structure. In certain embodiments, the binding molecule comprises the L1, L2 and L3 loops form a combination of canonical fold structures corresponding to the 7λ-1-4 combination of human canonical fold structures as found in the human 3MUG antibody structure.

In certain embodiments, the binding molecule is a Fab fragment which binds to human IL-6 with an off-rate ($k_{off}$ measured by surface Plasmon resonance) of less than $2\times10^{-5}$ $s^{-1}$. In certain embodiments, the binding molecule binds to the human IL-6 antigen with sub-picomolar binding affinity. In certain embodiments, the binding molecule binds to the human IL-6 antigen with single digit femtomolar binding affinity. In certain embodiments, the binding molecule comprises the hypervariable loops are obtained from the conventional antibody of the *Lama* without subsequent affinity maturation. In certain embodiments, the binding molecule inhibits IL-6-induced proliferation of B9 hybridoma cells with an IC50 of less than 0.1 pM.

In certain embodiments, the binding molecule exhibits a melting temperature (Tm) of greater than 65° C. In certain embodiments, the binding molecule is a germlined variant of a parental camelid antibody, said germlined variant having a higher melting temperature than the parental camelid antibody. In certain embodiments, the binding molecule is expressed at the level of at least 20 mg/ml following transient expression in a HEK293 cell. In certain embodiments, the binding molecule is characterized by an EpiBase® score of less than about 10.0, e.g., less than about 6.0. In certain embodiments, the binding molecule inhibits binding of IL-6 to an IL-6 receptor. In certain embodiments, the binding molecule inhibits binding of gp130 to an IL-6 receptor. In certain embodiments, the binding molecule binds specifically to human and cynomologus monkey IL-6. In certain embodiments, the binding molecule comprises at least one CDR from a camelid antibody that specifically binds to IL-6.

In another aspect, the invention provides, a pharmaceutical composition comprising the binding molecule of any of the preceding claims and one or more pharmaceutically acceptable carrier.

In another aspect, the invention provides, a method of treating an IL-6-associated disease or disorder, comprising administering to a subject in need of treatment thereof an effective amount of the pharmaceutical composition of the invention.

In another aspect, the invention provides, an isolated nucleic acid encoding a binding molecule disclosed herein.

In another aspect, the invention provides, a recombinant expression vector comprising a nucleic acid molecule of the invention.

In another aspect, the invention provides a host cell comprising a recombinant expression vector of the invention.

BRIEF DESCRIPTION OF THE FIGURES

FIG. 7A depicts the thermal stability of 68F2 and its germlined variant 129D3 as measured in Biacore with immobilized glycosylated human IL-6 with respect to other germlined variant IL-6 antibodies of the invention. The upper part of the figure depicts the melting curves, while the lower part lists the Tm value for each antibody.

FIG. 7B depicts the thermal stability of 68F2 and its germlined variant 129D3 as measured in Biacore with immobilized glycosylated human IL-6 with respect to other reference antibodies. The upper part of the figure depicts the melting curves, while the lower part lists the Tm value for each antibody.

FIG. 9 depicts the low immunogenicity (Epibase) scores for IL-6 antibodies of the invention as compared to reference antibodies (shown in bold), including the fully human antibody adalimumab (Humira).

FIG. 10A depicts an alignment of the VH and VL of 68F2 depicting the high level of sequence homology with the framework regions of its germlined variant 129D3. The minimal number of framework alterations introduced into the molecule (13 total) is also shown.

FIG. 10B depicts an alignment of the VH and VL of 61H7 depicting the high level of sequence homology with the framework regions of its germlined variant 111A7. The minimal number of framework alterations introduced into the molecule (13 total) is also shown.

FIG. 11A depicts an alignment of the VH and VK of CNTO328 depicting the high level of sequence homology with the framework regions of its germlined variant CNTO136. The minimal number of framework alterations introduced into the molecule (36 in total) is also shown.

FIG. 11B depicts an alignment of the VH and VK of VH rabbit (ALD518) depicting the high level of sequence homology with the framework regions of its germlined variant VH_human (ALD518). The minimal number of framework alterations introduced into the molecule (46 in total) is also shown.

DESCRIPTION OF THE INVENTION

I. Definitions

Figure 1:
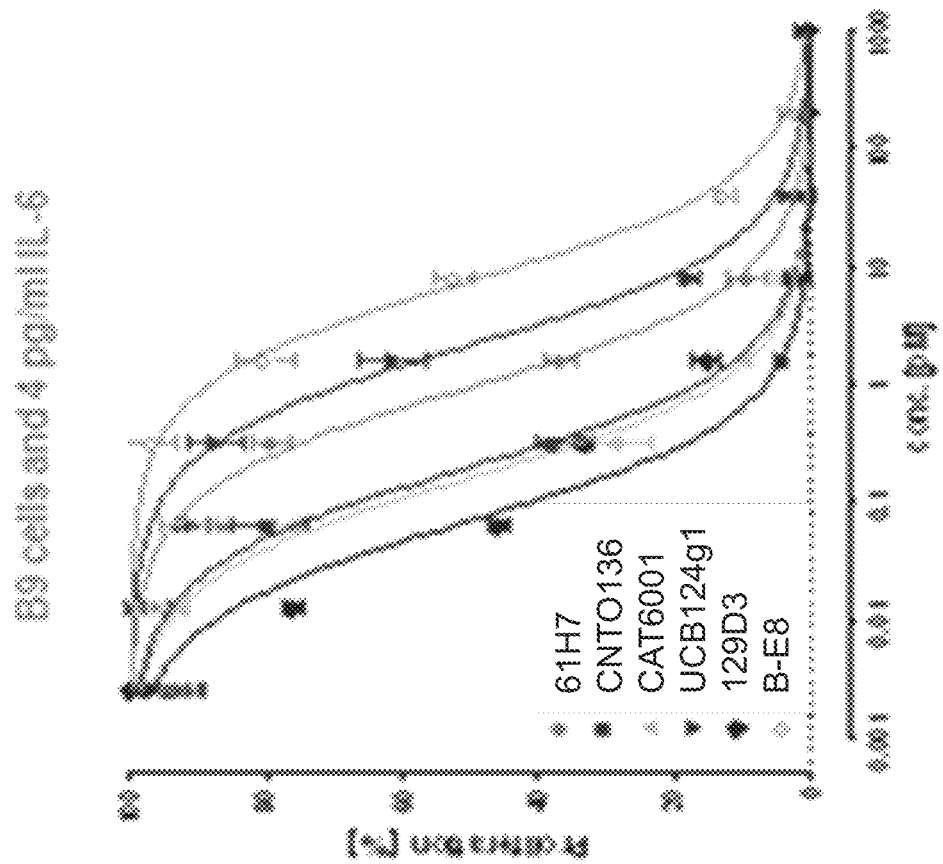
FIG. 1 depicts the results of cell proliferation assays measuring the in vitro IL-6 neutralizing activity of antibodies of the invention.

In order that the present invention may be more readily understood, certain terms are first defined.

As used herein, the term "IL-6" refers to interleukin-6. IL-6 nucleotide and polypeptide sequences are well known in the art. An exemplary human IL-6 amino sequence is set forth in GenBank deposit GI: 10834984 and an exemplary mouse IL-6 amino sequence is set forth in GenBank deposit GI: 13624311.

As used herein, the term "antibody" refers to immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (abbreviated VH) and a heavy chain constant region. The heavy chain constant region comprises three domains, CH1, CH2 and CH3. Each light chain comprises a light chain variable region (abbreviated VL) and a light chain constant region. The light chain constant region comprises one domain (CL1). The VH and VL regions can be further subdivided into regions of hypervariability, termed complementarity determining regions (CDRs), interspersed with regions that are more conserved, termed framework regions (FR).

As used herein, the term "antigen-binding fragment" of an antibody includes any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Non-limiting examples of antigen-binding portions include: (i) Fab fragments; (ii) F(ab')$_2$ fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR)). Other engineered molecules, such as diabodies, triabodies, tetrabodies and minibodies, are also encompassed within the expression "antigen-binding portion."

As used herein, the terms "variable region" or "variable domain" refer to the fact that certain portions of the variable domains VH and VL differ extensively in sequence among antibodies and are used in the binding and specificity of each particular antibody for its target antigen. However, the variability is not evenly distributed throughout the variable domains of antibodies. It is concentrated in three segments called "hypervariable loops" in each of the VL domain and the VH domain which form part of the antigen binding site. The first, second and third hypervariable loops of the VLambda light chain domain are referred to herein as L1(λ), L2(λ) and L3(λ) and may be defined as comprising residues 24-33 (L1(λ), consisting of 9, 10 or 11 amino acid residues), 49-53 (L2(λ), consisting of 3 residues) and 90-96 (L3(λ), consisting of 5 residues) in the VL domain (Morea et al., Methods 20:267-279 (2000)). The first, second and third hypervariable loops of the VKappa light chain domain are referred to herein as L1(κ), L2(κ) and L3(κ) and may be defined as comprising residues 25-33 (L1(κ), consisting of 6, 7, 8, 11, 12 or 13 residues), 49-53 (L2(κ), consisting of 3 residues) and 90-97 (L3(κ), consisting of 6 residues) in the VL domain (Morea et al., Methods 20:267-279 (2000)). The first, second and third hypervariable loops of the VH domain are referred to herein as H1, H2 and H3 and may be defined as comprising residues 25-33 (H1, consisting of 7, 8 or 9 residues), 52-56 (H2, consisting of 3 or 4 residues) and 91-105 (H3, highly variable in length) in the VH domain (Morea et al., Methods 20:267-279 (2000)).

Unless otherwise indicated, the terms L1, L2 and L3 respectively refer to the first, second and third hypervariable loops of a VL domain, and encompass hypervariable loops obtained from both Vkappa and Vlambda isotypes. The terms H1, H2 and H3 respectively refer to the first, second and third hypervariable loops of the VH domain, and encompass hypervariable loops obtained from any of the known heavy chain isotypes, including γ, ε, δ, α or μ.

The hypervariable loops L1, L2, L3, H1, H2 and H3 may each comprise part of a "complementarity determining region" or "CDR", as defined below. The terms "hypervariable loop" and "complementarity determining region" are not strictly synonymous, since the hypervariable loops (HVs) are defined on the basis of structure, whereas complementarity determining regions (CDRs) are defined based on sequence variability (Kabat et al., Sequences of Proteins of Immunological Interest, 5th Ed. Public Health Service, National Institutes of Health, Bethesda, Md., 1983) and the limits of the HVs and the CDRs may be different in some VH and VL domains.

The CDRs of the VL and VH domains can typically be defined as comprising the following amino acids: residues 24-34 (CDRL1), 50-56 (CDRL2) and 89-97 (CDRL3) in the light chain variable domain, and residues 31-35 or 31-35b (CDRH1), 50-65 (CDRH2) and 95-102 (CDRH3) in the heavy chain variable domain; (Kabat et al., Sequences of Proteins of Immunological Interest, 5th Ed. Public Health Service, National Institutes of Health, Bethesda, Md. (1991)). Thus, the HVs may be comprised within the corresponding CDRs and references herein to the "hypervariable loops" of VH and VL domains should be interpreted as also encompassing the corresponding CDRs, and vice versa, unless otherwise indicated.

The more highly conserved portions of variable domains are called the framework region (FR), as defined below. The variable domains of native heavy and light chains each comprise four FRs (FR1, FR2, FR3 and FR4, respectively), largely adopting a β-sheet configuration, connected by the three hypervariable loops. The hypervariable loops in each chain are held together in close proximity by the FRs and, with the hypervariable loops from the other chain, contribute to the formation of the antigen-binding site of antibodies. Structural analysis of antibodies revealed the relationship between the sequence and the shape of the binding site formed by the complementarity determining regions (Chothia et al., J. Mol. Biol. 227: 799-817 (1992)); Tramontano et al., J. Mol. Biol, 215:175-182 (1990)). Despite their high sequence variability, five of the six loops adopt just a small repertoire of main-chain conformations, called "canonical structures". These conformations are first of all determined by the length of the loops and secondly by the presence of key residues at certain positions in the loops and in the framework regions that determine the conformation through their packing, hydrogen bonding or the ability to assume unusual main-chain conformations.

As used herein, the terms "complementarity determining region" or "CDR" refer to the non-contiguous antigen combining sites found within the variable region of both heavy and light chain polypeptides. These particular regions have been described by Kabat et al., J. Biol. Chem. 252, 6609-6616 (1977) and Kabat et al., Sequences of protein of immunological interest. (1991), and by Chothia et al., J. Mol. Biol. 196:901-917 (1987) and by MacCallum et al., J. Mol. Biol. 262:732-745 (1996) where the definitions include overlapping or subsets of amino acid residues when compared against each other. The amino acid residues which encompass the CDRs as defined by each of the above cited references are set forth for comparison. Preferably, the term "CDR" is a CDR as defined by Kabat based on sequence comparisons.

TABLE 1

CDR definitions

| | CDR Definitions | | |
|---|---|---|---|
| | Kabat[1] | Chothia[2] | MacCallum[3] |
| $V_H$ CDR1 | 31-35 | 26-32 | 30-35 |
| $V_H$ CDR2 | 50-65 | 53-55 | 47-58 |
| $V_H$ CDR3 | 95-102 | 96-101 | 93-101 |
| $V_L$ CDR1 | 24-34 | 26-32 | 30-36 |
| $V_L$ CDR2 | 50-56 | 50-52 | 46-55 |
| $V_L$ CDR3 | 89-97 | 91-96 | 89-96 |

[1]Residue numbering follows the nomenclature of Kabat et al., supra
[2]Residue numbering follows the nomenclature of Chothia et al., supra
[3]Residue numbering follows the nomenclature of MacCallum et al., supra As used herein the terms "framework region" or "FR region" include the amino acid residues that are part of the variable region, but are not part of the CDRs (e.g., using the Kabat definition of CDRs). Therefore, a variable region framework is between about 100-120 amino acids in length but includes only those amino acids outside of the CDRs. For the specific example of a heavy chain variable region and for the CDRs as defined by Kabat et al., framework region 1 corresponds to the domain of the variable region encompassing amino acids 1-30; framework region 2 corresponds to the domain of the variable region encompassing amino acids 36-49; framework region 3 corresponds to the domain of the variable region encompassing amino acids 66-94, and framework region 4 corresponds to the domain of the variable region from amino acids 103 to the end of the variable region. The framework regions for the light chain are similarly separated by each of the light chain variable region CDRs. Similarly, using the definition of CDRs by Chothia et al. or McCallum et al. the framework region boundaries are separated by the respective CDR termini as described above. In preferred embodiments the CDRs are as defined by Kabat.

In naturally occurring antibodies, the six CDRs present on each monomeric antibody are short, non-contiguous sequences of amino acids that are specifically positioned to form the antigen binding site as the antibody assumes its three dimensional configuration in an aqueous environment. The remainder of the heavy and light variable domains show less inter-molecular variability in amino acid sequence and are termed the framework regions. The framework regions largely adopt a β-sheet conformation and the CDRs form loops which connect, and in some cases form part of, the β-sheet structure. Thus, these framework regions act to form a scaffold that provides for positioning the six CDRs in correct orientation by inter-chain, non-covalent interactions. The antigen binding site formed by the positioned CDRs defines a surface complementary to the epitope on the immunoreactive antigen. This complementary surface promotes the non-covalent binding of the antibody to the immunoreactive antigen epitope. The position of CDRs can be readily identified by one of ordinary skill in the art.

As used herein, the term "F229 cavity" refers to the surface cavity of human IL-6 that is occupied by the phenylalanine 229 residue of the human IL-6 receptor in the IL-6/IL-6 receptor complex set forth in Boulanger et al., 2003, Science 27, 2101-2104, which is incorporated by reference herein in its entirety.

As used herein, the term "F279 cavity" refers to the surface cavity of human IL-6 that is occupied by the phenylalanine 279 residue of the human IL-6 receptor in the IL-6/IL-6 receptor complex set forth in Boulanger et al., 2003, Science 27, 2101-2104, which is incorporated by reference herein in its entirety.

As used herein, the term "camelid-derived" refers to antibody variable region amino acid sequences (e.g., framework or CDR sequences) naturally present in antibody molecules of a camelid (e.g., llama). Camelid-derived antibodies may be obtained from any camelid species, including, without limitation, llama, dromedary, alpaca, vicuna, guanaco or camel. In certain embodiments, the camelid (e.g., llama) has been actively immunised with IL-6 (e.g., human IL-6). In certain embodiments, the term "camelid-derived" is limited to antibody sequences that are derived from the conventional antibody repertoire of a camelid and specifically excludes antibody sequences derived from the heavy chain-only antibody (VHH) repertoire of the camelid.

As used herein, the term "conventional antibody" refers to antibodies of any isotype, including IgA, IgG, IgD, IgE or IgM. Native or naturally occurring "conventional" camelid antibodies are usually heterotetrameric glycoproteins, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end (N-terminal) a variable domain (VH) followed by a number of constant domains. Each light chain has a variable domain (VL) at one end (N-terminal) and a constant domain (CL) at its other end; the constant domain of the light chain is aligned with the first constant domain of the heavy chain, and the light-chain variable domain is aligned with the variable domain of the heavy chain. Particular amino acid residues are believed to form an interface between the light- and heavy-chain variable domains.

As used herein, the term "specifically binds to" refers to the ability of an antibody or antigen binding fragment thereof to bind to an IL-6 with an KD of at least about $1\times10^{-6}$ (e.g, $1\times10^{-6}$ M, $1\times10^{-7}$ M, $1\times10^{-8}$ M, $1\times10^{-9}$ M, $1\times10^{-10}$ M, $1\times10^{-11}$ M, $1\times10^{-12}$ M, $1\times10^{-13}$ M, $1\times10^{-14}$ M, $1\times10^{-15}$ M or more), preferably between $1\times10^{-12}$ M and $1\times10^{-15}$ M or more and/or bind to IL-6 with an affinity that is at least two-fold greater than its affinity for a nonspecific antigen. It shall be understood, however, that an antibody or antigen binding fragment thereof is capable of specifically binding to two or more antigens which are related in sequence. For example, the antibodies or antigen binding fragments thereof disclosed herein can specifically bind to both human and a non-human (e.g., mouse or non-human primate) IL-6.

As used herein, the term "antigen" refers to the binding site or epitope recognized by an antibody variable region.

As used herein, the term "treat," "treating," and "treatment" refer to therapeutic or preventative measures described herein. The methods of "treatment" employ administration to a subject, an antibody or antigen binding fragment thereof of the present invention, for example, a subject having an IL-6-associated disease or disorder (e.g. inflammation and cancer) or predisposed to having such a disease or disorder, in order to prevent, cure, delay, reduce the severity of, or ameliorate one or more symptoms of the disease or disorder or recurring disease or disorder, or in order to prolong the survival of a subject beyond that expected in the absence of such treatment.

As used herein, the term "IL6-associated disease or disorder" includes disease states and/or symptoms associated with IL-6 activity. Exemplary IL6-associated diseases or disorders include, but are not limited to, inflammatory diseases (e.g., inflammatory autoimmune diseases such as rheumatoid arthritis and systemic lupus erythematosus), cancer (e.g., prostate cancer, diffuse large cell lymphoma, multiple myeloma, and renal cell cancer), and cancer-related disorders (e.g., anorexia and cachexia).

As used herein, the term "effective amount" refers to that amount of an antibody or antigen binding fragment thereof that is sufficient to effect treatment, prognosis or diagnosis of an IL-6-associated disease or disorder, as described herein, when administered to a subject. A therapeutically effective amount will vary depending upon the subject and disease condition being treated, the weight and age of the subject, the severity of the disease condition, the manner of administration and the like, which can readily be determined by one of ordinary skill in the art. The dosages for administration can range from, for example, about 1 ng to about 10,000 mg, about 1 ug to about 5,000 mg, about 1 mg to about 1,000 mg, about 10 mg to about 100 mg, of an antibody or antigen binding fragment thereof according to the invention. Dosage regiments may be adjusted to provide the optimum therapeutic response. An effective amount is also one in which any toxic or detrimental effects (i.e., side effects) of a binding polypeptide are minimized and/or outweighed by the beneficial effects.

As used herein, the term "subject" includes any human or non-human animal.

As used herein, the term "surface plasmon resonance" refers to an optical phenomenon that allows for the analysis of real-time interactions by detection of alterations in protein concentrations within a biosensor matrix, for example using the BIAcore™ system (Biacore Life Sciences division of GE Healthcare, Piscataway, N.J.).

As used herein, the term "$K_D$" refers to the equilibrium dissociation constant of a particular binding polypeptide/antigen interaction.

As used herein, the term "off-rate" is refers to the dissociation rate ($K_{off}$) for a particular binding interaction.

II. IL-6 Binding Molecules

In one aspect, the invention provides binding molecules (antibodies or antigen binding fragments thereof) that specifically bind to and inhibit the activity of IL-6. Such binding molecules generally comprise at least one CDR region amino acid sequence set forth in Tables 13-18, herein.

Analysis of the crystal structure of human IL-6 in complex with the human IL-6 receptor has shown that 2 residues of the IL-6 receptor, F229 and F279, are critical for the IL-6/IL-6 receptor interaction (see e.g., Boulanger et al., 2003, Science 27, 2101-2104, which is incorporated by reference herein in its entirety). In the IL-6/IL-6 receptor complex, F229 and F279 are buried in separate cavities on the surface of IL-6. In certain embodiments, the binding molecules of the invention utilize these cavities on IL-6 to achieve high affinity binding. In one particular embodiment, binding molecules of the invention comprise an antibody CDR region, wherein the CDR region comprises an amino acid residue that is buried in the F229 cavity or the F279 cavity on IL-6 when the binding molecule to bound to IL-6.

In general, the binding molecules of the invention inhibit IL-6 activity (e.g., by antagonizing the binding of IL-6 to an IL-6 receptor). In certain embodiments, the binding molecules also inhibit binding of gp130 to an IL-6 receptor. However, in other embodiments, the binding molecules can bind to IL-6 without inhibiting binding of gp130 to an IL-6 receptor.

Binding molecules of the invention generally have a high affinity for IL-6 and are generally highly potent at inhibiting IL-6 activity in vivo and in vitro. In certain embodiments, the binding molecules of the invention bind to human IL-6 with an off-rate (kw measured by surface Plasmon resonance) of less than about $1\times10^{-4}$ s$^{-1}$ (e.g., about $9\times10^{-5}$, $8\times10^{-5}$, $7\times10^{-5}$, $6\times10^{-5}$, $5\times10^{-5}$, $4\times10^{-5}$, $3\times10^{-5}$, $2\times10^{-5}$, and $1\times10^{-5}$). In other embodiments, the binding molecules of the invention inhibit IL-6-induced proliferation of B9 hybridoma cells with an IC50 of less than 0.1 pM. In certain other embodiments, the binding molecules of the invention compete with a predetermined antibody binding to IL-6 wherein such predetermined antibody containing a VH sequence and a VL sequence selected from VH and VL amino acid sequences set forth in Table 13-18. In certain other embodiments, the binding molecules of the invention compete away at least 30%, 40%, 50%, 60%, 70%, 80%, or 90% of the binding of the predetermined antibody binding to IL-6. In certain other embodiments, the binding molecules of the invention compete with the binding of 20A4, 24D10, 68F2, 61H7, 129D3 or 111A7 to IL-6, e.g., compete away at least 50%, 60%, 70%, 80% or 90% of the binding of one of these antibodies to IL-6. In certain other embodiments, the binding molecules of the invention compete with the binding of 17F10, 24C9, 18C11, 29B11, 28A6, or 126A3 to IL-6, e.g., compete away at least 50%, 60%, 70%, 80% or 90% of the binding of one of these antibodies to IL-6.

In general, the binding molecules of the invention also exhibit high thermal stability. In certain embodiments, the binding molecules exhibit a melting temperature (Tm) of greater than 55° C. (e.g., at least 56, 57, 58, 59, 60, 61, 62, 63, 64, 65, 66, 67, 68, 69, 70, 71, 72, 73, 74, 75 C or higher). In certain exemplary embodiments, the IL-6 binding molecules of the invention are germlined variants which exhibit a thermal stability that is comparable to, or higher than, their parental, camelid-derived counterparts. In certain exemplary embodiments, thermal stability is measured following incubation in a suitable buffer (e.g., PBS) at a concentration of 100 µg/ml for 1 hour. In other exemplary, embodiments the thermal stability of the IL-6 binding molecule is that exhibited in a full-length IgG format (e.g., comprising an IgG1 or IgG4 Fc region).

The binding molecules of the invention are also characterized by high expression levels of functional antibody, with low levels of non-functional contaminants such as high or low-molecular weight aggregates. For example, IL-6 binding molecules of the invention may be characterized by production levels of at least 20 mg/L (e.g., at least 20, 21, 22, 23, 24, 25, 26, 27, 28, 29, 30 mg/L or higher). In certain exemplary embodiments, the IL-6 binding molecules are germlined variants which exhibit an expression level that is comparable to, or higher than, their parental, camelid counterparts. In other exemplary embodiments, the expression level is determined using the full-length IgG format of an IL-6 binding molecule of the invention, e.g., by transient expression in a HEK293 cell.

Binding molecules of the invention are also generally characterized by low predicted immunogenicity. For example, IL-6 binding molecules of the invention exhibit EpiBase® scores (e.g., total DRB1 scores) of less than 15.0, least than about 12.0, or less than about 10.0. In certain exemplary embodiments, the binding molecules exhibit immunogenicity scores of about 9.0, about 8.0, about 7.0, or about 6.0. In yet other embodiments, the immunogenicity score is less than the immunogenicity score of Humira®, e.g., about 6.0, about 5.0, or about 4.0.

Binding molecules of the invention can bind to any IL-6 including, without limitation, human and cynomolgus monkey IL-6. Preferably, binding molecules can bind to both human and cynomolgus monkey IL-6.

i) IL-6 Antibodies or Antigen Binding Fragments Thereof

In certain embodiments, the invention provides antibodies or antigen binding fragments thereof that specifically bind to IL-6 (e.g., human IL-6) and antagonize the binding of IL-6 to an IL-6 receptor. The VH, VL and CDR sequences of exemplary Fab clones of the invention are set forth in Tables 13-18. Antibodies of the invention can comprise any of the framework and/or CDR amino acid sequences of these Fab clones.

Antibodies of the invention can comprise a CDR region sequence with an amino acid residue (e.g., an aromatic amino acid, such as tryptophan or tyrosine) that is buried in the F229 cavity on IL-6 when the antibody or fragment to bound to IL-6. Exemplary antibodies comprise a VH domain with a tryptophan at position 98 and/or VL domain with a tyrosine at position 30, according to Kabat. Such antibodies have particularly high affinity for IL-6.

Additionally or alternatively, antibodies of the invention can comprise a CDR region sequence with an amino acid residue that is buried in the F279 cavity on IL-6 when the antibody or fragment to bound to IL-6. Exemplary antibodies comprise a VH domain with a valine at position 99, according to Kabat.

In certain embodiments, the anti-IL-6 antibodies or fragments of the invention comprise a VH comprising 1, 2, or 3 CDR amino acid sequences from a VH set forth in Tables 13-16.

In certain embodiments, the anti-IL-6 antibodies or fragments of the invention comprise a VL comprising 1, 2, or 3 CDR amino acid sequences from a VL set forth in Tables 13-16.

In certain embodiments, the anti-IL-6 antibodies or fragments of the invention comprise: a VH comprising 1, 2, or 3 CDR amino acid sequences from a VH set forth in Tables 13-18; and a VL comprising 1, 2, or 3 CDR amino acid sequences from a VL set forth in Tables 13-18. In a preferred embodiment all six CDRs are from the same Fab clone.

In certain embodiments, the anti-IL-6 antibodies or fragments of the invention comprise a VH set forth in Tables 13-16.

In certain embodiments, the anti-IL-6 antibodies or fragments of the invention comprise a VL set forth in Tables 13-16.

In certain embodiments, the anti-IL-6 antibodies or fragments of the invention comprise a VH and VL set forth in Tables 13-16.

In certain embodiments, the anti-IL-6 antibodies or fragments of the invention comprise a VH and VL from a single Fab clone set forth in Tables 13-16.

In certain embodiments, the invention provides antibodies or antigen binding fragments thereof that specifically bind to IL-6, the antibodies or fragments comprising a sequence variant of a CDR, VH, and VL amino acid sequences set forth in Tables 13-18.

In certain embodiments, the sequence variant comprises a VH and/or VL amino acid sequence with about 80%, 85%, 86%, 87%, 88%, 89%, 90%, 91%, 92%, 93%, 94%, 95%, 96%, 97%, 98%, or 99% identity to a VH or VL region amino acid sequences set forth in Tables 13-16.

In other embodiments, the sequence variant comprises a VH, VL, or CDR amino acid sequence selected from Tables 13-18 which has been altered by the introduction of one or more conservative amino acid substitutions. Conservative amino acid substitutions include the substitution of an amino acid in one class by an amino acid of the same class, where a class is defined by common physicochemical amino acid side chain properties and high substitution frequencies in homologous proteins found in nature, as determined, for example, by a standard Dayhoff frequency exchange matrix or BLOSUM matrix. Six general classes of amino acid side chains have been categorized and include: Class I (Cys); Class II (Ser, Thr, Pro, Ala, Gly); Class III (Asn, Asp, Gln, Glu); Class IV (His, Arg, Lys); Class V (Ile, Leu, Val, Met); and Class VI (Phe, Tyr, Trp). For example, substitution of an Asp for another class III residue such as Asn, Gln, or Glu, is a conservative substitution. Thus, a predicted nonessential amino acid residue in an IL-6 antibody or antigen binding fragment thereof is preferably replaced with another amino acid residue from the same class. Methods of identifying amino acid conservative substitutions which do not eliminate antigen binding are well-known in the art (see, e.g., Brummell et al., Biochem. 32:1180-1187 (1993); Kobayashi et al. Protein Eng. 12(10):879-884 (1999); and Burks et al. Proc. Natl. Acad. Sci. USA 94:412-417 (1997)).

In other embodiments, the sequence variant comprises a VH, VL or CDR amino acid sequence selected from Tables 13-18 which has been altered to improve antibody production and/or manufacturing, e.g., exchange of a methionine to alanine, serine or leucine. In certain other embodiments, the sequence variant comprises a VH, VL or CDR amino acid sequence selected from Tables 13-18 which has been altered to improve antibody production, e.g., exchange of glutamine to glutamic acid or asparagine to alanine or related amino acids. In exemplary embodiments, one or more glutamines outside of CDR regions of VH amino acid sequences of Table 16 have been changed to glutamic acid(s), e.g., one or more glutamines at position 1, 3, 5, or 16 or any combination thereof of SEQ ID NO. 152 have been changed to glutamic acid(s) to improve antibody production or stability. In one particular embodiment, glutamine at position 1 of SEQ ID NO. 152 has been changed to glutamic acid.

ii) IL-6 Binding Molecules with High Human Homology

In certain aspects, the IL-6 binding molecules of the invention are antibodies (or antigen binding fragments) with high human homology. An antibody will be considered as having "high human homology" if the VH domains and the VL domains, taken together, exhibit at least 90% amino acid sequence identity to the closest matching human germline VH and VL sequences. Antibodies having high human homology may include antibodies comprising VH and VL domains of native non-human antibodies which exhibit sufficiently high % sequence identity human germline sequences, including for example antibodies comprising VH and VL domains of camelid conventional antibodies, as well as engineered, especially humanised, variants of such antibodies and also "fully human" antibodies.

In one embodiment the VH domain of the antibody with high human homology may exhibit an amino acid sequence identity or sequence homology of 80% or greater with one or more human VH domains across the framework regions FR1, FR2, FR3 and FR4. In other embodiments the amino acid sequence identity or sequence homology between the VH domain of the polypeptide of the invention and the closest matching human germline VH domain sequence may be 85% or greater, 90% or greater, 95% or greater, 97% or greater, or up to 99% or even 100%.

In one embodiment the VH domain of the antibody with high human homology may contain fewer than 10 (e.g. 10, 9, 8, 7, 6, 5, 4, 3, 2 or 1) amino acid sequence substitutions across the framework regions FR1, FR2, FR3 and FR4, in comparison to the closest matched human VH sequence.

In another embodiment the VL domain of the antibody with high human homology may exhibit a sequence identity or sequence homology of 80% or greater with one or more human VL domains across the framework regions FR1, FR2, FR3 and FR4. In other embodiments the amino acid sequence identity or sequence homology between the VL domain of the polypeptide of the invention and the closest matching human germline VL domain sequence may be 85% or greater 90% or greater, 95% or greater, 97% or greater, or up to 99% or even 100%.

In one embodiment the VL domain of the antibody with high human homology may contain fewer than 10 (e.g. 10, 9, 8, 7, 6, 5, 4, 3, 2 or 1) amino acid sequence substitutions across the framework regions FR1, FR2, FR3 and FR4, in comparison to the closest matched human VL sequence.

Antibodies with high human homology may also comprise hypervariable loops or CDRs having human or human-like canonical folds, as discussed in detail below. In one embodiment at least one hypervariable loop or CDR in either the VH domain or the VL domain of the antibody with high human homology may be obtained or derived from a VH or VL domain of a non-human antibody, for example a conventional antibody from a species of *Camelidae*, yet exhibit a predicted or actual canonical fold structure which is substantially identical to a canonical fold structure which occurs in human antibodies.

It should be noted that antibodies with high human homology do not necessarily possess human or human-like canonical folds structures. For example, primate antibodies have high sequence homology to human antibodies yet often do not possess human or human-like canonical folds structures.

It is well established in the art that although the primary amino acid sequences of hypervariable loops present in both VH domains and VL domains encoded by the human germline are, by definition, highly variable, all hypervariable loops, except CDR H3 of the VH domain, adopt only a few distinct structural conformations, termed canonical folds (Chothia et al., J. Mol. Biol. 196:901-917 (1987); Tramontano et al. Proteins 6:382-94 (1989)), which depend on both the length of the hypervariable loop and presence of the so-called canonical amino acid residues (Chothia et al., J. Mol. Biol. 196:901-917 (1987)). Actual canonical structures of the hypervariable loops in intact VH or VL domains can be determined by structural analysis (e.g. X-ray crystallography), but it is also possible to predict canonical structure on the basis of key amino acid residues which are characteristic of a particular structure (discussed further below). In essence, the specific pattern of residues that determines each canonical structure forms a "signature" which enables the canonical structure to be recognised in hypervariable loops of a VH or VL domain of unknown structure; canonical structures can therefore be predicted on the basis of primary amino acid sequence alone.

The predicted canonical fold structures for the hypervariable loops of any given VH or VL sequence in an antibody with high human homology can be analysed using algorithms which are publicly available from www.bioinf.org.uk/abs/chothia.html, www.biochem.ucl.ac.uk/~martin/antibodies.html and www.bioc.unizh.ch/antibody/Sequences/Germlines/Vbase_hVk.html. These tools permit query VH or VL sequences to be aligned against human VH or VL domain sequences of known canonical structure, and a prediction of canonical structure made for the hypervariable loops of the query sequence.

In the case of the VH domain, H1 and H2 loops may be scored as having a canonical fold structure "substantially identical" to a canonical fold structure known to occur in human antibodies if at least the first, and preferable both, of the following criteria are fulfilled:

1. An identical length, determined by the number of residues, to the closest matching human canonical structural class.
2. At least 33% identity, preferably at least 50% identity with the key amino acid residues described for the corresponding human H1 and H2 canonical structural classes.
(note for the purposes of the foregoing analysis the H1 and H2 loops are treated separately and each compared against its closest matching human canonical structural class)

The foregoing analysis relies on prediction of the canonical structure of the H1 and H2 loops of the antibody of interest. If the actual structures of the H1 and H2 loops in the antibody of interest are known, for example based on X-ray crystallography, then the H1 and H2 loops in the antibody of interest may also be scored as having a canonical fold structure "substantially identical" to a canonical fold structure known to occur in human antibodies if the length of the loop differs from that of the closest matching human canonical structural class (typically by ±1 or ±2 amino acids) but the actual structure of the H1 and H2 loops in the antibody of interest matches the structure of a human canonical fold.

Key amino acid residues found in the human canonical structural classes for the first and second hypervariable loops of human VH domains (H1 and H2) are described by Chothia et al., J. Mol. Biol. 227:799-817 (1992), the contents of which are incorporated herein in their entirety by reference. In particular, Table 3 on page 802 of Chothia et al., which is specifically incorporated herein by reference, lists preferred amino acid residues at key sites for H1 canonical structures found in the human germline, whereas Table 4 on page 803, also specifically incorporated by reference, lists preferred amino acid residues at key sites for CDR H2 canonical structures found in the human germline.

In one embodiment, both H1 and H2 in the VH domain of the antibody with high human homology exhibit a predicted or actual canonical fold structure which is substantially identical to a canonical fold structure which occurs in human antibodies.

Antibodies with high human homology may comprise a VH domain in which the hypervariable loops H1 and H2 form a combination of canonical fold structures which is identical to a combination of canonical structures known to occur in at least one human germline VH domain. It has been observed that only certain combinations of canonical fold structures at H1 and H2 actually occur in VH domains encoded by the human germline. In an embodiment H1 and H2 in the VH domain of the antibody with high human homology may be obtained from a VH domain of a non-human species, e.g. a *Camelidae* species, yet form a combination of predicted or actual canonical fold structures which is identical to a combination of canonical fold structures known to occur in a human germline or somatically mutated VH domain. In non-limiting embodiments H1 and H2 in the VH domain of the antibody with high human homology may be obtained from a VH domain of a non-human species, e.g. a *Camelidae* species, and form one of the following canonical fold combinations: 1-1, 1-2, 1-3, 1-6, 1-4, 2-1, 3-1 and 3-5.

An antibody with high human homology may contain a VH domain which exhibits both high sequence identity/sequence homology with human VH, and which contains hypervariable loops exhibiting structural homology with human VH.

It may be advantageous for the canonical folds present at H1 and H2 in the VH domain of the antibody with high human homology, and the combination thereof, to be "correct" for the human VH germline sequence which represents the closest match with the VH domain of the antibody with high human homology in terms of overall primary amino acid sequence identity. By way of example, if the closest sequence match is with a human germline VH3 domain, then it may be advantageous for H1 and H2 to form a combination of canonical folds which also occurs naturally in a human VH3 domain. This may be particularly important in the case of antibodies with high human homology which are derived from non-human species, e.g. antibodies containing VH and VL domains which are derived from camelid conventional antibodies, especially antibodies containing humanised camelid VH and VL domains.

Thus, in one embodiment the VH domain of the IL-6 antibody with high human homology may exhibit a sequence identity or sequence homology of 80% or greater, 85% or greater, 90% or greater, 95% or greater, 97% or greater, or up to 99% or even 100% with a human VH domain across the framework regions FR1, FR2, FR3 and FR4, and in addition H1 and H2 in the same antibody are obtained from a non-human VH domain (e.g. derived from a *Camelidae* species), but form a combination of predicted or actual canonical fold structures which is the same as a canonical fold combination known to occur naturally in the same human VH domain.

For example, in one exemplary embodiment, the H1 and H2 loops of an IL-6 antibody of the invention (e.g., 61H7) may comprise the 1-2 combination human canonical fold structures as found, for example, in the human antibody structure 1DFB. In another exemplary embodiment, the H1 and H2 of an IL-6 antibody of the invention (e.g., 68F2 or its germlined variant 129D3) loops may comprise the 3-1 combination of human canonical fold structures as found, for example, in the human antibody structure 1ACY.

In other embodiments, L1 and L2 in the VL domain of the antibody with high human homology are each obtained from a VL domain of a non-human species (e.g. a camelid-derived VL domain), and each exhibits a predicted or actual canonical fold structure which is substantially identical to a canonical fold structure which occurs in human antibodies.

As with the VH domains, the hypervariable loops of VL domains of both VLambda and VKappa types can adopt a limited number of conformations or canonical structures, determined in part by length and also by the presence of key amino acid residues at certain canonical positions.

Within an antibody of interest having high human homology, L1, L2 and L3 loops obtained from a VL domain of a non-human species, e.g. a *Camelidae* species, may be scored as having a canonical fold structure "substantially identical" to a canonical fold structure known to occur in human antibodies if at least the first, and preferable both, of the following criteria are fulfilled:

1. An identical length, determined by the number of amino acid residues, to the closest matching human structural class.
2. At least 33% identity, preferably at least 50% identity with the key amino acid residues described for the corresponding human L1 or L2 canonical structural classes, from either the VLambda or the VKappa repertoire.

(note for the purposes of the foregoing analysis the L1 and L2 loops are treated separately and each compared against its closest matching human canonical structural class).

The foregoing analysis relies on prediction of the canonical structure of the L1, L2 and L3 loops in the VL domain of the antibody of interest. If the actual structure of the L1, L2 and L3 loops is known, for example based on X-ray crystallography, then L1, L2 or L3 loops derived from the antibody of interest may also be scored as having a canonical fold structure "substantially identical" to a canonical fold structure known to occur in human antibodies if the length of the loop differs from that of the closest matching human canonical structural class (typically by ±1 or ±2 amino acids) but the actual structure of the *Camelidae* loops matches a human canonical fold.

Key amino acid residues found in the human canonical structural classes for the CDRs of human VLambda and VKappa domains are described by Morea et al. Methods, 20: 267-279 (2000) and Martin et al., J. Mol. Biol., 263:800-815 (1996). The structural repertoire of the human VKappa domain is also described by Tomlinson et al. EMBO J. 14:4628-4638 (1995), and that of the VLambda domain by Williams et al. J. Mol. Biol., 264:220-232 (1996). The contents of all these documents are to be incorporated herein by reference.

L1 and L2 in the VL domain of an antibody with high human homology may form a combination of predicted or actual canonical fold structures which is identical to a combination of canonical fold structures known to occur in a human germline VL domain. In non-limiting embodiments L1 and L2 in the VLambda domain of an antibody with high human homology (e.g. an antibody containing a camelid-derived VL domain or a humanised variant thereof) may form one of the following canonical fold combinations: 11-7, 13-7(A,B,C), 14-7(A,B), 12-11, 14-11 and 12-12 (as defined in Williams et al. J. Mol. Biol. 264:220-32 (1996) and as shown on http://www.bioc.uzh.ch/antibody/Sequences/Germlines/VBase_hVL.html). In non-limiting embodiments L1 and L2 in the Vkappa domain may form one of the following canonical fold combinations: 2-1, 3-1, 4-1 and 6-1 (as defined in Tomlinson et al. EMBO J. 14:4628-38 (1995) and as shown on http://www.bioc.uzh.ch/antibody/Sequences/Germlines/VBase_hVK.html). For example, in one exemplary embodiment, the L1 and L2 loops of an IL-6 antibody of the invention (e.g., 61H7) may comprise the 7λ-1 combination human canonical fold structures as found, for example, in the human antibody structure 1MFA. In another exemplary embodiment, the L1 and L2 of an IL-6 antibody of the invention (e.g., 68F2 or its germlined variant 129D3) loops may comprise the 6λ-1 combination of human canonical fold structures as found, for example, in the human antibody structure 3MUG.

In a further embodiment, all three of L1, L2 and L3 in the VL domain of an antibody with high human homology may exhibit a substantially human structure. It is preferred that the VL domain of the antibody with high human homology exhibits both high sequence identity/sequence homology with human VL, and also that the hypervariable loops in the VL domain exhibit structural homology with human VL. For example, in one exemplary embodiment, loops L1-L3 of an IL-6 antibody of the invention (e.g., 61H7) may comprise the 7λ-1-4 combination human canonical fold structures as found, for example, in the human antibody structure 1MFA. In another exemplary embodiment, the L1-L3 of an IL-6 antibody of the invention (e.g., 68F2 or its germlined variant 129D3) loops may comprise the 6λ-1-5 combination of human canonical fold structures as found, for example, in the human antibody structure 3MUG.

In one embodiment, the VL domain of a IL-6 antibody with high human homology may exhibit a sequence identity of 80% or greater, 85% or greater, 90% or greater, 95% or greater, 97% or greater, or up to 99% or even 100% with a human VL domain across the framework regions FR1, FR2, FR3 and FR4, and in addition hypervariable loop L1 and hypervariable loop L2 may form a combination of predicted or actual canonical fold structures which is the same as a canonical fold combination known to occur naturally in the same human VL domain.

It is, of course, envisaged that VH domains exhibiting high sequence identity/sequence homology with human VH, and also structural homology with hypervariable loops of human VH will be combined with VL domains exhibiting high sequence identity/sequence homology with human VL, and also structural homology with hypervariable loops of human VL to provide antibodies with high human homology containing VH/VL pairings (e.g camelid-derived VH/VL pairings) with maximal sequence and structural homology to human-encoded VH/VL pairings.

iii). Non-Immunoglobulin Binding Molecules

In a further aspect, the invention provides non-immunoglobulin binding molecules that specifically bind to IL-6. As used herein, the term "non-immunoglobulin binding molecules" are binding molecules whose binding sites comprise a portion (e.g., a scaffold or framework) derived from a polypeptide other than an immunoglobulin, but which may be engineered (e.g., by the addition of CDR region sequences) to confer a desired binding specificity to the binding molecule. The non-immunoglobulin binding molecules of the invention generally comprise one or more of the CDR regions set forth in Tables 13-18 grafted into a non-immunoglobulin polypeptide.

In certain embodiments, non-immunoglobulin binding molecules comprise binding site portions that are derived from a member of the immunoglobulin superfamily that is not an immunoglobulin (e.g. a T-cell receptor or a cell-adhesion protein (e.g., CTLA-4, N-CAM, telokin)). Such binding molecules comprise a binding site portion which retains the conformation of an immunoglobulin fold and is capable of specifically binding to IL-6 when modified to include one or more of the CDR region set forth in Tables 13-18. In other embodiments, non-immunoglobulin binding molecules of the invention comprise a binding site with a protein topology that is not based on the immunoglobulin fold (e.g. ankyrin repeat proteins, tetranectins, and fibronectins) but which nonetheless are capable of specifically binding to a target (e.g. IL-6) when modified to include one or more of the CDR region set forth in Tables 13-18.

In one embodiment, a binding molecule of the invention comprises a tetranectin molecule. Tetranectins are plasma proteins of trivalent structure. Each monomer of the tetranectin trimer comprises five distinct amino-acid loops that can be can be replaced by or engineered to contain antibody CDR sequences (e.g., CDR regions set forth in Tables 13-18). Methods for making tetranectin binding polypeptides are described, for example, in US20110086770, which is incorporated by reference herein in its entirety.

In one embodiment, a binding molecule of the invention comprises a fibronectin molecule. Fibronectin binding molecules (e.g., molecules comprising the Fibronectin type I, II, or III domains) display CDR-like loops which can be replaced by or engineered to contain antibody CDR sequences (e.g., CDR regions set forth in Tables 13-18). Methods for making fibronectin binding polypeptides are described, for example, in WO 01/64942 and in U.S. Pat. Nos. 6,673,901, 6,703,199, 7,078,490, and 7,119,171, which are each incorporated herein by reference in their entirety.

In another embodiment, a binding molecule of the invention comprises a binding site from an affibody. Affibodies are derived from the immunoglobulin binding domains of staphylococcal Protein A (SPA) (see e.g., Nord et al., Nat. Biotechnol., 15: 772-777 (1997)). Affibody binding sites employed in the invention may be synthesized by mutagenizing an SPA-related protein (e.g., Protein Z) derived from a domain of SPA (e.g., domain B) and selecting for mutant SPA-related polypeptides having binding affinity for IL-6. Other methods for making affibody binding sites are described in U.S. Pat. Nos. 6,740,734 and 6,602,977 and in WO 00/63243, each of which is incorporated herein by reference.

In another embodiment, a binding molecule of the invention comprises a binding site from an anticalin. Anticalins (also known as lipocalins) are members of a diverse beta-barrel protein family whose function is to bind target molecules in their barrel/loop region. Lipocalin binding sites may be engineered to bind IL-6 by randomizing loop sequences connecting the strands of the barrel (see e.g., Schlehuber et al., Drug Discov. Today, 10: 23-33 (2005); Beste et al., PNAS, 96: 1898-1903 (1999). Anticalin binding sites employed in the binding molecules of the invention may be obtainable starting from polypeptides of the lipocalin family which are mutated in four segments that correspond to the sequence positions of the linear polypeptide sequence comprising amino acid positions 28 to 45, 58 to 69, 86 to 99 and 114 to 129 of the Bilin-binding protein (BBP) of *Pieris brassica*. Other methods for making anticalin binding sites are described in WO99/16873 and WO 05/019254, each of which is incorporated herein by reference.

In another embodiment, a binding molecule of the invention comprises a binding site from a cysteine-rich polypeptide. Cysteine-rich domains employed in the practice of the present invention typically do not form an alpha-helix, a beta-sheet, or a beta-barrel structure. Typically, the disulfide bonds promote folding of the domain into a three-dimensional structure. Usually, cysteine-rich domains have at least two disulfide bonds, more typically at least three disulfide bonds. An exemplary cysteine-rich polypeptide is an A domain protein. A-domains (sometimes called "complement-type repeats") contain about 30-50 or 30-65 amino acids. In some embodiments, the domains comprise about 35-45 amino acids and in some cases about 40 amino acids. Within the 30-50 amino acids, there are about 6 cysteine residues. Of the six cysteines, disulfide bonds typically are found between the following cysteines: C1 and C3, C2 and C5, C4 and C6. The A domain constitutes a ligand binding moiety. The cysteine residues of the domain are disulfide linked to form a compact, stable, functionally independent moiety. Clusters of these repeats make up a ligand binding domain, and differential clustering can impart specificity with respect to the ligand binding. Exemplary proteins containing A-domains include, e.g., complement components (e.g., C6, C7, C8, C9, and Factor I), serine proteases (e.g., enteropeptidase, matriptase, and corin), transmembrane proteins (e.g., ST7, LRP3, LRPS and LRP6) and endocytic receptors (e.g., Sortilin-related receptor, LDL-receptor, VLDLR, LRP1, LRP2, and ApoER2). Methods for making A domain proteins of a desired binding specificity are disclosed, for example, in WO 02/088171 and WO 04/044011, each of which is incorporated herein by reference.

In other embodiments, a binding molecule of the invention comprises a binding site from a repeat protein. Repeat proteins are proteins that contain consecutive copies of small (e.g., about 20 to about 40 amino acid residues) structural units or repeats that stack together to form contiguous domains. Repeat proteins can be modified to suit a particular target binding site by adjusting the number of repeats in the protein. Exemplary repeat proteins include designed ankyrin repeat proteins (i.e., a DARPins) (see e.g., Binz et al., Nat. Biotechnol., 22: 575-582 (2004)) or leucine-rich repeat proteins (i.e., LRRPs) (see e.g., Pancer et al., Nature, 430: 174-180 (2004)). All so far determined tertiary structures of ankyrin repeat units share a characteristic composed of a beta-hairpin followed by two antiparallel alpha-helices and ending with a loop connecting the repeat unit with the next one. Domains built of ankyrin repeat units are formed by stacking the repeat units to an extended and curved structure. LRRP binding sites from part of the adaptive immune system of sea lampreys and other jawless fishes and resemble antibodies in that they are formed by recombination of a suite of leucine-rich repeat genes during lymphocyte maturation. Methods for making DARpin or LRRP binding sites are described in WO 02/20565 and WO 06/083275, each of which is incorporated herein by reference.

Other non-immunoglobulin binding sites which may be employed in binding molecules of the invention include binding sites derived from Src homology domains (e.g. SH2 or SH3 domains), PDZ domains, beta-lactamase, high affinity protease inhibitors, or small disulfide binding protein scaffolds such as scorpion toxins. Methods for making binding sites derived from these molecules have been disclosed in the art, see e.g., Panni et al, J. Biol. Chem., 277: 21666-21674 (2002), Schneider et al., Nat. Biotechnol., 17: 170-175 (1999); Legendre et al., Protein Sci., 11:1506-1518 (2002); Stoop et al., Nat. Biotechnol., 21: 1063-1068 (2003); and Vita et al., PNAS, 92: 6404-6408 (1995). Yet other binding sites may be derived from a binding domain selected from the group consisting of an EGF-like domain, a Kringle-domain, a PAN domain, a Gla domain, a SRCR domain, a Kunitz/Bovine pancreatic trypsin Inhibitor domain, a Kazal-type serine protease inhibitor domain, a Trefoil (P-type) domain, a von Willebrand factor type C domain, an Anaphylatoxin-like domain, a CUB domain, a thyroglobulin type I repeat, LDL-receptor class A domain, a Sushi domain, a Link domain, a Thrombospondin type I domain, an Immunoglobulin-like domain, a C-type lectin domain, a MAM domain, a von Willebrand factor type A domain, a Somatomedin B domain, a WAP-type four disulfide core domain, a F5/8 type C domain, a Hemopexin domain, a Laminin-type EGF-like domain, a C2 domain, and other such domains known to those of ordinary skill in the art, as well as derivatives and/or variants thereof.

Non-immunoglobulin binding molecules may be identified by selection or isolation of a target-binding variant from a library of binding molecules having artificially diversified binding sites. Diversified libraries can be generated incorporation of a library of CDR sequences (e.g., selected from those CDR sequences set forth in Tables 13-18) and/or completely random approaches (e.g., error-prone PCR, exon shuffling, or directed evolution) and/or aided by art-recognized design strategies. For example, amino acid positions that are usually involved when the binding site interacts with its cognate target molecule can be randomized by insertion of degenerate codons, trinucleotides, random peptides, or entire loops at corresponding positions within the nucleic acid which encodes the binding site (see e.g., U.S. Pub. No. 20040132028). The location of the amino acid positions can be identified by investigation of the crystal structure of the binding site in complex with the target molecule. Candidate positions for incorporation of CDR sequences (e.g., selected from those CDR sequences set forth in Tables 13-18) and/or randomization include loops, flat surfaces, helices, and binding cavities of the binding site. In certain embodiments, amino acids within the binding site that are likely candidates for diversification can be identified by their homology with the immunoglobulin fold. For example, residues within the CDR-like loops of fibronectin may be randomized to generate a library of fibronectin binding molecules (see, e.g., Koide et al., J. Mol. Biol., 284: 1141-1151 (1998)). Following incorporation of CDR sequences (e.g., selected from those CDR sequences set forth in Table 2-6) and/or randomization, the diversified library may then be subjected to a selection or screening procedure to obtain binding molecules with the desired binding characteristics, e.g. specific binding to IL-6. Selection can be achieved by art-recognized methods such as phage display, yeast display, or nucleic acid display.

iv. Germlining of Camelid-Derived VH and VL Domains

Camelid conventional antibodies provide an advantageous starting point for the preparation of antibodies with utility as human therapeutic agents due to the following factors (discussed in U.S. Ser. No. 12/497,239, which is incorporated herein by reference in its entirety):

1) High % sequence homology between camelid VH and VL domains and their human counterparts;

2) High degree of structural homology between CDRs of camelid VH and VL domains and their human counterparts (i.e. human-like canonical fold structures and human-like combinations of canonical folds).

The camelid (e.g. llama) platform also provides a significant advantage in terms of the functional diversity of the IL-6 antibodies which can be obtained.

The utility of IL-6 antibodies comprising camelid VH and/or camelid VL domains for human therapy can be improved still further by "germlining" of natural camelid VH and VL domains, for example to render them less immunogenic in a human host. The overall aim of germlining is to produce a molecule in which the VH and VL domains exhibit minimal immunogenicity when introduced into a human subject, while retaining the specificity and affinity of the antigen binding site formed by the parental VH and VL domains.

Determination of homology between a camelid VH (or VL) domain and human VH (or VL) domains is a critical step in the germlining process, both for selection of camelid amino acid residues to be changed (in a given VH or VL domain) and for selecting the appropriate replacement amino acid residue(s).

An approach to germlining of camelid conventional antibodies has been developed based on alignment of a large number of novel camelid VH (and VL) domain sequences, typically somatically mutated VH (or VL) domains which are known to bind a target antigen, with human germline VH (or VL) sequences, human VH (and VL) consensus sequences, as well as germline sequence information available for llama pacos.

The following passages outline the principles which can be applied to (i) select "camelid" amino acid residues for replacement in a camelid-derived VH or VL domain or a CDR thereof, and (ii) select replacement "human" amino acid residues to substitute in, when germlining any given camelid VH (or VL) domain. This approach can be used to prepare germlined variants of the VH and VL sequences set forth in Tables 13-16, herein.

Step 1. Select human (germline) family and member of this family that shows highest homology/identity to the mature camelid sequence to be germlined. A general procedure for identifying the closest matching human germline for any given camelid VH (or VL) domain is outlined below.
Step 2. Select specific human germline family member used to germline against. Preferably this is the germline with the highest homology or another germline family member from the same family.
Step 3. Identify the preferred positions considered for germlining on the basis of the table of amino acid utilisation for the camelid germline that is closest to the selected human germline.
Step 4. Try to change amino acids in the camelid germline that deviate from the closest human germline; germlining of FR residues is preferred over CDR residues.
a. Preferred are positions that are deviating from the selected human germline used to germline against, for which the amino acid found in the camelid sequence does not match with the selected germline and is not found in other germlines of the same subclass (both for V as well as for J encoded FR amino acids).
b. Positions that are deviating from the selected human germline family member but which are used in other germlines of the same family may also be addressed in the germlining process.
c. Additional mismatches (e.g. due to additional somatic mutations) towards the selected human germline may also be addressed.
The following approach may be used to determine the closest matching human germline for a given camelid VH (or VL) domain:

Before analyzing the percentage sequence identity between *Camelidae* and human germline VH and VL, the canonical folds may first be determined, which allows the identification of the family of human germline segments with the identical combination of canonical folds for H1 and H2 or L1 and L2 (and L3). Subsequently the human germline family member that has the highest degree of sequence homology with the *Camelidae* variable region of interest may be chosen for scoring sequence homology. The determination of Chothia canonical classes of hypervariable loops L1, L2, L3, H1 and H2 can be performed with the bioinformatics tools publicly available on webpage www.bioinf.org.uk/abs/chothia.html.page. The output of the program shows the key residue requirements in a datafile. In these datafiles, the key residue positions are shown with the allowed amino acids at each position. The sequence of the variable region of the antibody is given as input and is first aligned with a consensus antibody sequence to assign the Kabat numbering scheme. The analysis of the canonical folds uses a set of key residue templates derived by an automated method developed by Martin and Thornton (Martin et al., J. Mol. Biol. 263:800-815 (1996)). The boundaries of the individual framework regions may be assigned using the IMGT numbering scheme, which is an adaptation of the numbering scheme of Chothia (Lefranc et al., NAR 27: 209-212 (1999); imgt.cines.fr).

With the particular human germline V segment known, which uses the same combination of canonical folds for H1 and H2 or L1 and L2 (and L3), the best matching family member in terms of sequence homology can be determined. The percentage sequence identity between *Camelidae* VH and VL domain framework amino acid sequences and corresponding sequences encoded by the human germline can be determined using bioinformatic tools, but manual alignment of the sequences could also be used. Human immunoglobulin sequences can be identified from several protein data bases, such as VBase (vbase.mrc-cpe.cam.ac.uk/) or the Pluckthun/Honegger database (http://www.bioc.unizh.ch/antibody/Sequences/Germlines. To compare the human sequences to the V regions of *Camelidae* VH or VL domains a sequence alignment algorithm such as available via websites like www.expasy.ch/tools/#align can be used, but also manual alignment can also be performed with a limited set of sequences. Human germline light and heavy chain sequences of the families with the same combinations of canonical folds and with the highest degree of homology with the framework regions 1, 2, and 3 of each chain may be selected and compared with the *Camelidae* variable region of interest; also the FR4 is checked against the human germline JH and JK or JL regions.

Note that in the calculation of overall percent sequence homology the residues of FR1, FR2 and FR3 are evaluated using the closest match sequence from the human germline family with the identical combination of canonical folds. Only residues different from the closest match or other members of the same family with the same combination of canonical folds are scored (NB—excluding any primer-encoded differences). However, for the purposes of germlining, residues in framework regions identical to members of other human germline families, which do not have the same combination of canonical folds, can be considered for germlining, despite the fact that these are scored "negative" according to the stringent conditions described above. This assumption is based on the "mix and match" approach for germlining, in which each of FR1, FR2, FR3 and FR4 is separately compared to its closest matching human germline sequence and the germlined molecule therefore contains a combination of different FRs as was done by Qu and colleagues (Qu et al., Clin. Cancer Res. 5:3095-3100 (1999)) and Ono and colleagues (Ono et al., Mol. Immunol. 36:387-395 (1999)).

IV. Modified Binding Molecules

In certain embodiments, binding polypeptides of the invention may comprise one or more modifications. Modified forms of binding polypeptides of the invention can be made using any techniques known in the art.

i) Reducing Immunogenicity Risk

In certain embodiments, binding molecules (e.g., antibodies or antigen binding fragments thereof) of the invention are modified to further reduce their immunogenicity risk using art-recognized techniques. For example, antibodies, or fragments thereof, can be germlined according to the methods describe above. Alternatively, binding molecules of the invention can be chimericized, humanized, and/or deimmunized.

In one embodiment, an antibody, or antigen binding fragments thereof, of the invention may be chimeric. A chimeric antibody is an antibody in which different portions of the antibody are derived from different animal species, such as antibodies having a variable region derived from a camelid (e.g., llama) monoclonal antibody and a human immunoglobulin constant region. Methods for producing chimeric antibodies, or fragments thereof, are known in the art. See, e.g., Morrison, Science 229:1202 (1985); Oi et al., BioTechniques 4:214 (1986); Gillies et al., J. Immunol. Methods 125:191-202 (1989); U.S. Pat. Nos. 5,807,715; 4,816,567; and 4,816,397, which are incorporated herein by reference in their entireties. Techniques developed for the production of "chimeric antibodies" (Morrison et al., Proc. Natl. Acad. Sci. 81:851-855 (1984); Neuberger et al., Nature 312:604-608 (1984); Takeda et al., Nature 314:452-454 (1985)) may be employed for the synthesis of said molecules. For example, a genetic sequence encoding a binding specificity of a camelid anti-IL-6 antibody molecule may be fused together with a sequence from a human antibody molecule of appropriate biological activity. As used herein, a chimeric antibody is a molecule in which different portions are derived from different animal species, such as those having a variable region derived from a camelid (e.g., llama) monoclonal antibody and a human immunoglobulin constant region, e.g., germlined or humanized antibodies.

In another embodiment, an antibody, or antigen binding portion thereof, of the invention is humanized. Humanized antibodies have a binding specificity comprising one or more complementarity determining regions (CDRs) from a non-human antibody and framework regions from a human antibody molecule. Often, framework residues in the human framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riechmann et al., Nature 332:323 (1988), which are incorporated herein by reference in their entireties.) Antibodies can be humanized using a variety of techniques known in the art including, for example, CDR-grafting (EP 239,400; PCT publication WO 91/09967; U.S. Pat. Nos. 5,225,539; 5,530,101; and 5,585,089), veneering or resurfacing (EP 592,106; EP 519,596; Padlan, Molecular Immunology 28(4/5):489-498 (1991); Studnicka et al., Protein Engineering 7(6):805-814 (1994); Roguska. et al., PNAS 91:969-973 (1994)), and chain shuffling (U.S. Pat. No. 5,565,332).

In some embodiments, de-immunization can be used to further decrease the immunogenicity risk of IL-6 binding molecules (e.g., antibody, or antigen binding portion thereof). As used herein, the term "de-immunization" includes alteration of polypeptide (e.g., an antibody, or antigen binding portion thereof) to modify T cell epitopes (see, e.g., WO9852976A1, WO0034317A2). For example, VH and VL sequences from the starting IL-6-specific antibody, or antigen binding portion thereof, of the invention may be analyzed and a human T cell epitope "map" may be generated from each V region showing the location of epitopes in relation to complementarity-determining regions (CDRs) and other key residues within the sequence. Individual T cell epitopes from the T cell epitope map are analyzed in order to identify alternative amino acid substitutions with a low risk of altering activity of the final antibody. A range of alternative VH and VL sequences are designed comprising combinations of amino acid substitutions and these sequences are subsequently incorporated into a range of IL-6-specific antibodies or fragments thereof for use in the diagnostic and treatment methods disclosed herein, which are then tested for function. Typically, between 12 and 24 variant antibodies are generated and tested. Complete heavy and light chain genes comprising modified V and human C regions are then cloned into expression vectors and the subsequent plasmids introduced into cell lines for the production of whole antibody. The antibodies are then compared in appropriate biochemical and biological assays, and the optimal variant is identified.

ii) Effector Functions and Fc Modifications

In certain embodiments, binding molecules of the invention may comprise an antibody constant region (e.g. an IgG constant region e.g., a human IgG constant region, e.g., a human IgG1 or IgG4 constant region) which mediates one or more effector functions. For example, binding of the C1 component of complement to an antibody constant region may activate the complement system. Activation of complement is important in the opsonisation and lysis of cell pathogens. The activation of complement also stimulates the inflammatory response and may also be involved in autoimmune hypersensitivity. Further, antibodies bind to receptors on various cells via the Fc region, with a Fc receptor binding site on the antibody Fc region binding to a Fc receptor (FcR) on a cell. There are a number of Fc receptors which are specific for different classes of antibody, including IgG (gamma receptors), IgE (epsilon receptors), IgA (alpha receptors) and IgM (mu receptors). Binding of antibody to Fc receptors on cell surfaces triggers a number of important and diverse biological responses including engulfment and destruction of antibody-coated particles, clearance of immune complexes, lysis of antibody-coated target cells by killer cells (called antibody-dependent cell-mediated cytotoxicity, or ADCC), release of inflammatory mediators, placental transfer and control of immunoglobulin production. In preferred embodiments, the binding molecules (e.g., antibodies or antigen binding fragments thereof) of the invention bind to an Fc-gamma receptor. In alternative embodiments, binding molecules of the invention may comprise a constant region which is devoid of one or more effector functions (e.g., ADCC activity) and/or is unable to bind Fcγ receptor.

Certain embodiments of the invention include anti-IL-6 antibodies in which at least one amino acid in one or more of the constant region domains has been deleted or otherwise altered so as to provide desired biochemical characteristics such as reduced or enhanced effector functions, the ability to non-covalently dimerize, increased ability to localize at the site of a tumor, reduced serum half-life, or increased serum half-life when compared with a whole, unaltered antibody of approximately the same immunogenicity. For example, certain antibodies, or fragments thereof, for use in the diagnostic and treatment methods described herein are domain deleted antibodies which comprise a polypeptide chain similar to an immunoglobulin heavy chain, but which lack at least a portion of one or more heavy chain domains. For instance, in certain antibodies, one entire domain of the constant region of the modified antibody will be deleted, for example, all or part of the CH2 domain will be deleted.

In certain other embodiments, binding molecules comprise constant regions derived from different antibody isotypes (e.g., constant regions from two or more of a human IgG1, IgG2, IgG3, or IgG4). In other embodiments, binding molecules comprises a chimeric hinge (i.e., a hinge comprising hinge portions derived from hinge domains of different antibody isotypes, e.g., an upper hinge domain from an IgG4 molecule and an IgG1 middle hinge domain). In one embodiment, binding molecules comprise an Fc region or portion thereof from a human IgG4 molecule and a Ser228Pro mutation (EU numbering) in the core hinge region of the molecule.

In certain embodiments, the Fc portion may be mutated to increase or decrease effector function using techniques known in the art. For example, the deletion or inactivation (through point mutations or other means) of a constant region domain may reduce Fc receptor binding of the circulating modified antibody thereby increasing tumor localization. In other cases it may be that constant region modifications consistent with the instant invention moderate complement binding and thus reduce the serum half life and nonspecific association of a conjugated cytotoxin. Yet other modifications of the constant region may be used to modify disulfide linkages or oligosaccharide moieties that allow for enhanced localization due to increased antigen specificity or flexibility. The resulting physiological profile, bioavailability and other biochemical effects of the modifications, such as tumor localization, biodistribution and serum half-life, may easily be measured and quantified using well know immunological techniques without undue experimentation.

In certain embodiments, an Fc domain employed in an antibody of the invention is an Fc variant. As used herein, the term "Fc variant" refers to an Fc domain having at least one amino acid substitution relative to the wild-type Fc domain from which said Fc domain is derived. For example, wherein the Fc domain is derived from a human IgG1 antibody, the Fc variant of said human IgG1 Fc domain comprises at least one amino acid substitution relative to said Fc domain.

The amino acid substitution(s) of an Fc variant may be located at any position (i.e., any EU convention amino acid position) within the Fc domain. In one embodiment, the Fc variant comprises a substitution at an amino acid position located in a hinge domain or portion thereof. In another embodiment, the Fc variant comprises a substitution at an amino acid position located in a CH2 domain or portion thereof. In another embodiment, the Fc variant comprises a substitution at an amino acid position located in a CH3 domain or portion thereof. In another embodiment, the Fc variant comprises a substitution at an amino acid position located in a CH4 domain or portion thereof.

The binding molecules of the invention may employ any art-recognized Fc variant which is known to impart an improvement (e.g., reduction or enhancement) in effector function and/or FcR binding. Said Fc variants may include, for example, any one of the amino acid substitutions disclosed in International PCT Publications WO88/07089A1, WO96/14339A1, WO98/05787A1, WO98/23289A1, WO99/51642A1, WO99/58572A1, WO00/09560A2, WO00/32767A1, WO00/42072A2, WO02/44215A2, WO02/060919A2, WO03/074569A2, WO04/016750A2, WO04/029207A2, WO04/035752A2, WO04/063351A2, WO04/074455A2, WO04/099249A2, WO05/040217A2, WO05/070963A1, WO05/077981A2, WO05/092925A2, WO05/123780A2, WO06/019447A1, WO06/047350A2, and WO06/085967A2 or U.S. Pat. Nos. 5,648,260; 5,739,277; 5,834,250; 5,869,046; 6,096,871; 6,121,022; 6,194,551; 6,242,195; 6,277,375; 6,528,624; 6,538,124; 6,737,056; 6,821,505; 6,998,253; and 7,083,784, each of which is incorporated by reference herein. In one exemplary embodiment, a binding polypeptide of the invention may comprise an Fc variant comprising an amino acid substitution at EU position 268 (e.g., H268D or H268E). In another exemplary embodiment, a binding polypeptide of the invention may comprise an amino acid substitution at EU position 239 (e.g., S239D or S239E) and/or EU position 332 (e.g., I332D or I332Q).

In certain embodiments, a binding polypeptide of the invention may comprise an Fc variant comprising an amino acid substitution which alters the antigen-independent effector functions of the antibody, in particular the circulating half-life of the binding polypeptide. Such binding molecules exhibit either increased or decreased binding to FcRn when compared to binding molecules lacking these substitutions, therefore, have an increased or decreased half-life in serum, respectively. Fc variants with improved affinity for FcRn are anticipated to have longer serum half-lives, and such molecules have useful applications in methods of treating mammals where long half-life of the administered antibody is desired, e.g., to treat a chronic disease or disorder. In contrast, Fc variants with decreased FcRn binding affinity are expected to have shorter half-lives, and such molecules are also useful, for example, for administration to a mammal where a shortened circulation time may be advantageous, e.g. for in vivo diagnostic imaging or in situations where the starting antibody has toxic side effects when present in the circulation for prolonged periods. Fc variants with decreased FcRn binding affinity are also less likely to cross the placenta and, thus, are also useful in the treatment of diseases or disorders in pregnant women.

In addition, other applications in which reduced FcRn binding affinity may be desired include those applications in which localization the brain, kidney, and/or liver is desired. In one exemplary embodiment, the altered binding molecules (e.g., antibodies or antigen binding fragments thereof) of the invention exhibit reduced transport across the epithelium of kidney glomeruli from the vasculature. In another embodiment, the altered binding molecules (e.g., antibodies or antigen binding fragments thereof) of the invention exhibit reduced transport across the blood brain barrier (BBB) from the brain, into the vascular space. In one embodiment, an antibody with altered FcRn binding comprises an Fc domain having one or more amino acid substitutions within the "FcRn binding loop" of an Fc domain. The FcRn binding loop is comprised of amino acid residues 280-299 (according to EU numbering). Exemplary amino acid substitutions which altered FcRn binding activity are disclosed in International PCT Publication No. WO05/047327 which is incorporated by reference herein.

In certain exemplary embodiments, the binding molecules (e.g., antibodies or antigen binding fragments thereof) of the invention comprise an Fc domain having one or more of the following substitutions: V284E, H285E, N286D, K290E and S304D (EU numbering). In yet other exemplary embodiments, the binding molecules of the invention comprise a human Fc domain with the double mutation H433K/N434F (see, e.g., U.S. Pat. No. 8,163,881). In a particular embodiment, the binding molecules of the invention comprise one or more variable regions selected from Table 16 and a human Fc domain with the double mutation H433K/N434F. In another particular embodiment, the binding molecule of the invention comprise one or more CDR sequences from Table 17 and a human Fc domain with the double mutation H433K/N434F. In yet another particular embodiment, the binding molecule of the invention comprise a VH domain of SEQ ID NO. 152 and a human Fc domain with the double mutation H433K/N434F. In still another particular embodiment, the binding molecule of the invention comprise a VH domain of SEQ ID NO. 152 wherein glutamine at one or more positions, e.g., position 1, 3, 5, or 16 or any combination thereof has been changed to glutamic acid(s) and a human Fc domain with the double mutation H433K/N434F. In still yet another particular embodiment, the binding molecule of the invention comprise a VH domain of SEQ ID NO. 152 wherein glutamine at position 1 has been changed to glutamic acid and a human Fc domain with the double mutation H433K/N434F.

In other embodiments, binding molecules, for use in the diagnostic and treatment methods described herein have a constant region, e.g., an IgG1 or IgG4 heavy chain constant region, which is altered to reduce or eliminate glycosylation. For example, binding molecules (e.g., antibodies or antigen binding fragments thereof) of the invention may also comprise an Fc variant comprising an amino acid substitution which alters the glycosylation of the antibody Fc. For example, said Fc variant may have reduced glycosylation (e.g., N- or O-linked glycosylation). In exemplary embodiments, the Fc variant comprises reduced glycosylation of the N-linked glycan normally found at amino acid position 297 (EU numbering). In another embodiment, the antibody has an amino acid substitution near or within a glycosylation motif, for example, an N-linked glycosylation motif that contains the amino acid sequence NXT or NXS. In a particular embodiment, the antibody comprises an Fc variant with an amino acid substitution at amino acid position 228 or 299 (EU numbering). In more particular embodiments, the antibody comprises an IgG1 or IgG4 constant region comprising an S228P and a T299A mutation (EU numbering).

Exemplary amino acid substitutions which confer reduce or altered glycosylation are disclosed in International PCT Publication No. WO05/018572, which is incorporated by reference herein. In preferred embodiments, the antibodies, or fragments thereof, of the invention are modified to eliminate glycosylation. Such antibodies, or fragments thereof, may be referred to as "agly" antibodies, or fragments thereof, (e.g. "agly" antibodies). While not being bound by theory, it is believed that "agly" antibodies, or fragments thereof, may have an improved safety and stability profile in vivo. Agly antibodies can be of any isotype or subclass thereof, e.g., IgG1, IgG2, IgG3, or IgG4. In certain embodiments, agly antibodies, or fragments thereof, comprise an aglycosylated Fc region of an IgG4 antibody which is devoid of Fc-effector function thereby eliminating the potential for Fc mediated toxicity to the normal vital organs that express IL-6. In yet other embodiments, antibodies, or fragments thereof, of the invention comprise an altered glycan. For example, the antibody may have a reduced number of fucose residues on an N-glycan at Asn297 of the Fc region, i.e., is afucosylated. Afucosylation increases FcRgII binding on the NK cells and potently increase ADCC. It has been shown that a diabody comprising an anti-IL-6 scFv and an anti-CD3 scFv induces killing of IL-6 expressing cells by ADCC. Accordingly, in one embodiment, the afucosylated an anti-IL-6 antibody is be used to target and kill IL-6-expressing cells. In another embodiment, the antibody may have an altered number of sialic acid residues on the N-glycan at Asn297 of the Fc region. Numerous art-recognized methods are available for making "agly" antibodies or antibodies with altered glycans. For examples, genetically engineered host cells (e.g., modified yeast, e.g., *Picchia*, or CHO cells) with modified glycosylation pathways (e.g., glycosyltransferase deletions) can be used to produce such antibodies.

iii) Covalent Attachment

Binding molecules of the invention may be modified, e.g., by the covalent attachment of a molecule to the binding polypeptide such that covalent attachment does not prevent the binding polypeptide from specifically binding to its cognate epitope. For example, but not by way of limitation, the antibodies, or fragments thereof, of the invention may be modified by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, etc. Additionally, the derivative may contain one or more non-classical amino acids.

Binding polypeptide (e.g., antibodies, or fragments thereof) of the invention may further be recombinantly fused to a heterologous polypeptide at the N- or C-terminus or chemically conjugated (including covalent and non-covalent conjugations) to polypeptides or other compositions. For example, anti-IL-6 antibodies may be recombinantly fused or conjugated to molecules useful as labels in detection assays and effector molecules such as heterologous polypeptides, drugs, radionuclides, or toxins. See, e.g., PCT publications WO 92/08495; WO 91/14438; WO 89/12624; U.S. Pat. No. 5,314,995; and EP 396,387.

Binding molecules may be fused to heterologous polypeptides to increase the in vivo half life or for use in immunoassays using methods known in the art. For example, in one embodiment, PEG can be conjugated to the binding molecules of the invention to increase their half-life in vivo. Leong, S. R., et al., Cytokine 16:106 (2001); Adv. in Drug Deliv. Rev. 54:531 (2002); or Weir et al., Biochem. Soc. Transactions 30:512 (2002).

Moreover, binding molecules of the invention can be fused to marker sequences, such as a peptide to facilitate their purification or detection. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86:821-824 (1989), for instance, hexa-histidine provides for convenient purification of the fusion protein. Other peptide tags useful for purification include, but are not limited to, the "HA" tag, which corresponds to an epitope derived from the influenza hemagglutinin protein (Wilson et al., Cell 37:767 (1984)) and the "flag" tag.

Binding molecules of the invention may be used in non-conjugated form or may be conjugated to at least one of a variety of molecules, e.g., to improve the therapeutic properties of the molecule, to facilitate target detection, or for imaging or therapy of the patient. Binding molecules of the invention can be labeled or conjugated either before or after purification, when purification is performed. In particular, binding molecules of the invention may be conjugated to therapeutic agents, prodrugs, peptides, proteins, enzymes, viruses, lipids, biological response modifiers, pharmaceutical agents, or PEG.

The present invention further encompasses binding molecules of the invention conjugated to a diagnostic or therapeutic agent. The binding molecules can be used diagnostically to, for example, monitor the development or progression of a immune cell disorder (e.g., CLL) as part of a clinical testing procedure to, e.g., determine the efficacy of a given treatment and/or prevention regimen. Detection can be facilitated by coupling the binding molecules to a detectable substance. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions. See, for example, U.S. Pat. No. 4,741,900 for metal ions which can be conjugated to antibodies for use as diagnostics according to the present invention. Examples of suitable enzymes include horseradish peroxidase, alkaline phosphatase, .beta.-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include 125I, 131I, 111In or 99Tc.

Binding molecules for use in the diagnostic and treatment methods disclosed herein may be conjugated to cytotoxins (such as radioisotopes, cytotoxic drugs, or toxins) therapeutic agents, cytostatic agents, biological toxins, prodrugs, peptides, proteins, enzymes, viruses, lipids, biological response modifiers, pharmaceutical agents, immunologically active ligands (e.g., lymphokines or other antibodies wherein the resulting molecule binds to both the neoplastic cell and an effector cell such as a T cell), or PEG.

In another embodiment, an anti-IL-6 antibody for use in the diagnostic and treatment methods disclosed herein can be conjugated to a molecule that decreases tumor cell growth. In other embodiments, the disclosed compositions may comprise antibodies, or fragments thereof, coupled to drugs or prodrugs. Still other embodiments of the present invention comprise the use of antibodies, or fragments thereof, conjugated to specific biotoxins or their cytotoxic fragments such as ricin, gelonin, *Pseudomonas* exotoxin or diphtheria toxin. The selection of which conjugated or unconjugated antibody to use will depend on the type and stage of cancer, use of adjunct treatment (e.g., chemotherapy or external radiation) and patient condition. It will be appreciated that one skilled in the art could readily make such a selection in view of the teachings herein.

It will be appreciated that, in previous studies, anti-tumor antibodies labeled with isotopes have been used successfully to destroy tumor cells in animal models, and in some cases in humans. Exemplary radioisotopes include: 90Y, 125I, 131I, 123I, 111In, 105Rh, 153Sm, 67Cu, 67Ga, 166Ho, 177Lu, 186Re and 188Re. The radionuclides act by producing ionizing radiation which causes multiple strand breaks in nuclear DNA, leading to cell death. The isotopes used to produce therapeutic conjugates typically produce high energy alpha- or beta-particles which have a short path length. Such radionuclides kill cells to which they are in close proximity, for example neoplastic cells to which the conjugate has attached or has entered. They have little or no effect on non-localized cells. Radionuclides are essentially non-immunogenic.

V. Expression of Binding Molecules

Following manipulation of the isolated genetic material to provide binding molecules of the invention as set forth above, the genes are typically inserted in an expression vector for introduction into host cells that may be used to produce the desired quantity of the claimed antibodies, or fragments thereof.

The term "vector" or "expression vector" is used herein for the purposes of the specification and claims, to mean vectors used in accordance with the present invention as a vehicle for introducing into and expressing a desired gene in a cell. As known to those skilled in the art, such vectors may easily be selected from the group consisting of plasmids, phages, viruses and retroviruses. In general, vectors compatible with the instant invention will comprise a selection marker, appropriate restriction sites to facilitate cloning of the desired gene and the ability to enter and/or replicate in eukaryotic or prokaryotic cells.

Numerous expression vector systems may be employed for the purposes of this invention. For example, one class of vector utilizes DNA elements which are derived from animal viruses such as bovine papilloma virus, polyoma virus, adenovirus, vaccinia virus, baculovirus, retroviruses (RSV, MMTV or MOMLV) or SV40 virus. Others involve the use of polycistronic systems with internal ribosome binding sites. Additionally, cells which have integrated the DNA into their chromosomes may be selected by introducing one or more markers which allow selection of transfected host cells. The marker may provide for prototrophy to an auxotrophic host, biocide resistance (e.g., antibiotics) or resistance to heavy metals such as copper. The selectable marker gene can either be directly linked to the DNA sequences to be expressed, or introduced into the same cell by cotransformation. Additional elements may also be needed for optimal synthesis of mRNA. These elements may include signal sequences, splice signals, as well as transcriptional promoters, enhancers, and termination signals. In particularly preferred embodiments the cloned variable region genes are inserted into an expression vector along with the heavy and light chain constant region genes (preferably human) synthetic as discussed above.

In other preferred embodiments the binding molecules, or fragments thereof, of the invention may be expressed using polycistronic constructs. In such expression systems, multiple gene products of interest such as heavy and light chains of antibodies may be produced from a single polycistronic construct. These systems advantageously use an internal ribosome entry site (IRES) to provide relatively high levels of polypeptides of the invention in eukaryotic host cells. Compatible IRES sequences are disclosed in U.S. Pat. No. 6,193,980 which is incorporated by reference herein. Those skilled in the art will appreciate that such expression systems may be used to effectively produce the full range of polypeptides disclosed in the instant application.

More generally, once a vector or DNA sequence encoding an antibody, or fragment thereof, has been prepared, the expression vector may be introduced into an appropriate host cell. That is, the host cells may be transformed. Introduction of the plasmid into the host cell can be accomplished by various techniques well known to those of skill in the art. These include, but are not limited to, transfection (including electrophoresis and electroporation), protoplast fusion, calcium phosphate precipitation, cell fusion with enveloped DNA, microinjection, and infection with intact virus. See, Ridgway, A. A. G. "Mammalian Expression Vectors" Chapter 24.2, pp. 470-472 Vectors, Rodriguez and Denhardt, Eds. (Butterworths, Boston, Mass. 1988). Most preferably, plasmid introduction into the host is via electroporation. The transformed cells are grown under conditions appropriate to the production of the light chains and heavy chains, and assayed for heavy and/or light chain protein synthesis. Exemplary assay techniques include enzyme-linked immunosorbent assay (ELISA), radioimmunoassay (RIA), or fluorescence-activated cell sorter analysis (FACS), immunohistochemistry and the like.

As used herein, the term "transformation" shall be used in a broad sense to refer to the introduction of DNA into a recipient host cell that changes the genotype and consequently results in a change in the recipient cell.

Along those same lines, "host cells" refers to cells that have been transformed with vectors constructed using recombinant DNA techniques and encoding at least one heterologous gene. In descriptions of processes for isolation of polypeptides from recombinant hosts, the terms "cell" and "cell culture" are used interchangeably to denote the source of antibody unless it is clearly specified otherwise. In other words, recovery of polypeptide from the "cells" may mean either from spun down whole cells, or from the cell culture containing both the medium and the suspended cells.

In one embodiment, the host cell line used for antibody expression is of mammalian origin; those skilled in the art can determine particular host cell lines which are best suited for the desired gene product to be expressed therein. Exemplary host cell lines include, but are not limited to, DG44 and DUXB11 (Chinese Hamster Ovary lines, DHFR minus), HELA (human cervical carcinoma), CVI (monkey kidney line), COS (a derivative of CVI with SV40 T antigen), R1610 (Chinese hamster fibroblast) BALBC/3T3 (mouse fibroblast), HAK (hamster kidney line), SP2/0 (mouse myeloma), BFA-1c1BPT (bovine endothelial cells), RAJI (human lymphocyte), 293 (human kidney). In one embodiment, the cell line provides for altered glycosylation, e.g., afucosylation, of the antibody expressed therefrom (e.g., PER.C6® (Crucell) or FUT8-knock-out CHO cell lines (Potelligent® Cells) (Biowa, Princeton, N.J.)). In one embodiment NS0 cells may be used. CHO cells are particularly preferred. Host cell lines are typically available from commercial services, the American Tissue Culture Collection or from published literature.

In vitro production allows scale-up to give large amounts of the desired polypeptides. Techniques for mammalian cell cultivation under tissue culture conditions are known in the art and include homogeneous suspension culture, e.g. in an airlift reactor or in a continuous stirrer reactor, or immobilized or entrapped cell culture, e.g. in hollow fibers, microcapsules, on agarose microbeads or ceramic cartridges. If necessary and/or desired, the solutions of polypeptides can be purified by the customary chromatography methods, for example gel filtration, ion-exchange chromatography, chromatography over DEAE-cellulose and/or (immuno-)affinity chromatography.

Genes encoding the binding molecules, or fragments thereof, of the invention can also be expressed non-mammalian cells such as bacteria or yeast or plant cells. In this regard it will be appreciated that various unicellular non-mammalian microorganisms such as bacteria can also be transformed; i.e. those capable of being grown in cultures or fermentation. Bacteria, which are susceptible to transformation, include members of the enterobacteriaceae, such as strains of *Escherichia coli* or *Salmonella*; Bacillaceae, such as *Bacillus subtilis; Pneumococcus; Streptococcus*, and *Haemophilus influenzae*. It will further be appreciated that, when expressed in bacteria, the polypeptides can become part of inclusion bodies. The polypeptides must be isolated, purified and then assembled into functional molecules.

In addition to prokaryotes, eukaryotic microbes may also be used. *Saccharomyces cerevisiae*, or common baker's yeast, is the most commonly used among eukaryotic microorganisms although a number of other strains are commonly available. For expression in *Saccharomyces*, the plasmid YRp7, for example, (Stinchcomb et al., Nature, 282:39 (1979); Kingsman et al., Gene, 7:141 (1979); Tschemper et al., Gene, 10:157 (1980)) is commonly used. This plasmid already contains the TRP1 gene which provides a selection marker for a mutant strain of yeast lacking the ability to grow in tryptophan, for example ATCC No. 44076 or PEP4-1 (Jones, Genetics, 85:12 (1977)). The presence of the trpl lesion as a characteristic of the yeast host cell genome then provides an effective environment for detecting transformation by growth in the absence of tryptophan.

VI. Pharmaceutical Formulations and Methods of Administration of Binding Molecules In another aspect, the invention provides pharmaceutical compositions comprising a binding molecule (e.g., an antibody, or antigen binding fragment thereof).

Methods for preparing and administering binding molecules of the invention to a subject are well known to or are readily determined by those skilled in the art. The route of administration of the antibodies, or fragments thereof, of the invention may be oral, parenteral, by inhalation or topical. The term parenteral as used herein includes intravenous, intraarterial, intraperitoneal, intramuscular, subcutaneous, rectal or vaginal administration. The intravenous, intraarterial, subcutaneous and intramuscular forms of parenteral administration are generally preferred. While all these forms of administration are clearly contemplated as being within the scope of the invention, an exemplary form for administration would be a solution for injection, in particular for intravenous or intraarterial injection or drip. Usually, a suitable pharmaceutical composition for injection may comprise a buffer (e.g. acetate, phosphate or citrate buffer), a surfactant (e.g. polysorbate), optionally a stabilizer agent (e.g. human albumin), etc. In other methods compatible with the teachings herein, the polypeptides can be delivered directly to the site of the adverse cellular population thereby increasing the exposure of the diseased tissue to the therapeutic agent. For example, the high thermal stability and solubility properties of the binding molecules of invention make them ideal agents for local administration, e.g., via subcutaneous (Sub-Q) injections. In addition, the extremely high affinity and potency of the antibodies of the invention allow the use of a lower effective dose, thereby simplifying subcutaneous injection. Accordingly, the binding molecules are particularly well-suited for the treatment or prevention of inflammatory-related disorders (e.g., rheumatoid arthritis), cancers or associated symptoms (e.g., cachexia or anorexia) for which localized delivery of the binding molecule may be desirable.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. In the subject invention, pharmaceutically acceptable carriers include, but are not limited to, 0.01-0.1M and preferably 0.05M phosphate buffer or 0.8% saline. Other common parenteral vehicles include sodium phosphate solutions, Ringer's dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives may also be present such as for example, antimicrobials, antioxidants, chelating agents, and inert gases and the like. More particularly, pharmaceutical compositions suitable for injectable use include sterile aqueous solutions (where water soluble) or dispersions and sterile powders for the extemporaneous preparation of sterile injectable solutions or dispersions. In such cases, the composition must be sterile and should be fluid to the extent that easy syringability exists. It should be stable under the conditions of manufacture and storage and will preferably be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal and the like. In many cases, it will be preferable to include isotonic agents, for example, sugars, polyalcohols, such as manitol, sorbitol, or sodium chloride in the composition. Prolonged absorption of the injectable compositions can be brought about by including in the composition an agent which delays absorption, for example, aluminum monostearate and gelatin.

In any case, sterile injectable solutions can be prepared by incorporating an active compound (e.g., an antibody by itself or in combination with other active agents) in the required amount in an appropriate solvent with one or a combination of ingredients enumerated herein, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yields a powder of an active ingredient plus any additional desired ingredient from a previously sterile-filtered solution thereof. The preparations for injections are processed, filled into containers such as ampoules, bags, bottles, syringes or vials, and sealed under aseptic conditions according to methods known in the art. Further, the preparations may be packaged and sold in the form of a kit such as those described in U.S. Ser. No. 09/259,337 and U.S. Ser. No. 09/259,338 each of which is incorporated herein by reference. Such articles of manufacture will preferably have labels or package inserts indicating that the associated compositions are useful for treating a subject suffering from, or predisposed to autoimmune or neoplastic disorders.

The binding molecules of the invention can be formulated to a wide range of concentrations for pharmaceutical use. For example, the binding molecule may be formulated to a concentration of between 5 mg/ml and 50 mg/ml (e.g., 5, 10, 20, 50 mg/ml). Alternatively, the binding molecules of the invention may be adapted to higher concentration formulations for local (e.g., subcutaneous) administration. For example, the binding molecule may be formulated to a concentration of between 50 mg/ml and 200 mg/ml, e.g, about 50, about 75, about 100, about 150, about 175 or about 200 mg/ml).

Effective doses of the binding molecules of the present invention, for the treatment of the above described conditions, vary depending upon many different factors, including means of administration, target site, physiological state of the patient, whether the patient is human or an animal, other medications administered, and whether treatment is prophylactic or therapeutic. Usually, the patient is a human, but non-human mammals including transgenic mammals can also be treated. Treatment dosages may be titrated using routine methods known to those of skill in the art to optimize safety and efficacy.

For passive immunization with an antibody of the invention, the dosage may range, e.g., from about 0.0001 to 100 mg/kg, and more usually 0.01 to 5 mg/kg (e.g., 0.02 mg/kg, 0.25 mg/kg, 0.5 mg/kg, 0.75 mg/kg, 1 mg/kg, 2 mg/kg, etc.), of the host body weight. For example dosages can be 1 mg/kg body weight or 10 mg/kg body weight or within the range of 1-10 mg/kg, preferably at least 1 mg/kg. Doses intermediate in the above ranges are also intended to be within the scope of the invention.

Subjects can be administered such doses daily, on alternative days, weekly or according to any other schedule determined by empirical analysis. An exemplary treatment entails administration in multiple dosages over a prolonged period, for example, of at least six months. Additional exemplary treatment regimes entail administration once per every two weeks or once a month or once every 3 to 6 months. Exemplary dosage schedules include 1-10 mg/kg or 15 mg/kg on consecutive days, 30 mg/kg on alternate days or 60 mg/kg weekly. In some methods, two or more monoclonal antibodies with different binding specificities are administered simultaneously, in which case the dosage of each antibody administered may fall within the ranges indicated.

Binding molecules of the invention can be administered on multiple occasions. Intervals between single dosages can be, e.g., daily, weekly, monthly or yearly. Intervals can also be irregular as indicated by measuring blood levels of polypeptide or target molecule in the patient. In some methods, dosage is adjusted to achieve a certain plasma antibody or toxin concentration, e.g., 1-1000 µg/ml or 25-300 µg/ml. Alternatively, antibodies, or fragments thereof, can be administered as a sustained release formulation, in which case less frequent administration is required. Dosage and frequency vary depending on the half-life of the antibody in the patient. In general, germlined or humanized antibodies show the longest half-life, followed by chimeric antibodies and nonhuman antibodies. In one embodiment, the antibodies, or fragments thereof, of the invention can be administered in unconjugated form. In another embodiment, the antibodies of the invention can be administered multiple times in conjugated form. In still another embodiment, the antibodies, or fragments thereof, of the invention can be administered in unconjugated form, then in conjugated form, or vise versa.

The dosage and frequency of administration can vary depending on whether the treatment is prophylactic or therapeutic. In prophylactic applications, compositions containing the present antibodies or a cocktail thereof are administered to a patient not already in the disease state to enhance the patient's resistance. Such an amount is defined to be a "prophylactic effective dose." In this use, the precise amounts again depend upon the patient's state of health and general immunity, but generally range from 0.1 to 25 mg per dose, especially 0.5 to 2.5 mg per dose. A relatively low dosage is administered at relatively infrequent intervals over a long period of time. Some patients continue to receive treatment for the rest of their lives.

In therapeutic applications, a relatively high dosage (e.g., from about 1 to 400 mg/kg of antibody per dose, with dosages of from 5 to 25 mg being more commonly used for radioimmunoconjugates and higher doses for cytotoxin-drug conjugated molecules) at relatively short intervals is sometimes required until progression of the disease is reduced or terminated, and preferably until the patient shows partial or complete amelioration of symptoms of disease. Thereafter, the patent can be administered a prophylactic regime.

In one embodiment, a subject can be treated with a nucleic acid molecule encoding a polypeptide of the invention (e.g., in a vector). Doses for nucleic acids encoding polypeptides range from about 10 ng to 1 g, 100 ng to 100 mg, 1 μg to 10 mg, or 30-300 μg DNA per patient. Doses for infectious viral vectors vary from 10-100, or more, virions per dose.

Therapeutic agents can be administered by parenteral, topical, intravenous, oral, subcutaneous, intraarterial, intracranial, intraperitoneal, intranasal or intramuscular means for prophylactic and/or therapeutic treatment. Intramuscular injection or intravenous infusion are preferred for administration of an antibody of the invention. In some methods, therapeutic antibodies, or fragments thereof, are injected directly into the cranium. In some methods, antibodies, or fragments thereof, are administered as a sustained release composition or device, such as a Medipa™ device.

Agents of the invention can optionally be administered in combination with other agents that are effective in treating the disorder or condition in need of treatment (e.g., prophylactic or therapeutic). Preferred additional agents are those which are art recognized and are standardly administered for a particular disorder.

Effective single treatment dosages (i.e., therapeutically effective amounts) of $^{90}$Y-labeled antibodies of the invention range from between about 5 and about 75 mCi, more preferably between about 10 and about 40 mCi. Effective single treatment non-marrow ablative dosages of $^{131}$I-labeled antibodies range from between about 5 and about 70 mCi, more preferably between about 5 and about 40 mCi. Effective single treatment ablative dosages (i.e., may require autologous bone marrow transplantation) of $^{131}$I-labeled antibodies range from between about 30 and about 600 mCi, more preferably between about 50 and less than about 500 mCi.

While a great deal of clinical experience has been gained with $^{131}$I and $^{90}$Y, other radiolabels are known in the art and have been used for similar purposes. Still other radioisotopes are used for imaging. For example, additional radioisotopes which are compatible with the scope of the instant invention include, but are not limited to, $^{123}$I, $^{125}$I, $^{32}$P, $^{57}$Co, $^{64}$Cu, $^{67}$Cu, $^{77}$Br, $^{81}$Rb, $^{81}$Kr, $^{87}$Sr, $^{113}$In, $^{127}$Cs, $^{129}$Cs, $^{132}$I, $^{197}$Hg, $^{203}$Pb, $^{206}$Bi, $^{177}$Lu, $^{186}$Re, $^{212}$Pb, $^{212}$Bi, $^{47}$Sc, $^{105}$Rh, $^{109}$Pd, $^{153}$Sm, $^{188}$Re, $^{199}$Au, $^{225}$Ac, $^{211}$At, $^{213}$Bi. In this respect alpha, gamma and beta emitters are all compatible with the instant invention. Further, in view of the instant disclosure it is submitted that one skilled in the art could readily determine which radionuclides are compatible with a selected course of treatment without undue experimentation. To this end, additional radionuclides which have already been used in clinical diagnosis include $^{125}$I, $^{123}$I, $^{99}$Tc, $^{43}$K, $^{52}$Fe, $^{67}$Ga, $^{68}$Ga, as well as $^{111}$In. Antibodies have also been labeled with a variety of radionuclides for potential use in targeted immunotherapy (Peirersz et al. Immunol. Cell Biol. 65: 111-125 (1987)). These radionuclides include $^{188}$Re and $^{186}$Re as well as $^{199}$Au and $^{67}$Cu to a lesser extent. U.S. Pat. No. 5,460,785 provides additional data regarding such radioisotopes and is incorporated herein by reference.

As previously discussed, the binding molecules of the invention can be administered in a pharmaceutically effective amount for the in vivo treatment of mammalian disorders. In this regard, it will be appreciated that the disclosed antibodies, or fragments thereof, will be formulated so as to facilitate administration and promote stability of the active agent. Preferably, pharmaceutical compositions in accordance with the present invention comprise a pharmaceutically acceptable, non-toxic, sterile carrier such as physiological saline, non-toxic buffers, preservatives and the like. For the purposes of the instant application, a pharmaceutically effective amount of a antibody of the invention, conjugated or unconjugated to a therapeutic agent, shall be held to mean an amount sufficient to achieve effective binding to a target and to achieve a benefit, e.g., to ameliorate symptoms of a disease or disorder or to detect a substance or a cell. In the case of tumor cells, the polypeptide will be preferably be capable of interacting with selected immunoreactive antigens on neoplastic or immunoreactive cells and provide for an increase in the death of those cells. Of course, the pharmaceutical compositions of the present invention may be administered in single or multiple doses to provide for a pharmaceutically effective amount of the polypeptide.

In keeping with the scope of the present disclosure, the binding molecules of the invention may be administered to a human or other animal in accordance with the aforementioned methods of treatment in an amount sufficient to produce a therapeutic or prophylactic effect. The polypeptides of the invention can be administered to such human or other animal in a conventional dosage form prepared by combining the antibody of the invention with a conventional pharmaceutically acceptable carrier or diluent according to known techniques. It will be recognized by one of skill in the art that the form and character of the pharmaceutically acceptable carrier or diluent is dictated by the amount of active ingredient with which it is to be combined, the route of administration and other well-known variables. Those skilled in the art will further appreciate that a cocktail comprising one or more species of polypeptides according to the present invention may prove to be particularly effective.

VII. Methods of Treating IL-6-Associated Disease or Disorders

The binding molecules of the invention are useful for antagonizing IL-6 activity. Accordingly, in another aspect, the invention provides methods for treating IL-6-associated diseases or disorders by administering to a subject in need of thereof a pharmaceutical composition comprising one or more binding molecules of the invention.

IL-6-associated diseases or disorders amenable to treatment include, without limitation, inflammatory diseases and cancer.

One skilled in the art would be able, by routine experimentation, to determine what an effective, non-toxic amount of antibody (or additional therapeutic agent) would be for the purpose of treating an IL-6-associated disease or disorder. For example, a therapeutically active amount of a polypeptide may vary according to factors such as the disease stage (e.g., stage I versus stage IV), age, sex, medical complications (e.g., immunosuppressed conditions or diseases) and weight of the subject, and the ability of the antibody to elicit a desired response in the subject. The dosage regimen may be adjusted to provide the optimum therapeutic response. For example, several divided doses may be administered daily, or the dose may be proportionally reduced as indicated by the exigencies of the therapeutic situation. Generally, however, an effective dosage is expected to be in the range of about 0.05 to 100 milligrams per kilogram body weight per day and more preferably from about 0.5 to 10, milligrams per kilogram body weight per day.

VIII. Exemplification

Example 1 Generation and Selection of IL-6-Specific Antagonistic Fabs

Llamas were immunized with human IL-6 (either produced in *E. coli* purchased from MACS Miltenyi Biotec (Cat. No. 130-093-934) or produced in Human Embryonic kidney cells purchased from Humanzyme (Cat. No. HZ-1044)). Immunization of llamas and harvesting of peripheral blood lymphocytes (PBLs), as well as the subsequent extraction of RNA and amplification of antibody fragments, were performed as described by De Haard and colleagues (De Haard H, et al., JBC. 274:18218-30, 1999). After the last immunization, blood was collected and total RNA extracted from PBLs prepared using a Ficoll-Paque gradient and the method described by Chomczynski P et al. (Anal. Biochem. 162: 156-159, 1987). The extracted RNA was then used for random cDNA synthesis and PCR amplification of the V-regions of the heavy and the light chains (Vλ and Vκ) in order to construct Fab-containing phagemid libraries as described by De Haard H, et al. (Biol. Chem. 274, 1999).

Phage expressing Fabs were produced according to standard protocols and further selected on immobilized human IL-6 either biotinylated and captured by neutravidine or directly coated on maxisorp plates. Total or competitive elution of the IL-6 binding phage with trypsin was performed according to standard phage display protocols.

IL-6-specific Fabs were next screened for cross-competition with the IL-6 neutralizing antibody, B-E8 and IL-6 receptor using an ELISA-based competition assay. The VH and VL amino acid sequences of exemplary antagonistic IL-6-specific Fabs identified using this assay are set forth in Table 13 below.

The binding kinetics of IL-6-specific Fabs that were able to cross-compete with the B-E8 antibody was assessed using surface plasmon resonance (Biacore). Specifically, biotinylated (prokaryotic) IL-6 was captured on a streptavidin biacore sensor chip (CM5-SA) and different concentrations of purified Fabs were injected during 3 minutes following by a 5 minute wash with buffer. From the washing phase the off-rate (kd) was determined, while from the injection phase the on-rate (ka) was calculated using the concentration and off-rate as parameters. The measured off-rates and on-rates and calculated affinities of antagonistic Fabs are shown in Table 2. Fabs 24C9 and 24D10 have off-rates in the $10^{-5}$ $s^{-1}$ range and have affinities of 660 and 270 pM, respectively. The binding kinetics of antagonistic purified Fabs (Table 3) and periplasmic fractions of Fab-expressing bacteria (Table 4) were also evaluated by surface plasmon resonance (Biacore) using both bacterially and eukaryotically produced human IL-6 directly coated on a CMS chip. The Fabs tested had off-rates between $6\times10^{-4}$ and $2\times10^{-5}$ $s^{-1}$.

TABLE 2

Binding Kinetics of Selected Purified Antagonistic Fab Clones

| Fab | ka (1/Ms) | kd (1/s) | Rmax (RU) | KA (1/M) | KD (M) | Chi2 |
|---|---|---|---|---|---|---|
| 17B3 | 3.02E+04 | 2.92E−03 | 35.7 | 1.04E+07 | 9.65E−08 | 2.67 |
| 18C7 | 1.05E+05 | 1.85E−03 | 43.9 | 5.70E+07 | 1.75E−08 | 6.98 |
| 18F8 | 4.84E+04 | 7.84E−04 | 51.5 | 6.18E+07 | 1.62E−08 | 8.43 |
| 18C9 | 5.56E+04 | 1.19E−03 | 49.9 | 4.67E+07 | 2.14E−08 | 9.51 |
| 18C11 | 5.52E+04 | 7.84E−04 | 22.1 | 7.05E+07 | 1.42E−08 | 0.2 |
| 28C6 | 1.01E+05 | 2.50E−03 | 22.6 | 4.04E+07 | 2.48E−08 | 1.2 |
| 20A4 | 2.88E+05 | 1.68E−03 | 48.2 | 1.72E+08 | 5.82E−09 | 2.56 |
| 29B11 | 1.30E+05 | 2.98E−03 | 23.3 | 4.36E+07 | 2.29E−08 | 1.02 |
| 24C9 | 1.33E+05 | 8.77E−05 | 38.1 | 1.51E+09 | 6.61E−10 | 2.21 |
| 24D10 | 6.27E+04 | 1.69E−05 | 40.6 | 3.70E+09 | 2.70E−10 | 3.48 |
| 24E9 | 1.17E+05 | 1.39E−04 | 41 | 8.38E+08 | 1.19E−09 | 3.87 |

TABLE 3

Binding Kinetics of Selected Purified Antagonistic Fab Clones

| | $K_D$ | | $k_{off}$ | |
|---|---|---|---|---|
| | eukIL-6 | bactIL-6 | eukIL-6 | bactIL-6 |
| 17F10 | 6.0E−09 | 4.3E−08 | 7.2E−04 | 1.2E−03 |
| 18C7 | 7.7E−09 | 9.1E−09 | 1.0E−03 | 1.1E−03 |
| 18C9 | 2.4E−09 | 4.9E−09 | 2.1E−04 | 3.6E−04 |
| 20A4 | 8.1E−10 | 2.0E−09 | 3.0E−04 | 6.2E−04 |
| 24D10 | 8.5E−10 | 1.2E−09 | 1.7E−04 | 1.9E−04 |
| 24E9 | 7.1E−10 | 9.3E−10 | 2.4E−04 | 2.9E−04 |
| 24C9 | 1.7E−09 | 2.6E−09 | 3.0E−04 | 3.7E−04 |
| 24A3 | 5.9E−10 | 2.2E−10 | 1.1E−04 | 4.8E−05 |
| 29B11 | 5.1E−10 | 9.3E−10 | 1.0E−04 | 2.2E−04 |
| 29E7 | 6.6E−10 | 1.0E−09 | 1.5E−04 | 2.4E−04 |

TABLE 4

Binding Kinetics of Fab-Containing Periplasmic Fractions

| run | | ratio bact/euk | bact | euk | average binding |
|---|---|---|---|---|---|
| 55 | 28d4 | 1.02 | 1.79E−05 | 2.10E−05 | 43 |
| 64 | 28e5 | 2.80 | 1.84E−05 | −1.15E−03 | 1 |
| 62 | 28c5 | −2.93 | 1.86E−05 | 6.66E−04 | 1 |
| 16 | 28e8 | 0.97 | 2.07E−05 | 9.02E−05 | 52 |
| 45 | 28B3 | 1.00 | 2.93E−05 | 1.02E−04 | 46 |
| 1 | pur61H7 | 1.13 | 4.22E−05 | 3.68E−05 | 176 |
| 17 | 28f8 | 0.98 | 5.16E−05 | 7.46E−05 | 72 |
| 3 | purGL18fab | 1.08 | 6.44E−05 | 3.87E−05 | 169 |
| 56 | 28e4 | 1.01 | 6.87E−05 | 6.74E−05 | 28 |
| 49 | 28f3(28B6) | 1.00 | 7.71E−05 | 3.50E−05 | 43 |
| 18 | 28g8 | 0.97 | 8.13E−05 | 1.14E−04 | 59 |
| 30 | 28c10 | 1.00 | 8.16E−05 | 5.91E−05 | 86 |
| 12 | 28A8 | 1.01 | 8.19E−05 | 6.78E−05 | 96 |
| 33 | 28f10(24A3) | 1.20 | 8.42E−05 | 7.60E−05 | 286 |
| 48 | 28e3 | 0.99 | 8.46E−05 | 3.56E−05 | 27 |
| 5 | 28B7 | 1.04 | 8.62E−05 | 7.55E−05 | 115 |

TABLE 4-continued

Binding Kinetics of Fab-Containing Periplasmic Fractions

| run | | ratio bact/euk | bact | euk | average binding |
|---|---|---|---|---|---|
| 20 | 28A9 | 0.95 | 8.75E−05 | 7.10E−05 | 74 |
| 63 | 28d5 | −3.50 | 9.23E−05 | 2.19E−03 | 1 |
| 2 | purBE8fab | 1.05 | 9.41E−05 | 8.59E−05 | 207 |
| 28 | 28A10 | 1.01 | 9.53E−05 | 7.47E−05 | 99 |
| 31 | 28d10 | 0.99 | 9.54E−05 | 7.41E−05 | 81 |
| 42 | 28g12(24G3) | 0.96 | 1.12E−04 | 7.52E−05 | 46 |
| 44 | 28A3 | 0.94 | 1.29E−04 | 1.12E−04 | 34 |
| 68 | pur24d10 | 1.14 | 1.43E−04 | 1.25E−04 | 301 |
| 57 | 28f4 | 1.09 | 1.67E−04 | 3.69E−06 | 43 |
| 66 | 28g5 | 1.96 | 1.71E−04 | 8.71E−04 | 2 |
| 58 | 28g4 | 0.95 | 1.73E−04 | 1.60E−04 | 39 |
| 6 | 28c7 | 1.09 | 1.77E−04 | 1.52E−04 | 159 |
| 52 | 28A4 | 0.87 | 1.81E−04 | 1.18E−04 | 19 |
| 41 | 28f12(24D10) | 1.09 | 1.83E−04 | 1.44E−04 | 167 |
| 26 | 28g9 | 1.08 | 1.84E−04 | 1.58E−04 | 196 |

Example 2. VH/VL Shuffling for Improved Affinity

VL chain shuffling was used to improve the affinity of the Fabs 17F10, 18C7, 18C9, 18C11, 20A4, 29B11, 16D2 and 28A6. In this method, the heavy chain of these clones (as a VHCH1 fragment) was reintroduced into the primary phagemid-light chain library (see Example 1). Affinity selections were performed to select for chain shuffled Fabs with an improved affinity for IL-6. The binding kinetics of chain shuffled Fabs were evaluated by surface plasmon resonance (Biacore) using both bacterially and eukaryotically produced human IL-6, and cynomolgus monkey IL-6 (Tables 5-7). The VH and VL amino acid sequences of exemplary IL-6-specific Fabs selected by the VL chain shuffling method are set forth in Table 14 below.

VH chain shuffling was also used to improve the affinity of the Fab 24D10. In this method, the light chain of 24D10 was reintroduced into the primary phagemid-heavy chain library (see Example 1) and selected using an off-rate assay. In this type of selection, the phage were allowed to bind to antigen on a substrate for 1.5 to 2 hours. At round 2, after 15 washes with PBS-Tween, an additional wash was performed with the presence of excess soluble IL-6. The principle is that phage antibodies with inferior off-rates and therefore dissociating more rapidly are captured by the excess of soluble target and are removed during washing. This procedure avoids re-binding of such phage to the coated target. The time of the additional wash step was increased with the number of rounds performed and the temperature was also increased to 37° C., to select for more stable Fab variants. The binding kinetics of chain shuffled Fabs and the benchmark antibodies, BE8 and GL18, were evaluated by surface plasmon resonance (Biacore) using both bacterially and eukaryotically produced human IL-6 (Tables 8 and 9). The VH and VL amino acid sequences of exemplary IL-6-specific Fabs selected by the VH chain shuffling method are set forth in Table 14 below.

TABLE 5

Binding Kinetics of Purifed 17F10, 18C11, 18C7 and 20A4 Chain-Shuffled Fabs

| parental | Light Chain shuffled | $K_D$ (M) | | | $k_{off}$ (1/s) | | |
|---|---|---|---|---|---|---|---|
| | | eukIL-6 | HIS-huIL-6 | HIS-cyIL-6 | eukIL-6 | HIS-huIL-6 | HIS-cyIL-6 |
| 17F10 | | 6.0E−09 | 4.3E−08 | 6.2E−10 | 7.2E−04 | 1.2E−03 | 7.0E−04 |
| | 41E10/35B1 | 4.6E−10 | 5.4E−10 | 3.4E−10 | 1.6E−04 | 1.6E−04 | 1.2E−04 |
| | 41B5/35C1 | 4.1E−10 | 4.7E−10 | 2.8E−10 | 1.2E−04 | 1.1E−04 | 8.1E−05 |
| | 41B5 | 9.2E−10 | | 7.2E−10 | 2.0E−04 | | 1.7E−04 |
| 17F10 | pur Fab 68 nM | 1.4E−08 | 1.9E−08 | 1.4E−08 | 7.7E−04 | 8.8E−04 | 7.8E−04 |
| 18C11 | | 2.9E−09 | Nt | 3.4E−09 | 7.6E−04 | | 8.5E−04 |
| | 42H1/36A1 | 3.4E−10 | 7.5E−10 | 6.9E−10 | 1.1E−04 | 1.5E−04 | 1.5E−04 |
| 18C7 | (090423) | 7.7E−09 | 9.1E−09 | 5.3E−09 | 1.0E−03 | 1.1E−03 | 6.3E−04 |
| | (090429) | 5.2E−09 | | 4.9E−09 | 8.2E−04 | | 6.9E−04 |
| | 44C3 | 2.9E−09 | 3.9E−09 | 3.4E−09 | 4.5E−04 | 6.4E−04 | 4.9E−04 |
| | 44E3 | 3.1E−09 | 3.6E−09 | 3.6E−09 | 6.6E−04 | 7.6E−04 | 7.6E−04 |
| | 44D3 | 2.5E−09 | 3.1E−09 | 3.2E−09 | 5.2E−04 | 6.4E−04 | 6.0E−04 |
| 20A4 | | 8.1E−10 | 2.0E−09 | 1.7E−09 | 3.0E−04 | 6.2E−04 | 7.5E−04 |
| | 68F2 | | | | 3.3E−05 | 8.0E−05 | |

TABLE 6

Binding Kinetics of Periplasmic Fractions Containing 29B11 Chain Shuffled Fabs

| | ka (1/Ms) | kd (1/s) | KA (1/M) | KD (M) | Chi2 | FOLD IMPROVEMENT | | |
|---|---|---|---|---|---|---|---|---|
| | | | | | | ka (1/Ms) | kd (1/s) | KD (M) |
| 29B11 | | | | | | | | |
| bact | 2.51E+05 | 1.31E−04 | 1.91E+09 | 5.24E−10 | 35 | | | |
| euk | 1.87E+05 | 1.02E−04 | 1.83E+09 | 5.46E−10 | 48.4 | | | |
| cy | 1.13E+05 | 7.46E−04 | 1.51E+08 | 6.61E−09 | 59.5 | | | |

TABLE 6-continued

Binding Kinetics of Periplasmic Fractions Containing 29B11 Chain Shuffled Fabs

| | ka (1/Ms) | kd (1/s) | KA (1/M) | KD (M) | Chi2 | FOLD IMPROVEMENT | | |
|---|---|---|---|---|---|---|---|---|
| | | | | | | ka (1/Ms) | kd (1/s) | KD (M) |
| 55C1a | | | | | | | | |
| bact | 5.61E+05 | 7.38E−05 | 7.60E+09 | 1.32E−10 | 21 | 2.24 | 1.78 | 3.97 |
| euk | 4.40E+05 | 7.93E−05 | 5.55E+09 | 1.80E−10 | 37.7 | 2.35 | 1.29 | 3.03 |
| cyno | 4.75E+05 | 3.81E−04 | 1.25E+09 | 8.01E−10 | 32.4 | 4.20 | 1.96 | 8.25 |
| 55E2b | | | | | | | | |
| bact | 4.89E+05 | 6.72E−05 | 7.28E+09 | 1.37E−10 | 15.6 | 1.95 | 1.95 | 3.82 |
| euk | 4.14E+05 | 6.53E−05 | 6.34E+09 | 1.58E−10 | 29.2 | 2.21 | 1.56 | 3.46 |
| cy | 4.68E+05 | 3.36E−04 | 1.39E+09 | 7.17E−10 | 24.1 | 4.14 | 2.22 | 9.22 |
| 55H1c | | | | | | | | |
| bact | 1.28E+06 | 1.27E−04 | 1.00E+10 | 9.97E−11 | 17.2 | 5.10 | 1.03 | 5.26 |
| euk | 1.13E+06 | 1.11E−04 | 1.02E+10 | 9.77E−11 | 11.7 | 6.04 | 0.92 | 5.59 |
| cy | 1.16E+06 | 6.15E−04 | 1.89E+09 | 5.29E−10 | 29.9 | 10.27 | 1.21 | 12.50 |
| 47C2 (R4) | | | | | | | | |
| bact | 1.12E+06 | 3.15E−04 | 3.56E+09 | 2.81E−10 | 18.3 | 4.46 | 0.42 | 1.86 |
| euk | 8.49E+05 | 2.40E−04 | 3.54E+09 | 2.82E−10 | 16.6 | 4.54 | 0.43 | 1.94 |
| cy | 8.51E+05 | 1.31E−03 | 6.48E+08 | 1.54E−09 | 18.7 | 7.53 | 0.57 | 4.29 |
| 48C10 | | | | | | | | |
| bact | 2.62E+05 | 1.84E−04 | 1.43E+09 | 7.01E−10 | 29 | 1.04 | 0.71 | 0.75 |
| euk | bad fit . . . | | | | | | | |
| cy | 1.80E+05 | 4.40E−04 | 4.10E+08 | 2.44E−09 | 5.11 | 1.59 | 1.70 | 2.71 |

TABLE 7

Binding Kinetics of Periplasmic Fractions Containing 28A6 Chain-Shuffled Fabs

| | ka (1/Ms) | kd (1/s) | KA (1/M) | KD (M) | Chi2 | FOLD IMPROVEMENT | | |
|---|---|---|---|---|---|---|---|---|
| | | | | | | ka (1/Ms) | kd (1/s) | KD (M) |
| 28A6 (parental) | | | | | | | | |
| bact | 2.38E+05 | 1.78E−04 | 1.34E+09 | 7.49E−10 | 40.7 | | | |
| euk | 1.82E+05 | 1.05E−04 | 1.73E+09 | 5.80E−10 | 63.1 | | | |
| cyno | 1.28E+05 | 6.73E−04 | 1.91E+08 | 5.25E−09 | 74.5 | | | |
| 55A11d | | | | | | | | |
| BACT | 1.88E+05 | 6.76E−05 | 2.78E+09 | 3.59E−10 | 14.5 | 0.79 | 2.63 | 2.09 |
| euk | 1.01E+05 | 6.36E−05 | 1.59E+09 | 6.31E−10 | 9.18 | 0.55 | 1.65 | 0.92 |
| cyno | 1.44E+05 | 8.17E−05 | 1.77E+09 | 5.66E−10 | 5.69 | 1.13 | 8.24 | 9.28 |
| 55C10e | | | | | | | | |
| bact | 1.71E+05 | 6.99E−05 | 2.44E+09 | 4.09E−10 | 7.83 | 0.72 | 2.55 | 1.83 |
| euk | 1.39E+05 | 6.14E−05 | 2.26E+09 | 4.43E−10 | 15.2 | 0.76 | 1.71 | 1.31 |
| cy | 1.36E+05 | 8.67E−05 | 1.56E+09 | 6.39E−10 | 6.97 | 1.06 | 7.76 | 8.22 |
| 55C11f | | | | | | | | |
| bact | 2.28E+05 | 6.94E−05 | 3.29E+09 | 3.04E−10 | 6.56 | 0.96 | 2.56 | 2.46 |
| euk | 2.01E+05 | 6.47E−05 | 3.10E+09 | 3.23E−10 | 13.4 | 1.10 | 1.62 | 1.80 |
| cy | 2.85E+05 | 8.90E−05 | 3.20E+09 | 3.13E−10 | 26.7 | 2.23 | 7.56 | 16.77 |
| 55E10g1 | | | | | | | | |
| bact | 1.93E+05 | 6.09E−05 | 3.18E+09 | 3.15E−10 | 10.4 | 0.81 | 2.92 | 2.38 |
| euk | 1.46E+05 | 5.59E−05 | 2.62E+09 | 3.82E−10 | 8.45 | 0.80 | 1.88 | 1.52 |
| cyno | 1.45E+05 | 6.88E−05 | 2.10E+09 | 4.76E−10 | 9.6 | 1.13 | 9.78 | 11.03 |
| 55E11g3 | | | | | | | | |
| bact | 1.68E+05 | 7.05E−05 | 2.38E+09 | 4.21E−10 | 4.98 | 0.71 | 2.52 | 1.78 |
| euk | 1.38E+05 | 5.14E−05 | 2.68E+09 | 3.73E−10 | 8.62 | 0.76 | 2.04 | 1.55 |
| cy | 1.39E+05 | 7.46E−05 | 1.86E+09 | 5.38E−10 | 7.34 | 1.09 | 9.02 | 9.76 |

TABLE 7-continued

Binding Kinetics of Periplasmic Fractions Containing 28A6 Chain-Shuffled Fabs

| | ka (1/Ms) | kd (1/s) | KA (1/M) | KD (M) | Chi2 | FOLD IMPROVEMENT ka (1/Ms) | kd (1/s) | KD (M) |
|---|---|---|---|---|---|---|---|---|
| 48H1g2,R4 | | | | | | | | |
| bact | 2.06E+05 | 7.04E−05 | 2.93E+09 | 3.41E−10 | 8.93 | 0.87 | 2.53 | 2.20 |
| euk | 1.06E+05 | 6.80E−05 | 1.56E+09 | 6.40E−10 | 19.9 | 0.58 | 1.54 | 0.91 |
| cy | 1.12E+05 | 9.46E−05 | 1.18E+09 | 8.45E−10 | 15.7 | 0.88 | 7.11 | 6.21 |

TABLE 8

Binding Kinetics of Periplasmic Fractions Containing 24D10 Chain-Shuffled Fabs

| | RANKED Bact | euk | cyno | Average binding (RU) |
|---|---|---|---|---|
| 62B6 | 9.07E−05 | 5.58E−05 | 7.49E−05 | 214 |
| 62c6 | 1.20E−04 | 6.11E−05 | 1.05E−04 | 150 |
| 62f6 | 1.13E−04 | 7.19E−05 | 1.01E−04 | 154 |
| CAT-GL18Fab | 9.41E−05 | 7.30E−05 | 1.20E−04 | 547 |
| 62g6 | 1.78E−04 | 7.67E−05 | 8.58E−05 | 132 |
| 62f5 | 1.63E−04 | 7.96E−05 | 1.15E−04 | 139 |
| 62h5 | 1.57E−04 | 8.28E−05 | 1.28E−04 | 139 |
| BE8-Fab | 9.70E−05 | 8.39E−05 | 1.18E−04 | 338 |
| 62h6 | 1.53E−04 | 8.46E−05 | 9.76E−05 | 196 |
| BE8-Fab | 1.03E−04 | 8.72E−05 | 1.28E−04 | 340 |
| BE8-Fab | 9.29E−05 | 8.96E−05 | 1.04E−04 | 347 |
| 61h7 | 7.54E−05 | 9.32E−05 | 9.45E−05 | 635 |
| CAT-GL18Fab | 9.98E−05 | 9.33E−05 | 1.40E−04 | 486 |
| 62d6 | 1.30E−04 | 9.53E−05 | 1.02E−04 | 134 |
| 62g5 | 1.68E−04 | 9.78E−05 | 1.31E−04 | 150 |
| 61B7 | 9.07E−05 | 9.79E−05 | 1.16E−04 | 597 |
| 55H1c | 1.35E−04 | 1.01E−04 | 4.17E−04 | 773 |
| 62A6 | 1.62E−04 | 1.01E−04 | 1.39E−04 | 138 |
| 62A5 | 1.48E−04 | 1.05E−04 | 1.29E−04 | 138 |
| 62f3 | 1.75E−04 | 1.05E−04 | 1.16E−04 | 109 |
| 55H1c | 1.40E−04 | 1.06E−04 | 4.30E−04 | 770 |
| 62c5 | 9.95E−05 | 1.09E−04 | 1.17E−04 | 131 |
| 61g7 | 1.19E−04 | 1.10E−04 | 3.18E−04 | 139 |
| 62B5 | 1.30E−04 | 1.11E−04 | 1.46E−04 | 170 |
| 61f6 | 1.12E−04 | 1.13E−04 | 1.25E−04 | 606 |
| 55H1c | 1.26E−04 | 1.13E−04 | 3.90E−04 | 873 |
| 61g3 | 1.39E−04 | 1.15E−04 | 5.28E−04 | 687 |
| 61A3 | 1.34E−04 | 1.18E−04 | 5.19E−04 | 694 |
| 62d5 | 1.63E−04 | 1.18E−04 | 1.47E−04 | 129 |
| 62c2 | 1.37E−04 | 1.20E−04 | 5.44E−04 | 619 |
| 62g1 | 1.38E−04 | 1.21E−04 | 5.38E−04 | 629 |
| 61e1 | 1.39E−04 | 1.21E−04 | 5.36E−04 | 690 |
| 61B4 | 1.55E−04 | 1.21E−04 | 5.68E−04 | 561 |
| 62h1 | 1.41E−04 | 1.24E−04 | 5.40E−04 | 647 |
| 61g12 | 1.42E−04 | 1.27E−04 | 4.30E−04 | 138 |
| 62g4 | 1.51E−04 | 1.27E−04 | 5.51E−04 | 605 |
| 61g10 | 1.45E−04 | 1.30E−04 | 3.99E−04 | 159 |
| 61h9 | 1.31E−04 | 1.31E−04 | 4.12E−04 | 152 |
| 62e5 | 1.48E−04 | 1.32E−04 | 1.88E−04 | 148 |
| 62A1 | 1.73E−04 | 1.32E−04 | 6.41E−04 | 597 |
| 61g5 | 1.30E−04 | 1.39E−04 | 3.69E−04 | 229 |
| 61c12 | 1.43E−04 | 1.39E−04 | 4.44E−04 | 267 |

TABLE 9

Binding Kinetics of Purified 24D10 Chain-Shuffled Fabs

| clone | | ka (1/Ms) | kd (1/s) | KD (M) | Chi2 |
|---|---|---|---|---|---|
| 24D10 | Bact | 2.1E+05 | 1.0E−04 | 5.0E−10 | 5.4 |
| | Euk IL-6 | 2.5E+05 | 1.0E−04 | 4.1E−10 | 5.04 |
| 61B7 | Bact | 3.5E+05 | 5.7E−05 | 1.6E−10 | 2.04 |
| | euk | 3.3E+05 | 6.6E−05 | 2.0E−10 | 3.84 |
| 61H7 | Bact | 1.2E+05 | 2.0E−06 | 1.7E−11 | 1.3 |
| | Euk IL-6 | 1.2E+05 | 5.5E−05 | 4.5E−10 | 0.711 |
| BE8-Fab(D) | Bact | 2.8E+05 | 7.7E−05 | 2.8E−10 | 18.7 |
| | Euk IL-6 | 3.6E+05 | 7.7E−05 | 2.2E−10 | 12.3 |

Example 3 Crystal Structure of Fab 61H7 in Complex with IL-6 i) IL-6/Fab 61H7 Complex Characterization

Size exclusion chromatography was performed on an Alliance 2695 HPLC system (Waters) using a Silica Gel KW803 column (Shodex) eluted with 50 mM Tris-HCl pH 7.5, 150 mM NaCl at a flow rate of 0.5 ml/min. Detection was performed using a triple-angle light scattering detector (Mini-DAWN™ TREOS, Wyatt technology, Sanata Barbara, USA). Molecular weight determination was performed by ASTRA V software (Wyatt technology).

ii) Crystallization

Initial crystallization screening of the IL-6/Fab 61H7 complex was performed with commercial kits Structure screen 1 and 2, Proplex screen and Stura Footprint screen (Molecular Dimensions Ltd). Drops were set-up with a 1:1 (v:v) ratio of protein (8.45 mg/ml) to mother liquor in a total volume of 200 nl on Greiner 96-well plates using a Cartesian MicroSys SQ robot. Diffraction-quality crystals of complex were obtained by sitting-drop vapor diffusion at 277 K after optimization in 27.14% PEG MME 2K, 0.1M Na Hepes pH 7.14. Crystals belong to the C2 space group with unit cell dimensions: a=108.2 Å, b=47.5 Å, and c=148.3 Å and β=97°. They contain one ILF/Fab complex per asymmetric unit with a Vm value of 2.36 Å$^3$/Da which correspond to a solvent content of 48%.

iii) Analysis of the Structure of the IL-6:61H7 Complex

Figure 3A:
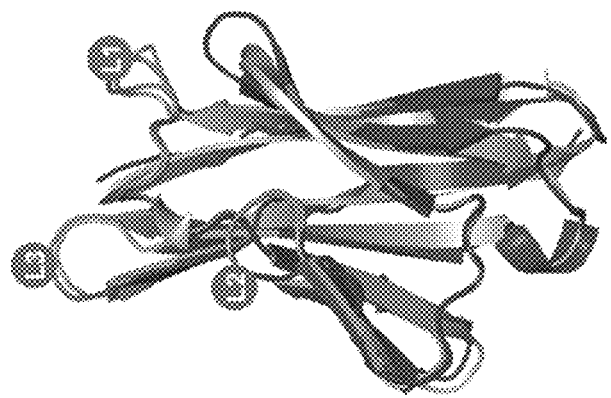
FIG. 3A shows that camelid-derived hypervariable loops L1-L3 of the 61H7 antibody of the invention adopt predicted canonical folds and canonical fold combinations of human antibodies.
Figure 3B:
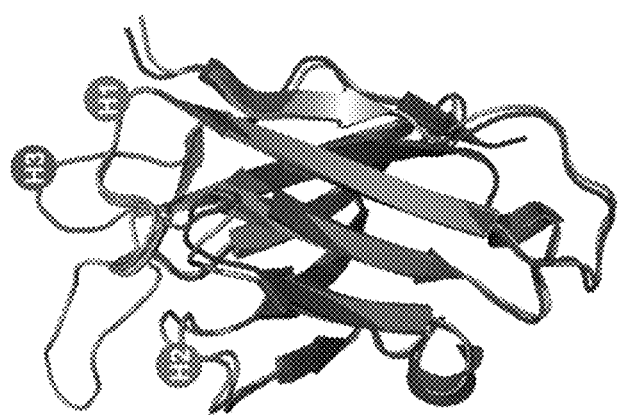
FIG. 3B shows that camelid-derived hypervariable loops H1 and H2 of the 61H7 antibody of the invention adopt predicted canonical folds and canonical fold combinations of human antibodies.

The canonical structures predicted for the CDR loops of 61H7 mAb are 1 and 3 for H1 and H2, respectively, and 7, 1, and 4 for L1, L2, and L3, respectively (www.bioinforg.uk/abs/chothia.html). The overlay of the 61H7 VH with Protein Data Bank (PDB) entry 1dfb (derived from a patient derived antibody against the HIV-1 protein gp41) shows that H1 and H2 adopt the predicted canonical folds (see FIG. 3A). The overlay of the 61H7 VL with Protein Data Bank (PDB) entry 1mfa demonstrates that all three light chain CDRs adopt the predicted conformations (see FIG. 3B). Accordingly, structural analysis confirms that the VH (a VH3 family member) of 61H7 belongs to the human 1-3 combination of canonical H1-H2 structures, while the VL (a VL8 family member) of 61H7 belongs to the human 7λ1-4 combination of human canonical structures.

IL-6 was previously crystallized and classified as a four helix bundle linked by loops and an additional mini-helix (Somers et al., 1997, EMBO Journal 16, 989-997, which is incorporated herein by reference in its entirety). Superposition of the apo IL-6 (pdb 1ALU) with the IL-6 from the IL-6:61H7 complex shows good agreement between both models (rms 0.54 Å). This confirms that the 61H7 Fab recognizes and binds the native conformation of IL-6.

The crystal structure of the IL-6 in complex with its receptor and the signalling receptor gp130 showed a hexameric complex (Boulanger et al., 2003, Science 27, 2101-2104, which is incorporated herein by reference in its entirety). IL-6 forms a non-signalling complex with IL-6R through site I. Site II is a composite epitope formed by the binary complex of IL-6 and IL-6R. Interaction of site III with gp130 forms the signalling complex.

Superposition of the IL-6:IL-6R structure (pdb 1P9M) with the IL-6:61H7 structure shows good agreement (rms 1.2 Å) between both IL-6 structures. Two loops differ in conformation. The first loop covering residues Asn48-Asn61, is a long loop that is unstructured in the apo IL-6 and IL-6:61H7 complex. This loop is stabilized in the IL-6:IL-6R structure by the binding of the IL-6R. The second loop that differs in conformation is the so called BC loop.

The crystallographic asymmetric unit contains a single 1:1 complex. The global architecture of the IL-6:61H7 complex shows that both the VH (60%) and the VL (40%) contribute to the large interaction surface (940 Å$^2$). From the crystal structure the residues important for the interaction with IL-6 were determined. The hydrogen bonds and salt bridges formed between the 61H7 Fab and the cytokine are listed in Table 10. The interactions are limited to the CDR1 and CDR3 of the light chain and the CDR1, CDR2 and CDR3 of the heavy chain.

61H7 Fab and the IL-6R. It is mainly the VL that gives a sterical clash with the IL-6R. Epitopes of IL-6R and 61H7 will be very close to each other. To verify if there is overlap between both epitopes, residues within 4.0 Å of the IL-6R and residues within 4.0 Å of the 61H7 Fab were mapped and searched for overlap between both epitopes. The overlap between both epitopes is rather small and is mainly formed by the VH paratope. The overlap concentrates around a cavity occupied by both the HCDR3 loop of the 61H7 and the IL-6R molecule. This binding site of IL-6R on IL-6 has been referred to as site I (Boulanger et al., 2003, Science 27, 2101-2104, which is incorporated herein by reference in its entirety). The cavity forming site I is occupied by the hydrophobic side chain of Phe 229 of IL-6R. This amino acid is called the hotspot residue by Boulanger et al, because mutagenesis studies have shown its critical role in the interaction between the receptor and the cytokine. Mutation of this residue to valine or serine completely abolished the IL-6R binding to IL-6 (Kalai et al., 1997, Blood, 1319-1333, which are both incorporated herein by reference in their entirety). Trp98 in the center of the heavy chain CDR3 loop of Fab 61H7 occupies the same cavity, suggesting that it hits thus the critical epitope in IL-6 to block its interaction with IL-6R (shown in FIG. 5). Trp98 is likely a key residue for the ultra high affinity of Fab61H7 for IL-6.

Example 4 Crystal Structures of Fabs 68F2 and 129D3 in Complex with IL-6 i) Generation, Data Collection and Structure Determination of the IL-6:68F2 Crystal 8 mg of 68F2 mAb (4 mg/ml) in Dulbecco's Phosphate buffered saline (d-PBS) pH 7.2 were buffer-exchanged to digestion buffer containing 20 mM cystein-HCl on a Zeba™ Desalt Spin Column (Pierce Fab Preparation Kit Thermo Scientific). Sample was incubated with Immobilized Papain (Pierce Thermo Scientific) and digested for 6 hours at 37° C.

TABLE 10

Hydrogen bonds and salt bridges in the 61H7:IL-6 complex

| | | 61H7 residue structure | Kabat numbering | Distance (Å) | IL-6 residue |
|---|---|---|---|---|---|
| Hydrogen bonds | Light chain-CDR1 | THR 30[OG1] | THR 28 | 3.21 | LYS 27[NZ] |
| | | SER 32[OG] | SER 30 | 2.66 | ASP 26[OD1] |
| | | ASN 33[ND2] | ASN 31 | 2.99 | GLU 23[OE2] |
| | | TYR 34[OH] | TYR 32 | 2.62 | ARG 30[NH1] |
| | | TYR 34[OH] | TYR 32 | 2.55 | ASP 26[OD2] |
| | Light chain-CDR3 | ASP 93[OD2] | ASP 91 | 2.72 | ARG 182[NH1] |
| | | ASP 93[OD2] | ASP 91 | 2.99 | ARG 182[NH2] |
| | | GLY 95[O] | GLY 93 | 3.45 | SER 22[N] |
| | | GLY 95[N] | GLY 93 | 2.91 | GLU 23[OE1] |
| | | GLY 95[O] | GLY 93 | 3.06 | GLU 23[N] |
| | | ASP 96[OD1] | ASP 94 | 3.04 | SER 22[OG] |
| | | ASP 96[OD1] | ASP 94 | 2.94 | SER 22[N] |
| | Heavy chain-CDR1 | THR 28[OG1] | THR 28 | 3.44 | GLN 75[NE2] |
| | | SER 31[OG] | SER 31 | 2.96 | GLN 75[O] |
| | | ARG 33[N] | ARG 33 | 2.73 | GLN 183[OE1] |
| | Heavy chain-CDR2 | ALA 53[N] | ALA 52a | 2.76 | GLN 183[O] |
| | | ALA 53[N] | ALA 52a | 3.66 | GLU 80[OE1] |
| | | GLY 54[N] | GLY 53 | 3.23 | GLU 80[OE1] |
| | | GLY 56[N] | GLY 55 | 2.78 | GLU 80[OE2] |
| | | TYR 59[OH] | TYR 58 | 3.54 | MET 184[O] |
| | Heavy chain-CDR3 | ARG 99[NH1] | ARG 95 | 2.71 | ARG 182[O] |
| | | ALA 100[O] | ALA 96 | 2.94 | GLN 183[NE2] |
| Salt bridges | Light chain-CDR3 | ASP 93[OD2] | ASP 91 | 2.72 | ARG 182[NH1] |
| | | ASP 93[OD2] | ASP 91 | 2.99 | ARG 182[NH2] |

Overlay of the IL-6:61H7 complex and the IL-6:IL-6R complex shows that there is sterical hindrance between the The Fc fragments were separated from the Fab fragments using a CaptureSelect human Fc affinity matrix (BAC BV Unilever) equilibrated in d-PBS. Fab fragments were recovered in the flow-through and Fc fragments were eluted using 0.1M glycine pH 2.0. Protein concentration was determined by UV spectrometry from the absorbance at 280 nm. 4.6 mg (>50%) of purified Fab 68F2 was recovered and concentrated to 1.53 mg/ml on an Amicon-Ultra (cut-off 10 kDa).

2.5 mg of rh IL-6 (Immunotools) was incubated with 2.6 mg of Fab 68F2 in Dulbecco's Phosphate buffered saline (d-PBS) pH 7.2 for 1 hour at 4° C. before being concentrate to 1 ml on a Amicon-Ultra (cut-off 10 kDa). The IL-6:68F2 complex was then separated from excess free IL-6 by gel filtration chromatography on a Superdex75 column in d-PBS and finally concentrated to 8.1 mg/ml on an Amicon-Ultra concentrator (cut-off 10 kDa). Purification of the complex was evaluated on SDS-PAGE.

Size exclusion chromatography was performed on an Alliance 2695 HPLC system (Waters) using a Silica Gel KW803 column (Shodex) eluted with 50 mM Tris-HCl pH 7.5, 150 mM NaCl at a flow rate of 0.5 ml/min. Detection was performed using a triple-angle light scattering detector (Mini-DAWN™ TREOS, Wyatt technology, Santa Barbara, USA). Molecular weight determination was performed by ASTRA V software (Wyatt technology). Initial crystallization screening of the IL-6:68F2 complex was performed with commercial kits Structure screen 1 and 2, Proplex screen and Stura Footprint screen (Molecular Dimensions Ltd). Drops were set-up with a 1:1 (v/v) ratio of protein (8.1 mg/ml) to mother liquor in a total volume of 200 nl on Greiner 96-well plates using a Cartesian MicroSys SQ robot. A diffraction-quality crystal of complex was obtained by sitting-drop vapor diffusion at 277 K after 9 months in 25% PEG 4K, 0.15M $(NH_4)_2SO_4$, 0.1M MES pH 5.5.

Crystals for data collection were transferred to liquor mother with 7.5% ethylene glycol and flash-frozen in liquid nitrogen. Diffraction data were collected under standard cryogenic conditions on beamline ID14-4, using an ADSC Quantum 4 detector at the ESRF synchrotron (Grenoble, France), processed using XDS and scaled with XSCALE. The crystal structure of IL-6 in complex with Fab 68F2 was determined from single-wavelength native diffraction experiments by molecular replacement with Fab 129D3 and the IL-6 structure using MOLREP (table 4). Refinement was performed with BUSTER. The IL-6:129D3 Crystal was similarly produced.

iii) Analysis of the Structure of the IL-6:68F2 and IL-6: 129D3 Complex

The crystal structure of the IL-6:68F2 complex has a resolution of 2.9 Å. The model was refined to an R-factor of 26.7% and an Rfree-factor of 29.6% with reasonable stereochemistry (meaning that more than 95% of the residues adopt allowed conformations). The crystal structure of the IL-6:129D3 complex has a resolution of 2.8 Å. The model was refined to an R-factor of 28.5% and an Rfree-factor of 31.3% with reasonable stereochemistry.

An overlay of the crystallized 68F2 and 129D3 Fabs (r.m.s.d. 1.4 Å), VH domain (r.m.s.d. 0.5 Å) and of the VL domain was made (r.m.s.d. 0.4). These superpositions show that there is no significant difference between the parental 68F2 and germlined 129D3 Fab structures.

Figure 4A:
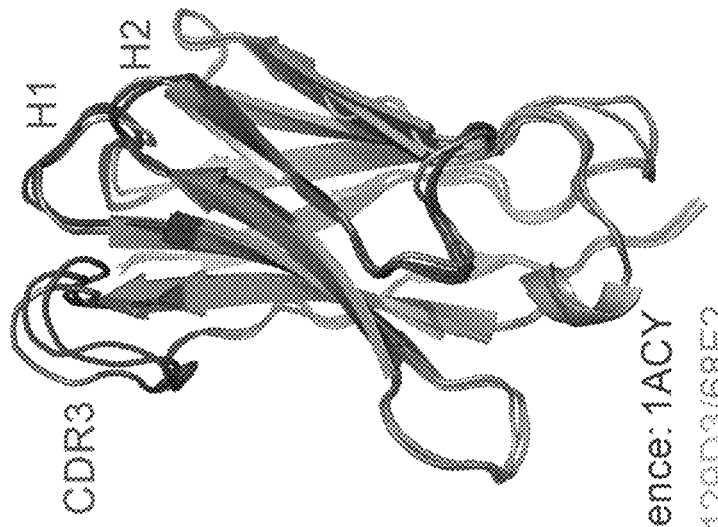
FIG. 4A shows that camelid-derived hypervariable loops L1-L3 of the 68F2 antibody of the invention and its germlined variant (129D3) adopt predicted canonical folds and canonical fold combinations of human antibodies.
Figure 4B:
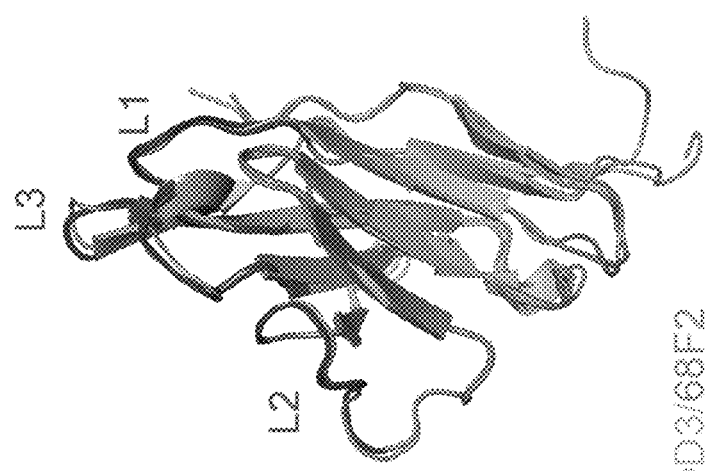
FIG. 4B shows that camelid-derived hypervariable loops H1 and H2 of the 68F2 antibody of the invention and its germlined variant (129D3) adopt predicted canonical folds and canonical fold combinations of human antibodies.

The canonical structures predicted for the CDR loops of the 68F2 mAb and its germlined variant 129D3 are 3 and 1 for H1 and H2, respectively, and 6λ, 1 and 5 for L1, L2 and L3, respectively. The canonical folds of the heavy chain were predicted by the server at www.bioinf.org.uk/abs/chothia.html, the canonical folds of the light chain were manually determined. The reference Fab (PG16) for comparison of the light chain canonical folds, was found manually by searching the Antibody Structure Summary Page (www.bioinforg.uk/abs/sacs/antibody_structure_summary_page.html). The overlay of the 68F2 and 129D3 VL with the VL of PG16 (Protein Data Bank (PDB) entry 3MUG) demonstrates that all three CDR's adopt the predicted conformations (see FIG. 4A). The overlay of the 68F2/129D3 VH with the reference PDB entry 1ACY shows that H1 and H2 adopt the predicted canonical folds (see FIG. 4B). Accordingly, structural analysis confirms that the VL (a VL2 family member) of 68F2/129D3 belongs to the human 6λ-1-5 combination of canonical L1-L3 structures, while the VH (a VH4 family member) of 68F2/129D3 belongs to the 3-1 combination of human canonical H1-H2 structures.

The crystallographic asymmetric unit contains a single 1:1 complex. The global architecture of the IL-6:68F2 complex shows that the VH (50%) and the VL (50%) contribute equally to the large interaction surface (1156 $Å^2$). The interaction surface is slightly bigger than the interaction surface of the 61H7 with IL-6 (940 $Å^2$). Analogous to the 61H7:IL-6 complex, only the L2 loop is not directly involved in the interaction with IL-6.

The interface between the heavy and light chain corresponds to 1764.7 $Å^2$ for the 68F2 and 1768.5 $Å^2$ for the 129D3 structure. This interface area was comparable to the areas measured for the 61H7 (1580.6 $Å^2$) and the 27B3 (1700.3 $Å^2$) antibodies. All interface areas were calculated with EMBL web service program PISA.

From the crystal structure the residues important for the interaction with IL-6 were determined. The hydrogen bonds and salt bridges formed between the 68F2 Fab and the cytokine are listed in Table 11. The interactions are limited to the CDR1 and CDR3 of the light chain and the CDR1, CDR2 and CDR3 of the heavy chain.

The VL shuffling of the 20A4 clone resulted in the 68F2 clone which has a 10× better affinity than the parental 20A4. Both antibodies differ mainly in their L1 and L2 CDRs. The light chain CDR2 loop does not contribute to the binding of IL-6, thus, the improvement in affinity is to be attributed to mutations in the L1 loop. Two out of the three residues that make important interactions with IL-6 are not conserved in the 20A4 clone: Asn26 that makes a hydrogen bond with Ser76 of IL-6 is a Ser in 20A4; and Thr31 that makes two hydrogen bonds with IL-6 is a Gly in the 20A4 parental L1. The addition of three new hydrogen bonds when changing these two residues likely explains some gain in affinity observed after the VL shuffling. Most importantly, the changes in L1 probably stabilize and/or position Y30 (Kabat numbering) properly in the F229 cavity allowing for extra high potency.

TABLE 11

Hydrogen bonds and salt bridges in the 68F2:IL-6 complex.

|  |  | 68F2 residue structure | Kabat numbering | Distance (Å) | IL-6 residue |
|---|---|---|---|---|---|
| Hydrogen bonds | Light chain-CDR1 | ASN 26[O] | ASN 27 | 3.60 | SER 76[OG] |
|  |  | TYR 32[OH] | TYR 30 | 3.43 | SER 176[O] |
|  |  | THR 31[N] | THR 29 | 3.55 | SER 76[OG] |
|  |  | THR 31[O] | THR 29 | 3.42 | GLN 75[N] |
|  | Light chain-CDR3 | ASN 95[ND2] | ASN 93 | 3.77 | MET 67[O] |
|  |  | ASN 97[OD1] | ASN 95 | 3.73 | ARG 179[NH2] |
|  | Heavy chain-CDR1 | TYR 33[OH] | TYR 33 | 3.47 | ARG 30[O] |
|  |  | TYR 33[OH] | TYR 33 | 2.16 | ASP 34[OD1] |
|  |  | ARG 32[NE] | ARG 32 | 3.20 | ASP 34[OD2] |
|  |  | ARG 32[NH2] | ARG 32 | 3.28 | ASP 34[OD2] |
|  | Heavy chain-CDR2 | TYR 60[OH] | TYR 58 | 2.59 | GLU 172[OE2] |
|  |  | ASP 54[OD2] | ASP 52 | 3.37 | LYS 171[NZ] |
|  |  | ASP 56[OD1] | ASP 54 | 2.90 | SER 37[OG] |
|  |  | ASP 58[OD1] | ASP 56 | 3.86 | HIS 164[NE2] |
|  |  | ASP 58[OD2] | ASP 56 | 3.42 | LYS 171[NZ] |
|  |  | THR 59[O] | THR 57 | 2.52 | ARG 168[NH2] |
|  |  | TYR 60[OH] | TYR 58 | 3.69 | ARG 168[NE] |
|  |  | TYR 60[OH] | TYR 58 | 3.15 | LYS 171[NZ] |
|  | Heavy chain-CDR3 | ASP 102[OD2] | ASP 97 | 2.77 | ARG 30[NH2] |
|  |  | VAL 104[O] | VAL 99 | 3.69 | ARG 179[NH1] |
| Salt bridges | Heavy chain-CDR1 | ARG 32[NE] | ARG 30 | 3.20 | ASP 34[OD2] |
|  |  | ARG 32[NH2] | ARG 30 | 3.28 | ASP 34[OD2] |
|  | Heavy chain-CDR2 | ASP 54[OD2] | ASP 52 | 3.37 | LYS 171[NZ] |
|  |  | ASP 58[OD1] | ASP 56 | 3.86 | HIS 164[NE2] |
|  |  | ASP 58[OD2] | ASP 56 | 3.42 | LYS 171[NZ] |
|  | Heavy chain-CDR3 | ASP 102[OD1] | ASP 97 | 3.40 | ARG 30[NH2] |
|  |  | ASP 102[OD2] | ASP 97 | 2.77 | ARG 30[NH2] |

Overlay of the IL-6:68F2 complex and the IL-6:IL-6R complex shows that there is steric hindrance between the 68F2 Fab and the IL-6R, as was observed for the 61H7:IL-6 complex. However, in contrast to the 61H7:IL-6 complex, it is mainly the VH of 68F2 that gives a sterical clash with the IL-6R in the 68F2:IL-6 complex. 68F2 Fab interacts with IL-6 exactly at the same site as IL-6R. Furthermore, 68F2 does not overlap with the gp130 binding sites and therefore competes specifically and only with the IL-6R.

Figure 5:
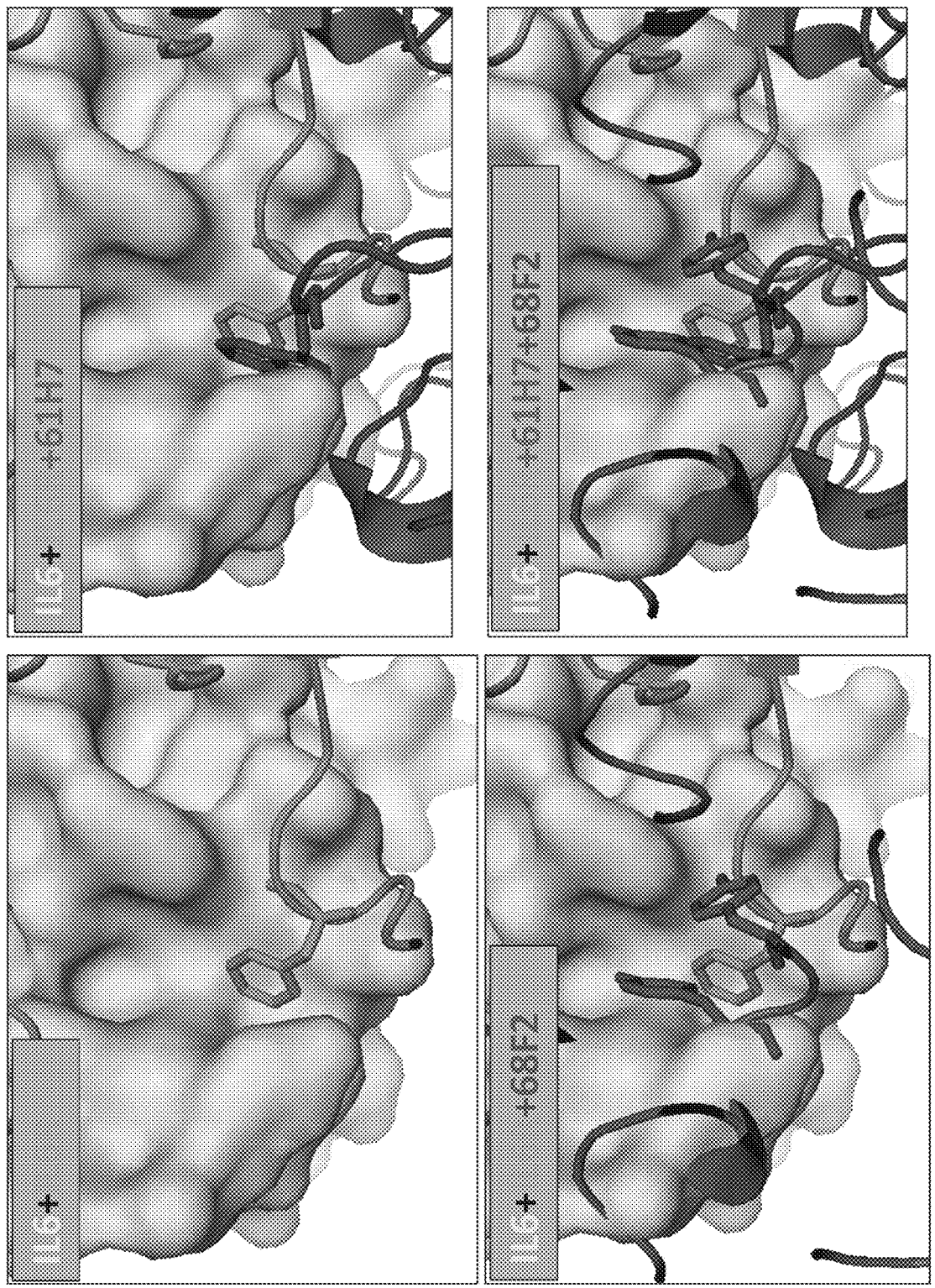
FIG. 5 depicts a space-fill model of IL-6 overlaid with: (top left) F229 of the IL-6 receptor; (top right) F229 of the IL-6 receptor and W98 of the 61H7 VH, (bottom left) F229 of the IL-6 receptor and Y30 of the 68F2 VL; and (bottom right) F229 of the IL-6 receptor, W98 of the 61H7 VH and V99 of the 68F2 VH, according to Kabat numbering.

Overlay of the IL-6:IL-6R and the IL-6:68F2 complexes suggests that the epitopes of IL-6R and 68F2 will be very close to each other. The residues belonging to both epitopes were mapped on IL-6 and the overlap determined. The overlap of the 68F2 epitope with the IL-6R is almost complete. The binding site of IL-6R on IL-6 has been called site I (Boulanger et al., 2003, Science 27, 2101-2104). The cavity forming site I is occupied by the hydrophobic side chain of Phe 229 of IL-6R. This amino acid is called the hotspot residue by Boulanger et al, since mutagenesis studies have shown its critical role in the interaction between the receptor and the cytokine. Mutation of this residue to valine or serine completely abolished the IL-6R binding to IL-6 (Kalai et al., 1997, Blood, 1319-1333). Inspection of the cavity described as site I in the IL-6:68F2 structure reveals that is occupied by the CDR1 loop of the light chain of Fab 68F2. In particular, Tyr32 (position 30 in Kabat numbering) in the CDR1 of the light chain plays a crucial role in binding this site (FIG. 5).

Figure 6:
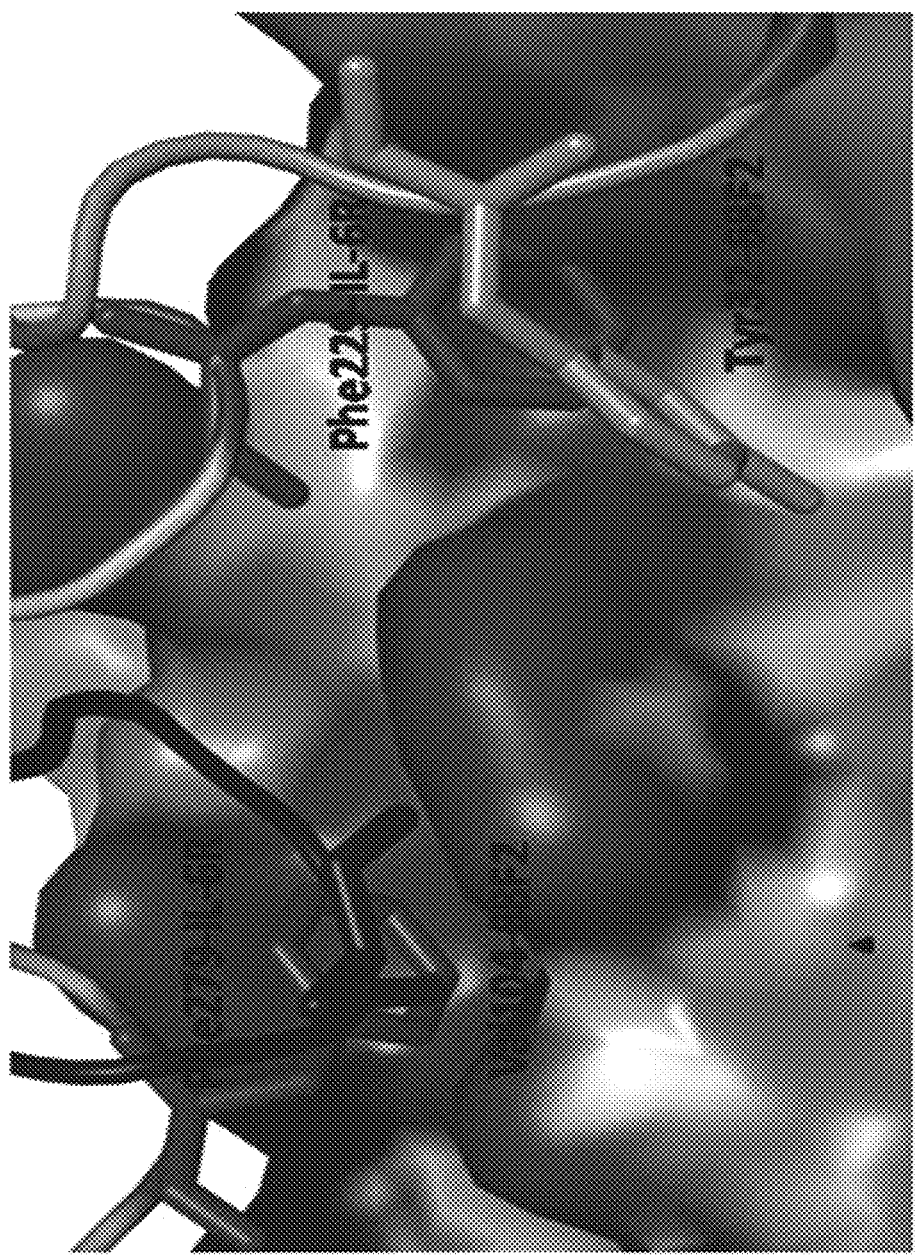
FIG. 6 depicts a space-fill model of the two surface binding cavities on IL-6 important for IL-6 receptor binding overlaid with residues F229 and F279 of the IL-6 receptor, and residues Y30 of the 68F2 VL and V99 of the 68F2 VH, according to Kabat numbering (Y32 and V104 in the structure).

Another key residue in the interaction between IL-6 and IL-6R is Phe279 of IL-6R. This residue represents 20% (129 Å$^2$) of the total binding interface (compared to 28% (174 Å$^2$) for Phe 229) making it the second most important interaction. Like Phe229, Phe279 also binds in a cavity formed on the surface of IL-6. This cavity is also occupied by a 68F2 residue, more particularly by Val104 (position 99 in Kabat numbering) of the CDR3 loop of the heavy chain (FIG. 6).

IL-6 was previously crystallized and classified as a four helix bundle linked by loops and an additional mini-helix (Somers et al., 1997, EMBO Journal 16, 989-997). The crystal structure of IL-6 in complex with its receptor and the signalling receptor gp130 has also been solved (Boulanger et al., 2003, Science 27, 2101-2104). IL-6 forms a non-signalling complex with IL-6R through site I. Site II is a composite epitope formed by the binary complex of IL-6 and IL-6R. Interaction of site III with gp130 forms the signalling complex.

Comparison of the structure of the IL-6:61H7 complex with the IL-6:68F2 structure shows that although both mAbs compete with IL-6R for binding to site I of IL-6, the two antibodies bind IL-6 at two different epitopes. 68F2 binds on the side of the barrel shaped IL-6 and exclusively competes for IL-6R binding, while 61H7 interacts more at the base of the barrel shaped IL-6, competing with both IL-6R and gp130. Interestingly, the unique overlapping epitope on IL-6 is the cavity that is filled by the hot spot residue Phe229 of IL-6R (FIG. 5). This suggests that binding to this cavity is key to the high potency observed for 68F2 and 61H7.

Example 5 Structure Function Analysis of W98 in HCDR3 of 61H7

A striking feature of the extremely highly potent antibodies disclosed herein is their capacity to occupy the cavity on IL-6 where F229 of the IL-6R binds (herein referred to as the F229 cavity). For 61H7 (and its germlined variants e.g., 111A7), the F229 cavity is occupied by the tryptophan 98 residue (W98) of the HCDR3. To assess the functional importance of W98 to 61H7 binding to IL-6, mutants of 111A7 were generated in which VH position 98 was mutated towards all the possible amino acids in the background of M100A or M100L. The binding kinetics of periplasmic fractions of bacteria containing the mutant Fabs were tested using surface Plasmon resonance (Biacore) and the off-rate for each mutant was determined. The results of the mutational analysis are set forth in Table 12. The data clearly show that the tryptophan (W) at position 98 is the best possible amino acid to achieve the best off-rate. Mutation of W98 was always detrimental to the binding of 111A7 to IL-6.

TABLE 12

Off-rate of 61H7 Fabs with VH mutations at Positions 98 and 100

| M100A/L | W98X | EUK_IL-6 (3-1) | | BACT_IL-6 (2-1) | | |
|---|---|---|---|---|---|---|
| | | Off rate (s−1) | Binding (RU) | Off rate (s−1) | Binding (RU) | |
| M | WGM | 4.67E−05 | 353 | 5.00E−05 | 127 | n = 3 |
| L | WGL | 5.50E−05 | 130 | 3.60E−05 | 51 | n = 1 |
| L | FGL | 2.20E−04 | 120 | 2.40E−04 | 40 | n = 1 |
| L | YGL | 3.10E−04 | 54 | 3.50E−04 | 18 | n = 1 |
| L | QGL | 4.20E−04 | 110 | 5.50E−04 | 36 | n = 1 |
| L | MGL | 5.90E−04 | 100 | 8.10E−04 | 31 | n = 1 |
| L | VGL | 7.17E−04 | 87 | 9.90E−04 | 25 | n = 3 |
| L | CGL | 7.70E−04 | 14 | 5.45E−04 | 2 | n = 2 |
| L | SGL | 7.77E−04 | 68 | 1.07E−03 | 20 | n = 5 |
| L | LGL | 8.35E−04 | 58 | 1.08E−03 | 16 | n = 6 |
| L | GGL | 9.46E−04 | 74 | 1.30E−03 | 21 | n = 7 |
| L | *GL | 9.53E−04 | 19 | 1.13E−03 | 4 | n = 3 |
| L | RGL | 1.00E−03 | 72 | 1.35E−03 | 19 | n = 2 |
| L | PGL | 1.10E−03 | 33 | 1.40E−03 | 10 | n = 2 |
| A | WGA | 8.30E−05 | 97 | 3.40E−05 | 33 | n = 1 |
| A | FGA | 9.20E−05 | 120 | 6.10E−05 | 32 | n = 1 |
| A | HGA | 2.83E−04 | 43 | 1.34E−04 | 8 | n = 3 |
| A | YGA | 3.75E−04 | 59 | 3.80E−04 | 15 | n = 2 |
| A | MGA | 7.35E−04 | 60 | 9.75E−04 | 15 | n = 2 |
| A | EGA | 7.45E−04 | 81 | 1.10E−03 | 18 | n = 2 |
| A | NGA | 9.50E−04 | 75 | 1.10E−03 | 16 | n = 1 |
| A | IGA | 9.63E−04 | 66 | 1.40E−03 | 15 | n = 3 |
| A | CGA | 9.95E−04 | 39 | 1.25E−03 | 6 | n = 2 |
| A | LGA | 1.05E−03 | 49 | 1.13E−03 | 11 | n = 5 |
| A | *GA | 1.05E−03 | 25 | 1.25E−03 | 4 | n = 2 |
| A | VGA | 1.23E−03 | 70 | 1.68E−03 | 14 | n = 4 |
| A | RGA | 1.25E−03 | 47 | 1.53E−03 | 9 | n = 5 |
| A | KGA | 1.45E−03 | 48 | 1.95E−03 | 9 | n = 2 |
| A | TGA | 1.55E−03 | 53 | 1.65E−03 | 10 | n = 2 |
| A | GGA | 1.77E−03 | 69 | 2.28E−03 | 13 | n = 6 |
| A | AGA | 1.85E−03 | 80 | 2.50E−03 | 15 | n = 2 |

Example 6 Germlining of the VH and VL of Fab Clones 61H7 and 68F2

The VH and VL sequences of clones 68F2 and 61H7 were aligned against human germline VH and VL sequences to identify the closest related germline sequences. The germlining process was performed as described in WO 2010/001251 and by Baca et al. (J. Biol. Chem. (1997) 272: 10678-10684) and Tsurushita et al. (J. Immunol. Methods (2004) 295: 9-19). A library/phage display approach was used, in which the deviating FR residues for both the human and the llama residues were incorporated.

The camelid derived IL-6 antibodies of the invention were remarkably human-like in sequence and structure. As a result, only a minimal number of sequence alterations (via germlining) were incorporated into final germlined variants. For example, of the 87 (VH) and 79 (VL) amino acids in VH and VL framework regions of the parental 68F2 antibody, only 6 (VH) and 7 (VL) amino acid changes were introduced (a total of 13 amino acid changes), resulting in a final germlined lead (129D3) with 93.1% and 91.1% identities in their respective VH and VL frameworks (see alignment of FIG. 10A). Similarly, of the 87 (VH) and 79 (VL) amino acids in the VH and VL framework regions of the parental 61H7 antibody, only 8 (VH) and 5 (VL) amino acid changes were introduced (a total of 13 amino acid changes), resulting in a final germlined lead (111A7) with 90.8 and 93.7% identities in their respective VH and VL frameworks (see alignment of FIG. 10B).

By contrast, art-recognized IL-6 antibodies require an extensive amount of engineering (CDR-grafting) and sequence alterations (backmutations) to generate variant suitable for therapeutic use. For example, the reference mouse IL-6 antibody CNTO-328 required 14 (VH) and 22 (VL) amino acid alterations (a total of 36) to generate the humanized variant CNTO136 with only 84% and 72.5% homology in its VH and VL frameworks (for alignment, see FIG. 11A). Another reference rabbit IL-6 antibody, ALD518, required a total of 46 framework changes (26 in VH and 20 in VL) to generate a final humanized variants with only 70.5% and 74% sequence homology to the parental antibody. Therefore, the IL-6 antibodies clearly require only minimal engineering and result in molecules which are much more human in sequence.

Furthermore, the small number of FR residues to be changed makes it possible to incorporate changes in CDR residues into the germlining process. Such CDR mutations can be used to remove amino acid introducing production variability (glycosylation site, oxidation, isomerisation, etc) or to change CDR residues toward amino acids found in different variant of the antibody to germline.

Phage display, applying stringent selection conditions, was used to select for additional functional Fabs. Individual clones were screened for off-rate and the best hits were sequenced to determine the human sequence identity. The VH and VL amino acid sequences of exemplary germlined IL-6-specific Fabs are set forth in Tables 15 and 16 below.

CDR region sequences from all identified VH and VL domains that are variant Fabs of 129D3 and 111A7 were compared and CDR amino acid consensus sequences determined. CDR variants of 129D3 and 111A7 and derived CDR consensus sequences are set forth in Tables 17 and 18 below.

Example 7 In Vitro Potency Assay

The in vitro efficacy of clones 129D3, 68F2, 61H7, 133A9, 133H2, 133E5 and 132E7 were determined using a cell-based neutralizing bioassay using the B9 cell line, essentially as described in Helle et al. 1988, Eur. J. Immunol 18; 1535-1540. B9 cells are derived from the murine B cell hybridoma cell line B13.29, which require IL-6 for survival and proliferation and respond to very low concentrations of human IL-6. The assay was performed using 10 pg/ml (or 0.5 pM) human IL-6 and a concentration series of purified 129D3, B-E8, CAT6001, CNTO136, 61H7, UCB124.g1. B9 cells were seeded in IL-6-free medium at 5000 cells/200 microl in flat-bottom wells in the presence of IL-6, with and without antibodies. Proliferation was measured by a [3H] thymidine pulse at 64-72 h. The results (shown in FIG. 1 and Table 23) demonstrate that all clones have high potency, with 129D3 having an IC50 in this assay of less than 0.1 pM. Interestingly, as shown in FIG. 1, the IC50 of clone 129D3 was superior to the benchmark CNTO136, CAT6001, UCB124, and B-E8 antibodies.

The in vitro efficacy of clones 133E5, 133A9, 133H2, 111B1, 104C1, 129D3, 68F2, 61H7, were also determined using a cell-based neutralizing bioassay using the 7TD1 cell line, essentially as described in Van Snick et al. PNAS; 83, :9679 (1986), which is hereby incorporated by reference in its entirety. 7TD1 cells are a murine hybridoma cell line formed by fusion of the mouse myeloma cell line Sp2/0-Ag14 with spleen cells from a C57BL/6 mouse immunized with *Escherichia coli* lipopolysaccharides three days before fusion. The 7TD1 cell line is dependent on IL-6 for its growth and IL-6 withdrawal leads to cell death by apoptosis. The assay was performed using 75 pg/ml human IL-6 and a concentration series of purified 133E5, 133A9, 133H2, 111B1, 104C1, 129D3, 68F2, 61H7, B-E8, GL18LB, CNTO136 and huIU.

Briefly, 7TD1 cells (7.10E3) were incubated for 2-4 h in RPMI1640 medium+10% FCS before addition of IL-6 (75 pg/ml final concentration) in microtiter plates (200 ul final volume). The cells were incubated 3 days at 37 C, before washing with PBS and addition of 60 ul of substrate solution (p-nitrophenyl-N-acetyl-β-D-glucosaminide (Sigma N-9376); 7.5 mM substrate in 0.05 M NaCitrate pH 5; 0.25 vol % triton X-100) for 4 h. The enzymatic reaction was stopped with 90 ul of stop solution (100 mM glycine+10 mM EDTA pH 10.4) and OD at 405 nm measured. The results (shown in Table 24) demonstrate that all clones have high potency in this assay, with IC50s of less than 1 pM.

Example 8 Epithelial Ovarian Cancer Mouse Xenograft Assay

Figure 2:
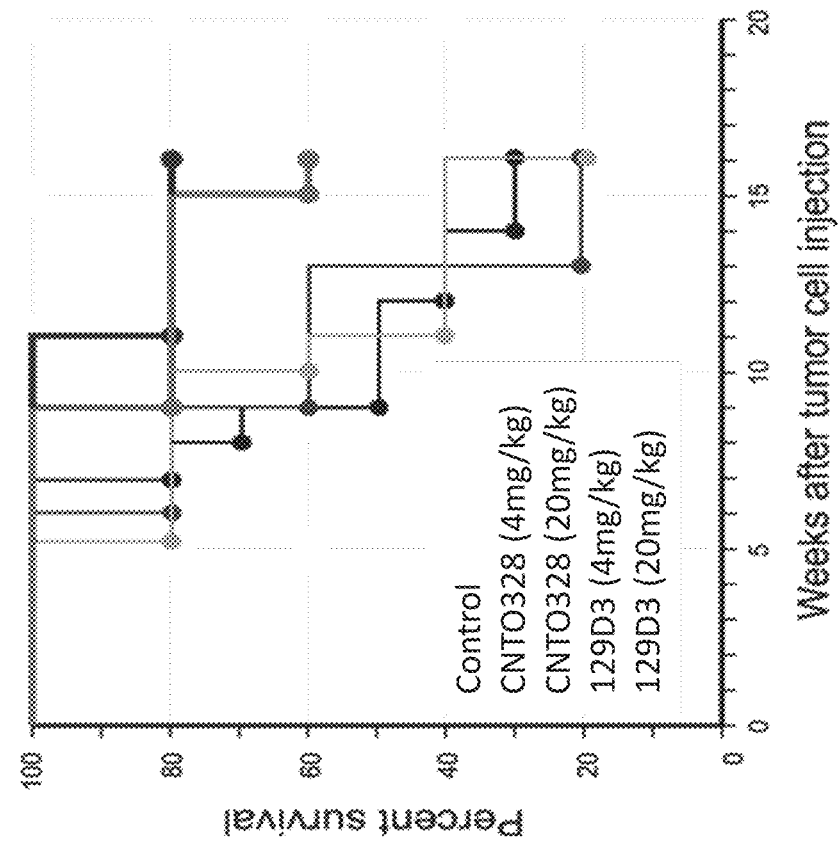
FIG. 2 depicts the results of epithelial ovarian cancer mouse tumor xenograft experiments measuring the in vivo efficacy of antibodies of the invention.

The in vivo potency of clone 129D3 was determined using a mouse xenogaft model. IGROV-1 epithelial cells ($5 \times 10^6$) were injected subcutaneously into nude mice. After three days, mice were administered 129D3 or CNT0328 biweekly, at a dosage of 4 or 20 mg/kg. There were 5 mice per group and 10 mice in the control group. Percentage survival of mice in each study group was determined each week and the results plotted as a survival curve. The results (shown in FIG. 2) demonstrate that 129D3 exhibits an in vivo potency that is superior to the benchmark CNT0328 IL-6 antibody.

Example 9. Immunogenicity Analysis

VH and VL regions of the IL-6 antibodies of the invention were scored for the presence of potential immunogenic sequences (e.g., putative HLA class II restricted epitopes, also known as TH-epitopes) and compared with immunogenicity scores for a variety of commercially-available reference antibodies using the Epibase® profiling method.

Profiling was done at the allotype level for 18 DRB1, 6 DRB3/4/5, 13 DQ and 5 DP, i.e. 42 HLA class II receptors in total. Strong and medium binders of DRB1, DRB3/4/5 were identified, as well as the strong binders of DQ and DP epitopes. Epitope counting was done separately for strong and medium affinity DRB1 binders. Peptides binding to multiple allotypes of the same group were counted as one. An approximate score expressing a worst-case immunogenic risk was calculated as follows: Score=Σ(epitope count×allotype frequency).

In other words, the number of epitopes affecting a particular HLA allotype is multiplied by the allele frequency of the affected allotype. For a given sequence, the products were summed for all DRB1 allotypes used in the study that are present in 2% or more of the Caucasian population.

DRB1 scores for the IL-6 antibodies of the invention and representative reference antibodies are provided in FIG. 9. Total DRB1 scores were a composite of the VH and VL scores for each antibody and low scores indicate low immunogenicity for the antibody. Accordingly, FIG. 9 demonstrates that IL-6 antibodies of the invention are equal to or less immunogenic than benchmark IL-6 antibodies as well as other commercially-available antibodies (e.g., Humira and Remicade).

Example 10. Manufacturability

The VH and VL of the germlined versions of 68F2 were recloned in pUPE Heavy Chain and Light Chain expression vectors, respectively, for transient expression of full-length IgG1 antibodies. After transient expression in HEK293E cells, IgG1 antibodies were purified with protein A and quantified by measurement of OD280. Table 19 below summarizes the production levels of the germlined derivatives together with the levels of the 68F2 parental antibody. Potencies (in pM) were also measured in a 7TD1 based proliferation assay for each antibody.

The variants 126A3, 127F1, 129D3 and 129F1, all selected from the germlined libraries under stringent conditions, were found to have similar potencies as the wild type 68F2 (i.e. between 0.5 and 0.7 pM). Moreover, all germlined variants expressed very well, i.e. between 24 and 28 µg/ml. The exception was germlined variant 129F2 that gave a production yield of 9 µg/ml.

Example 11. Stability Analysis

To examine the thermal stability of the germlined and the parental versions of 68F2 in full length human IgG1 format, antibody samples were incubated at a concentration of 100 µg/ml (in PBS) at 4, 50, 55, 60, 65, 70 and 75° C. for 1 hour. Following this, the samples were cooled down slowly during a period of 15 minutes to 25° C. and kept at this temperature for 2 hours, after which they were stored overnight at 4° C. Following centrifugation to remove precipitates (of denatured antibody), the concentration of functional antibody remaining in solution was measured using Biacore (1/10 dilution in PBS and 1/10 in HBSEP). The slope of the association curve obtained after injection on the IL-6 immobilized chip is a measure of the concentration of functional antibody.

As shown in FIG. 7A, the melting curves and the melting temperatures of wild type 68F2 and its germlined derivatives were clearly unaffected by germlining. Quite unexpectedly, the melting temperatures even seemed to be improved. For example, 129D3 has a Tm of around 70° C., which is 3° C. higher than the parental 68F2 antibody. The melting curves of the germline variant 129D3 and the parental 68F2 together were also compared with the reference antibodies GL18 and CNTO136 (see FIG. 7B). The favorable thermal stability of the SIMPLE antibody 68F2 and especially of its germlined variant 129D3 (Tm of 70° C.) was striking when compared to Tm of 65° C. for CNTO136 and the Tm of 61° C. for the GL18 antibody. Surprisingly, the extensive antibody engineering (e.g., humanization) and in vitro affinity maturation applied to both reference antibodies strongly affected their stability, whereas the in vivo generated SIMPLE antibody and the minimal engineering by germlining resulted in extremely good thermal stabilities.

Figure 8:
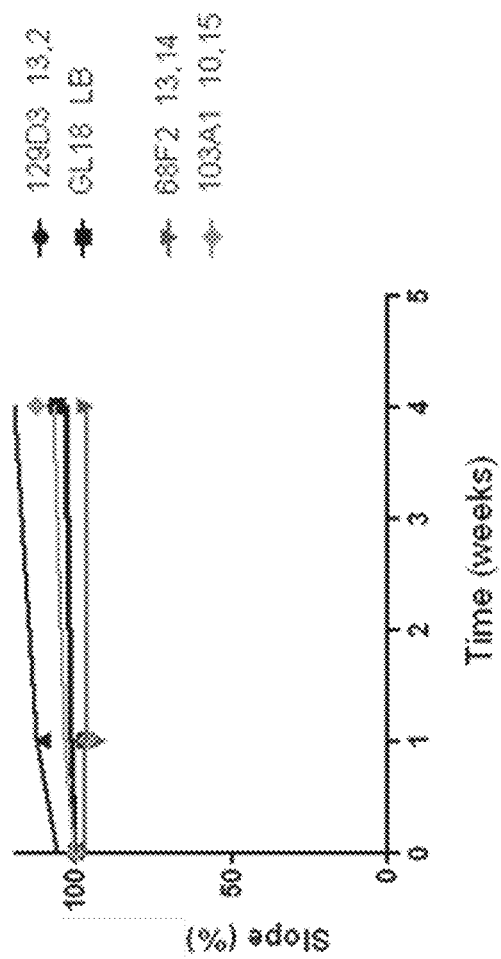
FIG. 8 depicts the serum stability of antibody clones 68F2, 129D3 (a germlined variant of 68F2), and 103A1 (a variant of 61H7). Also included is the reference antibody GL 18.

The serum stability of the full length human IgG1 versions of 68F2 and its germline variant (129D3) (and the germlined variant 103A1 derived from SIMPLE™ antibody lead 61H7) were compared to those of the reference antibodies. Following incubation at 37° C. in human serum. functional concentration of antibody was measured at weeks 1, 2, 4, 8, 12, 16, 24, 32 and 56 and compared to a pre-aliquoted standard. As depicted in FIG. 8, the serum stability for the antibodies of the invention compared favourably to that reference antibodies.

Example 12. CMC Optimization

Several residues or motifs are not recommended for CMC-quality manufacturing of antibodies. Among them is the presence of Methionine in the CDR loops of the antibody. Methionine can be oxidized leading to chemically-altered variant of the antibody with altered properties such as affinity, potency, and stability. Accordingly, the methionine present in CDR3 of 111A7 (and its germlined variant of 61H7) was mutated to Alanine (111A7MA), leucine (111A7ML) or Serine (111A7MS). The resultant CMC-optimized sequences are provided in Table 20 below. As shown in Table 21, the mutation of the methionine residue has a negligible effect on the binding to IL-6.

Example 13. Pharmacokinetic (PK) Study in Cynomolgus Monkeys of Clone 129D3 and Fc Mutants Thereof Pharmacokinetic analysis of antibody clone 129D3 formatted as various IgG1 molecules was performed. The following antibodies were analysed: Wild-type IgG1 129D3 (129D3-WT), IgG1 129D3 with the mutations M252Y/S254T/T256E in the Fc region (129D3-YTE), and IgG1 129D3 with the mutations H433K and N434F in the Fc region (129D3-HN).

Cynomolgus monkeys (3 per antibody tested) were injected intravenously with a single 5 mg/kg dose of 129D3-WT, 129D3-YTE, or 129D3-HN. Samples were taken at different time points and tested for plasma concentration of mAb by the ELISA. Specifically, a microtiterplate (Maxisorb Nunc) was coated with 1 ug/ml IL-6 (Immunotools) in PBS overnight at 4 C. The plate was washed 2 times with PBS-Tween and blocked for 2 hours with 300 µl PBS-1% casein. After 2 washes with PBS-Tween, the samples were applied. All dilutions were made in 1% pooled blank plasma (this is a pool from 3 naive cynomolgus monkeys, see chapter 4.2). The samples were allowed to bind for 2 hours at RT. Plates were then washed 5 times with PBS-Tween and goat biotinilated anti-human IgG heavy and light chain monkey adsorbed polyclonal antibodies were applied at a 1000-fold dilution (Bethyl, catno: A80-319B) and allowed to bind for 1 hour at RT. After washing the plates 5 times with PBS-Tween, streptavidin conjugated with HRP (Jackson Immunoresearch 016-030-084) was applied at a 300,000-fold dilution and allowed to bind for 1 hour at RT. Plates were then washed 5 times with PBS-Tween and a 1:1 mixture of TMB (calbiochem CL07)-s(HS)TMB weakener (SDT, #sTMB-W) was added. The staining was allowed to proceed for 10 minutes and then stopped with 0.5 M H2SO4, after which the Optical Density was measured at 450 nm. The samples were analysed four times and 129D3-WT (from the same batch that was injected into the animals) was used for a standard curve.

The relevant PK parameters for the non-compartmental analysis are shown in Table 22 below. The pharmacokinetic profiles for the different 129D3 IgG1 antibodies are shown graphically in FIG. 12 (the results are shown are the average result of the group of monkeys). This data clearly shows that 129D3-YTE and 129D3-HN have a longer mean residency time (MRT) than the parental 129D3-WT antibody. Moreover, 129D3-YTE and 129D3-HN have a slower elimination rate and thus a substantially prolonged half-life as compared to 129D3-WT.

Interestingly, although both antibodies contain a wild-type IgG1 Fc region, the half-life of 129D3-WT is significantly longer than the half-life of the MedImmune anti-IL-6 IgG1 antibody (GL18) described in US201200344212. Specifically, 129D3-WT has a half-life of about 15.6 days as compared to about 8.5 days for antibody GL18. Thus, the extended half-life of the antibodies of the invention appears to be due to the properties of their respective Fab regions.

Example 14. Serum Amyloid A (SAA) Mouse Model

The in vivo efficacy of clones 68F2 and 61H7 was further investigated by measuring the ability of these antibodies to block serum amyloid A (SAA) induction in response to injected IL-6. General methods for performing this assay are set forth in WO2006/119115A2, which is hereby incorporated by reference in its entirety. Specifically, Balb/c mice were injected intravenously with 68F2, 61H7, the benchmark antibodies GL18, or CNTO136, or salt solution (control). Four hours after administration of the antibody, the mice were injected with 0.1 ug of IL-6. After a further 16 hours, blood was taken from the mice and the concentration of Serum Amyloid A was determined by ELISA. The experimental groups, dosages and results are set forth in Table 26, herein. The dose responses are also graphically depicted in FIG. 13. The results show that antibody clones 68F2 and 61H7 have in vivo efficacy at least equal to the high potency benchmark controls GL18 and CNTO136.

Example 15. Humanized Mouse Psoriasis Xenograft Model

A mouse xenograft model was employed to evaluate the prophylactic efficacy of clone 68F2 on the development of induced psoriatic lesions. Specifically, BNX mice were transplanted with 5 mm diameter full-thickness skin biopsies from non-involved skin from psoriasis patients (1 per mouse). After 3 weeks, the transplants were injected with $0.5 \times 10^6$ activated PBMCs. Treatment of mice with clone 68F2, anti-TNF antibody (Remicade), or betamethasone dipropionate (positive control) was begun 1 day before the activated cells were injected into the transplants. Details of the treatment groups and regimes are shown in Table 25.

Treatment efficacy was determined by epidermal ridge thickness, as measured by light microscopy. Significance between groups was analyzed statistically using analysis of variance (ANOVA) followed by post-hoc Least Square Difference (LSD) tests to establish statistical significance differences between treatment groups. A value of p<0.05 denoted a significant difference between groups.

Figure 12:
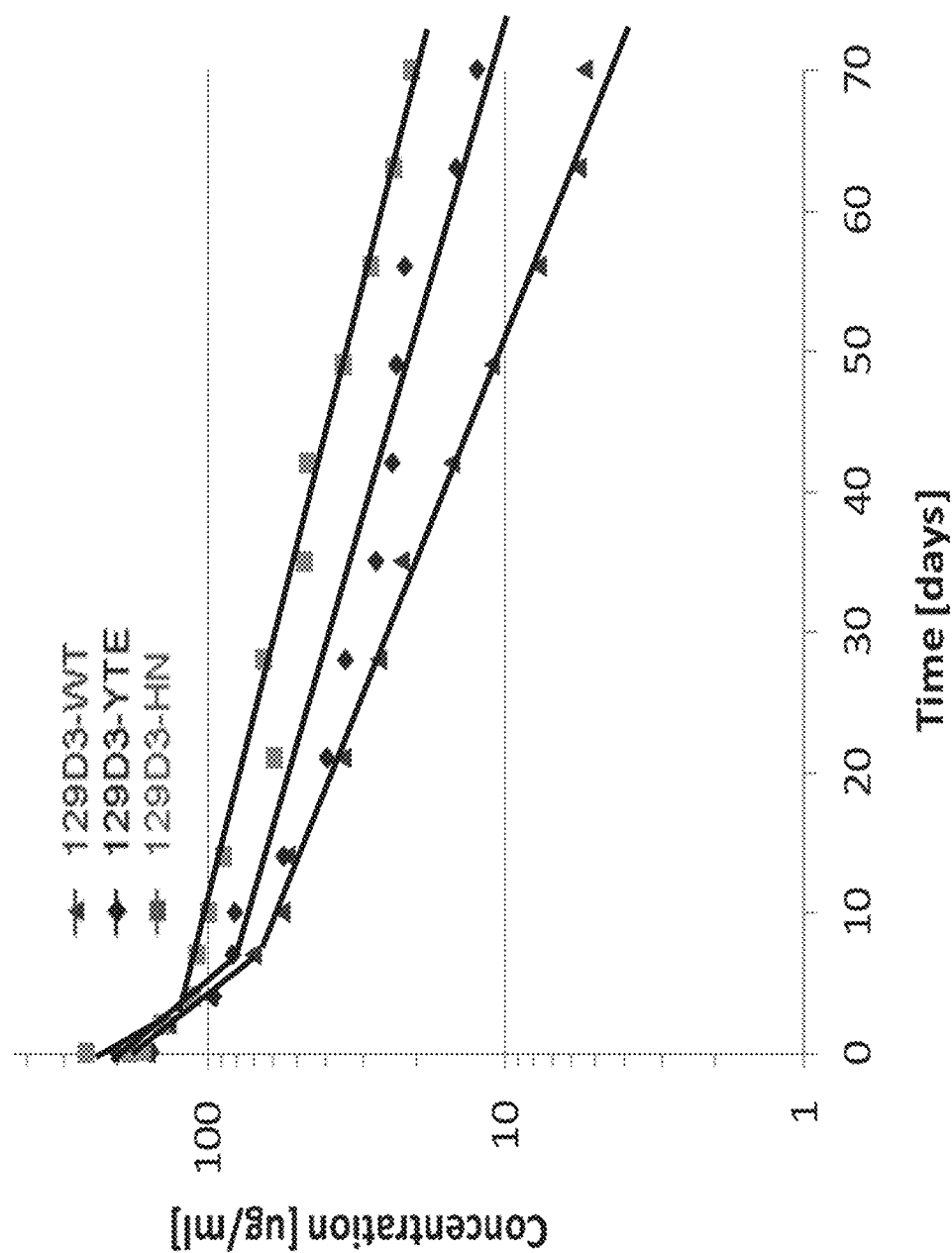
FIG. 12 depicts the pharmacokinetic profiles of 129D3 IgG1 antibodies and variants thereof in cynomolgus monkeys.
Figure 13:
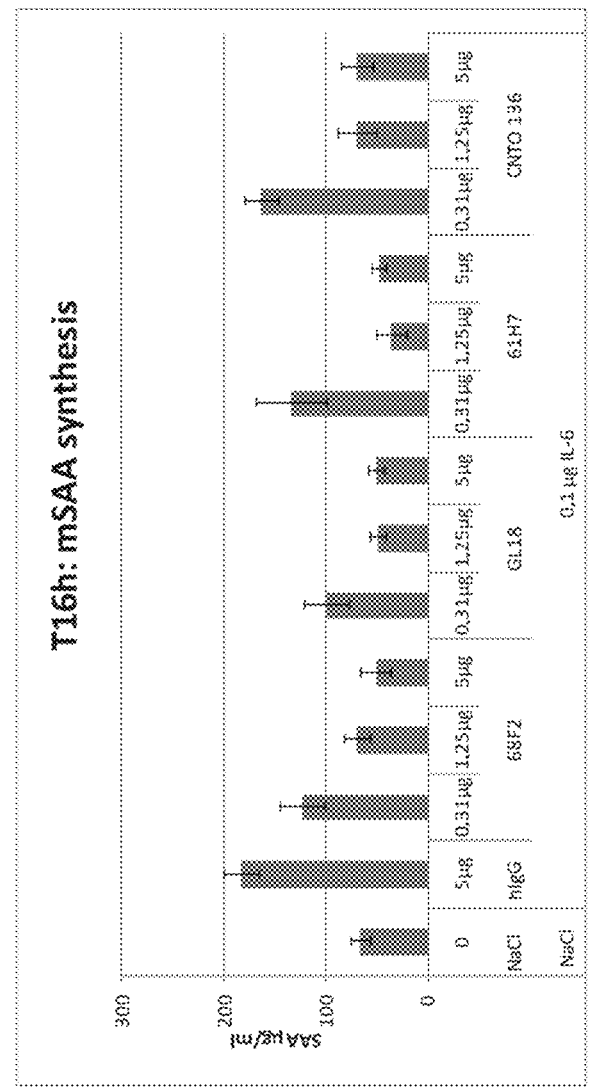
FIG. 13 depicts the results of serum amyloid A (SAA) mouse model experiments measuring the in vivo efficacy of antibodies of the invention.
Figure 14:
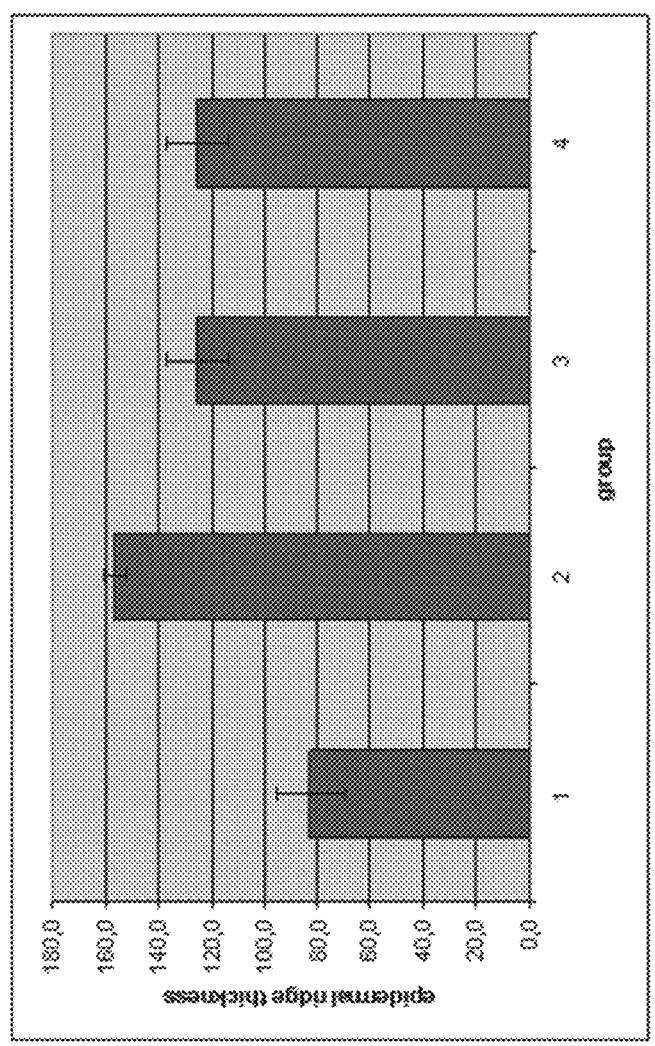
FIG. 14 depicts the results of mouse psoriasis xenograph experiments measuring the in vivo efficacy of antibodies of the invention.

The results of these experiments are set forth in FIG. 14, herein. The epidermal ridge thickness of the control group (group 2) was 156 µm±4 (mean±s.e.m.). Treatment with betamethasone (group 1, n=3) significantly reduced epidermal ridge thickness to 83 µm±13 (p<0.05) (FIGS. 12 and 13). The average epidermal ridge thicknesses of the Remicade treatment group (group 3) was 125 µm±12 and the 68F2 treatment group (group 4) was 125 µm±12. These data show that clone 68F2 is as efficacious as the anti-TNF antibody Remicade in a humanized mouse psoriasis model.

Example 16. Renal Cell Cancer Mouse Xenograft Model

The in vivo efficacy of clones 68F2 was investigated in a renal cell cancer mouse xenograft model. General methods for performing this assay are set forth in WO2008/144763, which is hereby incorporated by reference in its entirety. Briefly, RXF393 cells ($2 \times 10^6$) were injected subcutaneously at both lateral sides of a nude mouse. Tumors were allowed to grow to a volume between of 50 en 300 mm$^3$, prior to antibody administration. 90% of the injected mice developed a tumor. 40 mice were split into 5 groups of 8 mice. Each group was received intraperatoneal injection of either PBS (control) or a specific dose of clone 68F2 (1, 3, 10, or 30 mg/kg). Tumor size and survival was monitored twice per week.

Figure 15:
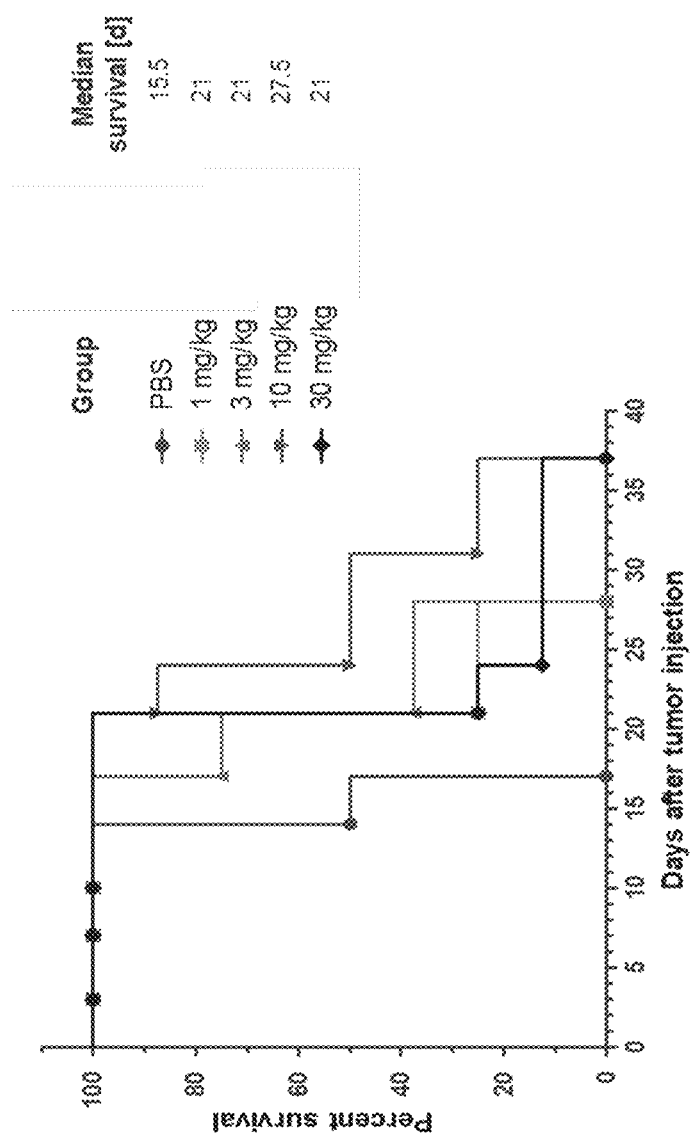
FIG. 15 depicts tumor growth data observed in experiments measuring the in vivo efficacy of antibodies of the invention in a renal cell cancer mouse tumor xenograph model.
Figure 16:
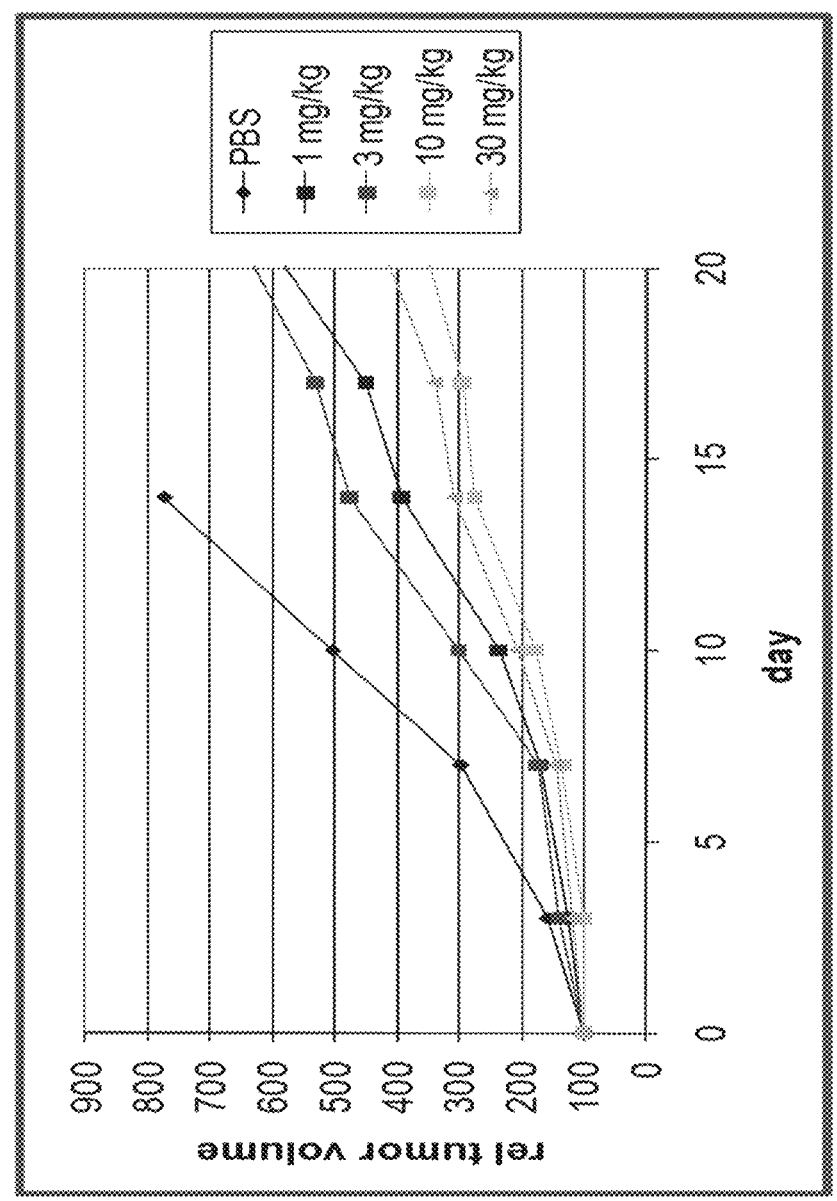
FIG. 16 depicts Kaplan-Meier plot of survival data observed in experiments measuring the in vivo efficacy of antibodies of the invention in a renal cell cancer mouse tumor xenograph model.
Figure 17:
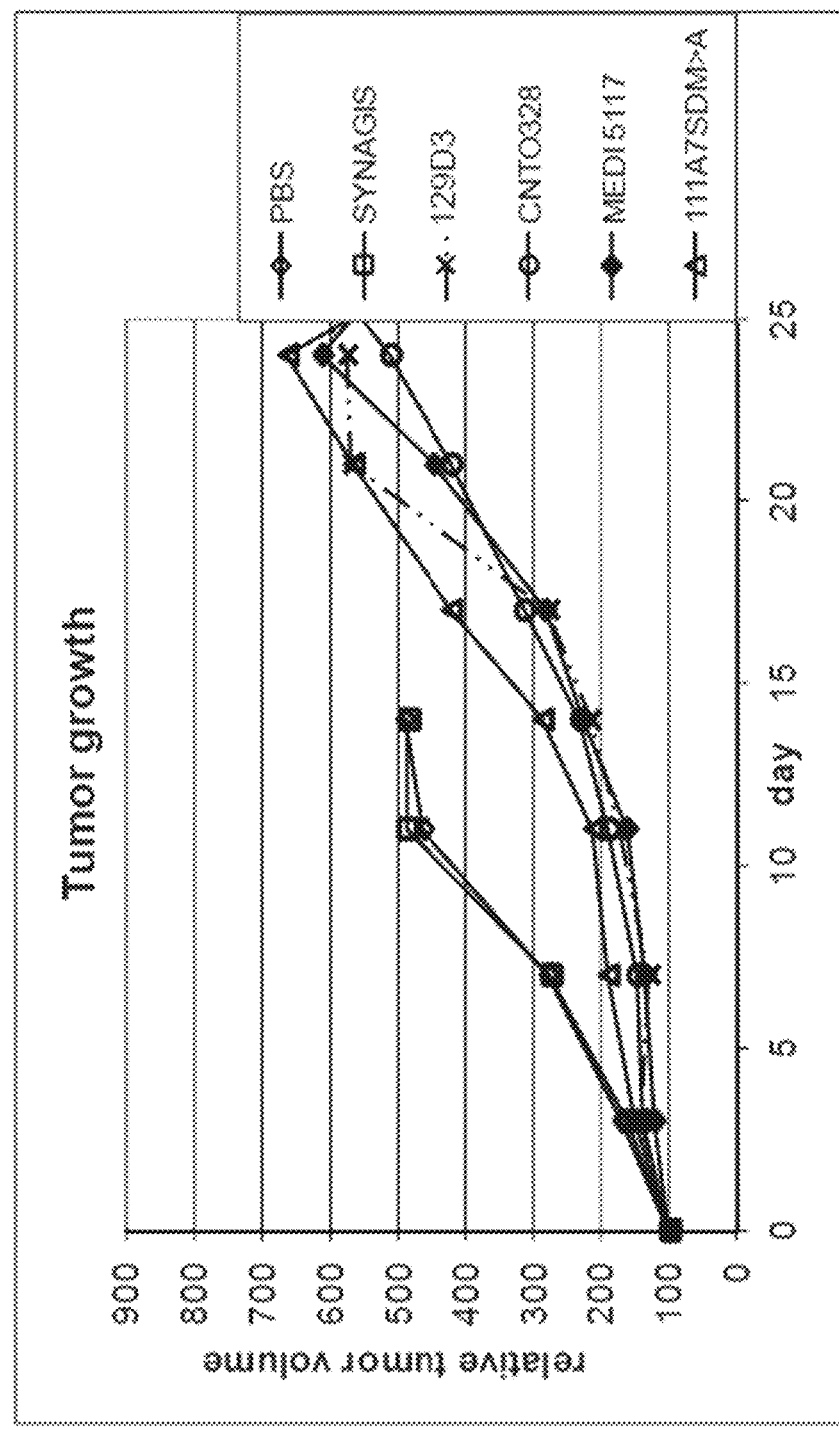
FIG. 17 depicts tumor growth data observed in experiments measuring the in vivo efficacy of antibodies of the invention in a renal cell cancer mouse tumor xenograph model with all agents dosed at 3 mg/kg.
Figure 18:
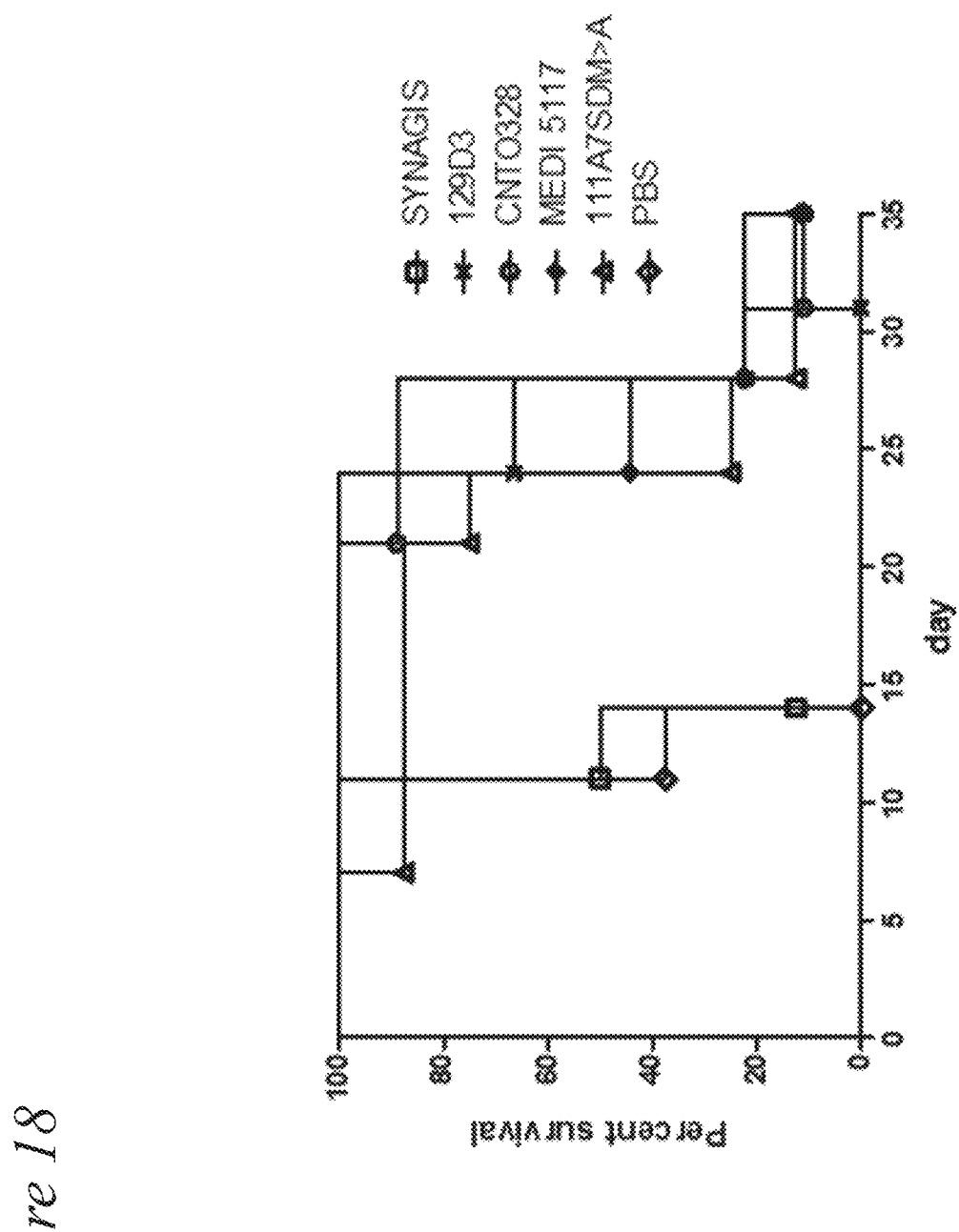
FIG. 18 depicts Kaplan-Meier plot of survival data observed in experiments measuring the in vivo efficacy of antibodies of the invention in a renal cell cancer mouse tumor xenograph model with all agents dosed at 3 mg/kg.

The survival data, set forth in FIG. 15 herein, show that 68F2 is effective at delaying death of mice relative to control. Specifically, the observed median survival times were 15.5 days for the PBS group, 21 days for the 1 mg/kg, 3 mg/kg and 30 mg/kg 68F2 group, and 27.5 days for the 10 mg/kg 68F2 group. The survival data, set forth in FIG. 18 herein, show that 129D3 and 111A7 dosed at 3 mg/kg are effective at delaying death of mice relative to control. The tumor growth rate data, set forth in FIG. 16 herein, shows that clone 68F2 is effective at inhibiting tumor outgrowth in a dose-dependent manner with saturating effects at 10 mg/kg dose. The tumor growth rate data, set forth in FIG. 17 herein, shows that clone 129D3 and 111A7SDMA>A are effective at inhibiting tumor outgrowth when dosed at 3 mg/kg. Additional Tables.

TABLE 13

VH and VL Amino Acid Sequences of Exemplary Anti-IL-6 Neutralizing Fabs.

| FAB CLONE | VH SEQUENCE | SEQ ID NO | VL SEQUENCE | SEQ ID NO |
|---|---|---|---|---|
| 17F10 | EVQLQESGPGLVKPSQTLSLTCTVSGGS IATSYYAWSWIRQPPGKGLEWMGVIDYD GDTYYKPSLKSRTSISRDTSKNQFSLQL SSVTPEDTAVYYCARAGLGDSYYLGTYY AMDYWGKGTLVTVSS | 1. | QAGLTQPPSVSGSPGKTVTISCAGTTSDVG TGNFVSWYQQLPGMAPKLLIYDVNKRASGI ADRFSGSKSGNTASLTISGLQSEDEADYYC ASYRSLNNVVFGGGTHLTVLG | 233. |
| 18C11 | EVQLVESGGGLVQPGGSLRLSCAASGFT FSSYAMSWVRQAPGKGLEWVSAINSGGG STSYADSVKGRFTISRDNAKNTLYLQMN SLKPEDTAVYYCAKEGDTGWKDPMYDYW GQGTQVTVSS | 2. | QSVVTQPSALSVTLGQTAKITCQGGGLRSS YAHWYQQKPGQAPVLVIYDDDSRPSGIPER FSGSSSGGRATLTISGAQAEDEGDYYCQSA DSSGNAAVFGGGTHLTVLG | 234. |
| 18C7 | EVQLVESGPGLVKPSQTLSLTCTVSGGS ITASFDAWSWIRQPPGKGLEWMGVIAYD GSTYYSPSLKSRTSISRDTSKNQFSLQL SSVTPEDTAVYYCARKSSWLIGYGMDYW GKGTLVTVSS | 3. | QAGLTQPSALSVTLGQTAKITCQGGSLGSS YAHWYQQKPGQAPVLVIYDDDSRPSGIPER FSGSSSGGRATLTISGAQAEDEGDYYCQSA DSSGNAAVFGGGTHLTVLG | 235. |
| 18C9 | EVQLVESGGGLVQPGGSLRLSCAASGFT FSRNAMSWVRQAPGKGLEWVSAINSGGG STSYADSVKGRFTISRDNAKNTLYLQMN SLKPEDTAVYYCAKEGYTGWKDPMYDYW GQGTQVTVSS | 4. | LNFMLTQPSALSVTLGQTAKITCQGGSLGS RYAHWYQQKPGQAPVLVIYDDDSRPSGIPE RFSGSSSGGRATLTISGAQAEDDGDYYCQS ADSSGNASVFGGGTHLTVLG | 236. |
| 18F8 | EVQLVESGGGLVQPGGSLRLSCAASGFT FSRNAMSWVRQAPGKGLEWVSAINSGGG STSYADSVKGRFTISRDNAKNTLYLQMN SLKPEDTAVYYCAKEGYTGWKDPMYDYW GQGTQVTVSS | 5. | QSALTQPSALSVTLGQTAKITCQGGSLGSR YAHWYQQKPGQAPVLVIYDDDSRPSGIPER FSGSSSGGRATLTISGAQAEDEGDYYCQSA DTSEHIVFGGGTHLTVLG | 237. |
| 20G2 | EVQLVESGGGLVQPGGSLRLSCAASGFT FSRNAMSWVRQAPGKGLEWVSAINSGGG STSYADSVKGRFTISRDNAKNTLYLQMN SLKPEDTAVYYCAKEGYTGWKDPMYDYW GQGTQVTVSS | 6. | ALNFMLTQPSALSVTLGQTAKITCQGGSLG SSYAHWYQQKPGQAPVLVIYDDDSRPSGIP ERFSGSSSGGRATLTISGAQAEDEGDYYCQ SADSSGNAVFGGGTHLTVLGQ | 238. |
| 18E12 | EVQLQESGPGLVKPSQTLSLTCTVSGGS ITTRYYAWSWIRQPPGKGLEWMGVIDYD GDTYYSPSLKSRTSISWDTSKNQFSLQL SSVTPEDTAVYYCARDPDVVTGFHYDYW GQGTQVTVSS | 7. | QSALTQPPSMSGTLGKTLTISCAGTSSDIG YGDYVSWYQQLPGTAPKLLIYKVSTRASGI PDRFSGSKSGNTASLTISGLQSEDEADYYC ASYRHYNNAVFGGGTHLTVLG | 239. |
| 20A4 | EVQLQESGPGLVKPSQTLSLTCTVSGGS ITTRYYAWSWIRQPPGKGLEWMGVIDYD GDTYYSPSLKSRTSISWDTSKNQFSLQL SSVTPEDTAVYYCARDPDVVTGFHYDYW GQGTQVTVSS | 8. | ALNFMLTQPPSVSGTLGKTVTISCAGTSSD IGGYNYVSWYQQLPGTAPKLLIHRVSTRAS GIPDRFSGSKSGNTASLTISGLRSEDEANY YCASYRNFNNAVFGGGTQLTVLG | 240. |
| 22C10 | QVQLQESGPGLVKPSQTLSLTCTVSGGS ITTSYYAWSWIRQPPGKGLEWMGVIGYD GSTYYSPSLKSRTSISRDTSKNQFSLQL SSVTPEDTAVYYCARDAGWYVGYEYDYW GQGTQVTVSS | 9. | ALPVLTQPPSVSGSPGQKFTISCTGSSSNI GENYVNWYQQLPGMAPKLLIYSNTNRASGV PDRFSGSKSGSSASLTITGLQVEDEADYYC SSWDDSLSGLVFGGGTKLTVLG | 241. |
| 22D11 | QLQLVESGGGLVQPGGSLRLSCAASGFT FDDYAMSWVRQAPGKGLEWVSDISWNGG NTYYAESMKGRFTISRDNAKNTLYLQMN SLKSEDTAVYYCAKEGGAVVAGTVGYYG MDYWGKGTLVTVSS | 10. | ALNFMLTQPPSLSASPGSSVRLTCTLSSGN SVGSYDISWYQQKAGSPPRYLLYYYSDSYK HQGSGVPSRFSGSKDASANAGLLLISGLQP EDEAAYYCSAYKSGSYVFGGGTKLTVLG | 242. |

TABLE 13-continued

VH and VL Amino Acid Sequences of Exemplary Anti-IL-6 Neutralizing Fabs.

| FAB CLONE | VH SEQUENCE | SEQ ID NO | VL SEQUENCE | SEQ ID NO |
|---|---|---|---|---|
| 24A3 | QVQVQESGGGLVQPGGSLRLSCAASGFTFSNYAMSWVRQAPGKGLEWVSGISFRGGMISYVDSVKGRFTISRDNAKNTLYLQMNSLKPEDTAVYYCAKNSGSSRSNALDAWGQGTLVTVSS | 11. | ALNFMLTQPPSVSGSPGQKFTIRCTGSFRSDSYVNWYQQLPGTAPKLLINYDDRRVSGVPSRFSGSKSGNSASLTIDGLQAEDEAEYYCSFWDHTFGGHVFGGGTKLTVLG | 243. |
| 24B9 | QVQLQESGGGLVQPGESLRLSCVASGFTFSSHRMYWVRQPPGKGLEWVSAISSSGVSTYYTDSVKGRFTISRDNAKNTVYLQMNSLKPEDTALYYCKRRTWYAGEYDYWGQGTQVTVSS | 12. | QTVVTQEPSLSVSPGGTVTLTCGLSSGSVTASNYPGWFQQTPGQAPRALIYSTNDRHSGVPSRFSGSISGNKAALTITGAQPEDEADYYCALDIGDITEFGGGTHLTVLG | 244. |
| 24C9 | QVQLVESGGGLVQPGGSLRLSCAASGFTFSSYRMYWVRQPPGKGLEWVSAISAGGGSTYYGDSVKGRFTISRDNAKNTVYLQMNSLKPEDTALYYCKKSTWADGESDYWGQGTQVTVSS | 13. | QTVVTQEPSLSVSPGGTVTLTCGLSSGSVTASNYPGWFQQTPGQAPRALIYSTNDRHSGVPSRFSGSISGNKAALTITGAQPEDEADYYCALDIGDITEFGGGTHLTVLG | 245. |
| 24D10 | QLQVVESGGGLVQPGGSLRLSCAASGFTFSSYAMSWVRQAPGKGPEWVSRISSGGGSTSYADSVKGRFTISRDNAKNTLYLQMNSLKPEDTAVYYCANRAGWGMGDYWGQGTQVTVSS | 14. | QTVVTQEPSLSVSPGGTVTLTCGLSSGSVTASNYPGWFQQTPGQAPRALIYSTNDRHSGVPSRFSGSISGNKAALTITGAQPEDEADYYCALDIGDITEFGGGTHLTVLG | 246. |
| 24D9 | EVQVQESGGGLVQPGESLRLSCAASGFTFSSHRMYWVRQPPGKGLEWVSAISSSGVSTYYADSVKGRFTISRDNAKNTVYLQMNSLKPEDTALYYCKRRTWYGGEYDYWGQGTQVTVSS | 15. | QTVVTQEPSLSVSPGGTVTLTCGLSSGSVTASNYPGWFQQTPGQAPRALIYSTNDRHSGVPSRFSGSISGNKAALTITGAQPEDEADYYCALDIGDITEFGGGTHLTVLG | 247. |
| 24E9 | EVQLVESGGGLVQPGGSLRLSCAASGFTFSTYAMSWVRQAPGKGPEWVSRISSGGGSTNYADSVKGRFTISRDNAKKTLYLQMKSLKPEDTAVYYCANRAGWGMGDYWGQGTQVTVSS | 16. | QTVVTQEPSLSVSPGGTVTLTCGLSSGSVTASNYPGWFQQTPGQAPRALIYSTNDRHSGVPSRFSGSISGNKAALTITGAQPEDEADYYCALDIGDITEFGGGTHLTVLG | 248. |
| 24F4 | EVQLVESGGGLVQPGESLRLSCAASGFTFSSHRMYWVRQPPGKGLEWVSAISSSGVSTYYADSVKGRFTISRDNAKNTVYLQMNSLKPEDTALYYCKRRTWYGGEYDYWGQGTQLTVAS | 17. | QTVVTQEPSLSVSPGGTVTLTCGLSSGSVTASNYPGWFQQTPGQAPRALIYSTNDRHSGVPSRFSGSISGNKAALTITGAQPEDEADYYCALDIGDITEFGGGTHLTVLG | 249. |
| 24G3 | QLQVVESGGGLVQPGSSLRLSCGASGFTFSSHRMYWVRQPPGKGLEWVSAISSSGVSTYYADSVKGRFTISRDNAKNTVYLQMNSLKPEDTALYYCKRRTWYGGEYDYWGQGTQVTVSS | 18. | QTVVTQEPSLSVSPGGTVTLTCGLSSGSVTASNYPGWFQQTPGQAPRALIYSTNDRHSGVPSRFSGSISGNKAALTITGAQPEDEADYYCALDIGDITEFGGGTHLTVLG | 250. |
| 24B3 | EVQLVESGGGLPXPGESLRLSCAASGFTFSSHRMYWVRQPPGKGLEWVSAISSSGVSTYYADSVKGRFTISRDNAKNTVYLQMNSLKPEDTALYYCKRRTWYGGEYDYWGQGTQLTVAS | 19. | QTVVTQEPSLSVSPGGTVTLTCGLSSGSVTASNYPGWFQQTPGQAPRALIYSTNDRHSGVPSRFSGSISGNKAALTITGAQPEDEADYYCALDIGDITEFGGGTHLTVLG | 251. |
| 29B11 | EVQLVESGGGLVQPGGSLRLSCAASGFTFSSYAMSWVRQAPGKGLEWVSRISSGGISTYYADSVKGRFTISRDNAKNTLYLQMNSLKPEDTAVYYCVRYAWGVQWAFDFWGQGTQVTVSS | 20. | QSVLTQPPSVSGSPGQTVTISCAGTSEDVGYGNYVSWYQQLPGMAPKLLIYDVNKRASGIADRFSGSKSGNTASLTISGLQSEDEADYYCASYRRTIDNIFGGGTHLTVLG | 252. |
| 28C6 | QVQLVESGGGLVQPGGSLRLSCAASGFTFSNYYMTWVRQAPGKGLEWVSSIYSFSGDTAYADSVKGRFTISRDNAKNTLYLQMKLKSEDTAVYYCTRDLGGVVVTANGYDYWGQGTQVTVSS | 21. | DIVMTQTPSSLSASLGDRVTITCQASQSISTELSWYQQKPGQTPKLLIYGASRLQTGVPARFSGSGSGTSFTLTISGLEAEDLATYYCLQDYSWPYSFGSGTRL | 253. |
| 28B6 | QVQLVESGGGLVQPGGSLRLSCAASGFTFSNYYMTWVRQAPGKGLEWVSSIYSFSGDTAYADSVKGRFTISRDNAKNTLYLQMNSLKSEDTAVYYCTRNLGGVVVTTNGYDYWGQGTQVTVSS | 22. | DIQLTQSPSSLSASLGDRVTITCQASQSISTELSWYQQKPGQTPKLLIYGASRLQTGVPARFSGSGSGTSFTLTISGLEAEDLATYYCLQDYSWPYSFGSGTRL | 254. |

TABLE 13-continued

VH and VL Amino Acid Sequences of Exemplary Anti-IL-6 Neutralizing Fabs.

| FAB CLONE | VH SEQUENCE | SEQ ID NO | VL SEQUENCE | SEQ ID NO |
|---|---|---|---|---|
| 28E6 | QVQLVESGGGLVQPGGSLRLSCAASGFTFSNYYMTWVRQAPGKGLEWVSSIYSFSGDTAYADSVKGRFTISRDNAKNTLYLQMNSLKSEDTAVYYCTRNLGGVVVTTNGYDYWGQGTQVTVSS | 23. | DIQMTQSPSSLSTSLGDRVTITCQASQAITTELSWYQQKPGQPPKLLIYGTSRLQTGVPSRFSGTGSGTSFTLTISDLEAEDLATYYCLQDYGWPFTFGQGTKV | 255. |
| 28F6 | QVQLVESGGGLVQPGGSLRLSCAASGFTFSNYYMTWVRQAPGKGLEWVSSIYSFSGDTAYADSVKGRFTISRDNAKNTLYLQMNSLKSEDTAVYYCTRNLGGVVVTTNGYDYWGQGTQVTVSS | 24. | DIVMTQSPSSLSASLGDRVTITCQTSQTISTELSWYQQKPGQAPKLLIYGASRLQTGVPSRFSGSGSGTSFTLTISGLEAEDLATYYCLQDYSWPFTFGQGTKV | 256. |
| 16A2 | ELQLVESGGGLVQPGGSLRLSCAASGYTFDDYAMGWVRQAPGKGLEWVSSIYSYSSDTYYADSVKGRFTISRDNAQNTVYLQMTSLKPEDTALYYCARCARDIGSAWCGGVDYWGKGTLVTVSS | 25. | DIVMTQSPFSLSASLGDRVTITCQASESILTEVSWYQQKPGQTPKLLIYGASGLQTGVPNRFSGSGSGTSFTLTISGLEAEDLATYYCLQDYRWPLTFGQGTKVELKR | 257. |
| 16B1 | ELQLVESGGGLVQPGGSLRLSCAASGYTFDDYAMGWVRQAPGKGLEWVSSIYSYSSDTYYADSVKGRFTISRDNAQNTVYLQMTSLKPEDTALYYCARCARDIGSAWCGGVDYWGKGTLVTVSS | 26. | DIVMTQSPSSLTASLGDRVTITCQASQSIRTDISWYQQKPGQTPKLLIYAASRLQTGVPSRFSGSGSGTSFTLTISGLEAEDLGTYYCLQDYSWPLTFGQGTKVELKR | 258. |
| 16D2 | ELQLVESGGGLVQPGGSLRLSCAASGYTFDDYAMGWVRQAPGKGLEWVSSIYSYSSDTYYADSVKGRFTISRDNAQNTVYLQMTSLKPEDTALYYCARCARDIGSAWCGGVDYWGKGTLVTVSS | 27. | DIVMTQSPSSLSASLGDRVTITCQASQSISTELSWYQQKPGQTPKLLIYGASRLQTGVPSSFSGSGSGTSFTLTISGLEAEDLATYYCLQDYNWPFTFGQGTKVELKR | 259. |
| 29G3 | ELQLVESGGGLVQPGGSLRLSCAASGFTFSSYAMSWVRQAPGKGLEWVSRISSGGISTYYADSVKGRFTISRDNAKNTLYLQMNSLKPEDTAVYYCARYAWGVQWAFDFWGQGTQVTVSS | 28. | DIQMTQSPSSVTASVGEKVTLNCKSSQSVVVRSDQKSYLNWYQQRPGQSPRLLIYYASTQESGIPDRFSGSGSTTDFTLTINSVQPEDAAVYYCQQASSAPYNFGSGTRL | 260. |

TABLE 14

VH and VL Amino Acid Sequences of Exemplary Anti-IL-6 Neutralizing Fabs Generated by VH or VL Shuffling

| FAB CLONE | VH SEQUENCE (clone name given in place of sequence if sequence identical to VH in another clone) | SEQ ID NO | VH SEQUENCE (clone name given in place of sequence if sequence identical to VL in another clone) | SEQ ID NO |
|---|---|---|---|---|
| 35C1 | VH_17F10 | 1. | QSALTQPPSMSGTLGKTLTISCNGTSSDIGSGDYVSWYQQLPGTTPKLLIEGVTTRASGIPDRFSASKSDNTASLTISGLQSEDEATYYCASYRETNNVVFGGGTHLTVLS | 261. |
| 35B1 | VH_17F10 | 1. | QAVLTQPPSMSGTLGKTLTISCNGTSSDIGSGNYVSWYQQLPGTTPKLLIEGVTTRVSGIPDRFSGSKSDNTASLTISGLQSEDEATYYCASYRETNNVVFGGGTHLTVLG | 262. |
| 35F5 | VH_17F10 | 1. | QAGLTQPPSVSGSPGKTVTISCAGTSSDVGYGNYVSWYQQLPGMAPKLLIYDVNKRASGIADRFSGSKSGNTASLTISRLQSEDEADYYCASYKTYNNVVFGGGTHLTVLG | 263. |
| 35D1 | VH_17F10 | 2. | QSVVTQPPSVSGTLGKTVTISCAGTTSDIGGYNYVSWYQQLPGTAPKFLIYEVSKRAAGIPDRFSGSKSGSTASLTISGLQSEDEADYYCASYRDTANVVFGGGTHLTVLG | 264. |
| 37A1 | VH_18C11 | 2. | ALNFMLTQPSALSVTLGQTAKITCQGGSLGNNYAHWYQQKPGQAPVLVIYDDDSRPSGIPERFSGSSSGGRATLTISGAQAEDEGDYYCQSADSSGNAVFGGGTHLTVLG | 265. |
| 36A1 | VH_18C11 | 2. | AQSALTQPSALSVTLGQTAKITCQGGSLGTRYAHWYQQKPGQAPVLVIYDDDSRPSGIPERFSGSSSGGRATLTISGAQAEDEGDYYCQSADSSGNASVFGGGTHLTVLG | 266. |

TABLE 14-continued

VH and VL Amino Acid Sequences of Exemplary Anti-IL-6 Neutralizing Fabs Generated by VH or VL Shuffling

| FAB CLONE | VH SEQUENCE (clone name given in place of sequence if sequence identical to VH in another clone) | SEQ ID NO | VH SEQUENCE (clone name given in place of sequence if sequence identical to VL in another clone) | SEQ ID NO |
|---|---|---|---|---|
| 36F8 | VH_18C11 | 2. | ALNFMLTQPSALSVTLGQTAKITCQGGSLGSRYAHWYQQ KPGQAPVLVIYDDDSRPSGIPERFSGSSSGGRATLTISG AQAEDEGDYYCQSADSSGNAAVFGGGTHLTVLG | 267. |
| 37D1 | VH_18C11 | 2. | AQAGLTQPSALSVTLGQTAKITCQGGSLGSSYAHWYQQK PGQAPVLVIYDDDSRPSGIPERFSGSSSGGRATLTISGA QAEDEGDYYCQSADSSGNAIVFGGGTHLTVLG | 268. |
| 37G1 | VH_18C11 | 2. | AQAVLTQPSALSVTLGQTAKITCQGGSLRSSYAHWYQQK PGQAPVLVIYDDDSRPSGIPERFSGSSSGGRATLTISGA QAEDEGDYYCQSADSSGNASVFGGGTHLTVLG | 269. |
| 20G2 | VH_18C11 | 2. | ALNFMLTQPSALSVTLGQTAKITCQGGSLGSSYAHWYQQ KPGQAPVLVIYDDDSRPSGIPERFSGSSSGGRATLTISG AQAEDEGDYYCQSADSSGNAVFGGGTHLTVLG | 270. |
| 44C6 | VH_18C7 | 3. | AQSALTQPSALSVTLGQTAKITCQGGSLGSSYAHWYQQK PGQAPVLVIYDDDSRPSGIPERFSGSSSGGRATLTISGA QAEDEGDYYCQSADSSGNASVFGGGTHLTVLG | 271. |
| 44E7 | VH_18C7 | 3. | ALNFMLTQPSALSVTLGQTAKITCQGGSLGSSYAHWYQQ KPGQAPVLVIYDDDSRPSGIPERFSGSSSGGRATLSISG AQAEDEGDYYCQSGDSSGNAAVFGGGTKLTVLG | 272. |
| 68F2 | EVQLQESGPGLVKPSQTLSLTCTVSGGSITTRYYAWSWIR QPPGKGLEWMGVIDYDGDTYYSPSLKSRTSISWDTSKNQF SLQLSSVTPEDTAVYYCARDPDVVTGFHYDYWGQGTQVTV SS (Identical to VH_20A4) | 8. | QSALTQPPLVSGTPGQVTISCAGANNDIGTYAYVSWYQ QLPGTAPKLLIYKVTTRASGIPSRFSGSKSGNTASLTIS GLQSEDEADYYCASYRNFNNAVFGRGTHLTVLG | 273. |
| 71C8 | VH_20A4 | 8. | QSALTQPPSVSGTLGKTLTISCAGTSSDVGYGNYVSWYQ QLPGTAPKLLIYRVSTRASGIPDRFSGSKSGNTASLTIS GLQSEDEADYYCASYRSSNNAVFGGGTHLTVLG | 274. |
| 70H2 | VH_20A4 | 8. | QSVLTQPPSVSGTLGKTVTISCAGTSSDVGYGNYVSWYQ QLPGTAPKLLIYAVSYRVSGIPDRFSGSKSGNTASLTIS GLQSEDEADYYCASYRNRNNAVFGGGTHLTVLG | 275. |
| 71D12 | VH_20A4 | 8. | QAVLTQPPSVSGTLGKTVTISCAGTSSDVGYGNYVSWYQ QLPGTAPKLVIYAVNYRASGIPDRFSGSKSGNTASLFIS GLQSEDEADYYCASYRDFNNAVFGGGTHLTVLG | 276. |
| 70B2 | VH_20A4 | 8. | QAVLTQPPSVSGSPGKTVTISCAGTSSDVGFGNYVSWYQ QLPGMAPKLLIYEVNKRTSGIPDRFSGSKSGNTASLTIS GLQSEDEADYHCASYRNFNNAVFGGGTHLTVLG | 277. |
| 71C3 | VH_20A4 | 8. | QSALTQPPSVSGSPGKTVTISCAGTSSDVGYGNYVSWYQ QLPGMAPKLLIYDVNKRASGIADRFSGSKSGNTASLTIS RLQSEDEADYYCASYKTYNNVVFGGGTHLTVLG | 278. |
| 69H4 | VH_20A4 | 8. | QSALTQPPSVSGTLGKTVTISCAGTSSDVGYGNYVSWYQ QLPGTAPKLLIYAVSYRASGIPDRFSGSKSGNTASLTIS GLQSEDEADYYCASYRYFNNAVFGGGTHLTVLG | 279. |
| 68G8 | VH_16D2 | 27. | LDIVMTQTPSSLSASLGDRVTITCQATQNINTELSWYQQ KPGQTPKLLIYDTSRLQTGVPSRFSGSGSRTTFTLTISG LEAEDLATYYCMQDYNWPLTFGQGTKVELKR | 280. |
| 68E10 | VH_16D2 | 27. | LDIVMTQTPSSLSASLGDRVTITCQASQSISTELSWYQQ KPGQSPKLLIYGASRLQIGVPSRFSGSGSGTSFTLTISG LEADDLATYYCLQDYNWPLSFGSGTRLEIK | 281. |
| 69H7 | VH_16D2 | 27. | LDIQMTQSPSSLSASLGDRVTITCQASQSISTELAWYQQ KPGQTPKLLIYGASKLQTGVPSRFSGSGSGTSFTLTISG LEAEDLATYYCLQDYNWPFTFGQGTKVELKR | 282. |
| 70B5 | VH_16D2 | 27. | LDIVMTQTPSSLSASLGDRVAITCQASQSINVDVSWYQQ KPGQTPKLLIYAASRLQTGVPSRFSGSGSGTSFALTISG LEAEDLASYYCLQDYSWPLTFGQGTKVELKR | 283. |
| 70C5 | VH_16D2 | 27. | LDIQMTQSPSSLSVFLGDRVTITCQASQRISTELSWYQQ KPGQTPKLLIWGASRLQTRVPSRFSGSGSGTSFTLTISG LEAEDLATYYCLQDYSWPLTFGQGTKVELKR | 284. |

TABLE 14-continued

VH and VL Amino Acid Sequences of Exemplary Anti-IL-6 Neutralizing Fabs Generated by VH or VL Shuffling

| FAB CLONE | VH SEQUENCE (clone name given in place of sequence if sequence identical to VH in another clone) | SEQ ID NO | VH SEQUENCE (clone name given in place of sequence if sequence identical to VL in another clone) | SEQ ID NO |
|---|---|---|---|---|
| 70C6 | VH_16D2 | 27. | LDIVMTQSPSSLSASLGDRVTITCQASQNIITELSWYQQ KPGQTPKLLIYGASRLQTGVPSRFSGSGSGTSFTLTISG LEAEDLATYYCLQDYNWPLTFGQGTKVELKR | 285. |
| 70H4 | VH_16D2 | 27. | LDIVMTQTPSSLSASLGDRVTITCQASQNINTDLSWYQQ KPGQTPKLLFYGASGLQTGIPSRFSGSGSGTSFTLAISG LEAEDLATYYCLQDYNWPLTFGQGTKVELKR | 286. |
| 72A4 | VH_16D2 | 27. | LEIVMTQSPSSLSASVGDRVTITCQASQSISTELSWYQQ KPGQTPKLLIYDASRLQTGVPSRFSGSRSGTTFTLTISG LEAEDLATYYCLQDYNWPLTFGQGTKVELK | 287. |
| 72B6 | VH_16D2 | 27. | LDIVMTQSPSSLSASLGDRVTITCQATQSISTELSWYQQ KPGQAPKLLIYDASKLQTGVPSRFSGSGSGRSFTLTISG LEAEDSATYYCLQDYNWPLSFGSGTRLEIK | 288. |
| 72D2 | VH_16D2 | 27. | LDIQLTQSPSSLSASLGDRVTITCQASQSINIDLSWYQQ KPGQTPKLLFYGASGLQAGVPSRFSGSGSGTSFTLTING LEAEDLATYYCLQDYNWPLTFGQGTKVELKR | 289. |
| 72G1 | VH_16D2 | 27. | LETTLTQSPSSLSVSLGDRVTITCQASQRISTELSWYQQ KPGQAPKLLIYDASTLQTGVPRFGGSGSGTSFTLTISG LEAEDLATYYCLQDYSWPLTFGQGTKVELNR | 290. |
| 47C2 | VH_29B11 | 20. | ALSYDLTQPPSVSGSPGKTVTISCAGTSSDVGYGNYVSW YQQLPGMAPKILIYDVNKRASGIADRFSGSKSGNTASLT ISGLQSEDEADYYCASYRRGETIVFGGGTHLTVLG | 291. |
| 47C3 | VH_29B11 | 20. | ALSYELTQPPSVSGSPGKTVTISCAGTSSDVGYGNYVSW YQQLPGMAPKLLIYDVNKRASGIADRFSGSKSGNTASLT ISGLQSEDEADYYCASYRLGNKYVFGGGTKLTVLG | 292. |
| 48C10 | VH_29B11 | 20. | AQSVLTQPPSVSGSPGQTVTISCAGTSEDVGYGNYVSWY QQLPGMAPKLLIYDVNKRASGIADRFSGSKSGNTASLTI SGLQSEDEADYYCASYRRTIDNIFGGGTHLTVLG | 293. |
| 47B2 | VH_29B11 | 20. | AQSALTQPPSVSGSPGKTVTISCAGTSSDIGYGNYVSWY QQFPGMAPKFLIYDVHRRASGIADRFSGSKSGNTASLTI SGLQPEDEAVYYCASYRRGSNAVFGGGTHLTVLG | 294. |
| 55C1 | VH_29B11 | 20. | ALNFMLTQPPSVSGSPGKTVTISCAGTSSDVGYGNYVSW YQQLPGTAPKLLIYNVNKRASGITDRFSGSKSGNTASLT ISGLQSEDEADYYCASYRTGDNAAFGGGTKLTVLG | 295. |
| 55E2 | VH_29B11 | 20. | AQSVLTQPPSVSGSPGMAPKTVTISCAGTSSDVGYGNYVSWY QQLPGMAPKLLIYDVNKRASGIADRFSGSKFANTASLTI SGLQSEDEADYYCASYKRGDNAVFGGGTKLTVLG | 296. |
| 55H1 | VH_29B11 | 20. | AQSVVTQPPSVSGSPGKTVTISCAGTSSDVGYGNYVSWY QQLPGMAPKLLIYDVSKRASGIADRFSGSKSGNTASLTI SGLQSEDEADYVCASYRRGGTAVFGGGTHLTVLG | 297. |
| 65B7 | QVQVQESGGGLVHPGESLRLSCAASGFTFSSHRMYWVRQP PGKGLEWVSAISSSGVSTYYADSVKGRFTISRDNAKNTVY LQMNSLKPEDTALYYCKRRTWYGGEYDYWGQGTQVTVSP | 29. | VL_24B9 | 12. |
| 65B12 | EVQLVESGGALVHPGGSLRLSCAASGFTFSSHRMYWVRQP PGKGLEWVSAISSSGVSTYYADSVKGRFTISRDNAKNTVY LQMNSLKPEDTALYYCKRRTWYGGEYDYWGQGTQVTVSS | 30. | VL_24B9 | 12. |
| 65H8 | QVQLVESGGGLVHPGESLRLSCAASGFTFSSHRMYWVRQP PGKGLEWVSAISSSGVSTYYADSVKGRFTISRDNAKNTVY LQMNSLKPEDTALYYCKRRTWYGGEYDYWGQGTQVTVSS | 31. | VL_24B9 | 12 |
| 77D1 | EVQLVESGGGLVQPGGSLRLSCAASGFTFSSYAMSWVRQA PGKGLEWVSRISSGGISTYYADSVKGRFTISRDNAKNTLY LQMNSLKPEDTAVYYCVRYAWGVQWAFDFWGQGTQVTVSS | 32. | VL_24B9 | 12 |
| 77D6 | EVQLVESGGGLVQPGGSLRLSCAASGFTFSSYAMSWVRQA PGKGLEWVSRISSGGISTYYADSVKGRFTISRDNAKNTLY LQMNSLKPEDTAVYYCVRYAWGVQWAFDFWGQGTQVTVSS | 33. | VL_24B9 | 12 |

TABLE 14-continued

VH and VL Amino Acid Sequences of Exemplary Anti-IL-6 Neutralizing Fabs Generated by VH or VL Shuffling

| FAB CLONE | VH SEQUENCE (clone name given in place of sequence if sequence identical to VH in another clone) | SEQ ID NO | VH SEQUENCE (clone name given in place of sequence if sequence identical to VL in another clone) | SEQ ID NO |
|---|---|---|---|---|
| 61A7 | QVQLVESGGGLVQPGGSLRLSCVASGFTFSSYAMSWVRQAPGKGPEWVSRISSGGGSTSYADSVKGRFTISRDNAKNTLYLQMNSLKPEDTAVYYCANRAGWGMGDYWGQGTQVTVSS | 34. | VL_24B9 | 12 |
| 61B7 | ELQLVESGGGLVQPGGSLRLSCAASGFTFSSYAMSWVRQAPGKGPEWVSRISSGGGSAYYADSVKGRFTISRDNAKNTLYLQMNSLKPEDTAVYYCANRAGWGMGDYWGQGTQVTVSS | 35. | VL_24B9 | 12 |
| 65F9 | QVQLVESGGGLVHPGGSLRLSCAASGFTFSSYAMSWVRQAPGKGPEWVSRISSGGGSAYYADSVKGRFTISRDNAKNTLYLQMNSLKPEDTAVYYCANRAGWGMGDYWGQGTQVTVSS | 36. | VL_24B9 | 12 |
| 61H7 | EVQLVESGGGLVQPGGSLRLSCAASGFTFSSYRMYWVRQPPGKGLEWVSAISAGGGSTYYGDSVKGRFTISRDNAKNTVYLQMNSLKPEDTAVYYCANRAGWGMGDYWGQGTQVTVSS | 37. | QTVVTQEPSLSVSPGGTVTLTCGLSSGSVTASNYPGWFQQTPGQAPRALIYSTNDRHSGVPSRFSGSISGNKAALTITGAQPEDEADYYCALDIGDITEFGGGTHLTVLG (IDENTICAL TO VL_24B9) | 12 |
| 65D7 | EVQLVESGGGLVQPGESLRLSCVASGFTFSSHRMYWVRQPPGKGLEWVSAISSSGVSTYYTDSVKGRFTISRDNAKNTVYLQMNSLKPEDTAVYYCANRAGWGMGDYWGQGTQVTVSS | 38. | VL_24B9 | 12 |
| 48H1 | VH_28B6 | | DVVMTQSPSSLPTSLGDSVTITCQASQSISDELSWYQQKPGQTPKLLIYGASKLQTGVPSRFSGSGSGTSFTLTISGLEAEDLATYYCLQGYSWPFMFGQGTKVELK | 298. |
| 55E10 | VH_28B6 | 22. | DIQMTQSPSSLPTSLGDSVTITCQASQSISDELSWYQQKPGQTPKLLIYGASKLQTGVPSRFSGSGSGTSFTLTISGLEAEDLATYYCLQGYSWPFMFGQGTKVELK | 299. |
| 55A11 | VH_28B6 | 22. | DIQMTQSPSSLPTSLGDSVTITCQASQSISDELSWYQQKPGQTPKLLIYGASRLQTGVPSRFSGRGSGTSFTLTISGLEAEDLATYYCLQGYSWPFMFGQGTKVELK | 300. |
| 55C11 | VH_28B6 | 22. | DIQLTQSPSSLSASLGDSVTITCQASQSISDELSWYQQKPGQTPKLLIYGASKLQTGVPSRFSGSGSGTSFTLTISGLEAEDLATYYCLQGYRWPFMFGQGTKVELK | 301. |
| 55C10 | VH_28B6 | 22. | DIQMTQSPSSLSTSLGDRVTITCQASQSISTELSWYQQKPGQTPKLLIYGASRLQTGVPSRFSGXGSGTSFTLTISGMEAEDLATYYCLQDYSWPYXFGXGTRVEIK | 302. |

TABLE 15

VH and VL Amino Acid Sequences of Exemplary Germlined Variants of Fab Clone 61H7.

| FAB CLONE | VH SEQUENCE | SEQ ID NO | VL SEQUENCE | SEQ ID NO |
|---|---|---|---|---|
| 100A8 | EVQLLESGGGLVQPGGSLRLSCAASGETFSSYAMYWVRQAPGKGPEWVSRISAGGGSTYYGDSVKGRFTISRDNAKNTLYLQMNSLRAEDTAVYYCANRAGWGMGDYWGQGTQVTVSS | 39. | QTVVTQEPSFSVSPGGTVTLTCGLSSGSVTASNYPGWYQQTPGQAPRTLIYSTNDRHSGVPSRFSGSISGNKAALTITGAQPDDEADYYCALDIGDITEFGGGTHLTVLG | 303. |
| 100E8 | EVQLLESGGGLVQPGGSLRLSCAASGETFSSYRMYWVRQPPGKGLEWVSAISAGGGSTYYGDSVKGRFTISRDNAKNTVYLQMNSLKPEDTAVYYCANRAGWGMGDYWGQGTQVTVSS | 40. | QTVVTQEPSFSVSPGGTVTLTCGLSSGSVTASNYPGWYQQTPGQAPRALIYSTNDRHSGVPSRFSGSILGNKAALTITGAQADDEADYYCALDIGDITEFGGGTHLTVLG | 304. |
| 100F2 | ELQLLESGGGLVQPGGSLRLSCAASGETFSSYAMYWVRQAPGKGPEWVSRISAGGGSTYYGDSVKGRFTISRDNAKNTLYLQMNSLKTENTAVYYCANRAGWGMGDYWGQGTLVTVSS | 41. | QTVVTQEPSFSVSPGGTVTLTCGLSSGSVTASNYPGWYQQTPGQAPRALIYSTNDRHSGVPSRFSGSISGNKAALTITGAQPEDSDYYCALDIGDITEFGGGTHLTVLG | 305. |
| 100G8 | EVQLVESGGGLVQPGGSLRLSCAASGETFSSYRMSWVRQPPGKGPEWVSAISSGGGSTYYGDSVKGRFTISRDNSKNTLYLQMNSLKTEDTAVYYCANRAGWGMGDYWGQGTQVTVSS | 42. | QTVVTQEPSFSVSPGGTVTLTCGLSSGSVTASNYPGWYQQTPGQAPRALIYSTNDRHSGVPDRFSGSISGNKAALTITGAQAEDEADYYCALDIGDITEFGGGTHLTVLG | 306. |

TABLE 15-continued

VH and VL Amino Acid Sequences of Exemplary Germlined Variants of Fab Clone 61H7.

| FAB CLONE | VH SEQUENCE | SEQ ID NO | VL SEQUENCE | SEQ ID NO |
|---|---|---|---|---|
| 101B2 | ELQLLESGGGLVQPGGSLRLSCAASGETFSSYAMYWVR QPPGKGPEWVSRISAGGGSTYYGDSVKGRFTISRDNAK NTVYLQMNTLKTEDTAVYYCANRAGWGMGDYWGQTLV TVSI | 43. | QTVVTQEPSLTVSPGGTVTLTCGLSSGSVTASNYPGWFQQ KPGQAPRALIYSTNDRHSWVPSRFSGSILGGKAALTLLGA QPEDEAEYYCALDIGDITEFGGGTQLTVLG | 307. |
| 101B8 | EVQLLESGGGLVQPGGSLRLSCAASGETFSSYAMSWVR QAPGKGPEWVSRISAGGGSTYYGDSVKGRFTISRDNAK NTVYLQMNSLRAENTAVYYCANRAGWGMGDYWGQTQV TVSS | 44. | QAVVTQEPSLSVSPGGTVTLTCGLSSGSVTASNYPGWFQQ TPGQAPRALIYSTNDRHSGVPSRFSGSILGNKAALTLTGA QPEDEAEYYCALDIGDITEFGGGTHLTVLG | 308. |
| 101D8 | EVQLVESGGGLVQPGGSLRLSCAASGETFSSYAMSWVR QAPGKGPEWVSRISSGGGSTYYGDSVKGRFTISRDNSK NTLYLQMNSLRAEDTAVYYCANRAGWGMGDYWGQTQV TVSS | 45. | QTVVTQEPSLTVSPGGTVTLTCGLSSGSVTASNYPGWFQQ KPGQAPRALIYSTNDRHSGVPARFSGSLLGGKAALTILGA QADDEAEYYCALDIGDITEFGGGTQLTVLG | 309. |
| 101G8 | EVQLLESGGGLVQPGGSLRLSCAASGETFSSYAMSWVR QAPGKGPEWVSRISSGGGSTYYGDSVKGRFTISRDNAK NTVYLQMNSLKTENTAVYYCANRAGWGMGDYWGQTQV TVSS | 46. | QTVVTQEPSLTVSPGGTVTLTCGLSSGSVTASNYPGWFQQ KPGQAPRALIYSTNDRHSGTPSRFSGSLSGGKAALTILGA QPEDEAEYYCALDIGDITEFGGGTKLTVLG | 310. |
| 104A5 | EVQLVESGGGLVQPGGSLRLSCAASGETFSSYRMSWVR QPPGKGLEWVSPISAGGGSTYYGDSVKGRFTISRDNAK NTVYLQMNSLKPEDTAVYYCANRAGWGMGDYWGQTQV TVSS | 47. | QTVVTQEPSLSVSPGGTVTLTCGLSSGSVTASNYPGWYQQ TPGQAPRALIYSTNDRHSGVPDRFSGSILGNKAALTITGA QPDDEADYYCALDIGDITEFGGGTQLTVLG | 311. |
| 104C1 | EVQLLESGGGLVQPGGSLRLSCAASGETFSSYAMYWVR QAPGKGLEWVSRISAGGGSTYYGDSVKGRFTISRDNAK NTVYLQMNSLKPEDTAVYYCANRAGWGMGDYWGQTQV TVSS | 48. | QTVVTQEPSFSVSPGGTVTLTCGLSSGSVTASNYPGWYQQ TPGQAPRALIYSTNDRHSGVPDRFSGSISGNKAALTITGA QADDESDYYCALDIGDITEFGGGTKLTVLG | 312. |
| 104C5 | EVQLVESGGGLVQPGGSLRLSCAASGETFSSYRMSWVR QPPGKGLEWVSAISAGGGSTYYGDSVKGRFTISRDNAK NTVYLQMNSLKPEDTAVYYCANRAGWGMGDYWGQTQV TVSS | 49. | QTVVTQEPSFSVSPGGTVTLTCGLSSGSVTASNYPGWYQQ TPGQAPRTLIYSTNDRHSGVPSRFSGSISGNKAALTITGA QPEDEADYYCALDIGDITEFGGGTHLTVLG | 313. |
| 104C7 | EVQLVESGGGLVQPGGSLRLSCAASGETFSSYAMYWVR QAPGKGLEWVSRISAGGGSTYYGDSVKGRFTISRDNSK NTVYLQMNSLKPEDTAVYYCANRAGWGMGDYWGQTQV TVSS | 50. | QTVVTQEPSFSVSPGGTVTLTCGLSSGSVTASNYPGWYQQ TPGQAPRALIYSTNDRHSGVPDRFSGSISGNKAALTITGA QADDESDYYCALDIGDITEFGGGTKLTVLG | 314. |
| 104D1 | EVQLVESGGGLVQPGGSLRLSCAASGETFSSYAMYWVR QAPGKGPEWVSRISAGGGSTYYGDSVKGRFTISRDNAK NTLYLQMNSLRAEDTAVYYCANRAGWGMGDYWGQTQV TVSS | 51. | QTVVTQEPSFSVSPGGTVTLTCGLSSGSVTASNYPGWYQQ TPGQAPRTLIYSTNDRHSGVPSRFSGSISGNKAALTITGA QPEDEADYYCALDIGDITEFGGGTHLTVLG | 315. |
| 104D5 | EVQLVESGGGLVQPGGSLRLSCAASGETFSSYAMSWVR QAPGKGLEWVSRISAGGGSTYYGDSVKGRFTISRDNSK NTLYLQMNSLKTEDTAVYYCANRAGWGMGDYWGQTQV TVSS | 52. | QTVVTQEPSFSVSPGGTVTLTCGLSSGSVTASNYPGWYQQ TPGQAPRALIYSTNDRHSGVPDRFSGSILGNKAALTITGA QAEDESDYYCALDIGDITEFGGGTHLTVLG | 316. |
| 104F11 | EVQLLESGGGLVQPGGSLRLSCAASGETFSSYAMSWVR QAPGKGPEWVSRISAGGGSTYYGDSVKGRFTISRDNAK NTVYLQMNSLRAEDTAVYYCANRAGWGMGDYWGQTQV TVSS | 53. | QTVVTQEPSLSVSPGGTVTLTCGLSSGSVTASNYPGWYQQ TPGQAPRALIYSTNDRHSGVPDRFSGSISGNKAALTITGA QPDDESDYYCALDIGDITEFGGGTQLTVLG | 317. |
| 104F7 | EVQLVESGGGLVQPGGSLRLSCAASGETFSSYAMYWVR QAPGKGPEWVSRISAGGGSTYYGDSVKGRFTISRDNSK NTVYLQMNSLKPEDTAVYYCANRAGWGMGDYWGQTQV TVSS | 54. | QTVVTQEPSFSVSPGGTVTLTCGLSSGSVTASNYPGWYQQ TPGQAPRALIYSTNDRHSGVPSRFSGSISGNKAALTITGA QAEDESDYYCALDIGDITEFGGGTHLTVLG | 318. |
| 104G7 | EVQLVESGGGLVQPGGSLRLSCAASGETFSSYAMSWVR QAPGKGPEWVSRISAGGGSTYYGDSVKGRFTISRDNSK NTLYLQMNSLRAEDTAVYYCANRAGWGMGDYWGQTQV TVSS | 55. | QTVVTQEPSFSVSPGGTVTLTCGLSSGSVTASNYPGWYQQ TPGQAPRTLIYSTNDRHSGVPSRFSGSILGNKAALTITGA QAEDEADYYCALDIGDITEFGGGTQLTVLG | 319. |
| 105A1 | EVQLVESGGGLVQPGGSLRLSCAASGETFSSYAMSWVR QAPGKGLEWVSRISAGGGSTYYGDSVKGRFTISRDNSK NTLYLQMNSLRAEDTAVYYCANRAGWGMGDYWGQTQV TVSS | 56. | QTVVTQEPSLSVSPGGTVTLTCGLSSGSVTASNYPGWYQQ TPGQAPRALIYSTNDRHSGVPSRFSGSISGNKAALTITGA QAEDEADYYCALDIGDITEFGGGTQLTVLG | 320. |

TABLE 15-continued

VH and VL Amino Acid Sequences of Exemplary Germlined Variants of Fab Clone 61H7.

| FAB CLONE | VH SEQUENCE | SEQ ID NO | VL SEQUENCE | SEQ ID NO |
|---|---|---|---|---|
| 105A5 | EVQLVESGGGLVQPGGSLRLSCAASGETFSSYAMSWVR QAPGKGLEWVSRISAGGGSTYYGDSVKGRFTISRDNSK NTVYLQMNSLKTEDTAVYYCANRAGWGMGDYWGQGTQV TVSS | 57. | QTVVTQEPSLSVSPGGTVTLTCGLSSGSVTASNYPGWFQQ TPGQAPRTLIYSTNDRHSGVPSRFSGSISGNKAALTITGA QADDEADYYCALDIGDITEFGGGTHLTVLG | 321. |
| 105A7 | EVQLLESGGGLVQPGGSLRLSCAASGETFSSYAMSWVR QAPGKGLEWVSRISAGGGSTYYGDSVKGRFTISRDNSK NTVYLQMNSLKPEDTAVYYCANRAGWGMGDYWGQGTQV TVSS | 58. | QAVVTQEPSLSVSPGGTVTLTCGLSSGSVTASNYPGWFQQ KPGQAPRALIYSTNDRHSGTPSRFSGSLSGNKAALTILGA QPEDEADYYCALDIGDITEFGGGTHLTVLG | 322. |
| 105B11 | EVQLVESGGGLVQPGGSLRLSCAASGETFSSYAMSWVR QAPGKGPEWVSRISSGGGSTYYGDSVKGRFTISRDNSK NTLYLQMNSLRAEDTAVYYCANRAGWGMGDYWGQGTQV TVSS | 59. | QAVVTQEPSLTVSPGGTVTLTCGLSSGSVTASNYPGWFQQ KPGQAPRALIYSTNDRHSGVPDRFSGSISGNKAALTITGA QPEDEAEYYCALDIGDITEFGGGTHLTVLG | 323. |
| 105B5 | EVQLVESGGGLVQPGGSLRLSCAASGETFSSYAMYWVR QPPGKGPEWVSRISAGGGSTYYGDSVKGRFTISRDNSK NTLYLQMNSLKPEDTAVYYCANRAGWGMGDYWGQGTQV TVSS | 60. | QTVVTQEPSLTVSPGGTVTLTCGLSSGSVTASNYPGWFQQ TPGQAPRALIYSTNDRHSGVPARFSGSISGGKAALTLLGA QPEDEAEYYCALDIGDITEFGGGTHLTVLG | 324. |
| 105B7 | EVQLVESGGGLVQPGGSLRLSCAASGETFSSYAMSWVR QAPGKGPEWVSRISSGGGSTYYGDSVKGRFTISRDNAK NTVYLQMNSLRAEDTAVYYCANRAGWGMGDYWGQGTLV TVSS | 61. | QTVVTQEPSLTVSPGGTVTLTCGLSSGSVTASNYPGWFQQ KPGQAPRALIYSTNDRHSGVPARFSGSLLGGKAALTILGA QADDEAEYYCALDIGDITEFGGGTQLTVLG | 325. |
| 105C1 | EVQLVESGGGLVQPGGSLRLSCAASGETFSSYAMYWVR QAPGKGLEWVSRISAGGGSTYYGDSVKGRFTISRDNSK NTVYLQMNSLKPEDTAVYYCANRAGWGMGDYWGQGTLV TVSS | 62. | QTVVTQEPSLSVSPGGTVTLTCGLSSGSVTASNYPGWFQQ TPGQAPRALIYSTNDRHSGVPARFSGSLSGKAALTITGA QAEDEAEYYCALDIGDITEFGGGTQLTVLG | 326. |
| 105C7 | EVQLLESGGGLVQPGGSLRLSCAASGETFSSYAMSWVR QAPGKGPEWVSRISSGGGSTYYGDSVKGRFTISRDNAK NTVYLQMNSLKTEDTAVYYCANRAGWGMGDYWGQGTLV TVSS | 63. | QTVVTQEPSFSVSPGGTVTLTCGLSSGSVTASNYPGWFQQ KPGQAPRALIYSTNDRHSWVPARFSGSLSGKAALTLLGA QPEDEAEYYCALDIGDITEFGGGTHLTVLG | 327. |
| 105D1 | ELQLVESGGGLVQPGGSLRLSCAASGETFSSYRMSWVR QAPGKGPEWVSAISAGGGSTYYGDSVKGRFTISRDNSK NTLYLQMNSLRAEDTAVYYCANRAGWGMGDYWGQGTQV TVSS | 64. | QTVVTQEPSLTVSPGGTVTLTCGLSSGSVTASNYPGWFQQ KPGQAPRALIYSTNDRHSWVPARFSGSLSGNKAALTLTGA QPEDEAEYYCALDIGDITEFGGGTHLTVLG | 328. |
| 105E5 | EVQLVESGGGLVQPGGSLRLSCAASGETFSSYAMYWVR QAPGKGPEWVSRISAGGGSTYYGDSVKGRFTISRDNSK NTVYLQMNSLKTEDTAVYYCANRAGWGMGDYWGQGTQV TVSS | 65. | QAVVTQEPSLSVSPGGTVTLTCGLSSGSVTASNYPGWFQQ KPGQAPRALIYSTNDRHSGVPARFSGSISGGKAALTLLGA QPDDEAEYYCALDIGDITEFGGGTKLTVLG | 329. |
| 105G1 | ELQLLESGGGLVQPGGSLRLSCAASGETFSSYAMSWVR QAPGKGPEWVSRISAGGGSTYYGDSVKGRFTISRDNAK NTLYLQMNSLKPEDTAVYYCANRAGWGMGDYWGQGTQV TVSS | 66. | QTVVTQEPSLTVSPGGTVTLTCGLSSGSVTASNYPGWFQQ KPGQAPRALIYSTNDRHSWVPSRFSGSLSGGKAALTLLGA QPEDEAEYYCALDIGDITEFGGGTQLTVLG | 330. |
| 105H11 | EVQLVESGGGLVQPGGSLRLSCAASGETFSSYAMSWVR QAPGKGPEWVSRISSGGGSTYYGDSVKGRFTISRDNSK NTLYLQMNSLRAEDTAVYYCANRAGWGMGDYWGQGTQV TVSS | 67. | QTVVTQEPSLSVSPGGTVTLTCGLSSGSVTASNYPGWFQQ TPGQAPRALIYSTNDRHSGVPARFSGSISGGKAALTLLGA QPEDEAEYYCALDIGDITEFGGGTQLTVLG | 331. |
| 105H5 | EVQLVESGGGLVQPGGSLRLSCAASGETFSSYRMSWVR QAPGKGPEWVSAISSGGGSTYYGDSVKGRFTISRDNSK NTVYLQMNSLKPEDTAVYYCANRAGWGMGDYWGQGTLV TVSS | 68. | QAVVTQEPSLSVSPGGTVTLTCGLSSGSVTASNYPGWFQQ TPGQAPRALIYSTNDRHSGVPARFSGSILGGKAALTILGA QPNDEAEYYCALDIGDITEFGGGTHLTVLG | 332. |
| 98C10 | EVQLVESGGGLVQPGGSLRLSCAASGETFSSYAMYWVR QPPGKGLEWVSRISAGGGSTYYGDSVKGRFTISRDNSK NTVYLQMNSLKPEDTAVYYCANRAGWGMGDYWGQGTQV TVSS | 69. | QTVVTQEPSLTVSPGGTVTLTCGLSSGSVTASNYPGWFQQ KPGQAPRALIYSTNDRHSGVPARFSGSLLGGKAALTILGA QADDEAEYYCALDIGDITEFGGGTQLTVLG | 333. |
| 98E10 | ELQLVESGGGLVQPGGSLRLSCAASGETFSSYAMYWVR QPPGKGLEWVSRISAGGGSTYYGDSVKGRFTISRDNSK NTVYLQMNSLKTEDTAVYYCANRAGWGMGDYWGQGTQV TVSS | 70. | QTVVTQEPSLSVSPGGTVTLTCGLSSGSVTASNYPGWFQQ KPGQAPRALIYSTNDRHSGVPARFSGSLSGNKAALTITGA QADDEADYYCALDIGDITEFGGGTQLTVLG | 334. |

TABLE 15-continued

VH and VL Amino Acid Sequences of Exemplary Germlined Variants of Fab Clone 61H7.

| FAB CLONE | VH SEQUENCE | SEQ ID NO | VL SEQUENCE | SEQ ID NO |
|---|---|---|---|---|
| 98F2 | EVQLVESGGGLVQPGGSLRLSCAASGETFSSYAMYWVR QPPGKGPEWVSRISAGGGSTYYGDSVKGRFTISRDNAK NTLYLQMNSLKTEDTAVYYCANRAGWGMGDYWGQTQV TVSS | 71. | QAVVTQEPSLTVSPGGTVTLTCGLSSGSVTASNYPGWFQQ TPGQAPRALIYSTNDRHSGTPARESGSLSGNKAALTITGA QPEDEADYYCALDIGDITEFGGGTKLTVLG | 335. |
| 99C10 | ELQLLESGGGLVQPGGSLRLSCAASGETFSSYAMYWVR QAPGKGLEWVSRISAGGGSTYYGDSVKGRFTISRDNSK NTVYLQMNSLKPEDTAVYYCANRAGWGMGDYWGQTLV TVST | 72. | QTVVTQEPSLSVSPGGTVTLTCGLSSGSVTASNYPGWFQQ KPGQAPRALIYSTNDRHSWVPARFSGSISGGKAALTLTGA QPEDEAEYYCALDIGDITEFGGGTQLTVLG | 336. |
| 104G5 | EVQLVESGGGLVQPGGSLRLSCAASGETFSSYRMSWVR QAPGKGPEWVSAISSGGGSTYYGDSVKGRFTISRDNAK NTVYLQMNSLRAEDTAVYYCANRAGWGMGDYWGQTQV TVSS | 73. | QTVVTQEPSFSVSPGGTVTLTCGLSSGSVTASNYPGWYQQ TPGQAPRALIYSTNDRHSGVPDRFSGSILGNKAALTITGA QADDESDYYCALDIGDITEFGGGTHLTVLG | 337. |
| 108A1 | EVQLVESGGGLVQPGGSLRLSCAASGETFSSYRMSWVR QAPGKGLEWVSAISAGGGSTYYGDSVKGRFTISRDNAK NTLYLQMNSLRAEDTAVYYCANRAGWGMGDYWGQTQV TVSS | 74. | QTVVTQEPSFSVSPGGTVTLTCGLSSGSVTASNYPGWYQQ TPGQAPRALIYSTNDRHSGVPSRFSGSISGNKAALTITGA QAEDEADYYCALDIGDITEFGGGTKLTVL | 338. |
| 108A3 | EVQLVESGGGLVQPGGSLRLSCAASGETFSSYRMSWVR QAPGKGPEWVSAISAGGGSTYYGDSVKGRFTISRDNSK NTLYLQMNSLRAEDTAVYYCANRAGWGMGDYWGQTQV TVSS | 75. | QTVVTQEPSFSVSPGGTVTLTCGLSSGSVTASNYPGWYQQ TPGQAPRALIYSTNDRHSGVPSRFSGSILGNKAALTITGA QAEDEADYYCALDIGDITEFGGGTHLTVL | 339. |
| 108A5 | EVQLVESGGGLVQPGGSLRLSCAASGETFSSYRMSWVR QPPGKGPEWVSAISAGGGSTYYGDSVKGRFTISRDNAK NTLYLQMNSLKPEDTAVYYCANRAGWGMGDYWGQTQV TVSS | 76. | QTVVTQEPSFSVSPGGTVTLTCGLSSGSVTASNYPGWFQQ TPGQAPRTLIYSTNDRHSGVPSRFSGSILGNKAALTITGA QPEDESDYYCALDIGDITEFGGGTHLTVL | 340. |
| 108A9 | EVQLLESGGGLVQPGGSLRLSCAASGETFSSYRMYWVR QAPGKGLEWVSAISAGGGSTYYGDSVKGRFTISRDNSK NTVYLQMNSLKPEDTAVYYCAKRAGWGMGDYWGQTQV TVSS | 77. | QAVVTQEPSLSVSPGGTVTLTCGLSSGSVTASNYPGWFQQ TPGQAPRALIYSTNDRHSGTPARESGSLSGNKAALTILGA QPEDEADYYCALDIGDITEFGGGTQLTVL | 341. |
| 108B1 | EVQLLESGGGLVQPGGSLRLSCAASGETFSSYRMSWVR QPPGKGPEWVSAISAGGGSTYYGDSVKGRFTISRDNSK NTVYLQMNSLRAEDTAVYYCANRAGWGMGDYWGQTQV TVSS | 78. | QTVVTQEPSFSVSPGGTVTLTCGLSSGSVTASNYPGWYQQ TPGQAPRALIYSTNDRHSGVPSRFSGSILGNKAALTITGA QAEDESDYYCALDIGDITEFGGGTHLTVL | 342. |
| 108B3 | EVQLLESGGGLVQPGGSLRLSCAASGETFSSYAMSWVR QAPGKGPEWVSRISAGGGSTYYGDSVKGRFTISRDNSK NTLYLQMNSLKPEDTAVYYCANRAGWGMGDYWGQTQV TVSS | 79. | QTVVTQEPRLSVSPGGTVTLTCGLSSGSVTASNYPGWYQQ TPGQAPRALIYSTNDRHSGVPDRFSGSISGNKAALTITGA QADDEADYYCALDIGDITEFGGGTQLTVL | 343. |
| 108B7 | EVQLVESGGGLVQPGGSLRLSCAASGETFSSYRMSWVR QAPGKGPEWVSAISAGGGSTYYGDSVKGRFTISRDNAK NTLYLQMNSLKPEDTAVYYCANRAGWGMGDYWGQTLV TVSS | 80. | QTVVTQEPSLTVSPGGTVTLTCGLSSGSVTASNYPGWFQQ TPGQAPRALIYSTNDRHSWVPARFSGSLSGGKAALTILGA QPEDEAEYYCALDIGDITEFGGGTHLTVL | 344. |
| 108B9 | EVQLLESGGGLVQPGGSLRLSCAASGETFSSYAMSWVR QAPGKGPEWVSRISAGGGSTYYGDSVKGRFTISRDNSK NTLYLQMNSLKPEDTAVYYCANRAGWGMGDYWGQTQV TVSS | 81. | QAVVTQEPSLSVSPGGTVTLTCGLSSGSVTASNYPGWFQQ KPGQAPRALIYSTNDRHSGVPARFSGSLSGNKAALTILGA QPEDEADYYCALDIGDITEFGGGTQLTVL | 345. |
| 108C5 | EVQLLESGGGLVQPGGSLRLSCAASGETFSSYRMSWVR QAPGKGLEWVSAISAGGGSTYYGDSVKGRFTISRDNSK NTLYLQMNSLKPEDTAVYYCANRAGWGMGDYWGQTQV TVSS | 82. | QTVVTQEPSFSVSPGGTVTLTCGLSSGSVTASNYPGWFQQ TPGQAPRTLIYSTNDRHSGVPDRFSGSISGNKAALTITGA QAEDESDYYCALDIGDITEFGGGTHLTVL | 346. |
| 108C9 | ELQLLESGGGLVQPGGSLRLSCAASGETFSSYAMYWVR QAPGKGLEWVSRISAGGGSTYYGDSVKGRFTISRDNSK NTLYLQMNSLRAEDTAVYYCANRAGWGMGDYWGQTQV TVSS | 83. | QTVVTQEPSLSVSPGGTVTLTCGLSSGSVTASNYPGWFQQ KPGQAPRALIYSTNDRHSGVPSRFSGSLSGNKAALTLTGA QPEDEAEYYCALDIGDITEFGGGTQLTVL | 347. |
| 111A11 | EVQLLESGGGLVQPGGSLRLSCAASGETFSSYRMSWVR QAPGKGLEWVSAISAGGGSTYYGDSVKGRFTISRDNSK NTLYLQMNSLKPEDTAVYYCANRAGWGMGDYWGQTLV TVSS | 84. | QTVVTQEPSFSVSPGGTVTLTCGLSSGSVTASNYPGWYQQ TPGQAPRALIYSTNDRHSGVPSRFSGSILGNKAALTITGA QAEDEADYYCALDIGDITEFGGGTHLTVL | 348. |

TABLE 15-continued

VH and VL Amino Acid Sequences of Exemplary Germlined Variants of Fab Clone 61H7.

| FAB CLONE | VH SEQUENCE | SEQ ID NO | VL SEQUENCE | SEQ ID NO |
|---|---|---|---|---|
| 111A5 | EVQLLESGGGLVQPGGSLRLSCAASGETFSSYAMYWVR QPPGKGPEWVSRISSGGGSTYYGDSVKGRFTISRDNSK NTLYLQMNSLKPEDTAVYYCAKRAGWGMGDYWGQGTQV TVSS | 85. | QTVVTQEPSLSVSPGGTVTLTCGLSSGSVTASNYPGWYQQ TPGQAPRTLIYSTNDRHSGVPDRFSGSISGNKAALTITGA QADDESDYYCALDIGDITEFGGGTKLTVL | 349. |
| 111A7 | EVQLLESGGGLVQPGGSLRLSCAASGETFSSYAMSWVR QAPGKGPEWVSRISAGGGSTYYGDSVKGRFTISRDNSK NTLYLQMNSLRAEDTAVYYCANRAGWGMGDYWGQGTLV TVSS | 86. | QTVVTQEPSFSVSPGGTVTLTCGLSSGSVTASNYPGWYQQ TPGQAPRALIYSTNDRHSGVPDRFSGSISGNKAALTITGA QAEDEADYYCALDIGDITEFGGGTQLTVL | 350. |
| 111B1 | EVQLLESGGGLVQPGGSLRLSCAASGETFSSYAMYWVR QPPGKGLEWVSRISAGGGSTYYGDSVKGRFTISRDNSK NTLYLQMNSLRAEDTAVYYCANRAGWGMGDYWGQGTLV TVSS | 87. | QTVVTQEPSFSVSPGGTVTLTCGLSSGSVTASNYPGWFQQ TPGQAPRALIYSTNDRHSGVPDRFSGSILGNKAALTITGA QAEDEADYYCALDIGDITEFGGGTQLTVL | 351. |
| 111B11 | EVQLLESGGGLVQPGGSLRLSCAASGETFSSYAMSWVR QAPGKGPEWVSRISAGGGSTYYGDSVKGRFTISRDNSK NTVYLQMNSLKPEDTAVYYCANRAGWGMGDYWGQGTQV TVSS | 88. | QTVVTQEPSLSVSPGGTVTLTCGLSSGSVTASNYPGWYQQ TPGQAPRALIYSTNDRHSGVPDRFSGSISGNKAALTITGA QPDDESDYYCALDIGDITEFGGGTKLTVL | 352. |
| 111B5 | EVQLLESGGGLVQPGGSLRLSCAASGETFSSYRMSWVR QAPGKGLEWVSAISSGGGSTYYGDSVKGRFTISRDNSK NTVYLQMNSLKTEDTAVYYCANRAGWGMGDYWGQGTQV TVSS | 89. | QTVVTQEPSFSVSPGGTVTLTCGLSSGSVTASNYPGWYQQ TPGQAPRALIYSTNDRHSGVPDRFSGSISGNKAALTITGA QAEDEADYYCALDIGDITEFGGGTQLTVL | 353. |
| 111B7 | ELQLLESGGGLVQPGGSLRLSCAASGETFSSYAMSWVR QAPGKGPEWVSRISAGGGSTYYGDSVKGRFTISRDNAK NTLYLQMNSLKPEDTAVYYCANRAGWGMGDYWGQGTQV TVSS | 90. | QTVVTQEPSFSVSPGGTVTLTCGLSSGSVTASNYPGWYQQ TPGQAPRALIYSTNDRHSGVPSRFSGSILGNKAALTITGA QPEDESDYYCALDIGDITEFGGGTHLTVL | 354. |
| 111C11 | EVQLLESGGGLVQPGGSLRLSCAASGETFSSYAMSWVR QAPGKGPEWVSRISAGGGSTYYGDSVKGRFTISRDNSK NTLYLQMNSLKPEDTAVYYCANRAGWGMGDYWGQGTLV TVSS | 91. | QTVVTQEPSFSVSPGGTVTLTCGLSSGSVTASNYPGWYQQ TPGQAPRALIYSTNDRHSGVPSRFSGSISGNKAALTITGA QPEDESDYYCALDIGDITEFGGGTQLTVL | 355. |
| 111C5 | EVQLVESGGGLVQPGGSLRLSCAASGETFSSYRMYWVR QAPGKGPEWVSAISAGGGSTYYGDSVKGRFTISRDNSK NTLYLQMNSLKPEDTAVYYCANRAGWGMGDYWGQGTQV TVSS | 92. | QTVVTQEPSLSVSPGGTVTLTCGLSSGSVTASNYPGWYQQ TPGQAPRTLIYSTNDRHSGVPDRFSGSISGNKAALTITGA QPDDEADYYCALDIGDITEFGGGTHLTVL | 356. |
| 111C9 | EVQLLESGGGLVQPGGSLRLSCAASGETFSSYAMSWVR QAPGKGPEWVSRISSGGGSTYYGDSVKGRFTISRDNSK NTVYLQMNSLKPEDTAVYYCANRAGWGMGDYWGQGTQV TVSS | 93. | QTVVTQEPSFSVSPGGTVTLTCGLSSGSVTASNYPGWFQQ TPGQAPRALIYSTNDRHSGVPDRFSGSISGNKAALTITGA QPDDEADYYCALDIGDITEFGGGTKLTVL | 357. |
| 111D7 | ELQLLESGGGLVQPGGSLRLSCAASGETFSSYAMYWVR QPPGKGLEWVSRISSGGGSTYYGDSVKGRFTISRDNAK NTLYLQMNSLKTEDTAVYYCANRAGWGMGDYWGQGTQV TVSS | 94. | QTVVTQEPSLSVSPGGTVTLTCGLSSGSVTASNYPGWYQQ TPGQAPRALIYSTNDRHSGVPSRFSGSISGNKAALTITGA QADDESDYYCALDIGDITEFGGGTHLTVL | 358. |
| 111D9 | EVQLVESGGGLVQPGGSLRLSCAASGETFSSYAMYWVR QAPGKGPEWVSRISAGGGSTYYGDSVKGRFTISRDNAK NTVYLQMNSLKPEDTAVYYCANRAGWGMGDYWGQGTQV TVSS | 95. | QTVVTQEPSFSVSPGGTVTLTCGLSSGSVTASNYPGWFQQ TPGQAPRALIYSTNDRHSGVPSRFSGSISGNKAALTITGA QAEDEADYYCALDIGDITEFGGGTKLTVL | 359. |
| 111E11 | EVQLVESGGGLVQPGGSLRLSCAASGETFSSYAMYWVR QAPGKGPEWVSRISAGGGSTYYGDSVKGRFTISRDNSK NTLYLQMNSLKPEDTAVYYCANRAGWGMGDYWGQGTLV TVSS | 96. | QTVVTQEPSFSVSPGGTVTLTCGLSSGSVTASNYPGWFQQ TPGQAPRALIYSTNDRHSGVPDRFSGSILGNKAALTITGA QPEDESDYYCALDIGDITEFGGGTQLTVL | 360. |
| 111E7 | EVQLLESGGGLVQPGGSLRLSCAASGETFSSYAMYWVR QAPGKGPEWVSRISAGGGSTYYGDSVKGRFTISRDNSK NTLYLQMNSLKPEDTAVYYCANRAGWGMGDYWGQGTQV TVSS | 97. | QTVVTQEPSFSVSPGGTVTLTCGLSSGSVTASNYPGWYQQ TPGQAPRALIYSTNDRHSGVPDRFSGSISGNKAALTITGA QPDDEADYYCALDIGDITEFGGGTHLTVL | 361. |
| 111E9 | EVQLLESGGGLVQPGGSLRLSCAASGETFSSYAMSWVR QAPGKGPEWVSRISSGGGSTYYGDSVKGRFTISRDNAK NTVYLQMNSLRAEDTAVYYCANRAGWGMGDYWGQGTQV TVSS | 98. | QTVVTQEPSFSVSPGGTVTLTCGLSSGSVTASNYPGWYQQ TPGQAPRALIYSTNDRHSGVPSRFSGSISGNKAALTITGA QAEDEADYYCALDIGDITEFGGGTKLTVL | 362. |
| 111F11 | EVQLVESGGGLVQPGGSLRLSCAASGETFSSYAMYWVR QAPGKGPEWVSRISSGGGSTYYGDSVKGRFTISRDNAK NTVYLQMNSLKTEDTAVYYCANRAGWGMGDYWGQGTQV TVSS | 99. | QTVVTQEPSFSVSPGGTVTLTCGLSSGSVTASNYPGWYQQ TPGQAPRTLIYSTNDRHSGVPDRFSGSISGNKAALTITGA QPDDESDYYCALDIGDITEFGGGTQLTVL | 363. |

TABLE 15-continued

VH and VL Amino Acid Sequences of Exemplary Germlined Variants of Fab Clone 61H7.

| FAB CLONE | VH SEQUENCE | SEQ ID NO | VL SEQUENCE | SEQ ID NO |
|---|---|---|---|---|
| 111F7 | EVQLLESGGGLVQPGGSLRLSCAASGETFSSYAMSWVR QAPGKGPEWVSRISAGGGSTYYGDSVKGRFTISRDNAK NTVYLQMNSLKTEDTAVYYCANRAGWGMGDYWGQGTQV TVSS | 100. | QTVVTQEPSFSVSPGGTVTLTCGLSSGSVTASNYPGWYQQ TPGQAPRALIYSTNDRHSGVPDRFSGSISGNKAALTITGA QADDESDYYCALDIGDITEFGGGTKLTVL | 364. |
| 111F9 | EVQLVESGGGLVQPGGSLRLSCAASGETFSSYRMYWVR QAPGKGLEWVSAISAGGGSTYYGDSVKGRFTISRDNSK NTVYLQMNSLRAEDTAVYYCANRAGWGMGDYWGQGTLV TVSS | 101. | QTVVTQEPSFSVSPGGTVTLTCGLSSGSVTASNYPGWYQQ TPGQAPRALIYSTNDRHSGVPDRFSGSILGNKAALTITGA QPEDEADYYCALDIGDITEFGGGTKLTVL | 365. |
| 111G1 | EVQLLESGGGLVQPGGSLRLSCAASGETFSSYAMYWVR QAPGKGPEWVSRISAGGGSTYYGDSVKGRFTISRDNSK NTVYLQMNSLKPEDTAVYYCANRAGWGMGDYWGQGTLV TVSS | 102. | QTVVTQEPSLSVSPGGTVTLTCGLSSGSVTASNYPGWYQQ TPGQAPRALIYSTNDRHSGVPSRFSGSILGNKAALTITGA QADDEADYYCALDIGDITEFGGGTHLTVL | 366. |
| 111G11 | EVQLVESGGGLVQPGGSLRLSCAASGETFSSYRMSWVR QAPGKGLEWVSAISAGGGSTYYGDSVKGRFTISRDNAK NTVYLQMNSLKTEDTAVYYCANRAGWGMGDYWGQGTQV TVSS | 103. | QTVVTQEPSFSVSPGGTVTLTCGLSSGSVTASNYPGWYQQ TPGQAPRALIYSTNDRHSGVPDRFSGSISGNKAALTITGA QADDESDYYCALDIGDITEFGGGTHLTVL | 367. |
| 111G7 | EVQLLESGGGLVQPGGSLRLSCAASGETFSSYAMYWVR QPPGKGPEWVSRISAGGGSTYYGDSVKGRFTISRDNAK NTVYLQMNSLKPEDTAVYYCANRAGWGMGDYWGQGTQV TVSS | 104. | QTVVTQEPSLSVSPGGTVTLTCGLSSGSVTASNYPGWYQQ TPGQAPRALIYSTNDRHSGVPDRFSGSISGNKAALTITGA QPDDESDYYCALDIGDITEFGGGTHLTVL | 368. |
| 111G9 | EVQLVESGGGLVQPGGSLRLSCAASGETFSSYRMYWVR QAPGKGLEWVSAISSGGGSTYYGDSVKGRFTISRDNAK NTVYLQMNSLKPEDTAVYYCANRAGWGMGDYWGQGTQV TVSS | 105. | QTVVTQEPSLSVSPGGTVTLTCGLSSGSVTASNYPGWYQQ TPGQAPRALIYSTNDRHSGVPSRFSGSILGNKAALTITGA QPEDEADYYCALDIGDITEFGGGTHLTVL | 369. |
| 111H7 | EVQLVESGGGLVQPGGSLRLSCAASGETFSSYAMYWVR QPPGKGPEWVSRISAGGGSTYYGDSVKGRFTISRDNSK NTVYLQMNSLKTEDTAVYYCANRAGWGMGDYWGQGTQV TVSS | 106. | QTVVTQEPSFSVSPGGTVTLTCGLSSGSVTASNYPGWYQQ TPGQAPRALIYSTNDRHSGVPSRFSGSILGNKAALTITGA QPDDEADYYCALDIGDITEFGGGTHLTVL | 370. |
| 111H9 | EVQLVESGGGLVQPGGSLRLSCAASGETFSSYRMSWVR QAPGKGLEWVSAISAGGGSTYYGDSVKGRFTISRDNAK NTVYLQMNSLKPEDTAVYYCANRAGWGMGDYWGQGTLV TVSS | 107. | QTVVTQEPSLSVSPGGTVTLTCGLSSGSVTASNYPGWFQQ TPGQAPRALIYSTNDRHSGVPDRFSGSISGNKAALTITGA QADDEADYYCALDIGDITEFGGGTHLTVL | 371. |
| 112A11 | EVQLVESGGGLVQPGGSLRLSCAASGETFSSYAMSWVR QAPGKGPEWVSRISSGGGSTYYGDSVKGRFTISRDNSK NTLYLQMNSLRAEDTAVYYCANRAGWGMGDYWGQGTQV TVSS | 108. | QTVVTQEPSLTVSPGGTVTLTCGLSSGSVTASNYPGWFQQ KPGQAPRALIYSTNDRHSGVPARFSGSLLGGKAALTILGA QADDEAEYYCALDIGDITEFGGGTQLTVL | 372. |
| 112A4 | EVQLVESGGGLVQPGGSLRLSCAASGETFSSYRMSWVR QAPGKGLEWVSAISAGGGSTYYGDSVKGRFTISRDNAK NTLYLQMNSLRAEDTAVYYCANRAGWGMGDYWGQGTQV TVSS | 109. | QTVVTQEPSLTVSPGGTVTLTCGLSSGSVTASNYPGWFQQ KPGQAPRALIYSTNDRHSWVPARFSGSISGGKAALTILGA QPEDEAEYYCALDIGDITEFGGGTQLTVL | 373. |
| 112A7 | EVQLVESGGGLVQPGGSLRLSCAASGETFSSYAMYWVR QAPGKGPEWVSRISSGGGSTYYGDSVKGRFTISRDNSK NTVYLQMNSLKPEDTAVYYCANRAGWGMGDYWGQGTQV TVSS | 110. | QTVVTQEPSLSVSPGGTVTLTCGLSSGSVTASNYPGWFQQ KPGQAPRALIYSTNDRHSGVPARFSGSLSGGKAALTILGA QPEDEADYYCALDIGDITEFGGGTHLTVL | 374. |
| 112B1 | EVQLLESGGGLVQPGGSLRLSCAASGETFSSYRMSWVR QAPGKGLEWVSAISAGGGSTYYGDSVKGRFTISRDNAK NTLYLQMNSLKPEDTAVYYCANRAGWGMGDYWGQGTLV TVSS | 111. | QTVVTQEPSLTVSPGGTVTLTCGLSSGSVTASNYPGWFQQ KPGQAPRALIYSTNDRHSWVPARFSGSLLGGKAALTITGA QPEDEAEYYCALDIGDITEFGGGTHLTVL | 375. |
| 112B11 | EVQLVESGGGLVQPGGSLRLSCAASGETFSSYAMSWVR QAPGKGPEWVSRISAGGGSTYYGDSVKGRFTISRDNAK NTVYLQMNSLKPEDTAVYYCANRAGWGMGDYWGQGTLV TVSS | 112. | QTVVTQEPSLTVSPGGTVTLTCGLSSGSVTASNYPGWFQQ KPGQAPRALIYSTNDRHSWVPARFSGSLSGGKAALTLTGA QPEDEAEYYCALDIGDITEFGGGTHLTVL | 376. |
| 112C11 | EVQLVESGGGLVQPGGSLRLSCAASGFTFSSYRLYWVR QPPGKGPEWVSAISAGGGSTYYGDSVKGRFTISRDNAK NTVYLQMNSLKPEDTAVYYCANRAGWGMGDYWGQGTQV TVSS | 113. | QTVVTQEPSLTVSPGGTVTLTCGLSSGSVTASNYPGWFQQ KPGQAPRALIYSTNDRHSWVPSRFSGSLSGGKAALTILGA QPEDEAEYYCALDIGDITEFGGGTQLTVL | 377. |

TABLE 15-continued

VH and VL Amino Acid Sequences of Exemplary Germlined Variants of Fab Clone 61H7.

| FAB CLONE | VH SEQUENCE | SEQ ID NO | VL SEQUENCE | SEQ ID NO |
|---|---|---|---|---|
| 112C7 | EVQLVESGGGLVQPGGSLRLSCAASGETFSSYAMYWVR QPPGKGPEWVSRISAGGGSTYYGDSVKGRFTISRDNAK NTLYLQMNSLKPEDTAVYYCANRAGWGMGDYWGQGTQV TVSS | 114. | QTVVTQEPSLTVSPGGTVTLTCGLSSGSVTASNYPGWFQQ TPGQAPRALIYSTNDRHSGVPARFSGSLSGGKAALTITGA QPEDEADYYCALDIGDITEFGGGTHLTVL | 378. |
| 112C9 | EVQLLESGGGLVQPGGSLRLSCAASGETFSSYAMYWVR QAPGKGPEWVSRISAGGGSTYYGDSVKGRFTISRDNAK NTLYLQMNSLRAEDTAVYYCANRAGWGMGDYWGQGTLV TVSS | 115. | QAVVTQEPSLTVSPGGTVTLTCGLSSGSVTASNYPGWFQQ TPGQAPRALIYSTNDRHSGVPARFSGSLSGNKAALTITGA QAEDEAEYYCALDIGDITEFGGGTHLTVL | 379. |
| 112D11 | EVQLLESGGGLVQPGGSLRLSCAASGETFSSYRMSWVR QPPGKGPEWVSAISSGGGSTYYGDSVKGRFTISRDNSK NTLYLQMNSLKPEDTAVYYCANRAGWGMGDYWGQGTQV TVSS | 116. | QTVVTQEPSLSVSPGGTVTLTCGLSSGSVTASNYPGWFQQ KPGQAPRALIYSTNDRHSGVPARFSGSLLGGKAALTLTGA QPEDEAEYYCALDIGDITEFGGGTQLTVL | 380. |
| 112D7 | EVQLVESGGGLVQPGGSLRLSCAASGETFSSYRMSWVR QAPGKGPEWVSAISSGGGSTYYGDSVKGRFTISRDNAK NTLYLQMNSLKPEDTAVYYCANRAGWGMGDYWGQGTLV TVSS | 117. | QTVVTQEPSLTVSPGGTVTLTCGLSSGSVTASNYPGWFQQ TPGQAPRALIYSTNDRHSWVPSRFSGSLLGGKAALTLTGA QPEDEAEYYCALDIGDITEFGGGTQLTVL | 381. |
| 112D9 | EVQLLESGGGLVQPGGSLRLSCAASGETFSSYAMYWVR QPPGKGLEWVSRISSGGGSTYYGDSVKGRFTISRDNAK NTVYLQMNSLKPEDTAVYYCANRAGWGMGDYWGQGTQV TVSS | 118. | QTVVTQEPSLTVSPGGTVTLTCGLSSGSVTASNYPGWFQQ KPGQAPRALIYSTNDRHSGVPSRFSGSLLGGKAALTLLGA QPEDEAEYYCALDIGDITEFGGGTQLTVL | 382. |
| 112E11 | EVQLVESGGGLVQPGGSLRLSCAASGETFSSYAMSWVR QAPGKGPEWVSRISAGGGSTYYGDSVKGRFTISRDNAK NTLYLQMNSLKTEDTAVYYCANRAGWGMGDYWGQGTQV TVSS | 119. | QTVVTQEPSLTVSPGGTVTLTCGLSSGSVTASNYPGWFQQ TPGQAPRALIYSTNDRHSWVPARFSGSLSGGKAALTITGA QPEDEADYYCALDIGDITEFGGGTKLTVL | 383. |
| 112E4 | EVQLVESGGGLVQPGGSLRLSCAASGETFSSYRMYWVR QPPGKGPEWVSAISSGGGSTYYGDSVKGRFTISRDNAK NTVYLQMNSLKTEDTAVYYCANRAGWGMGDYWGQGTQV TVSS | 120. | QAVVTQEPSLSVSPGGTVTLTCGLSSGSVTASNYPGWFQQ TPGQAPRALIYSTNDRHSWVPARFSGSLLGGKAALTITGA QPEDEAEYYCALDIGDITEFGGGTHLTVL | 384. |
| 112E7 | EVQLLESGGGLVQPGGSLRLSCAASGETFSSYAMYWVR QAPGKGLEWVSRISSGGGSTYYGDSVKGRFTISRDNSK NTLYLQMNSLKPEDTAVYYCANRAGWGMGDYWGQGTQV TVSS | 121. | QTVVTQEPSLSVSPGGTVTLTCGLSSGSVTASNYPGWFQQ TPGQAPRALIYSTNDRHSGVPARFSGSILGGKAALTILGA QPEDEAEYYCALDIGDITEFGGGTHLTVL | 385. |
| 112F11 | EVQLLESGGGLVQPGGSLRLSCAASGETFSSYAMSWVR QAPGKGPEWVSRISSGGGSTYYGDSVKGRFTISRDNAK NTVYLQMNSLKTEDTAVYYCANRAGWGMGDYWGQGTLV TVSS | 122. | QTVVTQEPSLTVSPGGTVTLTCGLSSGSVTASNYPGWFQQ TPGQAPRALIYSTNDRHSGVPSRFSGSILGGKAALTLTGA QPEDEAEYYCALDIGDITEFGGGTQLTVL | 386. |
| 112G11 | EVQLLESGGGLVQPGGSLRLSCAASGETFSSYAMSWVR QAPGKGLEWVSRISAGGGSTYYGDSVKGRFTISRDNSK NTVYLQMNSLKPEDTAVYYCANRAGWGMGDYWGQGTQV TVSS | 123. | QTVVTQEPSLSVSPGGTVTLTCGLSSGSVTASNYPGWFQQ TPGQAPRALIYSTNDRHSGVPARFSGSISGGKAALTLLGA QPEDEAEYYCALDIGDITEFGGGTQLTVL | 387. |
| 112G4 | EVQLLESGGGLVQPGGSLRLSCAASGETFSSYAMYWVR QPPGKGLEWVSRISAGGGSTYYGDSVKGRFTISRDNAK NTVYLQMNSLRAEDTAVYYCANRAGWGMGDYWGQGTLV TVSS | 124. | QTVVTQEPSLSVSPGGTVTLTCGLSSGSVTASNYPGWFQQ KPGQAPRALIYSTNDRHSGVPARFSGSISGGKAALTLLGA QAEDEAEYYCALDIGDITEFGGGTQLTVL | 388. |
| 112G7 | EVQLLESGGGLVQPGGSLRLSCAASGETFSSYAMYWVR QAPGKGPEWVSRISSGGGSTYYGDSVKGRFTISRDNSK NTLYLQMNSLKPEDTAVYYCANRAGWGMGDYWGQGTLV TVSS | 125. | QTVVTQEPSLSVSPGGTVTLTCGLSSGSVTASNYPGWFQQ TPGQAPRALIYSTNDRHSGVPARFSGSLSGNKAALTITGA QPEDEAEYYCALDIGDITEFGGGTQLTVL | 389. |
| 112H7 | ELQLLESGGGLVQPGGSLRLSCAASGETFSSYRMYWVR QPPGKGPEWVSAISAGGGSTYYGDSVKGRFTISRDNAK NTVYLQMNSLRAEDTAVYYCANRAGWGMGDYWGQGTQV TVSS | 126. | QAVVTQEPSLSVSPGGTVTLTCGLSSGSVTASNYPGWFQQ KPGQAPRALIYSTNDRHSGVPARFSGSILGGKAALTLTGA QPEDEADYYCALDIGDITEFGGGTHLTVL | 390. |

TABLE 16

VH and VL Amino Acid Sequences of Exemplary Germlined Variants of Fab Clone 68F2.

| FAB CLONE | VH SEQUENCE | SEQ ID NO | VL SEQUENCE | SEQ ID NO |
|---|---|---|---|---|
| 128B7 | QVQLQESGPGLVKPSQTLSLTCTVSGGSITTRYYAWSWIRQPPGKGLEWMGVIDYEGDTYYSPSLKSRVSISWDTSKNQFSLQLSSVTAEDTAVYYCARDPDVVTGFHYDYWGQGTQVTVSS | 127. | QSALTQPPSVSGTPGQRVTISCAGANNDIGTYAYVSWYQQLPGTAPKLLIYKVTTRASGVPDRFSGSKSGNTASLTITGLQSEDEADYYCASYRNFNNAVFGRGTKLTVL | 391. |
| 128B8 | QVQLQESGPGLVKPSQTLSLTCTVSGGSITSRYYAWSWIRQPPGKGLEWIGVIDYDGDTYYSPSLKSRVTISWDTSNNQFSLQLSSVTPEDTAVYYCARDPDVVTGFHYDYWGQGTLVTVSS | 128. | QSVLTQPPSVSGAPGQTVTISCAGANNDIGTYAYVSWYQQLPGTAPKLLIYKVTTRASGIPDRFSGSKSGATASLTITGLQAEDEADYYCASYRNFNNAVFGRGTHLTVL | 392. |
| 128C2 | QVQLQESGPGLVKPSQTLSLTCTVSGGSITTRYYAWSWIRQPPGKGLEWIGVIDYDGDTYYSPSLKSRTTISWDTSKNQFSLQLSSVTPEDTAVYYCARDPDVVTGFHYDYWGQGTMVTVSS | 129. | QSALTQPPLVSGTPGQRVTISCAGANNDIGTYAYVSWYQQLPGTAPRLLIYKVTTRASGVPDRFSGSKSGNTASLTITGLQSEDEADYYCASYRNFNNAVFGGGTKLTVL | 393. |
| 128D3 | QVQLQESGPGLVKPSQTLSLTCTVSGGSITSRYYAWSWIRQPPGKGLEWIGVIDYDGDTYYSPSLKSRTTISWDTSKNQFSLKLSSVTAADTAVYYCARDPDVVTGFHYDYWGQGTMVTVSS | 130. | QSALTHPPLVSGAPGQTVTISCAGANNDIGTYAYVSWYQQLPGTAPKLLIYKVTTRASGVPDRFSGSKSANTASLTITGLQAEDEADYYCASYRNFNNAVFGRGTKLTVL | 394. |
| 128D7 | EVQLQESGPGLVKPSQTLSLTCTVSGGSITSRYYAWSWIRQPPGKGLEWIGVIDYDGDTYYSPSLKSRTTISWDTSKNQFSLQLSSVTPEDTAVYYCARDPDVVTGFHYDYWGKGTLVTVSS | 131. | QSALTQPPLVSGAPGQRVTISCAGANNDIGTYAYVSWYQQLPGTAPKLLIYKVTTRASGVPSRFSGSKSGNTASLTISELQSEDEADYYCASYRNFNNAVFGGGTHLTVL | 395. |
| 128E10 | EVQLQESGPGLVKPSQTLSLTCTVSGGSITSRYYAWSWIRQPPGKGLEWIGVIDYDGDTYYSPSLKSRTTISWDTSKNQFSLKLSSVTPADTAVYYCARDPDVVTGFHYDYWGQGTLVTVSS | 132. | QSVLTQPPSVSGTPGQTVTISCAGANNDIGTYAYVSWYQQLPGTAPKLLIYKVTTRASGVPDRFSGSKSGNSASLTITGLQSEDEADYYCASYRNFNNAVFGGGTKLTVL | 396. |
| 128E2 | QVQLQESGPGLVKPSQTLSLTCTVSGGSITSRYYAWSWIRQPPGKGLEWIGVIDYDGDTYYSPSLKSRVSISWDTSKNQFSLQLSSVTAADTAVYYCARDPDVVTGFHYDYWGQGTMVTVSS | 133. | QSALTQPPLVSGAPGQTVTISCAGANNDIGTYAYVSWYQQLPGTAPKLLIYKVTTRASGVPDRFSGSKSGNTASLTITGLQAEDEADYYCASYRNFNNAVFGGGTKLTVL | 397. |
| 128E3 | EVQLQESGPGLVKPSQTLSLTCTVSGGSITSRYYAWSWIRQPPGKGLEWIGVIDYDGDTYYSPSLKSRTSISWDTSKNQFSLKLSSVTAEDTAVYYCARDPDVVTGFHYDYWGQGTTVTVSS | 134. | QSVLTQPPLVSGAPGQTVTISCAGANNDIGTYAYVSWYQQLPGTAPKLLIYKVTTRASGVPDRFSGSKSGNTASLAITGLQAEDEADYYCASYRNFNNAVFGGGTKLTVL | 398. |
| 128E7 | EVQLQESGPGLVKPSQTLSLTCTVSGGSITSRYYAWSWIRQPPGKGLEWIGVIDYDGDTYYSPSLKSRTTISVDTSKNQFSLHLSSVTAEDTAVYYCARDPDVVTGFHYDYWGQGTQVTVSS | 135. | QSVLTQPPLVSGAPGQTVTISCAGANNDIGTYAYVSWYQQLPGTAPKLLIYKVTTRASGVPDRFSGSKSGATASLTITGLQSEDEADYYCASYRNFNNAVFGRGTHLTVL | 399. |
| 128F3 | EVQLQESGPGLVKPSQTLSLTCTVSGGSITSRYYAWSWIRQPPGKGLEWIGVIDYDGDTYYSPSLKSRTSISVDTSKNQFSLQLSSVTAEDTAVYYCARDPDVVTGFHYDYWGQGTLVTVSS | 136. | QSVLTQPPLVSGAPGQTVTISCAGANNDIGTYAYVSWYQQLPGTAPKLLIYKVTTRASGIPSRFSGSKSGNSASLTISGLQAEDEADYYCASYRNFNNAVFGGGTKLTVL | 400. |
| 128F7 | EVQLQESGPGLVKPSQTLSLTCTVSGGSITTRYYAWSWIRQPPGKGLEWIGVIDYDGDTYYSPSLKSRVTISWDTSKNQFSLQLSSVTPEDTAVYYCARDPDVVTGFHYDYWGQGTTVTVSS | 137. | QSVLTQPPLVSGAPGQTVTISCAGANNDIGTYAYVSWYQQLPGTAPKLLIYKVTTRASGIPSRFSGSKSGNTASLTITGLQAEDEADYYCASYRNFNNAVFGRGTKLTVL | 401. |
| 128F8 | QVQLQESGPGLVKPSQTLSLTCTVSGGSITTRYYAWSWIRQPPGKGLEWIGVIDYDGDTYYSPSLKSRTTISWDTSKNQFSLQLSSVTPEDTAVYYCARDPDVVTGFHYDYWGQGTLVTVSS | 138. | QSVLTQPPLVSGTPGQRVTISCAGANNDIGTYAYVSWYQQLPGTAPKLLIYKVTTRASGIPDRFSGSKSGNTASLTITGLQAEDEADYYCASYRNFNNAVFGRGTHLTVL | 402. |
| 128G3 | EVQLQESGPGLVKPSQTLSLTCTVSGGSITTRYYAWSWIRQPPGKGLEWIGVIDYDGDTYYSPSLKSRTTISVDTSKNQFSLKLSSVTPEDTAVYYCARDPDVVTGFHYDYWGQGTMVTVSS | 139. | QSALTQPPSVSGAPGQTVTISCAGANNDIGTYAYVSWYQQLPGTAPKLLIYKVTTRASGVPDRFSGSKSGNTASLAISGLQAEDEADYYCASYRNFNNAVFGGGTHLTVL | 403. |
| 128H7 | EVQLQESGPGLVKPSQTLSLTCTVSGGSITTRYYAWSWIRQPPGKGLEWIGVIDYDGDTYYSPSLKSRTTISWDTSKNQFSLKLSSVTAEDTAVYYCARDPDVVTGFHYDYWGQGTQVTVSS | 140. | QSALTQPPLVSGSPGQSVTISCAGANNDIGTYAYVSWYQQLPGTAPKLLIYKVTTRASGIPDRFSGSKSGNTASLTISGLQSEDEADYYCASYRNFNNAVFGGGTKLTVL | 404. |
| 129A10 | EVQLQESGPGLVKPSQTLSLTCTVSGGSITSRYYAWSWIRQPPGKGLEWIGVIDYDGDTYYSPSLKSRTTISWDTSKNQFSLKLSSVTAADTAVYYCARDPDVVTGFHYDYWGQGTMVTVSS | 141. | QSALTQPPLVSGSPGQTVTISCAGANNDIGTYAYVSWYQQLPGTAPKLMIYKVTTRASGIPSRFSGSKSGNTASLTISGLQSEDEADYYCASYRNFNNAVFGTGTKLTVL | 405. |

TABLE 16-continued

VH and VL Amino Acid Sequences of Exemplary Germlined Variants of Fab Clone 68F2.

| FAB CLONE | VH SEQUENCE | SEQ ID NO | VL SEQUENCE | SEQ ID NO |
|---|---|---|---|---|
| 129A3 | EVQLQESGPGLVKPSQTLSLTCTVSGGSITTRYYAWSW IRQPPGKGLEWIGVIDYDGDTYYSPSLKSRTSISWDTS KNQFSLKLSSVTAADTAVYYCARDPDVVTGFHYDYWGP GTQVTVSS | 142. | QSALTQPPSVSGSPGQTVTISCAGANNDIGTYAYVSWYQQ LPGTAPKLMIYKVTTRASGIPDRFSGSKSGNTASLTISGL QSEDEADYYCASYRNFNNAVFGRGTHLTVL | 406. |
| 129A5 | EVQLQESGPGLVKPSQTLSLTCTVSGGSITSRYYAWSW IRQPPGKGLEWIGVIDYDGDTYYSPSLKSRTSISVDTS KNQFSLQLSSVTAEDTAVYYCARDPDVVTGFHYDYWGQ GTMVTVSS | 143. | QSALTQPPSVSGSPGQTVTISCAGANNDIGTYAYVSWYQQ LPGTAPKLLIYKVTTRASGIPSRFSGSKSGNTASLTISGL QSEDEADYYCASYRNFNNAVFGTGTKLTVL | 407. |
| 129A9 | QVQLQESGPGLVKPSQTLSLTCTVSGGSITTRYYAWSW IRQPPGKGLEWMGVIDYDGDTYYSPSLKSRVSISWDTS KNQFSLQLSSVTAEDTAVYYCARDPDVVTGFHYDYWGQ GTLVTVSS | 144. | QSALTQPPLVSGIPGQSVTISCAGANNDIGTYAYVSWYQQ LPGTAPKLLIYKVTTRASGVPDRFSGSKSGNTASLTISGL QSEDEADYYCASYRNFNNAVFGTGTKLTVL | 408. |
| 129B3 | EVQLQESGPGLVKPSQTLSLTCTVSGGSITTRYYAWSW IRQPPGKGLEWIGVIDYDGDTYYSPSLKSRVTISVDTS KNQFSLKLSSVTPEDTAVYYCARDPDVVTGFHYDYWGQ GTMVTVSS | 145. | QSALTQPPSVSGSPGQTVTISCAGANNDIGTYAYVSWYQQ LPGTAPKLMIYKVTTRASGIPSRFSGSKSGNTASLTISGL QAEDEADYYCASYRNFNNAVFGGGTKLTVL | 409. |
| 129B7 | EVQLQESGPGLVKPSQTLSLTCTVSGGSITTRYYAWSW IRQPPGKGLEWIGVIDYDGDTYYSPSLKSRTTISWDTS KNQFSLKLSSVTAEDTAVYYCARDPDVVTGFHYDYWGQ GTQVTVSS | 146. | QSALTQPPLVSGSPGQSVTISCAGANNDIGTYAYVSWYQQ LPGTAPKLMIYKVTTRASGVPDRFSGSKSGNTASLTISGL QSEDEADYYCASYRNFNNAVFGTGTKLTVL | 410. |
| 129B8 | EVQLQESGPGLVKPSQTLSLTCTVSGGSITSRYYAWSW IRQPPGKGLEWIGVIDYDGDTYYSPSLKSRTTISWDTS KNQFSLKLSSVTAEDTAVYYCARDPDVVTGFHYDYWGQ GTQVTVSS | 147. | QSALTQPPLVSGSPGQSVTISCAGANNDIGTYAYVSWYQQ LPGTAPKLLIYKVTTRASGVPDRFSGSKSGNTASLTISGL QSEDEADYYCASYRNFNNAVFGRGTKLTVL | 411. |
| 129C10 | QVQLQESGPGLVKPSQTLSLTCTVSGGSITSRYYAWSW IRQPPGKGLEWIGVIDYDGDTYYSPSLKSRTTISWDTS KNQFSLKLSSVTAEDTAVYYCARDPDVVTGFHYDYWGQ GTQVTVSS | 148. | QSAMTQPPSVSGSPGQSVTISCAGANNDIGTYAYVSWYQQ PPGTAPKLLIYKVTTRASGVPSRFSGSKSGNTASLTISGL QSEDEADYYCASYRNFNNAVFGTGTKLTVL | 412. |
| 129C11 | QVQLQESGPGLVKPSQTLSLTCTVSGGSITTRYYAWSW IRQPPGKGLEWIGVIDYDGDTYYSPSLKSRVTISVDTS KNQISLKLSSVTPEDTAVYYCARDPDVVTGFHYDYWGQ GTQVTVSS | 149. | QSALTQPPLVSGSPGQTVTISCAGANNDIGTYAYVSWYQQ LAGTAPKLMIYKVTTRASGIPSRFSGSKSGNTASLTISGL QAEDEADYYCASYRNFNNAVFGTGTHLTVL | 413. |
| 129D11 | EVQLQESGPGLVKPSQTLSLTCTVSGGSITSRYYAWSW IRQPPGKGLEWIGVIDYDGDTYYSPSLKSRVSISWDTS KNQFSLKLSSVTAEDTAVYYCARDPDVVTGFHYDYWGQ GTLVTVSS | 150. | QSALTQPPLVSGSPGQSVTISCAGANNDIGTYAYVSWYQQ LPGTAPKLMIYKVTTRASGVPSRFSGSKSGNTASLTISGL QSEDEADYYCASYRNFNNAVFGTGTHLTVL | 414. |
| 129D2 | EVQLQESGPGLVKPSQTLSLTCTVSGGSITPRYYVWTW IRHPPGKGLDWIGVIDYDGDTYYSPSLKSRTTISWDTS KNQFSLQLSSVTAEDTAVYYCARYPDVVTGFHYDYWGQ GTQVTVSS | 151. | QSALTQPPSVSGSPGQTVTISCAGANNDIGTYAYVSWYQQ LPGTAPKLMIYKVTTRASGVPSRFSGSISGNTASLTISGL QAEDEADYYCASYRNFNNAVFGGGTHLTVL | 415. |
| 129D3 | EVQLQESGPGLVKPSQTLSLTCTVSGGSITSRYYAWSW IRQPPGKGLEWIGVIDYDGDTYYSPSLKSRVSISWDTS KNQFSLKLSSVTPADTAVYYCARDPDVVTGFHYDYWGQ GTMVTVSS | 152. | QSALTQPPSVSGTPGQSVTISCAGANNDIGTYAYVSWYQQ LPGTAPKLMIYKVTTRASGIPDRFSGSKSGNTASLTISGL QAEDEADYYCASYRNFNNAVFGTGTKLTVL | 416. |
| 129D5 | EVQLQESGPGLVKPSQTLSLTCTVSGGSITSRYYAWSW IRQPPGKGLEWIGVIDYDGDTYYSPSLKSRTTISWDTS KNQFSLQLSSVTAADTAVYYCARDPDVVTGFHYDYWGQ GTLVTVSS | 153. | QSALTQPPSVSGSPGQSVTISCAGANNDIGTYAYVSWYQQ LPGTAPKLLIYKVTTRASGVPDRFSGSKSGNTASLTISGL QSEDEADYYCASYRNFNNGVFGTGTKLTVL | 417. |
| 129D8 | EVQLQESGPGLVKPSQTLSLTCTVSGGSITSRYYAWSW IRQPPGKGLEWIGVIDYDGDTYYSPSLKSRTSISWDTS KNQFSLQLSSVTPEDTAVYYCARDPDVVTGFHYDYWGQ GTTVTVSS | 154. | QSALTQPPLVSGSPGQSVTISCAGANNDIGTYAYVSWYQQ LPGTAPKLMIYKVTTRASGVPDRFSGSKSGNTASLTISGL QAEDEADYYCASYRNFNNAVFGRGTHLTVL | 418. |
| 129E11 | EVQLQESGPGLVKPSQTLSLTCTVSGGSITSRYYAWSW IRQPPGKGLEWMGVIDYDGDTYYSPSLKSRVSISVDTS KNQFSLKLSSVTAEDTAVYYCARDPDVVTGFHYDYWGQ GTLVTVSS | 155. | QSALTQPPLVSGSPGQTVTISCAGANNDIGTYAYVSWYQQ LPGTAPKLLIYKVTTRASGVPDRFSGSKSGNTASLTISGL QSEDEADYYCASYRNFNNAVFGTGTKLTVL | 419. |

TABLE 16-continued

VH and VL Amino Acid Sequences of Exemplary Germlined Variants of Fab Clone 68F2.

| FAB CLONE | VH SEQUENCE | SEQ ID NO | VL SEQUENCE | SEQ ID NO |
|---|---|---|---|---|
| 129E3 | EVQLQESGPGLVKPSQTLSLTCTVSGGSITSRYYAWSW IRQPPGKGLEWIGVIDYDGDTYYSPSLKSRVTISWDTS KNQFSLQLSSVTAEDTAVYYCARDPDVVTGFHYDYWGQ GTLVTVSS | 156. | QSALTQPPSVSGTPGQTVTISCAGANNDIGTYAYVSWYQQ PPGTAPKLLIYKVTTRASGIPDRFSGSKSGNTASLTISGL QAEDEADYYCASYRYFNNAVFGTGTKLTVL | 420. |
| 129F10 | EVQLQESGPGLVKPSQTLSLTCTVSGGSITSSYYAWSW IRQPPGKGLEWIGVIDYDGDTYYSPSLKSRTTISWDTS KNQFSLQLSSVTAEDTAVYYCARDPDVVTGFHYDYWGQ GTMVTVSS | 157. | QSALTQPPSVSGSPGQTVTISCAGANNDIGTYAYVSWYQQ LPGTAPKLMIYKVTTRASGVPSRFSGSKSGNTASLTISGL QSEDEADYYCSSYRNFNNAVFGTGTKLTVL | 421. |
| 129F11 | EVQLQESGPGLVKPSQTLSLTCTVSGGSITTRYYAWSW IRQPPGKGLEWIGVIDYDGDTYYSPSLKSRVSISWDTS KNQFSLKLSSVTAEDTAVYYCARDPDVVTGFHYDYWGQ GTQVTVSS | 158. | QSALTQPPSVSGSPGQTVTISCAGANNDIGTYAYVSWYQQ LPGTAPKLLIYKVTSRASGVPSRFSGSKSGNTASLSISGL QAEDEADYYCASYRNFNNAVFGSGTKLTVL | 422. |
| 129F2 | EVQLQESGPGLVKPSQTLSLTCTVSGGSITSRYYAWSW IRQPPGKGLEWIGVIDYDGDTYYSPSLKSRVTISWDTS KNQFSLKLSSVTAEDTAVYYCARDPDVVTGFHYDYWGQ GTMVTVSS | 159. | QSALTQPPSVSGTPGQTVTISCAGANNDIGTYAYVSWYQQ LPGTAPKLMIYKVTTRASGIPDRFSGSKSGNTASLTISGL QSEDEADYYCASYRNFNNAVFGGGTKLTVL | 423. |
| 129F3 | EVQLQESGPGLVKPSQTLSLTCTVSGGSITSRYYAWSW IRQPPGKGLEWIGVIDYDGDTYYSPSLKSRTTISWDTS KNQFSLQLSSVTAEDTAVYYCARDPDVVTGFHYDYWGQ GTQVTVSS | 160. | QSALTQPPSVSGSPGQTVTISCAGANNDIGTYAYVSWYQQ LPGTAPKLMIYKVTTRASGVPSRFSGSKSGNTASLTISGL QAEDEADYYCASYRNFNNAVFGRGTHLTVL | 424. |
| 129F5 | EVQLQESGPGLVKPSQTLSLTCTVSGGSITTRYYAWSW IRQPPGKGLEWIGVIDYDGDTYYSPSLKSRTTISWDTS KNQFSLKLSSVTAEDTAVYYCARDPDVVTGFHYDYWGQ GTQVTVSS | 161. | QSALTQPPLVSGTPGQSVTISCAGANNDIGTYAYVSWYQQ LPGTAPKLLIYKVTTRASGIPSRFSGSKSGNTASLTISGL QSEDEADYYCASYRNFNNAVFGTGTKLTVL | 425. |
| 129G7 | QVQLQESGPGLVKPSQTLSLTCTVSGGSITTRYYAWSW IRQPPGKGLEWIGVIDYDGDTYYSPSLKSRTTISVDTS KNQFSLQLSSVTAADTAVYYCARDPDVVTGFHYDYWGQ GTQVTVSS | 162. | QSALTQPPLVSGTPGQTVTISCAGANNDIGTYAYVSWYQQ LPGTAPKLMIYKVTTRASGVPDRFSGSKSGNTASLTISGL QAEDEADYYCASYRNFNNAVFGRGTKLTVL | 426. |
| 129G9 | EVQLQESGPGLVKPSQTLSLTCTVSGGSITSRYYAWSW IRQPPGKGLEWIGVIDYDGDTYYSPSLKSRTSISWDTS KNQFSLQLSSVTPEDTAVYYCARDPDVVTGFHYDYWGQ GTQVTVSS | 163. | QSALTQPPSVSGSPGQTVTISCAGANNDIGTYAYVSWYQQ PPGTAPKLMIYKVTTRASGVPSRFSGSKSGNTASLTISGL QAEDEADYYCASYRNFNNAVFGSGTHLTVL | 427. |
| 129H5 | QVQLQESGPGLVKPSQTLSLTCTVSGGSITSRYYAWSW IRQPPGKGLEWIGVIDYDGDTYYSPSLKSRTSISWDTS KNQFSLQLSSVTAEDTAVYYCARDPDVVTGFHYDYWGQ GTLVTVSS | 164. | QSALTQPPLVSGSPGQTVTISCAGANNDIGTYAYVSWYQQ LPGTAPKLMIYRVTTRASGVPDRFSGSKSGNTASLTISGL QAEDEADYYCASYRNFNNAVFGGGTHLTVL | 428. |
| 129H6 | EVQLQESGPGLVKPSQTLSLTCTVSGGSITTRYYAWSW IRQPPGKGLEWMGVIDYDGDTYYSPSLKSRTSISWDTS KNQFSLQLSSVTPEDTAVYYCARDPDVVTGFHYDYWGQ GTQVTVSS | 165. | QSALTQPPLVSGTPGQTVTISCAGANNDIGTYAYVSWYQQ LPGTAPKLLIYKVTTRASGIPSRFSGSKSGNTASLTISGL QSEDEADYYCASYRNFNNAVFGRGTHLTVL | 429. |
| 129H7 | QVQLQESGPGLVKPSQTLSLTCTVSGGSITRYYAWSW IRQPPGKGLEWIGVIDYDGDTYYSPSLKSRTTISWDTS KNQFSLKLSSVTAEDTAVYYCARDPDVVTGFHYDYWGQ GTQVTVSS | 166. | QSAMTQPPSVSGSPGQSVTISCAGANNDIGTYAYVSWYQQ PPGTAPKLLIYKVTTRASGVPSRFSGSKSGNTASLTISGL QSEDEADYYCASYRNFNNAVFGTGTKLTVL | 430. |
| 129H8 | EVQLQESGPGLVKPSQTLSLTCTVSGGSITTRYYAWSW IRQPPGKGLEWIGVIDYDGDTYYSPSLKSRVSISWDTS KNQFSLQLSSVTAEDTAVYYCARDPDVVTGFHYDYWGQ GTLVTVSS | 167. | QSALTQPPLVSGSPGQSVTISCAGANNDIGTYAYVSWYQQ LPGTAPKLLIYKVTTRASGVPSRFSGSKSGNTASLTISGL QSEDEADYYCASYRNFNNAVFGNGTQLTVL | 431. |
| 129H9 | EVQLQESGPGLVKPSQTLSLTCTVSGGSITTRYYAWSW IRQPPGKGLEWIGVIDYDGDTYYSPSLESRTTISWDTS KNQFSLNLSSVTAEDTAVYYCARDPDVVTGFHYDYWGQ GTLVTVSS | 168. | QSALTQPPSVSGSPGQTVTISCAGANNDIGTYAYVSWYQQ PPGTAPKLMIYKVTTRASGVPSRFSGSISGNTASLTISGL QAEDEADYYCASYRNFNNAVFGTGTHLTVL | 432. |
| 126F4 | EVQLQESGPGLVKPSQTLSLTCTVSGGSITSRYYAWSW IRQPPGKGLEWMGVIDYDGDTYYSPSLKSRVTISVDTS KNQFSLKLSSVTPADTAVYYCARDPDVVTGFHYDYWGQ GTLVTVSS | 169. | QSALTQPPLVSGSPGQSVTISCAGANNDIGTYAYVSWYQQ LPGTAPKLLIYKVTTRASGIPDRFSGSKSGNTASLTISGL QAEDEADYYCASYRNFNNAVFGGGTKLTVL | 433. |

TABLE 16-continued

VH and VL Amino Acid Sequences of Exemplary Germlined Variants of Fab Clone 68F2.

| FAB CLONE | VH SEQUENCE | SEQ ID NO | VL SEQUENCE | SEQ ID NO |
|---|---|---|---|---|
| 127D11 | EVQLQESGPGLVKPSQTLSLTCTVSGGSITSRYYAWSWIRQPPGKGLEWIGVIDYDGDTYYSPSLKSRVSISWDTSKNQFSLQLSSVTPEDTAVYYCARDPDVVTGFHYDYWGQGTKVTVSS | 170. | QSALTQPPSVSGSPGQTVTISCAGANNDIGTYAYVSWYQQLPGTAPKLMIYKVTTRASGVPSRFSGSKSGNTASLTISGLQSEDEADYYCASYRNFNNAVFGGGTHLTVL | 434. |
| 127H10 | EVQLQESGPGLVKPSQTLSLTCTVSGGSITTRYYAWSWIRQPPGKGLEWIGVIDYDGDTYYSPSLKSRTSISWDTSKNQFSLKLSSVTAEDTAVYYCARDPDVVTGFHYDYWGQGTQVTVSS | 171. | QSVLTQPPLVSGAPGQRVTSCAGANNDIGTYAYVSWYQQLPGTAPKLLIYKVTTRASGVPDRFSGSKSGNSASLTITGLQAEDEADYYCASYRNFNNAVFGGGTKLTVL | 435. |
| 127H1 | EVQLQESGPGLVKPSQTLSLTCTVSGGSITTRYYAWSWIRQPPGKGLEWIGVIDYDGDTYYSPSLKSRVSISWDTSKNQFSLQLSSVTAADTAVYYCARDPDVVTGFHYDYWGQGTQVTVSS | 172. | QSVLTQPPLVSGAPGQTVTISCAGANNDIGTYAYVSWYQQLPGTAPKLLIYKVTTRASGVPDRFSGSKSGNTASLTITGLQAEDEADYYCASYRNFNNAVFGRGTKLTVL | 436. |
| 127G1 | EVQLQESGPGLVKPSQTLSLTCTVSGGSITSRYYAWSWIRQPPGKGLEWIGVIDYDGDTYYSPSLKSRTTISVDTSKNQFSLQLSSVTPEDTAVYYCARDPDVVTGFHYDYWGQGTTVTVSS | 173. | QSVLTQPPLVSGTPGQTVTISCAGANNDIGTYAYVSWYQQLPGTAPKLLIYKVTTRASGIPDRFSGSKSGNTASLAISGLQAEDEADYYCASYRNFNNAVFGGGTKLTVL | 437. |
| 126H5 | QVQLQESGPGLVKPSQTLSLTCTVSGGSITSRYYAWSWIRQPPGKGLEWIGVIDYDGDTYYSPSLKSRTSISWDTSKNQFSLKLSSVTPEDTAVYYCARDPDVVTGFHYDYWGQGTTVTVSS | 174. | QSALTQPPSVSGSPGQSVTISCAGANNDIGTYAYVSWYQQLPGTAPKLLIYKVTTRASGIPDRFSGSKSGNTASLTISGLQAEDEADYYCASYRNFNNAVFGTGTHLTVL | 438. |
| 127B12 | EVQLQESGPGLVKPSQTLSLTCTVSGGSITSRYYAWSWIRQPPGKGLEWIGVIDYDGDTYYSPSLKSRVSISWDTSKNQFSLQLSSVTPEDTAVYYCARDPDVVTGFHYDYWGQGTKVTVSS | 175. | QSALTQPPSVSGSPGQTVTISCAGANNDIGTYAYVSWYQQLPGTAPKLMIYKVTTRASGVPSRFSGSKSGNTASLTISGLQSEDEADYYCASYRNFNNAVFGGGTHLTVL | 439. |
| 127F1 | EVQLQESGPGLVKPSQTLSLTCTVSGGSITTRYYAWSWIRQPPGKGLEWIGVIDYDGDTYYSPSLKSRVSISWDTSKNQFSLKLSSVTAADTAVYYCARDPDVVTGFHYDYWGQGTLVTVSS | 176. | QSVLTQPPSVSGTPGQRVTISCAGANNDIGTYAYVSWYQQLPGTAPKLLIYKVTTRASGVPDRFSGSKSGNSASLTITGLQSEDEADYYCASYRNFNNAVFGGGTHLTVL | 440. |
| 127D7 | QVQLQESGPGLVKPSQTLSLTCTVSGGSITSRYYAWSWIRQPPGKGLEWIGVIDYDGDTYYSPSLKSRVTISWDTSKNQFSLQLSSVTAADTAVYYCARDPDVVTGFHYDYWGQGTLVTVSS | 177. | QSALTQPPLVSGTPGQPVTISCAGANNDIGTYAYVSWYQQLPGTAPKLLISKVTTRASGVPDRFSGSKSGTTASLTITGLQSEDEADYYCASYRNFNNGVFGGGTHLTVL | 441. |
| 127F5 | QVQLQESGPGLVKPSQTLSLTCTVSGGSITSRYYAWSWIRQPPGKGLEWIGVIDYDGDTYYSPSLKSRTTISWDTSKNQFSLQLSSVTAEDTAVYYCARDPDVVTGFHYDYWGQGTLVTVSS | 178. | QSALTQPPLVSGTPGQTVTISCAGANNDIGTYAYVSWYQQLPGTAPKLLIYKVTTRASGVPSRFSGSKSGNTASLTISGLQSEDEADYYCASYRTFNNAVFGSGTHLTVL | 442. |
| 127C6 | QVQLQESGPGLVKPSQTLSLTCTVSGGSITSRYYAWSWIRQPPGKGLEWIGVIDYDGDTYYSPSLKSRVTISWDTSKNQFSLKLSSVTAEDTAVYYCARDPDVVTGFHYDYWGQGTQVTVSS | 179. | QSALTQPPLVSGSPGQTVTISCAGANNDIGTYAYVSWYQQPPGTAPKLLIYKVTTRASGIPDRFSGSISGNTASLTISGLQAEDEADYYCASYRNFNNAVFGRGTKLTVL | 443. |
| 127F3 | QVQLQESGPGLVKPSQTLSLTCTVSGGSITSRYYAWSWIRQPPGKGLEWIGVIDYDGDTYYSPSLKSRTSISVDTSKNQFSLKLSSVTPADTAVYYCARDPDVVTGFHYDYWGQGTLVTVSS | 180. | QSVLTQPPSVSGAPGQTVTISCAGANNDIGTYAYVSWYQQLPGTAPKLLIYKVTTRASGIPSRFSGSKSGNTASLTITGLQSEDEADYYCASYRNFNNAVFGGGTHLTVL | 444. |
| 127G5 | EVQLQESGPGLVKPSQTLSLTCTVSGGSITSRYYAWSWIRQPPGKGLEWMGVIDYDGDTYYSPSLKSRTTISWDTSKNQFSLQLSSVTAADTAVYYCARDPDVVTGFHYDYWGQGTLVTVSS | 181. | QSALTQPPSVSGTPGQSVTISCAGANNDIGTYAYVSWYQQPPGTAPKLLIYKVTTRASGIPSRFSGSKSGNTASLTISGLQSEDEADYYCASYRNFNNAVFGSGTHLTVL | 445. |
| 126H2 | QVQLQESGPGLVKPSQTLSLTCTVSGGSITTRYYAWSWIRQPPGKGLEWIGVIDYDGDTYYSPSLKSRTTISWDTSKNQFSLQLSSVTPEDTAVYYCARDPDVVTGFHYDYWGQGTQVTVSS | 182. | QSALTQPPLVSGSPGQSVTISCAGANNDIGTYAYVSWYQQLPGTAPKLLIYKVTTRASGIPDRFSGSKSGNTASLTISGLQAEDEADYYCASYRNFNNAVFGGGTKLTVL | 446. |
| 127D5 | EVQLQESGPGLVKPSQTLSLTCTVSGGSITSRYYAWSWIRQPPGKGLEWIGVIDYDGDTYYSPSLKSRTSISWDTSKNQFSLQLSSVTAEDTAVYYCARDPDVVTGFHYDYWGQGTLVTVSS | 183. | QSALTQPPLVSGSPGQSVTISCAGANNDIGTYAYVSWYQQLPGTAPKLMIYKVTTRASGIPDRFSGSKSGNTASLTISGLQSEDEADYYCASYRNFNNAVFGTGTKLTVL | 447. |

TABLE 16-continued

VH and VL Amino Acid Sequences of Exemplary Germlined Variants of Fab Clone 68F2.

| FAB CLONE | VH SEQUENCE | SEQ ID NO | VL SEQUENCE | SEQ ID NO |
|---|---|---|---|---|
| 127B5 | EVQLQESGPGLVKPSQTLSLTCTVSGGSITSRYYAWSW IRQPPGKGLEWIGVIDYDGDTYYSPSLKSRTTISWDTS KNQFSLKLSSVTAEDTAVYYCARDPDVVTGFHYDYWGQ GTTVTVSS | 184. | QSALTQPPLVSGSPGQSVTISCAGANNDIGTYAYVSWYQQ LPGTAPKLLIYKVTTRASGIPDRFSGSKSGNTASLTISGL QSEDEADYYCASYRNFNNAVFGSGTKLTVL | 448. |
| 126E1 | EVQLQESGPGLVKPSQTLSLTCTVSGGSITSRYYAWSW IRQPPGKGLEWIGVIDYDGDTYYSPSLKSRVTISWDTS KNQFSLQLSSVTAEDTAVYYCARDPDVVTGFHYDYWGQ GTQVTVSS | 185. | QSALTQPPLVSGAPGQTVTISCAGANNDIGTYAYVSWYQQ LPGTAPKLLIYKVTTRASGIPDRFSGSKSGNTASLTITGL QAEDEADYYCASYRNFNNAVFGGGTHLTVL | 449. |
| 126B5 | QVQLQESGPGLVKPSQTLSLTCTVSGGSITTRYYAWSW IRQPPGKGLEWIGVIDYDGDTYYSPSLKSRVTISWDTS KNQFSLQLSSVTPEDTAVYYCARDPDVVTGFHYDNWGQ GTLVTVSS | 186. | QSALTQPPLVSGSPGQSVTISCAGANNDIGTYAYVSWYQQ LPGTAPKLMIYKVTTRASGVPSRFSGSKSGNTASLTISGL QAEDEADYYCASYRNFNNAVFGSGTHLTVL | 450. |
| 127B8 | EVQLQESGPGLVKPSQTLSLTCTVSGGSITTRYYAWSW IRQPPGKGLEWIGVIDYDGDTYYSPSLKSRVSISWDTS KNQFSLKLSSVTAEDTAVYYCARDPDVVTGFHYDYWGQ GTQVTVSS | 187. | QSALTQPPSVSGSPGQTVTISCAGANNDIGTYAYVSWYQQ LPGTAPKLLIYKVTSRASGVPSRFSGSKSGNTASLSISGL QAEDEADYYCASYRNFNNAVFGSGTKLTVL | 451. |
| 127E1 | EVQLQESGPGLVKPSQTLSLTCTVSGGSITSRYYAWSW IRQPPGKGLEWIGVIDYDGDTYYSPSLKSRTTISWDTS KNQFSLQLSSVTPEDTAVYYCARDPDVVTGFHYDYWGQ GTQVTVSS | 188. | QSVLTQPPLVSGAPGQTVTISCAGANNDIGTYAYVSWYQQ LPGTAPKLLIYKVTTRASGIPDRFSGSKSGNSASLTITGL QSEDEADYYCASYRNFNNAVFGGGTKLTVL | 452. |
| 126G2 | EVQLQESGPGLVKPSQTLSLTCTVSGGSITSRYYAWSW IRQPPGKGLEWIGVIDYDGDTYYSPSLKSRVTISVDTS KNQFSLKLSSVTAADTAVYYCARDPDVVTGFHYDYWGQ GTMVTVSS | 189. | QSALTQPPLVSGSPGQTVTISCAGANNDIGTYAYVSWYQQ LPGTAPKLLIYKVTTRASGVPDRFSGSKSGNTASLTISGL QAEDEADYYCASYRNFNNAVFGTGTHLTVL | 453. |
| 126D2 | EVQLQESGPGLVKPSQTLSLTCTVSGGSITSRYYAWSW IRQPPGKGLEWIGVIDYDGDTYYSPSLKSRTTISWDTS KNQFSLKLSSVTAEDTAVYYCARDPDVVTGFHYDYWGQ GTQVTVSS | 190. | QSALTQPPLVSGSPGQTVTISCAGANNDIGTYAYVSWYQQ LPGTAPKLLIYKVTTRASGVPSRFSGSKSGNTASLTISGL QAEDEADYYCASYRNFNNAVFGGGTHLTVL | 454. |
| 126G3 | EVQLQESGPGLVKPSQTLSLTCTVSGGSITTRYYAWSW IRQPPGKGLEWIGVIDYDGDTYYSPSLKSRVTISVDTS KNQISLQLSSVTPEDTAVYYCARDPDVVTGFHYDYWGQ GTLVTVSS | 191. | QSALTQPPSVSGAPGQRVTISCAGANNDIGTYAYVSWYQQ LPGTAPKLLIYKVTTRASGVPSRFSGSKSGNSASLTITGL QSEDEADYYCASYRNFNNAVFGGGTHLTVL | 455. |
| 126D4 | EVQLQESGPGLVKPSQTLSLTCTVSGGSITTRYYAWSW IRQPPGKGLEWIGVIDYDGDTYYSPSLKSRVTISVDTS KNQFSLKLSSVTPADTAVYYCARDPDVVTGFHYDYWGQ GTTVTVSS | 192. | QFALTQPPLVSGTPGQSVTISCAGANNDIGTYAYVSWYQQ LPGTAPKLLIYKVTTRASGVPSRFSGSKSGNTASLTISGL QSEDEADYYCASYRNFNNAVFGTGTHLTVL | 456. |
| 127F2 | QVQLQESGPGLVKPSQTLSLTCTVSGGSITSRYYAWSW IRQPPGKGLEWIGVIDYDGDTYYSPSLKSRVTISWDTS KNQFSLKLSSVTPEDTAVYYCARDPDVVTGFHYDYWGQ GTQVTVSS | 193. | QSALTQPPLVSGSPGQTVTISCAGANNDIGTYAYVSWYQQ LPGTAPKLMIYKVTTRASGVPSRFSGSKSGNTASLTISGL QAEDEADYYCASYRNFNNAVFGSGTKLTVL | 457. |
| 127H2 | EVQLQESGPGLVKPSQTLSLTCTVSGGSITTRYYAWSW IRQPPGKGLEWMGVIDYDGDTYYSPSLKSRTTISWDTS KNQFSLQLSSVTAEDTAVYYCARDPDVVTGFHYDYWGQ GTMVTVSS | 194. | QSALTQPPLVSGSPGQTVTISCAGANNDIGTYAYVSWYQQ LPGTAPKLLIYKVTTRASGVPDRFSGSKSGNTASLTISGL QSEDEADYYCASYRNFNNAVFGRGTHLTVL | 458. |
| 127G2 | EVQLQESGPGLVKPSQTLSLTCTVSGGSITTRYYAWSW IRQPPGKGLEWIGVIDYDGDTYYSPSLKSRVSISWDTS KNQFSLHLSSVTPEDTAVYYCARDPDVVTGFHYDYWGQ GTLVTVSS | 195. | QSALTQPPSVSGSPGQTVTISCAGANNDIGTYAYVSWYQQ LPGTAPKLLIYKVTTRASGVPDRFSGSKSGNTASLTISGL QAEDEADYYCASYRNFNNAVFGGGTKLTVL | 459. |
| 126E5 | EVQLQESGPGLVKPSQTLSLTCTVSGGSITSRYYAWSW IRQPPGKGLEWMGVIDYDGDTYYSPSLKSRVSISWDTS KNQFSLQLSSVTAEDTAVYYCARDPDVVTGFHYDYWGQ GTQVTVSS | 196. | QSALTQPPLVSGTPGQTVTISCAGANNDIGTYAYVSWYQQ LPGTAPKLLIYKVTTRASGVPSRFSGSKSGNTASLTISGL QAEDEADYYCASYRNFNNGVFGTGTKLTVL | 460. |
| 127E9 | EVQLQESGPGLVKPSQTLSLTCTVSGGSITSRYYAWSW IRQPPGKGLEWIGVIDYDGDTYYSPSLKSRTTISWDTS KNQFSLKLSSVTAEDTAVYYCARDPDVVTGFHYDYWGQ GTQVTVSS | 197. | QSVLTQPPSVSGTPGQRVTISCAGANNDIGTYAYVSWYQQ LPGTAPKLLIYKVTTRASGIPSRFSGSKSGNTASLTITGL QAEDEADYYCASYRNFNNAVFGGGTKLTVL | 461. |

TABLE 16-continued

VH and VL Amino Acid Sequences of Exemplary Germlined Variants of Fab Clone 68F2.

| FAB CLONE | VH SEQUENCE | SEQ ID NO | VL SEQUENCE | SEQ ID NO |
|---|---|---|---|---|
| 127E8 | QVQLQESGPGLVKPSQTLSLTCTVSGGSITSRYYAWSW IRQPPGKGLEWMGVIDYDGDTYYSPSLKSRTTISWDTS KNQFSLKLSSVTAADTAVYYCARDPDVVTGFHYDYWGQ GTTVTVSS | 198. | QSALTQPPLVSGSPGQTVTISCAGANNDIGTYAYVSWYQQ LPGTAPKLLIYKVTTRASGVPDRFSGSKSGNTASLTISGL QSEDEADYYCASYRNFNNAVFGTGTKLTVL | 462. |
| 127E3 | EVQLQESGPGLVKPSQTLSLTCTVSGGSITTRYYAWSW IRQPPGKGLEWMGVIDYDGDTYYSPSLKSRVTISWDTS KNQFSLKLSSVTAEDTAVYYCARDPDVVTGFHYDYWGQ GTLVTVSS | 199. | QSVLTQPPSVSGTPGQTVTISCAGANNDIGTYAYVSWYQQ LPGTAPKLLIYKVTTRASGIPSRFSGSKSGNTASLAITGL QSEDEADYYCASYRNFNNAVFGGGTKLTVL | 463. |
| 126F3 | EVQLQESGPGLVKPSQTLSLTCTVSGGSITSRYYAWSW IRQPPGKGLEWIGVIDYDADTYYSPSLKSRTSISWDTS KNQFSLKLSSVTPEDTAVYYCARDPDVVTGFHYDYWGQ GTTVTVSS | 200. | QSALTQPPLVSGAPGQTVTISCAGANNDIGTYAYVSWYQQ LPGTAPKLLIYKVTTRASGIPDRFSGSKSGNTASLTITGL QAEDEADYYCASYRNFNNAVFGGGTHLTVL | 464. |
| 126A4 | EVQLQESGPGLVKPSQTLSLTCTVSGGSITSRYYAWSW IRQPPGKGLEWIGVIDYDGDTYYSPSLKSRTTISWDTS KNQFSLQLSSVTPADTAVYYCARDPDVVTGFHYDYWGQ GTQVTVSS | 201. | QSALTQPPLVSGSPGQTVTISCAGANNDIGTYAYVSWYQQ LPGTAPKLLIYKVTTRASGVPSRFSGSKSGNTASLTISGL QAEDEADYYCASYRNFNNAVFGGGTHLTVL | 465. |
| 127B4 | EVQLQESGPGLVKPSQTLSLTCTVSGGSITTRYYAWSW IRQPPGKGLEWIGVIDYDGDTYYSPSLKSRVTISWDTS KNQISLQLSSVTPEDTAVYYCARDPDVVTGFHYDYWGQ GTLVTVSS | 202. | QSALTQPPSVSGAPGQRVTISCAGANNDIGTYAYVSWYQQ LPGTAPKLLIYKVTTRASGVPSRFSGSKSGNSASLTITGL QSEDEADYYCASYRNFNNAVFGGGTHLTVL | 466. |
| 126A3 | EVQLQESGPGLVKPSQTLSLTCTVSGGSITTRYYAWSW IRQPPGKGLEWIGVIDYDGDTYYSPSLKSRVTISVDTS KNQFSLKLSSVTAADTAVYYCARDPDVVTGFHYDYWGQ GTMVTVSS | 203. | QSALTQPPSVSGAPGQTVTISCAGANNDIGTYAYVSWYQQ LPGTAPKLLIYKVTTRASGIPSRFSGSKSGNTASLTITGL QSEDEADYYCASYRNFNNAVFGRGTKLTVL | 467. |
| 127D6 | EVQLQESGPGLVKPSQTLSLTCTVSGGSITSRYYAWSW IRQPPGKGLEWIGVIDYDGDTYYSPSLKSRTTISWDTS KNQFSLQLSSVTPEDTAVYYCARDPDVVTGFHYDYWGQ GTQVTVSS | 204. | QSALTQPPSVSGSPGQTVTISCAGANNDIGTYAYVSWYQQ LPGTAPKLLIYKVTTRASGVPDRFSGSKSGNTASLTISGL QSEDEADYYCASYRNFNNAVFGGGTHLTVL | 468. |
| 126D5 | QVQLQESGPGLVKPSQTLSLTCTVSGGSITTRYYAWSW IRQPPGKGLEWMGVIDYDGDTYYSPSLKSRVTISVDTS KNHFSLKLSSVTAEDTAVYCATDPDVVTGFHYDYWGQ GTTVTVSS | 205. | QSALTQPPSVSGTPGQTVTISCAGANNDIGTYAYVSWYQQ LPGTAPKLLIYKVTTRASGVPDRFSGSKSGNTASLTISGL QSEDEADYYCASYRNFNNAVFGTGTKLTVL | 469. |
| 127D8 | EVQLQESGPGLVKPSQTLSLTCTVSGGSITSRYYAWSW IRQPPGKGLEWIGVIDYDGDTYYSPSLKSRVSISVDTS KNQFSLKLSSVTAEDTAVYYCARDPDVVTGFHYDNWGQ GTLVTVSS | 206. | QSALTQPPSVSGTPGQTVTISCAGANNDIGTYAYVSWYQQ LPGTAPKLMIYKVTTRASGVPVRFSGSKSGNTASLTISGL QAEDEADYYCASYRNFNNAVFGGGTKLTVL | 470. |
| 126E4 | EVQLQESGPGLVKPSQTLSLTCTVSGGSITSRYYAWSW IRQPPGKGLEWMGVIDYDGDTYYSPSLKSRVTISVDTS KNQFSLQLSSVTAEDTAVYYCARDPDVVTGFHYDYWGQ GTQVTVSS | 207. | QSALTQPPLVSGSPGQTVTISCAGANNDIGTYAYVSWYQQ LPGTAPKLLIYKVTTRASGVPDRFSGSKSGNTASLTISGL QAEDEADYYCASYRNFNNAVFGTGTHLTVL | 471. |
| 126F2 | QVQLQESGPGLVKPSQTLSLTCTVSGGSITTRYYAWSW IRQPPGKGLEWIGVIDYDGDTYYSPSLKSRTTISWDTS KNQFSLKLSSVTAEDTAVYYCARDPDVVTGFHYDYWGQ GTQVTVSS | 208. | QFALTQPPLVSGTPGQSVTISCAGANNDIGTYAYVSWYQQ LPGTAPKLLIYKVTTRASGVPSRFSGSKSGNTASLTISGL QSEDEADYYCASYRNFNNAVFGTGTHLTVL | 472. |
| 132A7 | EVQLQESGPGLVKPSQTLSLTCTVSGGSITSRYYAWSW IRQPPGKGLEWIGVIDYDGDTYYSPSLKSRTTISVDTS KNQFSLKLSSVTAEDTAVYYCARDPDVVTGFHYDYWGQ GTLVTVSS | 209. | QSVLTQPPLVSGTPGQRVTISCAGANNDIGTYAYVSWYQQ LPGTAPKLLIYKVTTRASGIPDRFSGSKSGNTASLTISGL QSEDEADYYCASYRNFNNAVFGGGTHLTVL | 473. |
| 132B1 | EVQLQESGPGLVKPSQTLSLTCTVSGGSITSRYYAWSW IRQPPGKGLEWIGVIDYDGDTYYSPSLKSRTTISVDTS KNQFSLKLSSVTAEDTAVYYCARDPDVVTGFHYDYWGQ GTLVTVSS | 210. | QSVLTQPPLVSGAPGQRVTISCAGANNDIGTYAYVSWYQQ LPGTAPKLLIYKVTTRASGVPDRFSGSKSGNTASLTISGL QAEDEADYYCASYRNFNNAVFGGGTHLTVL | 474. |
| 132B2 | EVQLQESGPGLVKPSQTLSLTCTVSGGSITTRYYAWSW IRQPPGKGLEWIGVIDYDGDTYYSPSLKSRTSISWDTS KNQFSLKLSSVTPEDTAVYYCARDPDVVTGFHYDYWGQ GTLVTVSS | 211. | QSALTQPPSVSGAPGQTVTISCAGANNDIGTYAYVSWYQQ LPGTAPKLLIYKVTTRASGIPDRFSGSKSSNTASLTISGL QAEDEADYYCASYRNFNNAVFGGGTHLTVL | 475. |

TABLE 16-continued

VH and VL Amino Acid Sequences of Exemplary Germlined Variants of Fab Clone 68F2.

| FAB CLONE | VH SEQUENCE | SEQ ID NO | VL SEQUENCE | SEQ ID NO |
|---|---|---|---|---|
| 132B7 | EVQLQESGPGLVKPSQTLSLTCTVSGGSITSRYYAWSW IRQPPGKGLEWIGVIDYDGDTYYSPSLKSRTTISWDTS KNQFSLQLSSVTAADTAVYYCARDPDVVTGFHYDYWGQ GTTVTVSS | 212. | QSVLTQPPSVSGTPGQTVTISCAGANNDIGTYAYVSWYQQ LPGTAPKLLIYKVTTRASGVPSRFSGSKSGATASLTISGL QSEDEADYYCASYRNFNNAVFGGGTHLTVL | 476. |
| 132D3 | EVQLQESGPGLVKPSQTLSLTCTVSGGSITSRYYAWSW IRQPPGKGLEWIGVIDYEGDTYYSPSLKSRTTISWDTS KNQFSLQLSSVTAEDTAVYYCARDPDVVTGFHYDYWGQ GTLVTVSS | 213. | QSALTQPPSVSGAPGQTVTISCAGANNDVGTYAYVSWYQQ LPGTAPKLLIYKVTTRASGVPDRFSGSKSGNSASLTITGL QSEDEADYYCASYRNFNNAVFGRGTHLTVL | 477. |
| 132E7 | EVQLQESGPGLVKPSQTLSLTCTVSGGSITSRYYAWSW IRQPPGKGLEWIGVIDYDGDTYYSPSLKSRVTISWDTS KNQFSLKLSSVTPADTAVYYCARDPDVVTGFHYDYWGQ GTTVTVSS | 214. | QSVLTQPPRVSGAPGQTVTISCAGANNDIGTYAYVSWYQQ LPGTAPKLLIYKVTTRASGVPDRFSGSKSGNSASLTITGL QAEDEADYYCASYRNFNNAVFGGGTKLTVL | 478. |
| 132F1 | EVQLEESGPGLVKPSQTLSLTCTVSGGSITTRYYAWSW IRQPPGKGLEWIGVIDYDGDTYYSPSLKSRVTISWDTS KNQFSLKLSSVTPEDTAVYYCARDPDVVTGFHYDYWGQ GTLVTVSS | 215. | QSVLTQPPLVSGAPGQRVTISCAGANNDIGTYAYVSWYQQ LPGTAPKLLIYKVTTRASGVPSRFSGSKSGNTASLTITGL QAEDEADYYCASYRNFNNAVFGRGTHLTVL | 479. |
| 132F2 | EVQLQESGPGLVKPSQTLSLTCTVSGGSITSRYYAWSW IRQPPGKGLEWIGVIDYDGDTYYSPSLKSRTTISWDTS KNQFSLQLSSVTAEDTAVYYCARDPDVVTGFHYDYWGQ GTTVTVSS | 216. | QSVLTQPPSVSGAPGQRVTISCAGANNDIGTYAYVSWYQQ LPGTAPKLLIYKVTTRASGIPSRFSGSKSGNTASLTITGL QSEDEADYYCASYRNFNNAVFGRGTHLTVL | 480. |
| 132G1 | EVQLQESGPGLVKPSQTLSLTCTVSGGSITTRYYAWSW IRQPPGKGLEWIGVIDYDGDTYYSPSLKSRTSISWDTS KNQFSLKLSSVTAADTAVYYCARDPDVVTGFHYDYWGQ GTTVTVSS | 217. | QSVLTQPPLVSGAPGQTVTISCAGANNDIGTYAYVSWYQQ LPGTAPKLLIYKVTTRASGIPNRFSGSKSGNTASLTITGL QAEDEADYYCASYRNFNNAVFGGGTHLTVL | 481. |
| 132G2 | EVQLQESGPGLVKPSQTLSLTCTVSGGSITSRYYAWSW IRQPPGKGLEWIGVIDYDGDTYYSPSLKSRTTISWDTS KNQFSLKLSSVTAEDTAVYYCARDPDVVTGFHYDYWGQ GTLVTVSS | 218. | QSVLTQPPLVSGTPGQRVTISCAGANNDIGTYAYVSWYQQ LPGTAPKLLIYKVTTRASGIPDRFSGSKSGNTASLTISGL QSEDEADYYCASYRNFNNAVFGGGTHLTVL | 482. |
| 132G3 | EVQLQESGPGLVKPSQTLSLTCTVSGGSITSRYYAWSW IRQPPGKGLEWIGVIDYDGDTYYSPSLKSRTTISWDTS KNQFSLQLSSVTAADTAVYYCARDPDVVTGFHYDYWGQ GTTVTVSS | 219. | QSVLTQPPLVSGAPGQTVTISCAGANNDIGTYAYVSWYQQ LPGTAPKLLIYKVTTRASGIPDRFSGSKSGNTASLTISGL QSEDEADYYCASYRNFNNAVFGGGTKLTVL | 483. |
| 132G7 | QVQLQESGPGLVKPSQTLSLTCTVSGGSITTRYYAWSW IRQPPGKGLEWIGVIDYDGDTYYSPSLKSRTTISWDTS KNQFSLQLSSVTPADTAVYYCARDPDVVTGFHYDYWGQ GTMVTVSS | 220. | QSALTQPPSVSGAPGQTVTISCAGANNDIGTYAYVSWYQQ LPGTAPKLLIYKVTTRASGIPDRFSGSKSGNTASLTISGL QAEDEADYYCASYRNFNNAVFGRGTKLTVL | 484. |
| 133A3 | EVQLQESGPGLVKPSQTLSLTCTVSGGSITTRYYAWSW IRQPPGKGLEWIGVIDYDGDTYYSPSLKSRTTISWDTS KNQFSLQLSSVTPEDTAVYYCARDPDVVTGFHYDYWGQ GTLVTVSS | 221. | QSALTQPPLVSGTPGQTVTISCAGANNDIGTYAYVSWYQQ LPGTAPKLLIYKVTTRASGVPDRFSGSISGNTASLTISGL QSEDEADYYCASYRNFNNGVFGTGTHLTVL | 485. |
| 133A7 | EVHLQESGPGLVKPSQTLSLTCTVSGGSITSRYYAWSW IRQPPGKGLEWIGVIYYEGDTYYSPSLKSRTSISWDTS KNQFSLQLSSVTPEDTAVYYCARDPDVVTGFHYDYWGQ GTLVTVSS | 222. | QSALTQPPLVSGSPGQTVTISCAGANNDIGTYAYVSWYQQ LPGTAPKLLIYKVTTRASGIPSRFSGSKSGNTASLTISGL QSEDEADYYCASYRNFNNAVFGRGTKLTVL | 486. |
| 133A9 | EVQLQESGPGLVKPSQTLSLTCTVSGGSITTRYYAWSW IRQPPGKGLEWIGVIDYEGDTYYSPSLKSRVTISVDTS KNQFSLKLSSVTAEDTAVYYCARDPDVVTGFHYDYWGQ GTMVTVSS | 223. | QSALTQPPLVSGSPGQTVTISCAGANNDIGTYAYVSWYQQ PPGTAPKLMIYKVTTRASGIPDRFSGSISGNTASLTISGL QSEDEADYYCASYRNFNNAVFGTGTKLTVL | 487. |
| 133D1 | EVQLQESGPGLVKPSQTLSLTCTVSGGSITSRYYAWSW IRQPPGKGLEWIGVINYDGDTYYSPSLKSRTTISWDTS KNQFSLQLSSVTPEDTAVYYCARYPDVVTGFHYDYWGQ GTQVTVSS | 224. | QSALTQPPLVSGSPGQTVTISCAGANNDIGTYAYVSWYQQ LPGTAPKLMIYKVTTRASGVPDRFSGSKSGNTASLTISGL QSEDEADYYCASYRNFNNAVFGRGTKLTVL | 488. |
| 133D8 | EVQLQESGPGLVKPSQTLSLTCTVSGGSITSRYYAWSW IRQPPGKGLEWIGVIDYDGDTYYSPSLKSRTTISWDTS KNQFSLQLSSVTAEDTAVYYCARDPDVVTGFHYDYWGQ GTLVTVSS | 225. | QSALTQPPLVSGSPGQSVTISCAGANNDIGTYAYVSWYQQ LPGTAPKLLIYKVTTRASGVPSRFSGSKSGNTASLTISGL QAEDEADYYCASYRNFNNAVFGRGTKLTVL | 489. |

TABLE 16-continued

VH and VL Amino Acid Sequences of Exemplary Germlined Variants of Fab Clone 68F2.

| FAB CLONE | VH SEQUENCE | SEQ ID NO | VL SEQUENCE | SEQ ID NO |
|---|---|---|---|---|
| 133E3 | EVQLQESGPGLVKPSQTLSLTCTVSGGSITSRYYAWSWIRQPPGKGLEWIGVIDYDGDTYYSPSLKSRTSISWDTSKNQFSLHLSSVTAEDTAVYYCARDPDVVTGFHYDYWGQGTQVTVSS | 226. | QSALTQPPSVSGSPGQSVTLSCAGANNDIGTYAYVSWYQQLPGTAPKLMIYKVTTRASGVPDRFSGSKSGNTASLTISGLQSEDEADYYCASYRNFNNAVFGSGTKLTVL | 490. |
| 133E5 | QVQLQESGPGLVKPSQTLSLTCTVSGGSITSRYYAWSWIRQPPGKGLEWIGVIDYDGDTYYSPSLKSRVTISWDTSKNQFSLKLSSVTPEDTAVYYCARDPDVVTGFHYDYWGQGTQVTVSS | 227. | QSALTQPPSVSGSPGQTVTISCAGANNDIGTYAYVSWYQQLPGTAPKLMIYKVTTRASGIPDRFSGSKSGNTASLTISGLQAEDEADYYCASYRNFNNAVFGRGTKLTVL | 491. |
| 133F2 | EVQLQESGPGLVKPSQTLSLTCTVSGGSITSRYYAWSWIRQPPGKGLEWIGVIDYDGDTYYSPSLKSRTTISWDTSKNQFSLQLSSVTPEDTAVYYCARDPDVVTGFHYDYWGQGTLVTVSS | 228. | QSALTQPPSVSGSPGQSVTISCAGANNDIGTYAYVSWYQQLPGTAPQLLIYKVTTRASGIPDRFSGSKSGNTASLTISGLQSEDEADYYCASYRNFNNAVFGGGTKLTVL | 492. |
| 133G8 | EVQLQESGPGLVKPSQTLSLTCTVSGGSITSRYYAWSWIRQPPGKGLEWIGVIDYDGDTYYSPSLKSRVTISWDTSKNQFSLQLSSVTAEDTAVYYCARDPDVVTGFHYDYWGQGTQVTVSS | 229. | QSALTQPPSVSGTPGQSVTISCAGANNDIGTYAYVSWYQQLPGTAPKLLIYKVTTRASGIPDRFSGSKSGNTASLTISGLQSEDEADYYCASYRNFNNAVFGGGTHLTVL | 493. |
| 133H2 | EVQLQESGPGLVKPSQTLSLTCTVSGGSITTRYYAWSWIRQPPGKGLEWIGVIDYDGDTYYSPSLKSRTTISWDTSKNQFSLKLSSVTPADTAVYYCARDPDVVTGFHYDYWGQGTTVTVSS | 230. | QSALTQPPLVSGSPGQTVTISCAGANNDIGTYAYVSWYQQPPGTAPKLMIYKVTTRASGIPDRFSGSKSGNTASLTISGLQAEDEADYYCASYRNFNNAVFGSGTKLTVL | 494. |
| 133H9 | QVQLQESGPGLVKPSQTLSLTCTVSGGSITTRYYAWSWIRQPPGKGLEWIGVIDYDGDTYYSPSLKSRTSISWDTSKNQFSLKLSSVTAEDTAVYYCARDPDVVTGFHYDYWGQGTQVTVSS | 231. | QSALTQPPSVSGSPGQTVTISCAGANNDIGTYAYVSWYQQPPGTAPKLLIYKVTTRASGVPDRFSGSKSGNTASLTISGLQSEDEADYYCASYRNFNNAVFGTGTHLTVL | 495. |
| 127E2 | EVQLQESGPGLVKPSQTLSLTCTVSGGSITTRYYAWSWIRQPPGKGLEWIGVIDYDGDTYYSPSLKSRVTISVDTSKNQFSLQLSSVTAEDTAVYYCARDPDVVTGFHYDYWGQGTQVTVSS | 232. | QSALTQPPSVSGSPGQTVTISCAGANNDIGTYAYVSWYQQPPGTAPKLLIYKVTTRASGVPDRFSGSKSGNTASLTISGLQAEDEADYYCASYRNFNNAVFGGGTHLTVL | 496. |

TABLE 17

Sequence Variants of Fab 129D3 CDR Amino Acid Sequences and CDR Consensus Sequences Thereof

| CDR | SEQUENCE | SEQ ID NO |
|---|---|---|
| HCDR3 | DPDVVTGFHYDY | 497. |
|  | YPDVVTGFHYDY | 498. |
|  | DPDVVTGFHYDN | 499. |
|  | $X_1$PDVVTGFHYD$X_2$ | 500. |
|  | Where: | |
|  | $X_1$ = D or Y | |
|  | $X_2$ = Y or N | |
| HCDR2 | VIDYDGDTYYSPSLKS | 501. |
|  | VIDYDGDTYYSPSLES | 502. |
|  | VIDYDADTYYSPSLKS | 503. |
|  | VIDYEGDTYYSPSLKS | 504. |
|  | VIYYEGDTYYSPSLKS | 505. |
|  | VINYDGDTYYSPSLKS | 506. |
|  | VI$X_1$Y$X_2$$X_3$DTYYSPSL$X_4$S | 507. |
|  | Where: | |
|  | $X_1$ = D, Y or N | |
|  | $X_2$ = D or E | |
|  | $X_3$ = A or G | |
|  | $X_4$ = E or K | |
| HCDR1 | SRYYAWS | 508. |
|  | TRYYAWS | 509. |
|  | PRYYVWT | 510. |
|  | SSYYAWS | 511. |
|  | $X_1$$X_2$YY$X_3$W$X_4$ | 512. |
|  | Where: | |
|  | $X_1$ = T, S or P | |
|  | $X_2$ = R or S | |
|  | $X_3$ = A or V | |
|  | $X_4$ = S or T | |
| LCDR3 | ASYRNFNNAV | 513. |
|  | ASYRHYNNAV | 514. |
|  | ASYRRTIDNI | 515. |
|  | ASYRSSNNAV | 516. |
|  | ASYRNRNNAV | 517. |
|  | ASYRDFNNAV | 518. |
|  | ASYKTYNNVV | 519. |
|  | ASYRYFNNAV | 520. |
|  | ASYRNFNNGV | 521. |
|  | SSYRNFNNAV | 522. |
|  | ASYRTFNNAV | 523. |
|  | ASY$X_1$$X_2$$X_3$$X_4$$X_5$$X_6$$X_7$ | 524. |
|  | Where: | |
|  | $X_1$ = R or K | |
|  | $X_2$ = N, H, R, S, D, T or Y | |
|  | $X_3$ = F, Y, T, S or R | |
|  | $X_4$ = N or I | |
|  | $X_5$ = N or D | |
|  | $X_6$ = V, N, G or A | |
|  | $X_7$ = V or I | |

TABLE 17-continued

Sequence Variants of Fab 129D3 CDR Amino Acid Sequences and CDR Consensus Sequences Thereof

| CDR | SEQUENCE | SEQ ID NO |
|---|---|---|
| LCDR2 | KVTTRAS | 525. |
| | KVSTRAS | 526. |
| | DVNKRAS | 527. |
| | RVSTRAS | 528. |
| | AVSYRVS | 529. |
| | AYNYRAS | 530. |
| | EVNKRTS | 531. |
| | AVSYRAS | 532. |
| | KVTSRAS | 533. |
| | RVTTRAS | 534. |
| | $X_1VX_2X_3RX_4S$ | 535. |
| | Where: | |
| | $X_1$ = R, K, D, A OR E | |
| | $X_2$ = S, N or T | |
| | $X_3$ = T, K or Y | |
| | $X_4$ = A, T or V | |
| LCDR1 | AGANNDIGTYAYVS | 536. |
| | AGTSSDIGGYNYVS | 537. |
| | AGTSSDIGYGDYVS | 538. |
| | AGTSEDVGYGNYVS | 539. |
| | AGTSSDVGYGNYVS | 540. |
| | AGTSSDVGFGNYVS | 541. |
| | $AGX_1X_2X_3DX_4GX_5X_6X_7YVS$ | 542. |
| | Where: | |
| | $X_1$ = A or T | |
| | $X_2$ = S or N | |
| | $X_3$ = S, E or N | |
| | $X_4$ = V or I | |
| | $X_5$ = G, Y, T or F | |
| | $X_6$ = G or Y | |
| | $X_7$ = N, D or A | |

TABLE 18

Sequence Variants of Fab 111A7 CDR Amino Acid Sequences and CDR Consensus Sequences Thereof

| CDR | SEQUENCE | SEQ ID NO |
|---|---|---|
| HCDR3 | RAGWGMGDY | 543. |
| | $RAGX_1GX_2G$ | 544. |
| | Where: | |
| | $X_1$ = any amino acid or no amino acid | |
| | $X_2$ = any amino acid | |
| HCDR2 | RISAGGGSTYYGDSVKG | 545. |
| | AISAGGGSTYYGDSVKG | 546. |
| | RISSGGGSTSYADSVKG | 547. |
| | RISSGGGSTNYADSVKG | 548. |
| | RISSGGGSAYYADSVKG | 549. |
| | AISSSGVSTYYTDSVKG | 550. |
| | AISSGGGSTYYGDSVKG | 551. |
| | RISSGGGSTYYGDSVKG | 552. |
| | PISAGGGSTYYGDSVKG | 553. |
| | $X_1ISX_2X_3GX_4SX_5X_6YX_7DSVKG$ | 554. |
| | Where: | |
| | $X_1$ = A, P or R | |
| | $X_2$ = A or S | |
| | $X_3$ = S or G | |
| | $X_4$ = G or V | |
| | $X_5$ = A or T | |
| | $X_6$ = Y, N or S | |
| | $X_7$ = G, A or T | |
| HCDR1 | SYAMS | 555. |
| | TYAMS | 556. |
| | SYRMY | 557. |
| | SHRMY | 558. |
| | SYAMY | 559. |
| | SYRMS | 560. |
| | SYRLY | 561. |
| | $X_1X_2X_3X_4X_5$ | 562. |
| | Where: | |
| | $X_1$ = S or T | |
| | $X_2$ = H or Y | |
| | $X_3$ = A or R | |
| | $X_4$ = M or L | |
| | $X_5$ = S or Y | |
| LCDR3 | ALDIGDITE | 563. |
| LCDR2 | STNDRHS | 564. |
| LCDR1 | GLSSGSVTASNYPG | 565. |

TABLE 19

Production levels and potencies (pM) of germlined 68F2 variants

| | Exp: | | | | | | | |
|---|---|---|---|---|---|---|---|---|
| | 22.06 (7TD1) | | 29.06 (7TD1) | | 7.07 (7TD1) | | Total identity | HEK (ug/ml) |
| Clone and batch date | IC50 | Rel. Potency | IC50 | Rel. Potency | IC50 | Rel. Potency | (%) | #1 | #2 |
| 129F2 (17.06) | 0.703 | 1.14 | 0.517 | 1.08 | | | 95.1 | 9.2 | |
| 126A3 (24.06) | | | 0.564 | 0.99 | 0.63 | 2.16 | 94.4 | | 28 |
| 129D3 (17.06) | 0.791 | 1.02 | 0.574 | 0.98 | | | 95.2 | 24 | |
| 127F1(24.06) | | | 0.637 | 0.88 | 1.49 | 0.91 | 95.1 | | 24 |
| 129E11 (24.06) | | | 0.857 | 0.65 | 1.55 | 0.88 | 94.5 | | 26 |
| 128G3 (17.06) | 1.344 | 0.60 | 1.073 | 0.52 | | | 94.5 | 6 | |
| 128G3 (24.06) | | | 1.464 | 0.38 | | | | | 34 |
| 127E2 (24.06) | | | 1.245 | 0.45 | | | 95.8 | | 15 |
| 127E2 (17.06) | 1.381 | 0.58 | 1.507 | 0.37 | | | | 0.8 | |
| 68F2 (#12.9) | 0.8026 | 1 | 0.521 | 1.08 | 1.46 | 0.93 | 88.5 | 48 | |
| 68F2 (24.06) | | | 0.560 | 1.00 | 1.36 | 1.00 | | | 48 |
| 68F2 (Dec batch) | | | 0.645 | 0.87 | | | | | |
| 68F2 (Large batch) | | | 1.311 | 0.43 | | | | | |

TABLE 20

CMC Optimized Sequence Variants of Fab 111A7

| CMC Variant | CDRH3 SEQUENCE | SEQ ID NO | VH SEQUENCE | SEQ ID NO |
|---|---|---|---|---|
| 111A7M_A | RAGWGAG | 566. | EVQLLESGGGLVQPGGSLRLSCAASGFTFSSYAMSWVRQAPGKGPEWVSRISAGGGSTYYGDSVKGRFTISRDNSKNTLYLQMNSLRAEDTAVYYCANRAGWGAGDYWGQGTLVTVSS | 569. |
| 111A7_M_L | RAGWGLG | 567. | EVQLLESGGGLVQPGGSLRLSCAASGFTFSSYAMSWVRQAPGKGPEWVSRISAGGGSTYYGDSVKGRFTISRDNSKNTLYLQMNSLRAEDTAVYYCANRAGWGLGDYWGQGTLVTVSS | 570. |
| 111A7_M_S | RAGWGSG | 568. | EVQLLESGGGLVQPGGSLRLSCAASGFTFSSYAMSWVRQAPGKGPEWVSRISAGGGSTYYGDSVKGRFTISRDNSKNTLYLQMNSLRAEDTAVYYCANRAGWGSGDYWGQGTLVTVSS | 571. |

TABLE 21

IL-6 Binding Kinetics of CMC Optimized Sequence Variants of Fab 111A7

| | Off rate (s$^{-1}$) | | | | |
|---|---|---|---|---|---|
| M98X: | bact-hIL-6 | euk-hIL-6 | bact-cy IL-6 | average binding | |
| C | 8.69E−05 | 3.72E−05 | 9.46E−05 | 42 | n = 1 |
| R | 8.05E−05 | 4.08E−05 | 1.21E−04 | 64 | n = 1 |
| A | 8.50E−05 | 4.77E−05 | 1.31E−04 | 102 | n = 3 |
| M | 9.11E−05 | 5.45E−05 | 1.38E−04 | 191 | n = 4 |
| S | 9.81E−05 | 5.46E−05 | 1.46E−04 | 118 | n = 5 |
| T | 1.03E−04 | 5.90E−05 | 1.44E−04 | 130 | n = 2 |
| Y | 1.06E−04 | 6.01E−05 | 1.58E−04 | 104 | n = 3 |
| w | 1.12E−04 | 6.12E−05 | 1.77E−04 | 26 | n = 1 |
| L | 1.17E−04 | 6.78E−05 | 1.84E−04 | 141 | n = 1 |
| N | 1.36E−04 | 7.74E−05 | 2.07E−04 | 137 | n = 1 |
| H | 1.39E−04 | 7.76E−05 | 2.22E−04 | 109 | n = 4 |
| F | 1.40E−04 | 8.17E−05 | 2.03E−04 | 144 | n = 1 |
| D | 1.54E−04 | 8.78E−05 | 2.34E−04 | 112 | n = 3 |
| G | 1.43E−04 | 8.80E−05 | 2.05E−04 | 109 | n = 3 |
| V | 1.16E−04 | 9.03E−05 | 2.42E−04 | 163 | n = 2 |
| P | 7.72E−04 | 5.20E−04 | 8.99E−04 | 66 | n = 5 |
| K | 4.61E−03 | 1.39E−03 | 4.17E−03 | 81 | n = 1 |

TABLE 22

Non-Compartmental PK Analysis of anti-IL-6 mAbs after Single Intravenous Administration Into Cynomolgus Monkey.

| Antibody | MRT [days] | Cl [ml/day] | k [day−1] | T½ [days] |
|---|---|---|---|---|
| 129D3-WT | 22.4 | 6.96 | 0.0468 | 15.6 |
| 129D3-YTE | 34.6 | 4.54 | 0.0303 | 24.0 |
| 129D3-HN | 35.9 | 3.34 | 0.0281 | 24.9 |

MRT = Mean Residence Time;
k = mean elimination rate constant;
t½ = elimination half-life;
Cl = elimination clearance

TABLE 23

In Vitro IL-6 Neutralization Assay Using B9 Cells

| Clone and batch | IC 50 (pM) | R$^2$ | Rel. potency | |
|---|---|---|---|---|
| 133A9 (A3.1) | ? | | R4 | |
| 133H2 (A1.8) | 0.37 | 0.9712 | 2.2 | germl |
| 133E5 (A2.1) | 0.19 | 0.9465 | 4.3 | 68F2 |
| 132E7 (A1.9) | 0.38 | 0.9849 | 2.1 | |
| 68F2 (12.9) | 0.98 | 0.9388 | 0.8 | (average IC50 = |
| 68F2 (A8.10) | 0.62 | 0.9731 | 1.3 | 0.8 pM) |
| 61H7 (12.8) | 1.83 | 0.8923 | 0.4 | |
| 61H7 (A8.11) | 1.57 | 0.9574 | 0.5 | |
| B-E8 P70822D1 | 5.106 | 0.9574 | 0.2 | |

TABLE 24

In Vitro IL-6 Neutralization Assay Using 7TD1 Cells

| | IC50 (pM) | Potency relative to 68F2 |
|---|---|---|
| VH_133E5#A2.1 | 0.10 | 6.69 |
| VH_133A9(QSV)#A3.3 | 0.17 | 4.00 |
| VH_133A9#A3.1 | 0.18 | 3.66 |
| CNTO136LB | 0.19 | 3.49 |
| 129D3U#15.1 | 0.23 | 2.91 |
| 129D3#A1.1 | 0.25 | 2.65 |
| Alder_hu1U#12.5 | 0.29 | 2.31 |
| VH_133H2#A1.8 | 0.35 | 1.94 |
| VH_132E7#A1.9 | 0.37 | 1.85 |
| 111B1_SDM #A6.7 | 0.38 | 1.79 |
| VH_133H2#A9.11 | 0.47 | 1.44 |
| 111B1_1 SDM M/L#A6.9 | 0.51 | 1.32 |
| 104C1_1 SDM M/L#A6.6 | 0.59 | 1.14 |
| 111B1_SDM2_M100L#A9.5 | 0.67 | 1.01 |
| 68F2#A8.10 | 0.67 | 1.00 |
| 104C1_SDM2_M100A#A9.2 | 0.73 | 0.93 |
| GL18LB | 0.76 | 0.89 |
| 104C1_SDM2_M100L#A9.3 | 0.98 | 0.69 |
| 111A7_SDM2_M100A#A9.7 | 1.57 | 0.43 |
| 61H7#A8.11 | 3.48 | 0.19 |

TABLE 25

Groups and Treatment Regimes Employed in Psoriasis Xenograft Model.

| Group | Treatment | group size | Dose-route | Treatment frequency |
|---|---|---|---|---|
| 1 | Betamethasone dipropionate | 3 | Topical | 2 × day, three weeks |
| 2 | PBS | 4 | i.p. | 200 μl, 2 × weeks, 3 weeks |
| 3 | Remicade (10 mg/kg) | 7 | i.p | 200 μl, 2 × weeks, 3 weeks |
| 4 | 68F2 (10 mg/kg) | 5 | i.p. | 200 μl, 2 × weeks, 3 weeks |

TABLE 26

In Vivo IL-6 Neutralization in an SAA Mouse Model

| Group | | | Ab dose/ mouse | Mouse1 | Mouse2 | Mouse3 | Mouse4 | Mouse5 | Mouse6 | Mean | SD |
|---|---|---|---|---|---|---|---|---|---|---|---|
| 1 | NaCl | NaCl | 0 | 61 | 52 | 64 | 73 | 77 | 72 | 66.5 | 9.3 |
| 2 | 0,.1 μg IL-6 | hIgG | 5 μg | 168 | 186 | 178 | 206 | 197 | 161 | 182.7 | 17.1 |
| 3 | | 68F2 | 0,.31 μg | 83 | 129 | 116 | 132 | 145 | 136 | 123.5 | 22.0 |
| 4 | | | 1,.25 μg | 69 | 67 | 81 | 73 | 47 | 83 | 70.0 | 12.9 |
| 5 | | | 5 μg | 76 | 38 | 46 | 63 | 43 | 40 | 51.0 | 15.2 |
| 6 | | GL18 | 0,.31 μg | 122 | 114 | 61 | 100 | 107 | 94 | 99.7 | 21.4 |
| 7 | | | 1,.25 μg | 59 | 51 | 40 | 44 | 44 | 59 | 49.5 | 8.2 |
| 8 | | | 5 μg | 53 | 49 | 36 | 58 | 51 | 56 | 50.5 | 7.8 |
| 9 | | 61H7 | 0,.31 μg | 184 | 148 | 124 | 140 | 133 | 76 | 134.2 | 35.2 |
| 10 | | | 1,.25 μg | 66 | 29 | 33 | 30 | 24 | 35 | 36.2 | 15.1 |
| 11 | | | 5 μg | 47 | 62 | 47 | 40 | 46 | 47 | 48.2 | 7.3 |
| 12 | | CNTO 136 | 0,.31 μg | 158 | 175 | 161 | 134 | 183 | 171 | 163.7 | 17.2 |
| 13 | | | 1,.25 μg | 107 | 54 | 67 | 56 | 62 | 71 | 69.5 | 19.5 |
| 14 | | | 5 μg | 80 | 80 | 45 | 55 | 70 | 84 | 69.0 | 15.7 |

We claim:

1. A method of treating an IL-6-associated disease or disorder selected from the group consisting of ovarian cancer, renal cell carcinoma, and psoriasis, comprising administering to a subject in need of treatment thereof an effective amount of an antibody or antigen binding fragment thereof that specifically binds to IL-6, comprising:
   a VH domain comprising the HCDR3 amino acid sequence set forth as SEQ ID NO: 497;
   the HCDR2 amino acid sequence set forth as SEQ ID NO: 501; and the HCDR1 amino acid sequence set forth as SEQ ID NO: 508, and
   a VL domain comprising the LCDR3 amino acid sequence set forth as SEQ ID NO: 513;
   the LCDR2 amino acid sequence set forth as SEQ ID NO: 525; and the LCDR1 amino acid sequence set forth as SEQ ID NO: 536.

2. The method of claim 1, wherein the antibody or antigen binding fragment thereof further comprises a human Fc domain comprising a H433K/N434F double mutation.

3. The method of claim 1, wherein the VH domain comprises the amino acid sequence set forth as SEQ ID NO: 152.

4. The method of claim 3, wherein the antibody or antigen binding fragment thereof further comprises a human Fc domain comprising a H433K/N434F double mutation.

5. The method of claim 3, wherein the glutamine at position 1 of SEQ ID NO: 152 has been changed to glutamic acid.

6. The method of claim 5, wherein the antibody or antigen binding fragment thereof further comprises a human Fc domain comprising a H433K/N434F double mutation.

7. The method of claim 1, wherein the VL domain comprises the amino acid sequence set forth as SEQ ID NO: 416.

8. The method of claim 7, wherein the antibody or antigen binding fragment thereof further comprises a human Fc domain comprising a H433K/N434F double mutation.

9. The method of claim 1, wherein the VH domain comprises the amino acid sequence set forth as SEQ ID NO: 152, and the VL domain comprises the amino acid sequence set forth as SEQ ID NO: 416.

10. The method of claim 9, wherein the antibody or antigen binding fragment thereof further comprises a human Fc domain comprising a H433K/N434F double mutation.

11. The method of claim 9, wherein the glutamine at position 1 of SEQ ID NO: 152 has been changed to glutamic acid.

12. The method of claim 11, wherein the antibody or antigen binding fragment further comprises a human Fc domain comprising a H433K/N434F double mutation.

13. The method of claim 1, wherein the IL-6-associated disease or disorder is psoriasis.

14. The method of claim 1, wherein the IL-6-associated disease or disorder is renal cell carcinoma.

15. The method of claim 1, wherein the IL-6-associated disease or disorder is ovarian cancer.

* * * * *

SEQUENCE LISTING

<160> NUMBER OF SEQ ID NOS: 571

<210> SEQ ID NO 1
<211> LENGTH: 127
<212> TYPE: PRT
<213> ORGANISM: Lama glama

<400> SEQUENCE: 1

Glu Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ala Thr Ser
            20                  25                  30

Tyr Tyr Ala Trp Ser Trp Ile Arg Gln Pro Pro Gly Lys Gly Leu Glu
        35                  40                  45

Trp Met Gly Val Ile Asp Tyr Asp Gly Asp Thr Tyr Tyr Lys Pro Ser
    50                  55                  60

Leu Lys Ser Arg Thr Ser Ile Ser Arg Asp Thr Ser Lys Asn Gln Phe
65                  70                  75                  80

Ser Leu Gln Leu Ser Ser Val Thr Pro Glu Asp Thr Ala Val Tyr Tyr
                85                  90                  95

Cys Ala Arg Ala Gly Leu Gly Asp Ser Tyr Tyr Leu Gly Thr Tyr Tyr
            100                 105                 110

Ala Met Asp Tyr Trp Gly Lys Gly Thr Leu Val Thr Val Ser Ser
        115                 120                 125

<210> SEQ ID NO 2
<211> LENGTH: 122
<212> TYPE: PRT
<213> ORGANISM: Lama glama

<400> SEQUENCE: 2

```
Glu Val Gln Leu Val Glu Ser Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Asn Ser Gly Gly Ser Thr Ser Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Asp Thr Ala Val Tyr Tyr Cys
                85                  90                  95

Ala Lys Glu Gly Asp Thr Gly Trp Lys Asp Pro Met Tyr Asp Tyr Trp
            100                 105                 110

Gly Gln Gly Thr Gln Val Thr Val Ser Ser
            115                 120
```

<210> SEQ ID NO 3
<211> LENGTH: 122
<212> TYPE: PRT
<213> ORGANISM: Lama glama

<400> SEQUENCE: 3

```
Glu Val Gln Leu Val Glu Ser Gly Pro Gly Leu Val Lys Pro Ser Gln
1               5                   10                  15

Thr Leu Ser Leu Thr Cys Thr Val Ser Gly Ser Ile Thr Ala Ser
            20                  25                  30

Phe Asp Ala Trp Ser Trp Ile Arg Gln Pro Pro Gly Lys Gly Leu Glu
        35                  40                  45

Trp Met Gly Val Ile Ala Tyr Asp Gly Ser Thr Tyr Tyr Ser Pro Ser
    50                  55                  60

Leu Lys Ser Arg Thr Ser Ile Ser Arg Asp Thr Ser Lys Asn Gln Phe
65                  70                  75                  80

Ser Leu Gln Leu Ser Ser Val Thr Pro Glu Asp Thr Ala Val Tyr Tyr
                85                  90                  95

Cys Ala Arg Lys Ser Ser Trp Leu Ile Gly Tyr Gly Met Asp Tyr Trp
            100                 105                 110

Gly Lys Gly Thr Leu Val Thr Val Ser Ser
            115                 120
```

<210> SEQ ID NO 4
<211> LENGTH: 122
<212> TYPE: PRT
<213> ORGANISM: Lama glama

<400> SEQUENCE: 4

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Asn
            20                  25                  30

Ala Met Ser Trp Val Arg Gln Ala Pro Gly Lys Gly Leu Glu Trp Val
        35                  40                  45

Ser Ala Ile Asn Ser Gly Gly Gly Ser Thr Ser Tyr Ala Asp Ser Val
    50                  55                  60
```

```
Lys Gly Arg Phe Thr Ile Ser Arg Asp Asn Ala Lys Asn Thr Leu Tyr
 65                  70                  75                  80

Leu Gln Met Asn Ser Leu Lys Pro Glu Asp Thr Ala Val Tyr Tyr Cys
                 85                  90                  95

Ala Lys Glu Gly Tyr Thr Gly Trp Lys Asp Pro Met Tyr Asp Tyr Trp
            100                 105                 110

Gly Gln Gly Thr Gln Val Thr Val Ser Ser
            115                 120

<210> SEQ ID NO 5
<211> LENGTH: 122
<212> TYPE: PRT
<213> ORGANISM: Lama glama

<400> SEQUENCE: 5

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Asn
            20                  25                  30

Ala Met Ser Trp Val Arg Gln Ala Pro Gly Lys Gly Leu Glu Trp Val
        35                  40                  45

Ser Ala Ile Asn Ser Gly Gly Gly Ser Thr Ser Tyr Ala Asp Ser Val
    50                  55                  60

Lys Gly Arg Phe Thr Ile Ser Arg Asp Asn Ala Lys Asn Thr Leu Tyr
 65                  70                  75                  80

Leu Gln Met Asn Ser Leu Lys Pro Glu Asp Thr Ala Val Tyr Tyr Cys
                 85                  90                  95

Ala Lys Glu Gly Tyr Thr Gly Trp Lys Asp Pro Met Tyr Asp Tyr Trp
            100                 105                 110

Gly Gln Gly Thr Gln Val Thr Val Ser Ser
            115                 120

<210> SEQ ID NO 6
<211> LENGTH: 122
<212> TYPE: PRT
<213> ORGANISM: Lama glama

<400> SEQUENCE: 6

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Asn
            20                  25                  30

Ala Met Ser Trp Val Arg Gln Ala Pro Gly Lys Gly Leu Glu Trp Val
        35                  40                  45

Ser Ala Ile Asn Ser Gly Gly Gly Ser Thr Ser Tyr Ala Asp Ser Val
    50                  55                  60

Lys Gly Arg Phe Thr Ile Ser Arg Asp Asn Ala Lys Asn Thr Leu Tyr
 65                  70                  75                  80

Leu Gln Met Asn Ser Leu Lys Pro Glu Asp Thr Ala Val Tyr Tyr Cys
                 85                  90                  95

Ala Lys Glu Gly Tyr Thr Gly Trp Lys Asp Pro Met Tyr Asp Tyr Trp
            100                 105                 110

Gly Gln Gly Thr Gln Val Thr Val Ser Ser
            115                 120

<210> SEQ ID NO 7
<211> LENGTH: 122
```

<212> TYPE: PRT
<213> ORGANISM: Lama glama

<400> SEQUENCE: 7

Glu Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Thr Thr Arg
            20                  25                  30

Tyr Tyr Ala Trp Ser Trp Ile Arg Gln Pro Pro Gly Lys Gly Leu Glu
        35                  40                  45

Trp Met Gly Val Ile Asp Tyr Asp Gly Asp Thr Tyr Tyr Ser Pro Ser
    50                  55                  60

Leu Lys Ser Arg Thr Ser Ile Ser Trp Asp Thr Ser Lys Asn Gln Phe
65                  70                  75                  80

Ser Leu Gln Leu Ser Ser Val Thr Pro Glu Asp Thr Ala Val Tyr Tyr
                85                  90                  95

Cys Ala Arg Asp Pro Asp Val Val Thr Gly Phe His Tyr Asp Tyr Trp
            100                 105                 110

Gly Gln Gly Thr Gln Val Thr Val Ser Ser
            115                 120

<210> SEQ ID NO 8
<211> LENGTH: 122
<212> TYPE: PRT
<213> ORGANISM: Lama glama

<400> SEQUENCE: 8

Glu Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Thr Thr Arg
            20                  25                  30

Tyr Tyr Ala Trp Ser Trp Ile Arg Gln Pro Pro Gly Lys Gly Leu Glu
        35                  40                  45

Trp Met Gly Val Ile Asp Tyr Asp Gly Asp Thr Tyr Tyr Ser Pro Ser
    50                  55                  60

Leu Lys Ser Arg Thr Ser Ile Ser Trp Asp Thr Ser Lys Asn Gln Phe
65                  70                  75                  80

Ser Leu Gln Leu Ser Ser Val Thr Pro Glu Asp Thr Ala Val Tyr Tyr
                85                  90                  95

Cys Ala Arg Asp Pro Asp Val Val Thr Gly Phe His Tyr Asp Tyr Trp
            100                 105                 110

Gly Gln Gly Thr Gln Val Thr Val Ser Ser
            115                 120

<210> SEQ ID NO 9
<211> LENGTH: 122
<212> TYPE: PRT
<213> ORGANISM: Lama glama

<400> SEQUENCE: 9

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Thr Thr Ser
            20                  25                  30

Tyr Tyr Ala Trp Ser Trp Ile Arg Gln Pro Pro Gly Lys Gly Leu Glu
        35                  40                  45

Trp Met Gly Val Ile Gly Tyr Asp Gly Ser Thr Tyr Tyr Ser Pro Ser

```
                    50                  55                  60
Leu Lys Ser Arg Thr Ser Ile Ser Arg Asp Thr Ser Lys Asn Gln Phe
 65                  70                  75                  80

Ser Leu Gln Leu Ser Ser Val Thr Pro Glu Asp Thr Ala Val Tyr Tyr
                     85                  90                  95

Cys Ala Arg Asp Ala Gly Trp Tyr Val Gly Tyr Glu Tyr Asp Tyr Trp
                    100                 105                 110

Gly Gln Gly Thr Gln Val Thr Val Ser Ser
                115                 120
```

<210> SEQ ID NO 10
<211> LENGTH: 126
<212> TYPE: PRT
<213> ORGANISM: Lama glama

<400> SEQUENCE: 10

```
Gln Leu Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Asp Asp Tyr
                20                  25                  30

Ala Met Ser Trp Val Arg Gln Ala Pro Gly Lys Gly Leu Glu Trp Val
             35                  40                  45

Ser Asp Ile Ser Trp Asn Gly Gly Asn Thr Tyr Tyr Ala Glu Ser Met
 50                  55                  60

Lys Gly Arg Phe Thr Ile Ser Arg Asp Asn Ala Lys Asn Thr Leu Tyr
 65                  70                  75                  80

Leu Gln Met Asn Ser Leu Lys Ser Glu Asp Thr Ala Val Tyr Tyr Cys
                 85                  90                  95

Ala Lys Glu Gly Gly Ala Val Val Ala Gly Thr Val Gly Tyr Tyr Gly
                100                 105                 110

Met Asp Tyr Trp Gly Lys Gly Thr Leu Val Thr Val Ser Ser
            115                 120                 125
```

<210> SEQ ID NO 11
<211> LENGTH: 121
<212> TYPE: PRT
<213> ORGANISM: Lama glama

<400> SEQUENCE: 11

```
Gln Val Gln Val Gln Glu Ser Gly Gly Gly Leu Val Gln Pro Gly Gly
 1               5                  10                  15

Ser Leu Arg Leu Ser Cys Ala Ala Ser Gly Phe Thr Phe Ser Asn Tyr
                20                  25                  30

Ala Met Ser Trp Val Arg Gln Ala Pro Gly Lys Gly Leu Glu Trp Val
             35                  40                  45

Ser Gly Ile Ser Phe Arg Gly Gly Met Ile Ser Tyr Val Asp Ser Val
 50                  55                  60

Lys Gly Arg Phe Thr Ile Ser Arg Asp Asn Ala Lys Asn Thr Leu Tyr
 65                  70                  75                  80

Leu Gln Met Asn Ser Leu Lys Pro Glu Asp Thr Ala Val Tyr Tyr Cys
                 85                  90                  95

Ala Lys Asn Ser Gly Ser Ser Arg Ser Asn Ala Leu Asp Ala Trp Gly
                100                 105                 110

Gln Gly Thr Leu Val Thr Val Ser Ser
            115                 120
```

-continued

```
<210> SEQ ID NO 12
<211> LENGTH: 119
<212> TYPE: PRT
<213> ORGANISM: Lama glama

<400> SEQUENCE: 12
```

Gln Val Gln Leu Gln Glu Ser Gly Gly Gly Leu Val Gln Pro Gly Glu
1               5                   10                  15

Ser Leu Arg Leu Ser Cys Val Ala Ser Gly Phe Thr Phe Ser Ser His
            20                  25                  30

Arg Met Tyr Trp Val Arg Gln Pro Pro Gly Lys Gly Leu Glu Trp Val
        35                  40                  45

Ser Ala Ile Ser Ser Gly Val Ser Thr Tyr Tyr Thr Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Leu Tyr Tyr Cys
                85                  90                  95

Lys Arg Arg Thr Trp Tyr Ala Gly Glu Tyr Asp Tyr Trp Gly Gln Gly
            100                 105                 110

Thr Gln Val Thr Val Ser Ser
            115

```
<210> SEQ ID NO 13
<211> LENGTH: 119
<212> TYPE: PRT
<213> ORGANISM: Lama glama

<400> SEQUENCE: 13
```

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Arg Met Tyr Trp Val Arg Gln Pro Pro Gly Lys Gly Leu Glu Trp Val
        35                  40                  45

Ser Ala Ile Ser Ala Gly Gly Gly Ser Thr Tyr Tyr Gly Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Leu Tyr Tyr Cys
                85                  90                  95

Lys Lys Ser Thr Trp Ala Asp Gly Glu Ser Asp Tyr Trp Gly Gln Gly
            100                 105                 110

Thr Gln Val Thr Val Ser Ser
            115

```
<210> SEQ ID NO 14
<211> LENGTH: 118
<212> TYPE: PRT
<213> ORGANISM: Lama glama

<400> SEQUENCE: 14
```

Gln Leu Gln Val Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Pro Glu Trp Val
        35                  40                  45

Ser Arg Ile Ser Ser Gly Gly Ser Thr Ser Tyr Ala Asp Ser Val
        50                  55                  60

Lys Gly Arg Phe Thr Ile Ser Arg Asp Asn Ala Lys Asn Thr Leu Tyr
 65                  70                  75                  80

Leu Gln Met Asn Ser Leu Lys Pro Glu Asp Thr Ala Val Tyr Tyr Cys
                     85                  90                  95

Ala Asn Arg Ala Gly Trp Gly Met Gly Asp Tyr Trp Gly Gln Gly Thr
            100                 105                 110

Gln Val Thr Val Ser Ser
            115

<210> SEQ ID NO 15
<211> LENGTH: 119
<212> TYPE: PRT
<213> ORGANISM: Lama glama

<400> SEQUENCE: 15

Glu Val Gln Val Gln Glu Ser Gly Gly Gly Leu Val Gln Pro Gly Glu
 1               5                   10                  15

Ser Leu Arg Leu Ser Cys Ala Ala Ser Gly Phe Thr Phe Ser Ser His
             20                  25                  30

Arg Met Tyr Trp Val Arg Gln Pro Pro Gly Lys Gly Leu Glu Trp Val
         35                  40                  45

Ser Ala Ile Ser Ser Gly Val Ser Thr Tyr Tyr Ala Asp Ser Val
        50                  55                  60

Lys Gly Arg Phe Thr Ile Ser Arg Asp Asn Ala Lys Asn Thr Val Tyr
 65                  70                  75                  80

Leu Gln Met Asn Ser Leu Lys Pro Glu Asp Thr Ala Leu Tyr Tyr Cys
                     85                  90                  95

Lys Arg Arg Thr Trp Tyr Gly Gly Glu Tyr Asp Tyr Trp Gly Gln Gly
            100                 105                 110

Thr Gln Val Thr Val Ser Ser
            115

<210> SEQ ID NO 16
<211> LENGTH: 118
<212> TYPE: PRT
<213> ORGANISM: Lama glama

<400> SEQUENCE: 16

Glu Val Gln Leu Val Glu Ser Gly Gly Gly Leu Val Gln Pro Gly Gly
 1               5                   10                  15

Ser Leu Arg Leu Ser Cys Ala Ala Ser Gly Phe Thr Phe Ser Thr Tyr
             20                  25                  30

Ala Met Ser Trp Val Arg Gln Ala Pro Gly Lys Gly Pro Glu Trp Val
         35                  40                  45

Ser Arg Ile Ser Ser Gly Gly Gly Ser Thr Asn Tyr Ala Asp Ser Val
        50                  55                  60

Lys Gly Arg Phe Thr Ile Ser Arg Asp Asn Ala Lys Lys Thr Leu Tyr
 65                  70                  75                  80

Leu Gln Met Lys Ser Leu Lys Pro Glu Asp Thr Ala Val Tyr Tyr Cys
                     85                  90                  95

Ala Asn Arg Ala Gly Trp Gly Met Gly Asp Tyr Trp Gly Gln Gly Thr
            100                 105                 110

Gln Val Thr Val Ser Ser
            115

<210> SEQ ID NO 17
<211> LENGTH: 119
<212> TYPE: PRT
<213> ORGANISM: Lama glama

<400> SEQUENCE: 17

Glu Val Gln Leu Val Glu Ser Gly Gly Gly Leu Val Gln Pro Gly Glu
1               5                   10                  15

Ser Leu Arg Leu Ser Cys Ala Ala Ser Gly Phe Thr Phe Ser Ser His
            20                  25                  30

Arg Met Tyr Trp Val Arg Gln Pro Pro Gly Lys Gly Leu Glu Trp Val
        35                  40                  45

Ser Ala Ile Ser Ser Ser Gly Val Ser Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Leu Tyr Tyr Cys
                85                  90                  95

Lys Arg Arg Thr Trp Tyr Gly Gly Glu Tyr Asp Tyr Trp Gly Gln Gly
            100                 105                 110

Thr Gln Leu Thr Val Ala Ser
        115

<210> SEQ ID NO 18
<211> LENGTH: 119
<212> TYPE: PRT
<213> ORGANISM: Lama glama

<400> SEQUENCE: 18

Gln Leu Gln Val Val Glu Ser Gly Gly Gly Leu Val Gln Pro Gly Ser
1               5                   10                  15

Ser Leu Arg Leu Ser Cys Gly Ala Ser Gly Phe Thr Phe Ser Ser His
            20                  25                  30

Arg Met Tyr Trp Val Arg Gln Pro Pro Gly Lys Gly Leu Glu Trp Val
        35                  40                  45

Ser Ala Ile Ser Ser Ser Gly Val Ser Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Leu Tyr Tyr Cys
                85                  90                  95

Lys Arg Arg Thr Trp Tyr Gly Gly Glu Tyr Asp Tyr Trp Gly Gln Gly
            100                 105                 110

Thr Gln Val Thr Val Ser Ser
        115

<210> SEQ ID NO 19
<211> LENGTH: 119
<212> TYPE: PRT
<213> ORGANISM: Lama glama
<220> FEATURE:
<221> NAME/KEY: misc_feature
<222> LOCATION: (13)..(13)
<223> OTHER INFORMATION: Xaa can be any naturally occurring amino acid

<400> SEQUENCE: 19

Glu Val Gln Leu Val Glu Ser Gly Gly Gly Leu Pro Xaa Pro Gly Glu
1               5                   10                  15

Ser Leu Arg Leu Ser Cys Ala Ala Ser Gly Phe Thr Phe Ser Ser His
            20                  25                  30

Arg Met Tyr Trp Val Arg Gln Pro Gly Lys Gly Leu Glu Trp Val
            35                  40                  45

Ser Ala Ile Ser Ser Ser Gly Val Ser Thr Tyr Tyr Ala Asp Ser Val
50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Leu Tyr Tyr Cys
                85                  90                  95

Lys Arg Thr Trp Tyr Gly Gly Glu Tyr Asp Tyr Trp Gly Gln Gly
            100                 105                 110

Thr Gln Leu Thr Val Ala Ser
            115

<210> SEQ ID NO 20
<211> LENGTH: 120
<212> TYPE: PRT
<213> ORGANISM: Lama glama

<400> SEQUENCE: 20

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
            35                  40                  45

Ser Arg Ile Ser Ser Gly Gly Ile Ser Thr Tyr Tyr Ala Asp Ser Val
50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Asp Thr Ala Val Tyr Tyr Cys
                85                  90                  95

Val Arg Tyr Ala Trp Gly Val Gln Trp Ala Phe Asp Phe Trp Gly Gln
            100                 105                 110

Gly Thr Gln Val Thr Val Ser Ser
            115                 120

<210> SEQ ID NO 21
<211> LENGTH: 123
<212> TYPE: PRT
<213> ORGANISM: Lama glama

<400> SEQUENCE: 21

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Tyr Met Thr Trp Val Arg Gln Ala Pro Gly Lys Gly Leu Glu Trp Val
            35                  40                  45

Ser Ser Ile Tyr Ser Phe Ser Gly Asp Thr Ala Tyr Ala Asp Ser Val
            50                  55                  60

Lys Gly Arg Phe Thr Ile Ser Arg Asp Asn Ala Lys Asn Thr Leu Tyr
65                  70                  75                  80

Leu Gln Met Asn Lys Leu Lys Ser Glu Asp Thr Ala Val Tyr Tyr Cys
                85                  90                  95

Thr Arg Asp Leu Gly Gly Val Val Thr Ala Asn Gly Tyr Asp Tyr
            100                 105                 110

Trp Gly Gln Gly Thr Gln Val Thr Val Ser Ser
            115                 120

<210> SEQ ID NO 22
<211> LENGTH: 123
<212> TYPE: PRT
<213> ORGANISM: Lama glama

<400> SEQUENCE: 22

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Tyr Met Thr Trp Val Arg Gln Ala Pro Gly Lys Gly Leu Glu Trp Val
            35                  40                  45

Ser Ser Ile Tyr Ser Phe Ser Gly Asp Thr Ala Tyr Ala Asp Ser Val
        50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Ser Glu Asp Thr Ala Val Tyr Tyr Cys
            85                  90                  95

Thr Arg Asn Leu Gly Gly Val Val Thr Thr Asn Gly Tyr Asp Tyr
            100                 105                 110

Trp Gly Gln Gly Thr Gln Val Thr Val Ser Ser
            115                 120

<210> SEQ ID NO 23
<211> LENGTH: 123
<212> TYPE: PRT
<213> ORGANISM: Lama glama

<400> SEQUENCE: 23

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Tyr Met Thr Trp Val Arg Gln Ala Pro Gly Lys Gly Leu Glu Trp Val
            35                  40                  45

Ser Ser Ile Tyr Ser Phe Ser Gly Asp Thr Ala Tyr Ala Asp Ser Val
        50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Ser Glu Asp Thr Ala Val Tyr Tyr Cys
            85                  90                  95

Thr Arg Asn Leu Gly Gly Val Val Thr Thr Asn Gly Tyr Asp Tyr
            100                 105                 110

Trp Gly Gln Gly Thr Gln Val Thr Val Ser Ser
            115                 120

<210> SEQ ID NO 24
<211> LENGTH: 123
<212> TYPE: PRT
<213> ORGANISM: Lama glama

<400> SEQUENCE: 24

-continued

```
Gln Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Ser Asn Tyr
            20                  25                  30
Tyr Met Thr Trp Val Arg Gln Ala Pro Gly Lys Gly Leu Glu Trp Val
        35                  40                  45
Ser Ser Ile Tyr Ser Phe Ser Gly Asp Thr Ala Tyr Ala Asp Ser Val
    50                  55                  60
Lys Gly Arg Phe Thr Ile Ser Arg Asp Asn Ala Lys Asn Thr Leu Tyr
65                  70                  75                  80
Leu Gln Met Asn Ser Leu Lys Ser Glu Asp Thr Ala Val Tyr Tyr Cys
                85                  90                  95
Thr Arg Asn Leu Gly Gly Val Val Thr Thr Asn Gly Tyr Asp Tyr
            100                 105                 110
Trp Gly Gln Gly Thr Gln Val Thr Val Ser Ser
            115                 120
```

<210> SEQ ID NO 25
<211> LENGTH: 124
<212> TYPE: PRT
<213> ORGANISM: Lama glama

<400> SEQUENCE: 25

```
Glu Leu Gln Leu Val Glu Ser Gly Gly Gly Leu Val Gln Pro Gly Gly
1               5                   10                  15
Ser Leu Arg Leu Ser Cys Ala Ala Ser Gly Tyr Thr Phe Asp Asp Tyr
            20                  25                  30
Ala Met Gly Trp Val Arg Gln Ala Pro Gly Lys Gly Leu Glu Trp Val
        35                  40                  45
Ser Ser Ile Tyr Ser Tyr Ser Ser Asp Thr Tyr Tyr Ala Asp Ser Val
    50                  55                  60
Lys Gly Arg Phe Thr Ile Ser Arg Asp Asn Ala Gln Asn Thr Val Tyr
65                  70                  75                  80
Leu Gln Met Thr Ser Leu Lys Pro Glu Asp Thr Ala Leu Tyr Tyr Cys
                85                  90                  95
Ala Arg Cys Ala Arg Asp Ile Gly Ser Ala Trp Cys Gly Val Asp
            100                 105                 110
Tyr Trp Gly Lys Gly Thr Leu Val Thr Val Ser Ser
            115                 120
```

<210> SEQ ID NO 26
<211> LENGTH: 124
<212> TYPE: PRT
<213> ORGANISM: Lama glama

<400> SEQUENCE: 26

```
Glu Leu Gln Leu Val Glu Ser Gly Gly Gly Leu Val Gln Pro Gly Gly
1               5                   10                  15
Ser Leu Arg Leu Ser Cys Ala Ala Ser Gly Tyr Thr Phe Asp Asp Tyr
            20                  25                  30
Ala Met Gly Trp Val Arg Gln Ala Pro Gly Lys Gly Leu Glu Trp Val
        35                  40                  45
Ser Ser Ile Tyr Ser Tyr Ser Ser Asp Thr Tyr Tyr Ala Asp Ser Val
    50                  55                  60
Lys Gly Arg Phe Thr Ile Ser Arg Asp Asn Ala Gln Asn Thr Val Tyr
65                  70                  75                  80
```

```
Leu Gln Met Thr Ser Leu Lys Pro Glu Asp Thr Ala Leu Tyr Tyr Cys
                85                  90                  95

Ala Arg Cys Ala Arg Asp Ile Gly Ser Ala Trp Cys Gly Gly Val Asp
            100                 105                 110

Tyr Trp Gly Lys Gly Thr Leu Val Thr Val Ser Ser
        115                 120
```

<210> SEQ ID NO 27
<211> LENGTH: 124
<212> TYPE: PRT
<213> ORGANISM: Lama glama

<400> SEQUENCE: 27

```
Glu Leu Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Asp Asp Tyr
            20                  25                  30

Ala Met Gly Trp Val Arg Gln Ala Pro Gly Lys Gly Leu Glu Trp Val
            35                  40                  45

Ser Ser Ile Tyr Ser Tyr Ser Ser Asp Thr Tyr Tyr Ala Asp Ser Val
        50                  55                  60

Lys Gly Arg Phe Thr Ile Ser Arg Asp Asn Ala Gln Asn Thr Val Tyr
65                  70                  75                  80

Leu Gln Met Thr Ser Leu Lys Pro Glu Asp Thr Ala Leu Tyr Tyr Cys
                85                  90                  95

Ala Arg Cys Ala Arg Asp Ile Gly Ser Ala Trp Cys Gly Gly Val Asp
            100                 105                 110

Tyr Trp Gly Lys Gly Thr Leu Val Thr Val Ser Ser
        115                 120
```

<210> SEQ ID NO 28
<211> LENGTH: 120
<212> TYPE: PRT
<213> ORGANISM: Lama glama

<400> SEQUENCE: 28

```
Glu Leu Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
            35                  40                  45

Ser Arg Ile Ser Ser Gly Gly Ile Ser Thr Tyr Tyr Ala Asp Ser Val
        50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Asp Thr Ala Val Tyr Tyr Cys
                85                  90                  95

Ala Arg Tyr Ala Trp Gly Val Gln Trp Ala Phe Asp Phe Trp Gly Gln
            100                 105                 110

Gly Thr Gln Val Thr Val Ser Ser
        115                 120
```

<210> SEQ ID NO 29
<211> LENGTH: 119
<212> TYPE: PRT
<213> ORGANISM: Lama glama

-continued

<400> SEQUENCE: 29

Gln Val Gln Val Gln Glu Ser Gly Gly Gly Leu Val His Pro Gly Glu
1               5                   10                  15

Ser Leu Arg Leu Ser Cys Ala Ala Ser Gly Phe Thr Phe Ser Ser His
            20                  25                  30

Arg Met Tyr Trp Val Arg Gln Pro Pro Gly Lys Gly Leu Glu Trp Val
        35                  40                  45

Ser Ala Ile Ser Ser Ser Gly Val Ser Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Leu Tyr Tyr Cys
                85                  90                  95

Lys Arg Arg Thr Trp Tyr Gly Gly Glu Tyr Asp Tyr Trp Gly Gln Gly
            100                 105                 110

Thr Gln Val Thr Val Ser Pro
        115

<210> SEQ ID NO 30
<211> LENGTH: 119
<212> TYPE: PRT
<213> ORGANISM: Lama glama

<400> SEQUENCE: 30

Glu Val Gln Leu Val Glu Ser Gly Gly Ala Leu Val His Pro Gly Gly
1               5                   10                  15

Ser Leu Arg Leu Ser Cys Ala Ala Ser Gly Phe Thr Phe Ser Ser His
            20                  25                  30

Arg Met Tyr Trp Val Arg Gln Pro Pro Gly Lys Gly Leu Glu Trp Val
        35                  40                  45

Ser Ala Ile Ser Ser Ser Gly Val Ser Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Leu Tyr Tyr Cys
                85                  90                  95

Lys Arg Arg Thr Trp Tyr Gly Gly Glu Tyr Asp Tyr Trp Gly Gln Gly
            100                 105                 110

Thr Gln Val Thr Val Ser Ser
        115

<210> SEQ ID NO 31
<211> LENGTH: 119
<212> TYPE: PRT
<213> ORGANISM: Lama glama

<400> SEQUENCE: 31

Gln Val Gln Leu Val Glu Ser Gly Gly Gly Leu Val His Pro Gly Glu
1               5                   10                  15

Ser Leu Arg Leu Ser Cys Ala Ala Ser Gly Phe Thr Phe Ser Ser His
            20                  25                  30

Arg Met Tyr Trp Val Arg Gln Pro Pro Gly Lys Gly Leu Glu Trp Val
        35                  40                  45

Ser Ala Ile Ser Ser Ser Gly Val Ser Thr Tyr Tyr Ala Asp Ser Val
    50                  55                  60

Lys Gly Arg Phe Thr Ile Ser Arg Asp Asn Ala Lys Asn Thr Val Tyr

```
            65                  70                  75                  80
Leu Gln Met Asn Ser Leu Lys Pro Glu Asp Thr Ala Leu Tyr Tyr Cys
                85                  90                  95

Lys Arg Arg Thr Trp Tyr Gly Glu Tyr Asp Tyr Trp Gly Gln Gly
               100                 105                 110

Thr Gln Val Thr Val Ser Ser
            115
```

<210> SEQ ID NO 32
<211> LENGTH: 120
<212> TYPE: PRT
<213> ORGANISM: Lama glama

<400> SEQUENCE: 32

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ser Arg Ile Ser Ser Gly Gly Ile Ser Thr Tyr Tyr Ala Asp Ser Val
        50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Asp Thr Ala Val Tyr Tyr Cys
                85                  90                  95

Val Arg Tyr Ala Trp Gly Val Gln Trp Ala Phe Asp Phe Trp Gly Gln
               100                 105                 110

Gly Thr Gln Val Thr Val Ser Ser
            115                 120
```

<210> SEQ ID NO 33
<211> LENGTH: 120
<212> TYPE: PRT
<213> ORGANISM: Lama glama

<400> SEQUENCE: 33

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ser Arg Ile Ser Ser Gly Gly Ile Ser Thr Tyr Tyr Ala Asp Ser Val
        50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Asp Thr Ala Val Tyr Tyr Cys
                85                  90                  95

Val Arg Tyr Ala Trp Gly Val Gln Trp Ala Phe Asp Phe Trp Gly Gln
               100                 105                 110

Gly Thr Gln Val Thr Val Ser Ser
            115                 120
```

<210> SEQ ID NO 34
<211> LENGTH: 118
<212> TYPE: PRT

<213> ORGANISM: Lama glama

<400> SEQUENCE: 34

Gln Val Gln Leu Val Glu Ser Gly Gly Gly Leu Val Gln Pro Gly Gly
1               5                   10                  15

Ser Leu Arg Leu Ser Cys Val Ala Ser Gly Phe Thr Phe Ser Ser Tyr
            20                  25                  30

Ala Met Ser Trp Val Arg Gln Ala Pro Gly Lys Gly Pro Glu Trp Val
        35                  40                  45

Ser Arg Ile Ser Ser Gly Gly Ser Thr Ser Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Asp Thr Ala Val Tyr Tyr Cys
                85                  90                  95

Ala Asn Arg Ala Gly Trp Gly Met Gly Asp Tyr Trp Gly Gln Gly Thr
            100                 105                 110

Gln Val Thr Val Ser Ser
        115

<210> SEQ ID NO 35
<211> LENGTH: 118
<212> TYPE: PRT
<213> ORGANISM: Lama glama

<400> SEQUENCE: 35

Glu Leu Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Pro Glu Trp Val
        35                  40                  45

Ser Arg Ile Ser Ser Gly Gly Ser Ala Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Asp Thr Ala Val Tyr Tyr Cys
                85                  90                  95

Ala Asn Arg Ala Gly Trp Gly Met Gly Asp Tyr Trp Gly Gln Gly Thr
            100                 105                 110

Gln Val Thr Val Ser Ser
        115

<210> SEQ ID NO 36
<211> LENGTH: 118
<212> TYPE: PRT
<213> ORGANISM: Lama glama

<400> SEQUENCE: 36

Gln Val Gln Leu Val Glu Ser Gly Gly Gly Leu Val His Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Pro Glu Trp Val
        35                  40                  45

Ser Arg Ile Ser Ser Gly Gly Ser Ala Tyr Tyr Ala Asp Ser Val
    50                  55                  60

```
Lys Gly Arg Phe Thr Ile Ser Arg Asp Asn Ala Lys Asn Thr Leu Tyr
 65                  70                  75                  80

Leu Gln Met Asn Ser Leu Lys Pro Glu Asp Thr Ala Val Tyr Tyr Cys
                 85                  90                  95

Ala Asn Arg Ala Gly Trp Gly Met Gly Asp Tyr Trp Gly Gln Gly Thr
            100                 105                 110

Gln Val Thr Val Ser Ser
        115

<210> SEQ ID NO 37
<211> LENGTH: 118
<212> TYPE: PRT
<213> ORGANISM: Lama glama

<400> SEQUENCE: 37

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Arg Met Tyr Trp Val Arg Gln Pro Pro Gly Lys Gly Leu Glu Trp Val
        35                  40                  45

Ser Ala Ile Ser Ala Gly Gly Ser Thr Tyr Tyr Gly Asp Ser Val
    50                  55                  60

Lys Gly Arg Phe Thr Ile Ser Arg Asp Asn Ala Lys Asn Thr Val Tyr
 65                  70                  75                  80

Leu Gln Met Asn Ser Leu Lys Pro Glu Asp Thr Ala Val Tyr Tyr Cys
                 85                  90                  95

Ala Asn Arg Ala Gly Trp Gly Met Gly Asp Tyr Trp Gly Gln Gly Thr
            100                 105                 110

Gln Val Thr Val Ser Ser
        115

<210> SEQ ID NO 38
<211> LENGTH: 118
<212> TYPE: PRT
<213> ORGANISM: Lama glama

<400> SEQUENCE: 38

Glu Val Gln Leu Val Glu Ser Gly Gly Gly Leu Val Gln Pro Gly Glu
1               5                   10                  15

Ser Leu Arg Leu Ser Cys Val Ala Ser Gly Phe Thr Phe Ser Ser His
            20                  25                  30

Arg Met Tyr Trp Val Arg Gln Pro Pro Gly Lys Gly Leu Glu Trp Val
        35                  40                  45

Ser Ala Ile Ser Ser Ser Gly Val Ser Thr Tyr Tyr Thr Asp Ser Val
    50                  55                  60

Lys Gly Arg Phe Thr Ile Ser Arg Asp Asn Ala Lys Asn Thr Val Tyr
 65                  70                  75                  80

Leu Gln Met Asn Ser Leu Lys Pro Glu Asp Thr Ala Val Tyr Tyr Cys
                 85                  90                  95

Ala Asn Arg Ala Gly Trp Gly Met Gly Asp Tyr Trp Gly Gln Gly Thr
            100                 105                 110

Gln Val Thr Val Ser Ser
        115

<210> SEQ ID NO 39
```

<211> LENGTH: 118
<212> TYPE: PRT
<213> ORGANISM: Lama glama

<400> SEQUENCE: 39

| Glu | Val | Gln | Leu | Leu | Glu | Ser | Gly | Gly | Gly | Leu | Val | Gln | Pro | Gly | Gly |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Ser | Leu | Arg | Leu | Ser | Cys | Ala | Ala | Ser | Gly | Phe | Thr | Phe | Ser | Ser | Tyr |
|     |     |     | 20  |     |     |     |     | 25  |     |     |     |     | 30  |     |     |

| Ala | Met | Tyr | Trp | Val | Arg | Gln | Ala | Pro | Gly | Lys | Gly | Pro | Glu | Trp | Val |
|     |     | 35  |     |     |     |     | 40  |     |     |     |     | 45  |     |     |     |

| Ser | Arg | Ile | Ser | Ala | Gly | Gly | Gly | Ser | Thr | Tyr | Tyr | Gly | Asp | Ser | Val |
| 50  |     |     |     |     | 55  |     |     |     |     | 60  |     |     |     |     |     |

| Lys | Gly | Arg | Phe | Thr | Ile | Ser | Arg | Asp | Asn | Ala | Lys | Asn | Thr | Leu | Tyr |
| 65  |     |     |     |     | 70  |     |     |     |     | 75  |     |     |     |     | 80  |

| Leu | Gln | Met | Asn | Ser | Leu | Arg | Ala | Glu | Asp | Thr | Ala | Val | Tyr | Tyr | Cys |
|     |     |     |     | 85  |     |     |     |     | 90  |     |     |     |     | 95  |     |

| Ala | Asn | Arg | Ala | Gly | Trp | Gly | Met | Gly | Asp | Tyr | Trp | Gly | Gln | Gly | Thr |
|     |     |     |     | 100 |     |     |     |     | 105 |     |     |     |     | 110 |     |

| Gln | Val | Thr | Val | Ser | Ser |
|     |     |     | 115 |     |     |

<210> SEQ ID NO 40
<211> LENGTH: 118
<212> TYPE: PRT
<213> ORGANISM: Lama glama

<400> SEQUENCE: 40

| Glu | Val | Gln | Leu | Leu | Glu | Ser | Gly | Gly | Gly | Leu | Val | Gln | Pro | Gly | Gly |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Ser | Leu | Arg | Leu | Ser | Cys | Ala | Ala | Ser | Gly | Phe | Thr | Phe | Ser | Ser | Tyr |
|     |     |     | 20  |     |     |     |     | 25  |     |     |     |     | 30  |     |     |

| Arg | Met | Tyr | Trp | Val | Arg | Gln | Pro | Pro | Gly | Lys | Gly | Leu | Glu | Trp | Val |
|     |     | 35  |     |     |     |     | 40  |     |     |     |     | 45  |     |     |     |

| Ser | Ala | Ile | Ser | Ala | Gly | Gly | Gly | Ser | Thr | Tyr | Tyr | Gly | Asp | Ser | Val |
| 50  |     |     |     |     | 55  |     |     |     |     | 60  |     |     |     |     |     |

| Lys | Gly | Arg | Phe | Thr | Ile | Ser | Arg | Asp | Asn | Ala | Lys | Asn | Thr | Val | Tyr |
| 65  |     |     |     |     | 70  |     |     |     |     | 75  |     |     |     |     | 80  |

| Leu | Gln | Met | Asn | Ser | Leu | Lys | Pro | Glu | Asp | Thr | Ala | Val | Tyr | Tyr | Cys |
|     |     |     |     | 85  |     |     |     |     | 90  |     |     |     |     | 95  |     |

| Ala | Asn | Arg | Ala | Gly | Trp | Gly | Met | Gly | Asp | Tyr | Trp | Gly | Gln | Gly | Thr |
|     |     |     |     | 100 |     |     |     |     | 105 |     |     |     |     | 110 |     |

| Gln | Val | Thr | Val | Ser | Ser |
|     |     |     | 115 |     |     |

<210> SEQ ID NO 41
<211> LENGTH: 118
<212> TYPE: PRT
<213> ORGANISM: Lama glama

<400> SEQUENCE: 41

| Glu | Leu | Gln | Leu | Leu | Glu | Ser | Gly | Gly | Gly | Leu | Val | Gln | Pro | Gly | Gly |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Ser | Leu | Arg | Leu | Ser | Cys | Ala | Ala | Ser | Gly | Phe | Thr | Phe | Ser | Ser | Tyr |
|     |     |     | 20  |     |     |     |     | 25  |     |     |     |     | 30  |     |     |

| Ala | Met | Tyr | Trp | Val | Arg | Gln | Ala | Pro | Gly | Lys | Gly | Pro | Glu | Trp | Val |
|     |     | 35  |     |     |     |     | 40  |     |     |     |     | 45  |     |     |     |

```
Ser Arg Ile Ser Ala Gly Gly Gly Ser Thr Tyr Tyr Gly Asp Ser Val
    50              55                  60

Lys Gly Arg Phe Thr Ile Ser Arg Asp Asn Ala Lys Asn Thr Leu Tyr
65              70                  75                  80

Leu Gln Met Asn Ser Leu Lys Thr Glu Asn Thr Ala Val Tyr Tyr Cys
                85                  90                  95

Ala Asn Arg Ala Gly Trp Gly Met Gly Asp Tyr Trp Gly Gln Gly Thr
            100                 105                 110

Leu Val Thr Val Ser Ser
        115

<210> SEQ ID NO 42
<211> LENGTH: 118
<212> TYPE: PRT
<213> ORGANISM: Lama glama

<400> SEQUENCE: 42

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Arg Met Ser Trp Val Arg Gln Pro Pro Gly Lys Gly Pro Glu Trp Val
            35                  40                  45

Ser Ala Ile Ser Ser Gly Gly Ser Thr Tyr Tyr Gly Asp Ser Val
    50              55                  60

Lys Gly Arg Phe Thr Ile Ser Arg Asp Asn Ser Lys Asn Thr Leu Tyr
65              70                  75                  80

Leu Gln Met Asn Ser Leu Lys Thr Glu Asp Thr Ala Val Tyr Tyr Cys
                85                  90                  95

Ala Asn Arg Ala Gly Trp Gly Met Gly Asp Tyr Trp Gly Gln Gly Thr
            100                 105                 110

Gln Val Thr Val Ser Ser
        115

<210> SEQ ID NO 43
<211> LENGTH: 118
<212> TYPE: PRT
<213> ORGANISM: Lama glama

<400> SEQUENCE: 43

Glu Leu Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Tyr Trp Val Arg Gln Pro Pro Gly Lys Gly Pro Glu Trp Val
            35                  40                  45

Ser Arg Ile Ser Ala Gly Gly Gly Ser Thr Tyr Tyr Gly Asp Ser Val
    50              55                  60

Lys Gly Arg Phe Thr Ile Ser Arg Asp Asn Ala Lys Asn Thr Val Tyr
65              70                  75                  80

Leu Gln Met Asn Thr Leu Lys Thr Glu Asp Thr Ala Val Tyr Tyr Cys
                85                  90                  95

Ala Asn Arg Ala Gly Trp Gly Met Gly Asp Tyr Trp Gly Gln Gly Thr
            100                 105                 110

Leu Val Thr Val Ser Ile
        115
```

-continued

<210> SEQ ID NO 44
<211> LENGTH: 118
<212> TYPE: PRT
<213> ORGANISM: Lama glama

<400> SEQUENCE: 44

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Pro Glu Trp Val
        35                  40                  45

Ser Arg Ile Ser Ala Gly Gly Gly Ser Thr Tyr Tyr Gly Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Arg Ala Glu Asn Thr Ala Val Tyr Tyr Cys
                85                  90                  95

Ala Asn Arg Ala Gly Trp Gly Met Gly Asp Tyr Trp Gly Gln Gly Thr
            100                 105                 110

Gln Val Thr Val Ser Ser
            115

<210> SEQ ID NO 45
<211> LENGTH: 118
<212> TYPE: PRT
<213> ORGANISM: Lama glama

<400> SEQUENCE: 45

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Pro Glu Trp Val
        35                  40                  45

Ser Arg Ile Ser Ser Gly Gly Gly Ser Thr Tyr Tyr Gly Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Asn Arg Ala Gly Trp Gly Met Gly Asp Tyr Trp Gly Gln Gly Thr
            100                 105                 110

Gln Val Thr Val Ser Ser
            115

<210> SEQ ID NO 46
<211> LENGTH: 118
<212> TYPE: PRT
<213> ORGANISM: Lama glama

<400> SEQUENCE: 46

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Pro Glu Trp Val

```
            35                  40                  45
Ser Arg Ile Ser Ser Gly Gly Ser Thr Tyr Tyr Gly Asp Ser Val
 50                  55                  60
Lys Gly Arg Phe Thr Ile Ser Arg Asp Asn Ser Lys Asn Thr Val Tyr
 65                  70                  75                  80
Leu Gln Met Asn Ser Leu Lys Thr Glu Asn Thr Ala Val Tyr Tyr Cys
                 85                  90                  95
Ala Asn Arg Ala Gly Trp Gly Met Gly Asp Tyr Trp Gly Gln Gly Thr
                100                 105                 110
Gln Val Thr Val Ser Ser
            115

<210> SEQ ID NO 47
<211> LENGTH: 118
<212> TYPE: PRT
<213> ORGANISM: Lama glama

<400> SEQUENCE: 47

Glu Val Gln Leu Val Glu Ser Gly Gly Gly Leu Val Gln Pro Gly Gly
 1               5                  10                  15
Ser Leu Arg Leu Ser Cys Ala Ala Ser Gly Phe Thr Phe Ser Ser Tyr
             20                  25                  30
Arg Met Ser Trp Val Arg Gln Pro Pro Gly Lys Gly Leu Glu Trp Val
            35                  40                  45
Ser Pro Ile Ser Ala Gly Gly Gly Ser Thr Tyr Tyr Gly Asp Ser Val
 50                  55                  60
Lys Gly Arg Phe Thr Ile Ser Arg Asp Asn Ala Lys Asn Thr Leu Tyr
 65                  70                  75                  80
Leu Gln Met Asn Ser Leu Lys Pro Glu Asp Thr Ala Val Tyr Tyr Cys
                 85                  90                  95
Ala Asn Arg Ala Gly Trp Gly Met Gly Asp Tyr Trp Gly Gln Gly Thr
                100                 105                 110
Gln Val Thr Val Ser Ser
            115

<210> SEQ ID NO 48
<211> LENGTH: 118
<212> TYPE: PRT
<213> ORGANISM: Lama glama

<400> SEQUENCE: 48

Glu Val Gln Leu Leu Glu Ser Gly Gly Gly Leu Val Gln Pro Gly Gly
 1               5                  10                  15
Ser Leu Arg Leu Ser Cys Ala Ala Ser Gly Phe Thr Phe Ser Ser Tyr
             20                  25                  30
Ala Met Tyr Trp Val Arg Gln Ala Pro Gly Lys Gly Leu Glu Trp Val
            35                  40                  45
Ser Arg Ile Ser Ala Gly Gly Gly Ser Thr Tyr Tyr Gly Asp Ser Val
 50                  55                  60
Lys Gly Arg Phe Thr Ile Ser Arg Asp Asn Ala Lys Asn Thr Val Tyr
 65                  70                  75                  80
Leu Gln Met Asn Ser Leu Lys Pro Glu Asp Thr Ala Val Tyr Tyr Cys
                 85                  90                  95
Ala Asn Arg Ala Gly Trp Gly Met Gly Asp Tyr Trp Gly Gln Gly Thr
                100                 105                 110
Gln Val Thr Val Ser Ser
```

<210> SEQ ID NO 49
<211> LENGTH: 118
<212> TYPE: PRT
<213> ORGANISM: Lama glama

<400> SEQUENCE: 49

| Glu | Val | Gln | Leu | Val | Glu | Ser | Gly | Gly | Gly | Leu | Val | Gln | Pro | Gly | Gly |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Ala | Ala | Ser | Gly | Phe | Thr | Phe | Ser | Ser | Tyr |
| | | | 20 | | | | | 25 | | | | | 30 | | |

| Arg | Met | Ser | Trp | Val | Arg | Gln | Pro | Pro | Gly | Lys | Gly | Leu | Glu | Trp | Val |
| | | 35 | | | | | 40 | | | | | 45 | | | |

| Ser | Ala | Ile | Ser | Ala | Gly | Gly | Gly | Ser | Thr | Tyr | Tyr | Gly | Asp | Ser | Val |
| | 50 | | | | | 55 | | | | | 60 | | | | |

| Lys | Gly | Arg | Phe | Thr | Ile | Ser | Arg | Asp | Asn | Ala | Lys | Asn | Thr | Val | Tyr |
| 65 | | | | | 70 | | | | | 75 | | | | | 80 |

| Leu | Gln | Met | Asn | Ser | Leu | Lys | Pro | Glu | Asp | Thr | Ala | Val | Tyr | Tyr | Cys |
| | | | | 85 | | | | | 90 | | | | | 95 | |

| Ala | Asn | Arg | Ala | Gly | Trp | Gly | Met | Gly | Asp | Tyr | Trp | Gly | Gln | Gly | Thr |
| | | | 100 | | | | | 105 | | | | | 110 | | |

| Gln | Val | Thr | Val | Ser | Ser |
|---|---|---|---|---|---|
| | | | 115 | | |

<210> SEQ ID NO 50
<211> LENGTH: 118
<212> TYPE: PRT
<213> ORGANISM: Lama glama

<400> SEQUENCE: 50

| Glu | Val | Gln | Leu | Val | Glu | Ser | Gly | Gly | Gly | Leu | Val | Gln | Pro | Gly | Gly |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Ala | Ala | Ser | Gly | Phe | Thr | Phe | Ser | Ser | Tyr |
| | | | 20 | | | | | 25 | | | | | 30 | | |

| Ala | Met | Tyr | Trp | Val | Arg | Gln | Ala | Pro | Gly | Lys | Gly | Leu | Glu | Trp | Val |
| | | 35 | | | | | 40 | | | | | 45 | | | |

| Ser | Arg | Ile | Ser | Ala | Gly | Gly | Gly | Ser | Thr | Tyr | Tyr | Gly | Asp | Ser | Val |
| | 50 | | | | | 55 | | | | | 60 | | | | |

| Lys | Gly | Arg | Phe | Thr | Ile | Ser | Arg | Asp | Asn | Ser | Lys | Asn | Thr | Val | Tyr |
| 65 | | | | | 70 | | | | | 75 | | | | | 80 |

| Leu | Gln | Met | Asn | Ser | Leu | Lys | Pro | Glu | Asp | Thr | Ala | Val | Tyr | Tyr | Cys |
| | | | | 85 | | | | | 90 | | | | | 95 | |

| Ala | Asn | Arg | Ala | Gly | Trp | Gly | Met | Gly | Asp | Tyr | Trp | Gly | Gln | Gly | Thr |
| | | | 100 | | | | | 105 | | | | | 110 | | |

| Gln | Val | Thr | Val | Ser | Ser |
|---|---|---|---|---|---|
| | | | 115 | | |

<210> SEQ ID NO 51
<211> LENGTH: 118
<212> TYPE: PRT
<213> ORGANISM: Lama glama

<400> SEQUENCE: 51

| Glu | Val | Gln | Leu | Val | Glu | Ser | Gly | Gly | Gly | Leu | Val | Gln | Pro | Gly | Gly |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Ala | Ala | Ser | Gly | Phe | Thr | Phe | Ser | Ser | Tyr |
| | | | 20 | | | | | 25 | | | | | 30 | | |

-continued

Ala Met Tyr Trp Val Arg Gln Ala Pro Gly Lys Gly Pro Glu Trp Val
            35                  40                  45

Ser Arg Ile Ser Ala Gly Gly Ser Thr Tyr Tyr Gly Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Asn Arg Ala Gly Trp Gly Met Gly Asp Tyr Trp Gly Gln Gly Thr
            100                 105                 110

Gln Val Thr Val Ser Ser
            115

<210> SEQ ID NO 52
<211> LENGTH: 118
<212> TYPE: PRT
<213> ORGANISM: Lama glama

<400> SEQUENCE: 52

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
            35                  40                  45

Ser Arg Ile Ser Ala Gly Gly Ser Thr Tyr Tyr Gly Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Lys Thr Glu Asp Thr Ala Val Tyr Tyr Cys
                85                  90                  95

Ala Asn Arg Ala Gly Trp Gly Met Gly Asp Tyr Trp Gly Gln Gly Thr
            100                 105                 110

Gln Val Thr Val Ser Ser
            115

<210> SEQ ID NO 53
<211> LENGTH: 118
<212> TYPE: PRT
<213> ORGANISM: Lama glama

<400> SEQUENCE: 53

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Pro Glu Trp Val
            35                  40                  45

Ser Arg Ile Ser Ala Gly Gly Ser Thr Tyr Tyr Gly Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Arg Ala Glu Asp Thr Ala Val Tyr Tyr Cys
                85                  90                  95

Ala Asn Arg Ala Gly Trp Gly Met Gly Asp Tyr Trp Gly Gln Gly Thr
            100                 105                 110

Gln Val Thr Val Ser Ser
        115

<210> SEQ ID NO 54
<211> LENGTH: 118
<212> TYPE: PRT
<213> ORGANISM: Lama glama

<400> SEQUENCE: 54

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Tyr Trp Val Arg Gln Ala Pro Gly Lys Gly Pro Glu Trp Val
        35                  40                  45

Ser Arg Ile Ser Ala Gly Gly Gly Ser Thr Tyr Tyr Gly Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Lys Pro Glu Asp Thr Ala Val Tyr Tyr Cys
                85                  90                  95

Ala Asn Arg Ala Gly Trp Gly Met Gly Asp Tyr Trp Gly Gln Gly Thr
            100                 105                 110

Gln Val Thr Val Ser Ser
        115

<210> SEQ ID NO 55
<211> LENGTH: 118
<212> TYPE: PRT
<213> ORGANISM: Lama glama

<400> SEQUENCE: 55

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Pro Glu Trp Val
        35                  40                  45

Ser Arg Ile Ser Ala Gly Gly Gly Ser Thr Tyr Tyr Gly Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Asn Arg Ala Gly Trp Gly Met Gly Asp Tyr Trp Gly Gln Gly Thr
            100                 105                 110

Gln Val Thr Val Ser Ser
        115

<210> SEQ ID NO 56
<211> LENGTH: 118
<212> TYPE: PRT
<213> ORGANISM: Lama glama

<400> SEQUENCE: 56

Glu Val Gln Leu Val Glu Ser Gly Gly Gly Leu Val Gln Pro Gly Gly
1               5                   10                  15

```
Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Arg Ile Ser Ala Gly Gly Gly Ser Thr Tyr Tyr Gly Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Asn Arg Ala Gly Trp Gly Met Gly Asp Tyr Trp Gly Gln Gly Thr
            100                 105                 110

Gln Val Thr Val Ser Ser
            115

<210> SEQ ID NO 57
<211> LENGTH: 118
<212> TYPE: PRT
<213> ORGANISM: Lama glama

<400> SEQUENCE: 57

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Arg Ile Ser Ala Gly Gly Gly Ser Thr Tyr Tyr Gly Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Lys Thr Glu Asp Thr Ala Val Tyr Tyr Cys
                85                  90                  95

Ala Asn Arg Ala Gly Trp Gly Met Gly Asp Tyr Trp Gly Gln Gly Thr
            100                 105                 110

Gln Val Thr Val Ser Ser
            115

<210> SEQ ID NO 58
<211> LENGTH: 118
<212> TYPE: PRT
<213> ORGANISM: Lama glama

<400> SEQUENCE: 58

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Arg Ile Ser Ala Gly Gly Gly Ser Thr Tyr Tyr Gly Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Lys Pro Glu Asp Thr Ala Val Tyr Tyr Cys
                85                  90                  95
```

Ala Asn Arg Ala Gly Trp Gly Met Gly Asp Tyr Trp Gly Gln Gly Thr
            100                 105                 110

Gln Val Thr Val Ser Ser
        115

<210> SEQ ID NO 59
<211> LENGTH: 118
<212> TYPE: PRT
<213> ORGANISM: Lama glama

<400> SEQUENCE: 59

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Pro Glu Trp Val
        35                  40                  45

Ser Arg Ile Ser Ser Gly Gly Ser Thr Tyr Tyr Gly Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Asn Arg Ala Gly Trp Gly Met Gly Asp Tyr Trp Gly Gln Gly Thr
            100                 105                 110

Gln Val Thr Val Ser Ser
        115

<210> SEQ ID NO 60
<211> LENGTH: 118
<212> TYPE: PRT
<213> ORGANISM: Lama glama

<400> SEQUENCE: 60

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Tyr Trp Val Arg Gln Pro Pro Gly Lys Gly Pro Glu Trp Val
        35                  40                  45

Ser Arg Ile Ser Ala Gly Gly Ser Thr Tyr Tyr Gly Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Lys Pro Glu Asp Thr Ala Val Tyr Tyr Cys
                85                  90                  95

Ala Asn Arg Ala Gly Trp Gly Met Gly Asp Tyr Trp Gly Gln Gly Thr
            100                 105                 110

Gln Val Thr Val Ser Ser
        115

<210> SEQ ID NO 61
<211> LENGTH: 118
<212> TYPE: PRT
<213> ORGANISM: Lama glama

<400> SEQUENCE: 61

Glu Val Gln Leu Val Glu Ser Gly Gly Gly Leu Val Gln Pro Gly Gly

-continued

```
              1               5                  10                 15
            Ser Leu Arg Leu Ser Cys Ala Ala Ser Gly Phe Thr Phe Ser Ser Tyr
                            20                  25                 30

Ala Met Ser Trp Val Arg Gln Ala Pro Gly Lys Gly Pro Glu Trp Val
                            35                  40                 45

Ser Arg Ile Ser Ser Gly Gly Ser Thr Tyr Tyr Gly Asp Ser Val
                50                          55                  60

Lys Gly Arg Phe Thr Ile Ser Arg Asp Asn Ala Lys Asn Thr Val Tyr
            65                          70                  75                 80

Leu Gln Met Asn Ser Leu Arg Ala Glu Asp Thr Ala Val Tyr Tyr Cys
                                    85                  90                 95

Ala Asn Arg Ala Gly Trp Gly Met Gly Asp Tyr Trp Gly Gln Gly Thr
                                100                 105                110

Leu Val Thr Val Ser Ser
                                115

<210> SEQ ID NO 62
<211> LENGTH: 118
<212> TYPE: PRT
<213> ORGANISM: Lama glama

<400> SEQUENCE: 62

Glu Val Gln Leu Val Glu Ser Gly Gly Gly Leu Val Gln Pro Gly Gly
            1               5                  10                 15

Ser Leu Arg Leu Ser Cys Ala Ala Ser Gly Phe Thr Phe Ser Ser Tyr
                            20                  25                 30

Ala Met Tyr Trp Val Arg Gln Ala Pro Gly Lys Gly Leu Glu Trp Val
                            35                  40                 45

Ser Arg Ile Ser Ala Gly Gly Ser Thr Tyr Tyr Gly Asp Ser Val
                50                          55                  60

Lys Gly Arg Phe Thr Ile Ser Arg Asp Asn Ser Lys Asn Thr Val Tyr
            65                          70                  75                 80

Leu Gln Met Asn Ser Leu Lys Pro Glu Asp Thr Ala Val Tyr Tyr Cys
                                    85                  90                 95

Ala Asn Arg Ala Gly Trp Gly Met Gly Asp Tyr Trp Gly Gln Gly Thr
                                100                 105                110

Leu Val Thr Val Ser Ser
                                115

<210> SEQ ID NO 63
<211> LENGTH: 118
<212> TYPE: PRT
<213> ORGANISM: Lama glama

<400> SEQUENCE: 63

Glu Val Gln Leu Leu Glu Ser Gly Gly Gly Leu Val Gln Pro Gly Gly
            1               5                  10                 15

Ser Leu Arg Leu Ser Cys Ala Ala Ser Gly Phe Thr Phe Ser Ser Tyr
                            20                  25                 30

Ala Met Ser Trp Val Arg Gln Ala Pro Gly Lys Gly Pro Glu Trp Val
                            35                  40                 45

Ser Arg Ile Ser Ser Gly Gly Ser Thr Tyr Tyr Gly Asp Ser Val
                50                          55                  60

Lys Gly Arg Phe Thr Ile Ser Arg Asp Asn Ala Lys Asn Thr Val Tyr
            65                          70                  75                 80

Leu Gln Met Asn Ser Leu Lys Thr Glu Asp Thr Ala Val Tyr Tyr Cys
```

```
                    85                  90                  95

Ala Asn Arg Ala Gly Trp Gly Met Gly Asp Tyr Trp Gly Gln Gly Thr
                100                 105                 110

Leu Val Thr Val Ser Ser
        115

<210> SEQ ID NO 64
<211> LENGTH: 118
<212> TYPE: PRT
<213> ORGANISM: Lama glama

<400> SEQUENCE: 64

Glu Leu Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Arg Met Ser Trp Val Arg Gln Ala Pro Gly Lys Gly Pro Glu Trp Val
        35                  40                  45

Ser Ala Ile Ser Ala Gly Gly Ser Thr Tyr Tyr Gly Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Asn Arg Ala Gly Trp Gly Met Gly Asp Tyr Trp Gly Gln Gly Thr
                100                 105                 110

Gln Val Thr Val Ser Ser
        115

<210> SEQ ID NO 65
<211> LENGTH: 118
<212> TYPE: PRT
<213> ORGANISM: Lama glama

<400> SEQUENCE: 65

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Tyr Trp Val Arg Gln Ala Pro Gly Lys Gly Pro Glu Trp Val
        35                  40                  45

Ser Arg Ile Ser Ala Gly Gly Gly Ser Thr Tyr Tyr Gly Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Lys Thr Glu Asp Thr Ala Val Tyr Tyr Cys
                85                  90                  95

Ala Asn Arg Ala Gly Trp Gly Met Gly Asp Tyr Trp Gly Gln Gly Thr
                100                 105                 110

Gln Val Thr Val Ser Ser
        115

<210> SEQ ID NO 66
<211> LENGTH: 118
<212> TYPE: PRT
<213> ORGANISM: Lama glama

<400> SEQUENCE: 66
```

Glu Leu Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Pro Glu Trp Val
        35                  40                  45

Ser Arg Ile Ser Ala Gly Gly Ser Thr Tyr Tyr Gly Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Asp Thr Ala Val Tyr Tyr Cys
            85                  90                  95

Ala Asn Arg Ala Gly Trp Gly Met Gly Asp Tyr Trp Gly Gln Gly Thr
        100                 105                 110

Gln Val Thr Val Ser Ser
        115

<210> SEQ ID NO 67
<211> LENGTH: 118
<212> TYPE: PRT
<213> ORGANISM: Lama glama

<400> SEQUENCE: 67

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Pro Glu Trp Val
        35                  40                  45

Ser Arg Ile Ser Ser Gly Gly Gly Ser Thr Tyr Tyr Gly Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Asn Arg Ala Gly Trp Gly Met Gly Asp Tyr Trp Gly Gln Gly Thr
        100                 105                 110

Gln Val Thr Val Ser Ser
        115

<210> SEQ ID NO 68
<211> LENGTH: 118
<212> TYPE: PRT
<213> ORGANISM: Lama glama

<400> SEQUENCE: 68

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Arg Met Ser Trp Val Arg Gln Ala Pro Gly Lys Gly Pro Glu Trp Val
        35                  40                  45

Ser Ala Ile Ser Ser Gly Gly Gly Ser Thr Tyr Tyr Gly Asp Ser Val
    50                  55                  60

Lys Gly Arg Phe Thr Ile Ser Arg Asp Asn Ser Lys Asn Thr Val Tyr
65                  70                  75                  80

-continued

Leu Gln Met Asn Ser Leu Lys Pro Glu Asp Thr Ala Val Tyr Tyr Cys
                85                  90                  95

Ala Asn Arg Ala Gly Trp Gly Met Gly Asp Tyr Trp Gly Gln Gly Thr
            100                 105                 110

Leu Val Thr Val Ser Ser
        115

<210> SEQ ID NO 69
<211> LENGTH: 118
<212> TYPE: PRT
<213> ORGANISM: Lama glama

<400> SEQUENCE: 69

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Tyr Trp Val Arg Gln Pro Pro Gly Lys Gly Leu Glu Trp Val
        35                  40                  45

Ser Arg Ile Ser Ala Gly Gly Gly Ser Thr Tyr Tyr Gly Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Lys Pro Glu Asp Thr Ala Val Tyr Tyr Cys
                85                  90                  95

Ala Asn Arg Ala Gly Trp Gly Met Gly Asp Tyr Trp Gly Gln Gly Thr
            100                 105                 110

Gln Val Thr Val Ser Ser
        115

<210> SEQ ID NO 70
<211> LENGTH: 118
<212> TYPE: PRT
<213> ORGANISM: Lama glama

<400> SEQUENCE: 70

Glu Leu Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Tyr Trp Val Arg Gln Pro Pro Gly Lys Gly Leu Glu Trp Val
        35                  40                  45

Ser Arg Ile Ser Ala Gly Gly Gly Ser Thr Tyr Tyr Gly Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Lys Thr Glu Asp Thr Ala Val Tyr Tyr Cys
                85                  90                  95

Ala Asn Arg Ala Gly Trp Gly Met Gly Asp Tyr Trp Gly Gln Gly Thr
            100                 105                 110

Gln Val Thr Val Ser Ser
        115

<210> SEQ ID NO 71
<211> LENGTH: 118
<212> TYPE: PRT
<213> ORGANISM: Lama glama

<400> SEQUENCE: 71

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Tyr Trp Val Arg Gln Pro Pro Gly Lys Gly Pro Glu Trp Val
        35                  40                  45

Ser Arg Ile Ser Ala Gly Gly Ser Thr Tyr Tyr Gly Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Thr Glu Asp Thr Ala Val Tyr Tyr Cys
                85                  90                  95

Ala Asn Arg Ala Gly Trp Gly Met Gly Asp Tyr Trp Gly Gln Gly Thr
            100                 105                 110

Gln Val Thr Val Ser Ser
        115

<210> SEQ ID NO 72
<211> LENGTH: 118
<212> TYPE: PRT
<213> ORGANISM: Lama glama

<400> SEQUENCE: 72

Glu Leu Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Tyr Trp Val Arg Gln Ala Pro Gly Lys Gly Leu Glu Trp Val
        35                  40                  45

Ser Arg Ile Ser Ala Gly Gly Gly Ser Thr Tyr Tyr Gly Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Lys Pro Glu Asp Thr Ala Val Tyr Tyr Cys
                85                  90                  95

Ala Asn Arg Ala Gly Trp Gly Met Gly Asp Tyr Trp Gly Gln Gly Thr
            100                 105                 110

Leu Val Thr Val Ser Thr
        115

<210> SEQ ID NO 73
<211> LENGTH: 118
<212> TYPE: PRT
<213> ORGANISM: Lama glama

<400> SEQUENCE: 73

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Arg Met Ser Trp Val Arg Gln Ala Pro Gly Lys Gly Pro Glu Trp Val
        35                  40                  45

Ser Ala Ile Ser Ser Gly Gly Gly Ser Thr Tyr Tyr Gly Asp Ser Val
    50                  55                  60

-continued

Lys Gly Arg Phe Thr Ile Ser Arg Asp Asn Ala Lys Asn Thr Val Tyr
65                  70                  75                  80

Leu Gln Met Asn Ser Leu Arg Ala Glu Asp Thr Ala Val Tyr Tyr Cys
                85                  90                  95

Ala Asn Arg Ala Gly Trp Gly Met Gly Asp Tyr Trp Gly Gln Gly Thr
            100                 105                 110

Gln Val Thr Val Ser Ser
            115

<210> SEQ ID NO 74
<211> LENGTH: 118
<212> TYPE: PRT
<213> ORGANISM: Lama glama

<400> SEQUENCE: 74

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Arg Met Ser Trp Val Arg Gln Ala Pro Gly Lys Gly Leu Glu Trp Val
        35                  40                  45

Ser Ala Ile Ser Ala Gly Gly Gly Ser Thr Tyr Tyr Gly Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Asn Arg Ala Gly Trp Gly Met Gly Asp Tyr Trp Gly Gln Gly Thr
            100                 105                 110

Gln Val Thr Val Ser Ser
            115

<210> SEQ ID NO 75
<211> LENGTH: 118
<212> TYPE: PRT
<213> ORGANISM: Lama glama

<400> SEQUENCE: 75

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Arg Met Ser Trp Val Arg Gln Ala Pro Gly Lys Gly Pro Glu Trp Val
        35                  40                  45

Ser Ala Ile Ser Ala Gly Gly Gly Ser Thr Tyr Tyr Gly Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Asn Arg Ala Gly Trp Gly Met Gly Asp Tyr Trp Gly Gln Gly Thr
            100                 105                 110

Gln Val Thr Val Ser Ser
            115

<210> SEQ ID NO 76
<211> LENGTH: 118

<212> TYPE: PRT
<213> ORGANISM: Lama glama

<400> SEQUENCE: 76

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Arg Met Ser Trp Val Arg Gln Pro Pro Gly Lys Gly Pro Glu Trp Val
        35                  40                  45

Ser Ala Ile Ser Ala Gly Gly Gly Ser Thr Tyr Tyr Gly Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Asp Thr Ala Val Tyr Tyr Cys
                85                  90                  95

Ala Asn Arg Ala Gly Trp Gly Met Gly Asp Tyr Trp Gly Gln Gly Thr
            100                 105                 110

Gln Val Thr Val Ser Ser
        115

<210> SEQ ID NO 77
<211> LENGTH: 118
<212> TYPE: PRT
<213> ORGANISM: Lama glama

<400> SEQUENCE: 77

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Arg Met Tyr Trp Val Arg Gln Ala Pro Gly Lys Gly Leu Glu Trp Val
        35                  40                  45

Ser Ala Ile Ser Ala Gly Gly Gly Ser Thr Tyr Tyr Gly Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Lys Pro Glu Asp Thr Ala Val Tyr Tyr Cys
                85                  90                  95

Ala Lys Arg Ala Gly Trp Gly Met Gly Asp Tyr Trp Gly Gln Gly Thr
            100                 105                 110

Gln Val Thr Val Ser Ser
        115

<210> SEQ ID NO 78
<211> LENGTH: 118
<212> TYPE: PRT
<213> ORGANISM: Lama glama

<400> SEQUENCE: 78

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Arg Met Ser Trp Val Arg Gln Pro Pro Gly Lys Gly Pro Glu Trp Val
        35                  40                  45

Ser Ala Ile Ser Ala Gly Gly Gly Ser Thr Tyr Tyr Gly Asp Ser Val

```
                50                  55                  60
Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Val Tyr Tyr Cys
                85                  90                  95

Ala Asn Arg Ala Gly Trp Gly Met Gly Asp Tyr Trp Gly Gln Gly Thr
            100                 105                 110

Gln Val Thr Val Ser Ser
        115

<210> SEQ ID NO 79
<211> LENGTH: 118
<212> TYPE: PRT
<213> ORGANISM: Lama glama

<400> SEQUENCE: 79

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Pro Glu Trp Val
        35                  40                  45

Ser Arg Ile Ser Ala Gly Gly Gly Ser Thr Tyr Tyr Gly Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Lys Pro Glu Asp Thr Ala Val Tyr Tyr Cys
                85                  90                  95

Ala Asn Arg Ala Gly Trp Gly Met Gly Asp Tyr Trp Gly Gln Gly Thr
            100                 105                 110

Gln Val Thr Val Ser Ser
        115

<210> SEQ ID NO 80
<211> LENGTH: 118
<212> TYPE: PRT
<213> ORGANISM: Lama glama

<400> SEQUENCE: 80

Glu Val Gln Leu Val Glu Ser Gly Gly Gly Leu Val Gln Pro Gly Gly
1               5                   10                  15

Ser Leu Arg Leu Ser Cys Ala Ser Gly Phe Thr Phe Ser Ser Tyr
            20                  25                  30

Arg Met Ser Trp Val Arg Gln Ala Pro Gly Lys Gly Pro Glu Trp Val
        35                  40                  45

Ser Ala Ile Ser Ala Gly Gly Gly Ser Thr Tyr Tyr Gly Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Asp Thr Ala Val Tyr Tyr Cys
                85                  90                  95

Ala Asn Arg Ala Gly Trp Gly Met Gly Asp Tyr Trp Gly Gln Gly Thr
            100                 105                 110

Leu Val Thr Val Ser Ser
        115
```

```
<210> SEQ ID NO 81
<211> LENGTH: 118
<212> TYPE: PRT
<213> ORGANISM: Lama glama

<400> SEQUENCE: 81

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Pro Glu Trp Val
        35                  40                  45

Ser Arg Ile Ser Ala Gly Gly Ser Thr Tyr Tyr Gly Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Lys Pro Glu Asp Thr Ala Val Tyr Tyr Cys
                85                  90                  95

Ala Asn Arg Ala Gly Trp Gly Met Gly Asp Tyr Trp Gly Gln Gly Thr
            100                 105                 110

Gln Val Thr Val Ser Ser
        115

<210> SEQ ID NO 82
<211> LENGTH: 118
<212> TYPE: PRT
<213> ORGANISM: Lama glama

<400> SEQUENCE: 82

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Arg Met Ser Trp Val Arg Gln Ala Pro Gly Lys Gly Leu Glu Trp Val
        35                  40                  45

Ser Ala Ile Ser Ala Gly Gly Ser Thr Tyr Tyr Gly Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Lys Pro Glu Asp Thr Ala Val Tyr Tyr Cys
                85                  90                  95

Ala Asn Arg Ala Gly Trp Gly Met Gly Asp Tyr Trp Gly Gln Gly Thr
            100                 105                 110

Gln Val Thr Val Ser Ser
        115

<210> SEQ ID NO 83
<211> LENGTH: 118
<212> TYPE: PRT
<213> ORGANISM: Lama glama

<400> SEQUENCE: 83

Glu Leu Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Tyr Trp Val Arg Gln Ala Pro Gly Lys Gly Leu Glu Trp Val
        35                  40                  45
```

Ser Arg Ile Ser Ala Gly Gly Ser Thr Tyr Tyr Gly Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Asn Arg Ala Gly Trp Gly Met Gly Asp Tyr Trp Gly Gln Gly Thr
            100                 105                 110

Gln Val Thr Val Ser Ser
            115

<210> SEQ ID NO 84
<211> LENGTH: 118
<212> TYPE: PRT
<213> ORGANISM: Lama glama

<400> SEQUENCE: 84

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
             20                  25                  30

Arg Met Ser Trp Val Arg Gln Ala Pro Gly Lys Gly Leu Glu Trp Val
         35                  40                  45

Ser Ala Ile Ser Ala Gly Gly Ser Thr Tyr Tyr Gly Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Lys Pro Glu Asp Thr Ala Val Tyr Tyr Cys
                 85                  90                  95

Ala Asn Arg Ala Gly Trp Gly Met Gly Asp Tyr Trp Gly Gln Gly Thr
            100                 105                 110

Leu Val Thr Val Ser Ser
            115

<210> SEQ ID NO 85
<211> LENGTH: 118
<212> TYPE: PRT
<213> ORGANISM: Lama glama

<400> SEQUENCE: 85

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
             20                  25                  30

Ala Met Tyr Trp Val Arg Gln Pro Pro Gly Lys Gly Pro Glu Trp Val
         35                  40                  45

Ser Arg Ile Ser Ser Gly Gly Gly Ser Thr Tyr Tyr Gly Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Lys Pro Glu Asp Thr Ala Val Tyr Tyr Cys
                 85                  90                  95

Ala Lys Arg Ala Gly Trp Gly Met Gly Asp Tyr Trp Gly Gln Gly Thr
            100                 105                 110

Gln Val Thr Val Ser Ser
            115

<210> SEQ ID NO 86
<211> LENGTH: 118
<212> TYPE: PRT
<213> ORGANISM: Lama glama

<400> SEQUENCE: 86

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Pro Glu Trp Val
        35                  40                  45

Ser Arg Ile Ser Ala Gly Gly Gly Ser Thr Tyr Tyr Gly Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Asn Arg Ala Gly Trp Gly Met Gly Asp Tyr Trp Gly Gln Gly Thr
            100                 105                 110

Leu Val Thr Val Ser Ser
        115

<210> SEQ ID NO 87
<211> LENGTH: 118
<212> TYPE: PRT
<213> ORGANISM: Lama glama

<400> SEQUENCE: 87

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Tyr Trp Val Arg Gln Pro Pro Gly Lys Gly Leu Glu Trp Val
        35                  40                  45

Ser Arg Ile Ser Ala Gly Gly Gly Ser Thr Tyr Tyr Gly Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Asn Arg Ala Gly Trp Gly Met Gly Asp Tyr Trp Gly Gln Gly Thr
            100                 105                 110

Leu Val Thr Val Ser Ser
        115

<210> SEQ ID NO 88
<211> LENGTH: 118
<212> TYPE: PRT
<213> ORGANISM: Lama glama

<400> SEQUENCE: 88

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Pro Glu Trp Val
            35                  40                  45

Ser Arg Ile Ser Ala Gly Gly Ser Thr Tyr Tyr Gly Asp Ser Val
 50                  55                  60

Lys Gly Arg Phe Thr Ile Ser Arg Asp Asn Ser Lys Asn Thr Val Tyr
 65                  70                  75                  80

Leu Gln Met Asn Ser Leu Lys Pro Glu Asp Thr Ala Val Tyr Tyr Cys
                 85                  90                  95

Ala Asn Arg Ala Gly Trp Gly Met Gly Asp Tyr Trp Gly Gln Gly Thr
            100                 105                 110

Gln Val Thr Val Ser Ser
        115

<210> SEQ ID NO 89
<211> LENGTH: 118
<212> TYPE: PRT
<213> ORGANISM: Lama glama

<400> SEQUENCE: 89

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Arg Met Ser Trp Val Arg Gln Ala Pro Gly Lys Gly Leu Glu Trp Val
            35                  40                  45

Ser Ala Ile Ser Ser Gly Gly Ser Thr Tyr Tyr Gly Asp Ser Val
 50                  55                  60

Lys Gly Arg Phe Thr Ile Ser Arg Asp Asn Ser Lys Asn Thr Val Tyr
 65                  70                  75                  80

Leu Gln Met Asn Ser Leu Lys Thr Glu Asp Thr Ala Val Tyr Tyr Cys
                 85                  90                  95

Ala Asn Arg Ala Gly Trp Gly Met Gly Asp Tyr Trp Gly Gln Gly Thr
            100                 105                 110

Gln Val Thr Val Ser Ser
        115

<210> SEQ ID NO 90
<211> LENGTH: 118
<212> TYPE: PRT
<213> ORGANISM: Lama glama

<400> SEQUENCE: 90

Glu Leu Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Pro Glu Trp Val
            35                  40                  45

Ser Arg Ile Ser Ala Gly Gly Gly Ser Thr Tyr Tyr Gly Asp Ser Val
 50                  55                  60

Lys Gly Arg Phe Thr Ile Ser Arg Asp Asn Ala Lys Asn Thr Val Tyr
 65                  70                  75                  80

Leu Gln Met Asn Ser Leu Lys Pro Glu Asp Thr Ala Val Tyr Tyr Cys
                 85                  90                  95

Ala Asn Arg Ala Gly Trp Gly Met Gly Asp Tyr Trp Gly Gln Gly Thr
            100                 105                 110

Gln Val Thr Val Ser Ser
        115

<210> SEQ ID NO 91
<211> LENGTH: 118
<212> TYPE: PRT
<213> ORGANISM: Lama glama

<400> SEQUENCE: 91

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Pro Glu Trp Val
        35                  40                  45

Ser Arg Ile Ser Ala Gly Gly Ser Thr Tyr Tyr Gly Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Lys Pro Glu Asp Thr Ala Val Tyr Tyr Cys
                85                  90                  95

Ala Asn Arg Ala Gly Trp Gly Met Gly Asp Tyr Trp Gly Gln Gly Thr
            100                 105                 110

Leu Val Thr Val Ser Ser
        115

<210> SEQ ID NO 92
<211> LENGTH: 118
<212> TYPE: PRT
<213> ORGANISM: Lama glama

<400> SEQUENCE: 92

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Arg Met Tyr Trp Val Arg Gln Ala Pro Gly Lys Gly Pro Glu Trp Val
        35                  40                  45

Ser Ala Ile Ser Ala Gly Gly Ser Thr Tyr Tyr Gly Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Lys Pro Glu Asp Thr Ala Val Tyr Tyr Cys
                85                  90                  95

Ala Asn Arg Ala Gly Trp Gly Met Gly Asp Tyr Trp Gly Gln Gly Thr
            100                 105                 110

Gln Val Thr Val Ser Ser
        115

<210> SEQ ID NO 93
<211> LENGTH: 118
<212> TYPE: PRT
<213> ORGANISM: Lama glama

<400> SEQUENCE: 93

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr

```
            20                  25                  30
Ala Met Ser Trp Val Arg Gln Ala Pro Gly Lys Gly Pro Glu Trp Val
            35                  40                  45

Ser Arg Ile Ser Ser Gly Gly Ser Thr Tyr Tyr Gly Asp Ser Val
        50                  55                  60

Lys Gly Arg Phe Thr Ile Ser Arg Asp Asn Ser Lys Asn Thr Val Tyr
 65                  70                  75                  80

Leu Gln Met Asn Ser Leu Lys Pro Glu Asp Thr Ala Val Tyr Tyr Cys
                85                  90                  95

Ala Asn Arg Ala Gly Trp Gly Met Gly Asp Tyr Trp Gly Gln Gly Thr
            100                 105                 110

Gln Val Thr Val Ser Ser
            115

<210> SEQ ID NO 94
<211> LENGTH: 118
<212> TYPE: PRT
<213> ORGANISM: Lama glama

<400> SEQUENCE: 94

Glu Leu Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Tyr Trp Val Arg Gln Pro Pro Gly Lys Gly Leu Glu Trp Val
            35                  40                  45

Ser Arg Ile Ser Ser Gly Gly Ser Thr Tyr Tyr Gly Asp Ser Val
        50                  55                  60

Lys Gly Arg Phe Thr Ile Ser Arg Asp Asn Ala Lys Asn Thr Leu Tyr
 65                  70                  75                  80

Leu Gln Met Asn Ser Leu Lys Thr Glu Asp Thr Ala Val Tyr Tyr Cys
                85                  90                  95

Ala Asn Arg Ala Gly Trp Gly Met Gly Asp Tyr Trp Gly Gln Gly Thr
            100                 105                 110

Gln Val Thr Val Ser Ser
            115

<210> SEQ ID NO 95
<211> LENGTH: 118
<212> TYPE: PRT
<213> ORGANISM: Lama glama

<400> SEQUENCE: 95

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Tyr Trp Val Arg Gln Ala Pro Gly Lys Gly Pro Glu Trp Val
            35                  40                  45

Ser Arg Ile Ser Ala Gly Gly Ser Thr Tyr Tyr Gly Asp Ser Val
        50                  55                  60

Lys Gly Arg Phe Thr Ile Ser Arg Asp Asn Ala Lys Asn Thr Val Tyr
 65                  70                  75                  80

Leu Gln Met Asn Ser Leu Lys Pro Glu Asp Thr Ala Val Tyr Tyr Cys
                85                  90                  95

Ala Asn Arg Ala Gly Trp Gly Met Gly Asp Tyr Trp Gly Gln Gly Thr
```

Gln Val Thr Val Ser Ser
        115

<210> SEQ ID NO 96
<211> LENGTH: 118
<212> TYPE: PRT
<213> ORGANISM: Lama glama

<400> SEQUENCE: 96

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Tyr Trp Val Arg Gln Ala Pro Gly Lys Gly Pro Glu Trp Val
        35                  40                  45

Ser Arg Ile Ser Ala Gly Gly Gly Ser Thr Tyr Tyr Gly Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Lys Pro Glu Asp Thr Ala Val Tyr Tyr Cys
                85                  90                  95

Ala Asn Arg Ala Gly Trp Gly Met Gly Asp Tyr Trp Gly Gln Gly Thr
            100                 105                 110

Leu Val Thr Val Ser Ser
        115

<210> SEQ ID NO 97
<211> LENGTH: 118
<212> TYPE: PRT
<213> ORGANISM: Lama glama

<400> SEQUENCE: 97

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Tyr Trp Val Arg Gln Ala Pro Gly Lys Gly Pro Glu Trp Val
        35                  40                  45

Ser Arg Ile Ser Ala Gly Gly Gly Ser Thr Tyr Tyr Gly Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Lys Pro Glu Asp Thr Ala Val Tyr Tyr Cys
                85                  90                  95

Ala Asn Arg Ala Gly Trp Gly Met Gly Asp Tyr Trp Gly Gln Gly Thr
            100                 105                 110

Gln Val Thr Val Ser Ser
        115

<210> SEQ ID NO 98
<211> LENGTH: 118
<212> TYPE: PRT
<213> ORGANISM: Lama glama

<400> SEQUENCE: 98

Glu Val Gln Leu Leu Glu Ser Gly Gly Gly Leu Val Gln Pro Gly Gly
1               5                   10                  15

-continued

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Pro Glu Trp Val
        35                  40                  45

Ser Arg Ile Ser Ala Gly Gly Ser Thr Tyr Tyr Gly Asp Ser Val
 50                  55                  60

Lys Gly Arg Phe Thr Ile Ser Arg Asp Asn Ala Lys Asn Thr Val Tyr
 65                  70                  75                  80

Leu Gln Met Asn Ser Leu Arg Ala Glu Asp Thr Ala Val Tyr Tyr Cys
                85                  90                  95

Ala Asn Arg Ala Gly Trp Gly Met Gly Asp Tyr Trp Gly Gln Gly Thr
            100                 105                 110

Gln Val Thr Val Ser Ser
        115

<210> SEQ ID NO 99
<211> LENGTH: 118
<212> TYPE: PRT
<213> ORGANISM: Lama glama

<400> SEQUENCE: 99

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Ala Met Tyr Trp Val Arg Gln Ala Pro Gly Lys Gly Pro Glu Trp Val
        35                  40                  45

Ser Arg Ile Ser Ser Gly Gly Gly Ser Thr Tyr Tyr Gly Asp Ser Val
 50                  55                  60

Lys Gly Arg Phe Thr Ile Ser Arg Asp Asn Ala Lys Asn Thr Val Tyr
 65                  70                  75                  80

Leu Gln Met Asn Ser Leu Lys Thr Glu Asp Thr Ala Val Tyr Tyr Cys
                85                  90                  95

Ala Asn Arg Ala Gly Trp Gly Met Gly Asp Tyr Trp Gly Gln Gly Thr
            100                 105                 110

Gln Val Thr Val Ser Ser
        115

<210> SEQ ID NO 100
<211> LENGTH: 118
<212> TYPE: PRT
<213> ORGANISM: Lama glama

<400> SEQUENCE: 100

Glu Val Gln Leu Leu Glu Ser Gly Gly Gly Leu Val Gln Pro Gly Gly
 1               5                  10                  15

Ser Leu Arg Leu Ser Cys Ala Ser Gly Phe Thr Phe Ser Ser Tyr
            20                  25                  30

Ala Met Ser Trp Val Arg Gln Ala Pro Gly Lys Gly Pro Glu Trp Val
        35                  40                  45

Ser Arg Ile Ser Ala Gly Gly Ser Thr Tyr Tyr Gly Asp Ser Val
 50                  55                  60

Lys Gly Arg Phe Thr Ile Ser Arg Asp Asn Ala Lys Asn Thr Val Tyr
 65                  70                  75                  80

Leu Gln Met Asn Ser Leu Lys Thr Glu Asp Thr Ala Val Tyr Tyr Cys
                85                  90                  95

Ala Asn Arg Ala Gly Trp Gly Met Gly Asp Tyr Trp Gly Gln Gly Thr
            100                 105                 110

Gln Val Thr Val Ser Ser
        115

<210> SEQ ID NO 101
<211> LENGTH: 118
<212> TYPE: PRT
<213> ORGANISM: Lama glama

<400> SEQUENCE: 101

Glu Val Gln Leu Val Glu Ser Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Arg Met Tyr Trp Val Arg Gln Ala Pro Gly Lys Gly Leu Glu Trp Val
            35                  40                  45

Ser Ala Ile Ser Ala Gly Gly Ser Thr Tyr Tyr Gly Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Val Tyr Tyr Cys
                85                  90                  95

Ala Asn Arg Ala Gly Trp Gly Met Gly Asp Tyr Trp Gly Gln Gly Thr
            100                 105                 110

Leu Val Thr Val Ser Ser
        115

<210> SEQ ID NO 102
<211> LENGTH: 118
<212> TYPE: PRT
<213> ORGANISM: Lama glama

<400> SEQUENCE: 102

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Tyr Trp Val Arg Gln Ala Pro Gly Lys Gly Pro Glu Trp Val
            35                  40                  45

Ser Arg Ile Ser Ala Gly Gly Gly Ser Thr Tyr Tyr Gly Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Lys Pro Glu Asp Thr Ala Val Tyr Tyr Cys
                85                  90                  95

Ala Asn Arg Ala Gly Trp Gly Met Gly Asp Tyr Trp Gly Gln Gly Thr
            100                 105                 110

Leu Val Thr Val Ser Ser
        115

<210> SEQ ID NO 103
<211> LENGTH: 118
<212> TYPE: PRT
<213> ORGANISM: Lama glama

<400> SEQUENCE: 103

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Arg Met Ser Trp Val Arg Gln Ala Pro Gly Lys Gly Leu Glu Trp Val
        35                  40                  45

Ser Ala Ile Ser Ala Gly Gly Ser Thr Tyr Tyr Gly Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Thr Glu Asp Thr Ala Val Tyr Tyr Cys
                85                  90                  95

Ala Asn Arg Ala Gly Trp Gly Met Gly Asp Tyr Trp Gly Gln Gly Thr
            100                 105                 110

Gln Val Thr Val Ser Ser
            115
```

<210> SEQ ID NO 104
<211> LENGTH: 118
<212> TYPE: PRT
<213> ORGANISM: Lama glama

<400> SEQUENCE: 104

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Tyr Trp Val Arg Gln Pro Pro Gly Lys Gly Pro Glu Trp Val
        35                  40                  45

Ser Arg Ile Ser Ala Gly Gly Ser Thr Tyr Tyr Gly Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Asn Arg Ala Gly Trp Gly Met Gly Asp Tyr Trp Gly Gln Gly Thr
            100                 105                 110

Gln Val Thr Val Ser Ser
            115
```

<210> SEQ ID NO 105
<211> LENGTH: 118
<212> TYPE: PRT
<213> ORGANISM: Lama glama

<400> SEQUENCE: 105

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Arg Met Tyr Trp Val Arg Gln Ala Pro Gly Lys Gly Leu Glu Trp Val
        35                  40                  45

Ser Ala Ile Ser Ser Gly Gly Gly Ser Thr Tyr Tyr Gly Asp Ser Val
    50                  55                  60

Lys Gly Arg Phe Thr Ile Ser Arg Asp Asn Ala Lys Asn Thr Val Tyr
65                  70                  75                  80
```

```
Leu Gln Met Asn Ser Leu Lys Pro Glu Asp Thr Ala Val Tyr Tyr Cys
                85                  90                  95

Ala Asn Arg Ala Gly Trp Gly Met Gly Asp Tyr Trp Gly Gln Gly Thr
            100                 105                 110

Gln Val Thr Val Ser Ser
        115
```

<210> SEQ ID NO 106
<211> LENGTH: 118
<212> TYPE: PRT
<213> ORGANISM: Lama glama

<400> SEQUENCE: 106

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Tyr Trp Val Arg Gln Pro Pro Gly Lys Gly Pro Glu Trp Val
        35                  40                  45

Ser Arg Ile Ser Ala Gly Gly Ser Thr Tyr Tyr Gly Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Lys Thr Glu Asp Thr Ala Val Tyr Tyr Cys
                85                  90                  95

Ala Asn Arg Ala Gly Trp Gly Met Gly Asp Tyr Trp Gly Gln Gly Thr
            100                 105                 110

Gln Val Thr Val Ser Ser
        115
```

<210> SEQ ID NO 107
<211> LENGTH: 118
<212> TYPE: PRT
<213> ORGANISM: Lama glama

<400> SEQUENCE: 107

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Arg Met Ser Trp Val Arg Gln Ala Pro Gly Lys Gly Leu Glu Trp Val
        35                  40                  45

Ser Ala Ile Ser Ala Gly Gly Ser Thr Tyr Tyr Gly Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Asn Arg Ala Gly Trp Gly Met Gly Asp Tyr Trp Gly Gln Gly Thr
            100                 105                 110

Leu Val Thr Val Ser Ser
        115
```

<210> SEQ ID NO 108
<211> LENGTH: 118
<212> TYPE: PRT
<213> ORGANISM: Lama glama

```
<400> SEQUENCE: 108

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Pro Glu Trp Val
        35                  40                  45

Ser Arg Ile Ser Ser Gly Gly Ser Thr Tyr Tyr Gly Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Asn Arg Ala Gly Trp Gly Met Gly Asp Tyr Trp Gly Gln Gly Thr
            100                 105                 110

Gln Val Thr Val Ser Ser
        115

<210> SEQ ID NO 109
<211> LENGTH: 118
<212> TYPE: PRT
<213> ORGANISM: Lama glama

<400> SEQUENCE: 109

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Arg Met Ser Trp Val Arg Gln Ala Pro Gly Lys Gly Leu Glu Trp Val
        35                  40                  45

Ser Ala Ile Ser Ala Gly Gly Ser Thr Tyr Tyr Gly Asp Ser Val
50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Asn Arg Ala Gly Trp Gly Met Gly Asp Tyr Trp Gly Gln Gly Thr
            100                 105                 110

Gln Val Thr Val Ser Ser
        115

<210> SEQ ID NO 110
<211> LENGTH: 118
<212> TYPE: PRT
<213> ORGANISM: Lama glama

<400> SEQUENCE: 110

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Tyr Trp Val Arg Gln Ala Pro Gly Lys Gly Pro Glu Trp Val
        35                  40                  45

Ser Arg Ile Ser Ser Gly Gly Gly Ser Thr Tyr Tyr Gly Asp Ser Val
50                  55                  60

Lys Gly Arg Phe Thr Ile Ser Arg Asp Asn Ser Lys Asn Thr Val Tyr
```

```
                65                  70                  75                  80
Leu Gln Met Asn Ser Leu Lys Pro Glu Asp Thr Ala Val Tyr Tyr Cys
                85                  90                  95

Ala Asn Arg Ala Gly Trp Gly Met Gly Asp Tyr Trp Gly Gln Gly Thr
            100                 105                 110

Gln Val Thr Val Ser Ser
        115

<210> SEQ ID NO 111
<211> LENGTH: 118
<212> TYPE: PRT
<213> ORGANISM: Lama glama

<400> SEQUENCE: 111

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Arg Met Ser Trp Val Arg Gln Ala Pro Gly Lys Gly Leu Glu Trp Val
        35                  40                  45

Ser Ala Ile Ser Ala Gly Gly Ser Thr Tyr Tyr Gly Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Asp Thr Ala Val Tyr Tyr Cys
                85                  90                  95

Ala Asn Arg Ala Gly Trp Gly Met Gly Asp Tyr Trp Gly Gln Gly Thr
            100                 105                 110

Leu Val Thr Val Ser Ser
        115

<210> SEQ ID NO 112
<211> LENGTH: 118
<212> TYPE: PRT
<213> ORGANISM: Lama glama

<400> SEQUENCE: 112

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Pro Glu Trp Val
        35                  40                  45

Ser Arg Ile Ser Ala Gly Gly Gly Ser Thr Tyr Tyr Gly Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Asn Arg Ala Gly Trp Gly Met Gly Asp Tyr Trp Gly Gln Gly Thr
            100                 105                 110

Leu Val Thr Val Ser Ser
        115

<210> SEQ ID NO 113
<211> LENGTH: 118
<212> TYPE: PRT
```

-continued

<213> ORGANISM: Lama glama

<400> SEQUENCE: 113

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Arg Leu Tyr Trp Val Arg Gln Pro Pro Gly Lys Gly Pro Glu Trp Val
        35                  40                  45

Ser Ala Ile Ser Ala Gly Gly Ser Thr Tyr Tyr Gly Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Asn Arg Ala Gly Trp Gly Met Gly Asp Tyr Trp Gly Gln Gly Thr
            100                 105                 110

Gln Val Thr Val Ser Ser
        115

<210> SEQ ID NO 114
<211> LENGTH: 118
<212> TYPE: PRT
<213> ORGANISM: Lama glama

<400> SEQUENCE: 114

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Tyr Trp Val Arg Gln Pro Pro Gly Lys Gly Pro Glu Trp Val
        35                  40                  45

Ser Arg Ile Ser Ala Gly Gly Ser Thr Tyr Tyr Gly Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Asp Thr Ala Val Tyr Tyr Cys
                85                  90                  95

Ala Asn Arg Ala Gly Trp Gly Met Gly Asp Tyr Trp Gly Gln Gly Thr
            100                 105                 110

Gln Val Thr Val Ser Ser
        115

<210> SEQ ID NO 115
<211> LENGTH: 118
<212> TYPE: PRT
<213> ORGANISM: Lama glama

<400> SEQUENCE: 115

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Tyr Trp Val Arg Gln Ala Pro Gly Lys Gly Pro Glu Trp Val
        35                  40                  45

Ser Arg Ile Ser Ala Gly Gly Ser Thr Tyr Tyr Gly Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Asn Arg Ala Gly Trp Gly Met Gly Asp Tyr Trp Gly Gln Gly Thr
            100                 105                 110

Leu Val Thr Val Ser Ser
        115

<210> SEQ ID NO 116
<211> LENGTH: 118
<212> TYPE: PRT
<213> ORGANISM: Lama glama

<400> SEQUENCE: 116

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Arg Met Ser Trp Val Arg Gln Pro Pro Gly Lys Gly Pro Glu Trp Val
        35                  40                  45

Ser Ala Ile Ser Ser Gly Gly Ser Thr Tyr Tyr Gly Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Lys Pro Glu Asp Thr Ala Val Tyr Tyr Cys
                85                  90                  95

Ala Asn Arg Ala Gly Trp Gly Met Gly Asp Tyr Trp Gly Gln Gly Thr
            100                 105                 110

Gln Val Thr Val Ser Ser
        115

<210> SEQ ID NO 117
<211> LENGTH: 118
<212> TYPE: PRT
<213> ORGANISM: Lama glama

<400> SEQUENCE: 117

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Arg Met Ser Trp Val Arg Gln Ala Pro Gly Lys Gly Pro Glu Trp Val
        35                  40                  45

Ser Ala Ile Ser Ser Gly Gly Ser Thr Tyr Tyr Gly Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Asp Thr Ala Val Tyr Tyr Cys
                85                  90                  95

Ala Asn Arg Ala Gly Trp Gly Met Gly Asp Tyr Trp Gly Gln Gly Thr
            100                 105                 110

Leu Val Thr Val Ser Ser
        115

<210> SEQ ID NO 118

<211> LENGTH: 118
<212> TYPE: PRT
<213> ORGANISM: Lama glama

<400> SEQUENCE: 118

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Tyr Trp Val Arg Gln Pro Pro Gly Lys Gly Leu Glu Trp Val
        35                  40                  45

Ser Arg Ile Ser Ser Gly Gly Ser Thr Tyr Tyr Gly Asp Ser Val
50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Asn Arg Ala Gly Trp Gly Met Gly Asp Tyr Trp Gly Gln Gly Thr
            100                 105                 110

Gln Val Thr Val Ser Ser
        115
```

<210> SEQ ID NO 119
<211> LENGTH: 118
<212> TYPE: PRT
<213> ORGANISM: Lama glama

<400> SEQUENCE: 119

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Pro Glu Trp Val
        35                  40                  45

Ser Arg Ile Ser Ala Gly Gly Ser Thr Tyr Tyr Gly Asp Ser Val
50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Thr Glu Asp Thr Ala Val Tyr Tyr Cys
                85                  90                  95

Ala Asn Arg Ala Gly Trp Gly Met Gly Asp Tyr Trp Gly Gln Gly Thr
            100                 105                 110

Gln Val Thr Val Ser Ser
        115
```

<210> SEQ ID NO 120
<211> LENGTH: 118
<212> TYPE: PRT
<213> ORGANISM: Lama glama

<400> SEQUENCE: 120

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Arg Met Tyr Trp Val Arg Gln Pro Pro Gly Lys Gly Pro Glu Trp Val
        35                  40                  45
```

```
Ser Ala Ile Ser Ser Gly Gly Gly Ser Thr Tyr Tyr Gly Asp Ser Val
 50                  55                  60

Lys Gly Arg Phe Thr Ile Ser Arg Asp Asn Ala Lys Asn Thr Val Tyr
 65                  70                  75                  80

Leu Gln Met Asn Ser Leu Lys Thr Glu Asp Thr Ala Val Tyr Tyr Cys
                 85                  90                  95

Ala Asn Arg Ala Gly Trp Gly Met Gly Asp Tyr Trp Gly Gln Gly Thr
                100                 105                 110

Gln Val Thr Val Ser Ser
                115

<210> SEQ ID NO 121
<211> LENGTH: 118
<212> TYPE: PRT
<213> ORGANISM: Lama glama

<400> SEQUENCE: 121

Glu Val Gln Leu Leu Glu Ser Gly Gly Leu Val Gln Pro Gly Gly
 1               5                  10                  15

Ser Leu Arg Leu Ser Cys Ala Ala Ser Gly Phe Thr Phe Ser Ser Tyr
                 20                  25                  30

Ala Met Tyr Trp Val Arg Gln Ala Pro Gly Lys Gly Leu Glu Trp Val
             35                  40                  45

Ser Arg Ile Ser Ser Gly Gly Ser Thr Tyr Tyr Gly Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Lys Pro Glu Asp Thr Ala Val Tyr Tyr Cys
                 85                  90                  95

Ala Asn Arg Ala Gly Trp Gly Met Gly Asp Tyr Trp Gly Gln Gly Thr
                100                 105                 110

Gln Val Thr Val Ser Ser
                115

<210> SEQ ID NO 122
<211> LENGTH: 118
<212> TYPE: PRT
<213> ORGANISM: Lama glama

<400> SEQUENCE: 122

Glu Val Gln Leu Leu Glu Ser Gly Gly Leu Val Gln Pro Gly Gly
 1               5                  10                  15

Ser Leu Arg Leu Ser Cys Ala Ala Ser Gly Phe Thr Phe Ser Ser Tyr
                 20                  25                  30

Ala Met Ser Trp Val Arg Gln Ala Pro Gly Lys Gly Pro Glu Trp Val
             35                  40                  45

Ser Arg Ile Ser Ser Gly Gly Gly Ser Thr Tyr Tyr Gly Asp Ser Val
 50                  55                  60

Lys Gly Arg Phe Thr Ile Ser Arg Asp Asn Ala Lys Asn Thr Val Tyr
 65                  70                  75                  80

Leu Gln Met Asn Ser Leu Lys Thr Glu Asp Thr Ala Val Tyr Tyr Cys
                 85                  90                  95

Ala Asn Arg Ala Gly Trp Gly Met Gly Asp Tyr Trp Gly Gln Gly Thr
                100                 105                 110

Leu Val Thr Val Ser Ser
                115
```

<210> SEQ ID NO 123
<211> LENGTH: 118
<212> TYPE: PRT
<213> ORGANISM: Lama glama

<400> SEQUENCE: 123

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Arg Ile Ser Ala Gly Gly Gly Ser Thr Tyr Tyr Gly Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Lys Pro Glu Asp Thr Ala Val Tyr Tyr Cys
                85                  90                  95

Ala Asn Arg Ala Gly Trp Gly Met Gly Asp Tyr Trp Gly Gln Gly Thr
            100                 105                 110

Gln Val Thr Val Ser Ser
        115

<210> SEQ ID NO 124
<211> LENGTH: 118
<212> TYPE: PRT
<213> ORGANISM: Lama glama

<400> SEQUENCE: 124

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Tyr Trp Val Arg Gln Pro Pro Gly Lys Gly Leu Glu Trp Val
        35                  40                  45

Ser Arg Ile Ser Ala Gly Gly Gly Ser Thr Tyr Tyr Gly Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Arg Ala Glu Asp Thr Ala Val Tyr Tyr Cys
                85                  90                  95

Ala Asn Arg Ala Gly Trp Gly Met Gly Asp Tyr Trp Gly Gln Gly Thr
            100                 105                 110

Leu Val Thr Val Ser Ser
        115

<210> SEQ ID NO 125
<211> LENGTH: 118
<212> TYPE: PRT
<213> ORGANISM: Lama glama

<400> SEQUENCE: 125

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Tyr Trp Val Arg Gln Ala Pro Gly Lys Gly Pro Glu Trp Val

```
                35                  40                  45
Ser Arg Ile Ser Ser Gly Gly Ser Thr Tyr Tyr Gly Asp Ser Val
 50                  55                  60
Lys Gly Arg Phe Thr Ile Ser Arg Asp Asn Ser Lys Asn Thr Leu Tyr
 65                  70                  75                  80
Leu Gln Met Asn Ser Leu Lys Pro Glu Asp Thr Ala Val Tyr Tyr Cys
                 85                  90                  95
Ala Asn Arg Ala Gly Trp Gly Met Gly Asp Tyr Trp Gly Gln Gly Thr
                100                 105                 110
Leu Val Thr Val Ser Ser
        115

<210> SEQ ID NO 126
<211> LENGTH: 118
<212> TYPE: PRT
<213> ORGANISM: Lama glama

<400> SEQUENCE: 126

Glu Leu Gln Leu Leu Glu Ser Gly Gly Gly Leu Val Gln Pro Gly Gly
 1               5                   10                  15
Ser Leu Arg Leu Ser Cys Ala Ala Ser Gly Phe Thr Phe Ser Ser Tyr
                20                  25                  30
Arg Met Tyr Trp Val Arg Gln Pro Pro Gly Lys Gly Pro Glu Trp Val
                35                  40                  45
Ser Ala Ile Ser Ala Gly Gly Ser Thr Tyr Tyr Gly Asp Ser Val
 50                  55                  60
Lys Gly Arg Phe Thr Ile Ser Arg Asp Asn Ala Lys Asn Thr Val Tyr
 65                  70                  75                  80
Leu Gln Met Asn Ser Leu Arg Ala Glu Asp Thr Ala Val Tyr Tyr Cys
                 85                  90                  95
Ala Asn Arg Ala Gly Trp Gly Met Gly Asp Tyr Trp Gly Gln Gly Thr
                100                 105                 110
Gln Val Thr Val Ser Ser
        115

<210> SEQ ID NO 127
<211> LENGTH: 122
<212> TYPE: PRT
<213> ORGANISM: Lama glama

<400> SEQUENCE: 127

Gln Val Gln Leu Gln Glu Ser Gly Pro Gly Leu Val Lys Pro Ser Gln
 1               5                   10                  15
Thr Leu Ser Leu Thr Cys Thr Val Ser Gly Gly Ser Ile Thr Thr Arg
                20                  25                  30
Tyr Tyr Ala Trp Ser Trp Ile Arg Gln Pro Pro Gly Lys Gly Leu Glu
                35                  40                  45
Trp Met Gly Val Ile Asp Tyr Glu Gly Asp Thr Tyr Tyr Ser Pro Ser
                50                  55                  60
Leu Lys Ser Arg Val Ser Ile Ser Trp Asp Thr Ser Lys Asn Gln Phe
 65                  70                  75                  80
Ser Leu Gln Leu Ser Ser Val Thr Ala Glu Asp Thr Ala Val Tyr Tyr
                 85                  90                  95
Cys Ala Arg Asp Pro Asp Val Val Thr Gly Phe His Tyr Asp Tyr Trp
                100                 105                 110
Gly Gln Gly Thr Gln Val Thr Val Ser Ser
```

115                 120

<210> SEQ ID NO 128
<211> LENGTH: 122
<212> TYPE: PRT
<213> ORGANISM: Lama glama

<400> SEQUENCE: 128

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Thr Ser Arg
            20                  25                  30

Tyr Tyr Ala Trp Ser Trp Ile Arg Gln Pro Pro Gly Lys Gly Leu Glu
        35                  40                  45

Trp Ile Gly Val Ile Asp Tyr Asp Gly Asp Thr Tyr Tyr Ser Pro Ser
    50                  55                  60

Leu Lys Ser Arg Val Thr Ile Ser Trp Asp Thr Ser Asn Asn Gln Phe
65                  70                  75                  80

Ser Leu Gln Leu Ser Ser Val Thr Pro Glu Asp Thr Ala Val Tyr Tyr
                85                  90                  95

Cys Ala Arg Asp Pro Asp Val Val Thr Gly Phe His Tyr Asp Tyr Trp
            100                 105                 110

Gly Gln Gly Thr Leu Val Thr Val Ser Ser
        115                 120

<210> SEQ ID NO 129
<211> LENGTH: 122
<212> TYPE: PRT
<213> ORGANISM: Lama glama

<400> SEQUENCE: 129

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Thr Thr Arg
            20                  25                  30

Tyr Tyr Ala Trp Ser Trp Ile Arg Gln Pro Pro Gly Lys Gly Leu Glu
        35                  40                  45

Trp Ile Gly Val Ile Asp Tyr Asp Gly Asp Thr Tyr Tyr Ser Pro Ser
    50                  55                  60

Leu Lys Ser Arg Thr Thr Ile Ser Trp Asp Thr Ser Lys Asn Gln Phe
65                  70                  75                  80

Ser Leu Gln Leu Ser Ser Val Thr Pro Glu Asp Thr Ala Val Tyr Tyr
                85                  90                  95

Cys Ala Arg Asp Pro Asp Val Val Thr Gly Phe His Tyr Asp Tyr Trp
            100                 105                 110

Gly Gln Gly Thr Met Val Thr Val Ser Ser
        115                 120

<210> SEQ ID NO 130
<211> LENGTH: 122
<212> TYPE: PRT
<213> ORGANISM: Lama glama

<400> SEQUENCE: 130

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Thr Ser Arg
            20                  25                  30

Tyr Tyr Ala Trp Ser Trp Ile Arg Gln Pro Pro Gly Lys Gly Leu Glu
                35                  40                  45

Trp Ile Gly Val Ile Asp Tyr Asp Gly Asp Thr Tyr Tyr Ser Pro Ser
 50                  55                  60

Leu Lys Ser Arg Thr Thr Ile Ser Trp Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Pro Asp Val Val Thr Gly Phe His Tyr Asp Tyr Trp
                100                 105                 110

Gly Gln Gly Thr Met Val Thr Val Ser Ser
            115                 120

<210> SEQ ID NO 131
<211> LENGTH: 122
<212> TYPE: PRT
<213> ORGANISM: Lama glama

<400> SEQUENCE: 131

Glu Val Gln Leu Gln Glu Ser Gly Pro Gly Leu Val Lys Pro Ser Gln
1               5                   10                  15

Thr Leu Ser Leu Thr Cys Thr Val Ser Gly Ser Ile Thr Ser Arg
                20                  25                  30

Tyr Tyr Ala Trp Ser Trp Ile Arg Gln Pro Pro Gly Lys Gly Leu Glu
                35                  40                  45

Trp Ile Gly Val Ile Asp Tyr Asp Gly Asp Thr Tyr Tyr Ser Pro Ser
 50                  55                  60

Leu Lys Ser Arg Thr Thr Ile Ser Trp Asp Thr Ser Lys Asn Gln Phe
65                  70                  75                  80

Ser Leu Gln Leu Ser Ser Val Thr Pro Glu Asp Thr Ala Val Tyr Tyr
                85                  90                  95

Cys Ala Arg Asp Pro Asp Val Val Thr Gly Phe His Tyr Asp Tyr Trp
                100                 105                 110

Gly Lys Gly Thr Leu Val Thr Val Ser Ser
            115                 120

<210> SEQ ID NO 132
<211> LENGTH: 122
<212> TYPE: PRT
<213> ORGANISM: Lama glama

<400> SEQUENCE: 132

Glu Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Thr Ser Arg
                20                  25                  30

Tyr Tyr Ala Trp Ser Trp Ile Arg Gln Pro Pro Gly Lys Gly Leu Glu
                35                  40                  45

Trp Ile Gly Val Ile Asp Tyr Asp Gly Asp Thr Tyr Tyr Ser Pro Ser
 50                  55                  60

Leu Lys Ser Arg Thr Thr Ile Ser Trp Asp Thr Ser Lys Asn Gln Phe
65                  70                  75                  80

Ser Leu Lys Leu Ser Ser Val Thr Pro Ala Asp Thr Ala Val Tyr Tyr
                85                  90                  95

Cys Ala Arg Asp Pro Asp Val Val Thr Gly Phe His Tyr Asp Tyr Trp
                100                 105                 110

-continued

Gly Gln Gly Thr Leu Val Thr Val Ser Ser
        115                 120

<210> SEQ ID NO 133
<211> LENGTH: 122
<212> TYPE: PRT
<213> ORGANISM: Lama glama

<400> SEQUENCE: 133

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Thr Ser Arg
            20                  25                  30

Tyr Tyr Ala Trp Ser Trp Ile Arg Gln Pro Pro Gly Lys Gly Leu Glu
        35                  40                  45

Trp Ile Gly Val Ile Asp Tyr Asp Gly Asp Thr Tyr Tyr Ser Pro Ser
    50                  55                  60

Leu Lys Ser Arg Val Ser Ile Ser Trp Asp Thr Ser Lys Asn Gln Phe
65                  70                  75                  80

Ser Leu Gln Leu Ser Ser Val Thr Ala Ala Asp Thr Ala Val Tyr Tyr
            85                  90                  95

Cys Ala Arg Asp Pro Asp Val Val Thr Gly Phe His Tyr Asp Tyr Trp
            100                 105                 110

Gly Gln Gly Thr Met Val Thr Val Ser Ser
        115                 120

<210> SEQ ID NO 134
<211> LENGTH: 122
<212> TYPE: PRT
<213> ORGANISM: Lama glama

<400> SEQUENCE: 134

Glu Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Thr Thr Arg
            20                  25                  30

Tyr Tyr Ala Trp Ser Trp Ile Arg Gln Pro Pro Gly Lys Gly Leu Glu
        35                  40                  45

Trp Ile Gly Val Ile Asp Tyr Asp Gly Asp Thr Tyr Tyr Ser Pro Ser
    50                  55                  60

Leu Lys Ser Arg Thr Ser Ile Ser Trp Asp Thr Ser Lys Asn Gln Phe
65                  70                  75                  80

Ser Leu Lys Leu Ser Ser Val Thr Ala Glu Asp Thr Ala Val Tyr Tyr
            85                  90                  95

Cys Ala Arg Asp Pro Asp Val Val Thr Gly Phe His Tyr Asp Tyr Trp
            100                 105                 110

Gly Gln Gly Thr Thr Val Thr Val Ser Ser
        115                 120

<210> SEQ ID NO 135
<211> LENGTH: 122
<212> TYPE: PRT
<213> ORGANISM: Lama glama

<400> SEQUENCE: 135

Glu Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Thr Ser Arg
            20                  25                  30

Tyr Tyr Ala Trp Ser Trp Ile Arg Gln Pro Pro Gly Lys Gly Leu Glu
        35                  40                  45

Trp Ile Gly Val Ile Asp Tyr Asp Gly Asp Thr Tyr Tyr Ser Pro Ser
    50                  55                  60

Leu Lys Ser Arg Thr Thr Ile Ser Val Asp Thr Ser Lys Asn Gln Phe
65                  70                  75                  80

Ser Leu His Leu Ser Ser Val Thr Ala Glu Asp Thr Ala Val Tyr Tyr
            85                  90                  95

Cys Ala Arg Asp Pro Asp Val Val Thr Gly Phe His Tyr Asp Tyr Trp
            100                 105                 110

Gly Gln Gly Thr Gln Val Thr Val Ser Ser
            115                 120

<210> SEQ ID NO 136
<211> LENGTH: 122
<212> TYPE: PRT
<213> ORGANISM: Lama glama

<400> SEQUENCE: 136

Glu Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Thr Ser Arg
            20                  25                  30

Tyr Tyr Ala Trp Ser Trp Ile Arg Gln Pro Pro Gly Lys Gly Leu Glu
        35                  40                  45

Trp Ile Gly Val Ile Asp Tyr Asp Gly Asp Thr Tyr Tyr Ser Pro Ser
    50                  55                  60

Leu Lys Ser Arg Thr Ser Ile Ser Val Asp Thr Ser Lys Asn Gln Phe
65                  70                  75                  80

Ser Leu Gln Leu Ser Ser Val Thr Ala Glu Asp Thr Ala Val Tyr Tyr
            85                  90                  95

Cys Ala Arg Asp Pro Asp Val Val Thr Gly Phe His Tyr Asp Tyr Trp
            100                 105                 110

Gly Gln Gly Thr Leu Val Thr Val Ser Ser
            115                 120

<210> SEQ ID NO 137
<211> LENGTH: 122
<212> TYPE: PRT
<213> ORGANISM: Lama glama

<400> SEQUENCE: 137

Glu Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Thr Thr Arg
            20                  25                  30

Tyr Tyr Ala Trp Ser Trp Ile Arg Gln Pro Pro Gly Lys Gly Leu Glu
        35                  40                  45

Trp Ile Gly Val Ile Asp Tyr Asp Gly Asp Thr Tyr Tyr Ser Pro Ser
    50                  55                  60

Leu Lys Ser Arg Val Thr Ile Ser Trp Asp Thr Ser Lys Asn Gln Phe
65                  70                  75                  80

Ser Leu Gln Leu Ser Ser Val Thr Pro Glu Asp Thr Ala Val Tyr Tyr
            85                  90                  95

```
Cys Ala Arg Asp Pro Asp Val Val Thr Gly Phe His Tyr Asp Tyr Trp
                100                 105                 110

Gly Gln Gly Thr Thr Val Thr Val Ser Ser
            115                 120
```

<210> SEQ ID NO 138
<211> LENGTH: 122
<212> TYPE: PRT
<213> ORGANISM: Lama glama

<400> SEQUENCE: 138

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Thr Thr Arg
            20                  25                  30

Tyr Tyr Ala Trp Ser Trp Ile Arg Gln Pro Pro Gly Lys Gly Leu Glu
            35                  40                  45

Trp Ile Gly Val Ile Asp Tyr Asp Gly Asp Thr Tyr Tyr Ser Pro Ser
    50                  55                  60

Leu Lys Ser Arg Thr Thr Ile Ser Trp Asp Thr Ser Lys Asn Gln Phe
65                  70                  75                  80

Ser Leu Gln Leu Ser Ser Val Thr Pro Glu Asp Thr Ala Val Tyr Tyr
                85                  90                  95

Cys Ala Arg Asp Pro Asp Val Val Thr Gly Phe His Tyr Asp Tyr Trp
                100                 105                 110

Gly Gln Gly Thr Leu Val Thr Val Ser Ser
            115                 120
```

<210> SEQ ID NO 139
<211> LENGTH: 122
<212> TYPE: PRT
<213> ORGANISM: Lama glama

<400> SEQUENCE: 139

```
Glu Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Thr Thr Arg
            20                  25                  30

Tyr Tyr Ala Trp Ser Trp Ile Arg Gln Pro Pro Gly Lys Gly Leu Glu
            35                  40                  45

Trp Ile Gly Val Ile Asp Tyr Asp Gly Asp Thr Tyr Tyr Ser Pro Ser
    50                  55                  60

Leu Lys Ser Arg Thr Thr Ile Ser Val Asp Thr Ser Lys Asn Gln Phe
65                  70                  75                  80

Ser Leu Lys Leu Ser Ser Val Thr Pro Glu Asp Thr Ala Val Tyr Tyr
                85                  90                  95

Cys Ala Arg Asp Pro Asp Val Val Thr Gly Phe His Tyr Asp Tyr Trp
                100                 105                 110

Gly Gln Gly Thr Met Val Thr Val Ser Ser
            115                 120
```

<210> SEQ ID NO 140
<211> LENGTH: 122
<212> TYPE: PRT
<213> ORGANISM: Lama glama

<400> SEQUENCE: 140

```
Glu Val Gln Leu Gln Glu Ser Gly Pro Gly Leu Val Lys Pro Ser Gln
```

```
                1               5                   10                  15
            Thr Leu Ser Leu Thr Cys Thr Val Ser Gly Gly Ser Ile Thr Thr Arg
                        20                  25                  30

Tyr Tyr Ala Trp Ser Trp Ile Arg Gln Pro Pro Gly Lys Gly Leu Glu
                        35                  40                  45

Trp Ile Gly Val Ile Asp Tyr Asp Gly Asp Thr Tyr Tyr Ser Pro Ser
                        50                  55                  60

Leu Lys Ser Arg Thr Thr Ile Ser Trp Asp Thr Ser Lys Asn Gln Phe
            65                  70                  75                  80

Ser Leu Lys Leu Ser Ser Val Thr Ala Glu Asp Thr Ala Val Tyr Tyr
                                85                  90                  95

Cys Ala Arg Asp Pro Asp Val Val Thr Gly Phe His Tyr Asp Tyr Trp
                        100                 105                 110

Gly Gln Gly Thr Gln Val Thr Val Ser Ser
                        115                 120

<210> SEQ ID NO 141
<211> LENGTH: 122
<212> TYPE: PRT
<213> ORGANISM: Lama glama

<400> SEQUENCE: 141

Glu Val Gln Leu Gln Glu Ser Gly Pro Gly Leu Val Lys Pro Ser Gln
            1               5                   10                  15

Thr Leu Ser Leu Thr Cys Thr Val Ser Gly Gly Ser Ile Thr Ser Arg
                        20                  25                  30

Tyr Tyr Ala Trp Ser Trp Ile Arg Gln Pro Pro Gly Lys Gly Leu Glu
                        35                  40                  45

Trp Ile Gly Val Ile Asp Tyr Asp Gly Asp Thr Tyr Tyr Ser Pro Ser
                        50                  55                  60

Leu Lys Ser Arg Thr Thr Ile Ser Trp Asp Thr Ser Lys Asn Gln Phe
            65                  70                  75                  80

Ser Leu Lys Leu Ser Ser Val Thr Ala Ala Asp Thr Ala Val Tyr Tyr
                                85                  90                  95

Cys Ala Arg Asp Pro Asp Val Val Thr Gly Phe His Tyr Asp Tyr Trp
                        100                 105                 110

Gly Gln Gly Thr Met Val Thr Val Ser Ser
                        115                 120

<210> SEQ ID NO 142
<211> LENGTH: 122
<212> TYPE: PRT
<213> ORGANISM: Lama glama

<400> SEQUENCE: 142

Glu Val Gln Leu Gln Glu Ser Gly Pro Gly Leu Val Lys Pro Ser Gln
            1               5                   10                  15

Thr Leu Ser Leu Thr Cys Thr Val Ser Gly Gly Ser Ile Thr Thr Arg
                        20                  25                  30

Tyr Tyr Ala Trp Ser Trp Ile Arg Gln Pro Pro Gly Lys Gly Leu Glu
                        35                  40                  45

Trp Ile Gly Val Ile Asp Tyr Asp Gly Asp Thr Tyr Tyr Ser Pro Ser
                        50                  55                  60

Leu Lys Ser Arg Thr Ser Ile Ser Trp Asp Thr Ser Lys Asn Gln Phe
            65                  70                  75                  80

Ser Leu Lys Leu Ser Ser Val Thr Ala Ala Asp Thr Ala Val Tyr Tyr
```

85                  90                  95

Cys Ala Arg Asp Pro Asp Val Val Thr Gly Phe His Tyr Asp Tyr Trp
            100                 105                 110

Gly Pro Gly Thr Gln Val Thr Val Ser Ser
            115                 120

<210> SEQ ID NO 143
<211> LENGTH: 122
<212> TYPE: PRT
<213> ORGANISM: Lama glama

<400> SEQUENCE: 143

Glu Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Thr Ser Arg
            20                  25                  30

Tyr Tyr Ala Trp Ser Trp Ile Arg Gln Pro Pro Gly Lys Gly Leu Glu
            35                  40                  45

Trp Ile Gly Val Ile Asp Tyr Asp Gly Asp Thr Tyr Tyr Ser Pro Ser
        50                  55                  60

Leu Lys Ser Arg Thr Ser Ile Ser Val Asp Thr Ser Lys Asn Gln Phe
65                  70                  75                  80

Ser Leu Gln Leu Ser Ser Val Thr Ala Glu Asp Thr Ala Val Tyr Tyr
                85                  90                  95

Cys Ala Arg Asp Pro Asp Val Val Thr Gly Phe His Tyr Asp Tyr Trp
            100                 105                 110

Gly Gln Gly Thr Met Val Thr Val Ser Ser
            115                 120

<210> SEQ ID NO 144
<211> LENGTH: 122
<212> TYPE: PRT
<213> ORGANISM: Lama glama

<400> SEQUENCE: 144

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Thr Thr Arg
            20                  25                  30

Tyr Tyr Ala Trp Ser Trp Ile Arg Gln Pro Pro Gly Lys Gly Leu Glu
            35                  40                  45

Trp Met Gly Val Ile Asp Tyr Asp Gly Asp Thr Tyr Tyr Ser Pro Ser
        50                  55                  60

Leu Lys Ser Arg Val Ser Ile Ser Trp Asp Thr Ser Lys Asn Gln Phe
65                  70                  75                  80

Ser Leu Gln Leu Ser Ser Val Thr Ala Glu Asp Thr Ala Val Tyr Tyr
                85                  90                  95

Cys Ala Arg Asp Pro Asp Val Val Thr Gly Phe His Tyr Asp Tyr Trp
            100                 105                 110

Gly Gln Gly Thr Leu Val Thr Val Ser Ser
            115                 120

<210> SEQ ID NO 145
<211> LENGTH: 122
<212> TYPE: PRT
<213> ORGANISM: Lama glama

<400> SEQUENCE: 145

```
Glu Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Thr Thr Arg
            20                  25                  30

Tyr Tyr Ala Trp Ser Trp Ile Arg Gln Pro Pro Gly Lys Gly Leu Glu
        35                  40                  45

Trp Ile Gly Val Ile Asp Tyr Asp Gly Asp Thr Tyr Tyr Ser Pro Ser
50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Pro Glu Asp Thr Ala Val Tyr Tyr
            85                  90                  95

Cys Ala Arg Asp Pro Asp Val Val Thr Gly Phe His Tyr Asp Tyr Trp
            100                 105                 110

Gly Gln Gly Thr Met Val Thr Val Ser Ser
            115                 120

<210> SEQ ID NO 146
<211> LENGTH: 122
<212> TYPE: PRT
<213> ORGANISM: Lama glama

<400> SEQUENCE: 146

Glu Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Thr Thr Arg
            20                  25                  30

Tyr Tyr Ala Trp Ser Trp Ile Arg Gln Pro Pro Gly Lys Gly Leu Glu
        35                  40                  45

Trp Ile Gly Val Ile Asp Tyr Asp Gly Asp Thr Tyr Tyr Ser Pro Ser
50                  55                  60

Leu Lys Ser Arg Thr Thr Ile Ser Trp Asp Thr Ser Lys Asn Gln Phe
65                  70                  75                  80

Ser Leu Lys Leu Ser Ser Val Thr Ala Glu Asp Thr Ala Val Tyr Tyr
            85                  90                  95

Cys Ala Arg Asp Pro Asp Val Val Thr Gly Phe His Tyr Asp Tyr Trp
            100                 105                 110

Gly Gln Gly Thr Gln Val Thr Val Ser Ser
            115                 120

<210> SEQ ID NO 147
<211> LENGTH: 122
<212> TYPE: PRT
<213> ORGANISM: Lama glama

<400> SEQUENCE: 147

Glu Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Thr Ser Arg
            20                  25                  30

Tyr Tyr Ala Trp Ser Trp Ile Arg Gln Pro Pro Gly Lys Gly Leu Glu
        35                  40                  45

Trp Ile Gly Val Ile Asp Tyr Asp Gly Asp Thr Tyr Tyr Ser Pro Ser
50                  55                  60

Leu Lys Ser Arg Thr Thr Ile Ser Trp Asp Thr Ser Lys Asn Gln Phe
65                  70                  75                  80
```

```
Ser Leu Gln Leu Ser Ser Val Thr Ala Glu Asp Thr Ala Val Tyr Tyr
                85                  90                  95

Cys Ala Arg Asp Pro Asp Val Val Thr Gly Phe His Tyr Asp Tyr Trp
            100                 105                 110

Gly Gln Gly Thr Gln Val Thr Val Ser Ser
        115                 120
```

<210> SEQ ID NO 148
<211> LENGTH: 122
<212> TYPE: PRT
<213> ORGANISM: Lama glama

<400> SEQUENCE: 148

```
Gln Val Gln Leu Gln Glu Ser Gly Pro Gly Leu Val Lys Pro Ser Gln
1               5                   10                  15

Thr Leu Ser Leu Thr Cys Val Ser Gly Gly Ser Ile Thr Ser Arg
            20                  25                  30

Tyr Tyr Ala Trp Ser Trp Ile Arg Gln Pro Pro Gly Lys Gly Leu Glu
        35                  40                  45

Trp Ile Gly Val Ile Asp Tyr Asp Gly Asp Thr Tyr Tyr Ser Pro Ser
    50                  55                  60

Leu Lys Ser Arg Thr Thr Ile Ser Trp Asp Thr Ser Lys Asn Gln Phe
65                  70                  75                  80

Ser Leu Lys Leu Ser Ser Val Thr Ala Glu Asp Thr Ala Val Tyr Tyr
                85                  90                  95

Cys Ala Arg Asp Pro Asp Val Val Thr Gly Phe His Tyr Asp Tyr Trp
            100                 105                 110

Gly Gln Gly Thr Gln Val Thr Val Ser Ser
        115                 120
```

<210> SEQ ID NO 149
<211> LENGTH: 122
<212> TYPE: PRT
<213> ORGANISM: Lama glama

<400> SEQUENCE: 149

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Thr Thr Arg
            20                  25                  30

Tyr Tyr Ala Trp Ser Trp Ile Arg Gln Pro Pro Gly Lys Gly Leu Glu
        35                  40                  45

Trp Ile Gly Val Ile Asp Tyr Asp Gly Asp Thr Tyr Tyr Ser Pro Ser
    50                  55                  60

Leu Lys Ser Arg Val Thr Ile Ser Val Asp Thr Ser Lys Asn Gln Ile
65                  70                  75                  80

Ser Leu Lys Leu Ser Ser Val Thr Pro Glu Asp Thr Ala Val Tyr Tyr
                85                  90                  95

Cys Ala Arg Asp Pro Asp Val Val Thr Gly Phe His Tyr Asp Tyr Trp
            100                 105                 110

Gly Gln Gly Thr Gln Val Thr Val Ser Ser
        115                 120
```

<210> SEQ ID NO 150
<211> LENGTH: 122
<212> TYPE: PRT
<213> ORGANISM: Lama glama -continued

<400> SEQUENCE: 150

Glu Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Thr Ser Arg
            20                  25                  30

Tyr Tyr Ala Trp Ser Trp Ile Arg Gln Pro Pro Gly Lys Gly Leu Glu
        35                  40                  45

Trp Ile Gly Val Ile Asp Tyr Asp Gly Asp Thr Tyr Tyr Ser Pro Ser
    50                  55                  60

Leu Lys Ser Arg Val Ser Ile Ser Trp Asp Thr Ser Lys Asn Gln Phe
65                  70                  75                  80

Ser Leu Lys Leu Ser Ser Val Thr Ala Glu Asp Thr Ala Val Tyr Tyr
                85                  90                  95

Cys Ala Arg Asp Pro Asp Val Val Thr Gly Phe His Tyr Asp Tyr Trp
            100                 105                 110

Gly Gln Gly Thr Leu Val Thr Val Ser Ser
            115                 120

<210> SEQ ID NO 151
<211> LENGTH: 122
<212> TYPE: PRT
<213> ORGANISM: Lama glama

<400> SEQUENCE: 151

Glu Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Thr Pro Arg
            20                  25                  30

Tyr Tyr Val Trp Thr Trp Ile Arg His Pro Pro Gly Lys Gly Leu Asp
        35                  40                  45

Trp Ile Gly Val Ile Asp Tyr Asp Gly Asp Thr Tyr Tyr Ser Pro Ser
    50                  55                  60

Leu Lys Ser Arg Thr Thr Ile Ser Trp Asp Thr Ser Lys Asn Gln Phe
65                  70                  75                  80

Ser Leu Gln Leu Ser Ser Val Thr Ala Glu Asp Thr Ala Val Tyr Tyr
                85                  90                  95

Cys Ala Arg Tyr Pro Asp Val Val Thr Gly Phe His Tyr Asp Tyr Trp
            100                 105                 110

Gly Gln Gly Thr Gln Val Thr Val Ser Ser
            115                 120

<210> SEQ ID NO 152
<211> LENGTH: 122
<212> TYPE: PRT
<213> ORGANISM: Lama glama

<400> SEQUENCE: 152

Glu Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Thr Ser Arg
            20                  25                  30

Tyr Tyr Ala Trp Ser Trp Ile Arg Gln Pro Pro Gly Lys Gly Leu Glu
        35                  40                  45

Trp Ile Gly Val Ile Asp Tyr Asp Gly Asp Thr Tyr Tyr Ser Pro Ser
    50                  55                  60

-continued

Leu Lys Ser Arg Val Ser Ile Ser Trp Asp Thr Ser Lys Asn Gln Phe
65                  70                  75                  80

Ser Leu Lys Leu Ser Ser Val Thr Pro Ala Asp Thr Ala Val Tyr Tyr
                85                  90                  95

Cys Ala Arg Asp Pro Asp Val Val Thr Gly Phe His Tyr Asp Tyr Trp
            100                 105                 110

Gly Gln Gly Thr Met Val Thr Val Ser Ser
        115                 120

<210> SEQ ID NO 153
<211> LENGTH: 122
<212> TYPE: PRT
<213> ORGANISM: Lama glama

<400> SEQUENCE: 153

Glu Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Thr Ser Arg
                20                  25                  30

Tyr Tyr Ala Trp Ser Trp Ile Arg Gln Pro Pro Gly Lys Gly Leu Glu
            35                  40                  45

Trp Ile Gly Val Ile Asp Tyr Asp Gly Asp Thr Tyr Tyr Ser Pro Ser
50                  55                  60

Leu Lys Ser Arg Thr Thr Ile Ser Trp Asp Thr Ser Lys Asn Gln Phe
65                  70                  75                  80

Ser Leu Gln Leu Ser Ser Val Thr Ala Ala Asp Thr Ala Val Tyr Tyr
                85                  90                  95

Cys Ala Arg Asp Pro Asp Val Val Thr Gly Phe His Tyr Asp Tyr Trp
            100                 105                 110

Gly Gln Gly Thr Leu Val Thr Val Ser Ser
        115                 120

<210> SEQ ID NO 154
<211> LENGTH: 122
<212> TYPE: PRT
<213> ORGANISM: Lama glama

<400> SEQUENCE: 154

Glu Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Thr Ser Arg
                20                  25                  30

Tyr Tyr Ala Trp Ser Trp Ile Arg Gln Pro Pro Gly Lys Gly Leu Glu
            35                  40                  45

Trp Ile Gly Val Ile Asp Tyr Asp Gly Asp Thr Tyr Tyr Ser Pro Ser
50                  55                  60

Leu Lys Ser Arg Thr Ser Ile Ser Trp Asp Thr Ser Lys Asn Gln Phe
65                  70                  75                  80

Ser Leu Gln Leu Ser Ser Val Thr Pro Glu Asp Thr Ala Val Tyr Tyr
                85                  90                  95

Cys Ala Arg Asp Pro Asp Val Val Thr Gly Phe His Tyr Asp Tyr Trp
            100                 105                 110

Gly Gln Gly Thr Thr Val Thr Val Ser Ser
        115                 120

<210> SEQ ID NO 155
<211> LENGTH: 122

```
<212> TYPE: PRT
<213> ORGANISM: Lama glama

<400> SEQUENCE: 155

Glu Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Thr Ser Arg
            20                  25                  30

Tyr Tyr Ala Trp Ser Trp Ile Arg Gln Pro Pro Gly Lys Gly Leu Glu
        35                  40                  45

Trp Met Gly Val Ile Asp Tyr Asp Gly Asp Thr Tyr Tyr Ser Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Glu Asp Thr Ala Val Tyr Tyr
                85                  90                  95

Cys Ala Arg Asp Pro Asp Val Val Thr Gly Phe His Tyr Asp Tyr Trp
            100                 105                 110

Gly Gln Gly Thr Leu Val Thr Val Ser Ser
        115                 120

<210> SEQ ID NO 156
<211> LENGTH: 122
<212> TYPE: PRT
<213> ORGANISM: Lama glama

<400> SEQUENCE: 156

Glu Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Thr Ser Arg
            20                  25                  30

Tyr Tyr Ala Trp Ser Trp Ile Arg Gln Pro Pro Gly Lys Gly Leu Glu
        35                  40                  45

Trp Ile Gly Val Ile Asp Tyr Asp Gly Asp Thr Tyr Tyr Ser Pro Ser
    50                  55                  60

Leu Lys Ser Arg Val Thr Ile Ser Trp Asp Thr Ser Lys Asn Gln Phe
65                  70                  75                  80

Ser Leu Gln Leu Ser Ser Val Thr Ala Glu Asp Thr Ala Val Tyr Tyr
                85                  90                  95

Cys Ala Arg Asp Pro Asp Val Val Thr Gly Phe His Tyr Asp Tyr Trp
            100                 105                 110

Gly Gln Gly Thr Leu Val Thr Val Ser Ser
        115                 120

<210> SEQ ID NO 157
<211> LENGTH: 122
<212> TYPE: PRT
<213> ORGANISM: Lama glama

<400> SEQUENCE: 157

Glu Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Thr Ser Ser
            20                  25                  30

Tyr Tyr Ala Trp Ser Trp Ile Arg Gln Pro Pro Gly Lys Gly Leu Glu
        35                  40                  45

Trp Ile Gly Val Ile Asp Tyr Asp Gly Asp Thr Tyr Tyr Ser Pro Ser
```

```
                50                  55                  60
Leu Lys Ser Arg Thr Thr Ile Ser Trp Asp Thr Ser Lys Asn Gln Phe
 65                  70                  75                  80

Ser Leu Gln Leu Ser Ser Val Thr Ala Glu Asp Thr Ala Val Tyr Tyr
                 85                  90                  95

Cys Ala Arg Asp Pro Asp Val Val Thr Gly Phe His Tyr Asp Tyr Trp
                100                 105                 110

Gly Gln Gly Thr Met Val Thr Val Ser Ser
            115                 120

<210> SEQ ID NO 158
<211> LENGTH: 122
<212> TYPE: PRT
<213> ORGANISM: Lama glama

<400> SEQUENCE: 158

Glu Val Gln Leu Gln Glu Ser Gly Pro Gly Leu Val Lys Pro Ser Gln
 1               5                  10                  15

Thr Leu Ser Leu Thr Cys Thr Val Ser Gly Gly Ser Ile Thr Thr Arg
                 20                  25                  30

Tyr Tyr Ala Trp Ser Trp Ile Arg Gln Pro Pro Gly Lys Gly Leu Glu
             35                  40                  45

Trp Ile Gly Val Ile Asp Tyr Asp Gly Asp Thr Tyr Tyr Ser Pro Ser
 50                  55                  60

Leu Lys Ser Arg Val Ser Ile Ser Trp Asp Thr Ser Lys Asn Gln Phe
 65                  70                  75                  80

Ser Leu Lys Leu Ser Ser Val Thr Ala Glu Asp Thr Ala Val Tyr Tyr
                 85                  90                  95

Cys Ala Arg Asp Pro Asp Val Val Thr Gly Phe His Tyr Asp Tyr Trp
                100                 105                 110

Gly Gln Gly Thr Gln Val Thr Val Ser Ser
            115                 120

<210> SEQ ID NO 159
<211> LENGTH: 122
<212> TYPE: PRT
<213> ORGANISM: Lama glama

<400> SEQUENCE: 159

Glu Val Gln Leu Gln Glu Ser Gly Pro Gly Leu Val Lys Pro Ser Gln
 1               5                  10                  15

Thr Leu Ser Leu Thr Cys Thr Val Ser Gly Gly Ser Ile Thr Ser Arg
                 20                  25                  30

Tyr Tyr Ala Trp Ser Trp Ile Arg Gln Pro Pro Gly Lys Gly Leu Glu
             35                  40                  45

Trp Ile Gly Val Ile Asp Tyr Asp Gly Asp Thr Tyr Tyr Ser Pro Ser
 50                  55                  60

Leu Lys Ser Arg Val Thr Ile Ser Trp Asp Thr Ser Lys Asn Gln Phe
 65                  70                  75                  80

Ser Leu Lys Leu Ser Ser Val Thr Ala Glu Asp Thr Ala Val Tyr Tyr
                 85                  90                  95

Cys Ala Arg Asp Pro Asp Val Val Thr Gly Phe His Tyr Asp Tyr Trp
                100                 105                 110

Gly Gln Gly Thr Met Val Thr Val Ser Ser
            115                 120
```

<210> SEQ ID NO 160
<211> LENGTH: 122
<212> TYPE: PRT
<213> ORGANISM: Lama glama

<400> SEQUENCE: 160

Glu Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Thr Ser Arg
            20                  25                  30

Tyr Tyr Ala Trp Ser Trp Ile Arg Gln Pro Pro Gly Lys Gly Leu Glu
        35                  40                  45

Trp Ile Gly Val Ile Asp Tyr Asp Gly Asp Thr Tyr Tyr Ser Pro Ser
    50                  55                  60

Leu Lys Ser Arg Thr Thr Ile Ser Trp Asp Thr Ser Lys Asn Gln Phe
65                  70                  75                  80

Ser Leu Gln Leu Ser Ser Val Thr Ala Glu Asp Thr Ala Val Tyr Tyr
                85                  90                  95

Cys Ala Arg Asp Pro Asp Val Val Thr Gly Phe His Tyr Asp Tyr Trp
            100                 105                 110

Gly Gln Gly Thr Gln Val Thr Val Ser Ser
        115                 120

<210> SEQ ID NO 161
<211> LENGTH: 122
<212> TYPE: PRT
<213> ORGANISM: Lama glama

<400> SEQUENCE: 161

Glu Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Thr Thr Arg
            20                  25                  30

Tyr Tyr Ala Trp Ser Trp Ile Arg Gln Pro Pro Gly Lys Gly Leu Glu
        35                  40                  45

Trp Ile Gly Val Ile Asp Tyr Asp Gly Asp Thr Tyr Tyr Ser Pro Ser
    50                  55                  60

Leu Lys Ser Arg Thr Thr Ile Ser Trp Asp Thr Ser Lys Asn Gln Phe
65                  70                  75                  80

Ser Leu Lys Leu Ser Ser Val Thr Ala Glu Asp Thr Ala Val Tyr Tyr
                85                  90                  95

Cys Ala Arg Asp Pro Asp Val Val Thr Gly Phe His Tyr Asp Tyr Trp
            100                 105                 110

Gly Gln Gly Thr Gln Val Thr Val Ser Ser
        115                 120

<210> SEQ ID NO 162
<211> LENGTH: 122
<212> TYPE: PRT
<213> ORGANISM: Lama glama

<400> SEQUENCE: 162

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Thr Thr Arg
            20                  25                  30

Tyr Tyr Ala Trp Ser Trp Ile Arg Gln Pro Pro Gly Lys Gly Leu Glu
        35                  40                  45

Trp Ile Gly Val Ile Asp Tyr Asp Gly Asp Thr Tyr Tyr Ser Pro Ser
            50                  55                  60

Leu Lys Ser Arg Thr Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                85                  90                  95

Cys Ala Arg Asp Pro Asp Val Val Thr Gly Phe His Tyr Asp Tyr Trp
                100                 105                 110

Gly Gln Gly Thr Gln Val Thr Val Ser Ser
            115                 120

<210> SEQ ID NO 163
<211> LENGTH: 122
<212> TYPE: PRT
<213> ORGANISM: Lama glama

<400> SEQUENCE: 163

Glu Val Gln Leu Gln Glu Ser Gly Pro Gly Leu Val Lys Pro Ser Gln
 1               5                  10                  15

Thr Leu Ser Leu Thr Cys Thr Val Ser Gly Gly Ser Ile Thr Ser Arg
                20                  25                  30

Tyr Tyr Ala Trp Ser Trp Ile Arg Gln Pro Pro Gly Lys Gly Leu Glu
                35                  40                  45

Trp Ile Gly Val Ile Asp Tyr Asp Gly Asp Thr Tyr Tyr Ser Pro Ser
            50                  55                  60

Leu Lys Ser Arg Thr Ser Ile Ser Trp Asp Thr Ser Lys Asn Gln Phe
 65                  70                  75                  80

Ser Leu Gln Leu Ser Ser Val Thr Pro Glu Asp Thr Ala Val Tyr Tyr
                85                  90                  95

Cys Ala Arg Asp Pro Asp Val Val Thr Gly Phe His Tyr Asp Tyr Trp
                100                 105                 110

Gly Gln Gly Thr Gln Val Thr Val Ser Ser
            115                 120

<210> SEQ ID NO 164
<211> LENGTH: 122
<212> TYPE: PRT
<213> ORGANISM: Lama glama

<400> SEQUENCE: 164

Gln Val Gln Leu Gln Glu Ser Gly Pro Gly Leu Val Lys Pro Ser Gln
 1               5                  10                  15

Thr Leu Ser Leu Thr Cys Thr Val Ser Gly Gly Ser Ile Thr Ser Arg
                20                  25                  30

Tyr Tyr Ala Trp Ser Trp Ile Arg Gln Pro Pro Gly Lys Gly Leu Glu
                35                  40                  45

Trp Ile Gly Val Ile Asp Tyr Asp Gly Asp Thr Tyr Tyr Ser Pro Ser
            50                  55                  60

Leu Lys Ser Arg Thr Ser Ile Ser Trp Asp Thr Ser Lys Asn Gln Phe
 65                  70                  75                  80

Ser Leu Gln Leu Ser Ser Val Thr Ala Glu Asp Thr Ala Val Tyr Tyr
                85                  90                  95

Cys Ala Arg Asp Pro Asp Val Val Thr Gly Phe His Tyr Asp Tyr Trp
                100                 105                 110

Gly Gln Gly Thr Leu Val Thr Val Ser Ser
            115                 120

<210> SEQ ID NO 165
<211> LENGTH: 122
<212> TYPE: PRT
<213> ORGANISM: Lama glama

<400> SEQUENCE: 165

Glu Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Thr Thr Arg
            20                  25                  30

Tyr Tyr Ala Trp Ser Trp Ile Arg Gln Pro Pro Gly Lys Gly Leu Glu
        35                  40                  45

Trp Met Gly Val Ile Asp Tyr Asp Gly Asp Thr Tyr Tyr Ser Pro Ser
    50                  55                  60

Leu Lys Ser Arg Thr Ser Ile Ser Trp Asp Thr Ser Lys Asn Gln Phe
65                  70                  75                  80

Ser Leu Gln Leu Ser Ser Val Thr Pro Glu Asp Thr Ala Val Tyr Tyr
                85                  90                  95

Cys Ala Arg Asp Pro Asp Val Val Thr Gly Phe His Tyr Asp Tyr Trp
            100                 105                 110

Gly Gln Gly Thr Gln Val Thr Val Ser Ser
        115                 120

<210> SEQ ID NO 166
<211> LENGTH: 122
<212> TYPE: PRT
<213> ORGANISM: Lama glama

<400> SEQUENCE: 166

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Thr Ser Arg
            20                  25                  30

Tyr Tyr Ala Trp Ser Trp Ile Arg Gln Pro Pro Gly Lys Gly Leu Glu
        35                  40                  45

Trp Ile Gly Val Ile Asp Tyr Asp Gly Asp Thr Tyr Tyr Ser Pro Ser
    50                  55                  60

Leu Lys Ser Arg Thr Thr Ile Ser Trp Asp Thr Ser Lys Asn Gln Phe
65                  70                  75                  80

Ser Leu Lys Leu Ser Ser Val Thr Ala Glu Asp Thr Ala Val Tyr Tyr
                85                  90                  95

Cys Ala Arg Asp Pro Asp Val Val Thr Gly Phe His Tyr Asp Tyr Trp
            100                 105                 110

Gly Gln Gly Thr Gln Val Thr Val Ser Ser
        115                 120

<210> SEQ ID NO 167
<211> LENGTH: 122
<212> TYPE: PRT
<213> ORGANISM: Lama glama

<400> SEQUENCE: 167

Glu Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Thr Thr Arg
            20                  25                  30

```
Tyr Tyr Ala Trp Ser Trp Ile Arg Gln Pro Pro Gly Lys Gly Leu Glu
            35                  40                  45

Trp Ile Gly Val Ile Asp Tyr Asp Gly Asp Thr Tyr Tyr Ser Pro Ser
 50                      55                  60

Leu Lys Ser Arg Val Ser Ile Ser Trp Asp Thr Ser Lys Asn Gln Phe
 65                  70                  75                  80

Ser Leu Gln Leu Ser Ser Val Thr Ala Glu Asp Thr Ala Val Tyr Tyr
                 85                  90                  95

Cys Ala Arg Asp Pro Asp Val Val Thr Gly Phe His Tyr Asp Tyr Trp
                100                 105                 110

Gly Gln Gly Thr Leu Val Thr Val Ser Ser
            115                 120
```

<210> SEQ ID NO 168
<211> LENGTH: 122
<212> TYPE: PRT
<213> ORGANISM: Lama glama

<400> SEQUENCE: 168

```
Glu Val Gln Leu Gln Glu Ser Gly Pro Gly Leu Val Lys Pro Ser Gln
 1               5                  10                  15

Thr Leu Ser Leu Thr Cys Thr Val Ser Gly Gly Ser Ile Thr Thr Arg
                 20                  25                  30

Tyr Tyr Ala Trp Ser Trp Ile Arg Gln Pro Pro Gly Lys Gly Leu Glu
            35                  40                  45

Trp Ile Gly Val Ile Asp Tyr Asp Gly Asp Thr Tyr Tyr Ser Pro Ser
 50                      55                  60

Leu Glu Ser Arg Thr Thr Ile Ser Trp Asp Thr Ser Lys Asn Gln Phe
 65                  70                  75                  80

Ser Leu Asn Leu Ser Ser Val Thr Ala Glu Asp Thr Ala Val Tyr Tyr
                 85                  90                  95

Cys Ala Arg Asp Pro Asp Val Val Thr Gly Phe His Tyr Asp Tyr Trp
                100                 105                 110

Gly Gln Gly Thr Leu Val Thr Val Ser Ser
            115                 120
```

<210> SEQ ID NO 169
<211> LENGTH: 122
<212> TYPE: PRT
<213> ORGANISM: Lama glama

<400> SEQUENCE: 169

```
Glu Val Gln Leu Gln Glu Ser Gly Pro Gly Leu Val Lys Pro Ser Gln
 1               5                  10                  15

Thr Leu Ser Leu Thr Cys Thr Val Ser Gly Gly Ser Ile Thr Ser Arg
                 20                  25                  30

Tyr Tyr Ala Trp Ser Trp Ile Arg Gln Pro Pro Gly Lys Gly Leu Glu
            35                  40                  45

Trp Met Gly Val Ile Asp Tyr Asp Gly Asp Thr Tyr Tyr Ser Pro Ser
 50                      55                  60

Leu Lys Ser Arg Val Thr Ile Ser Val Asp Thr Ser Lys Asn Gln Phe
 65                  70                  75                  80

Ser Leu Lys Leu Ser Ser Val Thr Pro Ala Asp Thr Ala Val Tyr Tyr
                 85                  90                  95

Cys Ala Arg Asp Pro Asp Val Val Thr Gly Phe His Tyr Asp Tyr Trp
                100                 105                 110
```

```
Gly Gln Gly Thr Leu Val Thr Val Ser Ser
        115                 120

<210> SEQ ID NO 170
<211> LENGTH: 122
<212> TYPE: PRT
<213> ORGANISM: Lama glama

<400> SEQUENCE: 170

Glu Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Thr Ser Arg
            20                  25                  30

Tyr Tyr Ala Trp Ser Trp Ile Arg Gln Pro Pro Gly Lys Gly Leu Glu
        35                  40                  45

Trp Ile Gly Val Ile Asp Tyr Asp Gly Asp Thr Tyr Tyr Ser Pro Ser
    50                  55                  60

Leu Lys Ser Arg Val Ser Ile Ser Trp Asp Thr Ser Lys Asn Gln Phe
65                  70                  75                  80

Ser Leu Gln Leu Ser Ser Val Thr Pro Glu Asp Thr Ala Val Tyr Tyr
                85                  90                  95

Cys Ala Arg Asp Pro Asp Val Val Thr Gly Phe His Tyr Asp Tyr Trp
            100                 105                 110

Gly Gln Gly Thr Lys Val Thr Val Ser Ser
        115                 120

<210> SEQ ID NO 171
<211> LENGTH: 122
<212> TYPE: PRT
<213> ORGANISM: Lama glama

<400> SEQUENCE: 171

Glu Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Thr Thr Arg
            20                  25                  30

Tyr Tyr Ala Trp Ser Trp Ile Arg Gln Pro Pro Gly Lys Gly Leu Glu
        35                  40                  45

Trp Ile Gly Val Ile Asp Tyr Asp Gly Asp Thr Tyr Tyr Ser Pro Ser
    50                  55                  60

Leu Lys Ser Arg Thr Ser Ile Ser Trp Asp Thr Ser Lys Asn Gln Phe
65                  70                  75                  80

Ser Leu Lys Leu Ser Ser Val Thr Ala Glu Asp Thr Ala Val Tyr Tyr
                85                  90                  95

Cys Ala Arg Asp Pro Asp Val Val Thr Gly Phe His Tyr Asp Tyr Trp
            100                 105                 110

Gly Gln Gly Thr Gln Val Thr Val Ser Ser
        115                 120

<210> SEQ ID NO 172
<211> LENGTH: 122
<212> TYPE: PRT
<213> ORGANISM: Lama glama

<400> SEQUENCE: 172

Glu Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Thr Thr Arg
            20                  25                  30
```

```
            20                  25                  30
Tyr Tyr Ala Trp Ser Trp Ile Arg Gln Pro Gly Lys Gly Leu Glu
            35                  40                  45

Trp Ile Gly Val Ile Asp Tyr Asp Gly Asp Thr Tyr Tyr Ser Pro Ser
        50                  55                  60

Leu Lys Ser Arg Val Ser Ile Ser Trp Asp Thr Ser Lys Asn Gln Phe
65                  70                  75                  80

Ser Leu Gln Leu Ser Ser Val Thr Ala Ala Asp Thr Ala Val Tyr Tyr
                85                  90                  95

Cys Ala Arg Asp Pro Asp Val Val Thr Gly Phe His Tyr Asp Tyr Trp
                100                 105                 110

Gly Gln Gly Thr Gln Val Thr Val Ser Ser
                115                 120

<210> SEQ ID NO 173
<211> LENGTH: 122
<212> TYPE: PRT
<213> ORGANISM: Lama glama

<400> SEQUENCE: 173

Glu Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Thr Ser Arg
            20                  25                  30

Tyr Tyr Ala Trp Ser Trp Ile Arg Gln Pro Pro Gly Lys Gly Leu Glu
            35                  40                  45

Trp Ile Gly Val Ile Asp Tyr Asp Gly Asp Thr Tyr Tyr Ser Pro Ser
        50                  55                  60

Leu Lys Ser Arg Thr Thr Ile Ser Val Asp Thr Ser Lys Asn Gln Phe
65                  70                  75                  80

Ser Leu Gln Leu Ser Ser Val Thr Pro Glu Asp Thr Ala Val Tyr Tyr
                85                  90                  95

Cys Ala Arg Asp Pro Asp Val Val Thr Gly Phe His Tyr Asp Tyr Trp
                100                 105                 110

Gly Gln Gly Thr Thr Val Thr Val Ser Ser
                115                 120

<210> SEQ ID NO 174
<211> LENGTH: 122
<212> TYPE: PRT
<213> ORGANISM: Lama glama

<400> SEQUENCE: 174

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Thr Ser Arg
            20                  25                  30

Tyr Tyr Ala Trp Ser Trp Ile Arg Gln Pro Pro Gly Lys Gly Leu Glu
            35                  40                  45

Trp Ile Gly Val Ile Asp Tyr Asp Gly Asp Thr Tyr Tyr Ser Pro Ser
        50                  55                  60

Leu Lys Ser Arg Thr Ser Ile Ser Val Asp Thr Ser Lys Asn Gln Phe
65                  70                  75                  80

Ser Leu Lys Leu Ser Ser Val Thr Pro Glu Asp Thr Ala Val Tyr Tyr
                85                  90                  95

Cys Ala Arg Asp Pro Asp Val Val Thr Gly Phe His Tyr Asp Tyr Trp
```

Gly Gln Gly Thr Thr Val Thr Val Ser Ser
            115                 120

<210> SEQ ID NO 175
<211> LENGTH: 122
<212> TYPE: PRT
<213> ORGANISM: Lama glama

<400> SEQUENCE: 175

Glu Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Thr Ser Arg
            20                  25                  30

Tyr Tyr Ala Trp Ser Trp Ile Arg Gln Pro Pro Gly Lys Gly Leu Glu
            35                  40                  45

Trp Ile Gly Val Ile Asp Tyr Asp Gly Asp Thr Tyr Tyr Ser Pro Ser
    50                  55                  60

Leu Lys Ser Arg Val Ser Ile Ser Trp Asp Thr Ser Lys Asn Gln Phe
65                  70                  75                  80

Ser Leu Gln Leu Ser Ser Val Thr Pro Glu Asp Thr Ala Val Tyr Tyr
                85                  90                  95

Cys Ala Arg Asp Pro Asp Val Val Thr Gly Phe His Tyr Asp Tyr Trp
            100                 105                 110

Gly Gln Gly Thr Lys Val Thr Val Ser Ser
            115                 120

<210> SEQ ID NO 176
<211> LENGTH: 122
<212> TYPE: PRT
<213> ORGANISM: Lama glama

<400> SEQUENCE: 176

Glu Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Thr Thr Arg
            20                  25                  30

Tyr Tyr Ala Trp Ser Trp Ile Arg Gln Pro Pro Gly Lys Gly Leu Glu
            35                  40                  45

Trp Ile Gly Val Ile Asp Tyr Asp Gly Asp Thr Tyr Tyr Ser Pro Ser
    50                  55                  60

Leu Lys Ser Arg Val Ser Ile Ser Trp Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Pro Asp Val Val Thr Gly Phe His Tyr Asp Tyr Trp
            100                 105                 110

Gly Gln Gly Thr Leu Val Thr Val Ser Ser
            115                 120

<210> SEQ ID NO 177
<211> LENGTH: 122
<212> TYPE: PRT
<213> ORGANISM: Lama glama

<400> SEQUENCE: 177

Gln Val Gln Leu Gln Glu Ser Gly Pro Gly Leu Val Lys Pro Ser Gln
1               5                   10                  15

```
Thr Leu Ser Leu Thr Cys Thr Val Ser Gly Ser Ile Thr Ser Arg
            20                  25                  30

Tyr Tyr Ala Trp Ser Trp Ile Arg Gln Pro Pro Gly Lys Gly Leu Glu
            35                  40                  45

Trp Ile Gly Val Ile Asp Tyr Asp Gly Asp Thr Tyr Tyr Ser Pro Ser
 50                  55                  60

Leu Lys Ser Arg Val Thr Ile Ser Trp Asp Thr Ser Lys Asn Gln Phe
 65                  70                  75                  80

Ser Leu Gln Leu Ser Ser Val Thr Ala Ala Asp Thr Ala Val Tyr Tyr
                85                  90                  95

Cys Ala Arg Asp Pro Asp Val Val Thr Gly Phe His Tyr Asp Tyr Trp
                100                 105                 110

Gly Gln Gly Thr Leu Val Thr Val Ser Ser
            115                 120
```

<210> SEQ ID NO 178
<211> LENGTH: 122
<212> TYPE: PRT
<213> ORGANISM: Lama glama

<400> SEQUENCE: 178

```
Gln Val Gln Leu Gln Glu Ser Gly Pro Gly Leu Val Lys Pro Ser Gln
 1               5                   10                  15

Thr Leu Ser Leu Thr Cys Thr Val Ser Gly Gly Ser Ile Thr Ser Arg
            20                  25                  30

Tyr Tyr Ala Trp Ser Trp Ile Arg Gln Pro Pro Gly Lys Gly Leu Glu
            35                  40                  45

Trp Ile Gly Val Ile Asp Tyr Asp Gly Asp Thr Tyr Tyr Ser Pro Ser
 50                  55                  60

Leu Lys Ser Arg Thr Thr Ile Ser Trp Asp Thr Ser Lys Asn Gln Phe
 65                  70                  75                  80

Ser Leu Gln Leu Ser Ser Val Thr Ala Glu Asp Thr Ala Val Tyr Tyr
                85                  90                  95

Cys Ala Arg Asp Pro Asp Val Val Thr Gly Phe His Tyr Asp Tyr Trp
                100                 105                 110

Gly Gln Gly Thr Leu Val Thr Val Ser Ser
            115                 120
```

<210> SEQ ID NO 179
<211> LENGTH: 122
<212> TYPE: PRT
<213> ORGANISM: Lama glama

<400> SEQUENCE: 179

```
Gln Val Gln Leu Gln Glu Ser Gly Pro Gly Leu Val Lys Pro Ser Gln
 1               5                   10                  15

Thr Leu Ser Leu Thr Cys Thr Val Ser Gly Gly Ser Ile Thr Ser Arg
            20                  25                  30

Tyr Tyr Ala Trp Ser Trp Ile Arg Gln Pro Pro Gly Lys Gly Leu Glu
            35                  40                  45

Trp Ile Gly Val Ile Asp Tyr Asp Gly Asp Thr Tyr Tyr Ser Pro Ser
 50                  55                  60

Leu Lys Ser Arg Val Thr Ile Ser Trp Asp Thr Ser Lys Asn Gln Phe
 65                  70                  75                  80

Ser Leu Lys Leu Ser Ser Val Thr Ala Glu Asp Thr Ala Val Tyr Tyr
                85                  90                  95
```

```
Cys Ala Arg Asp Pro Asp Val Val Thr Gly Phe His Tyr Asp Tyr Trp
                100                 105                 110

Gly Gln Gly Thr Gln Val Thr Val Ser Ser
        115                 120

<210> SEQ ID NO 180
<211> LENGTH: 122
<212> TYPE: PRT
<213> ORGANISM: Lama glama

<400> SEQUENCE: 180

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Thr Ser Arg
            20                  25                  30

Tyr Tyr Ala Trp Ser Trp Ile Arg Gln Pro Pro Gly Lys Gly Leu Glu
        35                  40                  45

Trp Ile Gly Val Ile Asp Tyr Asp Gly Asp Thr Tyr Tyr Ser Pro Ser
    50                  55                  60

Leu Lys Ser Arg Thr Ser Ile Ser Val Asp Thr Ser Lys Asn Gln Phe
65                  70                  75                  80

Ser Leu Lys Leu Ser Ser Val Thr Pro Ala Asp Thr Ala Val Tyr Tyr
                85                  90                  95

Cys Ala Arg Asp Pro Asp Val Val Thr Gly Phe His Tyr Asp Tyr Trp
                100                 105                 110

Gly Gln Gly Thr Leu Val Thr Val Ser Ser
        115                 120

<210> SEQ ID NO 181
<211> LENGTH: 122
<212> TYPE: PRT
<213> ORGANISM: Lama glama

<400> SEQUENCE: 181

Glu Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Thr Ser Arg
            20                  25                  30

Tyr Tyr Ala Trp Ser Trp Ile Arg Gln Pro Pro Gly Lys Gly Leu Glu
        35                  40                  45

Trp Met Gly Val Ile Asp Tyr Asp Gly Asp Thr Tyr Tyr Ser Pro Ser
    50                  55                  60

Leu Lys Ser Arg Thr Thr Ile Ser Trp Asp Thr Ser Lys Asn Gln Phe
65                  70                  75                  80

Ser Leu Gln Leu Ser Ser Val Thr Ala Ala Asp Thr Ala Val Tyr Tyr
                85                  90                  95

Cys Ala Arg Asp Pro Asp Val Val Thr Gly Phe His Tyr Asp Tyr Trp
                100                 105                 110

Gly Gln Gly Thr Leu Val Thr Val Ser Ser
        115                 120

<210> SEQ ID NO 182
<211> LENGTH: 122
<212> TYPE: PRT
<213> ORGANISM: Lama glama

<400> SEQUENCE: 182
```

-continued

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Ser Ile Thr Thr Arg
            20                  25                  30

Tyr Tyr Ala Trp Ser Trp Ile Arg Gln Pro Pro Gly Lys Gly Leu Glu
            35                  40                  45

Trp Ile Gly Val Ile Asp Tyr Asp Gly Asp Thr Tyr Tyr Ser Pro Ser
        50                  55                  60

Leu Lys Ser Arg Thr Thr Ile Ser Trp Asp Thr Ser Lys Asn Gln Phe
65                  70                  75                  80

Ser Leu Gln Leu Ser Ser Val Thr Pro Glu Asp Thr Ala Val Tyr Tyr
            85                  90                  95

Cys Ala Arg Asp Pro Asp Val Val Thr Gly Phe His Tyr Asp Tyr Trp
            100                 105                 110

Gly Gln Gly Thr Gln Val Thr Val Ser Ser
            115                 120
```

<210> SEQ ID NO 183
<211> LENGTH: 122
<212> TYPE: PRT
<213> ORGANISM: Lama glama

<400> SEQUENCE: 183

```
Glu Val Gln Leu Gln Glu Ser Gly Pro Gly Leu Val Lys Pro Ser Gln
1               5                   10                  15

Thr Leu Ser Leu Thr Cys Thr Val Ser Gly Ser Ile Thr Ser Arg
            20                  25                  30

Tyr Tyr Ala Trp Ser Trp Ile Arg Gln Pro Pro Gly Lys Gly Leu Glu
            35                  40                  45

Trp Ile Gly Val Ile Asp Tyr Asp Gly Asp Thr Tyr Tyr Ser Pro Ser
        50                  55                  60

Leu Lys Ser Arg Thr Ser Ile Ser Trp Asp Thr Ser Lys Asn Gln Phe
65                  70                  75                  80

Ser Leu Gln Leu Ser Ser Val Thr Ala Glu Asp Thr Ala Val Tyr Tyr
            85                  90                  95

Cys Ala Arg Asp Pro Asp Val Val Thr Gly Phe His Tyr Asp Tyr Trp
            100                 105                 110

Gly Gln Gly Thr Leu Val Thr Val Ser Ser
            115                 120
```

<210> SEQ ID NO 184
<211> LENGTH: 122
<212> TYPE: PRT
<213> ORGANISM: Lama glama

<400> SEQUENCE: 184

```
Glu Val Gln Leu Gln Glu Ser Gly Pro Gly Leu Val Lys Pro Ser Gln
1               5                   10                  15

Thr Leu Ser Leu Thr Cys Thr Val Ser Gly Ser Ile Thr Ser Arg
            20                  25                  30

Tyr Tyr Ala Trp Ser Trp Ile Arg Gln Pro Pro Gly Lys Gly Leu Glu
            35                  40                  45

Trp Ile Gly Val Ile Asp Tyr Asp Gly Asp Thr Tyr Tyr Ser Pro Ser
        50                  55                  60

Leu Lys Ser Arg Thr Thr Ile Ser Trp Asp Thr Ser Lys Asn Gln Phe
65                  70                  75                  80
```

```
Ser Leu Lys Leu Ser Ser Val Thr Ala Glu Asp Thr Ala Val Tyr Tyr
            85                  90                  95

Cys Ala Arg Asp Pro Asp Val Val Thr Gly Phe His Tyr Asp Tyr Trp
            100                 105                 110

Gly Gln Gly Thr Thr Val Thr Val Ser Ser
            115             120
```

<210> SEQ ID NO 185
<211> LENGTH: 122
<212> TYPE: PRT
<213> ORGANISM: Lama glama

<400> SEQUENCE: 185

```
Glu Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Thr Ser Arg
            20                  25                  30

Tyr Tyr Ala Trp Ser Trp Ile Arg Gln Pro Pro Gly Lys Gly Leu Glu
            35                  40                  45

Trp Ile Gly Val Ile Asp Tyr Asp Gly Asp Thr Tyr Tyr Ser Pro Ser
50                  55                  60

Leu Lys Ser Arg Val Thr Ile Ser Trp Asp Thr Ser Lys Asn Gln Phe
65                  70                  75                  80

Ser Leu Gln Leu Ser Ser Val Thr Ala Glu Asp Thr Ala Val Tyr Tyr
            85                  90                  95

Cys Ala Arg Asp Pro Asp Val Val Thr Gly Phe His Tyr Asp Tyr Trp
            100                 105                 110

Gly Gln Gly Thr Gln Val Thr Val Ser Ser
            115             120
```

<210> SEQ ID NO 186
<211> LENGTH: 122
<212> TYPE: PRT
<213> ORGANISM: Lama glama

<400> SEQUENCE: 186

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Thr Thr Arg
            20                  25                  30

Tyr Tyr Ala Trp Ser Trp Ile Arg Gln Pro Pro Gly Lys Gly Leu Glu
            35                  40                  45

Trp Ile Gly Val Ile Asp Tyr Asp Gly Asp Thr Tyr Tyr Ser Pro Ser
50                  55                  60

Leu Lys Ser Arg Val Thr Ile Ser Trp Asp Thr Ser Lys Asn Gln Phe
65                  70                  75                  80

Ser Leu Gln Leu Ser Ser Val Thr Pro Glu Asp Thr Ala Val Tyr Tyr
            85                  90                  95

Cys Ala Arg Asp Pro Asp Val Val Thr Gly Phe His Tyr Asp Asn Trp
            100                 105                 110

Gly Gln Gly Thr Leu Val Thr Val Ser Ser
            115             120
```

<210> SEQ ID NO 187
<211> LENGTH: 122
<212> TYPE: PRT
<213> ORGANISM: Lama glama -continued

<400> SEQUENCE: 187

Glu Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Thr Thr Arg
            20                  25                  30

Tyr Tyr Ala Trp Ser Trp Ile Arg Gln Pro Pro Gly Lys Gly Leu Glu
        35                  40                  45

Trp Ile Gly Val Ile Asp Tyr Asp Gly Asp Thr Tyr Tyr Ser Pro Ser
    50                  55                  60

Leu Lys Ser Arg Val Ser Ile Ser Trp Asp Thr Ser Lys Asn Gln Phe
65                  70                  75                  80

Ser Leu Lys Leu Ser Ser Val Thr Ala Glu Asp Thr Ala Val Tyr Tyr
                85                  90                  95

Cys Ala Arg Asp Pro Asp Val Val Thr Gly Phe His Tyr Asp Tyr Trp
            100                 105                 110

Gly Gln Gly Thr Gln Val Thr Val Ser Ser
            115                 120

<210> SEQ ID NO 188
<211> LENGTH: 122
<212> TYPE: PRT
<213> ORGANISM: Lama glama

<400> SEQUENCE: 188

Glu Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Thr Ser Arg
            20                  25                  30

Tyr Tyr Ala Trp Ser Trp Ile Arg Gln Pro Pro Gly Lys Gly Leu Glu
        35                  40                  45

Trp Ile Gly Val Ile Asp Tyr Asp Gly Asp Thr Tyr Tyr Ser Pro Ser
    50                  55                  60

Leu Lys Ser Arg Thr Thr Ile Ser Trp Asp Thr Ser Lys Asn Gln Phe
65                  70                  75                  80

Ser Leu Gln Leu Ser Ser Val Thr Pro Glu Asp Thr Ala Val Tyr Tyr
                85                  90                  95

Cys Ala Arg Asp Pro Asp Val Val Thr Gly Phe His Tyr Asp Tyr Trp
            100                 105                 110

Gly Gln Gly Thr Gln Val Thr Val Ser Ser
            115                 120

<210> SEQ ID NO 189
<211> LENGTH: 122
<212> TYPE: PRT
<213> ORGANISM: Lama glama

<400> SEQUENCE: 189

Glu Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Thr Thr Arg
            20                  25                  30

Tyr Tyr Ala Trp Ser Trp Ile Arg Gln Pro Pro Gly Lys Gly Leu Glu
        35                  40                  45

Trp Ile Gly Val Ile Asp Tyr Asp Gly Asp Thr Tyr Tyr Ser Pro Ser
    50                  55                  60

Leu Lys Ser Arg Val Thr Ile Ser Val Asp Thr Ser Lys Asn Gln Phe

```
                65                  70                  75                  80
Ser Leu Lys Leu Ser Ser Val Thr Ala Ala Asp Thr Ala Val Tyr Tyr
                    85                  90                  95

Cys Ala Arg Asp Pro Asp Val Val Thr Gly Phe His Tyr Asp Tyr Trp
                100                 105                 110

Gly Gln Gly Thr Met Val Thr Val Ser Ser
            115                 120

<210> SEQ ID NO 190
<211> LENGTH: 122
<212> TYPE: PRT
<213> ORGANISM: Lama glama

<400> SEQUENCE: 190

Glu Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Thr Ser Arg
            20                  25                  30

Tyr Tyr Ala Trp Ser Trp Ile Arg Gln Pro Pro Gly Lys Gly Leu Glu
        35                  40                  45

Trp Ile Gly Val Ile Asp Tyr Asp Gly Asp Thr Tyr Tyr Ser Pro Ser
    50                  55                  60

Leu Lys Ser Arg Thr Thr Ile Ser Trp Asp Thr Ser Lys Asn Gln Phe
65                  70                  75                  80

Ser Leu Lys Leu Ser Ser Val Thr Ala Glu Asp Thr Ala Val Tyr Tyr
                    85                  90                  95

Cys Ala Arg Asp Pro Asp Val Val Thr Gly Phe His Tyr Asp Tyr Trp
                100                 105                 110

Gly Gln Gly Thr Gln Val Thr Val Ser Ser
            115                 120

<210> SEQ ID NO 191
<211> LENGTH: 122
<212> TYPE: PRT
<213> ORGANISM: Lama glama

<400> SEQUENCE: 191

Glu Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Thr Thr Arg
            20                  25                  30

Tyr Tyr Ala Trp Ser Trp Ile Arg Gln Pro Pro Gly Lys Gly Leu Glu
        35                  40                  45

Trp Ile Gly Val Ile Asp Tyr Asp Gly Asp Thr Tyr Tyr Ser Pro Ser
    50                  55                  60

Leu Lys Ser Arg Val Thr Ile Ser Trp Asp Thr Ser Lys Asn Gln Ile
65                  70                  75                  80

Ser Leu Gln Leu Ser Ser Val Thr Pro Glu Asp Thr Ala Val Tyr Tyr
                    85                  90                  95

Cys Ala Arg Asp Pro Asp Val Val Thr Gly Phe His Tyr Asp Tyr Trp
                100                 105                 110

Gly Gln Gly Thr Leu Val Thr Val Ser Ser
            115                 120

<210> SEQ ID NO 192
<211> LENGTH: 122
<212> TYPE: PRT
```

<213> ORGANISM: Lama glama

<400> SEQUENCE: 192

Glu Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Thr Thr Arg
            20                  25                  30

Tyr Tyr Ala Trp Ser Trp Ile Arg Gln Pro Pro Gly Lys Gly Leu Glu
        35                  40                  45

Trp Ile Gly Val Ile Asp Tyr Asp Gly Asp Thr Tyr Tyr Ser Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Pro Ala Asp Thr Ala Val Tyr Tyr
            85                  90                  95

Cys Ala Arg Asp Pro Asp Val Val Thr Gly Phe His Tyr Asp Tyr Trp
            100                 105                 110

Gly Gln Gly Thr Thr Val Thr Val Ser Ser
            115                 120

<210> SEQ ID NO 193
<211> LENGTH: 122
<212> TYPE: PRT
<213> ORGANISM: Lama glama

<400> SEQUENCE: 193

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Thr Ser Arg
            20                  25                  30

Tyr Tyr Ala Trp Ser Trp Ile Arg Gln Pro Pro Gly Lys Gly Leu Glu
        35                  40                  45

Trp Ile Gly Val Ile Asp Tyr Asp Gly Asp Thr Tyr Tyr Ser Pro Ser
    50                  55                  60

Leu Lys Ser Arg Val Thr Ile Ser Trp Asp Thr Ser Lys Asn Gln Phe
65                  70                  75                  80

Ser Leu Lys Leu Ser Ser Val Thr Pro Glu Asp Thr Ala Val Tyr Tyr
            85                  90                  95

Cys Ala Arg Asp Pro Asp Val Val Thr Gly Phe His Tyr Asp Tyr Trp
            100                 105                 110

Gly Gln Gly Thr Gln Val Thr Val Ser Ser
            115                 120

<210> SEQ ID NO 194
<211> LENGTH: 122
<212> TYPE: PRT
<213> ORGANISM: Lama glama

<400> SEQUENCE: 194

Glu Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Thr Thr Arg
            20                  25                  30

Tyr Tyr Ala Trp Ser Trp Ile Arg Gln Pro Pro Gly Lys Gly Leu Glu
        35                  40                  45

Trp Met Gly Val Ile Asp Tyr Asp Gly Asp Thr Tyr Tyr Ser Pro Ser
    50                  55                  60

```
Leu Lys Ser Arg Thr Thr Ile Ser Trp Asp Thr Ser Lys Asn Gln Phe
 65                  70                  75                  80

Ser Leu Gln Leu Ser Ser Val Thr Ala Glu Asp Thr Ala Val Tyr Tyr
                 85                  90                  95

Cys Ala Arg Asp Pro Asp Val Val Thr Gly Phe His Tyr Asp Tyr Trp
            100                 105                 110

Gly Gln Gly Thr Met Val Thr Val Ser Ser
            115                 120
```

<210> SEQ ID NO 195
<211> LENGTH: 122
<212> TYPE: PRT
<213> ORGANISM: Lama glama

<400> SEQUENCE: 195

```
Glu Val Gln Leu Gln Glu Ser Gly Pro Gly Leu Val Lys Pro Ser Gln
 1               5                  10                  15

Thr Leu Ser Leu Thr Cys Thr Val Ser Gly Gly Ser Ile Thr Thr Arg
                 20                  25                  30

Tyr Tyr Ala Trp Ser Trp Ile Arg Gln Pro Pro Gly Lys Gly Leu Glu
             35                  40                  45

Trp Ile Gly Val Ile Asp Tyr Asp Gly Asp Thr Tyr Tyr Ser Pro Ser
         50                  55                  60

Leu Lys Ser Arg Val Ser Ile Ser Trp Asp Thr Ser Lys Asn Gln Phe
 65                  70                  75                  80

Ser Leu His Leu Ser Ser Val Thr Pro Glu Asp Thr Ala Val Tyr Tyr
                 85                  90                  95

Cys Ala Arg Asp Pro Asp Val Val Thr Gly Phe His Tyr Asp Tyr Trp
            100                 105                 110

Gly Gln Gly Thr Leu Val Thr Val Ser Ser
            115                 120
```

<210> SEQ ID NO 196
<211> LENGTH: 122
<212> TYPE: PRT
<213> ORGANISM: Lama glama

<400> SEQUENCE: 196

```
Glu Val Gln Leu Gln Glu Ser Gly Pro Gly Leu Val Lys Pro Ser Gln
 1               5                  10                  15

Thr Leu Ser Leu Thr Cys Thr Val Ser Gly Gly Ser Ile Thr Ser Arg
                 20                  25                  30

Tyr Tyr Ala Trp Ser Trp Ile Arg Gln Pro Pro Gly Lys Gly Leu Glu
             35                  40                  45

Trp Met Gly Val Ile Asp Tyr Asp Gly Asp Thr Tyr Tyr Ser Pro Ser
         50                  55                  60

Leu Lys Ser Arg Val Ser Ile Ser Trp Asp Thr Ser Lys Asn Gln Phe
 65                  70                  75                  80

Ser Leu Gln Leu Ser Ser Val Thr Ala Glu Asp Thr Ala Val Tyr Tyr
                 85                  90                  95

Cys Ala Arg Asp Pro Asp Val Val Thr Gly Phe His Tyr Asp Tyr Trp
            100                 105                 110

Gly Gln Gly Thr Gln Val Thr Val Ser Ser
            115                 120
```

<210> SEQ ID NO 197

```
<211> LENGTH: 122
<212> TYPE: PRT
<213> ORGANISM: Lama glama

<400> SEQUENCE: 197

Glu Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Thr Ser Arg
            20                  25                  30

Tyr Tyr Ala Trp Ser Trp Ile Arg Gln Pro Pro Gly Lys Gly Leu Glu
        35                  40                  45

Trp Ile Gly Val Ile Asp Tyr Asp Gly Asp Thr Tyr Tyr Ser Pro Ser
    50                  55                  60

Leu Lys Ser Arg Thr Thr Ile Ser Trp Asp Thr Ser Lys Asn Gln Phe
65                  70                  75                  80

Ser Leu Lys Leu Ser Ser Val Thr Ala Glu Asp Thr Ala Val Tyr Tyr
                85                  90                  95

Cys Ala Arg Asp Pro Asp Val Val Thr Gly Phe His Tyr Asp Tyr Trp
            100                 105                 110

Gly Gln Gly Thr Gln Val Thr Val Ser Ser
            115                 120

<210> SEQ ID NO 198
<211> LENGTH: 122
<212> TYPE: PRT
<213> ORGANISM: Lama glama

<400> SEQUENCE: 198

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Thr Ser Arg
            20                  25                  30

Tyr Tyr Ala Trp Ser Trp Ile Arg Gln Pro Pro Gly Lys Gly Leu Glu
        35                  40                  45

Trp Met Gly Val Ile Asp Tyr Asp Gly Asp Thr Tyr Tyr Ser Pro Ser
    50                  55                  60

Leu Lys Ser Arg Thr Thr Ile Ser Trp Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Pro Asp Val Val Thr Gly Phe His Tyr Asp Tyr Trp
            100                 105                 110

Gly Gln Gly Thr Thr Val Thr Val Ser Ser
            115                 120

<210> SEQ ID NO 199
<211> LENGTH: 122
<212> TYPE: PRT
<213> ORGANISM: Lama glama

<400> SEQUENCE: 199

Glu Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Thr Thr Arg
            20                  25                  30

Tyr Tyr Ala Trp Ser Trp Ile Arg Gln Pro Pro Gly Lys Gly Leu Glu
        35                  40                  45
```

```
Trp Met Gly Val Ile Asp Tyr Asp Gly Asp Thr Tyr Tyr Ser Pro Ser
        50                  55                  60

Leu Lys Ser Arg Val Thr Ile Ser Trp Asp Thr Ser Lys Asn Gln Phe
65                  70                  75                  80

Ser Leu Lys Leu Ser Ser Val Thr Ala Glu Asp Thr Ala Val Tyr Tyr
                    85                  90                  95

Cys Ala Arg Asp Pro Asp Val Val Thr Gly Phe His Tyr Asp Tyr Trp
                100                 105                 110

Gly Gln Gly Thr Leu Val Thr Val Ser Ser
                115                 120
```

<210> SEQ ID NO 200
<211> LENGTH: 122
<212> TYPE: PRT
<213> ORGANISM: Lama glama

<400> SEQUENCE: 200

```
Glu Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Thr Ser Arg
                20                  25                  30

Tyr Tyr Ala Trp Ser Trp Ile Arg Gln Pro Pro Gly Lys Gly Leu Glu
            35                  40                  45

Trp Ile Gly Val Ile Asp Tyr Asp Ala Asp Thr Tyr Tyr Ser Pro Ser
        50                  55                  60

Leu Lys Ser Arg Thr Ser Ile Ser Trp Asp Thr Ser Lys Asn Gln Phe
65                  70                  75                  80

Ser Leu Lys Leu Ser Ser Val Thr Pro Glu Asp Thr Ala Val Tyr Tyr
                    85                  90                  95

Cys Ala Arg Asp Pro Asp Val Val Thr Gly Phe His Tyr Asp Tyr Trp
                100                 105                 110

Gly Gln Gly Thr Thr Val Thr Val Ser Ser
                115                 120
```

<210> SEQ ID NO 201
<211> LENGTH: 122
<212> TYPE: PRT
<213> ORGANISM: Lama glama

<400> SEQUENCE: 201

```
Glu Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Thr Ser Arg
                20                  25                  30

Tyr Tyr Ala Trp Ser Trp Ile Arg Gln Pro Pro Gly Lys Gly Leu Glu
            35                  40                  45

Trp Ile Gly Val Ile Asp Tyr Asp Gly Asp Thr Tyr Tyr Ser Pro Ser
        50                  55                  60

Leu Lys Ser Arg Thr Thr Ile Ser Trp Asp Thr Ser Lys Asn Gln Phe
65                  70                  75                  80

Ser Leu Gln Leu Ser Ser Val Thr Pro Ala Asp Thr Ala Val Tyr Tyr
                    85                  90                  95

Cys Ala Arg Asp Pro Asp Val Val Thr Gly Phe His Tyr Asp Tyr Trp
                100                 105                 110

Gly Gln Gly Thr Gln Val Thr Val Ser Ser
                115                 120
```

<210> SEQ ID NO 202
<211> LENGTH: 122
<212> TYPE: PRT
<213> ORGANISM: Lama glama

<400> SEQUENCE: 202

Glu Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Thr Thr Arg
            20                  25                  30

Tyr Tyr Ala Trp Ser Trp Ile Arg Gln Pro Pro Gly Lys Gly Leu Glu
        35                  40                  45

Trp Ile Gly Val Ile Asp Tyr Asp Gly Asp Thr Tyr Tyr Ser Pro Ser
50                  55                  60

Leu Lys Ser Arg Val Thr Ile Ser Trp Asp Thr Ser Lys Asn Gln Ile
65                  70                  75                  80

Ser Leu Gln Leu Ser Ser Val Thr Pro Glu Asp Thr Ala Val Tyr Tyr
                85                  90                  95

Cys Ala Arg Asp Pro Asp Val Val Thr Gly Phe His Tyr Asp Tyr Trp
            100                 105                 110

Gly Gln Gly Thr Leu Val Thr Val Ser Ser
        115                 120

<210> SEQ ID NO 203
<211> LENGTH: 122
<212> TYPE: PRT
<213> ORGANISM: Lama glama

<400> SEQUENCE: 203

Glu Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Thr Thr Arg
            20                  25                  30

Tyr Tyr Ala Trp Ser Trp Ile Arg Gln Pro Pro Gly Lys Gly Leu Glu
        35                  40                  45

Trp Ile Gly Val Ile Asp Tyr Asp Gly Asp Thr Tyr Tyr Ser Pro Ser
50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Pro Asp Val Val Thr Gly Phe His Tyr Asp Tyr Trp
            100                 105                 110

Gly Gln Gly Thr Met Val Thr Val Ser Ser
        115                 120

<210> SEQ ID NO 204
<211> LENGTH: 122
<212> TYPE: PRT
<213> ORGANISM: Lama glama

<400> SEQUENCE: 204

Glu Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Thr Ser Arg
            20                  25                  30

Tyr Tyr Ala Trp Ser Trp Ile Arg Gln Pro Pro Gly Lys Gly Leu Glu

```
                35                  40                  45
Trp Ile Gly Val Ile Asp Tyr Asp Gly Asp Thr Tyr Tyr Ser Pro Ser
     50                  55                  60
Leu Lys Ser Arg Thr Thr Ile Ser Trp Asp Thr Ser Lys Asn Gln Phe
 65                  70                  75                  80
Ser Leu Gln Leu Ser Ser Val Thr Pro Glu Asp Thr Ala Val Tyr Tyr
                 85                  90                  95
Cys Ala Arg Asp Pro Asp Val Val Thr Gly Phe His Tyr Asp Tyr Trp
                100                 105                 110
Gly Gln Gly Thr Gln Val Thr Val Ser Ser
                115                 120

<210> SEQ ID NO 205
<211> LENGTH: 122
<212> TYPE: PRT
<213> ORGANISM: Lama glama

<400> SEQUENCE: 205

Gln Val Gln Leu Gln Glu Ser Gly Pro Gly Leu Val Lys Pro Ser Gln
 1               5                  10                  15
Thr Leu Ser Leu Thr Cys Thr Val Ser Gly Gly Ser Ile Thr Thr Arg
                20                  25                  30
Tyr Tyr Ala Trp Ser Trp Ile Arg Gln Pro Pro Gly Lys Gly Leu Glu
                35                  40                  45
Trp Met Gly Val Ile Asp Tyr Asp Gly Asp Thr Tyr Tyr Ser Pro Ser
     50                  55                  60
Leu Lys Ser Arg Val Thr Ile Ser Val Asp Thr Ser Lys Asn His Phe
 65                  70                  75                  80
Ser Leu Lys Leu Ser Ser Val Thr Ala Glu Asp Thr Ala Val Tyr Tyr
                 85                  90                  95
Cys Ala Thr Asp Pro Asp Val Val Thr Gly Phe His Tyr Asp Tyr Trp
                100                 105                 110
Gly Gln Gly Thr Thr Val Thr Val Ser Ser
                115                 120

<210> SEQ ID NO 206
<211> LENGTH: 122
<212> TYPE: PRT
<213> ORGANISM: Lama glama

<400> SEQUENCE: 206

Glu Val Gln Leu Gln Glu Ser Gly Pro Gly Leu Val Lys Pro Ser Gln
 1               5                  10                  15
Thr Leu Ser Leu Thr Cys Thr Val Ser Gly Gly Ser Ile Thr Ser Arg
                20                  25                  30
Tyr Tyr Ala Trp Ser Trp Ile Arg Gln Pro Pro Gly Lys Gly Leu Glu
                35                  40                  45
Trp Ile Gly Val Ile Asp Tyr Asp Gly Asp Thr Tyr Tyr Ser Pro Ser
     50                  55                  60
Leu Lys Ser Arg Val Ser Ile Ser Val Asp Thr Ser Lys Asn Gln Phe
 65                  70                  75                  80
Ser Leu Lys Leu Ser Ser Val Thr Ala Glu Asp Thr Ala Val Tyr Tyr
                 85                  90                  95
Cys Ala Arg Asp Pro Asp Val Val Thr Gly Phe His Tyr Asp Asn Trp
                100                 105                 110
Gly Gln Gly Thr Leu Val Thr Val Ser Ser
```

<210> SEQ ID NO 207
<211> LENGTH: 122
<212> TYPE: PRT
<213> ORGANISM: Lama glama

<400> SEQUENCE: 207

Glu Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Thr Ser Arg
            20                  25                  30

Tyr Tyr Ala Trp Ser Trp Ile Arg Gln Pro Pro Gly Lys Gly Leu Glu
        35                  40                  45

Trp Met Gly Val Ile Asp Tyr Asp Gly Asp Thr Tyr Tyr Ser Pro Ser
    50                  55                  60

Leu Lys Ser Arg Val Thr Ile Ser Val Asp Thr Ser Lys Asn Gln Phe
65                  70                  75                  80

Ser Leu Gln Leu Ser Ser Val Thr Ala Glu Asp Thr Ala Val Tyr Tyr
                85                  90                  95

Cys Ala Arg Asp Pro Asp Val Val Thr Gly Phe His Tyr Asp Tyr Trp
            100                 105                 110

Gly Gln Gly Thr Gln Val Thr Val Ser Ser
        115                 120

<210> SEQ ID NO 208
<211> LENGTH: 122
<212> TYPE: PRT
<213> ORGANISM: Lama glama

<400> SEQUENCE: 208

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Thr Thr Arg
            20                  25                  30

Tyr Tyr Ala Trp Ser Trp Ile Arg Gln Pro Pro Gly Lys Gly Leu Glu
        35                  40                  45

Trp Ile Gly Val Ile Asp Tyr Asp Gly Asp Thr Tyr Tyr Ser Pro Ser
    50                  55                  60

Leu Lys Ser Arg Thr Thr Ile Ser Trp Asp Thr Ser Lys Asn Gln Phe
65                  70                  75                  80

Ser Leu Lys Leu Ser Ser Val Thr Ala Glu Asp Thr Ala Val Tyr Tyr
                85                  90                  95

Cys Ala Arg Asp Pro Asp Val Val Thr Gly Phe His Tyr Asp Tyr Trp
            100                 105                 110

Gly Gln Gly Thr Gln Val Thr Val Ser Ser
        115                 120

<210> SEQ ID NO 209
<211> LENGTH: 122
<212> TYPE: PRT
<213> ORGANISM: Lama glama

<400> SEQUENCE: 209

Glu Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Thr Ser Arg
            20                  25                  30

Tyr Tyr Ala Trp Ser Trp Ile Arg Gln Pro Pro Gly Lys Gly Leu Glu
            35                  40                  45

Trp Ile Gly Val Ile Asp Tyr Asp Gly Asp Thr Tyr Tyr Ser Pro Ser
    50                  55                  60

Leu Lys Ser Arg Thr Thr Ile Ser Trp Asp Thr Ser Lys Asn Gln Phe
65                  70                  75                  80

Ser Leu Lys Leu Ser Ser Val Thr Ala Glu Asp Thr Ala Val Tyr Tyr
                85                  90                  95

Cys Ala Arg Asp Pro Asp Val Val Thr Gly Phe His Tyr Asp Tyr Trp
                100                 105                 110

Gly Gln Gly Thr Leu Val Thr Val Ser Ser
            115                 120

<210> SEQ ID NO 210
<211> LENGTH: 122
<212> TYPE: PRT
<213> ORGANISM: Lama glama

<400> SEQUENCE: 210

Glu Val Gln Leu Gln Glu Ser Gly Pro Gly Leu Val Lys Pro Ser Gln
1               5                   10                  15

Thr Leu Ser Leu Thr Cys Thr Val Ser Gly Ser Ile Thr Ser Arg
            20                  25                  30

Tyr Tyr Ala Trp Ser Trp Ile Arg Gln Pro Pro Gly Lys Gly Leu Glu
            35                  40                  45

Trp Ile Gly Val Ile Asp Tyr Asp Gly Asp Thr Tyr Tyr Ser Pro Ser
    50                  55                  60

Leu Lys Ser Arg Thr Thr Ile Ser Val Asp Thr Ser Lys Asn Gln Phe
65                  70                  75                  80

Ser Leu Lys Leu Ser Ser Val Thr Ala Glu Asp Thr Ala Val Tyr Tyr
                85                  90                  95

Cys Ala Arg Asp Pro Asp Val Val Thr Gly Phe His Tyr Asp Tyr Trp
                100                 105                 110

Gly Gln Gly Thr Leu Val Thr Val Ser Ser
            115                 120

<210> SEQ ID NO 211
<211> LENGTH: 122
<212> TYPE: PRT
<213> ORGANISM: Lama glama

<400> SEQUENCE: 211

Glu Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Thr Thr Arg
            20                  25                  30

Tyr Tyr Ala Trp Ser Trp Ile Arg Gln Pro Pro Gly Lys Gly Leu Glu
            35                  40                  45

Trp Ile Gly Val Ile Asp Tyr Asp Gly Asp Thr Tyr Tyr Ser Pro Ser
    50                  55                  60

Leu Lys Ser Arg Ser Ile Ser Trp Asp Thr Ser Lys Asn Gln Phe
65                  70                  75                  80

Ser Leu Lys Leu Ser Ser Val Thr Pro Glu Asp Thr Ala Val Tyr Tyr
                85                  90                  95

Cys Ala Arg Asp Pro Asp Val Val Thr Gly Phe His Tyr Asp Tyr Trp
                100                 105                 110

Gly Gln Gly Thr Leu Val Thr Val Ser Ser
        115                 120

<210> SEQ ID NO 212
<211> LENGTH: 122
<212> TYPE: PRT
<213> ORGANISM: Lama glama

<400> SEQUENCE: 212

Glu Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Thr Ser Arg
            20                  25                  30

Tyr Tyr Ala Trp Ser Trp Ile Arg Gln Pro Pro Gly Lys Gly Leu Glu
        35                  40                  45

Trp Ile Gly Val Ile Asp Tyr Asp Gly Asp Thr Tyr Tyr Ser Pro Ser
    50                  55                  60

Leu Lys Ser Arg Thr Thr Ile Ser Trp Asp Thr Ser Lys Asn Gln Phe
65                  70                  75                  80

Ser Leu Gln Leu Ser Ser Val Thr Ala Ala Asp Thr Ala Val Tyr Tyr
            85                  90                  95

Cys Ala Arg Asp Pro Asp Val Val Thr Gly Phe His Tyr Asp Tyr Trp
            100                 105                 110

Gly Gln Gly Thr Thr Val Thr Val Ser Ser
        115                 120

<210> SEQ ID NO 213
<211> LENGTH: 122
<212> TYPE: PRT
<213> ORGANISM: Lama glama

<400> SEQUENCE: 213

Glu Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Thr Ser Arg
            20                  25                  30

Tyr Tyr Ala Trp Ser Trp Ile Arg Gln Pro Pro Gly Lys Gly Leu Glu
        35                  40                  45

Trp Ile Gly Val Ile Asp Tyr Glu Gly Asp Thr Tyr Tyr Ser Pro Ser
    50                  55                  60

Leu Lys Ser Arg Thr Thr Ile Ser Trp Asp Thr Ser Lys Asn Gln Phe
65                  70                  75                  80

Ser Leu Gln Leu Ser Ser Val Thr Ala Glu Asp Thr Ala Val Tyr Tyr
            85                  90                  95

Cys Ala Arg Asp Pro Asp Val Val Thr Gly Phe His Tyr Asp Tyr Trp
            100                 105                 110

Gly Gln Gly Thr Leu Val Thr Val Ser Ser
        115                 120

<210> SEQ ID NO 214
<211> LENGTH: 122
<212> TYPE: PRT
<213> ORGANISM: Lama glama

<400> SEQUENCE: 214

Glu Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Thr Ser Arg
            20                  25                  30

Tyr Tyr Ala Trp Ser Trp Ile Arg Gln Pro Pro Gly Lys Gly Leu Glu
            35                  40                  45

Trp Ile Gly Val Ile Asp Tyr Asp Gly Asp Thr Tyr Tyr Ser Pro Ser
    50                  55                  60

Leu Lys Ser Arg Val Thr Ile Ser Trp Asp Thr Ser Lys Asn Gln Phe
65                  70                  75                  80

Ser Leu Lys Leu Ser Ser Val Thr Pro Ala Asp Thr Ala Val Tyr Tyr
            85                  90                  95

Cys Ala Arg Asp Pro Asp Val Val Thr Gly Phe His Tyr Asp Tyr Trp
            100                 105                 110

Gly Gln Gly Thr Thr Val Thr Val Ser Ser
            115                 120

<210> SEQ ID NO 215
<211> LENGTH: 122
<212> TYPE: PRT
<213> ORGANISM: Lama glama

<400> SEQUENCE: 215

Glu Val Gln Leu Glu Glu Ser Gly Pro Gly Leu Val Lys Pro Ser Gln
1               5                   10                  15

Thr Leu Ser Leu Thr Cys Thr Val Ser Gly Gly Ser Ile Thr Thr Arg
            20                  25                  30

Tyr Tyr Ala Trp Ser Trp Ile Arg Gln Pro Pro Gly Lys Gly Leu Glu
            35                  40                  45

Trp Ile Gly Val Ile Asp Tyr Asp Gly Asp Thr Tyr Tyr Ser Pro Ser
    50                  55                  60

Leu Lys Ser Arg Val Thr Ile Ser Trp Asp Thr Ser Lys Asn Gln Phe
65                  70                  75                  80

Ser Leu Lys Leu Ser Ser Val Thr Pro Glu Asp Thr Ala Val Tyr Tyr
            85                  90                  95

Cys Ala Arg Asp Pro Asp Val Val Thr Gly Phe His Tyr Asp Tyr Trp
            100                 105                 110

Gly Gln Gly Thr Leu Val Thr Val Ser Ser
            115                 120

<210> SEQ ID NO 216
<211> LENGTH: 122
<212> TYPE: PRT
<213> ORGANISM: Lama glama

<400> SEQUENCE: 216

Glu Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Thr Ser Arg
            20                  25                  30

Tyr Tyr Ala Trp Ser Trp Ile Arg Gln Pro Pro Gly Lys Gly Leu Glu
            35                  40                  45

Trp Ile Gly Val Ile Asp Tyr Asp Gly Asp Thr Tyr Tyr Ser Pro Ser
    50                  55                  60

Leu Lys Ser Arg Thr Thr Ile Ser Trp Asp Thr Ser Lys Asn Gln Phe
65                  70                  75                  80

Ser Leu Gln Leu Ser Ser Val Thr Ala Glu Asp Thr Ala Val Tyr Tyr
            85                  90                  95

Cys Ala Arg Asp Pro Asp Val Val Thr Gly Phe His Tyr Asp Tyr Trp
            100                 105                 110

Gly Gln Gly Thr Thr Val Thr Val Ser Ser
            115                 120

<210> SEQ ID NO 217
<211> LENGTH: 122
<212> TYPE: PRT
<213> ORGANISM: Lama glama

<400> SEQUENCE: 217

Glu Val Gln Leu Gln Glu Ser Gly Pro Gly Leu Val Lys Pro Ser Gln
1               5                   10                  15

Thr Leu Ser Leu Thr Cys Thr Val Ser Gly Ser Ile Thr Thr Arg
            20                  25                  30

Tyr Tyr Ala Trp Ser Trp Ile Arg Gln Pro Pro Gly Lys Gly Leu Glu
            35                  40                  45

Trp Ile Gly Val Ile Asp Tyr Asp Gly Asp Thr Tyr Tyr Ser Pro Ser
        50                  55                  60

Leu Lys Ser Arg Thr Ser Ile Ser Trp Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Pro Asp Val Val Thr Gly Phe His Tyr Asp Tyr Trp
            100                 105                 110

Gly Gln Gly Thr Thr Val Thr Val Ser Ser
            115                 120

<210> SEQ ID NO 218
<211> LENGTH: 122
<212> TYPE: PRT
<213> ORGANISM: Lama glama

<400> SEQUENCE: 218

Glu Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Thr Ser Arg
            20                  25                  30

Tyr Tyr Ala Trp Ser Trp Ile Arg Gln Pro Pro Gly Lys Gly Leu Glu
            35                  40                  45

Trp Ile Gly Val Ile Asp Tyr Asp Gly Asp Thr Tyr Tyr Ser Pro Ser
        50                  55                  60

Leu Lys Ser Arg Thr Thr Ile Ser Trp Asp Thr Ser Lys Asn Gln Phe
65                  70                  75                  80

Ser Leu Lys Leu Ser Ser Val Thr Ala Glu Asp Thr Ala Val Tyr Tyr
                85                  90                  95

Cys Ala Arg Asp Pro Asp Val Val Thr Gly Phe His Tyr Asp Tyr Trp
            100                 105                 110

Gly Gln Gly Thr Leu Val Thr Val Ser Ser
            115                 120

<210> SEQ ID NO 219
<211> LENGTH: 122
<212> TYPE: PRT
<213> ORGANISM: Lama glama

<400> SEQUENCE: 219

Glu Val Gln Leu Gln Glu Ser Gly Pro Gly Leu Val Lys Pro Ser Gln

```
                1               5                  10                  15
            Thr Leu Ser Leu Thr Cys Thr Val Ser Gly Gly Ser Ile Thr Ser Arg
                            20                  25                  30

Tyr Tyr Ala Trp Ser Trp Ile Arg Gln Pro Pro Gly Lys Gly Leu Glu
                        35                  40                  45

Trp Ile Gly Val Ile Asp Tyr Asp Gly Asp Thr Tyr Tyr Ser Pro Ser
                    50                  55                  60

Leu Lys Ser Arg Thr Thr Ile Ser Trp Asp Thr Ser Lys Asn Gln Phe
            65                  70                  75                  80

Ser Leu Gln Leu Ser Ser Val Thr Ala Ala Asp Thr Ala Val Tyr Tyr
                            85                  90                  95

Cys Ala Arg Asp Pro Asp Val Val Thr Gly Phe His Tyr Asp Tyr Trp
                            100                 105                 110

Gly Gln Gly Thr Thr Val Thr Val Ser Ser
                        115                 120

<210> SEQ ID NO 220
<211> LENGTH: 122
<212> TYPE: PRT
<213> ORGANISM: Lama glama

<400> SEQUENCE: 220

Gln Val Gln Leu Gln Glu Ser Gly Pro Gly Leu Val Lys Pro Ser Gln
            1               5                   10                  15

Thr Leu Ser Leu Thr Cys Thr Val Ser Gly Gly Ser Ile Thr Thr Arg
                            20                  25                  30

Tyr Tyr Ala Trp Ser Trp Ile Arg Gln Pro Pro Gly Lys Gly Leu Glu
                        35                  40                  45

Trp Ile Gly Val Ile Asp Tyr Asp Gly Asp Thr Tyr Tyr Ser Pro Ser
                    50                  55                  60

Leu Lys Ser Arg Thr Thr Ile Ser Trp Asp Thr Ser Lys Asn Gln Phe
            65                  70                  75                  80

Ser Leu Gln Leu Ser Ser Val Thr Pro Ala Asp Thr Ala Val Tyr Tyr
                            85                  90                  95

Cys Ala Arg Asp Pro Asp Val Val Thr Gly Phe His Tyr Asp Tyr Trp
                            100                 105                 110

Gly Gln Gly Thr Met Val Thr Val Ser Ser
                        115                 120

<210> SEQ ID NO 221
<211> LENGTH: 122
<212> TYPE: PRT
<213> ORGANISM: Lama glama

<400> SEQUENCE: 221

Glu Val Gln Leu Gln Glu Ser Gly Pro Gly Leu Val Lys Pro Ser Gln
            1               5                   10                  15

Thr Leu Ser Leu Thr Cys Thr Val Ser Gly Gly Ser Ile Thr Thr Arg
                            20                  25                  30

Tyr Tyr Ala Trp Ser Trp Ile Arg Gln Pro Pro Gly Lys Gly Leu Glu
                        35                  40                  45

Trp Ile Gly Val Ile Asp Tyr Asp Gly Asp Thr Tyr Tyr Ser Pro Ser
                    50                  55                  60

Leu Lys Ser Arg Thr Thr Ile Ser Trp Asp Thr Ser Lys Asn Gln Phe
            65                  70                  75                  80

Ser Leu Gln Leu Ser Ser Val Thr Pro Glu Asp Thr Ala Val Tyr Tyr
```

85                  90                  95

Cys Ala Arg Asp Pro Asp Val Val Thr Gly Phe His Tyr Asp Tyr Trp
            100                 105                 110

Gly Gln Gly Thr Leu Val Thr Val Ser Ser
            115                 120

<210> SEQ ID NO 222
<211> LENGTH: 122
<212> TYPE: PRT
<213> ORGANISM: Lama glama

<400> SEQUENCE: 222

Glu Val His Leu Gln Glu Ser Gly Pro Gly Leu Val Lys Pro Ser Gln
1               5                   10                  15

Thr Leu Ser Leu Thr Cys Thr Val Ser Gly Gly Ser Ile Thr Ser Arg
            20                  25                  30

Tyr Tyr Ala Trp Ser Trp Ile Arg Gln Pro Pro Gly Lys Gly Leu Glu
        35                  40                  45

Trp Ile Gly Val Ile Tyr Tyr Glu Gly Asp Thr Tyr Tyr Ser Pro Ser
    50                  55                  60

Leu Lys Ser Arg Thr Ser Ile Ser Trp Asp Thr Ser Lys Asn Gln Phe
65                  70                  75                  80

Ser Leu Gln Leu Ser Ser Val Thr Pro Glu Asp Thr Ala Val Tyr Tyr
                85                  90                  95

Cys Ala Arg Asp Pro Asp Val Val Thr Gly Phe His Tyr Asp Tyr Trp
            100                 105                 110

Gly Gln Gly Thr Leu Val Thr Val Ser Ser
            115                 120

<210> SEQ ID NO 223
<211> LENGTH: 122
<212> TYPE: PRT
<213> ORGANISM: Lama glama

<400> SEQUENCE: 223

Glu Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Thr Thr Arg
            20                  25                  30

Tyr Tyr Ala Trp Ser Trp Ile Arg Gln Pro Pro Gly Lys Gly Leu Glu
        35                  40                  45

Trp Ile Gly Val Ile Asp Tyr Glu Gly Asp Thr Tyr Tyr Ser Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Glu Asp Thr Ala Val Tyr Tyr
                85                  90                  95

Cys Ala Arg Asp Pro Asp Val Val Thr Gly Phe His Tyr Asp Tyr Trp
            100                 105                 110

Gly Gln Gly Thr Met Val Thr Val Ser Ser
            115                 120

<210> SEQ ID NO 224
<211> LENGTH: 122
<212> TYPE: PRT
<213> ORGANISM: Lama glama

<400> SEQUENCE: 224

Glu Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Thr Ser Arg
            20                  25                  30

Tyr Tyr Ala Trp Ser Trp Ile Arg Gln Pro Pro Gly Lys Gly Leu Glu
        35                  40                  45

Trp Ile Gly Val Ile Asn Tyr Asp Gly Asp Thr Tyr Tyr Ser Pro Ser
50                  55                  60

Leu Lys Ser Arg Thr Thr Ile Ser Trp Asp Thr Ser Lys Asn Gln Phe
65                  70                  75                  80

Ser Leu Gln Leu Ser Ser Val Thr Pro Glu Asp Thr Ala Val Tyr Tyr
            85                  90                  95

Cys Ala Arg Tyr Pro Asp Val Val Thr Gly Phe His Tyr Asp Tyr Trp
            100                 105                 110

Gly Gln Gly Thr Gln Val Thr Val Ser Ser
            115                 120

<210> SEQ ID NO 225
<211> LENGTH: 122
<212> TYPE: PRT
<213> ORGANISM: Lama glama

<400> SEQUENCE: 225

Glu Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Thr Ser Arg
            20                  25                  30

Tyr Tyr Ala Trp Ser Trp Ile Arg Gln Pro Pro Gly Lys Gly Leu Glu
        35                  40                  45

Trp Ile Gly Val Ile Asp Tyr Asp Gly Asp Thr Tyr Tyr Ser Pro Ser
50                  55                  60

Leu Lys Ser Arg Thr Thr Ile Ser Trp Asp Thr Ser Lys Asn Gln Phe
65                  70                  75                  80

Ser Leu Gln Leu Ser Ser Val Thr Ala Glu Asp Thr Ala Val Tyr Tyr
            85                  90                  95

Cys Ala Arg Asp Pro Asp Val Val Thr Gly Phe His Tyr Asp Tyr Trp
            100                 105                 110

Gly Gln Gly Thr Leu Val Thr Val Ser Ser
            115                 120

<210> SEQ ID NO 226
<211> LENGTH: 122
<212> TYPE: PRT
<213> ORGANISM: Lama glama

<400> SEQUENCE: 226

Glu Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Thr Ser Arg
            20                  25                  30

Tyr Tyr Ala Trp Ser Trp Ile Arg Gln Pro Pro Gly Lys Gly Leu Glu
        35                  40                  45

Trp Ile Gly Val Ile Asp Tyr Asp Gly Asp Thr Tyr Tyr Ser Pro Ser
50                  55                  60

Leu Lys Ser Arg Thr Ser Ile Ser Trp Asp Thr Ser Lys Asn Gln Phe
65                  70                  75                  80

```
Ser Leu His Leu Ser Ser Val Thr Ala Glu Asp Thr Ala Val Tyr Tyr
                85                  90                  95

Cys Ala Arg Asp Pro Asp Val Val Thr Gly Phe His Tyr Asp Tyr Trp
            100                 105                 110

Gly Gln Gly Thr Gln Val Thr Val Ser Ser
        115                 120
```

<210> SEQ ID NO 227
<211> LENGTH: 122
<212> TYPE: PRT
<213> ORGANISM: Lama glama

<400> SEQUENCE: 227

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Thr Ser Arg
            20                  25                  30

Tyr Tyr Ala Trp Ser Trp Ile Arg Gln Pro Pro Gly Lys Gly Leu Glu
        35                  40                  45

Trp Ile Gly Val Ile Asp Tyr Asp Gly Asp Thr Tyr Tyr Ser Pro Ser
    50                  55                  60

Leu Lys Ser Arg Val Thr Ile Ser Trp Asp Thr Ser Lys Asn Gln Phe
65                  70                  75                  80

Ser Leu Lys Leu Ser Ser Val Thr Pro Glu Asp Thr Ala Val Tyr Tyr
                85                  90                  95

Cys Ala Arg Asp Pro Asp Val Val Thr Gly Phe His Tyr Asp Tyr Trp
            100                 105                 110

Gly Gln Gly Thr Gln Val Thr Val Ser Ser
        115                 120
```

<210> SEQ ID NO 228
<211> LENGTH: 122
<212> TYPE: PRT
<213> ORGANISM: Lama glama

<400> SEQUENCE: 228

```
Glu Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Thr Ser Arg
            20                  25                  30

Tyr Tyr Ala Trp Ser Trp Ile Arg Gln Pro Pro Gly Lys Gly Leu Glu
        35                  40                  45

Trp Ile Gly Val Ile Asp Tyr Asp Gly Asp Thr Tyr Tyr Ser Pro Ser
    50                  55                  60

Leu Lys Ser Arg Thr Thr Ile Ser Trp Asp Thr Ser Lys Asn Gln Phe
65                  70                  75                  80

Ser Leu Gln Leu Ser Ser Val Thr Pro Glu Asp Thr Ala Val Tyr Tyr
                85                  90                  95

Cys Ala Arg Asp Pro Asp Val Val Thr Gly Phe His Tyr Asp Tyr Trp
            100                 105                 110

Gly Gln Gly Thr Leu Val Thr Val Ser Ser
        115                 120
```

<210> SEQ ID NO 229
<211> LENGTH: 122
<212> TYPE: PRT
<213> ORGANISM: Lama glama -continued

<400> SEQUENCE: 229

Glu Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Thr Ser Arg
            20                  25                  30

Tyr Tyr Ala Trp Ser Trp Ile Arg Gln Pro Pro Gly Lys Gly Leu Glu
        35                  40                  45

Trp Ile Gly Val Ile Asp Tyr Asp Gly Asp Thr Tyr Tyr Ser Pro Ser
50                  55                  60

Leu Lys Ser Arg Val Thr Ile Ser Trp Asp Thr Ser Lys Asn Gln Phe
65                  70                  75                  80

Ser Leu Gln Leu Ser Ser Val Thr Ala Glu Asp Thr Ala Val Tyr Tyr
                85                  90                  95

Cys Ala Arg Asp Pro Asp Val Val Thr Gly Phe His Tyr Asp Tyr Trp
            100                 105                 110

Gly Gln Gly Thr Gln Val Thr Val Ser Ser
            115                 120

<210> SEQ ID NO 230
<211> LENGTH: 122
<212> TYPE: PRT
<213> ORGANISM: Lama glama

<400> SEQUENCE: 230

Glu Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Thr Thr Arg
            20                  25                  30

Tyr Tyr Ala Trp Ser Trp Ile Arg Gln Pro Pro Gly Lys Gly Leu Glu
        35                  40                  45

Trp Ile Gly Val Ile Asp Tyr Asp Gly Asp Thr Tyr Tyr Ser Pro Ser
50                  55                  60

Leu Lys Ser Arg Thr Thr Ile Ser Trp Asp Thr Ser Lys Asn Gln Phe
65                  70                  75                  80

Ser Leu Lys Leu Ser Ser Val Thr Pro Ala Asp Thr Ala Val Tyr Tyr
                85                  90                  95

Cys Ala Arg Asp Pro Asp Val Val Thr Gly Phe His Tyr Asp Tyr Trp
            100                 105                 110

Gly Gln Gly Thr Thr Val Thr Val Ser Ser
            115                 120

<210> SEQ ID NO 231
<211> LENGTH: 122
<212> TYPE: PRT
<213> ORGANISM: Lama glama

<400> SEQUENCE: 231

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Thr Thr Arg
            20                  25                  30

Tyr Tyr Ala Trp Ser Trp Ile Arg Gln Pro Pro Gly Lys Gly Leu Glu
        35                  40                  45

Trp Ile Gly Val Ile Asp Tyr Asp Gly Asp Thr Tyr Tyr Ser Pro Ser
50                  55                  60

```
Leu Lys Ser Arg Thr Ser Ile Ser Trp Asp Thr Ser Lys Asn Gln Phe
 65                  70                  75                  80

Ser Leu Lys Leu Ser Ser Val Thr Ala Glu Asp Thr Ala Val Tyr Tyr
                 85                  90                  95

Cys Ala Arg Asp Pro Asp Val Val Thr Gly Phe His Tyr Asp Tyr Trp
            100                 105                 110

Gly Gln Gly Thr Gln Val Thr Val Ser Ser
            115                 120

<210> SEQ ID NO 232
<211> LENGTH: 122
<212> TYPE: PRT
<213> ORGANISM: Lama glama

<400> SEQUENCE: 232

Glu Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Thr Thr Arg
             20                  25                  30

Tyr Tyr Ala Trp Ser Trp Ile Arg Gln Pro Pro Gly Lys Gly Leu Glu
             35                  40                  45

Trp Ile Gly Val Ile Asp Tyr Asp Gly Asp Thr Tyr Tyr Ser Pro Ser
 50                  55                  60

Leu Lys Ser Arg Val Thr Ile Ser Val Asp Thr Ser Lys Asn Gln Phe
 65                  70                  75                  80

Ser Leu Gln Leu Ser Ser Val Thr Ala Glu Asp Thr Ala Val Tyr Tyr
                 85                  90                  95

Cys Ala Arg Asp Pro Asp Val Val Thr Gly Phe His Tyr Asp Tyr Trp
            100                 105                 110

Gly Gln Gly Thr Gln Val Thr Val Ser Ser
            115                 120

<210> SEQ ID NO 233
<211> LENGTH: 111
<212> TYPE: PRT
<213> ORGANISM: Lama glama

<400> SEQUENCE: 233

Gln Ala Gly Leu Thr Gln Pro Pro Ser Val Ser Gly Ser Pro Gly Lys
1               5                   10                  15

Thr Val Thr Ile Ser Cys Ala Gly Thr Thr Ser Asp Val Gly Thr Gly
             20                  25                  30

Asn Phe Val Ser Trp Tyr Gln Gln Leu Pro Gly Met Ala Pro Lys Leu
             35                  40                  45

Leu Ile Tyr Asp Val Asn Lys Arg Ala Ser Gly Ile Ala Asp Arg Phe
 50                  55                  60

Ser Gly Ser Lys Ser Gly Asn Thr Ala Ser Leu Thr Ile Ser Gly Leu
 65                  70                  75                  80

Gln Ser Glu Asp Glu Ala Asp Tyr Tyr Cys Ala Ser Tyr Arg Ser Leu
                 85                  90                  95

Asn Asn Val Val Phe Gly Gly Gly Thr His Leu Thr Val Leu Gly
            100                 105                 110

<210> SEQ ID NO 234
<211> LENGTH: 109
<212> TYPE: PRT
<213> ORGANISM: Lama glama
```

<400> SEQUENCE: 234

Gln Ser Val Val Thr Gln Pro Ser Ala Leu Ser Val Thr Leu Gly Gln
1               5                   10                  15

Thr Ala Lys Ile Thr Cys Gln Gly Gly Gly Leu Arg Ser Ser Tyr Ala
            20                  25                  30

His Trp Tyr Gln Gln Lys Pro Gly Gln Ala Pro Val Leu Val Ile Tyr
        35                  40                  45

Asp Asp Asp Ser Arg Pro Ser Gly Ile Pro Glu Arg Phe Ser Gly Ser
    50                  55                  60

Ser Ser Gly Gly Arg Ala Thr Leu Thr Ile Ser Gly Ala Gln Ala Glu
65                  70                  75                  80

Asp Glu Gly Asp Tyr Tyr Cys Gln Ser Ala Asp Ser Ser Gly Asn Ala
                85                  90                  95

Ala Val Phe Gly Gly Gly Thr His Leu Thr Val Leu Gly
            100                 105

<210> SEQ ID NO 235
<211> LENGTH: 109
<212> TYPE: PRT
<213> ORGANISM: Lama glama

<400> SEQUENCE: 235

Gln Ala Gly Leu Thr Gln Pro Ser Ala Leu Ser Val Thr Leu Gly Gln
1               5                   10                  15

Thr Ala Lys Ile Thr Cys Gln Gly Gly Ser Leu Gly Ser Ser Tyr Ala
            20                  25                  30

His Trp Tyr Gln Gln Lys Pro Gly Gln Ala Pro Val Leu Val Ile Tyr
        35                  40                  45

Asp Asp Asp Ser Arg Pro Ser Gly Ile Pro Glu Arg Phe Ser Gly Ser
    50                  55                  60

Ser Ser Gly Gly Arg Ala Thr Leu Thr Ile Ser Gly Ala Gln Ala Glu
65                  70                  75                  80

Asp Glu Gly Asp Tyr Tyr Cys Gln Ser Ala Asp Ser Ser Gly Asn Ala
                85                  90                  95

Ala Val Phe Gly Gly Gly Thr His Leu Thr Val Leu Gly
            100                 105

<210> SEQ ID NO 236
<211> LENGTH: 110
<212> TYPE: PRT
<213> ORGANISM: Lama glama

<400> SEQUENCE: 236

Leu Asn Phe Met Leu Thr Gln Pro Ser Ala Leu Ser Val Thr Leu Gly
1               5                   10                  15

Gln Thr Ala Lys Ile Thr Cys Gln Gly Gly Ser Leu Gly Ser Arg Tyr
            20                  25                  30

Ala His Trp Tyr Gln Gln Lys Pro Gly Gln Ala Pro Val Leu Val Ile
        35                  40                  45

Tyr Asp Asp Asp Ser Arg Pro Ser Gly Ile Pro Glu Arg Phe Ser Gly
    50                  55                  60

Ser Ser Ser Gly Gly Arg Ala Thr Leu Thr Ile Ser Gly Ala Gln Ala
65                  70                  75                  80

Glu Asp Asp Gly Asp Tyr Tyr Cys Gln Ser Ala Asp Ser Ser Gly Asn
                85                  90                  95

Ala Ser Val Phe Gly Gly Gly Thr His Leu Thr Val Leu Gly

<210> SEQ ID NO 237
<211> LENGTH: 108
<212> TYPE: PRT
<213> ORGANISM: Lama glama

<400> SEQUENCE: 237

Gln Ser Ala Leu Thr Gln Pro Ser Ala Leu Ser Val Thr Leu Gly Gln
1               5                   10                  15

Thr Ala Lys Ile Thr Cys Gln Gly Gly Ser Leu Gly Ser Arg Tyr Ala
            20                  25                  30

His Trp Tyr Gln Gln Lys Pro Gly Gln Ala Pro Val Leu Val Ile Tyr
        35                  40                  45

Asp Asp Asp Ser Arg Pro Ser Gly Ile Pro Glu Arg Phe Ser Gly Ser
    50                  55                  60

Ser Ser Gly Gly Arg Ala Thr Leu Thr Ile Ser Gly Ala Gln Ala Glu
65                  70                  75                  80

Asp Glu Gly Asp Tyr Tyr Cys Gln Ser Ala Asp Thr Ser Glu His Ile
                85                  90                  95

Val Phe Gly Gly Gly Thr His Leu Thr Val Leu Gly
            100                 105

<210> SEQ ID NO 238
<211> LENGTH: 111
<212> TYPE: PRT
<213> ORGANISM: Lama glama

<400> SEQUENCE: 238

Ala Leu Asn Phe Met Leu Thr Gln Pro Ser Ala Leu Ser Val Thr Leu
1               5                   10                  15

Gly Gln Thr Ala Lys Ile Thr Cys Gln Gly Gly Ser Leu Gly Ser Ser
            20                  25                  30

Tyr Ala His Trp Tyr Gln Gln Lys Pro Gly Gln Ala Pro Val Leu Val
        35                  40                  45

Ile Tyr Asp Asp Asp Ser Arg Pro Ser Gly Ile Pro Glu Arg Phe Ser
    50                  55                  60

Gly Ser Ser Ser Gly Gly Arg Ala Thr Leu Thr Ile Ser Gly Ala Gln
65                  70                  75                  80

Ala Glu Asp Glu Gly Asp Tyr Tyr Cys Gln Ser Ala Asp Ser Ser Gly
                85                  90                  95

Asn Ala Val Phe Gly Gly Gly Thr His Leu Thr Val Leu Gly Gln
            100                 105                 110

<210> SEQ ID NO 239
<211> LENGTH: 111
<212> TYPE: PRT
<213> ORGANISM: Lama glama

<400> SEQUENCE: 239

Gln Ser Ala Leu Thr Gln Pro Pro Ser Met Ser Gly Thr Leu Gly Lys
1               5                   10                  15

Thr Leu Thr Ile Ser Cys Ala Gly Thr Ser Ser Asp Ile Gly Tyr Gly
            20                  25                  30

Asp Tyr Val Ser Trp Tyr Gln Gln Leu Pro Gly Thr Ala Pro Lys Leu
        35                  40                  45

Leu Ile Tyr Lys Val Ser Thr Arg Ala Ser Gly Ile Pro Asp Arg Phe
    50                  55                  60

Ser Gly Ser Lys Ser Gly Asn Thr Ala Ser Leu Thr Ile Ser Gly Leu
65                  70                  75                  80

Gln Ser Glu Asp Glu Ala Asp Tyr Tyr Cys Ala Ser Tyr Arg His Tyr
                85                  90                  95

Asn Asn Ala Val Phe Gly Gly Gly Thr His Leu Thr Val Leu Gly
            100                 105                 110

<210> SEQ ID NO 240
<211> LENGTH: 113
<212> TYPE: PRT
<213> ORGANISM: Lama glama

<400> SEQUENCE: 240

Ala Leu Asn Phe Met Leu Thr Gln Pro Pro Ser Val Ser Gly Thr Leu
1               5                   10                  15

Gly Lys Thr Val Thr Ile Ser Cys Ala Gly Thr Ser Ser Asp Ile Gly
            20                  25                  30

Gly Tyr Asn Tyr Val Ser Trp Tyr Gln Gln Leu Pro Gly Thr Ala Pro
        35                  40                  45

Lys Leu Leu Ile His Arg Val Ser Thr Arg Ala Ser Gly Ile Pro Asp
50                  55                  60

Arg Phe Ser Gly Ser Lys Ser Gly Asn Thr Ala Ser Leu Thr Ile Ser
65                  70                  75                  80

Gly Leu Arg Ser Glu Asp Glu Ala Asn Tyr Tyr Cys Ala Ser Tyr Arg
                85                  90                  95

Asn Phe Asn Ala Val Phe Gly Gly Gly Thr Gln Leu Thr Val Leu
            100                 105                 110

Gly

<210> SEQ ID NO 241
<211> LENGTH: 112
<212> TYPE: PRT
<213> ORGANISM: Lama glama

<400> SEQUENCE: 241

Ala Leu Pro Val Leu Thr Gln Pro Pro Ser Val Ser Gly Ser Pro Gly
1               5                   10                  15

Gln Lys Phe Thr Ile Ser Cys Thr Gly Ser Ser Ser Asn Ile Gly Glu
            20                  25                  30

Asn Tyr Val Asn Trp Tyr Gln Gln Leu Pro Gly Met Ala Pro Lys Leu
        35                  40                  45

Leu Ile Tyr Ser Asn Thr Asn Arg Ala Ser Gly Val Pro Asp Arg Phe
50                  55                  60

Ser Gly Ser Lys Ser Gly Ser Ser Ala Ser Leu Thr Ile Thr Gly Leu
65                  70                  75                  80

Gln Val Glu Asp Glu Ala Asp Tyr Tyr Cys Ser Ser Trp Asp Asp Ser
                85                  90                  95

Leu Ser Gly Leu Val Phe Gly Gly Gly Thr Lys Leu Thr Val Leu Gly
            100                 105                 110

<210> SEQ ID NO 242
<211> LENGTH: 118
<212> TYPE: PRT
<213> ORGANISM: Lama glama

<400> SEQUENCE: 242

Ala Leu Asn Phe Met Leu Thr Gln Pro Pro Ser Leu Ser Ala Ser Pro

```
                1               5                  10                 15
Gly Ser Ser Val Arg Leu Thr Cys Thr Leu Ser Ser Gly Asn Ser Val
                20                 25                 30

Gly Ser Tyr Asp Ile Ser Trp Tyr Gln Gln Lys Ala Gly Ser Pro Pro
                35                 40                 45

Arg Tyr Leu Leu Tyr Tyr Ser Asp Ser Tyr Lys His Gln Gly Ser
        50                 55                 60

Gly Val Pro Ser Arg Phe Ser Gly Ser Lys Asp Ala Ser Ala Asn Ala
65                 70                 75                 80

Gly Leu Leu Leu Ile Ser Gly Leu Gln Pro Glu Asp Glu Ala Ala Tyr
                85                 90                 95

Tyr Cys Ser Ala Tyr Lys Ser Gly Ser Tyr Val Phe Gly Gly Gly Thr
                100                105                110

Lys Leu Thr Val Leu Gly
            115
```

<210> SEQ ID NO 243
<211> LENGTH: 111
<212> TYPE: PRT
<213> ORGANISM: Lama glama

<400> SEQUENCE: 243

```
Ala Leu Asn Phe Met Leu Thr Gln Pro Pro Ser Val Ser Gly Ser Pro
1               5                  10                 15

Gly Gln Lys Phe Thr Ile Arg Cys Thr Gly Ser Phe Arg Ser Asp Ser
                20                 25                 30

Tyr Val Asn Trp Tyr Gln Gln Leu Pro Gly Thr Ala Pro Lys Leu Leu
                35                 40                 45

Ile Asn Tyr Asp Asp Arg Arg Val Ser Gly Val Pro Ser Arg Phe Ser
        50                 55                 60

Gly Ser Lys Ser Gly Asn Ser Ala Ser Leu Thr Ile Asp Gly Leu Gln
65                 70                 75                 80

Ala Glu Asp Glu Ala Glu Tyr Tyr Cys Ser Phe Trp Asp His Thr Phe
                85                 90                 95

Gly Gly His Val Phe Gly Gly Gly Thr Lys Leu Thr Val Leu Gly
                100                105                110
```

<210> SEQ ID NO 244
<211> LENGTH: 110
<212> TYPE: PRT
<213> ORGANISM: Lama glama

<400> SEQUENCE: 244

```
Gln Thr Val Val Thr Gln Glu Pro Ser Leu Ser Val Ser Pro Gly Gly
1               5                  10                 15

Thr Val Thr Leu Thr Cys Gly Leu Ser Ser Gly Ser Val Thr Ala Ser
                20                 25                 30

Asn Tyr Pro Gly Trp Phe Gln Gln Thr Pro Gly Gln Ala Pro Arg Ala
                35                 40                 45

Leu Ile Tyr Ser Thr Asn Asp Arg His Ser Gly Val Pro Ser Arg Phe
        50                 55                 60

Ser Gly Ser Ile Ser Gly Asn Lys Ala Ala Leu Thr Ile Thr Gly Ala
65                 70                 75                 80

Gln Pro Glu Asp Glu Ala Asp Tyr Tyr Cys Ala Leu Asp Ile Gly Asp
                85                 90                 95

Ile Thr Glu Phe Gly Gly Gly Thr His Leu Thr Val Leu Gly
```

-continued

```
              100                 105                 110
```

<210> SEQ ID NO 245
<211> LENGTH: 110
<212> TYPE: PRT
<213> ORGANISM: Lama glama

<400> SEQUENCE: 245

```
Gln Thr Val Val Thr Gln Glu Pro Ser Leu Ser Val Ser Pro Gly Gly
1               5                   10                  15

Thr Val Thr Leu Thr Cys Gly Leu Ser Ser Gly Ser Val Thr Ala Ser
            20                  25                  30

Asn Tyr Pro Gly Trp Phe Gln Gln Thr Pro Gly Gln Ala Pro Arg Ala
        35                  40                  45

Leu Ile Tyr Ser Thr Asn Asp Arg His Ser Gly Val Pro Ser Arg Phe
    50                  55                  60

Ser Gly Ser Ile Ser Gly Asn Lys Ala Ala Leu Thr Ile Thr Gly Ala
65                  70                  75                  80

Gln Pro Glu Asp Glu Ala Asp Tyr Tyr Cys Ala Leu Asp Ile Gly Asp
                85                  90                  95

Ile Thr Glu Phe Gly Gly Gly Thr His Leu Thr Val Leu Gly
            100                 105                 110
```

<210> SEQ ID NO 246
<211> LENGTH: 110
<212> TYPE: PRT
<213> ORGANISM: Lama glama

<400> SEQUENCE: 246

```
Gln Thr Val Val Thr Gln Glu Pro Ser Leu Ser Val Ser Pro Gly Gly
1               5                   10                  15

Thr Val Thr Leu Thr Cys Gly Leu Ser Ser Gly Ser Val Thr Ala Ser
            20                  25                  30

Asn Tyr Pro Gly Trp Phe Gln Gln Thr Pro Gly Gln Ala Pro Arg Ala
        35                  40                  45

Leu Ile Tyr Ser Thr Asn Asp Arg His Ser Gly Val Pro Ser Arg Phe
    50                  55                  60

Ser Gly Ser Ile Ser Gly Asn Lys Ala Ala Leu Thr Ile Thr Gly Ala
65                  70                  75                  80

Gln Pro Glu Asp Glu Ala Asp Tyr Tyr Cys Ala Leu Asp Ile Gly Asp
                85                  90                  95

Ile Thr Glu Phe Gly Gly Gly Thr His Leu Thr Val Leu Gly
            100                 105                 110
```

<210> SEQ ID NO 247
<211> LENGTH: 110
<212> TYPE: PRT
<213> ORGANISM: Lama glama

<400> SEQUENCE: 247

```
Gln Thr Val Val Thr Gln Glu Pro Ser Leu Ser Val Ser Pro Gly Gly
1               5                   10                  15

Thr Val Thr Leu Thr Cys Gly Leu Ser Ser Gly Ser Val Thr Ala Ser
            20                  25                  30

Asn Tyr Pro Gly Trp Phe Gln Gln Thr Pro Gly Gln Ala Pro Arg Ala
        35                  40                  45

Leu Ile Tyr Ser Thr Asn Asp Arg His Ser Gly Val Pro Ser Arg Phe
    50                  55                  60
```

```
Ser Gly Ser Ile Ser Gly Asn Lys Ala Ala Leu Thr Ile Thr Gly Ala
 65                  70                  75                  80

Gln Pro Glu Asp Glu Ala Asp Tyr Tyr Cys Ala Leu Asp Ile Gly Asp
                 85                  90                  95

Ile Thr Glu Phe Gly Gly Gly Thr His Leu Thr Val Leu Gly
            100                 105                 110

<210> SEQ ID NO 248
<211> LENGTH: 110
<212> TYPE: PRT
<213> ORGANISM: Lama glama

<400> SEQUENCE: 248

Gln Thr Val Val Thr Gln Glu Pro Ser Leu Ser Val Ser Pro Gly Gly
 1               5                  10                  15

Thr Val Thr Leu Thr Cys Gly Leu Ser Ser Gly Ser Val Thr Ala Ser
             20                  25                  30

Asn Tyr Pro Gly Trp Phe Gln Gln Thr Pro Gly Gln Ala Pro Arg Ala
         35                  40                  45

Leu Ile Tyr Ser Thr Asn Asp Arg His Ser Gly Val Pro Ser Arg Phe
     50                  55                  60

Ser Gly Ser Ile Ser Gly Asn Lys Ala Ala Leu Thr Ile Thr Gly Ala
 65                  70                  75                  80

Gln Pro Glu Asp Glu Ala Asp Tyr Tyr Cys Ala Leu Asp Ile Gly Asp
                 85                  90                  95

Ile Thr Glu Phe Gly Gly Gly Thr His Leu Thr Val Leu Gly
            100                 105                 110

<210> SEQ ID NO 249
<211> LENGTH: 110
<212> TYPE: PRT
<213> ORGANISM: Lama glama

<400> SEQUENCE: 249

Gln Thr Val Val Thr Gln Glu Pro Ser Leu Ser Val Ser Pro Gly Gly
 1               5                  10                  15

Thr Val Thr Leu Thr Cys Gly Leu Ser Ser Gly Ser Val Thr Ala Ser
             20                  25                  30

Asn Tyr Pro Gly Trp Phe Gln Gln Thr Pro Gly Gln Ala Pro Arg Ala
         35                  40                  45

Leu Ile Tyr Ser Thr Asn Asp Arg His Ser Gly Val Pro Ser Arg Phe
     50                  55                  60

Ser Gly Ser Ile Ser Gly Asn Lys Ala Ala Leu Thr Ile Thr Gly Ala
 65                  70                  75                  80

Gln Pro Glu Asp Glu Ala Asp Tyr Tyr Cys Ala Leu Asp Ile Gly Asp
                 85                  90                  95

Ile Thr Glu Phe Gly Gly Gly Thr His Leu Thr Val Leu Gly
            100                 105                 110

<210> SEQ ID NO 250
<211> LENGTH: 110
<212> TYPE: PRT
<213> ORGANISM: Lama glama

<400> SEQUENCE: 250

Gln Thr Val Val Thr Gln Glu Pro Ser Leu Ser Val Ser Pro Gly Gly
 1               5                  10                  15
```

```
Thr Val Thr Leu Thr Cys Gly Leu Ser Ser Gly Ser Val Thr Ala Ser
            20                  25                  30

Asn Tyr Pro Gly Trp Phe Gln Gln Thr Pro Gly Gln Ala Pro Arg Ala
        35                  40                  45

Leu Ile Tyr Ser Thr Asn Asp Arg His Ser Gly Val Pro Ser Arg Phe
    50                  55                  60

Ser Gly Ser Ile Ser Gly Asn Lys Ala Ala Leu Thr Ile Thr Gly Ala
65              70                  75                  80

Gln Pro Glu Asp Glu Ala Asp Tyr Tyr Cys Ala Leu Asp Ile Gly Asp
                85                  90                  95

Ile Thr Glu Phe Gly Gly Gly Thr His Leu Thr Val Leu Gly
            100                 105                 110

<210> SEQ ID NO 251
<211> LENGTH: 110
<212> TYPE: PRT
<213> ORGANISM: Lama glama

<400> SEQUENCE: 251

Gln Thr Val Val Thr Gln Glu Pro Ser Leu Ser Val Ser Pro Gly Gly
1               5                   10                  15

Thr Val Thr Leu Thr Cys Gly Leu Ser Ser Gly Ser Val Thr Ala Ser
            20                  25                  30

Asn Tyr Pro Gly Trp Phe Gln Gln Thr Pro Gly Gln Ala Pro Arg Ala
        35                  40                  45

Leu Ile Tyr Ser Thr Asn Asp Arg His Ser Gly Val Pro Ser Arg Phe
    50                  55                  60

Ser Gly Ser Ile Ser Gly Asn Lys Ala Ala Leu Thr Ile Thr Gly Ala
65              70                  75                  80

Gln Pro Glu Asp Glu Ala Asp Tyr Tyr Cys Ala Leu Asp Ile Gly Asp
                85                  90                  95

Ile Thr Glu Phe Gly Gly Gly Thr His Leu Thr Val Leu Gly
            100                 105                 110

<210> SEQ ID NO 252
<211> LENGTH: 111
<212> TYPE: PRT
<213> ORGANISM: Lama glama

<400> SEQUENCE: 252

Gln Ser Val Leu Thr Gln Pro Pro Ser Val Ser Gly Ser Pro Gly Gln
1               5                   10                  15

Thr Val Thr Ile Ser Cys Ala Gly Thr Ser Glu Asp Val Gly Tyr Gly
            20                  25                  30

Asn Tyr Val Ser Trp Tyr Gln Gln Leu Pro Gly Met Ala Pro Lys Leu
        35                  40                  45

Leu Ile Tyr Asp Val Asn Lys Arg Ala Ser Gly Ile Ala Asp Arg Phe
    50                  55                  60

Ser Gly Ser Lys Ser Gly Asn Thr Ala Ser Leu Thr Ile Ser Gly Leu
65              70                  75                  80

Gln Ser Glu Asp Glu Ala Asp Tyr Tyr Cys Ala Ser Tyr Arg Arg Thr
                85                  90                  95

Ile Asp Asn Ile Phe Gly Gly Gly Thr His Leu Thr Val Leu Gly
            100                 105                 110

<210> SEQ ID NO 253
<211> LENGTH: 104
```

```
<212> TYPE: PRT
<213> ORGANISM: Lama glama

<400> SEQUENCE: 253

Asp Ile Val Met Thr Gln Thr Pro Ser Ser Leu Ser Ala Ser Leu Gly
1               5                   10                  15

Asp Arg Val Thr Ile Thr Cys Gln Ala Ser Gln Ser Ile Ser Thr Glu
            20                  25                  30

Leu Ser Trp Tyr Gln Gln Lys Pro Gly Gln Thr Pro Lys Leu Leu Ile
        35                  40                  45

Tyr Gly Ala Ser Arg Leu Gln Thr Gly Val Pro Ala Arg Phe Ser Gly
50                  55                  60

Ser Gly Ser Gly Thr Ser Phe Thr Leu Thr Ile Ser Gly Leu Glu Ala
65                  70                  75                  80

Glu Asp Leu Ala Thr Tyr Tyr Cys Leu Gln Asp Tyr Ser Trp Pro Tyr
                85                  90                  95

Ser Phe Gly Ser Gly Thr Arg Leu
            100

<210> SEQ ID NO 254
<211> LENGTH: 104
<212> TYPE: PRT
<213> ORGANISM: Lama glama

<400> SEQUENCE: 254

Asp Ile Gln Leu Thr Gln Ser Pro Ser Ser Leu Ser Ala Ser Leu Gly
1               5                   10                  15

Asp Arg Val Thr Ile Thr Cys Gln Ala Ser Gln Ser Ile Ser Thr Glu
            20                  25                  30

Leu Ser Trp Tyr Gln Gln Lys Pro Gly Gln Thr Pro Lys Leu Leu Ile
        35                  40                  45

Tyr Gly Ala Ser Arg Leu Gln Thr Gly Val Pro Ala Arg Phe Ser Gly
50                  55                  60

Ser Gly Ser Gly Thr Ser Phe Thr Leu Thr Ile Ser Gly Leu Glu Ala
65                  70                  75                  80

Glu Asp Leu Ala Thr Tyr Tyr Cys Leu Gln Asp Tyr Ser Trp Pro Tyr
                85                  90                  95

Ser Phe Gly Ser Gly Thr Arg Leu
            100

<210> SEQ ID NO 255
<211> LENGTH: 104
<212> TYPE: PRT
<213> ORGANISM: Lama glama

<400> SEQUENCE: 255

Asp Ile Gln Met Thr Gln Ser Pro Ser Ser Leu Ser Thr Ser Leu Gly
1               5                   10                  15

Asp Arg Val Thr Ile Thr Cys Gln Ala Ser Gln Ala Ile Thr Thr Glu
            20                  25                  30

Leu Ser Trp Tyr Gln Gln Lys Pro Gly Gln Pro Pro Lys Leu Leu Ile
        35                  40                  45

Tyr Gly Thr Ser Arg Leu Gln Thr Gly Val Pro Ser Arg Phe Ser Gly
50                  55                  60

Thr Gly Ser Gly Thr Ser Phe Thr Leu Thr Ile Ser Asp Leu Glu Ala
65                  70                  75                  80

Glu Asp Leu Ala Thr Tyr Tyr Cys Leu Gln Asp Tyr Gly Trp Pro Phe
```

```
                    85                  90                  95

Thr Phe Gly Gln Gly Thr Lys Val
            100

<210> SEQ ID NO 256
<211> LENGTH: 104
<212> TYPE: PRT
<213> ORGANISM: Lama glama

<400> SEQUENCE: 256

Asp Ile Val Met Thr Gln Ser Pro Ser Ser Leu Ser Ala Ser Leu Gly
1               5                   10                  15

Asp Arg Val Thr Ile Thr Cys Gln Thr Ser Gln Thr Ile Ser Thr Glu
            20                  25                  30

Leu Ser Trp Tyr Gln Gln Lys Pro Gly Gln Ala Pro Lys Leu Leu Ile
        35                  40                  45

Tyr Gly Ala Ser Arg Leu Gln Thr Gly Val Pro Ser Arg Phe Ser Gly
    50                  55                  60

Ser Gly Ser Gly Thr Ser Phe Thr Leu Thr Ile Ser Gly Leu Glu Ala
65                  70                  75                  80

Glu Asp Leu Ala Thr Tyr Tyr Cys Leu Gln Asp Tyr Ser Trp Pro Phe
                85                  90                  95

Thr Phe Gly Gln Gly Thr Lys Val
            100

<210> SEQ ID NO 257
<211> LENGTH: 108
<212> TYPE: PRT
<213> ORGANISM: Lama glama

<400> SEQUENCE: 257

Asp Ile Val Met Thr Gln Ser Pro Phe Ser Leu Ser Ala Ser Leu Gly
1               5                   10                  15

Asp Arg Val Thr Ile Thr Cys Gln Ala Ser Glu Ser Ile Leu Thr Glu
            20                  25                  30

Val Ser Trp Tyr Gln Gln Lys Pro Gly Gln Thr Pro Lys Leu Leu Ile
        35                  40                  45

Tyr Gly Ala Ser Gly Leu Gln Thr Gly Val Pro Asn Arg Phe Ser Gly
    50                  55                  60

Ser Gly Ser Gly Thr Ser Phe Thr Leu Thr Ile Ser Gly Leu Glu Ala
65                  70                  75                  80

Glu Asp Leu Ala Thr Tyr Tyr Cys Leu Gln Asp Tyr Arg Trp Pro Leu
                85                  90                  95

Thr Phe Gly Gln Gly Thr Lys Val Glu Leu Lys Arg
            100                 105

<210> SEQ ID NO 258
<211> LENGTH: 108
<212> TYPE: PRT
<213> ORGANISM: Lama glama

<400> SEQUENCE: 258

Asp Ile Val Met Thr Gln Ser Pro Ser Ser Leu Thr Ala Ser Leu Gly
1               5                   10                  15

Asp Arg Val Thr Ile Thr Cys Gln Ala Ser Gln Ser Ile Arg Thr Asp
            20                  25                  30

Ile Ser Trp Tyr Gln Gln Lys Pro Gly Gln Thr Pro Lys Leu Leu Ile
        35                  40                  45
```

```
Tyr Ala Ala Ser Arg Leu Gln Thr Gly Val Pro Ser Arg Phe Ser Gly
         50                  55                  60

Ser Gly Ser Gly Thr Ser Phe Thr Leu Thr Ile Ser Gly Leu Glu Ala
 65                  70                  75                  80

Glu Asp Leu Gly Thr Tyr Tyr Cys Leu Gln Asp Tyr Ser Trp Pro Leu
                 85                  90                  95

Thr Phe Gly Gln Gly Thr Lys Val Glu Leu Lys Arg
            100                 105
```

<210> SEQ ID NO 259
<211> LENGTH: 108
<212> TYPE: PRT
<213> ORGANISM: Lama glama

<400> SEQUENCE: 259

```
Asp Ile Val Met Thr Gln Ser Pro Ser Ser Leu Ser Ala Ser Leu Gly
 1               5                  10                  15

Asp Arg Val Thr Ile Thr Cys Gln Ala Ser Gln Ser Ile Ser Thr Glu
                 20                  25                  30

Leu Ser Trp Tyr Gln Gln Lys Pro Gly Gln Thr Pro Lys Leu Leu Ile
             35                  40                  45

Tyr Gly Ala Ser Arg Leu Gln Thr Gly Val Pro Ser Ser Phe Ser Gly
         50                  55                  60

Ser Gly Ser Gly Thr Ser Phe Thr Leu Thr Ile Ser Gly Leu Glu Ala
 65                  70                  75                  80

Glu Asp Leu Ala Thr Tyr Tyr Cys Leu Gln Asp Tyr Asn Trp Pro Phe
                 85                  90                  95

Thr Phe Gly Gln Gly Thr Lys Val Glu Leu Lys Arg
            100                 105
```

<210> SEQ ID NO 260
<211> LENGTH: 110
<212> TYPE: PRT
<213> ORGANISM: Lama glama

<400> SEQUENCE: 260

```
Asp Ile Gln Met Thr Gln Ser Pro Ser Ser Val Thr Ala Ser Val Gly
 1               5                  10                  15

Glu Lys Val Thr Leu Asn Cys Lys Ser Ser Gln Ser Val Val Val Arg
                 20                  25                  30

Ser Asp Gln Lys Ser Tyr Leu Asn Trp Tyr Gln Gln Arg Pro Gly Gln
             35                  40                  45

Ser Pro Arg Leu Leu Ile Tyr Tyr Ala Ser Thr Gln Glu Ser Gly Ile
         50                  55                  60

Pro Asp Arg Phe Ser Gly Ser Gly Ser Thr Thr Asp Phe Thr Leu Thr
 65                  70                  75                  80

Ile Asn Ser Val Gln Pro Glu Asp Ala Ala Val Tyr Tyr Cys Gln Gln
                 85                  90                  95

Ala Ser Ser Ala Pro Tyr Asn Phe Gly Ser Gly Thr Arg Leu
            100                 105                 110
```

<210> SEQ ID NO 261
<211> LENGTH: 111
<212> TYPE: PRT
<213> ORGANISM: Lama glama

<400> SEQUENCE: 261

Gln Ser Ala Leu Thr Gln Pro Pro Ser Met Ser Gly Thr Leu Gly Lys
1               5                   10                  15

Thr Leu Thr Ile Ser Cys Asn Gly Thr Ser Ser Asp Ile Gly Ser Gly
            20                  25                  30

Asp Tyr Val Ser Trp Tyr Gln Gln Leu Pro Gly Thr Thr Pro Lys Leu
        35                  40                  45

Leu Ile Glu Gly Val Thr Thr Arg Ala Ser Gly Ile Pro Asp Arg Phe
50                  55                  60

Ser Ala Ser Lys Ser Asp Asn Thr Ala Ser Leu Thr Ile Ser Gly Leu
65                  70                  75                  80

Gln Ser Glu Asp Glu Ala Thr Tyr Tyr Cys Ala Ser Tyr Arg Glu Thr
                85                  90                  95

Asn Asn Val Val Phe Gly Gly Gly Thr His Leu Thr Val Leu Ser
            100                 105                 110

<210> SEQ ID NO 262
<211> LENGTH: 111
<212> TYPE: PRT
<213> ORGANISM: Lama glama

<400> SEQUENCE: 262

Gln Ala Val Leu Thr Gln Pro Pro Ser Met Ser Gly Thr Leu Gly Lys
1               5                   10                  15

Thr Leu Thr Ile Ser Cys Asn Gly Thr Ser Ser Asp Ile Gly Ser Gly
            20                  25                  30

Asn Tyr Val Ser Trp Tyr Gln Gln Leu Pro Gly Thr Thr Pro Lys Leu
        35                  40                  45

Leu Ile Glu Gly Val Thr Thr Arg Val Ser Gly Ile Pro Asp Arg Phe
50                  55                  60

Ser Gly Ser Lys Ser Asp Asn Thr Ala Ser Leu Thr Ile Ser Gly Leu
65                  70                  75                  80

Gln Ser Glu Asp Glu Ala Thr Tyr Tyr Cys Ala Ser Tyr Arg Glu Thr
                85                  90                  95

Asn Asn Val Val Phe Gly Gly Gly Thr His Leu Thr Val Leu Gly
            100                 105                 110

<210> SEQ ID NO 263
<211> LENGTH: 111
<212> TYPE: PRT
<213> ORGANISM: Lama glama

<400> SEQUENCE: 263

Gln Ala Gly Leu Thr Gln Pro Pro Ser Val Ser Gly Ser Pro Gly Lys
1               5                   10                  15

Thr Val Thr Ile Ser Cys Ala Gly Thr Ser Ser Asp Val Gly Tyr Gly
            20                  25                  30

Asn Tyr Val Ser Trp Tyr Gln Gln Leu Pro Gly Met Ala Pro Lys Leu
        35                  40                  45

Leu Ile Tyr Asp Val Asn Lys Arg Ala Ser Gly Ile Ala Asp Arg Phe
50                  55                  60

Ser Gly Ser Lys Ser Gly Asn Thr Ala Ser Leu Thr Ile Ser Arg Leu
65                  70                  75                  80

Gln Ser Glu Asp Glu Ala Asp Tyr Tyr Cys Ala Ser Tyr Lys Thr Tyr
                85                  90                  95

Asn Asn Val Val Phe Gly Gly Gly Thr His Leu Thr Val Leu Gly
            100                 105                 110

<210> SEQ ID NO 264
<211> LENGTH: 111
<212> TYPE: PRT
<213> ORGANISM: Lama glama

<400> SEQUENCE: 264

Gln Ser Val Val Thr Gln Pro Pro Ser Val Ser Gly Thr Leu Gly Lys
1               5                   10                  15

Thr Val Thr Ile Ser Cys Ala Gly Thr Thr Ser Asp Ile Gly Gly Tyr
            20                  25                  30

Asn Tyr Val Ser Trp Tyr Gln Gln Leu Pro Gly Thr Ala Pro Lys Phe
        35                  40                  45

Leu Ile Tyr Glu Val Ser Lys Arg Ala Ala Gly Ile Pro Asp Arg Phe
    50                  55                  60

Ser Gly Ser Lys Ser Gly Ser Thr Ala Ser Leu Thr Ile Ser Gly Leu
65                  70                  75                  80

Gln Ser Glu Asp Glu Ala Asp Tyr Tyr Cys Ala Ser Tyr Arg Asp Thr
                85                  90                  95

Ala Asn Val Val Phe Gly Gly Gly Thr His Leu Thr Val Leu Gly
            100                 105                 110

<210> SEQ ID NO 265
<211> LENGTH: 110
<212> TYPE: PRT
<213> ORGANISM: Lama glama

<400> SEQUENCE: 265

Ala Leu Asn Phe Met Leu Thr Gln Pro Ser Ala Leu Ser Val Thr Leu
1               5                   10                  15

Gly Gln Thr Ala Lys Ile Thr Cys Gln Gly Gly Ser Leu Gly Asn Asn
            20                  25                  30

Tyr Ala His Trp Tyr Gln Gln Lys Pro Gly Gln Ala Pro Val Leu Val
        35                  40                  45

Ile Tyr Asp Asp Asp Ser Arg Pro Ser Gly Ile Pro Glu Arg Phe Ser
    50                  55                  60

Gly Ser Ser Ser Gly Gly Arg Ala Thr Leu Thr Ile Ser Gly Ala Gln
65                  70                  75                  80

Ala Glu Asp Glu Gly Asp Tyr Tyr Cys Gln Ser Ala Asp Ser Ser Gly
                85                  90                  95

Asn Ala Val Phe Gly Gly Gly Thr His Leu Thr Val Leu Gly
            100                 105                 110

<210> SEQ ID NO 266
<211> LENGTH: 110
<212> TYPE: PRT
<213> ORGANISM: Lama glama

<400> SEQUENCE: 266

Ala Gln Ser Ala Leu Thr Gln Pro Ser Ala Leu Ser Val Thr Leu Gly
1               5                   10                  15

Gln Thr Ala Lys Ile Thr Cys Gln Gly Gly Ser Leu Gly Thr Arg Tyr
            20                  25                  30

Ala His Trp Tyr Gln Gln Lys Pro Gly Gln Ala Pro Val Leu Val Ile
        35                  40                  45

Tyr Asp Asp Asp Ser Arg Pro Ser Gly Ile Pro Glu Arg Phe Ser Gly
    50                  55                  60

Ser Ser Ser Gly Gly Arg Ala Thr Leu Thr Ile Ser Gly Ala Gln Ala

```
                65                  70                  75                  80
Glu Asp Glu Gly Asp Tyr Tyr Cys Gln Ser Ala Asp Ser Ser Gly Asn
                    85                  90                  95

Ala Ser Val Phe Gly Gly Gly Thr His Leu Thr Val Leu Gly
                100                 105                 110
```

<210> SEQ ID NO 267
<211> LENGTH: 111
<212> TYPE: PRT
<213> ORGANISM: Lama glama

<400> SEQUENCE: 267

```
Ala Leu Asn Phe Met Leu Thr Gln Pro Ser Ala Leu Ser Val Thr Leu
1               5                   10                  15

Gly Gln Thr Ala Lys Ile Thr Cys Gln Gly Gly Ser Leu Gly Ser Arg
                20                  25                  30

Tyr Ala His Trp Tyr Gln Gln Lys Pro Gly Gln Ala Pro Val Leu Val
                35                  40                  45

Ile Tyr Asp Asp Asp Ser Arg Pro Ser Gly Ile Pro Glu Arg Phe Ser
                50                  55                  60

Gly Ser Ser Ser Gly Gly Arg Ala Thr Leu Thr Ile Ser Gly Ala Gln
65                  70                  75                  80

Ala Glu Asp Glu Gly Asp Tyr Tyr Cys Gln Ser Ala Asp Ser Ser Gly
                85                  90                  95

Asn Ala Ala Val Phe Gly Gly Gly Thr His Leu Thr Val Leu Gly
                100                 105                 110
```

<210> SEQ ID NO 268
<211> LENGTH: 110
<212> TYPE: PRT
<213> ORGANISM: Lama glama

<400> SEQUENCE: 268

```
Ala Gln Ala Gly Leu Thr Gln Pro Ser Ala Leu Ser Val Thr Leu Gly
1               5                   10                  15

Gln Thr Ala Lys Ile Thr Cys Gln Gly Gly Ser Leu Gly Ser Ser Tyr
                20                  25                  30

Ala His Trp Tyr Gln Gln Lys Pro Gly Gln Ala Pro Val Leu Val Ile
                35                  40                  45

Tyr Asp Asp Asp Ser Arg Pro Ser Gly Ile Pro Glu Arg Phe Ser Gly
                50                  55                  60

Ser Ser Ser Gly Gly Arg Ala Thr Leu Thr Ile Ser Gly Ala Gln Ala
65                  70                  75                  80

Glu Asp Glu Gly Asp Tyr Tyr Cys Gln Ser Ala Asp Ser Ser Gly Asn
                85                  90                  95

Ala Ile Val Phe Gly Gly Gly Thr His Leu Thr Val Leu Gly
                100                 105                 110
```

<210> SEQ ID NO 269
<211> LENGTH: 110
<212> TYPE: PRT
<213> ORGANISM: Lama glama

<400> SEQUENCE: 269

```
Ala Gln Ala Val Leu Thr Gln Pro Ser Ala Leu Ser Val Thr Leu Gly
1               5                   10                  15

Gln Thr Ala Lys Ile Thr Cys Gln Gly Gly Ser Leu Arg Ser Ser Tyr
                20                  25                  30
```

Ala His Trp Tyr Gln Gln Lys Pro Gly Gln Ala Pro Val Leu Val Ile
        35                  40                  45

Tyr Asp Asp Ser Arg Pro Ser Gly Ile Pro Glu Arg Phe Ser Gly
 50                  55                  60

Ser Ser Ser Gly Gly Arg Ala Thr Leu Thr Ile Ser Gly Ala Gln Ala
 65                  70                  75                  80

Glu Asp Glu Gly Asp Tyr Tyr Cys Gln Ser Ala Asp Ser Ser Gly Asn
                 85                  90                  95

Ala Ser Val Phe Gly Gly Gly Thr His Leu Thr Val Leu Gly
             100                 105                 110

<210> SEQ ID NO 270
<211> LENGTH: 110
<212> TYPE: PRT
<213> ORGANISM: Lama glama

<400> SEQUENCE: 270

Ala Leu Asn Phe Met Leu Thr Gln Pro Ser Ala Leu Ser Val Thr Leu
 1               5                  10                  15

Gly Gln Thr Ala Lys Ile Thr Cys Gln Gly Gly Ser Leu Gly Ser Ser
                 20                  25                  30

Tyr Ala His Trp Tyr Gln Gln Lys Pro Gly Gln Ala Pro Val Leu Val
                 35                  40                  45

Ile Tyr Asp Asp Ser Arg Pro Ser Gly Ile Pro Glu Arg Phe Ser
         50                  55                  60

Gly Ser Ser Ser Gly Gly Arg Ala Thr Leu Thr Ile Ser Gly Ala Gln
 65                  70                  75                  80

Ala Glu Asp Glu Gly Asp Tyr Tyr Cys Gln Ser Ala Asp Ser Ser Gly
                 85                  90                  95

Asn Ala Val Phe Gly Gly Gly Thr His Leu Thr Val Leu Gly
             100                 105                 110

<210> SEQ ID NO 271
<211> LENGTH: 110
<212> TYPE: PRT
<213> ORGANISM: Lama glama

<400> SEQUENCE: 271

Ala Gln Ser Ala Leu Thr Gln Pro Ser Ala Leu Ser Val Thr Leu Gly
 1               5                  10                  15

Gln Thr Ala Lys Ile Thr Cys Gln Gly Gly Ser Leu Gly Ser Ser Tyr
                 20                  25                  30

Ala His Trp Tyr Gln Gln Lys Pro Gly Gln Ala Pro Val Leu Val Ile
                 35                  40                  45

Tyr Asp Asp Ser Arg Pro Ser Gly Ile Pro Glu Arg Phe Ser Gly
 50                  55                  60

Ser Ser Ser Gly Gly Arg Ala Thr Leu Thr Ile Ser Gly Ala Gln Ala
 65                  70                  75                  80

Glu Asp Glu Gly Asp Tyr Tyr Cys Gln Ser Ala Asp Ser Ser Gly Asn
                 85                  90                  95

Ala Ser Val Phe Gly Gly Gly Thr His Leu Thr Val Leu Gly
             100                 105                 110

<210> SEQ ID NO 272
<211> LENGTH: 111
<212> TYPE: PRT
<213> ORGANISM: Lama glama

<400> SEQUENCE: 272

```
Ala Leu Asn Phe Met Leu Thr Gln Pro Ser Ala Leu Ser Val Thr Leu
1               5                   10                  15

Gly Gln Thr Ala Lys Ile Thr Cys Gln Gly Gly Ser Leu Gly Ser Ser
            20                  25                  30

Tyr Ala His Trp Tyr Gln Gln Lys Pro Gly Gln Ala Pro Val Leu Val
        35                  40                  45

Ile Tyr Asp Asp Asp Ser Arg Pro Ser Gly Ile Pro Glu Arg Phe Ser
    50                  55                  60

Gly Ser Ser Ser Gly Gly Arg Ala Thr Leu Ser Ile Ser Gly Ala Gln
65                  70                  75                  80

Ala Glu Asp Glu Gly Asp Tyr Tyr Cys Gln Ser Gly Asp Ser Ser Gly
                85                  90                  95

Asn Ala Ala Val Phe Gly Gly Gly Thr Lys Leu Thr Val Leu Gly
            100                 105                 110
```

<210> SEQ ID NO 273
<211> LENGTH: 111
<212> TYPE: PRT
<213> ORGANISM: Lama glama

<400> SEQUENCE: 273

```
Gln Ser Ala Leu Thr Gln Pro Pro Leu Val Ser Gly Thr Pro Gly Gln
1               5                   10                  15

Thr Val Thr Ile Ser Cys Ala Gly Ala Asn Asn Asp Ile Gly Thr Tyr
            20                  25                  30

Ala Tyr Val Ser Trp Tyr Gln Gln Leu Pro Gly Thr Ala Pro Lys Leu
        35                  40                  45

Leu Ile Tyr Lys Val Thr Thr Arg Ala Ser Gly Ile Pro Ser Arg Phe
    50                  55                  60

Ser Gly Ser Lys Ser Gly Asn Thr Ala Ser Leu Thr Ile Ser Gly Leu
65                  70                  75                  80

Gln Ser Glu Asp Glu Ala Asp Tyr Tyr Cys Ala Ser Tyr Arg Asn Phe
                85                  90                  95

Asn Asn Ala Val Phe Gly Arg Gly Thr His Leu Thr Val Leu Gly
            100                 105                 110
```

<210> SEQ ID NO 274
<211> LENGTH: 111
<212> TYPE: PRT
<213> ORGANISM: Lama glama

<400> SEQUENCE: 274

```
Gln Ser Ala Leu Thr Gln Pro Pro Ser Val Ser Gly Thr Leu Gly Lys
1               5                   10                  15

Thr Leu Thr Ile Ser Cys Ala Gly Thr Ser Ser Asp Val Gly Tyr Gly
            20                  25                  30

Asn Tyr Val Ser Trp Tyr Gln Gln Leu Pro Gly Thr Ala Pro Lys Leu
        35                  40                  45

Leu Ile Tyr Arg Val Ser Thr Arg Ala Ser Gly Ile Pro Asp Arg Phe
    50                  55                  60

Ser Gly Ser Lys Ser Gly Asn Thr Ala Ser Leu Thr Ile Ser Gly Leu
65                  70                  75                  80

Gln Ser Glu Asp Glu Ala Asp Tyr Tyr Cys Ala Ser Tyr Arg Ser Ser
                85                  90                  95
```

```
Asn Asn Ala Val Phe Gly Gly Gly Thr His Leu Thr Val Leu Gly
            100                 105                 110

<210> SEQ ID NO 275
<211> LENGTH: 111
<212> TYPE: PRT
<213> ORGANISM: Lama glama

<400> SEQUENCE: 275

Gln Ser Val Leu Thr Gln Pro Pro Ser Val Gly Thr Leu Gly Lys
1               5                   10                  15

Thr Val Thr Ile Ser Cys Ala Gly Thr Ser Ser Asp Val Gly Tyr Gly
            20                  25                  30

Asn Tyr Val Ser Trp Tyr Gln Gln Leu Pro Gly Thr Ala Pro Lys Leu
            35                  40                  45

Leu Ile Tyr Ala Val Ser Tyr Arg Val Ser Gly Ile Pro Asp Arg Phe
        50                  55                  60

Ser Gly Ser Lys Ser Gly Asn Thr Ala Ser Leu Thr Ile Ser Gly Leu
65                  70                  75                  80

Gln Ser Glu Asp Glu Ala Asp Tyr Tyr Cys Ala Ser Tyr Arg Asn Arg
                85                  90                  95

Asn Asn Ala Val Phe Gly Gly Gly Thr His Leu Thr Val Leu Gly
            100                 105                 110

<210> SEQ ID NO 276
<211> LENGTH: 111
<212> TYPE: PRT
<213> ORGANISM: Lama glama

<400> SEQUENCE: 276

Gln Ala Val Leu Thr Gln Pro Pro Ser Val Gly Thr Leu Gly Lys
1               5                   10                  15

Thr Val Thr Ile Ser Cys Ala Gly Thr Ser Ser Asp Val Gly Tyr Gly
            20                  25                  30

Asn Tyr Val Ser Trp Tyr Gln Gln Leu Pro Gly Thr Ala Pro Lys Leu
            35                  40                  45

Val Ile Tyr Ala Val Asn Tyr Arg Ala Ser Gly Ile Pro Asp Arg Phe
        50                  55                  60

Ser Gly Ser Lys Ser Gly Asn Thr Ala Ser Leu Phe Ile Ser Gly Leu
65                  70                  75                  80

Gln Ser Glu Asp Glu Ala Asp Tyr Tyr Cys Ala Ser Tyr Arg Asp Phe
                85                  90                  95

Asn Asn Ala Val Phe Gly Gly Gly Thr His Leu Thr Val Leu Gly
            100                 105                 110

<210> SEQ ID NO 277
<211> LENGTH: 111
<212> TYPE: PRT
<213> ORGANISM: Lama glama

<400> SEQUENCE: 277

Gln Ala Val Leu Thr Gln Pro Pro Ser Val Gly Ser Pro Gly Lys
1               5                   10                  15

Thr Val Thr Ile Ser Cys Ala Gly Thr Ser Ser Asp Val Gly Phe Gly
            20                  25                  30

Asn Tyr Val Ser Trp Tyr Gln Gln Leu Pro Gly Met Ala Pro Lys Leu
            35                  40                  45

Leu Ile Tyr Glu Val Asn Lys Arg Thr Ser Gly Ile Pro Asp Arg Phe
```

```
                50                  55                  60
Ser Gly Ser Lys Ser Gly Asn Thr Ala Ser Leu Thr Ile Ser Gly Leu
 65                  70                  75                  80

Gln Ser Glu Asp Glu Ala Asp Tyr His Cys Ala Ser Tyr Arg Asn Phe
                 85                  90                  95

Asn Asn Ala Val Phe Gly Gly Gly Thr His Leu Thr Val Leu Gly
                100                 105                 110

<210> SEQ ID NO 278
<211> LENGTH: 111
<212> TYPE: PRT
<213> ORGANISM: Lama glama

<400> SEQUENCE: 278

Gln Ser Ala Leu Thr Gln Pro Pro Ser Val Ser Gly Ser Pro Gly Lys
 1               5                  10                  15

Thr Val Thr Ile Ser Cys Ala Gly Thr Ser Ser Asp Val Gly Tyr Gly
                20                  25                  30

Asn Tyr Val Ser Trp Tyr Gln Gln Leu Pro Gly Met Ala Pro Lys Leu
             35                  40                  45

Leu Ile Tyr Asp Val Asn Lys Arg Ala Ser Gly Ile Ala Asp Arg Phe
         50                  55                  60

Ser Gly Ser Lys Ser Gly Asn Thr Ala Ser Leu Thr Ile Ser Arg Leu
 65                  70                  75                  80

Gln Ser Glu Asp Glu Ala Asp Tyr Tyr Cys Ala Ser Tyr Lys Thr Tyr
                 85                  90                  95

Asn Asn Val Val Phe Gly Gly Gly Thr His Leu Thr Val Leu Gly
                100                 105                 110

<210> SEQ ID NO 279
<211> LENGTH: 111
<212> TYPE: PRT
<213> ORGANISM: Lama glama

<400> SEQUENCE: 279

Gln Ser Ala Leu Thr Gln Pro Pro Ser Val Ser Gly Thr Leu Gly Lys
 1               5                  10                  15

Thr Val Thr Ile Ser Cys Ala Gly Thr Ser Ser Asp Val Gly Tyr Gly
                20                  25                  30

Asn Tyr Val Ser Trp Tyr Gln Gln Leu Pro Gly Thr Ala Pro Lys Leu
             35                  40                  45

Leu Ile Tyr Ala Val Ser Tyr Arg Ala Ser Gly Ile Pro Asp Arg Phe
         50                  55                  60

Ser Gly Ser Lys Ser Gly Asn Thr Ala Ser Leu Thr Ile Ser Gly Leu
 65                  70                  75                  80

Gln Ser Glu Asp Glu Ala Asp Tyr Tyr Cys Ala Ser Tyr Arg Tyr Phe
                 85                  90                  95

Asn Asn Ala Val Phe Gly Gly Gly Thr His Leu Thr Val Leu Gly
                100                 105                 110

<210> SEQ ID NO 280
<211> LENGTH: 109
<212> TYPE: PRT
<213> ORGANISM: Lama glama

<400> SEQUENCE: 280

Leu Asp Ile Val Met Thr Gln Thr Pro Ser Ser Leu Ser Ala Ser Leu
 1               5                  10                  15
```

```
Gly Asp Arg Val Thr Ile Thr Cys Gln Ala Thr Gln Asn Ile Asn Thr
            20                  25                  30

Glu Leu Ser Trp Tyr Gln Gln Lys Pro Gly Gln Thr Pro Lys Leu Leu
        35                  40                  45

Ile Tyr Asp Thr Ser Arg Leu Gln Thr Gly Val Pro Ser Arg Phe Ser
    50                  55                  60

Gly Ser Gly Ser Arg Thr Thr Phe Thr Leu Thr Ile Ser Gly Leu Glu
65                  70                  75                  80

Ala Glu Asp Leu Ala Thr Tyr Tyr Cys Met Gln Asp Tyr Asn Trp Pro
                85                  90                  95

Leu Thr Phe Gly Gln Gly Thr Lys Val Glu Leu Lys Arg
            100                 105

<210> SEQ ID NO 281
<211> LENGTH: 108
<212> TYPE: PRT
<213> ORGANISM: Lama glama

<400> SEQUENCE: 281

Leu Asp Ile Val Met Thr Gln Thr Pro Ser Ser Leu Ser Ala Ser Leu
1               5                   10                  15

Gly Asp Arg Val Thr Ile Thr Cys Gln Ala Ser Gln Ser Ile Ser Thr
            20                  25                  30

Glu Leu Ser Trp Tyr Gln Gln Lys Pro Gly Gln Ser Pro Lys Leu Leu
        35                  40                  45

Ile Tyr Gly Ala Ser Arg Leu Gln Ile Gly Val Pro Ser Arg Phe Ser
    50                  55                  60

Gly Ser Gly Ser Gly Thr Ser Phe Thr Leu Thr Ile Ser Gly Leu Glu
65                  70                  75                  80

Ala Asp Asp Leu Ala Thr Tyr Tyr Cys Leu Gln Asp Tyr Asn Trp Pro
                85                  90                  95

Leu Ser Phe Gly Ser Gly Thr Arg Leu Glu Ile Lys
            100                 105

<210> SEQ ID NO 282
<211> LENGTH: 109
<212> TYPE: PRT
<213> ORGANISM: Lama glama

<400> SEQUENCE: 282

Leu Asp Ile Gln Met Thr Gln Ser Pro Ser Ser Leu Ser Ala Ser Leu
1               5                   10                  15

Gly Asp Arg Val Thr Ile Thr Cys Gln Ala Ser Gln Ser Ile Ser Thr
            20                  25                  30

Glu Leu Ala Trp Tyr Gln Gln Lys Pro Gly Gln Thr Pro Lys Leu Leu
        35                  40                  45

Ile Tyr Gly Ala Ser Lys Leu Gln Thr Gly Val Pro Ser Arg Phe Ser
    50                  55                  60

Gly Ser Gly Ser Gly Thr Ser Phe Thr Leu Thr Ile Ser Gly Leu Glu
65                  70                  75                  80

Ala Glu Asp Leu Ala Thr Tyr Tyr Cys Leu Gln Asp Tyr Asn Trp Pro
                85                  90                  95

Phe Thr Phe Gly Gln Gly Thr Lys Val Glu Leu Lys Arg
            100                 105

<210> SEQ ID NO 283
```

```
<211> LENGTH: 109
<212> TYPE: PRT
<213> ORGANISM: Lama glama

<400> SEQUENCE: 283

Leu Asp Ile Val Met Thr Gln Thr Pro Ser Ser Leu Ser Ala Ser Leu
1               5                   10                  15

Gly Asp Arg Val Ala Ile Thr Cys Gln Ala Ser Gln Ser Ile Asn Val
                20                  25                  30

Asp Val Ser Trp Tyr Gln Gln Lys Pro Gly Gln Thr Pro Lys Leu Leu
            35                  40                  45

Ile Tyr Ala Ala Ser Arg Leu Gln Thr Gly Val Pro Ser Arg Phe Ser
        50                  55                  60

Gly Ser Gly Ser Gly Thr Ser Phe Ala Leu Thr Ile Ser Gly Leu Glu
65                  70                  75                  80

Ala Glu Asp Leu Ala Ser Tyr Tyr Cys Leu Gln Asp Tyr Ser Trp Pro
                85                  90                  95

Leu Thr Phe Gly Gln Gly Thr Lys Val Glu Leu Lys Arg
                100                 105

<210> SEQ ID NO 284
<211> LENGTH: 109
<212> TYPE: PRT
<213> ORGANISM: Lama glama

<400> SEQUENCE: 284

Leu Asp Ile Gln Met Thr Gln Ser Pro Ser Ser Leu Ser Val Phe Leu
1               5                   10                  15

Gly Asp Arg Val Thr Ile Thr Cys Gln Ala Ser Gln Arg Ile Ser Thr
                20                  25                  30

Glu Leu Ser Trp Tyr Gln Gln Lys Pro Gly Gln Thr Pro Lys Leu Leu
            35                  40                  45

Ile Trp Gly Ala Ser Arg Leu Gln Thr Arg Val Pro Ser Arg Phe Ser
        50                  55                  60

Gly Ser Gly Ser Gly Thr Ser Phe Thr Leu Thr Ile Ser Gly Leu Glu
65                  70                  75                  80

Ala Glu Asp Leu Ala Thr Tyr Tyr Cys Leu Gln Asp Tyr Ser Trp Pro
                85                  90                  95

Leu Thr Phe Gly Gln Gly Thr Lys Val Glu Leu Lys Arg
                100                 105

<210> SEQ ID NO 285
<211> LENGTH: 109
<212> TYPE: PRT
<213> ORGANISM: Lama glama

<400> SEQUENCE: 285

Leu Asp Ile Val Met Thr Gln Ser Pro Ser Ser Leu Ser Ala Ser Leu
1               5                   10                  15

Gly Asp Arg Val Thr Ile Thr Cys Gln Ala Ser Gln Asn Ile Ile Thr
                20                  25                  30

Glu Leu Ser Trp Tyr Gln Gln Lys Pro Gly Gln Thr Pro Lys Leu Leu
            35                  40                  45

Ile Tyr Gly Ala Ser Arg Leu Gln Thr Gly Val Pro Ser Arg Phe Ser
        50                  55                  60

Gly Ser Gly Ser Gly Thr Ser Phe Thr Leu Thr Ile Ser Gly Leu Glu
65                  70                  75                  80
```

-continued

Ala Glu Asp Leu Ala Thr Tyr Tyr Cys Leu Gln Asp Tyr Asn Trp Pro
            85                  90                  95

Leu Thr Phe Gly Gln Gly Thr Lys Val Glu Leu Lys Arg
            100                 105

<210> SEQ ID NO 286
<211> LENGTH: 109
<212> TYPE: PRT
<213> ORGANISM: Lama glama

<400> SEQUENCE: 286

Leu Asp Ile Val Met Thr Gln Thr Pro Ser Ser Leu Ser Ala Ser Leu
1               5                   10                  15

Gly Asp Arg Val Thr Ile Thr Cys Gln Ala Ser Gln Asn Ile Asn Thr
            20                  25                  30

Asp Leu Ser Trp Tyr Gln Gln Lys Pro Gly Gln Thr Pro Lys Leu Leu
        35                  40                  45

Phe Tyr Gly Ala Ser Gly Leu Gln Thr Gly Ile Pro Ser Arg Phe Ser
    50                  55                  60

Gly Ser Gly Ser Gly Thr Ser Phe Thr Leu Ala Ile Ser Gly Leu Glu
65                  70                  75                  80

Ala Glu Asp Leu Ala Thr Tyr Tyr Cys Leu Gln Asp Tyr Asn Trp Pro
            85                  90                  95

Leu Thr Phe Gly Gln Gly Thr Lys Val Glu Leu Lys Arg
            100                 105

<210> SEQ ID NO 287
<211> LENGTH: 108
<212> TYPE: PRT
<213> ORGANISM: Lama glama

<400> SEQUENCE: 287

Leu Glu Ile Val Met Thr Gln Ser Pro Ser Ser Leu Ser Ala Ser Val
1               5                   10                  15

Gly Asp Arg Val Thr Ile Thr Cys Gln Ala Ser Gln Ser Ile Ser Thr
            20                  25                  30

Glu Leu Ser Trp Tyr Gln Gln Lys Pro Gly Gln Thr Pro Lys Leu Leu
        35                  40                  45

Ile Tyr Asp Ala Ser Arg Leu Gln Thr Gly Val Pro Ser Arg Phe Ser
    50                  55                  60

Gly Ser Arg Ser Gly Thr Thr Phe Thr Leu Thr Ile Ser Gly Leu Glu
65                  70                  75                  80

Ala Glu Asp Leu Ala Thr Tyr Tyr Cys Leu Gln Asp Tyr Asn Trp Pro
            85                  90                  95

Leu Thr Phe Gly Gln Gly Thr Lys Val Glu Leu Lys
            100                 105

<210> SEQ ID NO 288
<211> LENGTH: 108
<212> TYPE: PRT
<213> ORGANISM: Lama glama

<400> SEQUENCE: 288

Leu Asp Ile Val Met Thr Gln Ser Pro Ser Ser Leu Ser Ala Ser Leu
1               5                   10                  15

Gly Asp Arg Val Thr Ile Thr Cys Gln Ala Thr Gln Ser Ile Ser Thr
            20                  25                  30

Glu Leu Ser Trp Tyr Gln Gln Lys Pro Gly Gln Ala Pro Lys Leu Leu

```
                35                  40                  45
Ile Tyr Asp Ala Ser Lys Leu Gln Thr Gly Val Pro Ser Arg Phe Ser
 50                  55                  60

Gly Ser Gly Ser Gly Arg Ser Phe Thr Leu Thr Ile Ser Gly Leu Glu
 65                  70                  75                  80

Ala Glu Asp Ser Ala Thr Tyr Tyr Cys Leu Gln Asp Tyr Asn Trp Pro
                 85                  90                  95

Leu Ser Phe Gly Ser Gly Thr Arg Leu Glu Ile Lys
                100                 105

<210> SEQ ID NO 289
<211> LENGTH: 109
<212> TYPE: PRT
<213> ORGANISM: Lama glama

<400> SEQUENCE: 289

Leu Asp Ile Gln Leu Thr Gln Ser Pro Ser Ser Leu Ser Ala Ser Leu
 1               5                  10                  15

Gly Asp Arg Val Thr Ile Thr Cys Gln Ala Ser Gln Ser Ile Asn Ile
                 20                  25                  30

Asp Leu Ser Trp Tyr Gln Gln Lys Pro Gly Gln Thr Pro Lys Leu Leu
             35                  40                  45

Phe Tyr Gly Ala Ser Gly Leu Gln Ala Gly Val Pro Ser Arg Phe Ser
 50                  55                  60

Gly Ser Gly Ser Gly Thr Ser Phe Thr Leu Thr Ile Asn Gly Leu Glu
 65                  70                  75                  80

Ala Glu Asp Leu Ala Thr Tyr Tyr Cys Leu Gln Asp Tyr Asn Trp Pro
                 85                  90                  95

Leu Thr Phe Gly Gln Gly Thr Lys Val Glu Leu Lys Arg
                100                 105

<210> SEQ ID NO 290
<211> LENGTH: 109
<212> TYPE: PRT
<213> ORGANISM: Lama glama

<400> SEQUENCE: 290

Leu Glu Thr Thr Leu Thr Gln Ser Pro Ser Ser Leu Ser Val Ser Leu
 1               5                  10                  15

Gly Asp Arg Val Thr Ile Thr Cys Gln Ala Ser Gln Arg Ile Ser Thr
                 20                  25                  30

Glu Leu Ser Trp Tyr Gln Gln Lys Pro Gly Gln Ala Pro Lys Leu Leu
             35                  40                  45

Ile Tyr Asp Ala Ser Thr Leu Gln Thr Gly Val Pro Phe Arg Phe Gly
 50                  55                  60

Gly Ser Gly Ser Gly Thr Ser Phe Thr Leu Thr Ile Ser Gly Leu Glu
 65                  70                  75                  80

Ala Glu Asp Leu Ala Thr Tyr Tyr Cys Leu Gln Asp Tyr Ser Trp Pro
                 85                  90                  95

Leu Thr Phe Gly Gln Gly Thr Lys Val Glu Leu Asn Arg
                100                 105

<210> SEQ ID NO 291
<211> LENGTH: 113
<212> TYPE: PRT
<213> ORGANISM: Lama glama

<400> SEQUENCE: 291
```

-continued

Ala Leu Ser Tyr Asp Leu Thr Gln Pro Pro Ser Val Ser Gly Ser Pro
1               5                   10                  15

Gly Lys Thr Val Thr Ile Ser Cys Ala Gly Thr Ser Ser Asp Val Gly
                20                  25                  30

Tyr Gly Asn Tyr Val Ser Trp Tyr Gln Gln Leu Pro Gly Met Ala Pro
            35                  40                  45

Lys Ile Leu Ile Tyr Asp Val Asn Lys Arg Ala Ser Gly Ile Ala Asp
        50                  55                  60

Arg Phe Ser Gly Ser Lys Ser Gly Asn Thr Ala Ser Leu Thr Ile Ser
65                  70                  75                  80

Gly Leu Gln Ser Glu Asp Glu Ala Asp Tyr Tyr Cys Ala Ser Tyr Arg
                85                  90                  95

Arg Gly Glu Thr Ile Val Phe Gly Gly Gly Thr His Leu Thr Val Leu
                100                 105                 110

Gly

<210> SEQ ID NO 292
<211> LENGTH: 113
<212> TYPE: PRT
<213> ORGANISM: Lama glama

<400> SEQUENCE: 292

Ala Leu Ser Tyr Glu Leu Thr Gln Pro Pro Ser Val Ser Gly Ser Pro
1               5                   10                  15

Gly Lys Thr Val Thr Ile Ser Cys Ala Gly Thr Ser Ser Asp Val Gly
                20                  25                  30

Tyr Gly Asn Tyr Val Ser Trp Tyr Gln Gln Leu Pro Gly Met Ala Pro
            35                  40                  45

Lys Leu Leu Ile Tyr Asp Val Asn Lys Arg Ala Ser Gly Ile Ala Asp
        50                  55                  60

Arg Phe Ser Gly Ser Lys Ser Gly Asn Thr Ala Ser Leu Thr Ile Ser
65                  70                  75                  80

Gly Leu Gln Ser Glu Asp Glu Ala Asp Tyr Tyr Cys Ala Ser Tyr Arg
                85                  90                  95

Leu Gly Asn Lys Tyr Val Phe Gly Gly Gly Thr Lys Leu Thr Val Leu
                100                 105                 110

Gly

<210> SEQ ID NO 293
<211> LENGTH: 112
<212> TYPE: PRT
<213> ORGANISM: Lama glama

<400> SEQUENCE: 293

Ala Gln Ser Val Leu Thr Gln Pro Pro Ser Val Ser Gly Ser Pro Gly
1               5                   10                  15

Gln Thr Val Thr Ile Ser Cys Ala Gly Thr Ser Glu Asp Val Gly Tyr
                20                  25                  30

Gly Asn Tyr Val Ser Trp Tyr Gln Gln Leu Pro Gly Met Ala Pro Lys
            35                  40                  45

Leu Leu Ile Tyr Asp Val Asn Lys Arg Ala Ser Gly Ile Ala Asp Arg
        50                  55                  60

Phe Ser Gly Ser Lys Ser Gly Asn Thr Ala Ser Leu Thr Ile Ser Gly
65                  70                  75                  80

Leu Gln Ser Glu Asp Glu Ala Asp Tyr Tyr Cys Ala Ser Tyr Arg Arg

```
                    85                  90                  95

Thr Ile Asp Asn Ile Phe Gly Gly Gly Thr His Leu Thr Val Leu Gly
                100                 105                 110

<210> SEQ ID NO 294
<211> LENGTH: 112
<212> TYPE: PRT
<213> ORGANISM: Lama glama

<400> SEQUENCE: 294

Ala Gln Ser Ala Leu Thr Gln Pro Pro Ser Val Ser Gly Ser Pro Gly
1               5                   10                  15

Lys Thr Val Thr Ile Ser Cys Ala Gly Thr Ser Ser Asp Ile Gly Tyr
                20                  25                  30

Gly Asn Tyr Val Ser Trp Tyr Gln Gln Phe Pro Gly Met Ala Pro Lys
            35                  40                  45

Phe Leu Ile Tyr Asp Val His Arg Arg Ala Ser Gly Ile Ala Asp Arg
        50                  55                  60

Phe Ser Gly Ser Lys Ser Gly Asn Thr Ala Ser Leu Thr Ile Ser Gly
65                  70                  75                  80

Leu Gln Pro Glu Asp Glu Ala Val Tyr Tyr Cys Ala Ser Tyr Arg Arg
                85                  90                  95

Gly Ser Asn Ala Val Phe Gly Gly Gly Thr His Leu Thr Val Leu Gly
                100                 105                 110

<210> SEQ ID NO 295
<211> LENGTH: 113
<212> TYPE: PRT
<213> ORGANISM: Lama glama

<400> SEQUENCE: 295

Ala Leu Asn Phe Met Leu Thr Gln Pro Pro Ser Val Ser Gly Ser Pro
1               5                   10                  15

Gly Lys Thr Val Thr Ile Ser Cys Ala Gly Thr Ser Ser Asp Val Gly
                20                  25                  30

Tyr Gly Asn Tyr Val Ser Trp Tyr Gln Gln Leu Pro Gly Thr Ala Pro
            35                  40                  45

Lys Leu Leu Ile Tyr Asn Val Asn Lys Arg Ala Ser Gly Ile Thr Asp
        50                  55                  60

Arg Phe Ser Gly Ser Lys Ser Gly Asn Thr Ala Ser Leu Thr Ile Ser
65                  70                  75                  80

Gly Leu Gln Ser Glu Asp Glu Ala Asp Tyr Tyr Cys Ala Ser Tyr Arg
                85                  90                  95

Thr Gly Asp Asn Ala Ala Phe Gly Gly Gly Thr Lys Leu Thr Val Leu
                100                 105                 110

Gly

<210> SEQ ID NO 296
<211> LENGTH: 112
<212> TYPE: PRT
<213> ORGANISM: Lama glama

<400> SEQUENCE: 296

Ala Gln Ser Val Leu Thr Gln Pro Pro Ser Val Ser Gly Ser Pro Gly
1               5                   10                  15

Lys Thr Val Thr Ile Ser Cys Ala Gly Thr Ser Ser Asp Val Gly Tyr
                20                  25                  30
```

Gly Asn Tyr Val Ser Trp Tyr Gln Gln Leu Pro Gly Met Ala Pro Lys
                35                  40                  45

Leu Leu Ile Tyr Asp Val Asn Lys Arg Ala Ser Gly Ile Ala Asp Arg
    50                  55                  60

Phe Ser Gly Ser Lys Phe Ala Asn Thr Ala Ser Leu Thr Ile Ser Gly
65                  70                  75                  80

Leu Gln Ser Glu Asp Glu Ala Asp Tyr Tyr Cys Ala Ser Tyr Lys Arg
                85                  90                  95

Gly Asp Asn Ala Val Phe Gly Gly Gly Thr Lys Leu Thr Val Leu Gly
                100                 105                 110

<210> SEQ ID NO 297
<211> LENGTH: 112
<212> TYPE: PRT
<213> ORGANISM: Lama glama

<400> SEQUENCE: 297

Ala Gln Ser Val Val Thr Gln Pro Pro Ser Val Ser Gly Ser Pro Gly
1               5                   10                  15

Lys Thr Val Thr Ile Ser Cys Ala Gly Thr Ser Ser Asp Val Gly Tyr
                20                  25                  30

Gly Asn Tyr Val Ser Trp Tyr Gln Gln Leu Pro Gly Met Ala Pro Lys
                35                  40                  45

Leu Leu Ile Tyr Asp Val Ser Lys Arg Ala Ser Gly Ile Ala Asp Arg
    50                  55                  60

Phe Ser Gly Ser Lys Ser Gly Asn Thr Ala Ser Leu Thr Ile Ser Gly
65                  70                  75                  80

Leu Gln Ser Glu Asp Glu Ala Asp Tyr Val Cys Ala Ser Tyr Arg Arg
                85                  90                  95

Gly Gly Thr Ala Val Phe Gly Gly Gly Thr His Leu Thr Val Leu Gly
                100                 105                 110

<210> SEQ ID NO 298
<211> LENGTH: 107
<212> TYPE: PRT
<213> ORGANISM: Lama glama

<400> SEQUENCE: 298

Asp Val Val Met Thr Gln Ser Pro Ser Ser Leu Pro Thr Ser Leu Gly
1               5                   10                  15

Asp Ser Val Thr Ile Thr Cys Gln Ala Ser Gln Ser Ile Ser Asp Glu
                20                  25                  30

Leu Ser Trp Tyr Gln Gln Lys Pro Gly Gln Thr Pro Lys Leu Leu Ile
                35                  40                  45

Tyr Gly Ala Ser Lys Leu Gln Thr Gly Val Pro Ser Arg Phe Ser Gly
    50                  55                  60

Ser Gly Ser Gly Thr Ser Phe Thr Leu Thr Ile Ser Gly Leu Glu Ala
65                  70                  75                  80

Glu Asp Leu Ala Thr Tyr Tyr Cys Leu Gln Gly Tyr Ser Trp Pro Phe
                85                  90                  95

Met Phe Gly Gln Gly Thr Lys Val Glu Leu Lys
                100                 105

<210> SEQ ID NO 299
<211> LENGTH: 107
<212> TYPE: PRT
<213> ORGANISM: Lama glama -continued

<400> SEQUENCE: 299

Asp Ile Gln Met Thr Gln Ser Pro Ser Leu Pro Thr Ser Leu Gly
1               5                   10                  15

Asp Ser Val Thr Ile Thr Cys Gln Ala Ser Gln Ser Ile Ser Asp Glu
            20                  25                  30

Leu Ser Trp Tyr Gln Gln Lys Pro Gly Gln Thr Pro Lys Leu Leu Ile
        35                  40                  45

Tyr Gly Ala Ser Lys Leu Gln Thr Gly Val Pro Ser Arg Phe Ser Gly
    50                  55                  60

Ser Gly Ser Gly Thr Ser Phe Thr Leu Thr Ile Ser Gly Leu Glu Ala
65                  70                  75                  80

Glu Asp Leu Ala Thr Tyr Tyr Cys Leu Gln Gly Tyr Ser Trp Pro Phe
                85                  90                  95

Met Phe Gly Gln Gly Thr Lys Val Glu Leu Lys
            100                 105

<210> SEQ ID NO 300
<211> LENGTH: 107
<212> TYPE: PRT
<213> ORGANISM: Lama glama

<400> SEQUENCE: 300

Asp Ile Gln Met Thr Gln Ser Pro Ser Leu Pro Thr Ser Leu Gly
1               5                   10                  15

Asp Ser Val Thr Ile Thr Cys Gln Ala Ser Gln Ser Ile Ser Asp Glu
            20                  25                  30

Leu Ser Trp Tyr Gln Gln Lys Pro Gly Gln Thr Pro Lys Leu Leu Ile
        35                  40                  45

Tyr Gly Ala Ser Arg Leu Gln Thr Gly Val Pro Ser Arg Phe Ser Gly
    50                  55                  60

Arg Gly Ser Gly Thr Ser Phe Thr Leu Thr Ile Ser Gly Leu Glu Ala
65                  70                  75                  80

Glu Asp Leu Ala Thr Tyr Tyr Cys Leu Gln Gly Tyr Ser Trp Pro Phe
                85                  90                  95

Met Phe Gly Gln Gly Thr Lys Val Glu Leu Lys
            100                 105

<210> SEQ ID NO 301
<211> LENGTH: 107
<212> TYPE: PRT
<213> ORGANISM: Lama glama

<400> SEQUENCE: 301

Asp Ile Gln Leu Thr Gln Ser Pro Ser Leu Ser Ala Ser Leu Gly
1               5                   10                  15

Asp Ser Val Thr Ile Thr Cys Gln Ala Ser Gln Ser Ile Ser Asp Glu
            20                  25                  30

Leu Ser Trp Tyr Gln Gln Lys Pro Gly Gln Thr Pro Lys Leu Leu Ile
        35                  40                  45

Tyr Gly Ala Ser Lys Leu Gln Thr Gly Val Pro Ser Arg Phe Ser Gly
    50                  55                  60

Ser Gly Ser Gly Thr Ser Phe Thr Leu Thr Ile Ser Gly Leu Glu Ala
65                  70                  75                  80

Glu Asp Leu Ala Thr Tyr Tyr Cys Leu Gln Gly Tyr Arg Trp Pro Phe
                85                  90                  95

Met Phe Gly Gln Gly Thr Lys Val Glu Leu Lys

```
<210> SEQ ID NO 302
<211> LENGTH: 107
<212> TYPE: PRT
<213> ORGANISM: Lama glama
<220> FEATURE:
<221> NAME/KEY: misc_feature
<222> LOCATION: (65)..(65)
<223> OTHER INFORMATION: Xaa can be any naturally occurring amino acid
<220> FEATURE:
<221> NAME/KEY: misc_feature
<222> LOCATION: (97)..(97)
<223> OTHER INFORMATION: Xaa can be any naturally occurring amino acid
<220> FEATURE:
<221> NAME/KEY: misc_feature
<222> LOCATION: (100)..(100)
<223> OTHER INFORMATION: Xaa can be any naturally occurring amino acid

<400> SEQUENCE: 302

Asp Ile Gln Met Thr Gln Ser Pro Ser Leu Ser Thr Ser Leu Gly
1               5                   10                  15

Asp Arg Val Thr Ile Thr Cys Gln Ala Ser Gln Ser Ile Ser Thr Glu
            20                  25                  30

Leu Ser Trp Tyr Gln Gln Lys Pro Gly Gln Thr Pro Lys Leu Leu Ile
        35                  40                  45

Tyr Gly Ala Ser Arg Leu Gln Thr Gly Val Pro Ser Arg Phe Ser Gly
    50                  55                  60

Xaa Gly Ser Gly Thr Ser Phe Thr Leu Thr Ile Ser Gly Met Glu Ala
65                  70                  75                  80

Glu Asp Leu Ala Thr Tyr Tyr Cys Leu Gln Asp Tyr Ser Trp Pro Tyr
                85                  90                  95

Xaa Phe Gly Xaa Gly Thr Arg Val Glu Ile Lys
            100                 105

<210> SEQ ID NO 303
<211> LENGTH: 110
<212> TYPE: PRT
<213> ORGANISM: Lama glama

<400> SEQUENCE: 303

Gln Thr Val Val Thr Gln Glu Pro Ser Phe Ser Val Ser Pro Gly Gly
1               5                   10                  15

Thr Val Thr Leu Thr Cys Gly Leu Ser Ser Gly Ser Val Thr Ala Ser
            20                  25                  30

Asn Tyr Pro Gly Trp Tyr Gln Gln Thr Pro Gly Gln Ala Pro Arg Thr
        35                  40                  45

Leu Ile Tyr Ser Thr Asn Asp Arg His Ser Gly Val Pro Ser Arg Phe
    50                  55                  60

Ser Gly Ser Ile Ser Gly Asn Lys Ala Ala Leu Thr Ile Thr Gly Ala
65                  70                  75                  80

Gln Pro Asp Asp Glu Ala Asp Tyr Tyr Cys Ala Leu Asp Ile Gly Asp
                85                  90                  95

Ile Thr Glu Phe Gly Gly Gly Thr His Leu Thr Val Leu Gly
            100                 105                 110

<210> SEQ ID NO 304
<211> LENGTH: 110
<212> TYPE: PRT
<213> ORGANISM: Lama glama

<400> SEQUENCE: 304
```

```
Gln Thr Val Val Thr Gln Glu Pro Ser Phe Ser Val Ser Pro Gly Gly
1               5                   10                  15

Thr Val Thr Leu Thr Cys Gly Leu Ser Ser Gly Ser Val Thr Ala Ser
            20                  25                  30

Asn Tyr Pro Gly Trp Tyr Gln Gln Thr Pro Gly Gln Ala Pro Arg Ala
        35                  40                  45

Leu Ile Tyr Ser Thr Asn Asp Arg His Ser Gly Val Pro Ser Arg Phe
    50                  55                  60

Ser Gly Ser Ile Leu Gly Asn Lys Ala Ala Leu Thr Ile Thr Gly Ala
65              70                  75                  80

Gln Ala Asp Asp Glu Ala Asp Tyr Tyr Cys Ala Leu Asp Ile Gly Asp
                85                  90                  95

Ile Thr Glu Phe Gly Gly Gly Thr His Leu Thr Val Leu Gly
            100                 105                 110
```

<210> SEQ ID NO 305
<211> LENGTH: 110
<212> TYPE: PRT
<213> ORGANISM: Lama glama

<400> SEQUENCE: 305

```
Gln Thr Val Val Thr Gln Glu Pro Ser Phe Ser Val Ser Pro Gly Gly
1               5                   10                  15

Thr Val Thr Leu Thr Cys Gly Leu Ser Ser Gly Ser Val Thr Ala Ser
            20                  25                  30

Asn Tyr Pro Gly Trp Tyr Gln Gln Thr Pro Gly Gln Ala Pro Arg Ala
        35                  40                  45

Leu Ile Tyr Ser Thr Asn Asp Arg His Ser Gly Val Pro Ser Arg Phe
    50                  55                  60

Ser Gly Ser Ile Ser Gly Asn Lys Ala Ala Leu Thr Ile Thr Gly Ala
65              70                  75                  80

Gln Pro Glu Asp Glu Ser Asp Tyr Tyr Cys Ala Leu Asp Ile Gly Asp
                85                  90                  95

Ile Thr Glu Phe Gly Gly Gly Thr His Leu Thr Val Leu Gly
            100                 105                 110
```

<210> SEQ ID NO 306
<211> LENGTH: 110
<212> TYPE: PRT
<213> ORGANISM: Lama glama

<400> SEQUENCE: 306

```
Gln Thr Val Val Thr Gln Glu Pro Ser Phe Ser Val Ser Pro Gly Gly
1               5                   10                  15

Thr Val Thr Leu Thr Cys Gly Leu Ser Ser Gly Ser Val Thr Ala Ser
            20                  25                  30

Asn Tyr Pro Gly Trp Tyr Gln Gln Thr Pro Gly Gln Ala Pro Arg Ala
        35                  40                  45

Leu Ile Tyr Ser Thr Asn Asp Arg His Ser Gly Val Pro Asp Arg Phe
    50                  55                  60

Ser Gly Ser Ile Ser Gly Asn Lys Ala Ala Leu Thr Ile Thr Gly Ala
65              70                  75                  80

Gln Ala Glu Asp Glu Ala Asp Tyr Tyr Cys Ala Leu Asp Ile Gly Asp
                85                  90                  95

Ile Thr Glu Phe Gly Gly Gly Thr His Leu Thr Val Leu Gly
            100                 105                 110
```

<210> SEQ ID NO 307
<211> LENGTH: 110
<212> TYPE: PRT
<213> ORGANISM: Lama glama

<400> SEQUENCE: 307

Gln Thr Val Val Thr Gln Glu Pro Ser Leu Thr Val Ser Pro Gly Gly
1               5                   10                  15

Thr Val Thr Leu Thr Cys Gly Leu Ser Ser Gly Ser Val Thr Ala Ser
            20                  25                  30

Asn Tyr Pro Gly Trp Phe Gln Gln Lys Pro Gly Gln Ala Pro Arg Ala
        35                  40                  45

Leu Ile Tyr Ser Thr Asn Asp Arg His Ser Trp Val Pro Ser Arg Phe
    50                  55                  60

Ser Gly Ser Ile Leu Gly Gly Lys Ala Ala Leu Thr Leu Leu Gly Ala
65                  70                  75                  80

Gln Pro Glu Asp Glu Ala Glu Tyr Tyr Cys Ala Leu Asp Ile Gly Asp
                85                  90                  95

Ile Thr Glu Phe Gly Gly Gly Thr Gln Leu Thr Val Leu Gly
            100                 105                 110

<210> SEQ ID NO 308
<211> LENGTH: 110
<212> TYPE: PRT
<213> ORGANISM: Lama glama

<400> SEQUENCE: 308

Gln Ala Val Val Thr Gln Glu Pro Ser Leu Ser Val Ser Pro Gly Gly
1               5                   10                  15

Thr Val Thr Leu Thr Cys Gly Leu Ser Ser Gly Ser Val Thr Ala Ser
            20                  25                  30

Asn Tyr Pro Gly Trp Phe Gln Gln Thr Pro Gly Gln Ala Pro Arg Ala
        35                  40                  45

Leu Ile Tyr Ser Thr Asn Asp Arg His Ser Gly Val Pro Ser Arg Phe
    50                  55                  60

Ser Gly Ser Ile Leu Gly Asn Lys Ala Ala Leu Thr Leu Thr Gly Ala
65                  70                  75                  80

Gln Pro Glu Asp Glu Ala Glu Tyr Tyr Cys Ala Leu Asp Ile Gly Asp
                85                  90                  95

Ile Thr Glu Phe Gly Gly Gly Thr His Leu Thr Val Leu Gly
            100                 105                 110

<210> SEQ ID NO 309
<211> LENGTH: 110
<212> TYPE: PRT
<213> ORGANISM: Lama glama

<400> SEQUENCE: 309

Gln Thr Val Val Thr Gln Glu Pro Ser Leu Thr Val Ser Pro Gly Gly
1               5                   10                  15

Thr Val Thr Leu Thr Cys Gly Leu Ser Ser Gly Ser Val Thr Ala Ser
            20                  25                  30

Asn Tyr Pro Gly Trp Phe Gln Gln Lys Pro Gly Gln Ala Pro Arg Ala
        35                  40                  45

Leu Ile Tyr Ser Thr Asn Asp Arg His Ser Gly Val Pro Ala Arg Phe
    50                  55                  60

Ser Gly Ser Leu Leu Gly Gly Lys Ala Ala Leu Thr Ile Leu Gly Ala
65                  70                  75                  80

Gln Ala Asp Asp Glu Ala Glu Tyr Tyr Cys Ala Leu Asp Ile Gly Asp
                85                  90                  95

Ile Thr Glu Phe Gly Gly Gly Thr Gln Leu Thr Val Leu Gly
            100                 105                 110

<210> SEQ ID NO 310
<211> LENGTH: 110
<212> TYPE: PRT
<213> ORGANISM: Lama glama

<400> SEQUENCE: 310

Gln Thr Val Val Thr Gln Glu Pro Ser Leu Thr Val Ser Pro Gly Gly
1               5                   10                  15

Thr Val Thr Leu Thr Cys Gly Leu Ser Ser Gly Ser Val Thr Ala Ser
                20                  25                  30

Asn Tyr Pro Gly Trp Phe Gln Gln Lys Pro Gly Gln Ala Pro Arg Ala
            35                  40                  45

Leu Ile Tyr Ser Thr Asn Asp Arg His Ser Gly Thr Pro Ser Arg Phe
50                  55                  60

Ser Gly Ser Leu Ser Gly Gly Lys Ala Ala Leu Thr Ile Leu Gly Ala
65                  70                  75                  80

Gln Pro Glu Asp Glu Ala Glu Tyr Tyr Cys Ala Leu Asp Ile Gly Asp
                85                  90                  95

Ile Thr Glu Phe Gly Gly Gly Thr Lys Leu Thr Val Leu Gly
            100                 105                 110

<210> SEQ ID NO 311
<211> LENGTH: 110
<212> TYPE: PRT
<213> ORGANISM: Lama glama

<400> SEQUENCE: 311

Gln Thr Val Val Thr Gln Glu Pro Ser Leu Ser Val Ser Pro Gly Gly
1               5                   10                  15

Thr Val Thr Leu Thr Cys Gly Leu Ser Ser Gly Ser Val Thr Ala Ser
                20                  25                  30

Asn Tyr Pro Gly Trp Tyr Gln Gln Thr Pro Gly Gln Ala Pro Arg Ala
            35                  40                  45

Leu Ile Tyr Ser Thr Asn Asp Arg His Ser Gly Val Pro Asp Arg Phe
50                  55                  60

Ser Gly Ser Ile Leu Gly Asn Lys Ala Ala Leu Thr Ile Thr Gly Ala
65                  70                  75                  80

Gln Pro Asp Asp Glu Ala Asp Tyr Tyr Cys Ala Leu Asp Ile Gly Asp
                85                  90                  95

Ile Thr Glu Phe Gly Gly Gly Thr Gln Leu Thr Val Leu Gly
            100                 105                 110

<210> SEQ ID NO 312
<211> LENGTH: 110
<212> TYPE: PRT
<213> ORGANISM: Lama glama

<400> SEQUENCE: 312

Gln Thr Val Val Thr Gln Glu Pro Ser Phe Ser Val Ser Pro Gly Gly
1               5                   10                  15

Thr Val Thr Leu Thr Cys Gly Leu Ser Ser Gly Ser Val Thr Ala Ser

```
                        20                  25                  30

Asn Tyr Pro Gly Trp Tyr Gln Gln Thr Pro Gly Gln Ala Pro Arg Ala
            35                  40                  45

Leu Ile Tyr Ser Thr Asn Asp Arg His Ser Gly Val Pro Asp Arg Phe
        50                  55                  60

Ser Gly Ser Ile Ser Gly Asn Lys Ala Ala Leu Thr Ile Thr Gly Ala
65                  70                  75                  80

Gln Ala Asp Asp Glu Ser Asp Tyr Tyr Cys Ala Leu Asp Ile Gly Asp
                85                  90                  95

Ile Thr Glu Phe Gly Gly Gly Thr Lys Leu Thr Val Leu Gly
                100                 105                 110

<210> SEQ ID NO 313
<211> LENGTH: 110
<212> TYPE: PRT
<213> ORGANISM: Lama glama

<400> SEQUENCE: 313

Gln Thr Val Val Thr Gln Glu Pro Ser Phe Ser Val Ser Pro Gly Gly
1               5                   10                  15

Thr Val Thr Leu Thr Cys Gly Leu Ser Ser Gly Ser Val Thr Ala Ser
            20                  25                  30

Asn Tyr Pro Gly Trp Tyr Gln Gln Thr Pro Gly Gln Ala Pro Arg Thr
            35                  40                  45

Leu Ile Tyr Ser Thr Asn Asp Arg His Ser Gly Val Pro Ser Arg Phe
        50                  55                  60

Ser Gly Ser Ile Ser Gly Asn Lys Ala Ala Leu Thr Ile Thr Gly Ala
65                  70                  75                  80

Gln Pro Glu Asp Glu Ala Asp Tyr Tyr Cys Ala Leu Asp Ile Gly Asp
                85                  90                  95

Ile Thr Glu Phe Gly Gly Gly Thr His Leu Thr Val Leu Gly
                100                 105                 110

<210> SEQ ID NO 314
<211> LENGTH: 110
<212> TYPE: PRT
<213> ORGANISM: Lama glama

<400> SEQUENCE: 314

Gln Thr Val Val Thr Gln Glu Pro Ser Phe Ser Val Ser Pro Gly Gly
1               5                   10                  15

Thr Val Thr Leu Thr Cys Gly Leu Ser Ser Gly Ser Val Thr Ala Ser
            20                  25                  30

Asn Tyr Pro Gly Trp Tyr Gln Gln Thr Pro Gly Gln Ala Pro Arg Ala
            35                  40                  45

Leu Ile Tyr Ser Thr Asn Asp Arg His Ser Gly Val Pro Asp Arg Phe
        50                  55                  60

Ser Gly Ser Ile Ser Gly Asn Lys Ala Ala Leu Thr Ile Thr Gly Ala
65                  70                  75                  80

Gln Ala Asp Asp Glu Ser Asp Tyr Tyr Cys Ala Leu Asp Ile Gly Asp
                85                  90                  95

Ile Thr Glu Phe Gly Gly Gly Thr Lys Leu Thr Val Leu Gly
                100                 105                 110

<210> SEQ ID NO 315
<211> LENGTH: 110
<212> TYPE: PRT
```

<213> ORGANISM: Lama glama

<400> SEQUENCE: 315

Gln Thr Val Val Thr Gln Glu Pro Ser Phe Ser Val Ser Pro Gly Gly
1               5                   10                  15

Thr Val Thr Leu Thr Cys Gly Leu Ser Ser Gly Ser Val Thr Ala Ser
            20                  25                  30

Asn Tyr Pro Gly Trp Tyr Gln Gln Thr Pro Gly Gln Ala Pro Arg Thr
        35                  40                  45

Leu Ile Tyr Ser Thr Asn Asp Arg His Ser Gly Val Pro Ser Arg Phe
    50                  55                  60

Ser Gly Ser Ile Ser Gly Asn Lys Ala Ala Leu Thr Ile Thr Gly Ala
65                  70                  75                  80

Gln Pro Glu Asp Glu Ala Asp Tyr Tyr Cys Ala Leu Asp Ile Gly Asp
                85                  90                  95

Ile Thr Glu Phe Gly Gly Gly Thr His Leu Thr Val Leu Gly
            100                 105                 110

<210> SEQ ID NO 316
<211> LENGTH: 110
<212> TYPE: PRT
<213> ORGANISM: Lama glama

<400> SEQUENCE: 316

Gln Thr Val Val Thr Gln Glu Pro Ser Phe Ser Val Ser Pro Gly Gly
1               5                   10                  15

Thr Val Thr Leu Thr Cys Gly Leu Ser Ser Gly Ser Val Thr Ala Ser
            20                  25                  30

Asn Tyr Pro Gly Trp Tyr Gln Gln Thr Pro Gly Gln Ala Pro Arg Ala
        35                  40                  45

Leu Ile Tyr Ser Thr Asn Asp Arg His Ser Gly Val Pro Asp Arg Phe
    50                  55                  60

Ser Gly Ser Ile Leu Gly Asn Lys Ala Ala Leu Thr Ile Thr Gly Ala
65                  70                  75                  80

Gln Ala Glu Asp Glu Ser Asp Tyr Tyr Cys Ala Leu Asp Ile Gly Asp
                85                  90                  95

Ile Thr Glu Phe Gly Gly Gly Thr His Leu Thr Val Leu Gly
            100                 105                 110

<210> SEQ ID NO 317
<211> LENGTH: 110
<212> TYPE: PRT
<213> ORGANISM: Lama glama

<400> SEQUENCE: 317

Gln Thr Val Val Thr Gln Glu Pro Ser Leu Ser Val Ser Pro Gly Gly
1               5                   10                  15

Thr Val Thr Leu Thr Cys Gly Leu Ser Ser Gly Ser Val Thr Ala Ser
            20                  25                  30

Asn Tyr Pro Gly Trp Tyr Gln Gln Thr Pro Gly Gln Ala Pro Arg Ala
        35                  40                  45

Leu Ile Tyr Ser Thr Asn Asp Arg His Ser Gly Val Pro Asp Arg Phe
    50                  55                  60

Ser Gly Ser Ile Ser Gly Asn Lys Ala Ala Leu Thr Ile Thr Gly Ala
65                  70                  75                  80

Gln Pro Asp Asp Glu Ser Asp Tyr Tyr Cys Ala Leu Asp Ile Gly Asp
                85                  90                  95

Ile Thr Glu Phe Gly Gly Gly Thr Gln Leu Thr Val Leu Gly
            100                 105                 110

<210> SEQ ID NO 318
<211> LENGTH: 110
<212> TYPE: PRT
<213> ORGANISM: Lama glama

<400> SEQUENCE: 318

Gln Thr Val Val Thr Gln Glu Pro Ser Phe Ser Val Ser Pro Gly Gly
1               5                   10                  15

Thr Val Thr Leu Thr Cys Gly Leu Ser Ser Gly Ser Val Thr Ala Ser
            20                  25                  30

Asn Tyr Pro Gly Trp Tyr Gln Gln Thr Pro Gly Gln Ala Pro Arg Ala
        35                  40                  45

Leu Ile Tyr Ser Thr Asn Asp Arg His Ser Gly Val Pro Ser Arg Phe
    50                  55                  60

Ser Gly Ser Ile Ser Gly Asn Lys Ala Ala Leu Thr Ile Thr Gly Ala
65                  70                  75                  80

Gln Ala Glu Asp Glu Ser Asp Tyr Tyr Cys Ala Leu Asp Ile Gly Asp
                85                  90                  95

Ile Thr Glu Phe Gly Gly Gly Thr His Leu Thr Val Leu Gly
            100                 105                 110

<210> SEQ ID NO 319
<211> LENGTH: 110
<212> TYPE: PRT
<213> ORGANISM: Lama glama

<400> SEQUENCE: 319

Gln Thr Val Val Thr Gln Glu Pro Ser Phe Ser Val Ser Pro Gly Gly
1               5                   10                  15

Thr Val Thr Leu Thr Cys Gly Leu Ser Ser Gly Ser Val Thr Ala Ser
            20                  25                  30

Asn Tyr Pro Gly Trp Tyr Gln Gln Thr Pro Gly Gln Ala Pro Arg Thr
        35                  40                  45

Leu Ile Tyr Ser Thr Asn Asp Arg His Ser Gly Val Pro Ser Arg Phe
    50                  55                  60

Ser Gly Ser Ile Leu Gly Asn Lys Ala Ala Leu Thr Ile Thr Gly Ala
65                  70                  75                  80

Gln Ala Glu Asp Glu Ala Asp Tyr Tyr Cys Ala Leu Asp Ile Gly Asp
                85                  90                  95

Ile Thr Glu Phe Gly Gly Gly Thr Gln Leu Thr Val Leu Gly
            100                 105                 110

<210> SEQ ID NO 320
<211> LENGTH: 110
<212> TYPE: PRT
<213> ORGANISM: Lama glama

<400> SEQUENCE: 320

Gln Thr Val Val Thr Gln Glu Pro Ser Leu Ser Val Ser Pro Gly Gly
1               5                   10                  15

Thr Val Thr Leu Thr Cys Gly Leu Ser Ser Gly Ser Val Thr Ala Ser
            20                  25                  30

Asn Tyr Pro Gly Trp Tyr Gln Gln Thr Pro Gly Gln Ala Pro Arg Ala
        35                  40                  45

Leu Ile Tyr Ser Thr Asn Asp Arg His Ser Gly Val Pro Ser Arg Phe
            50                  55                  60

Ser Gly Ser Ile Ser Gly Asn Lys Ala Ala Leu Thr Ile Thr Gly Ala
65                  70                  75                  80

Gln Ala Glu Asp Glu Ala Asp Tyr Tyr Cys Ala Leu Asp Ile Gly Asp
                85                  90                  95

Ile Thr Glu Phe Gly Gly Gly Thr Gln Leu Thr Val Leu Gly
            100                 105                 110

<210> SEQ ID NO 321
<211> LENGTH: 110
<212> TYPE: PRT
<213> ORGANISM: Lama glama

<400> SEQUENCE: 321

Gln Thr Val Val Thr Gln Glu Pro Ser Leu Ser Val Ser Pro Gly Gly
1               5                   10                  15

Thr Val Thr Leu Thr Cys Gly Leu Ser Ser Gly Ser Val Thr Ala Ser
            20                  25                  30

Asn Tyr Pro Gly Trp Phe Gln Gln Thr Pro Gly Gln Ala Pro Arg Thr
        35                  40                  45

Leu Ile Tyr Ser Thr Asn Asp Arg His Ser Gly Val Pro Ser Arg Phe
    50                  55                  60

Ser Gly Ser Ile Ser Gly Asn Lys Ala Ala Leu Thr Ile Thr Gly Ala
65                  70                  75                  80

Gln Ala Asp Asp Glu Ala Asp Tyr Tyr Cys Ala Leu Asp Ile Gly Asp
                85                  90                  95

Ile Thr Glu Phe Gly Gly Gly Thr His Leu Thr Val Leu Gly
            100                 105                 110

<210> SEQ ID NO 322
<211> LENGTH: 110
<212> TYPE: PRT
<213> ORGANISM: Lama glama

<400> SEQUENCE: 322

Gln Ala Val Val Thr Gln Glu Pro Ser Leu Ser Val Ser Pro Gly Gly
1               5                   10                  15

Thr Val Thr Leu Thr Cys Gly Leu Ser Ser Gly Ser Val Thr Ala Ser
            20                  25                  30

Asn Tyr Pro Gly Trp Phe Gln Gln Lys Pro Gly Gln Ala Pro Arg Ala
        35                  40                  45

Leu Ile Tyr Ser Thr Asn Asp Arg His Ser Gly Thr Pro Ser Arg Phe
    50                  55                  60

Ser Gly Ser Leu Ser Gly Asn Lys Ala Ala Leu Thr Ile Leu Gly Ala
65                  70                  75                  80

Gln Pro Glu Asp Glu Ala Asp Tyr Tyr Cys Ala Leu Asp Ile Gly Asp
                85                  90                  95

Ile Thr Glu Phe Gly Gly Gly Thr His Leu Thr Val Leu Gly
            100                 105                 110

<210> SEQ ID NO 323
<211> LENGTH: 110
<212> TYPE: PRT
<213> ORGANISM: Lama glama

<400> SEQUENCE: 323

Gln Ala Val Val Thr Gln Glu Pro Ser Leu Thr Val Ser Pro Gly Gly

```
   1               5                  10                 15
Thr Val Thr Leu Thr Cys Gly Leu Ser Ser Gly Ser Val Thr Ala Ser
                20                 25                 30

Asn Tyr Pro Gly Trp Phe Gln Gln Lys Pro Gly Gln Ala Pro Arg Ala
            35                 40                 45

Leu Ile Tyr Ser Thr Asn Asp Arg His Ser Gly Val Pro Asp Arg Phe
        50                 55                 60

Ser Gly Ser Ile Ser Gly Asn Lys Ala Ala Leu Thr Ile Thr Gly Ala
65                 70                 75                 80

Gln Pro Glu Asp Glu Ala Glu Tyr Tyr Cys Ala Leu Asp Ile Gly Asp
                85                 90                 95

Ile Thr Glu Phe Gly Gly Gly Thr His Leu Thr Val Leu Gly
                100                105                110

<210> SEQ ID NO 324
<211> LENGTH: 110
<212> TYPE: PRT
<213> ORGANISM: Lama glama

<400> SEQUENCE: 324

Gln Thr Val Val Thr Gln Glu Pro Ser Leu Thr Val Ser Pro Gly Gly
1               5                  10                 15

Thr Val Thr Leu Thr Cys Gly Leu Ser Ser Gly Ser Val Thr Ala Ser
                20                 25                 30

Asn Tyr Pro Gly Trp Phe Gln Gln Thr Pro Gly Gln Ala Pro Arg Ala
            35                 40                 45

Leu Ile Tyr Ser Thr Asn Asp Arg His Ser Gly Val Pro Ala Arg Phe
        50                 55                 60

Ser Gly Ser Ile Ser Gly Gly Lys Ala Ala Leu Thr Leu Leu Gly Ala
65                 70                 75                 80

Gln Pro Glu Asp Glu Ala Glu Tyr Tyr Cys Ala Leu Asp Ile Gly Asp
                85                 90                 95

Ile Thr Glu Phe Gly Gly Gly Thr His Leu Thr Val Leu Gly
                100                105                110

<210> SEQ ID NO 325
<211> LENGTH: 110
<212> TYPE: PRT
<213> ORGANISM: Lama glama

<400> SEQUENCE: 325

Gln Thr Val Val Thr Gln Glu Pro Ser Leu Thr Val Ser Pro Gly Gly
1               5                  10                 15

Thr Val Thr Leu Thr Cys Gly Leu Ser Ser Gly Ser Val Thr Ala Ser
                20                 25                 30

Asn Tyr Pro Gly Trp Phe Gln Gln Lys Pro Gly Gln Ala Pro Arg Ala
            35                 40                 45

Leu Ile Tyr Ser Thr Asn Asp Arg His Ser Gly Val Pro Ala Arg Phe
        50                 55                 60

Ser Gly Ser Leu Leu Gly Gly Lys Ala Ala Leu Thr Ile Leu Gly Ala
65                 70                 75                 80

Gln Ala Asp Asp Glu Ala Glu Tyr Tyr Cys Ala Leu Asp Ile Gly Asp
                85                 90                 95

Ile Thr Glu Phe Gly Gly Gly Thr Gln Leu Thr Val Leu Gly
                100                105                110
```

-continued

```
<210> SEQ ID NO 326
<211> LENGTH: 110
<212> TYPE: PRT
<213> ORGANISM: Lama glama

<400> SEQUENCE: 326

Gln Thr Val Val Thr Gln Glu Pro Ser Leu Ser Val Ser Pro Gly Gly
1               5                   10                  15

Thr Val Thr Leu Thr Cys Gly Leu Ser Ser Gly Ser Val Thr Ala Ser
            20                  25                  30

Asn Tyr Pro Gly Trp Phe Gln Gln Thr Pro Gly Gln Ala Pro Arg Ala
        35                  40                  45

Leu Ile Tyr Ser Thr Asn Asp Arg His Ser Gly Val Pro Ala Arg Phe
    50                  55                  60

Ser Gly Ser Leu Ser Gly Gly Lys Ala Ala Leu Thr Ile Thr Gly Ala
65                  70                  75                  80

Gln Ala Glu Asp Glu Ala Glu Tyr Tyr Cys Ala Leu Asp Ile Gly Asp
                85                  90                  95

Ile Thr Glu Phe Gly Gly Gly Thr Gln Leu Thr Val Leu Gly
            100                 105                 110

<210> SEQ ID NO 327
<211> LENGTH: 110
<212> TYPE: PRT
<213> ORGANISM: Lama glama

<400> SEQUENCE: 327

Gln Thr Val Val Thr Gln Glu Pro Ser Phe Ser Val Ser Pro Gly Gly
1               5                   10                  15

Thr Val Thr Leu Thr Cys Gly Leu Ser Ser Gly Ser Val Thr Ala Ser
            20                  25                  30

Asn Tyr Pro Gly Trp Phe Gln Gln Lys Pro Gly Gln Ala Pro Arg Ala
        35                  40                  45

Leu Ile Tyr Ser Thr Asn Asp Arg His Ser Trp Val Pro Ala Arg Phe
    50                  55                  60

Ser Gly Ser Leu Ser Gly Gly Lys Ala Ala Leu Thr Leu Leu Gly Ala
65                  70                  75                  80

Gln Pro Glu Asp Glu Ala Glu Tyr Tyr Cys Ala Leu Asp Ile Gly Asp
                85                  90                  95

Ile Thr Glu Phe Gly Gly Gly Thr His Leu Thr Val Leu Gly
            100                 105                 110

<210> SEQ ID NO 328
<211> LENGTH: 110
<212> TYPE: PRT
<213> ORGANISM: Lama glama

<400> SEQUENCE: 328

Gln Thr Val Val Thr Gln Glu Pro Ser Leu Thr Val Ser Pro Gly Gly
1               5                   10                  15

Thr Val Thr Leu Thr Cys Gly Leu Ser Ser Gly Ser Val Thr Ala Ser
            20                  25                  30

Asn Tyr Pro Gly Trp Phe Gln Gln Lys Pro Gly Gln Ala Pro Arg Ala
        35                  40                  45

Leu Ile Tyr Ser Thr Asn Asp Arg His Ser Trp Val Pro Ala Arg Phe
    50                  55                  60

Ser Gly Ser Leu Ser Gly Asn Lys Ala Ala Leu Thr Leu Thr Gly Ala
65                  70                  75                  80
```

Gln Pro Glu Asp Glu Ala Glu Tyr Tyr Cys Ala Leu Asp Ile Gly Asp
                85                  90                  95

Ile Thr Glu Phe Gly Gly Gly Thr His Leu Thr Val Leu Gly
            100                 105                 110

<210> SEQ ID NO 329
<211> LENGTH: 110
<212> TYPE: PRT
<213> ORGANISM: Lama glama

<400> SEQUENCE: 329

Gln Ala Val Val Thr Gln Glu Pro Ser Leu Ser Val Ser Pro Gly Gly
1               5                   10                  15

Thr Val Thr Leu Thr Cys Gly Leu Ser Ser Gly Ser Val Thr Ala Ser
            20                  25                  30

Asn Tyr Pro Gly Trp Phe Gln Gln Lys Pro Gly Gln Ala Pro Arg Ala
        35                  40                  45

Leu Ile Tyr Ser Thr Asn Asp Arg His Ser Gly Val Pro Ala Arg Phe
    50                  55                  60

Ser Gly Ser Ile Ser Gly Gly Lys Ala Ala Leu Thr Leu Thr Gly Ala
65                  70                  75                  80

Gln Pro Asp Asp Glu Ala Glu Tyr Tyr Cys Ala Leu Asp Ile Gly Asp
                85                  90                  95

Ile Thr Glu Phe Gly Gly Gly Thr Lys Leu Thr Val Leu Gly
            100                 105                 110

<210> SEQ ID NO 330
<211> LENGTH: 110
<212> TYPE: PRT
<213> ORGANISM: Lama glama

<400> SEQUENCE: 330

Gln Thr Val Val Thr Gln Glu Pro Ser Leu Thr Val Ser Pro Gly Gly
1               5                   10                  15

Thr Val Thr Leu Thr Cys Gly Leu Ser Ser Gly Ser Val Thr Ala Ser
            20                  25                  30

Asn Tyr Pro Gly Trp Phe Gln Gln Lys Pro Gly Gln Ala Pro Arg Ala
        35                  40                  45

Leu Ile Tyr Ser Thr Asn Asp Arg His Ser Trp Val Pro Ser Arg Phe
    50                  55                  60

Ser Gly Ser Leu Ser Gly Gly Lys Ala Ala Leu Thr Leu Leu Gly Ala
65                  70                  75                  80

Gln Pro Glu Asp Glu Ala Glu Tyr Tyr Cys Ala Leu Asp Ile Gly Asp
                85                  90                  95

Ile Thr Glu Phe Gly Gly Gly Thr Gln Leu Thr Val Leu Gly
            100                 105                 110

<210> SEQ ID NO 331
<211> LENGTH: 110
<212> TYPE: PRT
<213> ORGANISM: Lama glama

<400> SEQUENCE: 331

Gln Thr Val Val Thr Gln Glu Pro Ser Leu Ser Val Ser Pro Gly Gly
1               5                   10                  15

Thr Val Thr Leu Thr Cys Gly Leu Ser Ser Gly Ser Val Thr Ala Ser
            20                  25                  30

Asn Tyr Pro Gly Trp Phe Gln Gln Thr Pro Gly Gln Ala Pro Arg Ala
            35                  40                  45

Leu Ile Tyr Ser Thr Asn Asp Arg His Ser Gly Val Pro Ala Arg Phe
 50                  55                  60

Ser Gly Ser Ile Ser Gly Gly Lys Ala Ala Leu Thr Leu Leu Gly Ala
 65                  70                  75                  80

Gln Pro Glu Asp Glu Ala Glu Tyr Tyr Cys Ala Leu Asp Ile Gly Asp
                 85                  90                  95

Ile Thr Glu Phe Gly Gly Gly Thr Gln Leu Thr Val Leu Gly
            100                 105                 110

<210> SEQ ID NO 332
<211> LENGTH: 110
<212> TYPE: PRT
<213> ORGANISM: Lama glama

<400> SEQUENCE: 332

Gln Ala Val Val Thr Gln Glu Pro Ser Leu Ser Val Ser Pro Gly Gly
 1               5                   10                  15

Thr Val Thr Leu Thr Cys Gly Leu Ser Ser Gly Ser Val Thr Ala Ser
            20                  25                  30

Asn Tyr Pro Gly Trp Phe Gln Gln Thr Pro Gly Gln Ala Pro Arg Ala
            35                  40                  45

Leu Ile Tyr Ser Thr Asn Asp Arg His Ser Gly Val Pro Ala Arg Phe
 50                  55                  60

Ser Gly Ser Ile Leu Gly Gly Lys Ala Ala Leu Thr Ile Leu Gly Ala
 65                  70                  75                  80

Gln Pro Asn Asp Glu Ala Glu Tyr Tyr Cys Ala Leu Asp Ile Gly Asp
                 85                  90                  95

Ile Thr Glu Phe Gly Gly Gly Thr His Leu Thr Val Leu Gly
            100                 105                 110

<210> SEQ ID NO 333
<211> LENGTH: 110
<212> TYPE: PRT
<213> ORGANISM: Lama glama

<400> SEQUENCE: 333

Gln Thr Val Val Thr Gln Glu Pro Ser Leu Thr Val Ser Pro Gly Gly
 1               5                   10                  15

Thr Val Thr Leu Thr Cys Gly Leu Ser Ser Gly Ser Val Thr Ala Ser
            20                  25                  30

Asn Tyr Pro Gly Trp Phe Gln Lys Pro Gly Gln Ala Pro Arg Ala
            35                  40                  45

Leu Ile Tyr Ser Thr Asn Asp Arg His Ser Gly Val Pro Ala Arg Phe
 50                  55                  60

Ser Gly Ser Leu Leu Gly Gly Lys Ala Ala Leu Thr Ile Leu Gly Ala
 65                  70                  75                  80

Gln Ala Asp Asp Glu Ala Glu Tyr Tyr Cys Ala Leu Asp Ile Gly Asp
                 85                  90                  95

Ile Thr Glu Phe Gly Gly Gly Thr Gln Leu Thr Val Leu Gly
            100                 105                 110

<210> SEQ ID NO 334
<211> LENGTH: 110
<212> TYPE: PRT
<213> ORGANISM: Lama glama

```
<400> SEQUENCE: 334

Gln Thr Val Val Thr Gln Glu Pro Ser Leu Ser Val Ser Pro Gly Gly
1               5                  10                  15

Thr Val Thr Leu Thr Cys Gly Leu Ser Ser Gly Ser Val Thr Ala Ser
            20                  25                  30

Asn Tyr Pro Gly Trp Phe Gln Lys Pro Gly Gln Ala Pro Arg Ala
        35                  40                  45

Leu Ile Tyr Ser Thr Asn Asp Arg His Ser Gly Val Pro Ala Arg Phe
    50                  55                  60

Ser Gly Ser Leu Ser Gly Asn Lys Ala Ala Leu Thr Ile Thr Gly Ala
65                  70                  75                  80

Gln Ala Asp Asp Glu Ala Asp Tyr Tyr Cys Ala Leu Asp Ile Gly Asp
                85                  90                  95

Ile Thr Glu Phe Gly Gly Gly Thr Gln Leu Thr Val Leu Gly
            100                 105                 110

<210> SEQ ID NO 335
<211> LENGTH: 110
<212> TYPE: PRT
<213> ORGANISM: Lama glama

<400> SEQUENCE: 335

Gln Ala Val Val Thr Gln Glu Pro Ser Leu Thr Val Ser Pro Gly Gly
1               5                  10                  15

Thr Val Thr Leu Thr Cys Gly Leu Ser Ser Gly Ser Val Thr Ala Ser
            20                  25                  30

Asn Tyr Pro Gly Trp Phe Gln Thr Pro Gly Gln Ala Pro Arg Ala
        35                  40                  45

Leu Ile Tyr Ser Thr Asn Asp Arg His Ser Gly Thr Pro Ala Arg Phe
    50                  55                  60

Ser Gly Ser Leu Ser Gly Asn Lys Ala Ala Leu Thr Ile Thr Gly Ala
65                  70                  75                  80

Gln Pro Glu Asp Glu Ala Asp Tyr Tyr Cys Ala Leu Asp Ile Gly Asp
                85                  90                  95

Ile Thr Glu Phe Gly Gly Gly Thr Lys Leu Thr Val Leu Gly
            100                 105                 110

<210> SEQ ID NO 336
<211> LENGTH: 110
<212> TYPE: PRT
<213> ORGANISM: Lama glama

<400> SEQUENCE: 336

Gln Thr Val Val Thr Gln Glu Pro Ser Leu Ser Val Ser Pro Gly Gly
1               5                  10                  15

Thr Val Thr Leu Thr Cys Gly Leu Ser Ser Gly Ser Val Thr Ala Ser
            20                  25                  30

Asn Tyr Pro Gly Trp Phe Gln Lys Pro Gly Gln Ala Pro Arg Ala
        35                  40                  45

Leu Ile Tyr Ser Thr Asn Asp Arg His Ser Trp Val Pro Ala Arg Phe
    50                  55                  60

Ser Gly Ser Ile Ser Gly Lys Ala Ala Leu Thr Leu Thr Gly Ala
65                  70                  75                  80

Gln Pro Glu Asp Glu Ala Glu Tyr Tyr Cys Ala Leu Asp Ile Gly Asp
                85                  90                  95

Ile Thr Glu Phe Gly Gly Gly Thr Gln Leu Thr Val Leu Gly
```

```
                    100                 105                 110

<210> SEQ ID NO 337
<211> LENGTH: 110
<212> TYPE: PRT
<213> ORGANISM: Lama glama

<400> SEQUENCE: 337

Gln Thr Val Val Thr Gln Glu Pro Ser Phe Ser Val Ser Pro Gly Gly
1               5                   10                  15

Thr Val Thr Leu Thr Cys Gly Leu Ser Ser Gly Ser Val Thr Ala Ser
            20                  25                  30

Asn Tyr Pro Gly Trp Tyr Gln Gln Thr Pro Gly Gln Ala Pro Arg Ala
        35                  40                  45

Leu Ile Tyr Ser Thr Asn Asp Arg His Ser Gly Val Pro Asp Arg Phe
    50                  55                  60

Ser Gly Ser Ile Leu Gly Asn Lys Ala Ala Leu Thr Ile Thr Gly Ala
65                  70                  75                  80

Gln Ala Asp Asp Glu Ser Asp Tyr Tyr Cys Ala Leu Asp Ile Gly Asp
                85                  90                  95

Ile Thr Glu Phe Gly Gly Gly Thr His Leu Thr Val Leu Gly
            100                 105                 110

<210> SEQ ID NO 338
<211> LENGTH: 109
<212> TYPE: PRT
<213> ORGANISM: Lama glama

<400> SEQUENCE: 338

Gln Thr Val Val Thr Gln Glu Pro Ser Phe Ser Val Ser Pro Gly Gly
1               5                   10                  15

Thr Val Thr Leu Thr Cys Gly Leu Ser Ser Gly Ser Val Thr Ala Ser
            20                  25                  30

Asn Tyr Pro Gly Trp Tyr Gln Gln Thr Pro Gly Gln Ala Pro Arg Ala
        35                  40                  45

Leu Ile Tyr Ser Thr Asn Asp Arg His Ser Gly Val Pro Ser Arg Phe
    50                  55                  60

Ser Gly Ser Ile Ser Gly Asn Lys Ala Ala Leu Thr Ile Thr Gly Ala
65                  70                  75                  80

Gln Ala Glu Asp Glu Ala Asp Tyr Tyr Cys Ala Leu Asp Ile Gly Asp
                85                  90                  95

Ile Thr Glu Phe Gly Gly Gly Thr Lys Leu Thr Val Leu
            100                 105

<210> SEQ ID NO 339
<211> LENGTH: 109
<212> TYPE: PRT
<213> ORGANISM: Lama glama

<400> SEQUENCE: 339

Gln Thr Val Val Thr Gln Glu Pro Ser Phe Ser Val Ser Pro Gly Gly
1               5                   10                  15

Thr Val Thr Leu Thr Cys Gly Leu Ser Ser Gly Ser Val Thr Ala Ser
            20                  25                  30

Asn Tyr Pro Gly Trp Tyr Gln Gln Thr Pro Gly Gln Ala Pro Arg Ala
        35                  40                  45

Leu Ile Tyr Ser Thr Asn Asp Arg His Ser Gly Val Pro Ser Arg Phe
    50                  55                  60
```

Ser Gly Ser Ile Leu Gly Asn Lys Ala Ala Leu Thr Ile Thr Gly Ala
65                  70                  75                  80

Gln Ala Glu Asp Glu Ala Asp Tyr Tyr Cys Ala Leu Asp Ile Gly Asp
                85                  90                  95

Ile Thr Glu Phe Gly Gly Gly Thr His Leu Thr Val Leu
            100                 105

<210> SEQ ID NO 340
<211> LENGTH: 109
<212> TYPE: PRT
<213> ORGANISM: Lama glama

<400> SEQUENCE: 340

Gln Thr Val Val Thr Gln Glu Pro Ser Phe Ser Val Ser Pro Gly Gly
1               5                   10                  15

Thr Val Thr Leu Thr Cys Gly Leu Ser Ser Gly Ser Val Thr Ala Ser
                20                  25                  30

Asn Tyr Pro Gly Trp Phe Gln Gln Thr Pro Gly Gln Ala Pro Arg Thr
            35                  40                  45

Leu Ile Tyr Ser Thr Asn Asp Arg His Ser Gly Val Pro Ser Arg Phe
50                  55                  60

Ser Gly Ser Ile Leu Gly Asn Lys Ala Ala Leu Thr Ile Thr Gly Ala
65                  70                  75                  80

Gln Pro Glu Asp Glu Ser Asp Tyr Tyr Cys Ala Leu Asp Ile Gly Asp
                85                  90                  95

Ile Thr Glu Phe Gly Gly Gly Thr His Leu Thr Val Leu
            100                 105

<210> SEQ ID NO 341
<211> LENGTH: 109
<212> TYPE: PRT
<213> ORGANISM: Lama glama

<400> SEQUENCE: 341

Gln Ala Val Val Thr Gln Glu Pro Ser Leu Ser Val Ser Pro Gly Gly
1               5                   10                  15

Thr Val Thr Leu Thr Cys Gly Leu Ser Ser Gly Ser Val Thr Ala Ser
                20                  25                  30

Asn Tyr Pro Gly Trp Phe Gln Gln Thr Pro Gly Gln Ala Pro Arg Ala
            35                  40                  45

Leu Ile Tyr Ser Thr Asn Asp Arg His Ser Gly Thr Pro Ala Arg Phe
50                  55                  60

Ser Gly Ser Leu Ser Gly Asn Lys Ala Ala Leu Thr Ile Leu Gly Ala
65                  70                  75                  80

Gln Pro Glu Asp Glu Ala Asp Tyr Tyr Cys Ala Leu Asp Ile Gly Asp
                85                  90                  95

Ile Thr Glu Phe Gly Gly Gly Thr Gln Leu Thr Val Leu
            100                 105

<210> SEQ ID NO 342
<211> LENGTH: 109
<212> TYPE: PRT
<213> ORGANISM: Lama glama

<400> SEQUENCE: 342

Gln Thr Val Val Thr Gln Glu Pro Ser Phe Ser Val Ser Pro Gly Gly
1               5                   10                  15

-continued

```
Thr Val Thr Leu Thr Cys Gly Leu Ser Ser Gly Ser Val Thr Ala Ser
            20                  25                  30

Asn Tyr Pro Gly Trp Tyr Gln Gln Thr Pro Gly Gln Ala Pro Arg Ala
        35                  40                  45

Leu Ile Tyr Ser Thr Asn Asp Arg His Ser Gly Val Pro Ser Arg Phe
    50                  55                  60

Ser Gly Ser Ile Leu Gly Asn Lys Ala Ala Leu Thr Ile Thr Gly Ala
65              70                  75                  80

Gln Ala Glu Asp Glu Ser Asp Tyr Tyr Cys Ala Leu Asp Ile Gly Asp
                85                  90                  95

Ile Thr Glu Phe Gly Gly Gly Thr His Leu Thr Val Leu
            100                 105
```

<210> SEQ ID NO 343
<211> LENGTH: 109
<212> TYPE: PRT
<213> ORGANISM: Lama glama

<400> SEQUENCE: 343

```
Gln Thr Val Val Thr Gln Glu Pro Arg Leu Ser Val Ser Pro Gly Gly
1               5                   10                  15

Thr Val Thr Leu Thr Cys Gly Leu Ser Ser Gly Ser Val Thr Ala Ser
            20                  25                  30

Asn Tyr Pro Gly Trp Tyr Gln Gln Thr Pro Gly Gln Ala Pro Arg Ala
        35                  40                  45

Leu Ile Tyr Ser Thr Asn Asp Arg His Ser Gly Val Pro Asp Arg Phe
    50                  55                  60

Ser Gly Ser Ile Ser Gly Asn Lys Ala Ala Leu Thr Ile Thr Gly Ala
65              70                  75                  80

Gln Ala Asp Asp Glu Ala Asp Tyr Tyr Cys Ala Leu Asp Ile Gly Asp
                85                  90                  95

Ile Thr Glu Phe Gly Gly Gly Thr Gln Leu Thr Val Leu
            100                 105
```

<210> SEQ ID NO 344
<211> LENGTH: 109
<212> TYPE: PRT
<213> ORGANISM: Lama glama

<400> SEQUENCE: 344

```
Gln Thr Val Val Thr Gln Glu Pro Ser Leu Thr Val Ser Pro Gly Gly
1               5                   10                  15

Thr Val Thr Leu Thr Cys Gly Leu Ser Ser Gly Ser Val Thr Ala Ser
            20                  25                  30

Asn Tyr Pro Gly Trp Phe Gln Gln Thr Pro Gly Gln Ala Pro Arg Ala
        35                  40                  45

Leu Ile Tyr Ser Thr Asn Asp Arg His Ser Trp Val Pro Ala Arg Phe
    50                  55                  60

Ser Gly Ser Leu Ser Gly Gly Lys Ala Ala Leu Thr Ile Leu Gly Ala
65              70                  75                  80

Gln Pro Glu Asp Glu Ala Glu Tyr Tyr Cys Ala Leu Asp Ile Gly Asp
                85                  90                  95

Ile Thr Glu Phe Gly Gly Gly Thr His Leu Thr Val Leu
            100                 105
```

<210> SEQ ID NO 345
<211> LENGTH: 109

```
<212> TYPE: PRT
<213> ORGANISM: Lama glama

<400> SEQUENCE: 345

Gln Ala Val Val Thr Gln Glu Pro Ser Leu Ser Val Ser Pro Gly Gly
1               5                   10                  15

Thr Val Thr Leu Thr Cys Gly Leu Ser Ser Gly Ser Val Thr Ala Ser
            20                  25                  30

Asn Tyr Pro Gly Trp Phe Gln Gln Lys Pro Gly Gln Ala Pro Arg Ala
        35                  40                  45

Leu Ile Tyr Ser Thr Asn Asp Arg His Ser Gly Val Pro Ala Arg Phe
    50                  55                  60

Ser Gly Ser Leu Ser Gly Asn Lys Ala Ala Leu Thr Ile Leu Gly Ala
65              70                  75                  80

Gln Pro Glu Asp Glu Ala Asp Tyr Tyr Cys Ala Leu Asp Ile Gly Asp
                85                  90                  95

Ile Thr Glu Phe Gly Gly Gly Thr Gln Leu Thr Val Leu
            100                 105

<210> SEQ ID NO 346
<211> LENGTH: 109
<212> TYPE: PRT
<213> ORGANISM: Lama glama

<400> SEQUENCE: 346

Gln Thr Val Val Thr Gln Glu Pro Ser Phe Ser Val Ser Pro Gly Gly
1               5                   10                  15

Thr Val Thr Leu Thr Cys Gly Leu Ser Ser Gly Ser Val Thr Ala Ser
            20                  25                  30

Asn Tyr Pro Gly Trp Phe Gln Gln Thr Pro Gly Gln Ala Pro Arg Thr
        35                  40                  45

Leu Ile Tyr Ser Thr Asn Asp Arg His Ser Gly Val Pro Asp Arg Phe
    50                  55                  60

Ser Gly Ser Ile Ser Gly Asn Lys Ala Ala Leu Thr Ile Thr Gly Ala
65              70                  75                  80

Gln Ala Glu Asp Glu Ser Asp Tyr Tyr Cys Ala Leu Asp Ile Gly Asp
                85                  90                  95

Ile Thr Glu Phe Gly Gly Gly Thr His Leu Thr Val Leu
            100                 105

<210> SEQ ID NO 347
<211> LENGTH: 109
<212> TYPE: PRT
<213> ORGANISM: Lama glama

<400> SEQUENCE: 347

Gln Thr Val Val Thr Gln Glu Pro Ser Leu Ser Val Ser Pro Gly Gly
1               5                   10                  15

Thr Val Thr Leu Thr Cys Gly Leu Ser Ser Gly Ser Val Thr Ala Ser
            20                  25                  30

Asn Tyr Pro Gly Trp Phe Gln Gln Lys Pro Gly Gln Ala Pro Arg Ala
        35                  40                  45

Leu Ile Tyr Ser Thr Asn Asp Arg His Ser Gly Val Pro Ser Arg Phe
    50                  55                  60

Ser Gly Ser Leu Ser Gly Asn Lys Ala Ala Leu Thr Leu Thr Gly Ala
65              70                  75                  80

Gln Pro Glu Asp Glu Ala Glu Tyr Tyr Cys Ala Leu Asp Ile Gly Asp
```

```
                85                  90                  95

Ile Thr Glu Phe Gly Gly Gly Thr Gln Leu Thr Val Leu
            100                 105

<210> SEQ ID NO 348
<211> LENGTH: 109
<212> TYPE: PRT
<213> ORGANISM: Lama glama

<400> SEQUENCE: 348

Gln Thr Val Val Thr Gln Glu Pro Ser Phe Ser Val Ser Pro Gly Gly
1               5                   10                  15

Thr Val Thr Leu Thr Cys Gly Leu Ser Ser Gly Ser Val Thr Ala Ser
            20                  25                  30

Asn Tyr Pro Gly Trp Tyr Gln Gln Thr Pro Gly Gln Ala Pro Arg Ala
        35                  40                  45

Leu Ile Tyr Ser Thr Asn Asp Arg His Ser Gly Val Pro Ser Arg Phe
    50                  55                  60

Ser Gly Ser Ile Leu Gly Asn Lys Ala Ala Leu Thr Ile Thr Gly Ala
65                  70                  75                  80

Gln Ala Glu Asp Glu Ala Asp Tyr Tyr Cys Ala Leu Asp Ile Gly Asp
                85                  90                  95

Ile Thr Glu Phe Gly Gly Gly Thr His Leu Thr Val Leu
            100                 105

<210> SEQ ID NO 349
<211> LENGTH: 109
<212> TYPE: PRT
<213> ORGANISM: Lama glama

<400> SEQUENCE: 349

Gln Thr Val Val Thr Gln Glu Pro Ser Leu Ser Val Ser Pro Gly Gly
1               5                   10                  15

Thr Val Thr Leu Thr Cys Gly Leu Ser Ser Gly Ser Val Thr Ala Ser
            20                  25                  30

Asn Tyr Pro Gly Trp Tyr Gln Gln Thr Pro Gly Gln Ala Pro Arg Thr
        35                  40                  45

Leu Ile Tyr Ser Thr Asn Asp Arg His Ser Gly Val Pro Asp Arg Phe
    50                  55                  60

Ser Gly Ser Ile Ser Gly Asn Lys Ala Ala Leu Thr Ile Thr Gly Ala
65                  70                  75                  80

Gln Ala Asp Asp Glu Ser Asp Tyr Tyr Cys Ala Leu Asp Ile Gly Asp
                85                  90                  95

Ile Thr Glu Phe Gly Gly Gly Thr Lys Leu Thr Val Leu
            100                 105

<210> SEQ ID NO 350
<211> LENGTH: 109
<212> TYPE: PRT
<213> ORGANISM: Lama glama

<400> SEQUENCE: 350

Gln Thr Val Val Thr Gln Glu Pro Ser Phe Ser Val Ser Pro Gly Gly
1               5                   10                  15

Thr Val Thr Leu Thr Cys Gly Leu Ser Ser Gly Ser Val Thr Ala Ser
            20                  25                  30

Asn Tyr Pro Gly Trp Tyr Gln Gln Thr Pro Gly Gln Ala Pro Arg Ala
        35                  40                  45
```

```
Leu Ile Tyr Ser Thr Asn Asp Arg His Ser Gly Val Pro Asp Arg Phe
        50                  55                  60
Ser Gly Ser Ile Ser Gly Asn Lys Ala Ala Leu Thr Ile Thr Gly Ala
65                  70                  75                  80
Gln Ala Glu Asp Glu Ala Asp Tyr Tyr Cys Ala Leu Asp Ile Gly Asp
                85                  90                  95
Ile Thr Glu Phe Gly Gly Gly Thr Gln Leu Thr Val Leu
            100                 105
```

<210> SEQ ID NO 351
<211> LENGTH: 109
<212> TYPE: PRT
<213> ORGANISM: Lama glama

<400> SEQUENCE: 351

```
Gln Thr Val Val Thr Gln Glu Pro Ser Phe Ser Val Ser Pro Gly Gly
1               5                   10                  15
Thr Val Thr Leu Thr Cys Gly Leu Ser Ser Gly Ser Val Thr Ala Ser
                20                  25                  30
Asn Tyr Pro Gly Trp Phe Gln Gln Thr Pro Gly Gln Ala Pro Arg Ala
            35                  40                  45
Leu Ile Tyr Ser Thr Asn Asp Arg His Ser Gly Val Pro Asp Arg Phe
        50                  55                  60
Ser Gly Ser Ile Leu Gly Asn Lys Ala Ala Leu Thr Ile Thr Gly Ala
65                  70                  75                  80
Gln Ala Glu Asp Glu Ala Asp Tyr Tyr Cys Ala Leu Asp Ile Gly Asp
                85                  90                  95
Ile Thr Glu Phe Gly Gly Gly Thr Gln Leu Thr Val Leu
            100                 105
```

<210> SEQ ID NO 352
<211> LENGTH: 109
<212> TYPE: PRT
<213> ORGANISM: Lama glama

<400> SEQUENCE: 352

```
Gln Thr Val Val Thr Gln Glu Pro Ser Leu Ser Val Ser Pro Gly Gly
1               5                   10                  15
Thr Val Thr Leu Thr Cys Gly Leu Ser Ser Gly Ser Val Thr Ala Ser
                20                  25                  30
Asn Tyr Pro Gly Trp Tyr Gln Gln Thr Pro Gly Gln Ala Pro Arg Ala
            35                  40                  45
Leu Ile Tyr Ser Thr Asn Asp Arg His Ser Gly Val Pro Asp Arg Phe
        50                  55                  60
Ser Gly Ser Ile Ser Gly Asn Lys Ala Ala Leu Thr Ile Thr Gly Ala
65                  70                  75                  80
Gln Pro Asp Asp Glu Ser Asp Tyr Tyr Cys Ala Leu Asp Ile Gly Asp
                85                  90                  95
Ile Thr Glu Phe Gly Gly Gly Thr Lys Leu Thr Val Leu
            100                 105
```

<210> SEQ ID NO 353
<211> LENGTH: 109
<212> TYPE: PRT
<213> ORGANISM: Lama glama

<400> SEQUENCE: 353

Gln Thr Val Val Thr Gln Glu Pro Ser Phe Ser Val Ser Pro Gly Gly
1               5                   10                  15

Thr Val Thr Leu Thr Cys Gly Leu Ser Ser Gly Ser Val Thr Ala Ser
                20                  25                  30

Asn Tyr Pro Gly Trp Tyr Gln Gln Thr Pro Gly Gln Ala Pro Arg Ala
            35                  40                  45

Leu Ile Tyr Ser Thr Asn Asp Arg His Ser Gly Val Pro Asp Arg Phe
        50                  55                  60

Ser Gly Ser Ile Ser Gly Asn Lys Ala Ala Leu Thr Ile Thr Gly Ala
65                  70                  75                  80

Gln Ala Glu Asp Glu Ala Asp Tyr Tyr Cys Ala Leu Asp Ile Gly Asp
                85                  90                  95

Ile Thr Glu Phe Gly Gly Gly Thr Gln Leu Thr Val Leu
            100                 105

<210> SEQ ID NO 354
<211> LENGTH: 109
<212> TYPE: PRT
<213> ORGANISM: Lama glama

<400> SEQUENCE: 354

Gln Thr Val Val Thr Gln Glu Pro Ser Leu Ser Val Ser Pro Gly Gly
1               5                   10                  15

Thr Val Thr Leu Thr Cys Gly Leu Ser Ser Gly Ser Val Thr Ala Ser
                20                  25                  30

Asn Tyr Pro Gly Trp Tyr Gln Gln Thr Pro Gly Gln Ala Pro Arg Ala
            35                  40                  45

Leu Ile Tyr Ser Thr Asn Asp Arg His Ser Gly Val Pro Ser Arg Phe
        50                  55                  60

Ser Gly Ser Ile Leu Gly Asn Lys Ala Ala Leu Thr Ile Thr Gly Ala
65                  70                  75                  80

Gln Pro Glu Asp Glu Ser Asp Tyr Tyr Cys Ala Leu Asp Ile Gly Asp
                85                  90                  95

Ile Thr Glu Phe Gly Gly Gly Thr His Leu Thr Val Leu
            100                 105

<210> SEQ ID NO 355
<211> LENGTH: 109
<212> TYPE: PRT
<213> ORGANISM: Lama glama

<400> SEQUENCE: 355

Gln Thr Val Val Thr Gln Glu Pro Ser Phe Ser Val Ser Pro Gly Gly
1               5                   10                  15

Thr Val Thr Leu Thr Cys Gly Leu Ser Ser Gly Ser Val Thr Ala Ser
                20                  25                  30

Asn Tyr Pro Gly Trp Tyr Gln Gln Thr Pro Gly Gln Ala Pro Arg Ala
            35                  40                  45

Leu Ile Tyr Ser Thr Asn Asp Arg His Ser Gly Val Pro Ser Arg Phe
        50                  55                  60

Ser Gly Ser Ile Ser Gly Asn Lys Ala Ala Leu Thr Ile Thr Gly Ala
65                  70                  75                  80

Gln Pro Glu Asp Glu Ser Asp Tyr Tyr Cys Ala Leu Asp Ile Gly Asp
                85                  90                  95

Ile Thr Glu Phe Gly Gly Gly Thr Gln Leu Thr Val Leu
            100                 105

<210> SEQ ID NO 356
<211> LENGTH: 109
<212> TYPE: PRT
<213> ORGANISM: Lama glama

<400> SEQUENCE: 356

```
Gln Thr Val Val Thr Gln Glu Pro Ser Leu Ser Val Ser Pro Gly Gly
1               5                   10                  15

Thr Val Thr Leu Thr Cys Gly Leu Ser Ser Gly Ser Val Thr Ala Ser
            20                  25                  30

Asn Tyr Pro Gly Trp Tyr Gln Gln Thr Pro Gly Gln Ala Pro Arg Thr
        35                  40                  45

Leu Ile Tyr Ser Thr Asn Asp Arg His Ser Gly Val Pro Asp Arg Phe
    50                  55                  60

Ser Gly Ser Ile Ser Gly Asn Lys Ala Ala Leu Thr Ile Thr Gly Ala
65                  70                  75                  80

Gln Pro Asp Asp Glu Ala Asp Tyr Tyr Cys Ala Leu Asp Ile Gly Asp
                85                  90                  95

Ile Thr Glu Phe Gly Gly Gly Thr His Leu Thr Val Leu
            100                 105
```

<210> SEQ ID NO 357
<211> LENGTH: 109
<212> TYPE: PRT
<213> ORGANISM: Lama glama

<400> SEQUENCE: 357

```
Gln Thr Val Val Thr Gln Glu Pro Ser Phe Ser Val Ser Pro Gly Gly
1               5                   10                  15

Thr Val Thr Leu Thr Cys Gly Leu Ser Ser Gly Ser Val Thr Ala Ser
            20                  25                  30

Asn Tyr Pro Gly Trp Phe Gln Gln Thr Pro Gly Gln Ala Pro Arg Ala
        35                  40                  45

Leu Ile Tyr Ser Thr Asn Asp Arg His Ser Gly Val Pro Asp Arg Phe
    50                  55                  60

Ser Gly Ser Ile Ser Gly Asn Lys Ala Ala Leu Thr Ile Thr Gly Ala
65                  70                  75                  80

Gln Pro Asp Asp Glu Ala Asp Tyr Tyr Cys Ala Leu Asp Ile Gly Asp
                85                  90                  95

Ile Thr Glu Phe Gly Gly Gly Thr Lys Leu Thr Val Leu
            100                 105
```

<210> SEQ ID NO 358
<211> LENGTH: 109
<212> TYPE: PRT
<213> ORGANISM: Lama glama

<400> SEQUENCE: 358

```
Gln Thr Val Val Thr Gln Glu Pro Ser Leu Ser Val Ser Pro Gly Gly
1               5                   10                  15

Thr Val Thr Leu Thr Cys Gly Leu Ser Ser Gly Ser Val Thr Ala Ser
            20                  25                  30

Asn Tyr Pro Gly Trp Tyr Gln Gln Thr Pro Gly Gln Ala Pro Arg Ala
        35                  40                  45

Leu Ile Tyr Ser Thr Asn Asp Arg His Ser Gly Val Pro Ser Arg Phe
    50                  55                  60

Ser Gly Ser Ile Ser Gly Asn Lys Ala Ala Leu Thr Ile Thr Gly Ala
```

65                  70                  75                  80

Gln Ala Asp Asp Glu Ser Asp Tyr Tyr Cys Ala Leu Asp Ile Gly Asp
                85                  90                  95

Ile Thr Glu Phe Gly Gly Gly Thr His Leu Thr Val Leu
            100                 105

<210> SEQ ID NO 359
<211> LENGTH: 109
<212> TYPE: PRT
<213> ORGANISM: Lama glama

<400> SEQUENCE: 359

Gln Thr Val Val Thr Gln Glu Pro Ser Phe Ser Val Ser Pro Gly Gly
1               5                   10                  15

Thr Val Thr Leu Thr Cys Gly Leu Ser Ser Gly Ser Val Thr Ala Ser
            20                  25                  30

Asn Tyr Pro Gly Trp Phe Gln Gln Thr Pro Gly Gln Ala Pro Arg Ala
            35                  40                  45

Leu Ile Tyr Ser Thr Asn Asp Arg His Ser Gly Val Pro Ser Arg Phe
        50                  55                  60

Ser Gly Ser Ile Ser Gly Asn Lys Ala Ala Leu Thr Ile Thr Gly Ala
65                  70                  75                  80

Gln Ala Glu Asp Glu Ala Asp Tyr Tyr Cys Ala Leu Asp Ile Gly Asp
                85                  90                  95

Ile Thr Glu Phe Gly Gly Gly Thr Lys Leu Thr Val Leu
            100                 105

<210> SEQ ID NO 360
<211> LENGTH: 109
<212> TYPE: PRT
<213> ORGANISM: Lama glama

<400> SEQUENCE: 360

Gln Thr Val Val Thr Gln Glu Pro Ser Phe Ser Val Ser Pro Gly Gly
1               5                   10                  15

Thr Val Thr Leu Thr Cys Gly Leu Ser Ser Gly Ser Val Thr Ala Ser
            20                  25                  30

Asn Tyr Pro Gly Trp Phe Gln Gln Thr Pro Gly Gln Ala Pro Arg Ala
            35                  40                  45

Leu Ile Tyr Ser Thr Asn Asp Arg His Ser Gly Val Pro Asp Arg Phe
        50                  55                  60

Ser Gly Ser Ile Leu Gly Asn Lys Ala Ala Leu Thr Ile Thr Gly Ala
65                  70                  75                  80

Gln Pro Glu Asp Glu Ser Asp Tyr Tyr Cys Ala Leu Asp Ile Gly Asp
                85                  90                  95

Ile Thr Glu Phe Gly Gly Gly Thr Gln Leu Thr Val Leu
            100                 105

<210> SEQ ID NO 361
<211> LENGTH: 109
<212> TYPE: PRT
<213> ORGANISM: Lama glama

<400> SEQUENCE: 361

Gln Thr Val Val Thr Gln Glu Pro Ser Phe Ser Val Ser Pro Gly Gly
1               5                   10                  15

Thr Val Thr Leu Thr Cys Gly Leu Ser Ser Gly Ser Val Thr Ala Ser
            20                  25                  30

Asn Tyr Pro Gly Trp Tyr Gln Gln Thr Pro Gly Gln Ala Pro Arg Ala
        35                  40                  45

Leu Ile Tyr Ser Thr Asn Asp Arg His Ser Gly Val Pro Asp Arg Phe
    50                  55                  60

Ser Gly Ser Ile Ser Gly Asn Lys Ala Ala Leu Thr Ile Thr Gly Ala
65                  70                  75                  80

Gln Pro Asp Asp Glu Ala Asp Tyr Tyr Cys Ala Leu Asp Ile Gly Asp
                85                  90                  95

Ile Thr Glu Phe Gly Gly Gly Thr His Leu Thr Val Leu
            100                 105

<210> SEQ ID NO 362
<211> LENGTH: 109
<212> TYPE: PRT
<213> ORGANISM: Lama glama

<400> SEQUENCE: 362

Gln Thr Val Val Thr Gln Glu Pro Ser Phe Ser Val Ser Pro Gly Gly
1               5                   10                  15

Thr Val Thr Leu Thr Cys Gly Leu Ser Ser Gly Ser Val Thr Ala Ser
            20                  25                  30

Asn Tyr Pro Gly Trp Tyr Gln Gln Thr Pro Gly Gln Ala Pro Arg Ala
        35                  40                  45

Leu Ile Tyr Ser Thr Asn Asp Arg His Ser Gly Val Pro Ser Arg Phe
    50                  55                  60

Ser Gly Ser Ile Ser Gly Asn Lys Ala Ala Leu Thr Ile Thr Gly Ala
65                  70                  75                  80

Gln Ala Glu Asp Glu Ala Asp Tyr Tyr Cys Ala Leu Asp Ile Gly Asp
                85                  90                  95

Ile Thr Glu Phe Gly Gly Gly Thr Lys Leu Thr Val Leu
            100                 105

<210> SEQ ID NO 363
<211> LENGTH: 109
<212> TYPE: PRT
<213> ORGANISM: Lama glama

<400> SEQUENCE: 363

Gln Thr Val Val Thr Gln Glu Pro Ser Phe Ser Val Ser Pro Gly Gly
1               5                   10                  15

Thr Val Thr Leu Thr Cys Gly Leu Ser Ser Gly Ser Val Thr Ala Ser
            20                  25                  30

Asn Tyr Pro Gly Trp Tyr Gln Gln Thr Pro Gly Gln Ala Pro Arg Thr
        35                  40                  45

Leu Ile Tyr Ser Thr Asn Asp Arg His Ser Gly Val Pro Asp Arg Phe
    50                  55                  60

Ser Gly Ser Ile Ser Gly Asn Lys Ala Ala Leu Thr Ile Thr Gly Ala
65                  70                  75                  80

Gln Pro Asp Asp Glu Ser Asp Tyr Tyr Cys Ala Leu Asp Ile Gly Asp
                85                  90                  95

Ile Thr Glu Phe Gly Gly Gly Thr Gln Leu Thr Val Leu
            100                 105

<210> SEQ ID NO 364
<211> LENGTH: 109
<212> TYPE: PRT
<213> ORGANISM: Lama glama

<400> SEQUENCE: 364

Gln Thr Val Val Thr Gln Glu Pro Ser Phe Ser Val Ser Pro Gly Gly
1               5                   10                  15

Thr Val Thr Leu Thr Cys Gly Leu Ser Ser Gly Ser Val Thr Ala Ser
            20                  25                  30

Asn Tyr Pro Gly Trp Tyr Gln Gln Thr Pro Gly Gln Ala Pro Arg Ala
        35                  40                  45

Leu Ile Tyr Ser Thr Asn Asp Arg His Ser Gly Val Pro Asp Arg Phe
    50                  55                  60

Ser Gly Ser Ile Ser Gly Asn Lys Ala Ala Leu Thr Ile Thr Gly Ala
65                  70                  75                  80

Gln Ala Asp Asp Glu Ser Asp Tyr Tyr Cys Ala Leu Asp Ile Gly Asp
                85                  90                  95

Ile Thr Glu Phe Gly Gly Gly Thr Lys Leu Thr Val Leu
            100                 105

<210> SEQ ID NO 365
<211> LENGTH: 109
<212> TYPE: PRT
<213> ORGANISM: Lama glama

<400> SEQUENCE: 365

Gln Thr Val Val Thr Gln Glu Pro Ser Phe Ser Val Ser Pro Gly Gly
1               5                   10                  15

Thr Val Thr Leu Thr Cys Gly Leu Ser Ser Gly Ser Val Thr Ala Ser
            20                  25                  30

Asn Tyr Pro Gly Trp Tyr Gln Gln Thr Pro Gly Gln Ala Pro Arg Ala
        35                  40                  45

Leu Ile Tyr Ser Thr Asn Asp Arg His Ser Gly Val Pro Asp Arg Phe
    50                  55                  60

Ser Gly Ser Ile Leu Gly Asn Lys Ala Ala Leu Thr Ile Thr Gly Ala
65                  70                  75                  80

Gln Pro Glu Asp Glu Ala Asp Tyr Tyr Cys Ala Leu Asp Ile Gly Asp
                85                  90                  95

Ile Thr Glu Phe Gly Gly Gly Thr Lys Leu Thr Val Leu
            100                 105

<210> SEQ ID NO 366
<211> LENGTH: 109
<212> TYPE: PRT
<213> ORGANISM: Lama glama

<400> SEQUENCE: 366

Gln Thr Val Val Thr Gln Glu Pro Ser Leu Ser Val Ser Pro Gly Gly
1               5                   10                  15

Thr Val Thr Leu Thr Cys Gly Leu Ser Ser Gly Ser Val Thr Ala Ser
            20                  25                  30

Asn Tyr Pro Gly Trp Tyr Gln Gln Thr Pro Gly Gln Ala Pro Arg Ala
        35                  40                  45

Leu Ile Tyr Ser Thr Asn Asp Arg His Ser Gly Val Pro Ser Arg Phe
    50                  55                  60

Ser Gly Ser Ile Leu Gly Asn Lys Ala Ala Leu Thr Ile Thr Gly Ala
65                  70                  75                  80

Gln Ala Asp Asp Glu Ala Asp Tyr Tyr Cys Ala Leu Asp Ile Gly Asp
                85                  90                  95

Ile Thr Glu Phe Gly Gly Gly Thr His Leu Thr Val Leu
            100                 105

<210> SEQ ID NO 367
<211> LENGTH: 109
<212> TYPE: PRT
<213> ORGANISM: Lama glama

<400> SEQUENCE: 367

Gln Thr Val Val Thr Gln Glu Pro Ser Phe Ser Val Ser Pro Gly Gly
1               5                   10                  15

Thr Val Thr Leu Thr Cys Gly Leu Ser Ser Gly Ser Val Thr Ala Ser
            20                  25                  30

Asn Tyr Pro Gly Trp Tyr Gln Gln Thr Pro Gly Gln Ala Pro Arg Ala
        35                  40                  45

Leu Ile Tyr Ser Thr Asn Asp Arg His Ser Gly Val Pro Asp Arg Phe
    50                  55                  60

Ser Gly Ser Ile Ser Gly Asn Lys Ala Ala Leu Thr Ile Thr Gly Ala
65                  70                  75                  80

Gln Ala Asp Asp Glu Ser Asp Tyr Tyr Cys Ala Leu Asp Ile Gly Asp
                85                  90                  95

Ile Thr Glu Phe Gly Gly Gly Thr His Leu Thr Val Leu
            100                 105

<210> SEQ ID NO 368
<211> LENGTH: 109
<212> TYPE: PRT
<213> ORGANISM: Lama glama

<400> SEQUENCE: 368

Gln Thr Val Val Thr Gln Glu Pro Ser Leu Ser Val Ser Pro Gly Gly
1               5                   10                  15

Thr Val Thr Leu Thr Cys Gly Leu Ser Ser Gly Ser Val Thr Ala Ser
            20                  25                  30

Asn Tyr Pro Gly Trp Tyr Gln Gln Thr Pro Gly Gln Ala Pro Arg Ala
        35                  40                  45

Leu Ile Tyr Ser Thr Asn Asp Arg His Ser Gly Val Pro Asp Arg Phe
    50                  55                  60

Ser Gly Ser Ile Ser Gly Asn Lys Ala Ala Leu Thr Ile Thr Gly Ala
65                  70                  75                  80

Gln Pro Asp Asp Glu Ser Asp Tyr Tyr Cys Ala Leu Asp Ile Gly Asp
                85                  90                  95

Ile Thr Glu Phe Gly Gly Gly Thr His Leu Thr Val Leu
            100                 105

<210> SEQ ID NO 369
<211> LENGTH: 109
<212> TYPE: PRT
<213> ORGANISM: Lama glama

<400> SEQUENCE: 369

Gln Thr Val Val Thr Gln Glu Pro Ser Leu Ser Val Ser Pro Gly Gly
1               5                   10                  15

Thr Val Thr Leu Thr Cys Gly Leu Ser Ser Gly Ser Val Thr Ala Ser
            20                  25                  30

Asn Tyr Pro Gly Trp Tyr Gln Gln Thr Pro Gly Gln Ala Pro Arg Ala
        35                  40                  45

Leu Ile Tyr Ser Thr Asn Asp Arg His Ser Gly Val Pro Ser Arg Phe

```
                      50                  55                  60
Ser Gly Ser Ile Leu Gly Asn Lys Ala Ala Leu Thr Ile Thr Gly Ala
 65                  70                  75                  80
Gln Pro Glu Asp Glu Ala Asp Tyr Tyr Cys Ala Leu Asp Ile Gly Asp
                 85                  90                  95
Ile Thr Glu Phe Gly Gly Gly Thr His Leu Thr Val Leu
            100                 105
```

<210> SEQ ID NO 370
<211> LENGTH: 109
<212> TYPE: PRT
<213> ORGANISM: Lama glama

<400> SEQUENCE: 370

```
Gln Thr Val Val Thr Gln Glu Pro Ser Phe Ser Val Ser Pro Gly Gly
 1               5                  10                  15
Thr Val Thr Leu Thr Cys Gly Leu Ser Ser Gly Ser Val Thr Ala Ser
             20                  25                  30
Asn Tyr Pro Gly Trp Tyr Gln Gln Thr Pro Gly Gln Ala Pro Arg Ala
         35                  40                  45
Leu Ile Tyr Ser Thr Asn Asp Arg His Ser Gly Val Pro Ser Arg Phe
     50                  55                  60
Ser Gly Ser Ile Leu Gly Asn Lys Ala Ala Leu Thr Ile Thr Gly Ala
 65                  70                  75                  80
Gln Pro Asp Asp Glu Ala Asp Tyr Tyr Cys Ala Leu Asp Ile Gly Asp
                 85                  90                  95
Ile Thr Glu Phe Gly Gly Gly Thr His Leu Thr Val Leu
            100                 105
```

<210> SEQ ID NO 371
<211> LENGTH: 109
<212> TYPE: PRT
<213> ORGANISM: Lama glama

<400> SEQUENCE: 371

```
Gln Thr Val Val Thr Gln Glu Pro Ser Leu Ser Val Ser Pro Gly Gly
 1               5                  10                  15
Thr Val Thr Leu Thr Cys Gly Leu Ser Ser Gly Ser Val Thr Ala Ser
             20                  25                  30
Asn Tyr Pro Gly Trp Phe Gln Gln Thr Pro Gly Gln Ala Pro Arg Ala
         35                  40                  45
Leu Ile Tyr Ser Thr Asn Asp Arg His Ser Gly Val Pro Asp Arg Phe
     50                  55                  60
Ser Gly Ser Ile Ser Gly Asn Lys Ala Ala Leu Thr Ile Thr Gly Ala
 65                  70                  75                  80
Gln Ala Asp Asp Glu Ala Asp Tyr Tyr Cys Ala Leu Asp Ile Gly Asp
                 85                  90                  95
Ile Thr Glu Phe Gly Gly Gly Thr His Leu Thr Val Leu
            100                 105
```

<210> SEQ ID NO 372
<211> LENGTH: 109
<212> TYPE: PRT
<213> ORGANISM: Lama glama

<400> SEQUENCE: 372

```
Gln Thr Val Val Thr Gln Glu Pro Ser Leu Thr Val Ser Pro Gly Gly
 1               5                  10                  15
```

```
Thr Val Thr Leu Thr Cys Gly Leu Ser Ser Gly Ser Val Thr Ala Ser
             20                  25                  30

Asn Tyr Pro Gly Trp Phe Gln Lys Pro Gly Gln Ala Pro Arg Ala
         35                  40                  45

Leu Ile Tyr Ser Thr Asn Asp Arg His Ser Gly Val Pro Ala Arg Phe
 50                  55                  60

Ser Gly Ser Leu Leu Gly Gly Lys Ala Ala Leu Thr Ile Leu Gly Ala
 65                  70                  75                  80

Gln Ala Asp Asp Glu Ala Glu Tyr Tyr Cys Ala Leu Asp Ile Gly Asp
                 85                  90                  95

Ile Thr Glu Phe Gly Gly Gly Thr Gln Leu Thr Val Leu
            100                 105
```

<210> SEQ ID NO 373
<211> LENGTH: 109
<212> TYPE: PRT
<213> ORGANISM: Lama glama

<400> SEQUENCE: 373

```
Gln Thr Val Val Thr Gln Glu Pro Ser Leu Thr Val Ser Pro Gly Gly
 1               5                  10                  15

Thr Val Thr Leu Thr Cys Gly Leu Ser Ser Gly Ser Val Thr Ala Ser
             20                  25                  30

Asn Tyr Pro Gly Trp Phe Gln Lys Pro Gly Gln Ala Pro Arg Ala
         35                  40                  45

Leu Ile Tyr Ser Thr Asn Asp Arg His Ser Trp Val Pro Ala Arg Phe
 50                  55                  60

Ser Gly Ser Ile Ser Gly Gly Lys Ala Ala Leu Thr Ile Leu Gly Ala
 65                  70                  75                  80

Gln Pro Glu Asp Glu Ala Glu Tyr Tyr Cys Ala Leu Asp Ile Gly Asp
                 85                  90                  95

Ile Thr Glu Phe Gly Gly Gly Thr Gln Leu Thr Val Leu
            100                 105
```

<210> SEQ ID NO 374
<211> LENGTH: 109
<212> TYPE: PRT
<213> ORGANISM: Lama glama

<400> SEQUENCE: 374

```
Gln Thr Val Val Thr Gln Glu Pro Ser Leu Ser Val Ser Pro Gly Gly
 1               5                  10                  15

Thr Val Thr Leu Thr Cys Gly Leu Ser Ser Gly Ser Val Thr Ala Ser
             20                  25                  30

Asn Tyr Pro Gly Trp Phe Gln Lys Pro Gly Gln Ala Pro Arg Ala
         35                  40                  45

Leu Ile Tyr Ser Thr Asn Asp Arg His Ser Gly Val Pro Ala Arg Phe
 50                  55                  60

Ser Gly Ser Leu Ser Gly Gly Lys Ala Ala Leu Thr Ile Leu Gly Ala
 65                  70                  75                  80

Gln Pro Glu Asp Glu Ala Asp Tyr Tyr Cys Ala Leu Asp Ile Gly Asp
                 85                  90                  95

Ile Thr Glu Phe Gly Gly Gly Thr His Leu Thr Val Leu
            100                 105
```

<210> SEQ ID NO 375

```
<211> LENGTH: 109
<212> TYPE: PRT
<213> ORGANISM: Lama glama

<400> SEQUENCE: 375
```

Gln Thr Val Val Thr Gln Glu Pro Ser Leu Thr Val Ser Pro Gly Gly
1               5                   10                  15

Thr Val Thr Leu Thr Cys Gly Leu Ser Ser Gly Ser Val Thr Ala Ser
            20                  25                  30

Asn Tyr Pro Gly Trp Phe Gln Gln Lys Pro Gly Gln Ala Pro Arg Ala
        35                  40                  45

Leu Ile Tyr Ser Thr Asn Asp Arg His Ser Trp Val Pro Ala Arg Phe
    50                  55                  60

Ser Gly Ser Leu Leu Gly Gly Lys Ala Ala Leu Thr Ile Thr Gly Ala
65                  70                  75                  80

Gln Pro Glu Asp Glu Ala Glu Tyr Tyr Cys Ala Leu Asp Ile Gly Asp
                85                  90                  95

Ile Thr Glu Phe Gly Gly Gly Thr His Leu Thr Val Leu
            100                 105

```
<210> SEQ ID NO 376
<211> LENGTH: 109
<212> TYPE: PRT
<213> ORGANISM: Lama glama

<400> SEQUENCE: 376
```

Gln Thr Val Val Thr Gln Glu Pro Ser Leu Thr Val Ser Pro Gly Gly
1               5                   10                  15

Thr Val Thr Leu Thr Cys Gly Leu Ser Ser Gly Ser Val Thr Ala Ser
            20                  25                  30

Asn Tyr Pro Gly Trp Phe Gln Gln Lys Pro Gly Gln Ala Pro Arg Ala
        35                  40                  45

Leu Ile Tyr Ser Thr Asn Asp Arg His Ser Trp Val Pro Ala Arg Phe
    50                  55                  60

Ser Gly Ser Leu Ser Gly Gly Lys Ala Ala Leu Thr Leu Thr Gly Ala
65                  70                  75                  80

Gln Pro Glu Asp Glu Ala Glu Tyr Tyr Cys Ala Leu Asp Ile Gly Asp
                85                  90                  95

Ile Thr Glu Phe Gly Gly Gly Thr His Leu Thr Val Leu
            100                 105

```
<210> SEQ ID NO 377
<211> LENGTH: 109
<212> TYPE: PRT
<213> ORGANISM: Lama glama

<400> SEQUENCE: 377
```

Gln Thr Val Val Thr Gln Glu Pro Ser Leu Thr Val Ser Pro Gly Gly
1               5                   10                  15

Thr Val Thr Leu Thr Cys Gly Leu Ser Ser Gly Ser Val Thr Ala Ser
            20                  25                  30

Asn Tyr Pro Gly Trp Phe Gln Gln Lys Pro Gly Gln Ala Pro Arg Ala
        35                  40                  45

Leu Ile Tyr Ser Thr Asn Asp Arg His Ser Trp Val Pro Ser Arg Phe
    50                  55                  60

Ser Gly Ser Leu Ser Gly Gly Lys Ala Ala Leu Thr Ile Thr Gly Ala
65                  70                  75                  80

Gln Pro Glu Asp Glu Ala Glu Tyr Tyr Cys Ala Leu Asp Ile Gly Asp
                85                  90                  95

Ile Thr Glu Phe Gly Gly Gly Thr Gln Leu Thr Val Leu
            100                 105

<210> SEQ ID NO 378
<211> LENGTH: 109
<212> TYPE: PRT
<213> ORGANISM: Lama glama

<400> SEQUENCE: 378

Gln Thr Val Val Thr Gln Glu Pro Ser Leu Thr Val Ser Pro Gly Gly
1               5                   10                  15

Thr Val Thr Leu Thr Cys Gly Leu Ser Ser Gly Ser Val Thr Ala Ser
            20                  25                  30

Asn Tyr Pro Gly Trp Phe Gln Gln Thr Pro Gly Gln Ala Pro Arg Ala
        35                  40                  45

Leu Ile Tyr Ser Thr Asn Asp Arg His Ser Gly Val Pro Ala Arg Phe
    50                  55                  60

Ser Gly Ser Leu Ser Gly Gly Lys Ala Ala Leu Thr Ile Thr Gly Ala
65                  70                  75                  80

Gln Pro Glu Asp Glu Ala Asp Tyr Tyr Cys Ala Leu Asp Ile Gly Asp
                85                  90                  95

Ile Thr Glu Phe Gly Gly Gly Thr His Leu Thr Val Leu
            100                 105

<210> SEQ ID NO 379
<211> LENGTH: 109
<212> TYPE: PRT
<213> ORGANISM: Lama glama

<400> SEQUENCE: 379

Gln Ala Val Val Thr Gln Glu Pro Ser Leu Thr Val Ser Pro Gly Gly
1               5                   10                  15

Thr Val Thr Leu Thr Cys Gly Leu Ser Ser Gly Ser Val Thr Ala Ser
            20                  25                  30

Asn Tyr Pro Gly Trp Phe Gln Gln Thr Pro Gly Gln Ala Pro Arg Ala
        35                  40                  45

Leu Ile Tyr Ser Thr Asn Asp Arg His Ser Gly Val Pro Ala Arg Phe
    50                  55                  60

Ser Gly Ser Leu Ser Gly Asn Lys Ala Ala Leu Thr Ile Thr Gly Ala
65                  70                  75                  80

Gln Ala Glu Asp Glu Ala Glu Tyr Tyr Cys Ala Leu Asp Ile Gly Asp
                85                  90                  95

Ile Thr Glu Phe Gly Gly Gly Thr His Leu Thr Val Leu
            100                 105

<210> SEQ ID NO 380
<211> LENGTH: 109
<212> TYPE: PRT
<213> ORGANISM: Lama glama

<400> SEQUENCE: 380

Gln Thr Val Val Thr Gln Glu Pro Ser Leu Ser Val Ser Pro Gly Gly
1               5                   10                  15

Thr Val Thr Leu Thr Cys Gly Leu Ser Ser Gly Ser Val Thr Ala Ser
            20                  25                  30

Asn Tyr Pro Gly Trp Phe Gln Gln Lys Pro Gly Gln Ala Pro Arg Ala

```
                35                  40                  45

Leu Ile Tyr Ser Thr Asn Asp Arg His Ser Gly Val Pro Ala Arg Phe
        50                  55                  60

Ser Gly Ser Leu Leu Gly Gly Lys Ala Ala Leu Thr Leu Thr Gly Ala
 65                  70                  75                  80

Gln Pro Glu Asp Glu Ala Glu Tyr Tyr Cys Ala Leu Asp Ile Gly Asp
                 85                  90                  95

Ile Thr Glu Phe Gly Gly Gly Thr Gln Leu Thr Val Leu
                100                 105
```

<210> SEQ ID NO 381
<211> LENGTH: 109
<212> TYPE: PRT
<213> ORGANISM: Lama glama

<400> SEQUENCE: 381

```
Gln Thr Val Val Thr Gln Glu Pro Ser Leu Thr Val Ser Pro Gly Gly
 1               5                  10                  15

Thr Val Thr Leu Thr Cys Gly Leu Ser Ser Gly Ser Val Thr Ala Ser
                20                  25                  30

Asn Tyr Pro Gly Trp Phe Gln Gln Thr Pro Gly Gln Ala Pro Arg Ala
                35                  40                  45

Leu Ile Tyr Ser Thr Asn Asp Arg His Ser Trp Val Pro Ser Arg Phe
        50                  55                  60

Ser Gly Ser Leu Leu Gly Gly Lys Ala Ala Leu Thr Leu Thr Gly Ala
 65                  70                  75                  80

Gln Pro Glu Asp Glu Ala Glu Tyr Tyr Cys Ala Leu Asp Ile Gly Asp
                 85                  90                  95

Ile Thr Glu Phe Gly Gly Gly Thr Gln Leu Thr Val Leu
                100                 105
```

<210> SEQ ID NO 382
<211> LENGTH: 109
<212> TYPE: PRT
<213> ORGANISM: Lama glama

<400> SEQUENCE: 382

```
Gln Thr Val Val Thr Gln Glu Pro Ser Leu Thr Val Ser Pro Gly Gly
 1               5                  10                  15

Thr Val Thr Leu Thr Cys Gly Leu Ser Ser Gly Ser Val Thr Ala Ser
                20                  25                  30

Asn Tyr Pro Gly Trp Phe Gln Gln Lys Pro Gly Gln Ala Pro Arg Ala
                35                  40                  45

Leu Ile Tyr Ser Thr Asn Asp Arg His Ser Gly Val Pro Ser Arg Phe
        50                  55                  60

Ser Gly Ser Leu Leu Gly Gly Lys Ala Ala Leu Thr Leu Leu Gly Ala
 65                  70                  75                  80

Gln Pro Glu Asp Glu Ala Glu Tyr Tyr Cys Ala Leu Asp Ile Gly Asp
                 85                  90                  95

Ile Thr Glu Phe Gly Gly Gly Thr Gln Leu Thr Val Leu
                100                 105
```

<210> SEQ ID NO 383
<211> LENGTH: 109
<212> TYPE: PRT
<213> ORGANISM: Lama glama

<400> SEQUENCE: 383

Gln Thr Val Val Thr Gln Glu Pro Ser Leu Thr Val Ser Pro Gly Gly
1               5                   10                  15

Thr Val Thr Leu Thr Cys Gly Leu Ser Ser Gly Ser Val Thr Ala Ser
            20                  25                  30

Asn Tyr Pro Gly Trp Phe Gln Gln Thr Pro Gly Gln Ala Pro Arg Ala
        35                  40                  45

Leu Ile Tyr Ser Thr Asn Asp Arg His Ser Trp Val Pro Ala Arg Phe
    50                  55                  60

Ser Gly Ser Leu Ser Gly Gly Lys Ala Ala Leu Thr Leu Thr Gly Ala
65              70                  75                  80

Gln Pro Glu Asp Glu Ala Asp Tyr Tyr Cys Ala Leu Asp Ile Gly Asp
                85                  90                  95

Ile Thr Glu Phe Gly Gly Gly Thr Lys Leu Thr Val Leu
            100                 105

<210> SEQ ID NO 384
<211> LENGTH: 109
<212> TYPE: PRT
<213> ORGANISM: Lama glama

<400> SEQUENCE: 384

Gln Ala Val Val Thr Gln Glu Pro Ser Leu Ser Val Ser Pro Gly Gly
1               5                   10                  15

Thr Val Thr Leu Thr Cys Gly Leu Ser Ser Gly Ser Val Thr Ala Ser
            20                  25                  30

Asn Tyr Pro Gly Trp Phe Gln Gln Thr Pro Gly Gln Ala Pro Arg Ala
        35                  40                  45

Leu Ile Tyr Ser Thr Asn Asp Arg His Ser Trp Val Pro Ala Arg Phe
    50                  55                  60

Ser Gly Ser Leu Leu Gly Gly Lys Ala Ala Leu Thr Ile Thr Gly Ala
65              70                  75                  80

Gln Pro Glu Asp Glu Ala Glu Tyr Tyr Cys Ala Leu Asp Ile Gly Asp
                85                  90                  95

Ile Thr Glu Phe Gly Gly Gly Thr His Leu Thr Val Leu
            100                 105

<210> SEQ ID NO 385
<211> LENGTH: 109
<212> TYPE: PRT
<213> ORGANISM: Lama glama

<400> SEQUENCE: 385

Gln Thr Val Val Thr Gln Glu Pro Ser Leu Ser Val Ser Pro Gly Gly
1               5                   10                  15

Thr Val Thr Leu Thr Cys Gly Leu Ser Ser Gly Ser Val Thr Ala Ser
            20                  25                  30

Asn Tyr Pro Gly Trp Phe Gln Gln Thr Pro Gly Gln Ala Pro Arg Ala
        35                  40                  45

Leu Ile Tyr Ser Thr Asn Asp Arg His Ser Gly Val Pro Ala Arg Phe
    50                  55                  60

Ser Gly Ser Ile Leu Gly Gly Lys Ala Ala Leu Thr Ile Leu Gly Ala
65              70                  75                  80

Gln Pro Glu Asp Glu Ala Glu Tyr Tyr Cys Ala Leu Asp Ile Gly Asp
                85                  90                  95

Ile Thr Glu Phe Gly Gly Gly Thr His Leu Thr Val Leu
            100                 105

<210> SEQ ID NO 386
<211> LENGTH: 109
<212> TYPE: PRT
<213> ORGANISM: Lama glama

<400> SEQUENCE: 386

```
Gln Thr Val Val Thr Gln Glu Pro Ser Leu Ser Val Ser Pro Gly Gly
1               5                   10                  15

Thr Val Thr Leu Thr Cys Gly Leu Ser Ser Gly Ser Val Thr Ala Ser
            20                  25                  30

Asn Tyr Pro Gly Trp Phe Gln Gln Thr Pro Gly Gln Ala Pro Arg Ala
        35                  40                  45

Leu Ile Tyr Ser Thr Asn Asp Arg His Ser Gly Val Pro Ser Arg Phe
    50                  55                  60

Ser Gly Ser Ile Leu Gly Gly Lys Ala Ala Leu Thr Leu Thr Gly Ala
65                  70                  75                  80

Gln Pro Glu Asp Glu Ala Glu Tyr Tyr Cys Ala Leu Asp Ile Gly Asp
                85                  90                  95

Ile Thr Glu Phe Gly Gly Gly Thr Gln Leu Thr Val Leu
            100                 105
```

<210> SEQ ID NO 387
<211> LENGTH: 109
<212> TYPE: PRT
<213> ORGANISM: Lama glama

<400> SEQUENCE: 387

```
Gln Thr Val Val Thr Gln Glu Pro Ser Leu Ser Val Ser Pro Gly Gly
1               5                   10                  15

Thr Val Thr Leu Thr Cys Gly Leu Ser Ser Gly Ser Val Thr Ala Ser
            20                  25                  30

Asn Tyr Pro Gly Trp Phe Gln Gln Thr Pro Gly Gln Ala Pro Arg Ala
        35                  40                  45

Leu Ile Tyr Ser Thr Asn Asp Arg His Ser Gly Val Pro Ala Arg Phe
    50                  55                  60

Ser Gly Ser Ile Ser Gly Gly Lys Ala Ala Leu Thr Leu Leu Gly Ala
65                  70                  75                  80

Gln Pro Glu Asp Glu Ala Glu Tyr Tyr Cys Ala Leu Asp Ile Gly Asp
                85                  90                  95

Ile Thr Glu Phe Gly Gly Gly Thr Gln Leu Thr Val Leu
            100                 105
```

<210> SEQ ID NO 388
<211> LENGTH: 109
<212> TYPE: PRT
<213> ORGANISM: Lama glama

<400> SEQUENCE: 388

```
Gln Thr Val Val Thr Gln Glu Pro Ser Leu Ser Val Ser Pro Gly Gly
1               5                   10                  15

Thr Val Thr Leu Thr Cys Gly Leu Ser Ser Gly Ser Val Thr Ala Ser
            20                  25                  30

Asn Tyr Pro Gly Trp Phe Gln Gln Lys Pro Gly Gln Ala Pro Arg Ala
        35                  40                  45

Leu Ile Tyr Ser Thr Asn Asp Arg His Ser Gly Val Pro Ala Arg Phe
    50                  55                  60
```

```
Ser Gly Ser Ile Ser Gly Gly Lys Ala Ala Leu Thr Leu Leu Gly Ala
 65                  70                  75                  80

Gln Ala Glu Asp Glu Ala Glu Tyr Tyr Cys Ala Leu Asp Ile Gly Asp
                 85                  90                  95

Ile Thr Glu Phe Gly Gly Gly Thr Gln Leu Thr Val Leu
            100                 105
```

<210> SEQ ID NO 389
<211> LENGTH: 109
<212> TYPE: PRT
<213> ORGANISM: Lama glama

<400> SEQUENCE: 389

```
Gln Thr Val Val Thr Gln Glu Pro Ser Leu Ser Val Ser Pro Gly Gly
 1               5                  10                  15

Thr Val Thr Leu Thr Cys Gly Leu Ser Ser Gly Ser Val Thr Ala Ser
                20                  25                  30

Asn Tyr Pro Gly Trp Phe Gln Gln Thr Pro Gly Gln Ala Pro Arg Ala
            35                  40                  45

Leu Ile Tyr Ser Thr Asn Asp Arg His Ser Gly Val Pro Ala Arg Phe
 50                  55                  60

Ser Gly Ser Leu Ser Gly Asn Lys Ala Ala Leu Thr Ile Thr Gly Ala
 65                  70                  75                  80

Gln Pro Glu Asp Glu Ala Glu Tyr Tyr Cys Ala Leu Asp Ile Gly Asp
                 85                  90                  95

Ile Thr Glu Phe Gly Gly Gly Thr Gln Leu Thr Val Leu
            100                 105
```

<210> SEQ ID NO 390
<211> LENGTH: 109
<212> TYPE: PRT
<213> ORGANISM: Lama glama

<400> SEQUENCE: 390

```
Gln Ala Val Val Thr Gln Glu Pro Ser Leu Ser Val Ser Pro Gly Gly
 1               5                  10                  15

Thr Val Thr Leu Thr Cys Gly Leu Ser Ser Gly Ser Val Thr Ala Ser
                20                  25                  30

Asn Tyr Pro Gly Trp Phe Gln Gln Lys Pro Gly Gln Ala Pro Arg Ala
            35                  40                  45

Leu Ile Tyr Ser Thr Asn Asp Arg His Ser Gly Val Pro Ala Arg Phe
 50                  55                  60

Ser Gly Ser Ile Leu Gly Gly Lys Ala Ala Leu Thr Leu Thr Gly Ala
 65                  70                  75                  80

Gln Pro Glu Asp Glu Ala Asp Tyr Tyr Cys Ala Leu Asp Ile Gly Asp
                 85                  90                  95

Ile Thr Glu Phe Gly Gly Gly Thr His Leu Thr Val Leu
            100                 105
```

<210> SEQ ID NO 391
<211> LENGTH: 110
<212> TYPE: PRT
<213> ORGANISM: Lama glama

<400> SEQUENCE: 391

```
Gln Ser Ala Leu Thr Gln Pro Pro Ser Val Ser Gly Thr Pro Gly Gln
 1               5                  10                  15

Arg Val Thr Ile Ser Cys Ala Gly Ala Asn Asn Asp Ile Gly Thr Tyr
```

```
                20                  25                  30
Ala Tyr Val Ser Trp Tyr Gln Gln Leu Pro Gly Thr Ala Pro Lys Leu
            35                  40                  45

Leu Ile Tyr Lys Val Thr Thr Arg Ala Ser Gly Val Pro Asp Arg Phe
        50                  55                  60

Ser Gly Ser Lys Ser Gly Asn Thr Ala Ser Leu Thr Ile Thr Gly Leu
65                  70                  75                  80

Gln Ser Glu Asp Glu Ala Asp Tyr Tyr Cys Ala Ser Tyr Arg Asn Phe
                85                  90                  95

Asn Asn Ala Val Phe Gly Arg Gly Thr Lys Leu Thr Val Leu
            100                 105                 110

<210> SEQ ID NO 392
<211> LENGTH: 110
<212> TYPE: PRT
<213> ORGANISM: Lama glama

<400> SEQUENCE: 392

Gln Ser Val Leu Thr Gln Pro Pro Ser Val Ser Gly Ala Pro Gly Gln
1               5                   10                  15

Thr Val Thr Ile Ser Cys Ala Gly Ala Asn Asn Asp Ile Gly Thr Tyr
            20                  25                  30

Ala Tyr Val Ser Trp Tyr Gln Gln Leu Pro Gly Thr Ala Pro Lys Leu
            35                  40                  45

Leu Ile Tyr Lys Val Thr Thr Arg Ala Ser Gly Ile Pro Asp Arg Phe
        50                  55                  60

Ser Gly Ser Lys Ser Gly Ala Thr Ala Ser Leu Thr Ile Thr Gly Leu
65                  70                  75                  80

Gln Ala Glu Asp Glu Ala Asp Tyr Tyr Cys Ala Ser Tyr Arg Asn Phe
                85                  90                  95

Asn Asn Ala Val Phe Gly Arg Gly Thr His Leu Thr Val Leu
            100                 105                 110

<210> SEQ ID NO 393
<211> LENGTH: 110
<212> TYPE: PRT
<213> ORGANISM: Lama glama

<400> SEQUENCE: 393

Gln Ser Ala Leu Thr Gln Pro Pro Leu Val Ser Gly Thr Pro Gly Gln
1               5                   10                  15

Arg Val Thr Ile Ser Cys Ala Gly Ala Asn Asn Asp Ile Gly Thr Tyr
            20                  25                  30

Ala Tyr Val Ser Trp Tyr Gln Gln Leu Pro Gly Thr Ala Pro Arg Leu
            35                  40                  45

Leu Ile Tyr Lys Val Thr Thr Arg Ala Ser Gly Val Pro Asp Arg Phe
        50                  55                  60

Ser Gly Ser Lys Ser Gly Asn Thr Ala Ser Leu Thr Ile Thr Gly Leu
65                  70                  75                  80

Gln Ser Glu Asp Glu Ala Asp Tyr Tyr Cys Ala Ser Tyr Arg Asn Phe
                85                  90                  95

Asn Asn Ala Val Phe Gly Gly Gly Thr Lys Leu Thr Val Leu
            100                 105                 110

<210> SEQ ID NO 394
<211> LENGTH: 110
<212> TYPE: PRT
```

<213> ORGANISM: Lama glama

<400> SEQUENCE: 394

```
Gln Ser Ala Leu Thr His Pro Pro Leu Val Ser Gly Ala Pro Gly Gln
1               5                   10                  15

Thr Val Thr Ile Ser Cys Ala Gly Ala Asn Asn Asp Ile Gly Thr Tyr
            20                  25                  30

Ala Tyr Val Ser Trp Tyr Gln Gln Leu Pro Gly Thr Ala Pro Lys Leu
        35                  40                  45

Leu Ile Tyr Lys Val Thr Thr Arg Ala Ser Gly Val Pro Asp Arg Phe
    50                  55                  60

Ser Gly Ser Lys Ser Ala Asn Thr Ala Ser Leu Thr Ile Thr Gly Leu
65                  70                  75                  80

Gln Ala Glu Asp Glu Ala Asp Tyr Tyr Cys Ala Ser Tyr Arg Asn Phe
                85                  90                  95

Asn Asn Ala Val Phe Gly Arg Gly Thr Lys Leu Thr Val Leu
            100                 105                 110
```

<210> SEQ ID NO 395
<211> LENGTH: 110
<212> TYPE: PRT
<213> ORGANISM: Lama glama

<400> SEQUENCE: 395

```
Gln Ser Ala Leu Thr Gln Pro Pro Leu Val Ser Gly Ala Pro Gly Gln
1               5                   10                  15

Arg Val Thr Ile Ser Cys Ala Gly Ala Asn Asn Asp Ile Gly Thr Tyr
            20                  25                  30

Ala Tyr Val Ser Trp Tyr Gln Gln Leu Pro Gly Thr Ala Pro Lys Leu
        35                  40                  45

Leu Ile Tyr Lys Val Thr Thr Arg Ala Ser Gly Val Pro Ser Arg Phe
    50                  55                  60

Ser Gly Ser Lys Ser Gly Asn Thr Ala Ser Leu Thr Ile Ser Glu Leu
65                  70                  75                  80

Gln Ser Glu Asp Glu Ala Asp Tyr Tyr Cys Ala Ser Tyr Arg Asn Phe
                85                  90                  95

Asn Asn Ala Val Phe Gly Gly Gly Thr His Leu Thr Val Leu
            100                 105                 110
```

<210> SEQ ID NO 396
<211> LENGTH: 110
<212> TYPE: PRT
<213> ORGANISM: Lama glama

<400> SEQUENCE: 396

```
Gln Ser Val Leu Thr Gln Pro Pro Ser Val Ser Gly Thr Pro Gly Gln
1               5                   10                  15

Thr Val Thr Ile Ser Cys Ala Gly Ala Asn Asn Asp Ile Gly Thr Tyr
            20                  25                  30

Ala Tyr Val Ser Trp Tyr Gln Gln Leu Pro Gly Thr Ala Pro Lys Leu
        35                  40                  45

Leu Ile Tyr Lys Val Thr Thr Arg Ala Ser Gly Val Pro Asp Arg Phe
    50                  55                  60

Ser Gly Ser Lys Ser Gly Asn Ser Ala Ser Leu Thr Ile Thr Gly Leu
65                  70                  75                  80

Gln Ser Glu Asp Glu Ala Asp Tyr Tyr Cys Ala Ser Tyr Arg Asn Phe
                85                  90                  95
```

```
Asn Asn Ala Val Phe Gly Gly Gly Thr Lys Leu Thr Val Leu
            100                 105                 110

<210> SEQ ID NO 397
<211> LENGTH: 110
<212> TYPE: PRT
<213> ORGANISM: Lama glama

<400> SEQUENCE: 397

Gln Ser Ala Leu Thr Gln Pro Pro Leu Val Ser Gly Ala Pro Gly Gln
1               5                   10                  15

Thr Val Thr Ile Ser Cys Ala Gly Ala Asn Asn Asp Ile Gly Thr Tyr
            20                  25                  30

Ala Tyr Val Ser Trp Tyr Gln Gln Leu Pro Gly Thr Ala Pro Lys Leu
        35                  40                  45

Leu Ile Tyr Lys Val Thr Thr Arg Ala Ser Gly Val Pro Asp Arg Phe
    50                  55                  60

Ser Gly Ser Lys Ser Gly Asn Thr Ala Ser Leu Thr Ile Thr Gly Leu
65                  70                  75                  80

Gln Ala Glu Asp Glu Ala Asp Tyr Tyr Cys Ala Ser Tyr Arg Asn Phe
                85                  90                  95

Asn Asn Ala Val Phe Gly Gly Gly Thr Lys Leu Thr Val Leu
            100                 105                 110

<210> SEQ ID NO 398
<211> LENGTH: 110
<212> TYPE: PRT
<213> ORGANISM: Lama glama

<400> SEQUENCE: 398

Gln Ser Val Leu Thr Gln Pro Pro Leu Val Ser Gly Ala Pro Gly Gln
1               5                   10                  15

Thr Val Thr Ile Ser Cys Ala Gly Ala Asn Asn Asp Ile Gly Thr Tyr
            20                  25                  30

Ala Tyr Val Ser Trp Tyr Gln Gln Leu Pro Gly Thr Ala Pro Lys Leu
        35                  40                  45

Leu Ile Tyr Lys Val Thr Thr Arg Ala Ser Gly Val Pro Asp Arg Phe
    50                  55                  60

Ser Gly Ser Lys Ser Gly Asn Thr Ala Ser Leu Ala Ile Thr Gly Leu
65                  70                  75                  80

Gln Ala Glu Asp Glu Ala Asp Tyr Tyr Cys Ala Ser Tyr Arg Asn Phe
                85                  90                  95

Asn Asn Ala Val Phe Gly Arg Gly Thr Lys Leu Thr Val Leu
            100                 105                 110

<210> SEQ ID NO 399
<211> LENGTH: 110
<212> TYPE: PRT
<213> ORGANISM: Lama glama

<400> SEQUENCE: 399

Gln Ser Val Leu Thr Gln Pro Pro Leu Val Ser Gly Ala Pro Gly Gln
1               5                   10                  15

Thr Val Thr Ile Ser Cys Ala Gly Ala Asn Asn Asp Ile Gly Thr Tyr
            20                  25                  30

Ala Tyr Val Ser Trp Tyr Gln Gln Leu Pro Gly Thr Ala Pro Lys Leu
        35                  40                  45
```

```
Leu Ile Tyr Lys Val Thr Thr Arg Ala Ser Gly Val Pro Asp Arg Phe
 50                  55                  60

Ser Gly Ser Lys Ser Gly Ala Thr Ala Ser Leu Thr Ile Thr Gly Leu
 65                  70                  75                  80

Gln Ser Glu Asp Glu Ala Asp Tyr Tyr Cys Ala Ser Tyr Arg Asn Phe
                 85                  90                  95

Asn Asn Ala Val Phe Gly Arg Gly Thr His Leu Thr Val Leu
            100                 105                 110

<210> SEQ ID NO 400
<211> LENGTH: 110
<212> TYPE: PRT
<213> ORGANISM: Lama glama

<400> SEQUENCE: 400

Gln Ser Val Leu Thr Gln Pro Pro Leu Val Ser Gly Ala Pro Gly Gln
  1               5                  10                  15

Thr Val Thr Ile Ser Cys Ala Gly Ala Asn Asn Asp Ile Gly Thr Tyr
                 20                  25                  30

Ala Tyr Val Ser Trp Tyr Gln Gln Leu Pro Gly Thr Ala Pro Lys Leu
             35                  40                  45

Leu Ile Tyr Lys Val Thr Thr Arg Ala Ser Gly Ile Pro Ser Arg Phe
 50                  55                  60

Ser Gly Ser Lys Ser Gly Asn Ser Ala Ser Leu Thr Ile Ser Gly Leu
 65                  70                  75                  80

Gln Ala Glu Asp Glu Ala Asp Tyr Tyr Cys Ala Ser Tyr Arg Asn Phe
                 85                  90                  95

Asn Asn Ala Val Phe Gly Gly Gly Thr Lys Leu Thr Val Leu
            100                 105                 110

<210> SEQ ID NO 401
<211> LENGTH: 110
<212> TYPE: PRT
<213> ORGANISM: Lama glama

<400> SEQUENCE: 401

Gln Ser Val Leu Thr Gln Pro Pro Leu Val Ser Gly Ala Pro Gly Gln
  1               5                  10                  15

Thr Val Thr Ile Ser Cys Ala Gly Ala Asn Asn Asp Ile Gly Thr Tyr
                 20                  25                  30

Ala Tyr Val Ser Trp Tyr Gln Gln Leu Pro Gly Thr Ala Pro Lys Leu
             35                  40                  45

Leu Ile Tyr Lys Val Thr Thr Arg Ala Ser Gly Ile Pro Ser Arg Phe
 50                  55                  60

Ser Gly Ser Lys Ser Gly Asn Thr Ala Ser Leu Thr Ile Thr Gly Leu
 65                  70                  75                  80

Gln Ala Glu Asp Glu Ala Asp Tyr Tyr Cys Ala Ser Tyr Arg Asn Phe
                 85                  90                  95

Asn Asn Ala Val Phe Gly Arg Gly Thr Lys Leu Thr Val Leu
            100                 105                 110

<210> SEQ ID NO 402
<211> LENGTH: 110
<212> TYPE: PRT
<213> ORGANISM: Lama glama

<400> SEQUENCE: 402

Gln Ser Val Leu Thr Gln Pro Pro Leu Val Ser Gly Thr Pro Gly Gln
  1               5                  10                  15
```

```
1               5                  10                 15
Arg Val Thr Ile Ser Cys Ala Gly Ala Asn Asn Asp Ile Gly Thr Tyr
            20                  25                 30

Ala Tyr Val Ser Trp Tyr Gln Gln Leu Pro Gly Thr Ala Pro Lys Leu
            35                  40                 45

Leu Ile Tyr Lys Val Thr Thr Arg Ala Ser Gly Ile Pro Asp Arg Phe
            50                  55                 60

Ser Gly Ser Lys Ser Gly Asn Thr Ala Ser Leu Thr Ile Thr Gly Leu
65                  70                  75                 80

Gln Ala Glu Asp Glu Ala Asp Tyr Tyr Cys Ala Ser Tyr Arg Asn Phe
            85                  90                 95

Asn Asn Ala Val Phe Gly Arg Gly Thr His Leu Thr Val Leu
            100                 105                110

<210> SEQ ID NO 403
<211> LENGTH: 110
<212> TYPE: PRT
<213> ORGANISM: Lama glama

<400> SEQUENCE: 403

Gln Ser Ala Leu Thr Gln Pro Pro Ser Val Ser Gly Ala Pro Gly Gln
1               5                  10                 15

Thr Val Thr Ile Ser Cys Ala Gly Ala Asn Asn Asp Ile Gly Thr Tyr
            20                  25                 30

Ala Tyr Val Ser Trp Tyr Gln Gln Leu Pro Gly Thr Ala Pro Lys Leu
            35                  40                 45

Leu Ile Tyr Lys Val Thr Thr Arg Ala Ser Gly Val Pro Asp Arg Phe
            50                  55                 60

Ser Gly Ser Lys Ser Gly Asn Thr Ala Ser Leu Ala Ile Ser Gly Leu
65                  70                  75                 80

Gln Ala Glu Asp Glu Ala Asp Tyr Tyr Cys Ala Ser Tyr Arg Asn Phe
            85                  90                 95

Asn Asn Ala Val Phe Gly Gly Gly Thr His Leu Thr Val Leu
            100                 105                110

<210> SEQ ID NO 404
<211> LENGTH: 110
<212> TYPE: PRT
<213> ORGANISM: Lama glama

<400> SEQUENCE: 404

Gln Ser Ala Leu Thr Gln Pro Pro Leu Val Ser Gly Ser Pro Gly Gln
1               5                  10                 15

Ser Val Thr Ile Ser Cys Ala Gly Ala Asn Asn Asp Ile Gly Thr Tyr
            20                  25                 30

Ala Tyr Val Ser Trp Tyr Gln Gln Leu Pro Gly Thr Ala Pro Lys Leu
            35                  40                 45

Leu Ile Tyr Lys Val Thr Thr Arg Ala Ser Gly Ile Pro Asp Arg Phe
            50                  55                 60

Ser Gly Ser Lys Ser Gly Asn Thr Ala Ser Leu Thr Ile Ser Gly Leu
65                  70                  75                 80

Gln Ser Glu Asp Glu Ala Asp Tyr Tyr Cys Ala Ser Tyr Arg Asn Phe
            85                  90                 95

Asn Asn Ala Val Phe Gly Gly Gly Thr Lys Leu Thr Val Leu
            100                 105                110
```

```
<210> SEQ ID NO 405
<211> LENGTH: 110
<212> TYPE: PRT
<213> ORGANISM: Lama glama

<400> SEQUENCE: 405

Gln Ser Ala Leu Thr Gln Pro Pro Leu Val Ser Gly Ser Pro Gly Gln
1               5                   10                  15

Thr Val Thr Ile Ser Cys Ala Gly Ala Asn Asn Asp Ile Gly Thr Tyr
            20                  25                  30

Ala Tyr Val Ser Trp Tyr Gln Gln Leu Pro Gly Thr Ala Pro Lys Leu
        35                  40                  45

Met Ile Tyr Lys Val Thr Thr Arg Ala Ser Gly Ile Pro Ser Arg Phe
    50                  55                  60

Ser Gly Ser Lys Ser Gly Asn Thr Ala Ser Leu Thr Ile Ser Gly Leu
65                  70                  75                  80

Gln Ser Glu Asp Glu Ala Asp Tyr Tyr Cys Ala Ser Tyr Arg Asn Phe
                85                  90                  95

Asn Asn Ala Val Phe Gly Thr Gly Thr Lys Leu Thr Val Leu
            100                 105                 110

<210> SEQ ID NO 406
<211> LENGTH: 110
<212> TYPE: PRT
<213> ORGANISM: Lama glama

<400> SEQUENCE: 406

Gln Ser Ala Leu Thr Gln Pro Pro Ser Val Ser Gly Ser Pro Gly Gln
1               5                   10                  15

Thr Val Thr Ile Ser Cys Ala Gly Ala Asn Asn Asp Ile Gly Thr Tyr
            20                  25                  30

Ala Tyr Val Ser Trp Tyr Gln Gln Leu Pro Gly Thr Ala Pro Lys Leu
        35                  40                  45

Met Ile Tyr Lys Val Thr Thr Arg Ala Ser Gly Ile Pro Asp Arg Phe
    50                  55                  60

Ser Gly Ser Lys Ser Gly Asn Thr Ala Ser Leu Thr Ile Ser Gly Leu
65                  70                  75                  80

Gln Ser Glu Asp Glu Ala Asp Tyr Tyr Cys Ala Ser Tyr Arg Asn Phe
                85                  90                  95

Asn Asn Ala Val Phe Gly Arg Gly Thr His Leu Thr Val Leu
            100                 105                 110

<210> SEQ ID NO 407
<211> LENGTH: 110
<212> TYPE: PRT
<213> ORGANISM: Lama glama

<400> SEQUENCE: 407

Gln Ser Ala Leu Thr Gln Pro Pro Ser Val Ser Gly Ser Pro Gly Gln
1               5                   10                  15

Thr Val Thr Ile Ser Cys Ala Gly Ala Asn Asn Asp Ile Gly Thr Tyr
            20                  25                  30

Ala Tyr Val Ser Trp Tyr Gln Gln Leu Pro Gly Thr Ala Pro Lys Leu
        35                  40                  45

Leu Ile Tyr Lys Val Thr Thr Arg Ala Ser Gly Ile Pro Ser Arg Phe
    50                  55                  60

Ser Gly Ser Lys Ser Gly Asn Thr Ala Ser Leu Thr Ile Ser Gly Leu
65                  70                  75                  80
```

Gln Ser Glu Asp Glu Ala Asp Tyr Tyr Cys Ala Ser Tyr Arg Asn Phe
                85                  90                  95

Asn Asn Ala Val Phe Gly Thr Gly Thr Lys Leu Thr Val Leu
            100                 105                 110

<210> SEQ ID NO 408
<211> LENGTH: 110
<212> TYPE: PRT
<213> ORGANISM: Lama glama

<400> SEQUENCE: 408

Gln Ser Ala Leu Thr Gln Pro Pro Leu Val Ser Gly Ile Pro Gly Gln
1               5                   10                  15

Ser Val Thr Ile Ser Cys Ala Gly Ala Asn Asn Asp Ile Gly Thr Tyr
            20                  25                  30

Ala Tyr Val Ser Trp Tyr Gln Gln Leu Pro Gly Thr Ala Pro Lys Leu
        35                  40                  45

Leu Ile Tyr Lys Val Thr Thr Arg Ala Ser Gly Val Pro Asp Arg Phe
50                  55                  60

Ser Gly Ser Lys Ser Gly Asn Thr Ala Ser Leu Thr Ile Ser Gly Leu
65                  70                  75                  80

Gln Ser Glu Asp Glu Ala Asp Tyr Tyr Cys Ala Ser Tyr Arg Asn Phe
                85                  90                  95

Asn Asn Ala Val Phe Gly Thr Gly Thr Lys Leu Thr Val Leu
            100                 105                 110

<210> SEQ ID NO 409
<211> LENGTH: 110
<212> TYPE: PRT
<213> ORGANISM: Lama glama

<400> SEQUENCE: 409

Gln Ser Ala Leu Thr Gln Pro Pro Ser Val Ser Gly Ser Pro Gly Gln
1               5                   10                  15

Thr Val Thr Ile Ser Cys Ala Gly Ala Asn Asn Asp Ile Gly Thr Tyr
            20                  25                  30

Ala Tyr Val Ser Trp Tyr Gln Gln Leu Pro Gly Thr Ala Pro Lys Leu
        35                  40                  45

Met Ile Tyr Lys Val Thr Thr Arg Ala Ser Gly Ile Pro Ser Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ala Ser Tyr Arg Asn Phe
                85                  90                  95

Asn Asn Ala Val Phe Gly Gly Gly Thr Lys Leu Thr Val Leu
            100                 105                 110

<210> SEQ ID NO 410
<211> LENGTH: 110
<212> TYPE: PRT
<213> ORGANISM: Lama glama

<400> SEQUENCE: 410

Gln Ser Ala Leu Thr Gln Pro Pro Leu Val Ser Gly Ser Pro Gly Gln
1               5                   10                  15

Ser Val Thr Ile Ser Cys Ala Gly Ala Asn Asn Asp Ile Gly Thr Tyr
            20                  25                  30

```
Ala Tyr Val Ser Trp Tyr Gln Gln Leu Pro Gly Thr Ala Pro Lys Leu
        35                  40                  45

Met Ile Tyr Lys Val Thr Thr Arg Ala Ser Gly Val Pro Asp Arg Phe
 50                  55                  60

Ser Gly Ser Lys Ser Gly Asn Thr Ala Ser Leu Thr Ile Ser Gly Leu
 65                  70                  75                  80

Gln Ser Glu Asp Glu Ala Asp Tyr Tyr Cys Ala Ser Tyr Arg Asn Phe
                 85                  90                  95

Asn Asn Ala Val Phe Gly Thr Gly Thr Lys Leu Thr Val Leu
                100                 105                 110

<210> SEQ ID NO 411
<211> LENGTH: 110
<212> TYPE: PRT
<213> ORGANISM: Lama glama

<400> SEQUENCE: 411

Gln Ser Ala Leu Thr Gln Pro Pro Leu Val Ser Gly Ser Pro Gly Gln
 1               5                  10                  15

Thr Val Thr Ile Ser Cys Ala Gly Ala Asn Asn Asp Ile Gly Thr Tyr
                20                  25                  30

Ala Tyr Val Ser Trp Tyr Gln Gln Leu Pro Gly Thr Ala Pro Lys Leu
        35                  40                  45

Leu Ile Tyr Lys Val Thr Thr Arg Ala Ser Gly Val Pro Asp Arg Phe
 50                  55                  60

Ser Gly Ser Lys Ser Gly Asn Thr Ala Ser Leu Thr Ile Ser Gly Leu
 65                  70                  75                  80

Gln Ser Glu Asp Glu Ala Asp Tyr Tyr Cys Ala Ser Tyr Arg Asn Phe
                 85                  90                  95

Asn Asn Ala Val Phe Gly Arg Gly Thr Lys Leu Thr Val Leu
                100                 105                 110

<210> SEQ ID NO 412
<211> LENGTH: 110
<212> TYPE: PRT
<213> ORGANISM: Lama glama

<400> SEQUENCE: 412

Gln Ser Ala Met Thr Gln Pro Pro Ser Val Ser Gly Ser Pro Gly Gln
 1               5                  10                  15

Ser Val Thr Ile Ser Cys Ala Gly Ala Asn Asn Asp Ile Gly Thr Tyr
                20                  25                  30

Ala Tyr Val Ser Trp Tyr Gln Gln Pro Pro Gly Thr Ala Pro Lys Leu
        35                  40                  45

Leu Ile Tyr Lys Val Thr Thr Arg Ala Ser Gly Val Pro Ser Arg Phe
 50                  55                  60

Ser Gly Ser Lys Ser Gly Asn Thr Ala Ser Leu Thr Ile Ser Gly Leu
 65                  70                  75                  80

Gln Ser Glu Asp Glu Ala Asp Tyr Tyr Cys Ala Ser Tyr Arg Asn Phe
                 85                  90                  95

Asn Asn Ala Val Phe Gly Thr Gly Thr Lys Leu Thr Val Leu
                100                 105                 110

<210> SEQ ID NO 413
<211> LENGTH: 110
<212> TYPE: PRT
<213> ORGANISM: Lama glama
```

<400> SEQUENCE: 413

Gln Ser Ala Leu Thr Gln Pro Pro Leu Val Ser Gly Ser Pro Gly Gln
1               5                   10                  15

Thr Val Thr Ile Ser Cys Ala Gly Ala Asn Asn Asp Ile Gly Thr Tyr
            20                  25                  30

Ala Tyr Val Ser Trp Tyr Gln Gln Leu Ala Gly Thr Ala Pro Lys Leu
        35                  40                  45

Met Ile Tyr Lys Val Thr Thr Arg Ala Ser Gly Ile Pro Ser Arg Phe
50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ala Ser Tyr Arg Asn Phe
                85                  90                  95

Asn Asn Ala Val Phe Gly Thr Gly Thr His Leu Thr Val Leu
            100                 105                 110

<210> SEQ ID NO 414
<211> LENGTH: 110
<212> TYPE: PRT
<213> ORGANISM: Lama glama

<400> SEQUENCE: 414

Gln Ser Ala Leu Thr Gln Pro Pro Leu Val Ser Gly Ser Pro Gly Gln
1               5                   10                  15

Ser Val Thr Ile Ser Cys Ala Gly Ala Asn Asn Asp Ile Gly Thr Tyr
            20                  25                  30

Ala Tyr Val Ser Trp Tyr Gln Gln Leu Pro Gly Thr Ala Pro Lys Leu
        35                  40                  45

Met Ile Tyr Lys Val Thr Thr Arg Ala Ser Gly Val Pro Ser Arg Phe
50                  55                  60

Ser Gly Ser Lys Ser Gly Asn Thr Ala Ser Leu Thr Ile Ser Gly Leu
65                  70                  75                  80

Gln Ser Glu Asp Glu Ala Asp Tyr Tyr Cys Ala Ser Tyr Arg Asn Phe
                85                  90                  95

Asn Asn Ala Val Phe Gly Thr Gly Thr His Leu Thr Val Leu
            100                 105                 110

<210> SEQ ID NO 415
<211> LENGTH: 110
<212> TYPE: PRT
<213> ORGANISM: Lama glama

<400> SEQUENCE: 415

Gln Ser Ala Leu Thr Gln Pro Pro Ser Val Ser Gly Ser Pro Gly Gln
1               5                   10                  15

Thr Val Thr Ile Ser Cys Ala Gly Ala Asn Asn Asp Ile Gly Thr Tyr
            20                  25                  30

Ala Tyr Val Ser Trp Tyr Gln Gln Leu Pro Gly Thr Ala Pro Lys Leu
        35                  40                  45

Met Ile Tyr Lys Val Thr Thr Arg Ala Ser Gly Val Pro Ser Arg Phe
50                  55                  60

Ser Gly Ser Ile Ser Gly Asn Thr Ala Ser Leu Thr Ile Ser Gly Leu
65                  70                  75                  80

Gln Ala Glu Asp Glu Ala Asp Tyr Tyr Cys Ala Ser Tyr Arg Asn Phe
                85                  90                  95

Asn Asn Ala Val Phe Gly Gly Gly Thr His Leu Thr Val Leu

<210> SEQ ID NO 416
<211> LENGTH: 110
<212> TYPE: PRT
<213> ORGANISM: Lama glama

<400> SEQUENCE: 416

Gln Ser Ala Leu Thr Gln Pro Pro Ser Val Ser Gly Thr Pro Gly Gln
1               5                   10                  15

Ser Val Thr Ile Ser Cys Ala Gly Ala Asn Asn Asp Ile Gly Thr Tyr
            20                  25                  30

Ala Tyr Val Ser Trp Tyr Gln Gln Leu Pro Gly Thr Ala Pro Lys Leu
        35                  40                  45

Met Ile Tyr Lys Val Thr Thr Arg Ala Ser Gly Ile Pro Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ala Ser Tyr Arg Asn Phe
                85                  90                  95

Asn Asn Ala Val Phe Gly Thr Gly Thr Lys Leu Thr Val Leu
            100                 105                 110

<210> SEQ ID NO 417
<211> LENGTH: 110
<212> TYPE: PRT
<213> ORGANISM: Lama glama

<400> SEQUENCE: 417

Gln Ser Ala Leu Thr Gln Pro Pro Ser Val Ser Gly Ser Pro Gly Gln
1               5                   10                  15

Ser Val Thr Ile Ser Cys Ala Gly Ala Asn Asn Asp Ile Gly Thr Tyr
            20                  25                  30

Ala Tyr Val Ser Trp Tyr Gln Gln Leu Pro Gly Thr Ala Pro Lys Leu
        35                  40                  45

Leu Ile Tyr Lys Val Thr Thr Arg Ala Ser Gly Val Pro Asp Arg Phe
    50                  55                  60

Ser Gly Ser Lys Ser Gly Asn Thr Ala Ser Leu Thr Ile Ser Gly Leu
65                  70                  75                  80

Gln Ser Glu Asp Glu Ala Asp Tyr Tyr Cys Ala Ser Tyr Arg Asn Phe
                85                  90                  95

Asn Asn Gly Val Phe Gly Thr Gly Thr Lys Leu Thr Val Leu
            100                 105                 110

<210> SEQ ID NO 418
<211> LENGTH: 110
<212> TYPE: PRT
<213> ORGANISM: Lama glama

<400> SEQUENCE: 418

Gln Ser Ala Leu Thr Gln Pro Pro Leu Val Ser Gly Ser Pro Gly Gln
1               5                   10                  15

Ser Val Thr Ile Ser Cys Ala Gly Ala Asn Asn Asp Ile Gly Thr Tyr
            20                  25                  30

Ala Tyr Val Ser Trp Tyr Gln Gln Leu Pro Gly Thr Ala Pro Lys Leu
        35                  40                  45

Met Ile Tyr Lys Val Thr Thr Arg Ala Ser Gly Val Pro Asp Arg Phe
    50                  55                  60

-continued

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ala Ser Tyr Arg Asn Phe
                85                  90                  95

Asn Asn Ala Val Phe Gly Arg Gly Thr His Leu Thr Val Leu
            100                 105                 110

<210> SEQ ID NO 419
<211> LENGTH: 110
<212> TYPE: PRT
<213> ORGANISM: Lama glama

<400> SEQUENCE: 419

Gln Ser Ala Leu Thr Gln Pro Pro Leu Val Ser Gly Pro Gly Gln
1               5                   10                  15

Thr Val Thr Ile Ser Cys Ala Gly Ala Asn Asn Asp Ile Gly Thr Tyr
                20                  25                  30

Ala Tyr Val Ser Trp Tyr Gln Gln Leu Pro Gly Thr Ala Pro Lys Leu
            35                  40                  45

Leu Ile Tyr Lys Val Thr Thr Arg Ala Ser Gly Val Pro Asp Arg Phe
        50                  55                  60

Ser Gly Ser Lys Ser Gly Asn Thr Ala Ser Leu Thr Ile Ser Gly Leu
65                  70                  75                  80

Gln Ser Glu Asp Glu Ala Asp Tyr Tyr Cys Ala Ser Tyr Arg Asn Phe
                85                  90                  95

Asn Asn Ala Val Phe Gly Thr Gly Thr Lys Leu Thr Val Leu
            100                 105                 110

<210> SEQ ID NO 420
<211> LENGTH: 110
<212> TYPE: PRT
<213> ORGANISM: Lama glama

<400> SEQUENCE: 420

Gln Ser Ala Leu Thr Gln Pro Pro Ser Val Ser Gly Thr Pro Gly Gln
1               5                   10                  15

Thr Val Thr Ile Ser Cys Ala Gly Ala Asn Asn Asp Ile Gly Thr Tyr
                20                  25                  30

Ala Tyr Val Ser Trp Tyr Gln Gln Pro Pro Gly Thr Ala Pro Lys Leu
            35                  40                  45

Leu Ile Tyr Lys Val Thr Thr Arg Ala Ser Gly Ile Pro Asp Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ala Ser Tyr Arg Tyr Phe
                85                  90                  95

Asn Asn Ala Val Phe Gly Thr Gly Thr Lys Leu Thr Val Leu
            100                 105                 110

<210> SEQ ID NO 421
<211> LENGTH: 110
<212> TYPE: PRT
<213> ORGANISM: Lama glama

<400> SEQUENCE: 421

Gln Ser Ala Leu Thr Gln Pro Pro Ser Val Ser Gly Pro Gly Gln
1               5                   10                  15

-continued

Thr Val Thr Ile Ser Cys Ala Gly Ala Asn Asn Asp Ile Gly Thr Tyr
            20                  25                  30

Ala Tyr Val Ser Trp Tyr Gln Gln Leu Pro Gly Thr Ala Pro Lys Leu
        35                  40                  45

Met Ile Tyr Lys Val Thr Thr Arg Ala Ser Gly Val Pro Ser Arg Phe
    50                  55                  60

Ser Gly Ser Lys Ser Gly Asn Thr Ala Ser Leu Thr Ile Ser Gly Leu
65                  70                  75                  80

Gln Ser Glu Asp Glu Ala Asp Tyr Tyr Cys Ser Ser Tyr Arg Asn Phe
                85                  90                  95

Asn Asn Ala Val Phe Gly Thr Gly Thr Lys Leu Thr Val Leu
                100                 105                 110

<210> SEQ ID NO 422
<211> LENGTH: 110
<212> TYPE: PRT
<213> ORGANISM: Lama glama

<400> SEQUENCE: 422

Gln Ser Ala Leu Thr Gln Pro Pro Ser Val Ser Gly Ser Pro Gly Gln
1               5                   10                  15

Thr Val Thr Ile Ser Cys Ala Gly Ala Asn Asn Asp Ile Gly Thr Tyr
            20                  25                  30

Ala Tyr Val Ser Trp Tyr Gln Gln Leu Pro Gly Thr Ala Pro Lys Leu
        35                  40                  45

Leu Ile Tyr Lys Val Thr Ser Arg Ala Ser Gly Val Pro Ser Arg Phe
    50                  55                  60

Ser Gly Ser Lys Ser Gly Asn Thr Ala Ser Leu Ser Ile Ser Gly Leu
65                  70                  75                  80

Gln Ala Glu Asp Glu Ala Asp Tyr Tyr Cys Ala Ser Tyr Arg Asn Phe
                85                  90                  95

Asn Asn Ala Val Phe Gly Ser Gly Thr Lys Leu Thr Val Leu
                100                 105                 110

<210> SEQ ID NO 423
<211> LENGTH: 110
<212> TYPE: PRT
<213> ORGANISM: Lama glama

<400> SEQUENCE: 423

Gln Ser Ala Leu Thr Gln Pro Pro Ser Val Ser Gly Thr Pro Gly Gln
1               5                   10                  15

Thr Val Thr Ile Ser Cys Ala Gly Ala Asn Asn Asp Ile Gly Thr Tyr
            20                  25                  30

Ala Tyr Val Ser Trp Tyr Gln Gln Leu Pro Gly Thr Ala Pro Lys Leu
        35                  40                  45

Met Ile Tyr Lys Val Thr Thr Arg Ala Ser Gly Ile Pro Asp Arg Phe
    50                  55                  60

Ser Gly Ser Lys Ser Gly Asn Thr Ala Ser Leu Thr Ile Ser Gly Leu
65                  70                  75                  80

Gln Ser Glu Asp Glu Ala Asp Tyr Tyr Cys Ala Ser Tyr Arg Asn Phe
                85                  90                  95

Asn Asn Ala Val Phe Gly Gly Gly Thr Lys Leu Thr Val Leu
                100                 105                 110

<210> SEQ ID NO 424
<211> LENGTH: 110

<212> TYPE: PRT
<213> ORGANISM: Lama glama

<400> SEQUENCE: 424

Gln Ser Ala Leu Thr Gln Pro Pro Ser Val Ser Gly Ser Pro Gly Gln
1               5                   10                  15

Thr Val Thr Ile Ser Cys Ala Gly Ala Asn Asn Asp Ile Gly Thr Tyr
            20                  25                  30

Ala Tyr Val Ser Trp Tyr Gln Gln Leu Pro Gly Thr Ala Pro Lys Leu
        35                  40                  45

Met Ile Tyr Lys Val Thr Thr Arg Ala Ser Gly Val Pro Ser Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ala Ser Tyr Arg Asn Phe
                85                  90                  95

Asn Asn Ala Val Phe Gly Arg Gly Thr His Leu Thr Val Leu
            100                 105                 110

<210> SEQ ID NO 425
<211> LENGTH: 110
<212> TYPE: PRT
<213> ORGANISM: Lama glama

<400> SEQUENCE: 425

Gln Ser Ala Leu Thr Gln Pro Pro Leu Val Ser Gly Thr Pro Gly Gln
1               5                   10                  15

Ser Val Thr Ile Ser Cys Ala Gly Ala Asn Asn Asp Ile Gly Thr Tyr
            20                  25                  30

Ala Tyr Val Ser Trp Tyr Gln Gln Leu Pro Gly Thr Ala Pro Lys Leu
        35                  40                  45

Leu Ile Tyr Lys Val Thr Thr Arg Ala Ser Gly Ile Pro Ser Arg Phe
    50                  55                  60

Ser Gly Ser Lys Ser Gly Asn Thr Ala Ser Leu Thr Ile Ser Gly Leu
65                  70                  75                  80

Gln Ser Glu Asp Glu Ala Asp Tyr Tyr Cys Ala Ser Tyr Arg Asn Phe
                85                  90                  95

Asn Asn Ala Val Phe Gly Thr Gly Thr Lys Leu Thr Val Leu
            100                 105                 110

<210> SEQ ID NO 426
<211> LENGTH: 110
<212> TYPE: PRT
<213> ORGANISM: Lama glama

<400> SEQUENCE: 426

Gln Ser Ala Leu Thr Gln Pro Pro Leu Val Ser Gly Thr Pro Gly Gln
1               5                   10                  15

Thr Val Thr Ile Ser Cys Ala Gly Ala Asn Asn Asp Ile Gly Thr Tyr
            20                  25                  30

Ala Tyr Val Ser Trp Tyr Gln Gln Leu Pro Gly Thr Ala Pro Lys Leu
        35                  40                  45

Met Ile Tyr Lys Val Thr Thr Arg Ala Ser Gly Val Pro Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ala Ser Tyr Arg Asn Phe

```
                    85                  90                  95

Asn Asn Ala Val Phe Gly Arg Gly Thr Lys Leu Thr Val Leu
                100                 105                 110

<210> SEQ ID NO 427
<211> LENGTH: 110
<212> TYPE: PRT
<213> ORGANISM: Lama glama

<400> SEQUENCE: 427

Gln Ser Ala Leu Thr Gln Pro Pro Ser Val Ser Gly Ser Pro Gly Gln
1               5                   10                  15

Thr Val Thr Ile Ser Cys Ala Gly Ala Asn Asn Asp Ile Gly Thr Tyr
                20                  25                  30

Ala Tyr Val Ser Trp Tyr Gln Gln Pro Pro Gly Thr Ala Pro Lys Leu
            35                  40                  45

Met Ile Tyr Lys Val Thr Thr Arg Ala Ser Gly Val Pro Ser Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ala Ser Tyr Arg Asn Phe
                85                  90                  95

Asn Asn Ala Val Phe Gly Ser Gly Thr His Leu Thr Val Leu
                100                 105                 110

<210> SEQ ID NO 428
<211> LENGTH: 110
<212> TYPE: PRT
<213> ORGANISM: Lama glama

<400> SEQUENCE: 428

Gln Ser Ala Leu Thr Gln Pro Pro Leu Val Ser Gly Ser Pro Gly Gln
1               5                   10                  15

Thr Val Thr Ile Ser Cys Ala Gly Ala Asn Asn Asp Ile Gly Thr Tyr
                20                  25                  30

Ala Tyr Val Ser Trp Tyr Gln Gln Leu Pro Gly Thr Ala Pro Lys Leu
            35                  40                  45

Met Ile Tyr Arg Val Thr Thr Arg Ala Ser Gly Val Pro Asp Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ala Ser Tyr Arg Asn Phe
                85                  90                  95

Asn Asn Ala Val Phe Gly Gly Gly Thr His Leu Thr Val Leu
                100                 105                 110

<210> SEQ ID NO 429
<211> LENGTH: 110
<212> TYPE: PRT
<213> ORGANISM: Lama glama

<400> SEQUENCE: 429

Gln Ser Ala Leu Thr Gln Pro Pro Leu Val Ser Gly Ser Pro Gly Gln
1               5                   10                  15

Thr Val Thr Ile Ser Cys Ala Gly Ala Asn Asn Asp Ile Gly Thr Tyr
                20                  25                  30

Ala Tyr Val Ser Trp Tyr Gln Gln Leu Pro Gly Thr Ala Pro Lys Leu
            35                  40                  45
```

```
Leu Ile Tyr Lys Val Thr Thr Arg Ala Ser Gly Ile Pro Ser Arg Phe
         50                  55                  60

Ser Gly Ser Lys Ser Gly Asn Thr Ala Ser Leu Thr Ile Ser Gly Leu
 65                  70                  75                  80

Gln Ser Glu Asp Glu Ala Asp Tyr Tyr Cys Ala Ser Tyr Arg Asn Phe
                 85                  90                  95

Asn Asn Ala Val Phe Gly Arg Gly Thr His Leu Thr Val Leu
            100                 105                 110

<210> SEQ ID NO 430
<211> LENGTH: 110
<212> TYPE: PRT
<213> ORGANISM: Lama glama

<400> SEQUENCE: 430

Gln Ser Ala Met Thr Gln Pro Pro Ser Val Ser Gly Ser Pro Gly Gln
 1               5                  10                  15

Ser Val Thr Ile Ser Cys Ala Gly Ala Asn Asn Asp Ile Gly Thr Tyr
                 20                  25                  30

Ala Tyr Val Ser Trp Tyr Gln Gln Pro Pro Gly Thr Ala Pro Lys Leu
             35                  40                  45

Leu Ile Tyr Lys Val Thr Thr Arg Ala Ser Gly Val Pro Ser Arg Phe
         50                  55                  60

Ser Gly Ser Lys Ser Gly Asn Thr Ala Ser Leu Thr Ile Ser Gly Leu
 65                  70                  75                  80

Gln Ser Glu Asp Glu Ala Asp Tyr Tyr Cys Ala Ser Tyr Arg Asn Phe
                 85                  90                  95

Asn Asn Ala Val Phe Gly Thr Gly Thr Lys Leu Thr Val Leu
            100                 105                 110

<210> SEQ ID NO 431
<211> LENGTH: 110
<212> TYPE: PRT
<213> ORGANISM: Lama glama

<400> SEQUENCE: 431

Gln Ser Ala Leu Thr Gln Pro Pro Leu Val Ser Gly Ser Pro Gly Gln
 1               5                  10                  15

Ser Val Thr Ile Ser Cys Ala Gly Ala Asn Asn Asp Ile Gly Thr Tyr
                 20                  25                  30

Ala Tyr Val Ser Trp Tyr Gln Gln Leu Pro Gly Thr Ala Pro Lys Leu
             35                  40                  45

Leu Ile Tyr Lys Val Thr Thr Arg Ala Ser Gly Val Pro Ser Arg Phe
         50                  55                  60

Ser Gly Ser Lys Ser Gly Asn Thr Ala Ser Leu Thr Ile Ser Gly Leu
 65                  70                  75                  80

Gln Ser Glu Asp Glu Ala Asp Tyr Tyr Cys Ala Ser Tyr Arg Asn Phe
                 85                  90                  95

Asn Asn Ala Val Phe Gly Asn Gly Thr Gln Leu Thr Val Leu
            100                 105                 110

<210> SEQ ID NO 432
<211> LENGTH: 110
<212> TYPE: PRT
<213> ORGANISM: Lama glama

<400> SEQUENCE: 432
```

Gln Ser Ala Leu Thr Gln Pro Pro Ser Val Ser Gly Ser Pro Gly Gln
1               5                   10                  15

Thr Val Thr Ile Ser Cys Ala Gly Ala Asn Asn Asp Ile Gly Thr Tyr
            20                  25                  30

Ala Tyr Val Ser Trp Tyr Gln Gln Pro Pro Gly Thr Ala Pro Lys Leu
        35                  40                  45

Met Ile Tyr Lys Val Thr Thr Arg Ala Ser Gly Val Pro Ser Arg Phe
    50                  55                  60

Ser Gly Ser Ile Ser Gly Asn Thr Ala Ser Leu Thr Ile Ser Gly Leu
65              70                  75                  80

Gln Ala Glu Asp Glu Ala Asp Tyr Tyr Cys Ala Ser Tyr Arg Asn Phe
                85                  90                  95

Asn Asn Ala Val Phe Gly Thr Gly Thr His Leu Thr Val Leu
            100                 105                 110

<210> SEQ ID NO 433
<211> LENGTH: 110
<212> TYPE: PRT
<213> ORGANISM: Lama glama

<400> SEQUENCE: 433

Gln Ser Ala Leu Thr Gln Pro Pro Leu Val Ser Gly Ser Pro Gly Gln
1               5                   10                  15

Ser Val Thr Ile Ser Cys Ala Gly Ala Asn Asn Asp Ile Gly Thr Tyr
            20                  25                  30

Ala Tyr Val Ser Trp Tyr Gln Gln Leu Pro Gly Thr Ala Pro Lys Leu
        35                  40                  45

Leu Ile Tyr Lys Val Thr Thr Arg Ala Ser Gly Ile Pro Asp Arg Phe
    50                  55                  60

Ser Gly Ser Lys Ser Gly Asn Thr Ala Ser Leu Thr Ile Ser Gly Leu
65              70                  75                  80

Gln Ala Glu Asp Glu Ala Asp Tyr Tyr Cys Ala Ser Tyr Arg Asn Phe
                85                  90                  95

Asn Asn Ala Val Phe Gly Gly Gly Thr Lys Leu Thr Val Leu
            100                 105                 110

<210> SEQ ID NO 434
<211> LENGTH: 110
<212> TYPE: PRT
<213> ORGANISM: Lama glama

<400> SEQUENCE: 434

Gln Ser Ala Leu Thr Gln Pro Pro Ser Val Ser Gly Ser Pro Gly Gln
1               5                   10                  15

Thr Val Thr Ile Ser Cys Ala Gly Ala Asn Asn Asp Ile Gly Thr Tyr
            20                  25                  30

Ala Tyr Val Ser Trp Tyr Gln Gln Leu Pro Gly Thr Ala Pro Lys Leu
        35                  40                  45

Met Ile Tyr Lys Val Thr Thr Arg Ala Ser Gly Val Pro Ser Arg Phe
    50                  55                  60

Ser Gly Ser Lys Ser Gly Asn Thr Ala Ser Leu Thr Ile Ser Gly Leu
65              70                  75                  80

Gln Ser Glu Asp Glu Ala Asp Tyr Tyr Cys Ala Ser Tyr Arg Asn Phe
                85                  90                  95

Asn Asn Ala Val Phe Gly Gly Gly Thr His Leu Thr Val Leu
            100                 105                 110

<210> SEQ ID NO 435
<211> LENGTH: 110
<212> TYPE: PRT
<213> ORGANISM: Lama glama

<400> SEQUENCE: 435

Gln Ser Val Leu Thr Gln Pro Pro Leu Val Ser Gly Ala Pro Gly Gln
1               5                   10                  15

Arg Val Thr Ile Ser Cys Ala Gly Ala Asn Asn Asp Ile Gly Thr Tyr
            20                  25                  30

Ala Tyr Val Ser Trp Tyr Gln Gln Leu Pro Gly Thr Ala Pro Lys Leu
        35                  40                  45

Leu Ile Tyr Lys Val Thr Thr Arg Ala Ser Gly Val Pro Asp Arg Phe
    50                  55                  60

Ser Gly Ser Lys Ser Gly Asn Ser Ala Ser Leu Thr Ile Thr Gly Leu
65                  70                  75                  80

Gln Ala Glu Asp Glu Ala Asp Tyr Tyr Cys Ala Ser Tyr Arg Asn Phe
                85                  90                  95

Asn Asn Ala Val Phe Gly Gly Gly Thr Lys Leu Thr Val Leu
            100                 105                 110

<210> SEQ ID NO 436
<211> LENGTH: 110
<212> TYPE: PRT
<213> ORGANISM: Lama glama

<400> SEQUENCE: 436

Gln Ser Val Leu Thr Gln Pro Pro Leu Val Ser Gly Ala Pro Gly Gln
1               5                   10                  15

Thr Val Thr Ile Ser Cys Ala Gly Ala Asn Asn Asp Ile Gly Thr Tyr
            20                  25                  30

Ala Tyr Val Ser Trp Tyr Gln Gln Leu Pro Gly Thr Ala Pro Lys Leu
        35                  40                  45

Leu Ile Tyr Lys Val Thr Thr Arg Ala Ser Gly Val Pro Asp Arg Phe
    50                  55                  60

Ser Gly Ser Lys Ser Gly Asn Thr Ala Ser Leu Thr Ile Thr Gly Leu
65                  70                  75                  80

Gln Ala Glu Asp Glu Ala Asp Tyr Tyr Cys Ala Ser Tyr Arg Asn Phe
                85                  90                  95

Asn Asn Ala Val Phe Gly Arg Gly Thr Lys Leu Thr Val Leu
            100                 105                 110

<210> SEQ ID NO 437
<211> LENGTH: 110
<212> TYPE: PRT
<213> ORGANISM: Lama glama

<400> SEQUENCE: 437

Gln Ser Val Leu Thr Gln Pro Pro Leu Val Ser Gly Thr Pro Gly Gln
1               5                   10                  15

Thr Val Thr Ile Ser Cys Ala Gly Ala Asn Asn Asp Ile Gly Thr Tyr
            20                  25                  30

Ala Tyr Val Ser Trp Tyr Gln Gln Leu Pro Gly Thr Ala Pro Lys Leu
        35                  40                  45

Leu Ile Tyr Lys Val Thr Thr Arg Ala Ser Gly Ile Pro Asp Arg Phe
    50                  55                  60

Ser Gly Ser Lys Ser Gly Asn Thr Ala Ser Leu Ala Ile Ser Gly Leu 65                  70                  75                  80

Gln Ala Glu Asp Glu Ala Asp Tyr Tyr Cys Ala Ser Tyr Arg Asn Phe
                85                  90                  95

Asn Asn Ala Val Phe Gly Gly Gly Thr Lys Leu Thr Val Leu
                100                 105                 110

<210> SEQ ID NO 438
<211> LENGTH: 110
<212> TYPE: PRT
<213> ORGANISM: Lama glama

<400> SEQUENCE: 438

Gln Ser Ala Leu Thr Gln Pro Pro Ser Val Gly Ser Pro Gly Gln
1               5                   10                  15

Ser Val Thr Ile Ser Cys Ala Gly Ala Asn Asn Asp Ile Gly Thr Tyr
                20                  25                  30

Ala Tyr Val Ser Trp Tyr Gln Gln Leu Pro Gly Thr Ala Pro Lys Leu
            35                  40                  45

Leu Ile Tyr Lys Val Thr Thr Arg Ala Ser Gly Ile Pro Asp Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ala Ser Tyr Arg Asn Phe
                85                  90                  95

Asn Asn Ala Val Phe Gly Thr Gly Thr His Leu Thr Val Leu
                100                 105                 110

<210> SEQ ID NO 439
<211> LENGTH: 110
<212> TYPE: PRT
<213> ORGANISM: Lama glama

<400> SEQUENCE: 439

Gln Ser Ala Leu Thr Gln Pro Pro Ser Val Gly Ser Pro Gly Gln
1               5                   10                  15

Thr Val Thr Ile Ser Cys Ala Gly Ala Asn Asn Asp Ile Gly Thr Tyr
                20                  25                  30

Ala Tyr Val Ser Trp Tyr Gln Gln Leu Pro Gly Thr Ala Pro Lys Leu
            35                  40                  45

Met Ile Tyr Lys Val Thr Thr Arg Ala Ser Gly Val Pro Ser Arg Phe
        50                  55                  60

Ser Gly Ser Lys Ser Gly Asn Thr Ala Ser Leu Thr Ile Ser Gly Leu
65                  70                  75                  80

Gln Ser Glu Asp Glu Ala Asp Tyr Tyr Cys Ala Ser Tyr Arg Asn Phe
                85                  90                  95

Asn Asn Ala Val Phe Gly Gly Gly Thr His Leu Thr Val Leu
                100                 105                 110

<210> SEQ ID NO 440
<211> LENGTH: 110
<212> TYPE: PRT
<213> ORGANISM: Lama glama

<400> SEQUENCE: 440

Gln Ser Val Leu Thr Gln Pro Pro Ser Val Gly Thr Pro Gly Gln
1               5                   10                  15

Arg Val Thr Ile Ser Cys Ala Gly Ala Asn Asn Asp Ile Gly Thr Tyr
                20                  25                  30

-continued

Ala Tyr Val Ser Trp Tyr Gln Gln Leu Pro Gly Thr Ala Pro Lys Leu
         35                  40                  45

Leu Ile Tyr Lys Val Thr Thr Arg Ala Ser Gly Val Pro Asp Arg Phe
 50                  55                  60

Ser Gly Ser Lys Ser Gly Asn Ser Ala Ser Leu Thr Ile Thr Gly Leu
 65                  70                  75                  80

Gln Ser Glu Asp Glu Ala Asp Tyr Tyr Cys Ala Ser Tyr Arg Asn Phe
                 85                  90                  95

Asn Asn Ala Val Phe Gly Gly Gly Thr His Leu Thr Val Leu
             100                 105                 110

<210> SEQ ID NO 441
<211> LENGTH: 110
<212> TYPE: PRT
<213> ORGANISM: Lama glama

<400> SEQUENCE: 441

Gln Ser Ala Leu Thr Gln Pro Pro Leu Val Ser Gly Thr Pro Gly Gln
 1               5                  10                  15

Pro Val Thr Ile Ser Cys Ala Gly Ala Asn Asn Asp Ile Gly Thr Tyr
                 20                  25                  30

Ala Tyr Val Ser Trp Tyr Gln Gln Leu Pro Gly Thr Ala Pro Lys Leu
         35                  40                  45

Leu Ile Ser Lys Val Thr Thr Arg Ala Ser Gly Val Pro Asp Arg Phe
 50                  55                  60

Ser Gly Ser Lys Ser Gly Thr Thr Ala Ser Leu Thr Ile Thr Gly Leu
 65                  70                  75                  80

Gln Ser Glu Asp Glu Ala Asp Tyr Tyr Cys Ala Ser Tyr Arg Asn Phe
                 85                  90                  95

Asn Asn Gly Val Phe Gly Gly Gly Thr His Leu Thr Val Leu
             100                 105                 110

<210> SEQ ID NO 442
<211> LENGTH: 110
<212> TYPE: PRT
<213> ORGANISM: Lama glama

<400> SEQUENCE: 442

Gln Ser Ala Leu Thr Gln Pro Pro Leu Val Ser Gly Thr Pro Gly Gln
 1               5                  10                  15

Thr Val Thr Ile Ser Cys Ala Gly Ala Asn Asn Asp Ile Gly Thr Tyr
                 20                  25                  30

Ala Tyr Val Ser Trp Tyr Gln Gln Leu Pro Gly Thr Ala Pro Lys Leu
         35                  40                  45

Leu Ile Tyr Lys Val Thr Thr Arg Ala Ser Gly Val Pro Ser Arg Phe
 50                  55                  60

Ser Gly Ser Lys Ser Gly Asn Thr Ala Ser Leu Thr Ile Ser Gly Leu
 65                  70                  75                  80

Gln Ser Glu Asp Glu Ala Asp Tyr Tyr Cys Ala Ser Tyr Arg Thr Phe
                 85                  90                  95

Asn Asn Ala Val Phe Gly Ser Gly Thr His Leu Thr Val Leu
             100                 105                 110

<210> SEQ ID NO 443
<211> LENGTH: 110
<212> TYPE: PRT
<213> ORGANISM: Lama glama -continued

<400> SEQUENCE: 443

Gln Ser Ala Leu Thr Gln Pro Pro Leu Val Ser Gly Ser Pro Gly Gln
1               5                   10                  15

Thr Val Thr Ile Ser Cys Ala Gly Ala Asn Asn Asp Ile Gly Thr Tyr
            20                  25                  30

Ala Tyr Val Ser Trp Tyr Gln Gln Pro Pro Gly Thr Ala Pro Lys Leu
        35                  40                  45

Leu Ile Tyr Lys Val Thr Thr Arg Ala Ser Gly Ile Pro Asp Arg Phe
    50                  55                  60

Ser Gly Ser Ile Ser Gly Asn Thr Ala Ser Leu Thr Ile Ser Gly Leu
65                  70                  75                  80

Gln Ala Glu Asp Glu Ala Asp Tyr Tyr Cys Ala Ser Tyr Arg Asn Phe
                85                  90                  95

Asn Asn Ala Val Phe Gly Arg Gly Thr Lys Leu Thr Val Leu
            100                 105                 110

<210> SEQ ID NO 444
<211> LENGTH: 110
<212> TYPE: PRT
<213> ORGANISM: Lama glama

<400> SEQUENCE: 444

Gln Ser Val Leu Thr Gln Pro Pro Ser Val Ser Gly Ala Pro Gly Gln
1               5                   10                  15

Thr Val Thr Ile Ser Cys Ala Gly Ala Asn Asn Asp Ile Gly Thr Tyr
            20                  25                  30

Ala Tyr Val Ser Trp Tyr Gln Gln Leu Pro Gly Thr Ala Pro Lys Leu
        35                  40                  45

Leu Ile Tyr Lys Val Thr Thr Arg Ala Ser Gly Ile Pro Ser Arg Phe
    50                  55                  60

Ser Gly Ser Lys Ser Gly Asn Thr Ala Ser Leu Thr Ile Thr Gly Leu
65                  70                  75                  80

Gln Ser Glu Asp Glu Ala Asp Tyr Tyr Cys Ala Ser Tyr Arg Asn Phe
                85                  90                  95

Asn Asn Ala Val Phe Gly Gly Gly Thr His Leu Thr Val Leu
            100                 105                 110

<210> SEQ ID NO 445
<211> LENGTH: 110
<212> TYPE: PRT
<213> ORGANISM: Lama glama

<400> SEQUENCE: 445

Gln Ser Ala Leu Thr Gln Pro Pro Ser Val Ser Gly Thr Pro Gly Gln
1               5                   10                  15

Ser Val Thr Ile Ser Cys Ala Gly Ala Asn Asn Asp Ile Gly Thr Tyr
            20                  25                  30

Ala Tyr Val Ser Trp Tyr Gln Gln Pro Pro Gly Thr Ala Pro Lys Leu
        35                  40                  45

Leu Ile Tyr Lys Val Thr Thr Arg Ala Ser Gly Ile Pro Ser Arg Phe
    50                  55                  60

Ser Gly Ser Lys Ser Gly Asn Thr Ala Ser Leu Thr Ile Ser Gly Leu
65                  70                  75                  80

Gln Ser Glu Asp Glu Ala Asp Tyr Tyr Cys Ala Ser Tyr Arg Asn Phe
                85                  90                  95

Asn Asn Ala Val Phe Gly Ser Gly Thr His Leu Thr Val Leu
            100                 105                 110

<210> SEQ ID NO 446
<211> LENGTH: 110
<212> TYPE: PRT
<213> ORGANISM: Lama glama

<400> SEQUENCE: 446

Gln Ser Ala Leu Thr Gln Pro Pro Leu Val Ser Gly Ser Pro Gly Gln
1               5                   10                  15

Ser Val Thr Ile Ser Cys Ala Gly Ala Asn Asn Asp Ile Gly Thr Tyr
            20                  25                  30

Ala Tyr Val Ser Trp Tyr Gln Gln Leu Pro Gly Thr Ala Pro Lys Leu
        35                  40                  45

Leu Ile Tyr Lys Val Thr Thr Arg Ala Ser Gly Ile Pro Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ala Ser Tyr Arg Asn Phe
                85                  90                  95

Asn Asn Ala Val Phe Gly Gly Gly Thr Lys Leu Thr Val Leu
            100                 105                 110

<210> SEQ ID NO 447
<211> LENGTH: 110
<212> TYPE: PRT
<213> ORGANISM: Lama glama

<400> SEQUENCE: 447

Gln Ser Ala Leu Thr Gln Pro Pro Leu Val Ser Gly Ser Pro Gly Gln
1               5                   10                  15

Ser Val Thr Ile Ser Cys Ala Gly Ala Asn Asn Asp Ile Gly Thr Tyr
            20                  25                  30

Ala Tyr Val Ser Trp Tyr Gln Gln Leu Pro Gly Thr Ala Pro Lys Leu
        35                  40                  45

Met Ile Tyr Lys Val Thr Thr Arg Ala Ser Gly Ile Pro Asp Arg Phe
    50                  55                  60

Ser Gly Ser Lys Ser Gly Asn Thr Ala Ser Leu Thr Ile Ser Gly Leu
65                  70                  75                  80

Gln Ser Glu Asp Glu Ala Asp Tyr Tyr Cys Ala Ser Tyr Arg Asn Phe
                85                  90                  95

Asn Asn Ala Val Phe Gly Thr Gly Thr Lys Leu Thr Val Leu
            100                 105                 110

<210> SEQ ID NO 448
<211> LENGTH: 110
<212> TYPE: PRT
<213> ORGANISM: Lama glama

<400> SEQUENCE: 448

Gln Ser Ala Leu Thr Gln Pro Pro Leu Val Ser Gly Ser Pro Gly Gln
1               5                   10                  15

Ser Val Thr Ile Ser Cys Ala Gly Ala Asn Asn Asp Ile Gly Thr Tyr
            20                  25                  30

Ala Tyr Val Ser Trp Tyr Gln Gln Leu Pro Gly Thr Ala Pro Lys Leu
        35                  40                  45

Leu Ile Tyr Lys Val Thr Thr Arg Ala Ser Gly Ile Pro Asp Arg Phe

```
                50                  55                  60
Ser Gly Ser Lys Ser Gly Asn Thr Ala Ser Leu Thr Ile Ser Gly Leu
 65                  70                  75                  80

Gln Ser Glu Asp Glu Ala Asp Tyr Tyr Cys Ala Ser Tyr Arg Asn Phe
                 85                  90                  95

Asn Asn Ala Val Phe Gly Ser Gly Thr Lys Leu Thr Val Leu
                100                 105                 110
```

<210> SEQ ID NO 449
<211> LENGTH: 110
<212> TYPE: PRT
<213> ORGANISM: Lama glama

<400> SEQUENCE: 449

```
Gln Ser Ala Leu Thr Gln Pro Pro Leu Val Ser Gly Ala Pro Gly Gln
 1               5                  10                  15

Thr Val Thr Ile Ser Cys Ala Gly Ala Asn Asn Asp Ile Gly Thr Tyr
                20                  25                  30

Ala Tyr Val Ser Trp Tyr Gln Gln Leu Pro Gly Thr Ala Pro Lys Leu
                35                  40                  45

Leu Ile Tyr Lys Val Thr Thr Arg Ala Ser Gly Ile Pro Asp Arg Phe
     50                  55                  60

Ser Gly Ser Lys Ser Gly Asn Thr Ala Ser Leu Thr Ile Thr Gly Leu
 65                  70                  75                  80

Gln Ala Glu Asp Glu Ala Asp Tyr Tyr Cys Ala Ser Tyr Arg Asn Phe
                 85                  90                  95

Asn Asn Ala Val Phe Gly Gly Gly Thr His Leu Thr Val Leu
                100                 105                 110
```

<210> SEQ ID NO 450
<211> LENGTH: 110
<212> TYPE: PRT
<213> ORGANISM: Lama glama

<400> SEQUENCE: 450

```
Gln Ser Ala Leu Thr Gln Pro Pro Leu Val Ser Gly Ser Pro Gly Gln
 1               5                  10                  15

Ser Val Thr Ile Ser Cys Ala Gly Ala Asn Asn Asp Ile Gly Thr Tyr
                20                  25                  30

Ala Tyr Val Ser Trp Tyr Gln Gln Leu Pro Gly Thr Ala Pro Lys Leu
                35                  40                  45

Met Ile Tyr Lys Val Thr Thr Arg Ala Ser Gly Val Pro Ser Arg Phe
     50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ala Ser Tyr Arg Asn Phe
                 85                  90                  95

Asn Asn Ala Val Phe Gly Ser Gly Thr His Leu Thr Val Leu
                100                 105                 110
```

<210> SEQ ID NO 451
<211> LENGTH: 110
<212> TYPE: PRT
<213> ORGANISM: Lama glama

<400> SEQUENCE: 451

```
Gln Ser Ala Leu Thr Gln Pro Pro Ser Val Ser Gly Ser Pro Gly Gln
 1               5                  10                  15
```

```
Thr Val Thr Ile Ser Cys Ala Gly Ala Asn Asn Asp Ile Gly Thr Tyr
            20                  25                  30

Ala Tyr Val Ser Trp Tyr Gln Gln Leu Pro Gly Thr Ala Pro Lys Leu
        35                  40                  45

Leu Ile Tyr Lys Val Thr Ser Arg Ala Ser Gly Val Pro Ser Arg Phe
    50                  55                  60

Ser Gly Ser Lys Ser Gly Asn Thr Ala Ser Leu Ser Ile Ser Gly Leu
65                  70                  75                  80

Gln Ala Glu Asp Glu Ala Asp Tyr Tyr Cys Ala Ser Tyr Arg Asn Phe
                85                  90                  95

Asn Asn Ala Val Phe Gly Ser Gly Thr Lys Leu Thr Val Leu
            100                 105                 110

<210> SEQ ID NO 452
<211> LENGTH: 110
<212> TYPE: PRT
<213> ORGANISM: Lama glama

<400> SEQUENCE: 452

Gln Ser Val Leu Thr Gln Pro Pro Leu Val Ser Gly Ala Pro Gly Gln
1               5                   10                  15

Thr Val Thr Ile Ser Cys Ala Gly Ala Asn Asn Asp Ile Gly Thr Tyr
            20                  25                  30

Ala Tyr Val Ser Trp Tyr Gln Gln Leu Pro Gly Thr Ala Pro Lys Leu
        35                  40                  45

Leu Ile Tyr Lys Val Thr Thr Arg Ala Ser Gly Ile Pro Asp Arg Phe
    50                  55                  60

Ser Gly Ser Lys Ser Gly Asn Ser Ala Ser Leu Thr Ile Thr Gly Leu
65                  70                  75                  80

Gln Ser Glu Asp Glu Ala Asp Tyr Tyr Cys Ala Ser Tyr Arg Asn Phe
                85                  90                  95

Asn Asn Ala Val Phe Gly Gly Gly Thr Lys Leu Thr Val Leu
            100                 105                 110

<210> SEQ ID NO 453
<211> LENGTH: 110
<212> TYPE: PRT
<213> ORGANISM: Lama glama

<400> SEQUENCE: 453

Gln Ser Ala Leu Thr Gln Pro Pro Leu Val Ser Gly Ser Pro Gly Gln
1               5                   10                  15

Thr Val Thr Ile Ser Cys Ala Gly Ala Asn Asn Asp Ile Gly Thr Tyr
            20                  25                  30

Ala Tyr Val Ser Trp Tyr Gln Gln Leu Pro Gly Thr Ala Pro Lys Leu
        35                  40                  45

Leu Ile Tyr Lys Val Thr Thr Arg Ala Ser Gly Val Pro Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ala Ser Tyr Arg Asn Phe
                85                  90                  95

Asn Asn Ala Val Phe Gly Thr Gly Thr His Leu Thr Val Leu
            100                 105                 110

<210> SEQ ID NO 454
```

```
<211> LENGTH: 110
<212> TYPE: PRT
<213> ORGANISM: Lama glama

<400> SEQUENCE: 454

Gln Ser Ala Leu Thr Gln Pro Pro Leu Val Ser Gly Ser Pro Gly Gln
1               5                   10                  15

Thr Val Thr Ile Ser Cys Ala Gly Ala Asn Asn Asp Ile Gly Thr Tyr
            20                  25                  30

Ala Tyr Val Ser Trp Tyr Gln Gln Leu Pro Gly Thr Ala Pro Lys Leu
        35                  40                  45

Leu Ile Tyr Lys Val Thr Thr Arg Ala Ser Gly Val Pro Ser Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ala Ser Tyr Arg Asn Phe
                85                  90                  95

Asn Asn Ala Val Phe Gly Gly Gly Thr His Leu Thr Val Leu
            100                 105                 110

<210> SEQ ID NO 455
<211> LENGTH: 110
<212> TYPE: PRT
<213> ORGANISM: Lama glama

<400> SEQUENCE: 455

Gln Ser Ala Leu Thr Gln Pro Pro Ser Val Ser Gly Ala Pro Gly Gln
1               5                   10                  15

Arg Val Thr Ile Ser Cys Ala Gly Ala Asn Asn Asp Ile Gly Thr Tyr
            20                  25                  30

Ala Tyr Val Ser Trp Tyr Gln Gln Leu Pro Gly Thr Ala Pro Lys Leu
        35                  40                  45

Leu Ile Tyr Lys Val Thr Thr Arg Ala Ser Gly Val Pro Ser Arg Phe
    50                  55                  60

Ser Gly Ser Lys Ser Gly Asn Ser Ala Ser Leu Thr Ile Thr Gly Leu
65                  70                  75                  80

Gln Ser Glu Asp Glu Ala Asp Tyr Tyr Cys Ala Ser Tyr Arg Asn Phe
                85                  90                  95

Asn Asn Ala Val Phe Gly Gly Gly Thr His Leu Thr Val Leu
            100                 105                 110

<210> SEQ ID NO 456
<211> LENGTH: 110
<212> TYPE: PRT
<213> ORGANISM: Lama glama

<400> SEQUENCE: 456

Gln Phe Ala Leu Thr Gln Pro Pro Leu Val Ser Gly Thr Pro Gly Gln
1               5                   10                  15

Ser Val Thr Ile Ser Cys Ala Gly Ala Asn Asn Asp Ile Gly Thr Tyr
            20                  25                  30

Ala Tyr Val Ser Trp Tyr Gln Gln Leu Pro Gly Thr Ala Pro Lys Leu
        35                  40                  45

Leu Ile Tyr Lys Val Thr Thr Arg Ala Ser Gly Val Pro Ser Arg Phe
    50                  55                  60

Ser Gly Ser Lys Ser Gly Asn Thr Ala Ser Leu Thr Ile Ser Gly Leu
65                  70                  75                  80
```

-continued

Gln Ser Glu Asp Glu Ala Asp Tyr Tyr Cys Ala Ser Tyr Arg Asn Phe
                85                  90                  95

Asn Asn Ala Val Phe Gly Thr Gly Thr His Leu Thr Val Leu
            100                 105                 110

<210> SEQ ID NO 457
<211> LENGTH: 110
<212> TYPE: PRT
<213> ORGANISM: Lama glama

<400> SEQUENCE: 457

Gln Ser Ala Leu Thr Gln Pro Pro Leu Val Ser Gly Ser Pro Gly Gln
1               5                   10                  15

Thr Val Thr Ile Ser Cys Ala Gly Ala Asn Asn Asp Ile Gly Thr Tyr
            20                  25                  30

Ala Tyr Val Ser Trp Tyr Gln Gln Leu Pro Gly Thr Ala Pro Lys Leu
        35                  40                  45

Met Ile Tyr Lys Val Thr Thr Arg Ala Ser Gly Val Pro Ser Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ala Ser Tyr Arg Asn Phe
                85                  90                  95

Asn Asn Ala Val Phe Gly Ser Gly Thr Lys Leu Thr Val Leu
            100                 105                 110

<210> SEQ ID NO 458
<211> LENGTH: 110
<212> TYPE: PRT
<213> ORGANISM: Lama glama

<400> SEQUENCE: 458

Gln Ser Ala Leu Thr Gln Pro Pro Leu Val Ser Gly Ser Pro Gly Gln
1               5                   10                  15

Thr Val Thr Ile Ser Cys Ala Gly Ala Asn Asn Asp Ile Gly Thr Tyr
            20                  25                  30

Ala Tyr Val Ser Trp Tyr Gln Gln Leu Pro Gly Thr Ala Pro Lys Leu
        35                  40                  45

Leu Ile Tyr Lys Val Thr Thr Arg Ala Ser Gly Val Pro Asp Arg Phe
    50                  55                  60

Ser Gly Ser Lys Ser Gly Asn Thr Ala Ser Leu Thr Ile Ser Gly Leu
65                  70                  75                  80

Gln Ser Glu Asp Glu Ala Asp Tyr Tyr Cys Ala Ser Tyr Arg Asn Phe
                85                  90                  95

Asn Asn Ala Val Phe Gly Arg Gly Thr His Leu Thr Val Leu
            100                 105                 110

<210> SEQ ID NO 459
<211> LENGTH: 110
<212> TYPE: PRT
<213> ORGANISM: Lama glama

<400> SEQUENCE: 459

Gln Ser Ala Leu Thr Gln Pro Pro Ser Val Ser Gly Ser Pro Gly Gln
1               5                   10                  15

Thr Val Thr Ile Ser Cys Ala Gly Ala Asn Asn Asp Ile Gly Thr Tyr
            20                  25                  30

Ala Tyr Val Ser Trp Tyr Gln Gln Leu Pro Gly Thr Ala Pro Lys Leu

-continued

```
                35                  40                  45

Leu Ile Tyr Lys Val Thr Thr Arg Ala Ser Gly Val Pro Asp Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ala Ser Tyr Arg Asn Phe
                 85                  90                  95

Asn Asn Ala Val Phe Gly Gly Gly Thr Lys Leu Thr Val Leu
                100                 105                 110

<210> SEQ ID NO 460
<211> LENGTH: 110
<212> TYPE: PRT
<213> ORGANISM: Lama glama

<400> SEQUENCE: 460

Gln Ser Ala Leu Thr Gln Pro Pro Leu Val Ser Gly Thr Pro Gly Gln
 1               5                  10                  15

Thr Val Thr Ile Ser Cys Ala Gly Ala Asn Asn Asp Ile Gly Thr Tyr
                 20                  25                  30

Ala Tyr Val Ser Trp Tyr Gln Gln Leu Pro Gly Thr Ala Pro Lys Leu
                 35                  40                  45

Leu Ile Tyr Lys Val Thr Thr Arg Ala Ser Gly Val Pro Ser Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ala Ser Tyr Arg Asn Phe
                 85                  90                  95

Asn Asn Gly Val Phe Gly Thr Gly Thr Lys Leu Thr Val Leu
                100                 105                 110

<210> SEQ ID NO 461
<211> LENGTH: 110
<212> TYPE: PRT
<213> ORGANISM: Lama glama

<400> SEQUENCE: 461

Gln Ser Val Leu Thr Gln Pro Pro Ser Val Ser Gly Thr Pro Gly Gln
 1               5                  10                  15

Arg Val Thr Ile Ser Cys Ala Gly Ala Asn Asn Asp Ile Gly Thr Tyr
                 20                  25                  30

Ala Tyr Val Ser Trp Tyr Gln Gln Leu Pro Gly Thr Ala Pro Lys Leu
                 35                  40                  45

Leu Ile Tyr Lys Val Thr Thr Arg Ala Ser Gly Ile Pro Ser Arg Phe
 50                  55                  60

Ser Gly Ser Lys Ser Gly Asn Thr Ala Ser Leu Thr Ile Thr Gly Leu
 65                  70                  75                  80

Gln Ala Glu Asp Glu Ala Asp Tyr Tyr Cys Ala Ser Tyr Arg Asn Phe
                 85                  90                  95

Asn Asn Ala Val Phe Gly Gly Gly Thr Lys Leu Thr Val Leu
                100                 105                 110

<210> SEQ ID NO 462
<211> LENGTH: 110
<212> TYPE: PRT
<213> ORGANISM: Lama glama

<400> SEQUENCE: 462
```

Gln Ser Ala Leu Thr Gln Pro Pro Leu Val Ser Gly Ser Pro Gly Gln
1               5                   10                  15

Thr Val Thr Ile Ser Cys Ala Gly Ala Asn Asn Asp Ile Gly Thr Tyr
            20                  25                  30

Ala Tyr Val Ser Trp Tyr Gln Gln Leu Pro Gly Thr Ala Pro Lys Leu
        35                  40                  45

Leu Ile Tyr Lys Val Thr Thr Arg Ala Ser Gly Val Pro Asp Arg Phe
50                  55                  60

Ser Gly Ser Lys Ser Gly Asn Thr Ala Ser Leu Thr Ile Ser Gly Leu
65                  70                  75                  80

Gln Ser Glu Asp Glu Ala Asp Tyr Tyr Cys Ala Ser Tyr Arg Asn Phe
                85                  90                  95

Asn Asn Ala Val Phe Gly Thr Gly Thr Lys Leu Thr Val Leu
            100                 105                 110

<210> SEQ ID NO 463
<211> LENGTH: 110
<212> TYPE: PRT
<213> ORGANISM: Lama glama

<400> SEQUENCE: 463

Gln Ser Val Leu Thr Gln Pro Pro Ser Val Ser Gly Thr Pro Gly Gln
1               5                   10                  15

Thr Val Thr Ile Ser Cys Ala Gly Ala Asn Asn Asp Ile Gly Thr Tyr
            20                  25                  30

Ala Tyr Val Ser Trp Tyr Gln Gln Leu Pro Gly Thr Ala Pro Lys Leu
        35                  40                  45

Leu Ile Tyr Lys Val Thr Thr Arg Ala Ser Gly Ile Pro Ser Arg Phe
50                  55                  60

Ser Gly Ser Lys Ser Gly Asn Thr Ala Ser Leu Ala Ile Thr Gly Leu
65                  70                  75                  80

Gln Ser Glu Asp Glu Ala Asp Tyr Tyr Cys Ala Ser Tyr Arg Asn Phe
                85                  90                  95

Asn Asn Ala Val Phe Gly Gly Gly Thr Lys Leu Thr Val Leu
            100                 105                 110

<210> SEQ ID NO 464
<211> LENGTH: 110
<212> TYPE: PRT
<213> ORGANISM: Lama glama

<400> SEQUENCE: 464

Gln Ser Ala Leu Thr Gln Pro Pro Leu Val Ser Gly Ala Pro Gly Gln
1               5                   10                  15

Thr Val Thr Ile Ser Cys Ala Gly Ala Asn Asn Asp Ile Gly Thr Tyr
            20                  25                  30

Ala Tyr Val Ser Trp Tyr Gln Gln Leu Pro Gly Thr Ala Pro Lys Leu
        35                  40                  45

Leu Ile Tyr Lys Val Thr Thr Arg Ala Ser Gly Ile Pro Asp Arg Phe
50                  55                  60

Ser Gly Ser Lys Ser Gly Asn Thr Ala Ser Leu Thr Ile Thr Gly Leu
65                  70                  75                  80

Gln Ala Glu Asp Glu Ala Asp Tyr Tyr Cys Ala Ser Tyr Arg Asn Phe
                85                  90                  95

Asn Asn Ala Val Phe Gly Gly Gly Thr His Leu Thr Val Leu
            100                 105                 110

<210> SEQ ID NO 465
<211> LENGTH: 110
<212> TYPE: PRT
<213> ORGANISM: Lama glama

<400> SEQUENCE: 465

Gln Ser Ala Leu Thr Gln Pro Pro Leu Val Ser Gly Ser Pro Gly Gln
1               5                   10                  15

Thr Val Thr Ile Ser Cys Ala Gly Ala Asn Asn Asp Ile Gly Thr Tyr
            20                  25                  30

Ala Tyr Val Ser Trp Tyr Gln Gln Leu Pro Gly Thr Ala Pro Lys Leu
        35                  40                  45

Leu Ile Tyr Lys Val Thr Thr Arg Ala Ser Gly Val Pro Ser Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ala Ser Tyr Arg Asn Phe
                85                  90                  95

Asn Asn Ala Val Phe Gly Gly Gly Thr His Leu Thr Val Leu
            100                 105                 110

<210> SEQ ID NO 466
<211> LENGTH: 110
<212> TYPE: PRT
<213> ORGANISM: Lama glama

<400> SEQUENCE: 466

Gln Ser Ala Leu Thr Gln Pro Pro Ser Val Ser Gly Ala Pro Gly Gln
1               5                   10                  15

Arg Val Thr Ile Ser Cys Ala Gly Ala Asn Asn Asp Ile Gly Thr Tyr
            20                  25                  30

Ala Tyr Val Ser Trp Tyr Gln Gln Leu Pro Gly Thr Ala Pro Lys Leu
        35                  40                  45

Leu Ile Tyr Lys Val Thr Thr Arg Ala Ser Gly Val Pro Ser Arg Phe
    50                  55                  60

Ser Gly Ser Lys Ser Gly Asn Ser Ala Ser Leu Thr Ile Thr Gly Leu
65                  70                  75                  80

Gln Ser Glu Asp Glu Ala Asp Tyr Tyr Cys Ala Ser Tyr Arg Asn Phe
                85                  90                  95

Asn Asn Ala Val Phe Gly Gly Gly Thr His Leu Thr Val Leu
            100                 105                 110

<210> SEQ ID NO 467
<211> LENGTH: 110
<212> TYPE: PRT
<213> ORGANISM: Lama glama

<400> SEQUENCE: 467

Gln Ser Ala Leu Thr Gln Pro Pro Ser Val Ser Gly Ala Pro Gly Gln
1               5                   10                  15

Thr Val Thr Ile Ser Cys Ala Gly Ala Asn Asn Asp Ile Gly Thr Tyr
            20                  25                  30

Ala Tyr Val Ser Trp Tyr Gln Gln Leu Pro Gly Thr Ala Pro Lys Leu
        35                  40                  45

Leu Ile Tyr Lys Val Thr Thr Arg Ala Ser Gly Ile Pro Ser Arg Phe
    50                  55                  60

```
Ser Gly Ser Lys Ser Gly Asn Thr Ala Ser Leu Thr Ile Thr Gly Leu
 65                  70                  75                  80

Gln Ser Glu Asp Glu Ala Asp Tyr Tyr Cys Ala Ser Tyr Arg Asn Phe
                 85                  90                  95

Asn Asn Ala Val Phe Gly Arg Gly Thr Lys Leu Thr Val Leu
            100                 105                 110

<210> SEQ ID NO 468
<211> LENGTH: 110
<212> TYPE: PRT
<213> ORGANISM: Lama glama

<400> SEQUENCE: 468

Gln Ser Ala Leu Thr Gln Pro Pro Ser Val Ser Gly Ser Pro Gly Gln
 1               5                  10                  15

Thr Val Thr Ile Ser Cys Ala Gly Ala Asn Asn Asp Ile Gly Thr Tyr
                 20                  25                  30

Ala Tyr Val Ser Trp Tyr Gln Gln Leu Pro Gly Thr Ala Pro Lys Leu
            35                  40                  45

Leu Ile Tyr Lys Val Thr Thr Arg Ala Ser Gly Val Pro Asp Arg Phe
         50                  55                  60

Ser Gly Ser Lys Ser Gly Asn Thr Ala Ser Leu Thr Ile Ser Gly Leu
 65                  70                  75                  80

Gln Ser Glu Asp Glu Ala Asp Tyr Tyr Cys Ala Ser Tyr Arg Asn Phe
                 85                  90                  95

Asn Asn Ala Val Phe Gly Gly Gly Thr His Leu Thr Val Leu
            100                 105                 110

<210> SEQ ID NO 469
<211> LENGTH: 110
<212> TYPE: PRT
<213> ORGANISM: Lama glama

<400> SEQUENCE: 469

Gln Ser Ala Leu Thr Gln Pro Pro Ser Val Ser Gly Thr Pro Gly Gln
 1               5                  10                  15

Thr Val Thr Ile Ser Cys Ala Gly Ala Asn Asn Asp Ile Gly Thr Tyr
                 20                  25                  30

Ala Tyr Val Ser Trp Tyr Gln Gln Leu Pro Gly Thr Ala Pro Lys Leu
            35                  40                  45

Leu Ile Tyr Lys Val Thr Thr Arg Ala Ser Gly Val Pro Asp Arg Phe
         50                  55                  60

Ser Gly Ser Lys Ser Gly Asn Thr Ala Ser Leu Thr Ile Ser Gly Leu
 65                  70                  75                  80

Gln Ser Glu Asp Glu Ala Asp Tyr Tyr Cys Ala Ser Tyr Arg Asn Phe
                 85                  90                  95

Asn Asn Ala Val Phe Gly Thr Gly Thr Lys Leu Thr Val Leu
            100                 105                 110

<210> SEQ ID NO 470
<211> LENGTH: 110
<212> TYPE: PRT
<213> ORGANISM: Lama glama

<400> SEQUENCE: 470

Gln Ser Ala Leu Thr Gln Pro Pro Ser Val Ser Gly Thr Pro Gly Gln
 1               5                  10                  15

Thr Val Thr Ile Ser Cys Ala Gly Ala Asn Asn Asp Ile Gly Thr Tyr
```

20                  25                  30

Ala Tyr Val Ser Trp Tyr Gln Gln Leu Pro Gly Thr Ala Pro Lys Leu
            35                  40                  45

Met Ile Tyr Lys Val Thr Thr Arg Ala Ser Gly Val Pro Val Arg Phe
         50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ala Ser Tyr Arg Asn Phe
                 85                  90                  95

Asn Asn Ala Val Phe Gly Gly Gly Thr Lys Leu Thr Val Leu
            100                 105                 110

<210> SEQ ID NO 471
<211> LENGTH: 110
<212> TYPE: PRT
<213> ORGANISM: Lama glama

<400> SEQUENCE: 471

Gln Ser Ala Leu Thr Gln Pro Pro Leu Val Ser Gly Ser Pro Gly Gln
 1               5                  10                  15

Thr Val Thr Ile Ser Cys Ala Gly Ala Asn Asn Asp Ile Gly Thr Tyr
            20                  25                  30

Ala Tyr Val Ser Trp Tyr Gln Gln Leu Pro Gly Thr Ala Pro Lys Leu
            35                  40                  45

Leu Ile Tyr Lys Val Thr Thr Arg Ala Ser Gly Val Pro Asp Arg Phe
         50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ala Ser Tyr Arg Asn Phe
                 85                  90                  95

Asn Asn Ala Val Phe Gly Thr Gly Thr His Leu Thr Val Leu
            100                 105                 110

<210> SEQ ID NO 472
<211> LENGTH: 110
<212> TYPE: PRT
<213> ORGANISM: Lama glama

<400> SEQUENCE: 472

Gln Phe Ala Leu Thr Gln Pro Pro Leu Val Ser Gly Thr Pro Gly Gln
 1               5                  10                  15

Ser Val Thr Ile Ser Cys Ala Gly Ala Asn Asn Asp Ile Gly Thr Tyr
            20                  25                  30

Ala Tyr Val Ser Trp Tyr Gln Gln Leu Pro Gly Thr Ala Pro Lys Leu
            35                  40                  45

Leu Ile Tyr Lys Val Thr Thr Arg Ala Ser Gly Val Pro Ser Arg Phe
         50                  55                  60

Ser Gly Ser Lys Ser Gly Asn Thr Ala Ser Leu Thr Ile Ser Gly Leu
 65                  70                  75                  80

Gln Ser Glu Asp Glu Ala Asp Tyr Tyr Cys Ala Ser Tyr Arg Asn Phe
                 85                  90                  95

Asn Asn Ala Val Phe Gly Thr Gly Thr His Leu Thr Val Leu
            100                 105                 110

<210> SEQ ID NO 473
<211> LENGTH: 110
<212> TYPE: PRT

<213> ORGANISM: Lama glama

<400> SEQUENCE: 473

Gln Ser Val Leu Thr Gln Pro Pro Leu Val Ser Gly Thr Pro Gly Gln
1               5                   10                  15

Arg Val Thr Ile Ser Cys Ala Gly Ala Asn Asn Asp Ile Gly Thr Tyr
            20                  25                  30

Ala Tyr Val Ser Trp Tyr Gln Gln Leu Pro Gly Thr Ala Pro Lys Leu
        35                  40                  45

Leu Ile Tyr Lys Val Thr Thr Arg Ala Ser Gly Ile Pro Asp Arg Phe
    50                  55                  60

Ser Gly Ser Lys Ser Gly Asn Thr Ala Ser Leu Thr Ile Ser Gly Leu
65                  70                  75                  80

Gln Ser Glu Asp Glu Ala Asp Tyr Tyr Cys Ala Ser Tyr Arg Asn Phe
                85                  90                  95

Asn Asn Ala Val Phe Gly Gly Gly Thr His Leu Thr Val Leu
            100                 105                 110

<210> SEQ ID NO 474
<211> LENGTH: 110
<212> TYPE: PRT
<213> ORGANISM: Lama glama

<400> SEQUENCE: 474

Gln Ser Val Leu Thr Gln Pro Pro Leu Val Ser Gly Ala Pro Gly Gln
1               5                   10                  15

Arg Val Thr Ile Ser Cys Ala Gly Ala Asn Asn Asp Ile Gly Thr Tyr
            20                  25                  30

Ala Tyr Val Ser Trp Tyr Gln Gln Leu Pro Gly Thr Ala Pro Lys Leu
        35                  40                  45

Leu Ile Tyr Lys Val Thr Thr Arg Ala Ser Gly Val Pro Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ala Ser Tyr Arg Asn Phe
                85                  90                  95

Asn Asn Ala Val Phe Gly Gly Gly Thr His Leu Thr Val Leu
            100                 105                 110

<210> SEQ ID NO 475
<211> LENGTH: 110
<212> TYPE: PRT
<213> ORGANISM: Lama glama

<400> SEQUENCE: 475

Gln Ser Ala Leu Thr Gln Pro Pro Ser Val Ser Gly Ala Pro Gly Gln
1               5                   10                  15

Thr Val Thr Ile Ser Cys Ala Gly Ala Asn Asn Asp Ile Gly Thr Tyr
            20                  25                  30

Ala Tyr Val Ser Trp Tyr Gln Gln Leu Pro Gly Thr Ala Pro Lys Leu
        35                  40                  45

Leu Ile Tyr Lys Val Thr Thr Arg Ala Ser Gly Ile Pro Asp Arg Phe
    50                  55                  60

Ser Gly Ser Lys Ser Ser Asn Thr Ala Ser Leu Thr Ile Ser Gly Leu
65                  70                  75                  80

Gln Ala Glu Asp Glu Ala Asp Tyr Tyr Cys Ala Ser Tyr Arg Asn Phe
                85                  90                  95

```
Asn Asn Ala Val Phe Gly Gly Gly Thr His Leu Thr Val Leu
            100                 105                 110
```

```
<210> SEQ ID NO 476
<211> LENGTH: 110
<212> TYPE: PRT
<213> ORGANISM: Lama glama

<400> SEQUENCE: 476

Gln Ser Val Leu Thr Gln Pro Pro Ser Val Ser Gly Thr Pro Gly Gln
1               5                   10                  15

Thr Val Thr Ile Ser Cys Ala Gly Ala Asn Asn Asp Ile Gly Thr Tyr
            20                  25                  30

Ala Tyr Val Ser Trp Tyr Gln Gln Leu Pro Gly Thr Ala Pro Lys Leu
        35                  40                  45

Leu Ile Tyr Lys Val Thr Thr Arg Ala Ser Gly Val Pro Ser Arg Phe
    50                  55                  60

Ser Gly Ser Lys Ser Gly Ala Thr Ala Ser Leu Thr Ile Ser Gly Leu
65                  70                  75                  80

Gln Ser Glu Asp Glu Ala Asp Tyr Tyr Cys Ala Ser Tyr Arg Asn Phe
                85                  90                  95

Asn Asn Ala Val Phe Gly Gly Gly Thr His Leu Thr Val Leu
            100                 105                 110
```

```
<210> SEQ ID NO 477
<211> LENGTH: 110
<212> TYPE: PRT
<213> ORGANISM: Lama glama

<400> SEQUENCE: 477

Gln Ser Ala Leu Thr Gln Pro Pro Ser Val Ser Gly Ala Pro Gly Gln
1               5                   10                  15

Thr Val Thr Ile Ser Cys Ala Gly Ala Asn Asn Asp Val Gly Thr Tyr
            20                  25                  30

Ala Tyr Val Ser Trp Tyr Gln Gln Leu Pro Gly Thr Ala Pro Lys Leu
        35                  40                  45

Leu Ile Tyr Lys Val Thr Thr Arg Ala Ser Gly Val Pro Asp Arg Phe
    50                  55                  60

Ser Gly Ser Lys Ser Gly Asn Ser Ala Ser Leu Thr Ile Thr Gly Leu
65                  70                  75                  80

Gln Ser Glu Asp Glu Ala Asp Tyr Tyr Cys Ala Ser Tyr Arg Asn Phe
                85                  90                  95

Asn Asn Ala Val Phe Gly Arg Gly Thr His Leu Thr Val Leu
            100                 105                 110
```

```
<210> SEQ ID NO 478
<211> LENGTH: 110
<212> TYPE: PRT
<213> ORGANISM: Lama glama

<400> SEQUENCE: 478

Gln Ser Val Leu Thr Gln Pro Pro Arg Val Ser Gly Ala Pro Gly Gln
1               5                   10                  15

Thr Val Thr Ile Ser Cys Ala Gly Ala Asn Asn Asp Ile Gly Thr Tyr
            20                  25                  30

Ala Tyr Val Ser Trp Tyr Gln Gln Leu Pro Gly Thr Ala Pro Lys Leu
        35                  40                  45
```

Leu Ile Tyr Lys Val Thr Thr Arg Ala Ser Gly Val Pro Asp Arg Phe
        50                  55                  60

Ser Gly Ser Lys Ser Gly Asn Ser Ala Ser Leu Thr Ile Thr Gly Leu
 65                  70                  75                  80

Gln Ala Glu Asp Glu Ala Asp Tyr Tyr Cys Ala Ser Tyr Arg Asn Phe
                 85                  90                  95

Asn Asn Ala Val Phe Gly Gly Gly Thr Lys Leu Thr Val Leu
            100                 105                 110

<210> SEQ ID NO 479
<211> LENGTH: 110
<212> TYPE: PRT
<213> ORGANISM: Lama glama

<400> SEQUENCE: 479

Gln Ser Val Leu Thr Gln Pro Pro Leu Val Ser Gly Ala Pro Gly Gln
 1               5                   10                  15

Arg Val Thr Ile Ser Cys Ala Gly Ala Asn Asn Asp Ile Gly Thr Tyr
                 20                  25                  30

Ala Tyr Val Ser Trp Tyr Gln Gln Leu Pro Gly Thr Ala Pro Lys Leu
             35                  40                  45

Leu Ile Tyr Lys Val Thr Thr Arg Ala Ser Gly Val Pro Ser Arg Phe
        50                  55                  60

Ser Gly Ser Lys Ser Gly Asn Thr Ala Ser Leu Thr Ile Thr Gly Leu
 65                  70                  75                  80

Gln Ala Glu Asp Glu Ala Asp Tyr Tyr Cys Ala Ser Tyr Arg Asn Phe
                 85                  90                  95

Asn Asn Ala Val Phe Gly Arg Gly Thr His Leu Thr Val Leu
            100                 105                 110

<210> SEQ ID NO 480
<211> LENGTH: 110
<212> TYPE: PRT
<213> ORGANISM: Lama glama

<400> SEQUENCE: 480

Gln Ser Val Leu Thr Gln Pro Pro Ser Val Ser Gly Ala Pro Gly Gln
 1               5                   10                  15

Arg Val Thr Ile Ser Cys Ala Gly Ala Asn Asn Asp Ile Gly Thr Tyr
                 20                  25                  30

Ala Tyr Val Ser Trp Tyr Gln Gln Leu Pro Gly Thr Ala Pro Lys Leu
             35                  40                  45

Leu Ile Tyr Lys Val Thr Thr Arg Ala Ser Gly Ile Pro Ser Arg Phe
        50                  55                  60

Ser Gly Ser Lys Ser Gly Asn Thr Ala Ser Leu Thr Ile Thr Gly Leu
 65                  70                  75                  80

Gln Ser Glu Asp Glu Ala Asp Tyr Tyr Cys Ala Ser Tyr Arg Asn Phe
                 85                  90                  95

Asn Asn Ala Val Phe Gly Arg Gly Thr His Leu Thr Val Leu
            100                 105                 110

<210> SEQ ID NO 481
<211> LENGTH: 110
<212> TYPE: PRT
<213> ORGANISM: Lama glama

<400> SEQUENCE: 481

Gln Ser Val Leu Thr Gln Pro Pro Leu Val Ser Gly Ala Pro Gly Gln
 1               5                   10                  15

```
1               5                   10                  15
Thr Val Thr Ile Ser Cys Ala Gly Ala Asn Asn Asp Ile Gly Thr Tyr
                20                  25                  30
Ala Tyr Val Ser Trp Tyr Gln Gln Leu Pro Gly Thr Ala Pro Lys Leu
                35                  40                  45
Leu Ile Tyr Lys Val Thr Thr Arg Ala Ser Gly Ile Pro Asn Arg Phe
                50                  55                  60
Ser Gly Ser Lys Ser Gly Asn Thr Ala Ser Leu Thr Ile Thr Gly Leu
65                  70                  75                  80
Gln Ala Glu Asp Glu Ala Asp Tyr Tyr Cys Ala Ser Tyr Arg Asn Phe
                85                  90                  95
Asn Asn Ala Val Phe Gly Gly Gly Thr His Leu Thr Val Leu
                100                 105                 110
```

<210> SEQ ID NO 482
<211> LENGTH: 110
<212> TYPE: PRT
<213> ORGANISM: Lama glama

<400> SEQUENCE: 482

```
Gln Ser Val Leu Thr Gln Pro Pro Leu Val Ser Gly Thr Pro Gly Gln
1               5                   10                  15
Arg Val Thr Ile Ser Cys Ala Gly Ala Asn Asn Asp Ile Gly Thr Tyr
                20                  25                  30
Ala Tyr Val Ser Trp Tyr Gln Gln Leu Pro Gly Thr Ala Pro Lys Leu
                35                  40                  45
Leu Ile Tyr Lys Val Thr Thr Arg Ala Ser Gly Ile Pro Asp Arg Phe
                50                  55                  60
Ser Gly Ser Lys Ser Gly Asn Thr Ala Ser Leu Thr Ile Ser Gly Leu
65                  70                  75                  80
Gln Ser Glu Asp Glu Ala Asp Tyr Tyr Cys Ala Ser Tyr Arg Asn Phe
                85                  90                  95
Asn Asn Ala Val Phe Gly Gly Gly Thr His Leu Thr Val Leu
                100                 105                 110
```

<210> SEQ ID NO 483
<211> LENGTH: 110
<212> TYPE: PRT
<213> ORGANISM: Lama glama

<400> SEQUENCE: 483

```
Gln Ser Val Leu Thr Gln Pro Pro Leu Val Ser Gly Ala Pro Gly Gln
1               5                   10                  15
Thr Val Thr Ile Ser Cys Ala Gly Ala Asn Asn Asp Ile Gly Thr Tyr
                20                  25                  30
Ala Tyr Val Ser Trp Tyr Gln Gln Leu Pro Gly Thr Ala Pro Lys Leu
                35                  40                  45
Leu Ile Tyr Lys Val Thr Thr Arg Ala Ser Gly Ile Pro Asp Arg Phe
                50                  55                  60
Ser Gly Ser Lys Ser Gly Asn Thr Ala Ser Leu Thr Ile Ser Gly Leu
65                  70                  75                  80
Gln Ser Glu Asp Glu Ala Asp Tyr Tyr Cys Ala Ser Tyr Arg Asn Phe
                85                  90                  95
Asn Asn Ala Val Phe Gly Gly Gly Thr Lys Leu Thr Val Leu
                100                 105                 110
```

<210> SEQ ID NO 484
<211> LENGTH: 110
<212> TYPE: PRT
<213> ORGANISM: Lama glama

<400> SEQUENCE: 484

Gln Ser Ala Leu Thr Gln Pro Pro Ser Val Gly Ala Pro Gly Gln
1               5                   10                  15

Thr Val Thr Ile Ser Cys Ala Gly Ala Asn Asn Asp Ile Gly Thr Tyr
            20                  25                  30

Ala Tyr Val Ser Trp Tyr Gln Gln Leu Pro Gly Thr Ala Pro Lys Leu
        35                  40                  45

Leu Ile Tyr Lys Val Thr Thr Arg Ala Ser Gly Ile Pro Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ala Ser Tyr Arg Asn Phe
                85                  90                  95

Asn Asn Ala Val Phe Gly Arg Gly Thr Lys Leu Thr Val Leu
            100                 105                 110

<210> SEQ ID NO 485
<211> LENGTH: 110
<212> TYPE: PRT
<213> ORGANISM: Lama glama

<400> SEQUENCE: 485

Gln Ser Ala Leu Thr Gln Pro Pro Leu Val Ser Gly Thr Pro Gly Gln
1               5                   10                  15

Thr Val Thr Ile Ser Cys Ala Gly Ala Asn Asn Asp Ile Gly Thr Tyr
            20                  25                  30

Ala Tyr Val Ser Trp Tyr Gln Gln Leu Pro Gly Thr Ala Pro Lys Leu
        35                  40                  45

Leu Ile Tyr Lys Val Thr Thr Arg Ala Ser Gly Val Pro Asp Arg Phe
    50                  55                  60

Ser Gly Ser Ile Ser Gly Asn Thr Ala Ser Leu Thr Ile Ser Gly Leu
65                  70                  75                  80

Gln Ser Glu Asp Glu Ala Asp Tyr Tyr Cys Ala Ser Tyr Arg Asn Phe
                85                  90                  95

Asn Asn Gly Val Phe Gly Thr Gly Thr His Leu Thr Val Leu
            100                 105                 110

<210> SEQ ID NO 486
<211> LENGTH: 110
<212> TYPE: PRT
<213> ORGANISM: Lama glama

<400> SEQUENCE: 486

Gln Ser Ala Leu Thr Gln Pro Pro Leu Val Ser Gly Ser Pro Gly Gln
1               5                   10                  15

Thr Val Thr Ile Ser Cys Ala Gly Ala Asn Asn Asp Ile Gly Thr Tyr
            20                  25                  30

Ala Tyr Val Ser Trp Tyr Gln Gln Leu Pro Gly Thr Ala Pro Lys Leu
        35                  40                  45

Leu Ile Tyr Lys Val Thr Thr Arg Ala Ser Gly Ile Pro Ser Arg Phe
    50                  55                  60

Ser Gly Ser Lys Ser Gly Asn Thr Ala Ser Leu Thr Ile Ser Gly Leu
65                  70                  75                  80

```
Gln Ser Glu Asp Glu Ala Asp Tyr Tyr Cys Ala Ser Tyr Arg Asn Phe
                85                  90                  95

Asn Asn Ala Val Phe Gly Arg Gly Thr Lys Leu Thr Val Leu
            100                 105                 110

<210> SEQ ID NO 487
<211> LENGTH: 110
<212> TYPE: PRT
<213> ORGANISM: Lama glama

<400> SEQUENCE: 487

Gln Ser Ala Leu Thr Gln Pro Pro Leu Val Ser Gly Ser Pro Gly Gln
1               5                   10                  15

Thr Val Thr Ile Ser Cys Ala Gly Ala Asn Asn Asp Ile Gly Thr Tyr
            20                  25                  30

Ala Tyr Val Ser Trp Tyr Gln Gln Pro Pro Gly Thr Ala Pro Lys Leu
        35                  40                  45

Met Ile Tyr Lys Val Thr Thr Arg Ala Ser Gly Ile Pro Asp Arg Phe
    50                  55                  60

Ser Gly Ser Ile Ser Gly Asn Thr Ala Ser Leu Thr Ile Ser Gly Leu
65                  70                  75                  80

Gln Ser Glu Asp Glu Ala Asp Tyr Tyr Cys Ala Ser Tyr Arg Asn Phe
                85                  90                  95

Asn Asn Ala Val Phe Gly Thr Gly Thr Lys Leu Thr Val Leu
            100                 105                 110

<210> SEQ ID NO 488
<211> LENGTH: 110
<212> TYPE: PRT
<213> ORGANISM: Lama glama

<400> SEQUENCE: 488

Gln Ser Ala Leu Thr Gln Pro Pro Leu Val Ser Gly Ser Pro Gly Gln
1               5                   10                  15

Thr Val Thr Ile Ser Cys Ala Gly Ala Asn Asn Asp Ile Gly Thr Tyr
            20                  25                  30

Ala Tyr Val Ser Trp Tyr Gln Gln Leu Pro Gly Thr Ala Pro Lys Leu
        35                  40                  45

Met Ile Tyr Lys Val Thr Thr Arg Ala Ser Gly Val Pro Asp Arg Phe
    50                  55                  60

Ser Gly Ser Lys Ser Gly Asn Thr Ala Ser Leu Thr Ile Ser Gly Leu
65                  70                  75                  80

Gln Ser Glu Asp Glu Ala Asp Tyr Tyr Cys Ala Ser Tyr Arg Asn Phe
                85                  90                  95

Asn Asn Ala Val Phe Gly Arg Gly Thr Lys Leu Thr Val Leu
            100                 105                 110

<210> SEQ ID NO 489
<211> LENGTH: 110
<212> TYPE: PRT
<213> ORGANISM: Lama glama

<400> SEQUENCE: 489

Gln Ser Ala Leu Thr Gln Pro Pro Leu Val Ser Gly Ser Pro Gly Gln
1               5                   10                  15

Ser Val Thr Ile Ser Cys Ala Gly Ala Asn Asn Asp Ile Gly Thr Tyr
            20                  25                  30
```

-continued

Ala Tyr Val Ser Trp Tyr Gln Gln Leu Pro Gly Thr Ala Pro Lys Leu
            35                  40                  45

Leu Ile Tyr Lys Val Thr Thr Arg Ala Ser Gly Val Pro Ser Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ala Ser Tyr Arg Asn Phe
                85                  90                  95

Asn Asn Ala Val Phe Gly Arg Gly Thr Lys Leu Thr Val Leu
                100                 105                 110

<210> SEQ ID NO 490
<211> LENGTH: 110
<212> TYPE: PRT
<213> ORGANISM: Lama glama

<400> SEQUENCE: 490

Gln Ser Ala Leu Thr Gln Pro Pro Ser Val Ser Gly Ser Pro Gly Gln
 1               5                  10                  15

Ser Val Thr Leu Ser Cys Ala Gly Ala Asn Asn Asp Ile Gly Thr Tyr
                20                  25                  30

Ala Tyr Val Ser Trp Tyr Gln Gln Leu Pro Gly Thr Ala Pro Lys Leu
            35                  40                  45

Met Ile Tyr Lys Val Thr Thr Arg Ala Ser Gly Val Pro Asp Arg Phe
 50                  55                  60

Ser Gly Ser Lys Ser Gly Asn Thr Ala Ser Leu Thr Ile Ser Gly Leu
 65                  70                  75                  80

Gln Ser Glu Asp Glu Ala Asp Tyr Tyr Cys Ala Ser Tyr Arg Asn Phe
                85                  90                  95

Asn Asn Ala Val Phe Gly Ser Gly Thr Lys Leu Thr Val Leu
                100                 105                 110

<210> SEQ ID NO 491
<211> LENGTH: 110
<212> TYPE: PRT
<213> ORGANISM: Lama glama

<400> SEQUENCE: 491

Gln Ser Ala Leu Thr Gln Pro Pro Ser Val Ser Gly Ser Pro Gly Gln
 1               5                  10                  15

Thr Val Thr Ile Ser Cys Ala Gly Ala Asn Asn Asp Ile Gly Thr Tyr
                20                  25                  30

Ala Tyr Val Ser Trp Tyr Gln Gln Leu Pro Gly Thr Ala Pro Lys Leu
            35                  40                  45

Met Ile Tyr Lys Val Thr Thr Arg Ala Ser Gly Ile Pro Asp Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ala Ser Tyr Arg Asn Phe
                85                  90                  95

Asn Asn Ala Val Phe Gly Arg Gly Thr Lys Leu Thr Val Leu
                100                 105                 110

<210> SEQ ID NO 492
<211> LENGTH: 110
<212> TYPE: PRT
<213> ORGANISM: Lama glama

<400> SEQUENCE: 492

```
Gln Ser Ala Leu Thr Gln Pro Pro Ser Val Ser Gly Ser Pro Gly Gln
1               5                   10                  15

Ser Val Thr Ile Ser Cys Ala Gly Ala Asn Asn Asp Ile Gly Thr Tyr
            20                  25                  30

Ala Tyr Val Ser Trp Tyr Gln Gln Leu Pro Gly Thr Ala Pro Gln Leu
        35                  40                  45

Leu Ile Tyr Lys Val Thr Thr Arg Ala Ser Gly Ile Pro Asp Arg Phe
    50                  55                  60

Ser Gly Ser Lys Ser Gly Asn Thr Ala Ser Leu Thr Ile Ser Gly Leu
65                  70                  75                  80

Gln Ser Glu Asp Glu Ala Asp Tyr Tyr Cys Ala Ser Tyr Arg Asn Phe
                85                  90                  95

Asn Asn Ala Val Phe Gly Gly Gly Thr Lys Leu Thr Val Leu
            100                 105                 110
```

<210> SEQ ID NO 493
<211> LENGTH: 110
<212> TYPE: PRT
<213> ORGANISM: Lama glama

<400> SEQUENCE: 493

```
Gln Ser Ala Leu Thr Gln Pro Pro Ser Val Ser Gly Thr Pro Gly Gln
1               5                   10                  15

Ser Val Thr Ile Ser Cys Ala Gly Ala Asn Asn Asp Ile Gly Thr Tyr
            20                  25                  30

Ala Tyr Val Ser Trp Tyr Gln Gln Leu Pro Gly Thr Ala Pro Lys Leu
        35                  40                  45

Leu Ile Tyr Lys Val Thr Thr Arg Ala Ser Gly Ile Pro Asp Arg Phe
    50                  55                  60

Ser Gly Ser Lys Ser Gly Asn Thr Ala Ser Leu Thr Ile Ser Gly Leu
65                  70                  75                  80

Gln Ser Glu Asp Glu Ala Asp Tyr Tyr Cys Ala Ser Tyr Arg Asn Phe
                85                  90                  95

Asn Asn Ala Val Phe Gly Gly Gly Thr His Leu Thr Val Leu
            100                 105                 110
```

<210> SEQ ID NO 494
<211> LENGTH: 110
<212> TYPE: PRT
<213> ORGANISM: Lama glama

<400> SEQUENCE: 494

```
Gln Ser Ala Leu Thr Gln Pro Pro Leu Val Ser Gly Ser Pro Gly Gln
1               5                   10                  15

Thr Val Thr Ile Ser Cys Ala Gly Ala Asn Asn Asp Ile Gly Thr Tyr
            20                  25                  30

Ala Tyr Val Ser Trp Tyr Gln Gln Pro Pro Gly Thr Ala Pro Lys Leu
        35                  40                  45

Met Ile Tyr Lys Val Thr Thr Arg Ala Ser Gly Ile Pro Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ala Ser Tyr Arg Asn Phe
                85                  90                  95

Asn Asn Ala Val Phe Gly Ser Gly Thr Lys Leu Thr Val Leu
```

<210> SEQ ID NO 495
<211> LENGTH: 110
<212> TYPE: PRT
<213> ORGANISM: Lama glama

<400> SEQUENCE: 495

Gln Ser Ala Leu Thr Gln Pro Pro Ser Val Ser Gly Ser Pro Gly Gln
1               5                   10                  15

Thr Val Thr Ile Ser Cys Ala Gly Ala Asn Asn Asp Ile Gly Thr Tyr
            20                  25                  30

Ala Tyr Val Ser Trp Tyr Gln Gln Pro Pro Gly Thr Ala Pro Lys Leu
        35                  40                  45

Leu Ile Tyr Lys Val Thr Thr Arg Ala Ser Gly Val Pro Asp Arg Phe
    50                  55                  60

Ser Gly Ser Lys Ser Gly Asn Thr Ala Ser Leu Thr Ile Ser Gly Leu
65                  70                  75                  80

Gln Ser Glu Asp Glu Ala Asp Tyr Tyr Cys Ala Ser Tyr Arg Asn Phe
                85                  90                  95

Asn Asn Ala Val Phe Gly Thr Gly Thr His Leu Thr Val Leu
            100                 105                 110

<210> SEQ ID NO 496
<211> LENGTH: 110
<212> TYPE: PRT
<213> ORGANISM: Lama glama

<400> SEQUENCE: 496

Gln Ser Ala Leu Thr Gln Pro Pro Ser Val Ser Gly Ser Pro Gly Gln
1               5                   10                  15

Thr Val Thr Ile Ser Cys Ala Gly Ala Asn Asn Asp Ile Gly Thr Tyr
            20                  25                  30

Ala Tyr Val Ser Trp Tyr Gln Gln Pro Pro Gly Thr Ala Pro Lys Leu
        35                  40                  45

Leu Ile Tyr Lys Val Thr Thr Arg Ala Ser Gly Val Pro Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ala Ser Tyr Arg Asn Phe
                85                  90                  95

Asn Asn Ala Val Phe Gly Gly Gly Thr His Leu Thr Val Leu
            100                 105                 110

<210> SEQ ID NO 497
<211> LENGTH: 12
<212> TYPE: PRT
<213> ORGANISM: Lama glama

<400> SEQUENCE: 497

Asp Pro Asp Val Val Thr Gly Phe His Tyr Asp Tyr
1               5                   10

<210> SEQ ID NO 498
<211> LENGTH: 12
<212> TYPE: PRT
<213> ORGANISM: Lama glama

<400> SEQUENCE: 498

```
Tyr Pro Asp Val Val Thr Gly Phe His Tyr Asp Tyr
1               5                   10
```

<210> SEQ ID NO 499
<211> LENGTH: 12
<212> TYPE: PRT
<213> ORGANISM: Lama glama

<400> SEQUENCE: 499

```
Asp Pro Asp Val Val Thr Gly Phe His Tyr Asp Asn
1               5                   10
```

<210> SEQ ID NO 500
<211> LENGTH: 12
<212> TYPE: PRT
<213> ORGANISM: Lama glama
<220> FEATURE:
<221> NAME/KEY: misc_feature
<222> LOCATION: (1)..(1)
<223> OTHER INFORMATION: Xaa can be any naturally occurring amino acid,
      preferably Asp or Tyr
<220> FEATURE:
<221> NAME/KEY: misc_feature
<222> LOCATION: (12)..(12)
<223> OTHER INFORMATION: Xaa can be any naturally occurring amino acid,
      preferably Tyr or Asn

<400> SEQUENCE: 500

```
Xaa Pro Asp Val Val Thr Gly Phe His Tyr Asp Xaa
1               5                   10
```

<210> SEQ ID NO 501
<211> LENGTH: 16
<212> TYPE: PRT
<213> ORGANISM: Lama glama

<400> SEQUENCE: 501

```
Val Ile Asp Tyr Asp Gly Asp Thr Tyr Tyr Ser Pro Ser Leu Lys Ser
1               5                   10                  15
```

<210> SEQ ID NO 502
<211> LENGTH: 16
<212> TYPE: PRT
<213> ORGANISM: Lama glama

<400> SEQUENCE: 502

```
Val Ile Asp Tyr Asp Gly Asp Thr Tyr Tyr Ser Pro Ser Leu Glu Ser
1               5                   10                  15
```

<210> SEQ ID NO 503
<211> LENGTH: 16
<212> TYPE: PRT
<213> ORGANISM: Lama glama

<400> SEQUENCE: 503

```
Val Ile Asp Tyr Asp Ala Asp Thr Tyr Tyr Ser Pro Ser Leu Lys Ser
1               5                   10                  15
```

<210> SEQ ID NO 504
<211> LENGTH: 16
<212> TYPE: PRT
<213> ORGANISM: Lama glama

<400> SEQUENCE: 504

```
Val Ile Asp Tyr Glu Gly Asp Thr Tyr Tyr Ser Pro Ser Leu Lys Ser
1               5                   10                  15
```

<210> SEQ ID NO 505
<211> LENGTH: 16
<212> TYPE: PRT
<213> ORGANISM: Lama glama

<400> SEQUENCE: 505

Val Ile Tyr Tyr Glu Gly Asp Thr Tyr Tyr Ser Pro Ser Leu Lys Ser
1               5                   10                  15

<210> SEQ ID NO 506
<211> LENGTH: 16
<212> TYPE: PRT
<213> ORGANISM: Lama glama

<400> SEQUENCE: 506

Val Ile Asn Tyr Asp Gly Asp Thr Tyr Tyr Ser Pro Ser Leu Lys Ser
1               5                   10                  15

<210> SEQ ID NO 507
<211> LENGTH: 16
<212> TYPE: PRT
<213> ORGANISM: Lama glama
<220> FEATURE:
<221> NAME/KEY: MISC_FEATURE
<222> LOCATION: (3)..(3)
<223> OTHER INFORMATION: Xaa can be any naturally occurring amino acid,
      preferably Asp, Tyr or Asn
<220> FEATURE:
<221> NAME/KEY: MISC_FEATURE
<222> LOCATION: (5)..(5)
<223> OTHER INFORMATION: Xaa can be any naturally occurring amino acid,
      preferably Asp or Glu
<220> FEATURE:
<221> NAME/KEY: MISC_FEATURE
<222> LOCATION: (6)..(6)
<223> OTHER INFORMATION: Xaa can be any naturally occurring amino acid,
      preferably Ala or Gly
<220> FEATURE:
<221> NAME/KEY: MISC_FEATURE
<222> LOCATION: (15)..(15)
<223> OTHER INFORMATION: Xaa can be any naturally occurring amino acid,
      preferably Glu or Lys

<400> SEQUENCE: 507

Val Ile Xaa Tyr Xaa Xaa Asp Thr Tyr Tyr Ser Pro Ser Leu Xaa Ser
1               5                   10                  15

<210> SEQ ID NO 508
<211> LENGTH: 7
<212> TYPE: PRT
<213> ORGANISM: Lama glama

<400> SEQUENCE: 508

Ser Arg Tyr Tyr Ala Trp Ser
1               5

<210> SEQ ID NO 509
<211> LENGTH: 7
<212> TYPE: PRT
<213> ORGANISM: Lama glama

<400> SEQUENCE: 509

Thr Arg Tyr Tyr Ala Trp Ser
1               5

<210> SEQ ID NO 510
<211> LENGTH: 7
<212> TYPE: PRT

<213> ORGANISM: Lama glama

<400> SEQUENCE: 510

Pro Arg Tyr Tyr Val Trp Thr
1               5

<210> SEQ ID NO 511
<211> LENGTH: 7
<212> TYPE: PRT
<213> ORGANISM: Lama glama

<400> SEQUENCE: 511

Ser Ser Tyr Tyr Ala Trp Ser
1               5

<210> SEQ ID NO 512
<211> LENGTH: 7
<212> TYPE: PRT
<213> ORGANISM: Lama glama
<220> FEATURE:
<221> NAME/KEY: MISC_FEATURE
<222> LOCATION: (1)..(1)
<223> OTHER INFORMATION: Xaa can be any naturally occurring amino acid,
      preferably Thr, Ser or Pro
<220> FEATURE:
<221> NAME/KEY: MISC_FEATURE
<222> LOCATION: (2)..(2)
<223> OTHER INFORMATION: Xaa can be any naturally occurring amino acid,
      preferably Arg or Ser
<220> FEATURE:
<221> NAME/KEY: MISC_FEATURE
<222> LOCATION: (5)..(5)
<223> OTHER INFORMATION: Xaa can be any naturally occurring amino acid,
      preferably Ala or val
<220> FEATURE:
<221> NAME/KEY: MISC_FEATURE
<222> LOCATION: (7)..(7)
<223> OTHER INFORMATION: Xaa can be any naturally occurring amino acid,
      preferably Ser or Thr

<400> SEQUENCE: 512

Xaa Xaa Tyr Tyr Xaa Trp Xaa
1               5

<210> SEQ ID NO 513
<211> LENGTH: 10
<212> TYPE: PRT
<213> ORGANISM: Lama glama

<400> SEQUENCE: 513

Ala Ser Tyr Arg Asn Phe Asn Asn Ala Val
1               5                   10

<210> SEQ ID NO 514
<211> LENGTH: 10
<212> TYPE: PRT
<213> ORGANISM: Lama glama

<400> SEQUENCE: 514

Ala Ser Tyr Arg His Tyr Asn Asn Ala Val
1               5                   10

<210> SEQ ID NO 515
<211> LENGTH: 10
<212> TYPE: PRT
<213> ORGANISM: Lama glama

<400> SEQUENCE: 515

Ala Ser Tyr Arg Arg Thr Ile Asp Asn Ile
1               5                   10

<210> SEQ ID NO 516
<211> LENGTH: 10
<212> TYPE: PRT
<213> ORGANISM: Lama glama

<400> SEQUENCE: 516

Ala Ser Tyr Arg Ser Ser Asn Asn Ala Val
1               5                   10

<210> SEQ ID NO 517
<211> LENGTH: 10
<212> TYPE: PRT
<213> ORGANISM: Lama glama

<400> SEQUENCE: 517

Ala Ser Tyr Arg Asn Arg Asn Asn Ala Val
1               5                   10

<210> SEQ ID NO 518
<211> LENGTH: 10
<212> TYPE: PRT
<213> ORGANISM: Lama glama

<400> SEQUENCE: 518

Ala Ser Tyr Arg Asp Phe Asn Asn Ala Val
1               5                   10

<210> SEQ ID NO 519
<211> LENGTH: 10
<212> TYPE: PRT
<213> ORGANISM: Lama glama

<400> SEQUENCE: 519

Ala Ser Tyr Lys Thr Tyr Asn Asn Val Val
1               5                   10

<210> SEQ ID NO 520
<211> LENGTH: 10
<212> TYPE: PRT
<213> ORGANISM: Lama glama

<400> SEQUENCE: 520

Ala Ser Tyr Arg Tyr Phe Asn Asn Ala Val
1               5                   10

<210> SEQ ID NO 521
<211> LENGTH: 10
<212> TYPE: PRT
<213> ORGANISM: Lama glama

<400> SEQUENCE: 521

Ala Ser Tyr Arg Asn Phe Asn Asn Gly Val
1               5                   10

<210> SEQ ID NO 522
<211> LENGTH: 10
<212> TYPE: PRT
<213> ORGANISM: Lama glama

<400> SEQUENCE: 522

Ser Ser Tyr Arg Asn Phe Asn Asn Ala Val
1               5                   10

```
<210> SEQ ID NO 523
<211> LENGTH: 10
<212> TYPE: PRT
<213> ORGANISM: Lama glama

<400> SEQUENCE: 523

Ala Ser Tyr Arg Thr Phe Asn Asn Ala Val
1               5                   10

<210> SEQ ID NO 524
<211> LENGTH: 10
<212> TYPE: PRT
<213> ORGANISM: Lama glama
<220> FEATURE:
<221> NAME/KEY: MISC_FEATURE
<222> LOCATION: (4)..(4)
<223> OTHER INFORMATION: Xaa can be any naturally occurring amino acid,
      preferably Arg or Lys
<220> FEATURE:
<221> NAME/KEY: MISC_FEATURE
<222> LOCATION: (5)..(5)
<223> OTHER INFORMATION: Xaa can be any naturally occurring amino acid,
      preferably Asn, His, Arg, Ser, Asp, Thr or Tyr
<220> FEATURE:
<221> NAME/KEY: MISC_FEATURE
<222> LOCATION: (6)..(6)
<223> OTHER INFORMATION: Xaa can be any naturally occurring amino acid,
      preferably Phe, Tyr, Thr, Ser or Arg
<220> FEATURE:
<221> NAME/KEY: MISC_FEATURE
<222> LOCATION: (7)..(7)
<223> OTHER INFORMATION: Xaa can be any naturally occurring amino acid,
      preferably Asn or Ile
<220> FEATURE:
<221> NAME/KEY: MISC_FEATURE
<222> LOCATION: (8)..(8)
<223> OTHER INFORMATION: Xaa can be any naturally occurring amino acid,
      preferably Asn or Asp
<220> FEATURE:
<221> NAME/KEY: MISC_FEATURE
<222> LOCATION: (9)..(9)
<223> OTHER INFORMATION: Xaa can be any naturally occurring amino acid,
      preferably Val, Asn, Gly or Ala
<220> FEATURE:
<221> NAME/KEY: MISC_FEATURE
<222> LOCATION: (10)..(10)
<223> OTHER INFORMATION: Xaa can be any naturally occurring amino acid,
      preferably Val or Ile

<400> SEQUENCE: 524

Ala Ser Tyr Xaa Xaa Xaa Xaa Xaa Xaa Xaa
1               5                   10

<210> SEQ ID NO 525
<211> LENGTH: 7
<212> TYPE: PRT
<213> ORGANISM: Lama glama

<400> SEQUENCE: 525

Lys Val Thr Thr Arg Ala Ser
1               5

<210> SEQ ID NO 526
<211> LENGTH: 7
<212> TYPE: PRT
<213> ORGANISM: Lama glama

<400> SEQUENCE: 526

Lys Val Ser Thr Arg Ala Ser
1               5
```

<210> SEQ ID NO 527
<211> LENGTH: 7
<212> TYPE: PRT
<213> ORGANISM: Lama glama

<400> SEQUENCE: 527

Asp Val Asn Lys Arg Ala Ser
1               5

<210> SEQ ID NO 528
<211> LENGTH: 7
<212> TYPE: PRT
<213> ORGANISM: Lama glama

<400> SEQUENCE: 528

Arg Val Ser Thr Arg Ala Ser
1               5

<210> SEQ ID NO 529
<211> LENGTH: 7
<212> TYPE: PRT
<213> ORGANISM: Lama glama

<400> SEQUENCE: 529

Ala Val Ser Tyr Arg Val Ser
1               5

<210> SEQ ID NO 530
<211> LENGTH: 7
<212> TYPE: PRT
<213> ORGANISM: Lama glama

<400> SEQUENCE: 530

Ala Val Asn Tyr Arg Ala Ser
1               5

<210> SEQ ID NO 531
<211> LENGTH: 7
<212> TYPE: PRT
<213> ORGANISM: Lama glama

<400> SEQUENCE: 531

Glu Val Asn Lys Arg Thr Ser
1               5

<210> SEQ ID NO 532
<211> LENGTH: 7
<212> TYPE: PRT
<213> ORGANISM: Lama glama

<400> SEQUENCE: 532

Ala Val Ser Tyr Arg Ala Ser
1               5

<210> SEQ ID NO 533
<211> LENGTH: 7
<212> TYPE: PRT
<213> ORGANISM: Lama glama

<400> SEQUENCE: 533

Lys Val Thr Ser Arg Ala Ser
1               5

-continued

<210> SEQ ID NO 534
<211> LENGTH: 7
<212> TYPE: PRT
<213> ORGANISM: Lama glama

<400> SEQUENCE: 534

Arg Val Thr Thr Arg Ala Ser
1               5

<210> SEQ ID NO 535
<211> LENGTH: 7
<212> TYPE: PRT
<213> ORGANISM: Lama glama
<220> FEATURE:
<221> NAME/KEY: MISC_FEATURE
<222> LOCATION: (1)..(1)
<223> OTHER INFORMATION: Xaa can be any naturally occurring amino acid,
      preferably Arg, Lys, Asp, Ala or Glu
<220> FEATURE:
<221> NAME/KEY: MISC_FEATURE
<222> LOCATION: (3)..(3)
<223> OTHER INFORMATION: Xaa can be any naturally occurring amino acid,
      preferably Ser, Asn or Thr
<220> FEATURE:
<221> NAME/KEY: MISC_FEATURE
<222> LOCATION: (4)..(4)
<223> OTHER INFORMATION: Xaa can be any naturally occurring amino acid,
      preferably Thr, Lys or Tyr
<220> FEATURE:
<221> NAME/KEY: MISC_FEATURE
<222> LOCATION: (6)..(6)
<223> OTHER INFORMATION: Xaa can be any naturally occurring amino acid,
      preferably Ala, Thr or Val

<400> SEQUENCE: 535

Xaa Val Xaa Xaa Arg Xaa Ser
1               5

<210> SEQ ID NO 536
<211> LENGTH: 14
<212> TYPE: PRT
<213> ORGANISM: Lama glama

<400> SEQUENCE: 536

Ala Gly Ala Asn Asn Asp Ile Gly Thr Tyr Ala Tyr Val Ser
1               5                   10

<210> SEQ ID NO 537
<211> LENGTH: 14
<212> TYPE: PRT
<213> ORGANISM: Lama glama

<400> SEQUENCE: 537

Ala Gly Thr Ser Ser Asp Ile Gly Gly Tyr Asn Tyr Val Ser
1               5                   10

<210> SEQ ID NO 538
<211> LENGTH: 14
<212> TYPE: PRT
<213> ORGANISM: Lama glama

<400> SEQUENCE: 538

Ala Gly Thr Ser Ser Asp Ile Gly Tyr Gly Asp Tyr Val Ser
1               5                   10

<210> SEQ ID NO 539
<211> LENGTH: 14
<212> TYPE: PRT
<213> ORGANISM: Lama glama

```
<400> SEQUENCE: 539

Ala Gly Thr Ser Glu Asp Val Gly Tyr Gly Asn Tyr Val Ser
1               5                   10

<210> SEQ ID NO 540
<211> LENGTH: 14
<212> TYPE: PRT
<213> ORGANISM: Lama glama

<400> SEQUENCE: 540

Ala Gly Thr Ser Ser Asp Val Gly Tyr Gly Asn Tyr Val Ser
1               5                   10

<210> SEQ ID NO 541
<211> LENGTH: 14
<212> TYPE: PRT
<213> ORGANISM: Lama glama

<400> SEQUENCE: 541

Ala Gly Thr Ser Ser Asp Val Gly Phe Gly Asn Tyr Val Ser
1               5                   10

<210> SEQ ID NO 542
<211> LENGTH: 14
<212> TYPE: PRT
<213> ORGANISM: Lama glama
<220> FEATURE:
<221> NAME/KEY: MISC_FEATURE
<222> LOCATION: (3)..(3)
<223> OTHER INFORMATION: Xaa can be any naturally occurring amino acid,
      preferably Ala or Thr
<220> FEATURE:
<221> NAME/KEY: MISC_FEATURE
<222> LOCATION: (4)..(4)
<223> OTHER INFORMATION: Xaa can be any naturally occurring amino acid,
      preferably Ser or Asn
<220> FEATURE:
<221> NAME/KEY: MISC_FEATURE
<222> LOCATION: (5)..(5)
<223> OTHER INFORMATION: Xaa can be any naturally occurring amino acid,
      preferably Ser, Glu or Asn
<220> FEATURE:
<221> NAME/KEY: MISC_FEATURE
<222> LOCATION: (7)..(7)
<223> OTHER INFORMATION: Xaa can be any naturally occurring amino acid,
      preferably Val or Ile
<220> FEATURE:
<221> NAME/KEY: MISC_FEATURE
<222> LOCATION: (9)..(9)
<223> OTHER INFORMATION: Xaa can be any naturally occurring amino acid,
      preferably Gly, Tyr, Thr or Phe
<220> FEATURE:
<221> NAME/KEY: MISC_FEATURE
<222> LOCATION: (10)..(10)
<223> OTHER INFORMATION: Xaa can be any naturally occurring amino acid,
      preferably Gly or Tyr
<220> FEATURE:
<221> NAME/KEY: MISC_FEATURE
<222> LOCATION: (11)..(11)
<223> OTHER INFORMATION: Xaa can be any naturally occurring amino acid,
      preferably Asn, Asp or Ala

<400> SEQUENCE: 542

Ala Gly Xaa Xaa Xaa Asp Xaa Gly Xaa Xaa Xaa Tyr Val Ser
1               5                   10

<210> SEQ ID NO 543
<211> LENGTH: 9
<212> TYPE: PRT
<213> ORGANISM: Lama glama
```

```
<400> SEQUENCE: 543

Arg Ala Gly Trp Gly Met Gly Asp Tyr
1               5

<210> SEQ ID NO 544
<211> LENGTH: 7
<212> TYPE: PRT
<213> ORGANISM: Lama glama
<220> FEATURE:
<221> NAME/KEY: MISC_FEATURE
<222> LOCATION: (4)..(4)
<223> OTHER INFORMATION: Xaa can be any naturally occurring amino acid,
      preferably Trp
<220> FEATURE:
<221> NAME/KEY: MISC_FEATURE
<222> LOCATION: (6)..(6)
<223> OTHER INFORMATION: Xaa can be any naturally occurring amino acid,
      preferably Met, Ala, Leu, Ser or Asn

<400> SEQUENCE: 544

Arg Ala Gly Xaa Gly Xaa Gly
1               5

<210> SEQ ID NO 545
<211> LENGTH: 17
<212> TYPE: PRT
<213> ORGANISM: Lama glama

<400> SEQUENCE: 545

Arg Ile Ser Ala Gly Gly Gly Ser Thr Tyr Tyr Gly Asp Ser Val Lys
1               5                   10                  15

Gly

<210> SEQ ID NO 546
<211> LENGTH: 17
<212> TYPE: PRT
<213> ORGANISM: Lama glama

<400> SEQUENCE: 546

Ala Ile Ser Ala Gly Gly Gly Ser Thr Tyr Tyr Gly Asp Ser Val Lys
1               5                   10                  15

Gly

<210> SEQ ID NO 547
<211> LENGTH: 17
<212> TYPE: PRT
<213> ORGANISM: Lama glama

<400> SEQUENCE: 547

Arg Ile Ser Ser Gly Gly Gly Ser Thr Ser Tyr Ala Asp Ser Val Lys
1               5                   10                  15

Gly

<210> SEQ ID NO 548
<211> LENGTH: 17
<212> TYPE: PRT
<213> ORGANISM: Lama glama

<400> SEQUENCE: 548

Arg Ile Ser Ser Gly Gly Gly Ser Thr Asn Tyr Ala Asp Ser Val Lys
1               5                   10                  15

Gly
```

<210> SEQ ID NO 549
<211> LENGTH: 17
<212> TYPE: PRT
<213> ORGANISM: Lama glama

<400> SEQUENCE: 549

Arg Ile Ser Ser Gly Gly Gly Ser Ala Tyr Tyr Ala Asp Ser Val Lys
1               5                   10                  15

Gly

<210> SEQ ID NO 550
<211> LENGTH: 17
<212> TYPE: PRT
<213> ORGANISM: Lama glama

<400> SEQUENCE: 550

Ala Ile Ser Ser Ser Gly Val Ser Thr Tyr Tyr Thr Asp Ser Val Lys
1               5                   10                  15

Gly

<210> SEQ ID NO 551
<211> LENGTH: 17
<212> TYPE: PRT
<213> ORGANISM: Lama glama

<400> SEQUENCE: 551

Ala Ile Ser Ser Gly Gly Gly Ser Thr Tyr Tyr Gly Asp Ser Val Lys
1               5                   10                  15

Gly

<210> SEQ ID NO 552
<211> LENGTH: 17
<212> TYPE: PRT
<213> ORGANISM: Lama glama

<400> SEQUENCE: 552

Arg Ile Ser Ser Gly Gly Gly Ser Thr Tyr Tyr Gly Asp Ser Val Lys
1               5                   10                  15

Gly

<210> SEQ ID NO 553
<211> LENGTH: 17
<212> TYPE: PRT
<213> ORGANISM: Lama glama

<400> SEQUENCE: 553

Pro Ile Ser Ala Gly Gly Gly Ser Thr Tyr Tyr Gly Asp Ser Val Lys
1               5                   10                  15

Gly

<210> SEQ ID NO 554
<211> LENGTH: 17
<212> TYPE: PRT
<213> ORGANISM: Lama glama
<220> FEATURE:
<221> NAME/KEY: MISC_FEATURE
<222> LOCATION: (1)..(1)
<223> OTHER INFORMATION: Xaa can be any naturally occurring amino acid,
      preferably Ala, Pro or Arg
<220> FEATURE:
<221> NAME/KEY: MISC_FEATURE
<222> LOCATION: (4)..(4)
<223> OTHER INFORMATION: Xaa can be any naturally occurring amino acid,

```
      preferably Ala or Ser
<220> FEATURE:
<221> NAME/KEY: MISC_FEATURE
<222> LOCATION: (5)..(5)
<223> OTHER INFORMATION: Xaa can be any naturally occurring amino acid,
      preferably Ser or Gly
<220> FEATURE:
<221> NAME/KEY: MISC_FEATURE
<222> LOCATION: (7)..(7)
<223> OTHER INFORMATION: Xaa can be any naturally occurring amino acid,
      preferably Gly or Val
<220> FEATURE:
<221> NAME/KEY: MISC_FEATURE
<222> LOCATION: (9)..(9)
<223> OTHER INFORMATION: Xaa can be any naturally occurring amino acid,
      preferably Ala or Thr
<220> FEATURE:
<221> NAME/KEY: MISC_FEATURE
<222> LOCATION: (10)..(10)
<223> OTHER INFORMATION: Xaa can be any naturally occurring amino acid,
      preferably Tyr, Asn or Ser
<220> FEATURE:
<221> NAME/KEY: MISC_FEATURE
<222> LOCATION: (12)..(12)
<223> OTHER INFORMATION: Xaa can be any naturally occurring amino acid,
      preferably Gly, Ala or Thr

<400> SEQUENCE: 554

Xaa Ile Ser Xaa Xaa Gly Xaa Ser Xaa Xaa Tyr Xaa Asp Ser Val Lys
1               5                   10                  15

Gly

<210> SEQ ID NO 555
<211> LENGTH: 5
<212> TYPE: PRT
<213> ORGANISM: Lama glama

<400> SEQUENCE: 555

Ser Tyr Ala Met Ser
1               5

<210> SEQ ID NO 556
<211> LENGTH: 5
<212> TYPE: PRT
<213> ORGANISM: Lama glama

<400> SEQUENCE: 556

Thr Tyr Ala Met Ser
1               5

<210> SEQ ID NO 557
<211> LENGTH: 5
<212> TYPE: PRT
<213> ORGANISM: Lama glama

<400> SEQUENCE: 557

Ser Tyr Arg Met Tyr
1               5

<210> SEQ ID NO 558
<211> LENGTH: 5
<212> TYPE: PRT
<213> ORGANISM: Lama glama

<400> SEQUENCE: 558

Ser His Arg Met Tyr
1               5
```

```
<210> SEQ ID NO 559
<211> LENGTH: 5
<212> TYPE: PRT
<213> ORGANISM: Lama glama

<400> SEQUENCE: 559

Ser Tyr Ala Met Tyr
1               5

<210> SEQ ID NO 560
<211> LENGTH: 5
<212> TYPE: PRT
<213> ORGANISM: Lama glama

<400> SEQUENCE: 560

Ser Tyr Arg Met Ser
1               5

<210> SEQ ID NO 561
<211> LENGTH: 5
<212> TYPE: PRT
<213> ORGANISM: Lama glama

<400> SEQUENCE: 561

Ser Tyr Arg Leu Tyr
1               5

<210> SEQ ID NO 562
<211> LENGTH: 5
<212> TYPE: PRT
<213> ORGANISM: Lama glama
<220> FEATURE:
<221> NAME/KEY: MISC_FEATURE
<222> LOCATION: (1)..(1)
<223> OTHER INFORMATION: Xaa can be any naturally occurring amino acid,
      preferably Ser or Thr
<220> FEATURE:
<221> NAME/KEY: MISC_FEATURE
<222> LOCATION: (2)..(2)
<223> OTHER INFORMATION: Xaa can be any naturally occurring amino acid,
      preferably His or Tyr
<220> FEATURE:
<221> NAME/KEY: MISC_FEATURE
<222> LOCATION: (3)..(3)
<223> OTHER INFORMATION: Xaa can be any naturally occurring amino acid,
      preferably Ala or Arg
<220> FEATURE:
<221> NAME/KEY: MISC_FEATURE
<222> LOCATION: (4)..(4)
<223> OTHER INFORMATION: Xaa can be any naturally occurring amino acid,
      preferably Met or Leu
<220> FEATURE:
<221> NAME/KEY: MISC_FEATURE
<222> LOCATION: (5)..(5)
<223> OTHER INFORMATION: Xaa can be any naturally occurring amino acid,
      preferably Ser or Tyr

<400> SEQUENCE: 562

Xaa Xaa Xaa Xaa Xaa
1               5

<210> SEQ ID NO 563
<211> LENGTH: 9
<212> TYPE: PRT
<213> ORGANISM: Lama glama

<400> SEQUENCE: 563

Ala Leu Asp Ile Gly Asp Ile Thr Glu
1               5
```

<210> SEQ ID NO 564
<211> LENGTH: 7
<212> TYPE: PRT
<213> ORGANISM: Lama glama

<400> SEQUENCE: 564

Ser Thr Asn Asp Arg His Ser
1               5

<210> SEQ ID NO 565
<211> LENGTH: 14
<212> TYPE: PRT
<213> ORGANISM: Lama glama

<400> SEQUENCE: 565

Gly Leu Ser Ser Gly Ser Val Thr Ala Ser Asn Tyr Pro Gly
1               5                   10

<210> SEQ ID NO 566
<211> LENGTH: 7
<212> TYPE: PRT
<213> ORGANISM: Lama glama

<400> SEQUENCE: 566

Arg Ala Gly Trp Gly Ala Gly
1               5

<210> SEQ ID NO 567
<211> LENGTH: 7
<212> TYPE: PRT
<213> ORGANISM: Lama glama

<400> SEQUENCE: 567

Arg Ala Gly Trp Gly Leu Gly
1               5

<210> SEQ ID NO 568
<211> LENGTH: 7
<212> TYPE: PRT
<213> ORGANISM: Lama glama

<400> SEQUENCE: 568

Arg Ala Gly Trp Gly Ser Gly
1               5

<210> SEQ ID NO 569
<211> LENGTH: 118
<212> TYPE: PRT
<213> ORGANISM: Lama glama

<400> SEQUENCE: 569

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Pro Glu Trp Val
        35                  40                  45

Ser Arg Ile Ser Ala Gly Gly Ser Thr Tyr Tyr Gly Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys

```
                85                  90                  95
Ala Asn Arg Ala Gly Trp Gly Ala Gly Asp Tyr Trp Gly Gln Gly Thr
            100                 105                 110

Leu Val Thr Val Ser Ser
        115

<210> SEQ ID NO 570
<211> LENGTH: 118
<212> TYPE: PRT
<213> ORGANISM: Lama glama

<400> SEQUENCE: 570

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Pro Glu Trp Val
        35                  40                  45

Ser Arg Ile Ser Ala Gly Gly Gly Ser Thr Tyr Tyr Gly Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Asn Arg Ala Gly Trp Gly Leu Gly Asp Tyr Trp Gly Gln Gly Thr
            100                 105                 110

Leu Val Thr Val Ser Ser
        115

<210> SEQ ID NO 571
<211> LENGTH: 118
<212> TYPE: PRT
<213> ORGANISM: Lama glama

<400> SEQUENCE: 571

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Pro Glu Trp Val
        35                  40                  45

Ser Arg Ile Ser Ala Gly Gly Gly Ser Thr Tyr Tyr Gly Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Asn Arg Ala Gly Trp Gly Ser Gly Asp Tyr Trp Gly Gln Gly Thr
            100                 105                 110

Leu Val Thr Val Ser Ser
        115
```